US012807616B2

(12) United States Patent
Wang et al.

(10) Patent No.: US 12,807,616 B2
(45) Date of Patent: Nov. 24, 2026

(54) TYK-2 INHIBITOR

(71) Applicant: BEIGENE, LTD., Camana Bay (KY)

(72) Inventors: Qiuwen Wang, Beijing (CN); Yunhang Guo, Beijing (CN); Zhiwei Wang, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 676 days.

(21) Appl. No.: 18/011,590

(22) PCT Filed: Jun. 21, 2021

(86) PCT No.: PCT/CN2021/101282
§ 371 (c)(1),
(2) Date: Dec. 20, 2022

(87) PCT Pub. No.: WO2021/259208
PCT Pub. Date: Dec. 30, 2021

(65) Prior Publication Data

US 2024/0043435 A1 Feb. 8, 2024

(30) Foreign Application Priority Data

Jun. 22, 2020 (WO) ................ PCT/CN2020/097557
Sep. 30, 2020 (WO) ................ PCT/CN2020/119750
May 14, 2021 (WO) ................ PCT/CN2021/093815

(51) Int. Cl.

| | |
|---|---|
| ***C07D 213/75*** | (2006.01) |
| ***A61K 31/436*** | (2006.01) |
| ***A61K 31/443*** | (2006.01) |
| ***A61K 31/4433*** | (2006.01) |
| ***A61K 31/4439*** | (2006.01) |
| ***A61K 31/444*** | (2006.01) |
| ***A61K 31/497*** | (2006.01) |
| ***A61K 31/4985*** | (2006.01) |
| ***A61K 31/501*** | (2006.01) |
| ***A61K 31/5025*** | (2006.01) |
| ***A61K 31/506*** | (2006.01) |
| ***A61K 31/519*** | (2006.01) |
| ***A61K 31/5355*** | (2006.01) |
| ***A61K 31/5365*** | (2006.01) |
| ***A61K 31/537*** | (2006.01) |
| ***A61P 29/00*** | (2006.01) |
| ***A61P 37/00*** | (2006.01) |
| ***C07D 401/04*** | (2006.01) |
| ***C07D 401/14*** | (2006.01) |
| ***C07D 405/04*** | (2006.01) |
| ***C07D 405/14*** | (2006.01) |
| ***C07D 407/14*** | (2006.01) |
| ***C07D 409/14*** | (2006.01) |
| ***C07D 413/14*** | (2006.01) |
| ***C07D 417/14*** | (2006.01) |
| ***C07D 487/04*** | (2006.01) |
| ***C07D 487/06*** | (2006.01) |

(Continued)

(52) U.S. Cl.
CPC ....... *C07D 491/056* (2013.01); *C07D 401/14* (2013.01); *C07D 405/14* (2013.01); *C07D 409/14* (2013.01); *C07D 413/14* (2013.01); *C07D 417/14* (2013.01); *C07D 487/04* (2013.01); *C07D 491/147* (2013.01); *C07D 495/04* (2013.01); *C07D 498/04* (2013.01); *C07D 513/04* (2013.01); *C07D 513/14* (2013.01); *C07D 519/00* (2013.01)

(58) Field of Classification Search
CPC .. C07D 213/75; C07D 401/04; C07D 401/14; C07D 405/04; C07D 405/14; C07D 407/14; C07D 409/14; C07D 413/14; C07D 417/14; C07D 487/04; C07D 487/06; C07D 491/048; C07D 491/052; C07D 491/056; C07D 491/06; C07D 491/08; C07D 491/147; C07D 493/04; C07D 495/04; C07D 497/04; C07D 498/04; C07D 498/08; C07D 498/10; C07D 513/04; C07D 513/14; C07D 519/00; A61K 31/444; A61K 31/4433; A61K 31/5355; A61K 31/497; A61K 31/443; A61K 31/501; A61K 31/506; A61K 31/4439; A61K 31/436; A61K 31/5025; A61K 31/5365; A61K 31/4985; A61K 31/519; A61K 31/537; A61P 29/00; A61P 37/00
See application file for complete search history.

(56) References Cited

U.S. PATENT DOCUMENTS

2019/0276450 A1 9/2019 Argiriadi
2025/0059199 A1 * 2/2025 Wang ................ C07D 491/056

FOREIGN PATENT DOCUMENTS

JP 6557436 B1 8/2019
WO 2012117059 A1 9/2012

(Continued)

OTHER PUBLICATIONS

Bryan et al., 2018, "Kinase Inhibitors for the Treatment of Immunological Disorders: Recent Advances", J Med. Chem., 61: 9030-9058.

(Continued)

*Primary Examiner* — Brenda L Coleman
(74) *Attorney, Agent, or Firm* — McNeill PLLC

(57) ABSTRACT

Disclosed herein is a compound of Formula (I) for inhibiting TYK2 and treating a disease associated with the undesirable tyk-2 activity (tyk-2 related diseases), a method of using the compounds disclosed herein for treating inflammatory or autoimmune disease, and a pharmaceutical composition comprising the same.

20 Claims, No Drawings

(51) Int. Cl.

| | |
|---|---|
| ***C07D 491/048*** | (2006.01) |
| ***C07D 491/052*** | (2006.01) |
| ***C07D 491/056*** | (2006.01) |
| ***C07D 491/06*** | (2006.01) |
| ***C07D 491/08*** | (2006.01) |
| ***C07D 491/147*** | (2006.01) |
| ***C07D 493/04*** | (2006.01) |
| ***C07D 495/04*** | (2006.01) |
| ***C07D 497/04*** | (2006.01) |
| ***C07D 498/04*** | (2006.01) |
| ***C07D 498/08*** | (2006.01) |
| ***C07D 498/10*** | (2006.01) |
| ***C07D 513/04*** | (2006.01) |
| ***C07D 513/14*** | (2006.01) |
| ***C07D 519/00*** | (2006.01) |

(56) References Cited

FOREIGN PATENT DOCUMENTS

| | | | |
|---|---|---|---|
| WO | 2013054351 | | 4/2013 |
| WO | 2014074661 | A1 | 5/2014 |
| WO | 2018071794 | A1 | 4/2018 |
| WO | 2018183649 | A1 | 10/2018 |
| WO | 2018183656 | A1 | 10/2018 |
| WO | 2019178079 | A1 | 9/2019 |
| WO | 2019178079 | A9 | 12/2019 |
| WO | 2019232138 | A1 | 12/2019 |
| WO | 2020051572 | A1 | 3/2020 |
| WO | 2020086616 | A1 | 4/2020 |

OTHER PUBLICATIONS

Extended European Search Report issued in App. No. EP21829711, dated Jul. 11, 2024, 6 pages.
He et al., 2013, "Efficacy and Safety of Tofacitinib in the Treatment of Rheumatoid Arthritis: A Systematic Review and Meta-Analysis", BMC Musculoskelet Disorders, 14: 12 pages.
International Search Report for PCT/CN2021/101282 dated Dec. 3, 2021 (4 pages).
Ishizaki et al., 2011, "Involvement of Tyrosine Kinase-2 in Both the IL-12/TH1 and IL-23/TH17 Axes in vivo", J. Immunol., 187: 181-189.
Lochmuller et al., 1975, "Chromatographic Resolution of Enantiomers", Journal of Chromatography, 113: 283-302.
Minegishi et al., 2006, "Human tyrosine kinase 2 deficiency reveals its requisite roles in multiple cytokine signals involved in innate acquired immunity", Immunity, 25: 745-755.
Neubauer et al., 1998, "JAK2 deficiency defines an essential developmental checkpoint in definitive hematopoiesis", Cell, 93: 397-409.
Oyamada et al., 2009, "Tyrosine kinase 2 plays critical roles in the pathogenic CD4 T cell responses for the development of experimental autoimmune encephalomyelitis", J. Immunol., 183: 7539-7546.
Prchal-Murphy et al., 2012, "TYK2 kinase activity is required for functional type I interferon responses in vivo", PloS one, 7 (12 pages).
Wollenhaupt et al., 2014, "Safety and efficacy of tofacitinib, an oral Janus Kinase Inhibitor, for the treatment of rheumatoid arthritis in open-label", J. Rheumatol., 41: 837-852.
Zerbini et al., 2012, "Tofacitinib for the treatment of rheumatoid arthritis", Expert Rev Clin. Immunol., 8: 319-331. Abstract only.

* cited by examiner

TYK-2 INHIBITOR

CROSS-REFERENCE TO RELATED APPLICATIONS

This application is a U.S. National Stage Application under 35 U.S.C. § 371 of International Application No. PCT/CN2021/101282, filed Jun. 21, 2021, which claims priority to Patent Application Nos. PCT/CN2020/097557 (CN), filed Jun. 22, 2020, PCT/CN2020/119750 (CN), filed Sep. 30, 2020, and PCT/CN2021/093815 (CN), filed May 14, 2021.

FIELD OF THE DISCLOSURE

Disclosed herein is a compound of Formula (I) for inhibiting TYK2 and treating a disease associated with the undesirable tyk-2 activity (tyk-2 related diseases), a method of using the compounds disclosed herein for treating inflammatory or autoimmune diseases, and a pharmaceutical composition comprising the same.

BACKGROUND OF THE DISCLOSURE

Janus family of kinases includes JAK1, JAK2, JAK3, and tyrosine kinase 2 (Tyk2) and are nonreceptor tyrosine kinases that bind to the intracellular portion of cell surface cytokine receptors. In response to the stimulation of these receptors, the Janus kinases phosphorylate signal transducer and activator of transcription (STAT) proteins, which then dimerize, translocate to the nucleus, and activate gene transcription. Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/TH1 and IL-23/TH17 Axes in vivo", *J. Immunol.,* 187: 181-189 (2011); Prchal-Murphyl, M. et al., "TYK2 kinase activity is required for functional type I interferon responses in vivo", *PloS one,* 7:e39141 (2012)) and humans (Minegishi, Y. et al., "Human tyrosine kinase 2 deficiency reveals its requisite roles in multiple cytokine signals involved in innate acquired immunity", *Immunity,* 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental model of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/TH1 and IL-23/TH17 Axes in vivo", *J. Immunol.,* 187: 181-189 (2011); Oyamada, A. et al., "Tyrosine kinase 2 plays critical roles in the pathogenic CD4 T cell responses for the development of experimental autoimmune encephalomyelitis", *J. Immunol.,* 2009, 183, 7539-7546).

To date, most of the known small molecule JAK inhibitors that have progressed into development are active site-directed inhibitors that bind to the adenosine triphosphate (ATP) site of the catalytic domain (also referred to as the JH1 or "Janus Homology 1" domain) of the JAK protein, which prevents catalytic activity of the kinase by blocking ATP, downstream phosphorylation, and resulting pathway signal transduction (Bryan, M. et al., "Kinase Inhibitors for the Treatment of Immunological Disorders: Recent Advances", *J Med. Chem.* 2018, 61, 9030-9058). It's well-known that JAK2 is involved in hematopoiesis (Neubauer, H.; et al., "JAK2 deficiency defines an essential developmental checkpoint in definitive hematopoiesis", *Cell* 1998, 93, 397-409) and the inhibition of JAK2 can cause side effects such as anemia, neutropenia, and increased infection risk and dyslipidemia (Wollenhaupt, J., et al., "Safety and efficacy of tofacitinib, an oral Janus Kinase Inhibitor, for the treatment of rheumatoid arthritis in open-label. *J. Rheumatol.* 2014, 41, 837-852; He, Y., et al., Efficacy and safety of tofacitinib in the treatment of rheumatoid arthritis: a systematic review and meta-analysis. *BMC Musculoskelet. Disord.* 2013, 14, 298; Zerbini, C. A, et al., Tofacitinib for the treatment of rheumatoid arthritis. *Expert Rev Clin. Immunol.* 2012, 8, 319-331).

Small molecule inhibitors of TYK2-JH2 domain are being developed for treating autoimmune diseases. BMS986165 (WO2014074661A1, WO2018183649A1, WO2018183656A1 and WO2019232138A1) is a first-in-class of TYK2-JH2 inhibitor, currently undergoing multiple clinical trials in psoriasis, ulcerative colitis (UC), lupus and systemic lupus erythematosus. The other TYK2-JH2 inhibitor which entered clinical trials is ABBV-712 (See, for example, WO2019178079A1, WO2019178079A9, JP6557436B1, and US2019276450A1) and it is in a clinical trial for psoriasis.

SUMMARY OF THE DISCLOSURE

Disclosed herein provides a serial of compounds which inhibit the pseudokinase (JH2) domain of TYK2. These compounds showed picomolar to nanomolar biochemical activity in TYK2-JH2 binding assay and also showed nanomolar activity in cellular assay. In the meanwhile, these compounds showed excellent selectivity against JAK1 in biochemical assay and excellent selectivity against JAK2 in cellular assay.

In the present discourse, compounds bind to the pseudokinase (JH2) domain of TYK2 and inhibit its function through an allosteric mechanism. In the meanwhile, these compounds have greatly improved selectivity over other JAK family members (JAK1, JAK2 and JAK3).

In the first aspect, disclosed herein a compound of Formula (I)

(I)

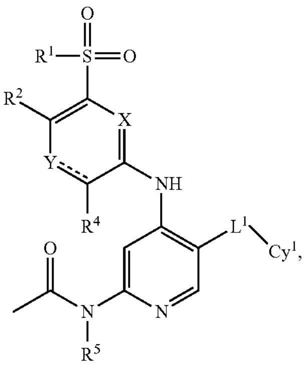

or a stereoisomer or a pharmaceutically acceptable salt thereof, wherein:

X is N or CH;

Y is N, $NR^3$ or $CR^3$;

$L^1$ is a direct bond, $—(CR^aR^b)—$, —O—, —S—, —S(O)—, $—SO_2—$, —C(O)—, C(O)O—, —OC(O)—, $—NR^a—$, $—O—(CR^aR^b)_q$, $—S—(CR^aR^b)_q—$, $—S(O)—(CR^aR^b)_q—$, $—SO_2—(CR^aR^b)_q—$, $—C(O)—(CR^aR^b)_q—$, $C(O)O—(CR^aR^b)_q—$, $—OC(O)—(CR^aR^b)_q—$, $—NR^a—(CR^aR^b)_6—$, $—C(O)NR^a—$, $—NR^aC(O)—$, $—NR^aC(O)O—$, $—NR^aC(O)NR^b—$, $—SO_2NR^a—$, $—NR^aSO_2—$, $—NR^aS(O)_2NR^b—$, $—NR^aS(O)NR^b—$, $—C(O)NR^aSO_2—$, $—C(O)NR^aSO—$, or $—C(=NR^a)NR^b—$, wherein q is a number of 1 to 7, and, $R^a$ and $R^b$ are independently hydrogen, $—C_{1-6}$alkyl, $—C_{2-6}$alkenyl, $—C_{2-6}$alkynyl, cycloalkyl, heterocyclyl, aryl, or heteroaryl;

$R^1$ is $—C_{1-6}$alkyl, -halo$C_{1-6}$alkyl, $—C_{1-6}$ alkoxy, -halo$C_{1-6}$ alkoxyl, $—C_{3-6}$ cycloalkyl, aryl, or $—NR^cR^d$;

each of $R^2$, $R^3$, and $R^4$ is independently hydrogen, cyano, halogen, $—C_{1-6}$alkyl, $—C_{2-6}$alkenyl, $—C_{2-6}$alkynyl, $—C_{3-8}$cycloalkyl, heterocyclyl, aryl, heteroaryl, oxo, $—NO_2$, $—OR^e$, $—SO_2R^e$, $—COR^e$, $—CO_2R^e$, $—CONR^eR^f$, $—C(=NR^e)NR^fR^g$, $—NR^eR^f$, $—NR^eCOR^f$, $—NR^eCONR^fR^g$, $—NR^eCO_2R^f$, $—NR^eSONR^fR^g$, $—NR^eSO_2NR^fR^g$, or $—NR^eSO_2R^f$, wherein each of $—C_{1-6}$alkyl, $—C_{2-6}$alkenyl, $—C_{2-6}$alkynyl, $—C_{3-8}$cycloalkyl, heterocyclyl, aryl, or heteroaryl is independently and optionally substituted with at least one substituent selected from i) cyano, -oxo-, halogen, $—NR^{m}R^{n}$, $—OR^h$, $—C(O)NR^{m}R^{n}$;

ii) heterocyclyl optionally substituted with at least one substituent independently selected from cyano, -oxo, halogen, hydroxy, $—NR^{m}R^{n}$, substituted or unsubstituted $—C_{1-6}$alkyl, substituted or unsubstituted $—C_{1-6}$ alkoxy or $—C(O)NR^{m}R^{n}$; or, iii) $C_{1-6}$alkyl optionally substituted with at least one substitution independently selected from cyano, halogen, hydroxy, $—NH_2$ or $C_{1-6}$alkoxy;

wherein $R^h$ is hydrogen, hydroxy, $—NH_2$, $—C_{1-6}$alkyl, $C_{1-6}$alkyl substituted with hydroxy, or heterocyclyl, $R^e$, $R^f$, and $R^g$ are each independently hydrogen, $—C_{1-6}$alkyl, $—C_{1-6}$alkoxy, $—C_{2-6}$alkenyl, $—C_{2-6}$alkynyl, cycloalkyl, heterocyclyl, aryl, or heteroaryl, wherein each of $—C_{1-6}$alkyl, $—C_{2-6}$alkenyl, $—C_{2-6}$alkynyl, cycloalkyl, heterocyclyl, aryl, or heteroaryl is optionally independently substituted with one to three substituents selected from cyano, -oxo-, halogen, hydroxy, $—NR^{m}R^{n}$, $—C_{1-6}$alkyl, $—C_{1-6}$alkoxy, $—C_{3-6}$cycloalkyl optionally substituted with halogen, hydroxy or $—C_{1-6}$alkoxy, $—C(O)NR^{m}R^{n}$, or heterocyclyl;

$R^5$ is hydrogen or $C_{1-6}$alkyl;

$Cy^1$ is 6- to 12-membered aryl or 5- to 14-membered heteroaryl, or 5- to 14-membered heterocyclyl, each of which is optionally substituted with at least one substituent $R^i$, $R^i$ is independently halogen, cyano, $—C_{1-6}$alkyl, $—C_{2-6}$ alkenyl, $—C_{2-6}$alkynyl, $—C_{3-6}$cycloalkyl, heterocyclyl, aryl, heteroaryl, oxo, cyano (—CN), $—NO_2$, $—OR^j$, $—SO_2R^j$, $—COR^j$, $—CO_2R^k$, $—CONR^jR^k$, $—C(=NR^j)NR^kR^l$, $—NR^jR^k$, $—NR^jCOR^k$, $—NR^jCONR^kR^l$, $—NR^jCO_2R^k$, $—NR^jSONR^kR^l$, $—NR^jSO_2NR^kR^l$, or $—NR^jSO_2R^k$, wherein each of $—C_{1-6}$alkyl, $—C_{2-6}$alkenyl, $—C_{2-6}$alkynyl, $—C_{3-8}$cycloalkyl, heterocyclyl, aryl, or heteroaryl is optionally substituted with halogen, $—OR^m$, $—C(O)R^m$, $—NR^{m}R^{n}$, $—C_{1-6}$alkyl, $C_{1-6}$alkoxy-, $C_{1-6}$alkyl substituted with $—C_{1-6}$alkoxy or -oxo-;

$R^j$, $R^k$, $R^l$, $R^m$, $R^n$ are each independently hydrogen, $—C_{1-6}$alkyl, $C_{1-6}$alkoxy-$C_{1-6}$alkyl-, $—C_{2-6}$alkenyl, $—C_{2-6}$alkynyl, cycloalkyl, heterocyclyl, aryl, or heteroaryl;

or ($R^1$ and $R^2$), or ($R^2$ and $R^3$), or ($R^3$ and $R^4$), together with the atoms to which they are attached, form a fused ring system, said fused ring system comprises 0-4 heteroatoms selected from oxygen (O), nitrogen (N) or sulfur (S) as ring member(s) and is optionally and independently substituted with halogen, $—C_{1-6}$ alkyl, $—C_{1-6}$alkoxy, $C_{1-6}$alkyl substituted with halogen, $C_{1-6}$alkoxy substituted with halogen or $—C_{3-6}$cycloalkyl;

any of the said alkyl or alkoxy is optionally enriched in deuterium.

In some embodiments, disclosed herein is a compound of Formula (I-A)

(I-A)

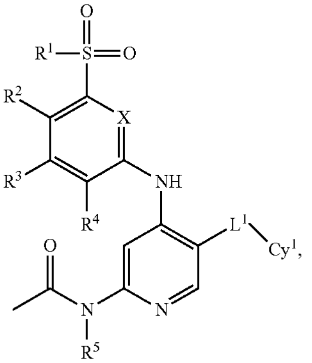

or a stereoisomer or a pharmaceutically acceptable salt thereof, wherein:

X is N or CH;

$L^1$ is a direct bond, $—(CR^aR^b)_q—$, —O—, —S—, —S(O)—, $—SO_2—$, —C(O)—, C(O)O—, —OC(O)—, $—NR^a—$, $—O—(CR^aR^b)_q—$, $—S—(CR^aR^b)_q—$, $—S(O)—(CR^aR^b)_q—$, $—SO_2—(CR^aR^b)_q—$, $—C(O)—(CR^aR^b)_q—$, $C(O)O—(CR^aR^b)_q—$, $—OC(O)—(CR^aR^b)_q—$, $—NR^a—(CR^aR^b)_q—$, $—C(O)NR^a—$, $—NR^aC(O)—$, $—NR^aC(O)O—$, $—NR^aC(O)NR^b—$, $—SO_2NR^a—$, $—NR^aSO_2—$, $—NR^aS(O)_2NR^b—$, $—NR^aS(O)NR^b—$, $—C(O)NR^aSO_2—$, $—C(O)NR^aSO—$, or $—C(=NR^a)NR^b—$, wherein q is a number of 1 to 7, and, $R^a$ and $R^b$ are independently hydrogen, $—C_{1-6}$alkyl, $—C_{2-6}$alkenyl, $—C_{2-6}$alkynyl, cycloalkyl, heterocyclyl, aryl, or heteroaryl;

$R^1$ is $—C_{1-6}$alkyl, -halo$C_{1-6}$alkyl, $—C_{1-6}$alkoxy, -halo$C_{1-6}$ alkoxyl, $—C_3$ cycloalkyl, aryl, or $—NR^{m}R^{n}$;

each of $R^2$, $R^3$, and $R^4$ is independently hydrogen, halogen, $—C_{1-6}$alkyl, $—C_{2-6}$alkenyl, $—C_{2-6}$alkynyl, $—C_{3-8}$ cycloalkyl, heterocyclyl, aryl, heteroaryl, -oxo-, —CN, $—NO_2$, $—OR^e$, $—SO_2R^e$, $—COR^e$, $—CO_2R^e$, $—CONR^eR^f$, $—C(=NR^e)NR^fR^g$, $—NR^eR^f$, $—NR^eCOR^f$, $—NR^eCONR^fR^g$, $—NR^eCO_2R^f$, $—NR^eSONR^fR^g$, $—NR^eSO_2NR^fR^g$, or $—NR^eSO_2R^f$, wherein each of $—C_{1-6}$alkyl, $—C_{2-6}$alkenyl, $—C_{2-6}$alkynyl, $—C_{3-8}$cycloalkyl, heterocyclyl, aryl, or heteroaryl is independently and optionally substituted with at least one substituents selected from cyano, oxo, halogen, $C_{1-6}$alkyl optionally substituted with halogen, $C_{1-6}$alkyl substituted with hydroxy (preferably, hydroxymethyl, hydroxyethyl), —$OR^h$, —C(O)NR'''R", —$NH_2$, —$C_{1-6}$ alkyl substituted with —$NH_2$ or —$C_{1-6}$alkyl substituted with —$C_{1-6}$alkoxy-;

wherein $R^h$ is hydrogen, alkyl, hydroxy-$C_{1-6}$alkyl or heterocyclyl, $R^e$, $R^f$, and $R^g$ are each independently hydrogen, —$C_{1-6}$ alkyl, —$C_{1-6}$alkoxy, —$C_{2-6}$alkenyl, —$C_{2-6}$alkynyl, cycloalkyl, heterocyclyl, aryl, or heteroaryl, wherein each of —$C_{1-6}$alkyl, —$C_{2-6}$alkenyl, —$C_{2-6}$alkynyl, cycloalkyl, heterocyclyl, aryl, or heteroaryl is optionally independently substituted with one to three substituents selected from halogen, hydroxy, cyano, or —$C_{1-6}$alkoxy; —$C_{3-6}$cycloalkyl optionally substituted with halogen, hydroxy, or $C_{1-6}$alkoxy, or heterocyclyl;

$R^5$ is hydrogen or $C_{1-6}$alkyl;

$Cy^1$ is 6- to 12-membered aryl or 5- to 14-membered heteroaryl, or 5- to 14-membered heterocyclyl, each of which is optionally substituted with at least one substituent $R^i$, $R^i$ is independently halogen, cyano, —$C_{1-6}$alkyl, —$C_{2-6}$ alkenyl, —$C_{2-6}$alkynyl, —$C_{3-6}$cycloalkyl, heterocyclyl, aryl, heteroaryl, oxo, —CN, —$NO_2$, —$OR^j$, —$SO_2R^j$, —$COR^j$, —$CO_2R^k$, —$CONR^jR^k$, —C(=$NR^j$)$NR^kR^l$, —$NR^jR^k$, —$NR^jCOR^k$, —$NR^jCONR^kR^l$, —$NR^jCO_2R^k$, —$NR^jSONR^kR^l$, —$NR^jSO_2NR^kR^l$, or —$NR^jSO_2R^k$, wherein each of said —$C_{1-6}$alkyl, —$C_{2-6}$alkenyl, —$C_{2-6}$ alkynyl, —$C_{3-8}$cycloalkyl, heterocyclyl, aryl, or heteroaryl is optionally substituted with halogen, $OR^m$, $C(O)R^m$, —$NR^mR^n$, —$C_{1-6}$alkyl, $C_{1-6}$alkoxy-, $C_{1-6}$alkoxy-$C_{1-6}$ alkyl-, or oxo;

$R^j$, $R^k$, $R^l$, $R^m$, $R^n$ are each independently hydrogen, —$C_{1-6}$alkyl, —$C_{1-6}$alkyl substituted with $C_{1-6}$alkoxy, —$C_{2-6}$alkenyl, —$C_{2-6}$alkynyl, cycloalkyl, heterocyclyl, aryl, or heteroaryl;

or ($R^1$ and $R^2$), or ($R^2$ and $R^3$), or ($R^3$ and $R^4$), together with the atoms to which they are attached, form a fused ring system, said fused ring system comprises 0-4 heteroatoms selected from oxygen, nitrogen or sulfur as ring member(s) and is optionally and independently substituted with halogen, —$C_{1-6}$alkyl, —$C_{1-6}$alkoxy, -halo$C_{1-6}$alkyl, -halo$C_{1-6}$alkoxy, or —$C_{3-6}$cycloalkyl;

any of the said alkyl or alkoxy is optionally enriched in deuterium.

In some embodiments, X is N and Y is $CR^3$. In some embodiments, X is N and Y is N. In some embodiments, X is CH and Y is N.

In some embodiments, $R^1$ is —$C_{1-3}$ alkyl, —$NR^cR^d$ or —$C_{3-6}$ cycloalkyl, preferably —$NH_2$, methyl, ethyl, propyl, isopropyl, cyclopropyl or cyclopentyl.

In some embodiments, $R^2$ and $R^4$ are each independently hydrogen, halogen, —$C_{1-6}$alkyl, or —$C_{1-6}$alkoxy, preferably hydrogen, fluoro, methyl, methoxy, ethoxy, or isopropoxy.

In some embodiments, $R^3$ is hydrogen;

cyano;

halogen;

—$C_{1-4}$ alkyl optionally substituted with at least one substituent independently selected from halogen, 3- to 6-membered heterocyclyl or —$OR^h$, wherein 3- to 6-membered heterocyclyl comprises one or two heteroatoms selected from oxygen (O), nitrogen (N) or sulfur (O) as ring member(s), optionally substituted with at least one substituent independently selected from cyano, -oxo, halogen, hydroxy, —$NR^mR^n$, $C_{1-6}$alkyl, —$C_{1-6}$alkoxy or —C(O)$NR^mR^n$, wherein —$C_{1-6}$alkyl or —$C_{1-6}$alkoxy is substituted with at least one substitution independently selected from cyano, halogen, hydroxy, —$NH_2$, —$C_{1-6}$alkyl or $C_{1-6}$alkoxy; and $R^h$ is hydrogen, alkyl, or heterocyclyl;

—$C_{3-6}$cycloalkyl, optionally substituted with at least one substituent independently selected from cyano, -oxo, halogen, —$NR^mR^n$, hydroxy, —$C_{1-6}$alkyl, —$C_{1-6}$ alkoxy or —C(O)$NR^mR^n$, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

heterocyclyl comprising one or two heteroatoms selected from oxygen (O), nitrogen (N) or sulfur (S) as ring member(s), optionally substituted with at least one substituent independently selected from cyano, -oxo-, halogen, hydroxy, $C_{1-6}$alkyl, alkoxy, —$NRR^mR^n$, or —C(O)$NR^mR^n$, and wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

—$OR^e$, wherein $R^e$ is —$C_{1-6}$alkyl, —$C_{3-6}$cycloalkyl, 3- to 6-membered heterocyclyl, or aryl, wherein i) —$C_{1-6}$alkyl is optionally substituted with cyano, -oxo-, halogen, hydroxy, —$NR^mR^n$, —$C_{1-6}$alkoxy-, —$C_{3-6}$cycloalkyl optionally substituted with cyano, -oxo, halogen, hydroxy, —$NR^mR^n$, —$C_{1-6}$alkyl, $C_{1-6}$alkoxy or —C(O)$NR^mR^n$, 4- to 6-membered heterocyclyl optionally substituted with cyano, halogen, hydroxy, $C_{1-6}$alkyl or $C_{1-6}$alkoxy; and, ii) —$C_{3-6}$cycloalkyl or 3- to 6-membered heterocyclyl is optionally substituted with cyano, -oxo, halogen, hydroxy, —$NR^mR^n$, $C_{1-6}$alkyl, $C_{1-6}$alkoxy or —C(O)$NR^mR^n$, wherein —$C_{1-6}$alkyl or $C_{1-6}$alkoxy is substituted with at least one substitution independently selected from cyano, halogen, hydroxy, —$NH_2$, —$C_{1-6}$ alkyl or $C_{1-6}$alkoxy;

—$C_{5-10}$aryl; or heteroaryl comprising one oxygen (O), nitrogen (N) or sulfur (S) heteroatom as ring member, optionally substituted with at least one substitution independently selected from cyano, -oxo, halogen, hydroxy, —$NR^mR^n$, —$C_{1-6}$alkyl, —$C_{1-6}$alkoxy or —C(O)$NR^mR^n$, wherein —$C_{1-6}$alkyl or $C_{1-6}$alkoxy is substituted with at least one substitution independently selected from cyano, halogen, hydroxy, —$NH_2$, —$C_{1-6}$ alkyl or $C_{1-6}$alkoxy;

and wherein $R^m$ and $R^n$ are independently selected from hydrogen or $C_{1-3}$alkyl;

any of the said alkyl or alkoxy is optionally enriched in deuterium.

In some embodiments, $R^3$ is hydrogen;

cyano;

halogen;

—$C_{1-4}$ alkyl optionally substituted with at least one substituent independently selected from halogen, 3- to 6-membered heterocyclyl or —OR, wherein said 3- to 6-membered heterocyclyl comprises one or two heteroatoms selected from oxygen (O), nitrogen (N) or sulfur (O) as ring member(s), optionally substituted with at least one substituent independently selected from cyano, -oxo, halogen, hydroxy, —$NR^mR^n$, $C_{1-6}$alkyl, —$C_{1-6}$alkoxy or —C(O)$NR^mR^n$, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy, and, $R^h$ is hydrogen, alkyl or heterocyclyl (preferably 3- to 6-membered heterocyclyl, e.g., tetrahydrofuranyl, thiazolidinyl);

—$C_{3-6}$cycloalkyl, optionally substituted with at least one substituent independently selected from cyano, -oxo, halogen, —NR‴R″, hydroxy, —$C_{1-6}$alkyl, —$C_{1-6}$ alkoxy or —C(O)NR‴R″, wherein —$C_{1-6}$alkyl or $C_{1-6}$ alkoxy is substituted with at least one substitution independently selected from cyano, halogen, hydroxy, —$NH_2$, —$C_{1-6}$alkyl or $C_{1-6}$alkoxy;

heterocyclyl, preferably 4- to 6-membered monocyclic saturated heterocyclyl, saturated mono-spiro heterocyclyl, saturated bicyclic fused heterocyclyl, or saturated bridged heterocyclyl, comprising one or two heteroatoms selected from oxygen (O), nitrogen (N) or sulfur (S) as ring member(s), more preferably morpholinyl, tetrahydrofuranyl, tetrahydropyranyl, pyrrolidinyl, 1,4-dioxanyl, piperidinyl or azetidinyl, optionally substituted with at least one substituent independently selected from cyano, -oxo, halogen, hydroxy, —$C_{1-6}$ alkyl, alkoxy, —NR‴R″, or —C(O)NR‴R″, and wherein —$C_{1-6}$alkyl or —$C_{1-6}$-alkoxy is substituted with at least one substitution independently selected from cyano, halogen, hydroxy, —$NH_2$, —$C_{1-6}$ alkyl or $C_{1-6}$alkoxy;

—$OR^e$, wherein $R^e$ is —$C_{1-6}$alkyl, —$C_{3-6}$cycloalkyl, 3- to 6-membered heterocyclyl (preferably 4- to 6-membered monocyclic saturated heterocyclyl comprising one oxygen heteroatom as ring member), or aryl, wherein i) —$C_{1-6}$alkyl is optionally substituted with cyano, -oxo-, halogen, hydroxy, —NR‴R″, —$C_{1-6}$alkoxy-, —$C_{3-6}$cycloalkyl optionally substituted with cyano, -oxo, halogen, hydroxy, —NR‴R″, —$C_{1-6}$alkyl, $C_{1-6}$alkoxy or —C(O) NR‴R″, 4- to 6-membered heterocyclyl optionally substituted with cyano, halogen, hydroxy, —$C_{1-6}$ alkyl or —$C_{1-6}$ alkoxy; and, ii) —$C_{3-6}$cycloalkyl or 3- to 6-membered heterocyclyl is optionally substituted with cyano, -oxo, halogen, hydroxy, NR‴R″, $C_{1-6}$alkyl, $C_{1-6}$alkoxy or —C(O)NR‴R″, wherein —$C_{1-6}$alkyl or $C_{1-6}$alkoxy is substituted with at least one substitution independently selected from cyano, halogen, hydroxy, —$NH_2$, —$C_{1-6}$ alkyl or $C_{1-6}$alkoxy;

—$C_{5-10}$aryl; or heteroaryl, preferably 5- to 6-membered heteroaryl comprising one oxygen (O), nitrogen (N) or sulfur (S) heteroatom as ring member, optionally substituted with at least one substitution independently selected from cyano, -oxo, halogen, hydroxy, —NR‴R″, —$C_{1-6}$alkyl, —$C_{1-6}$alkoxy or —C(O)NR‴R″, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

and wherein R‴ and R″ are independently selected from hydrogen or $C_{1-3}$alkyl.

In some embodiments, $R^3$ is hydrogen, cyano, halogen;

—$C_{1-4}$ alkyl optionally substituted with at least one substituent independently selected from halogen, 3- to 6-membered heterocyclyl or —$OR^h$, wherein Said 3- to 6-membered heterocyclyl is selected from morpholinyl, tetrahydrofuranyl, tetrahydropyranyl, pyrrolidinyl, 1,4-dioxanyl, piperidinyl, thiazolidinyl or azetidinyl, each of which is optionally substituted with at least one substituent independently selected from cyano, -oxo, halogen, hydroxy, —NR‴R″, $C_{1-6}$ alkyl, —$C_{1-6}$alkoxy or —C(O)NR‴R″, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy, and, $R^h$ is hydrogen, $C_{1-6}$alkyl or 3- to 6-membered heterocyclyl (e.g., tetrahydrofuranyl or thiazolidinyl);

—$C_{3-6}$cycloalkyl, optionally substituted with at least one substituent independently selected from cyano, -oxo, halogen, NR‴R″, hydroxy, —$C_{1-6}$alkyl, —$C_{1-6}$alkoxy or —C(O)NR‴R″, hydroxy, or $C_{1-6}$alkoxy, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

heterocyclyl is selected from morpholinyl, tetrahydrofuranyl, tetrahydropyranyl, pyrrolidinyl, 1,4-dioxanyl, piperidinyl or azetidinyl, optionally substituted with at least one substituent independently selected from cyano, -oxo, halogen, hydroxy, $C_{1-6}$alkyl, alkoxy, —NRR‴R″, or —C(O)NR‴R″, and wherein —$C_{1-6}$ alkyl or —$C_{1-6}$alkoxy is substituted with at least one substitution independently selected from cyano, halogen, hydroxy, —$NH_2$, —$C_{1-6}$alkyl or —$C_{1-6}$alkoxy;

—$OR^e$, wherein $R^e$ is —$C_{1-6}$alkyl, —$C_{3-6}$cycloalkyl, 4- to 6-membered monocyclic saturated heterocyclyl comprising one oxygen heteroatom as ring member, or $C_{6-10}$aryl, wherein i) —$C_{1-6}$alkyl is optionally substituted with cyano, -oxo-, halogen, hydroxy, —NR‴R″, —$C_{1-6}$alkoxy-, —$C_{3-6}$cycloalkyl optionally substituted with cyano, -oxo, halogen, hydroxy, —NR‴R″, —$C_{1-6}$alkyl, —$C_{1-6}$alkoxy or —C(O) NR‴R″, 4- to 6-membered heterocyclyl optionally substituted with cyano, halogen, hydroxy, —$C_{1-6}$ alkyl or —$C_{1-6}$ alkoxy; and, ii) —$C_{3-6}$cycloalkyl or 3- to 6-membered heterocyclyl is optionally substituted with cyano, -oxo, halogen, hydroxy, NR‴R″, $C_{1-6}$alkyl, $C_{1-6}$alkoxy or —C(O)NR‴R″, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

—$C_{6-10}$aryl; or 5- to 6-membered heteroaryl selected from pyridinyl, pyridazinyl, pyrazinyl, thiazolyl or isoxazolyl, each of which is optionally substituted with at least one substitution independently selected from cyano, -oxo, halogen, hydroxy, —NR‴R″, —$C_{1-6}$alkyl, —$C_{1-6}$ alkoxy or —C(O)NR‴R″, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

and wherein R‴ and R″ are independently selected from hydrogen or —$C_{1-3}$alkyl.

In some embodiments, $R^3$ is hydrogen, cyano, halogen;

—$C_{1-4}$ alkyl optionally substituted with at least one substituent independently selected from halogen, hydroxy, $C_{1-3}$alkoxy, thiazolidin-3-yl optionally substituted with at least one substituent independently selected from cyano, -oxo, halogen, hydroxy, —NR‴R″, or —$C_{1-3}$ alkyl;

—$C_{3-6}$cycloalkyl, optionally substituted with at least one substituent independently selected from cyano, -oxo, halogen, —NR‴R″, hydroxy, —$C_{1-6}$alkyl, or —$C_{1-6}$ alkoxy, wherein —$C_{1-6}$alkyl or $C_{1-6}$alkoxy is substituted with at least one substitution independently selected from cyano, halogen, hydroxy, —$NH_2$, —$C_{1-6}$alkyl or —$C_{1-3}$alkoxy;

heterocyclyl is selected from morpholinyl, tetrahydrofuranyl, tetrahydropyranyl, pyrrolidinyl, 1,4-dioxanyl, piperidinyl or azetidinyl, optionally substituted with at least one substituent independently selected from cyano, -oxo, halogen, hydroxy, $C_{1-6}$alkyl, alkoxy, —NR‴R″, or —C(O)NR‴R″, and wherein —$C_{1-6}$ alkyl or $C_{1-6}$alkoxy is substituted with at least one substitution independently selected from cyano, halogen, hydroxy, —$NH_2$, —$C_{1-6}$alkyl or —$C_{1-6}$alkoxy;

—$OR^e$, wherein $R^e$ is —$C_{1-6}$alkyl, —$C_{3-6}$cycloalkyl, 4- to 6-membered monocyclic saturated heterocyclyl comprising one oxygen heteroatom as ring member, or $C_{6-10}$aryl, wherein i) —$C_{1-6}$alkyl is optionally substituted with cyano, -oxo-, halogen, hydroxy, —NR‴R″, —$C_{1-6}$alkoxy-, —$C_{3-6}$cycloalkyl optionally substituted with cyano, -oxo, halogen, hydroxy, —NR‴R″, —$C_{1-6}$alkyl, —$C_{1-6}$alkoxy or —C(O) NR‴R″, 4- to 6-membered heterocyclyl optionally substituted with cyano, halogen, hydroxy, —$C_{1-6}$ alkyl or —$C_{1-6}$ alkoxy; and, ii) —$C_{3-6}$cycloalkyl or 3- to 6-membered heterocyclyl is optionally substituted with cyano, -oxo, halogen, hydroxy, —NR‴R″, —$C_{1-6}$alkyl, —$C_{1-6}$alkoxy or —C(O)NR‴R″, wherein —$C_{1-6}$alkyl or —$C_{1-6}$alkoxy is substituted with at least one substitution independently selected from cyano, halogen, hydroxy, —$NH_2$, —$C_{1-6}$alkyl or —$C_{1-6}$alkoxy;

—$C_{6-10}$aryl; or 5- to 6-membered heteroaryl selected from pyridinyl, pyridazinyl, pyrazinyl, thiazolyl or isoxazolyl, each of which is optionally substituted with at least one substitution independently selected from cyano, -oxo, halogen, hydroxy, —NR‴R″, —$C_{1-6}$alkyl, —$C_{1-6}$ alkoxy or —C(O)NR‴R″, wherein —$C_{1-6}$alkyl or —$C_{1-6}$alkoxy is substituted with at least one substitution independently selected from cyano, halogen, hydroxy, —$NH_2$, —$C_{1-6}$alkyl or —$C_{1-6}$alkoxy;

and wherein R‴ and R″ are independently selected from hydrogen or —$C_{1-3}$alkyl.

In some embodiments, $R^3$ is hydrogen, cyano, halogen;

methyl, ethyl, propyl or butyl, each of which optionally substituted with at least one substituent independently selected from halogen, hydroxy, methoxy, ethoxy, propoxy, or 2,4-dioxothiazolidin-3-yl;

cyclopropyl, cyclobutyl, cyclopentyl or cyclohexyl, each of which is optionally substituted with at least one substituent independently selected from cyano, -oxo, halogen, —NR‴R″, hydroxy, —$C_{1-3}$alkyl, or —$C_{1-3}$ alkoxy, wherein —$C_{1-3}$alkyl or $C_{1-3}$alkoxy is optionally substituted with at least one substitution independently selected from cyano, halogen, hydroxy, —$NH_2$, —$C_{1-3}$alkyl or —$C_{1-3}$alkoxy;

heterocyclyl is selected from morpholin-2-yl, morpholin-3-yl, morpholin-4-yl, tetrahydrofuran-2-yl, tetrahydrofuran-3-yl, tetrahydropyran-2-yl, tetrahydropyran-3-yl, tetrahydropyran-4-yl, pyrrolidine-1-yl, pyrrolidin-2-yl, pyrrolidin-3-yl, 1,4-dioxan-2-yl, piperidin-1-yl, piperidin-2-yl, piperidin-3-yl, piperidin-4-yl, azetidin-1-yl, azetidine-2-yl, azetidin-3-yl, 5-azaspiro[2.4]heptanyl, 3-azabicyclo[3.1.0]hexan-3-yl or 2-azabicyclo[3.1.0] hexan-2-yl, each of which is optionally substituted with at least one substituent independently selected from cyano, -oxo, halogen, hydroxy, —$C_{1-6}$alkyl, —$C_{1-6}$ alkoxy, —NR‴R″, or —C(O)NR‴R″, and wherein —$C_{1-6}$alkyl or $C_{1-6}$alkoxy is substituted with at least one substitution independently selected from cyano, halogen, hydroxy, —$NH_2$, —$C_{1-6}$alkyl or —$C_{1-6}$ alkoxy;

—$OR^e$, wherein $R^e$ is i) methyl, ethyl, propyl (iso-propyl), butyl, pentyl or hexyl, each of which is optionally substituted with deuterium, cyano, -oxo-, halogen, hydroxy, —NR‴R″, —$C_{1-3}$alkoxy-, —$C_{3-6}$cycloalkyl optionally substituted with cyano, -oxo, halogen, hydroxy, —NR‴R″, —$C_{1-3}$alkyl, —$C_{1-3}$alkoxy or —C(O)NR‴R″, or 4- to 6-membered heterocyclyl optionally substituted with cyano, halogen, hydroxy, —$C_{1-3}$alkyl or —$C_{1-3}$alkoxy; or, ii) cyclopropyl, cyclobutyl, cyclopentyl, cyclohexyl, morpholin-2-yl, morpholin-3-yl, morpholin-4-yl, tetrahydrofuran-2-yl, tetrahydrofuran-3-yl, tetrahydropyran-2-yl, tetrahydropyran-3-yl, tetrahydropyran-4-yl, pyrrolidin-1-yl, pyrrolidin-2-yl, pyrrolidin-3-yl, 1,4-dioxan-2-yl, piperidin-1-yl, piperidin-2-yl, piperidin-3-yl, piperidin-4-yl, azetidin-1-yl, azetidine-2-yl or azetidin-3-yl, each of which is optionally substituted with cyano, -oxo, halogen, hydroxy, —NR‴R″, —$C_{1-3}$alkyl, —$C_{1-3}$alkoxy or —C(O)NR‴R″, wherein —$C_{1-3}$alkyl or —$C_{1-3}$alkoxy is substituted with at least one substitution independently selected from cyano, halogen, hydroxy, —$NH_2$, —$C_{1-3}$alkyl or —$C_{1-3}$alkoxy;

—$C_{6-10}$aryl; or 5- to 6-membered heteroaryl selected from pyridin-1-yl, pyridin-2-yl, pyridin-3-yl, pyridin-4-yl, pyridazin-1-yl, pyridazin-2-yl, pyridazin-3-yl, pyridazin-4-yl, pyrazin-1-yl, pyrazin-2-yl, thiazol-2-yl, thiazol-3-yl, thiazol-4-yl, isoxazol-2-yl, isoxazol-3-yl or isoxazol-4-yl, each of which is optionally substituted with at least one substitution independently selected from cyano, -oxo, halogen, hydroxy, —NR‴R″, —$C_{1-3}$alkyl, —$C_{1-3}$ alkoxy or —C(O)NR‴R″, wherein —$C_{1-3}$alkyl or —$C_{1-3}$alkoxy is substituted with at least one substitution independently selected from cyano, halogen, hydroxy, —$NH_2$, —$C_{1-3}$alkyl or $C_{1-3}$alkoxy; and wherein R‴ and R″ are independently selected from hydrogen or —$C_{1-3}$alkyl.

In some embodiments, $R^3$ is

Hydrogen;

Methyl, 1-methoxyethyl, 2-hydroxypropan-2-yl, 1-methoxyethyl, or (2,4-dioxothiazolidin-3-yl)methyl;

Isopropoxy, methoxy-d3, methoxy, ethoxy, difluoromethoxy, 2-methoxyethoxy, 2-methoxy-2-methylpropoxy, 2-hydroxy-2-methylpropoxy, cyclopropylmethoxy, (1,4-dioxan-2-yl)methoxy, (4-hydroxycyclohexyl)oxy, (cis-4-hydroxycyclohexyl) oxy, (trans-4-hydroxycyclohexyl)oxy, (4-methoxycyclohexyl)oxy, (cis-4-methoxycyclohexyl)oxy, (trans-4-methoxycyclohexyl)oxy, or (3-methyloxetan-3-yl) methoxy;

cyano 3-methoxycyclobutyl, (trans)-3-methoxycyclobutyl, (cis)-3-methoxycyclobutyl, 2,2-dichlorocyclopropyl, or 1-cyanocyclopropyl;

Morpholino, 3-methyl-morpholino, 3(R)-methyl-morpholino, 3(S)-methyl-morpholino, 3,3-dimethylmorpho;

tetrahydro-2H-pyran-4-yl, tetrahydro-2H-pyran-3-yl, (R)-tetrahydro-2H-pyran-3-yl, (S)-tetrahydro-2H-pyran-3-yl, 2,2,6,6-tetramethyltetrahydro-2H-pyran-4-yl;

3-methoxypyrrolidin-1-yl, 3(R)-methoxypyrrolidin-1-yl, 3(S)-methoxypyrrolidin-1-yl, 3-hydroxy-3-methylpyrrolidin-1-yl, 3-(2-hydroxyethoxy)pyrrolidin-1-yl, 3-(trifluoromethoxy)pyrrolidin-1-yl, 3(R)-(trifluoromethoxy)pyrrolidin-1-yl, 3(S)-(trifluoromethoxy)pyrrolidin-1-yl, 2-(aminocarbonyl)pyrrolidin-1-yl, 2(R)-(aminocarbonyl) pyrrolidin-1-yl, 2(S)-(aminocarbonyl)pyrrolidin-1-yl, 3-(methoxymethyl)pyrrolidin-1-yl, 3(R)-(methoxymethyl)pyrrolidin-1-yl, 3(S)-(methoxymethyl)pyrrolidin-1-yl, 3-cyano-4-hydroxypyrrolidin-1-yl, cis-3-cyano-4-hydroxypyrrolidin-1-yl, trans-3-cyano-4-hydroxypyrrolidin-1-yl, 3-cyano-4-methoxypyrrolidin-1-yl, cis-3-cyano-4-methoxypyrrolidin-1-yl, trans-3-cyano-4-methoxypyrrolidin-1-yl, 2-(methoxymethyl)pyrrolidin-1-yl, 2(R)-(methoxymethyl)pyrrolidin-1-yl, 2(S)-(methoxymethyl)pyrrolidin-1-yl, 3-methylpyrrolidin-1-yl, 3(R)-methylpyrrolidin-1-yl, 3(S)-methylpyrrolidin-1-yl, pyrrolidin-1-yl, 3-(cyanomethoxy)pyrrolidin-1-yl;

5-azaspiro[2.4]heptan-5-yl;

tetrahydrofuran-3-yl;

3-methoxyazetidin-1-yl, 3-hydroxy-3-methylazetidin-1-yl;

1,4-dioxan-2-yl;

4-aminotetrahydro-2H-pyran-4-yl, 4-(aminomethyl)tetrahydro-2H-pyran-4-yl, 4-methoxypiperidin-1-yl, 4-hydroxy-4-methylpiperidin-1-yl, 1-(2,2,2-trifluoroethyl)piperidin-4-yl, 3-methoxypiperidin-1-yl, 3(R)-methoxypiperidin-1-yl, 3(S)-methoxypiperidin-1-yl, 3-ethoxypiperidin-1-yl, 3(R)-ethoxypiperidin-1-yl, 3(S)-ethoxypiperidin-1-yl;

3-cyano-2-azabicyclo[3.1.0]hexan-2-yl, (3R)-3-cyano-2-azabicyclo[3.1.0]hexan-2-yl, (3S)-3-cyano-2-azabicyclo[3.1.0]hexan-2-yl, 3-azabicyclo[3.1.0]hexan-3-yl; 4-methylpyridin-3-yl, 5-methylpyridazin-4-yl, 5-methoxypyridazin-4-yl, 3,5-dimethylisoxazol-4-yl, 4-methoxypyridin-3-yl, 4-(2-hydroxypropan-2-yl)pyridin-3-yl, 6-cyanopyridin-3-yl, 4-cyanopyridin-3-yl, 2-cyanopyridin-3-yl, 3-methylpyrazin-2-yl, 5-cyanopyridazin-4-yl, 5-fluoropyridazin-4-yl, 4-fluoropyridin-3-yl, 4-isopropylpyridin-3-yl, 4-(1-hydroxyethyl)pyridin-3-yl, 4-(1-methoxyethyl)pyridin-3-yl, pyridin-2-yl, or thiazol-4-yl.

In some embodiments, ($R^1$ and $R^2$), or ($R^2$ and $R^3$), or ($R^3$ and $R^4$), together with the atoms to which they are attached, form a fused 5- to 7-membered ring system, said fused ring system comprises 0-2 oxygen heteroatoms as ring member(s) and is optionally and independently substituted with halogen, $-C_{1-6}$ alkyl, $-C_{1-6}$alkoxy, -halo$C_{1-6}$alkyl, -halo$C_{1-6}$alkoxy, or $-C_{3-6}$cycloalkyl.

In some embodiments, $R^1$ and $R^2$, together with the atoms to which they are attached, form a fused ring system selected from

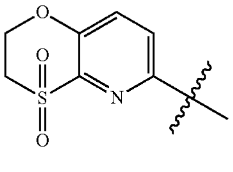

,

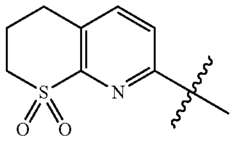

, or

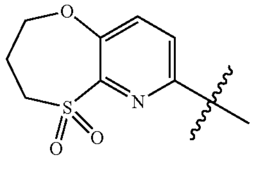

;

or $R^2$ and $R^3$, together with the atoms to which they are attached, form a fused ring system

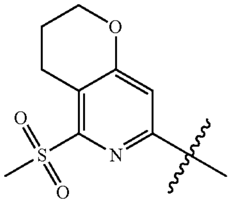

;

$R^3$ and $R^4$, together with the atoms to which they are attached, form a fused ring system selected from

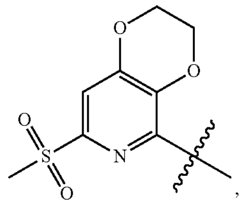

,

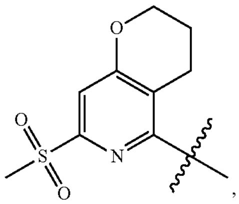

,

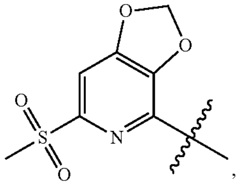

, or

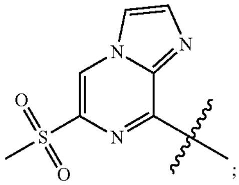

;

and wherein each of fused ring system is optionally and independently substituted with halogen, $-C_{1-6}$alkyl, $-C_{1-6}$ alkoxy, -halo$C_{1-6}$alkyl, -halo$C_{1-6}$alkoxy, or $-C_{3-6}$cycloalkyl.

In some embodiments, $Cy^1$ is a 5- to 7-membered monocyclic heterocyclyl or heteroaryl comprising 1, 2, 3 or 4 heteroatoms selected from oxygen, nitrogen or sulfur as ring member(s), or 7- to 14-membered bicyclic or tricyclic heterocyclyl or heteroaryl having 1, 2, or 3 heteroatoms selected from oxygen, nitrogen or sulfur as ring member(s), each of which is optionally substituted with at least one substituent $R^i$.

In some embodiments, $Cy^1$ is said 5- to 7-membered monocyclic heteroaryl comprising 1, 2, 3 or 4 heteroatom(s) selected from oxygen (O), nitrogen (N) or sulfur (S) as ring member(s), preferably pyrazolyl, triazolyl, imidazolyl, thiazolyl, oxazolyl, furanyl, pyridinyl, pyridazinyl, pyrazinyl or pyrimidinyl, said monocyclic heteroaryl is optionally substituted with one or two substituents selected from i. halogen;

ii. cyano;

iii. $-C_{1-6}$alkyl optionally substituted with halogen, hydroxy, $-C_{1-6}$alkoxy, $-C(O)R'''$ (preferably $R'''$ is morpholinyl), or $-NR'''R''$;

iv. heterocyclyl optionally substituted with halogen, $C_{1-6}$alkyl-, $-C_{1-6}$alkyl substituted with $-C_{1-6}$alkoxy, or oxo; preferably said heterocyclyl is selected from tetrahydrofuranyl (preferably tetrahydrofuran-3-yl), morpholinyl (preferably morpholino), 2-oxa-5-azabicyclo[2.2.1]heptanyl (preferably 2-oxa-5-azabicyclo[2.2.1]heptan-2-yl), 8-oxa-3-azabicyclo[3.2.1]octanyl (preferably 8-oxa-3-azabicyclo[3.2.1]octan-8-yl), isoindolinyl (preferably isoindolin-2-yl), each of which is optionally substituted with methyl, ethyl, propyl, isopropyl, isobutyl, tert-butyl, n-butyl, methoxymethyl, methoxyethyl, ethoxymethyl, ethoxyethyl, or oxo;

v. —$C_{3-6}$cycloalkyl optionally substituted with halogen, -oxo, —$C_{1-6}$alkyl, $C_{1-6}$alkoxy-, or —$C_{1-6}$alkyl substituted with —$C_{1-6}$alkoxy; or vi. —$OR^j$, wherein $R^j$ is —$C_{1-6}$alkyl, —$C_{1-6}$alkyl substituted with —$C_{1-6}$alkoxy, or heterocyclyl;

vii. oxo;

said 7- to 14-membered bicyclic or tricyclic heteroaryl comprising 1, 2, or 3 heteroatom(s) as ring member(s), preferably benzoimidazolyl, imidazopyrimidinyl, pyrazolopyrazinyl, pyrazolopyrimidinyl, benzothiophenyl, benzothiazolyl, benzoisoxazolyl, benzooxazolyl, benzoisothiazolyl, imidazopyridazinyl, imidazopyridazinyl; dihydro-4H-furo[3,2-c]pyranyl, 6,7-dihydro-4H-thieno[3,2-c]pyranyl, 2,3-dihydropyrazolo[5,1-b]oxazolyl, 4,5,6,7-tetrahydrofuro[3,2-c]pyridinyl, 1,3a, 4,6,7,7a-hexahydropyrano[4,3-c]pyrazolyl, 4,5,6,7-tetrahydropyrazolo[1,5-a]pyrazinyl, 4,5,6,7-tetrahydropyrazolo[1,5-a]pyrimidinyl, 4,5,6,7-tetrahydropyrazolo[1,5-a]pyrazinyl, 4,5,6,7-tetrahydrothiazolo[5,4-c]pyridinyl, 4,5,6,7-tetrahydropyrazolo[1,5-a]pyrazinyl, 6,7-dihydro-4H-pyrazolo[5,1-c][1,4]oxazinyl, 2,3-dihydropyrazolo[5,1-b]oxazolyl, 2,3-dihydropyrazolo[5,1-b]oxazolyl, 1,3a,4,6,7,7a-hexahydropyrano[4,3-c]pyrazolyl, 6,7-dihydro-4H-pyrano[4,3-d]thiazolyl, [1,3]dioxolo[4,5-c]pyridinyl, 2,3-dihydro-[1,4]dioxino[2,3-c]pyridinyl, 3,4-dihydro-2H-pyrido[3,2-b][1,4]oxazinyl, 2,3-dihydro-[1,4]dioxino[2,3-b]pyridinyl, 2,3-dihydro-[1,4]dioxino[2,3-b]pyridin-6-yl, 3,4-dihydro-2H-pyrido[4,3-b][1,4]oxazinyl, or 2H-pyrido[3,2-b][1,4]oxazin-4(3H)-yl, each of which is optionally substituted with halogen, —$C_{1-6}$alkyl, —$NH_2$, or —$C(O)R'''$, wherein $R'''$ is $C_{1-6}$alkyl.

In some embodiments, $Cy^1$ is a 7- to 14-membered bicyclic heteroaryl which is a pyridinyl, pyrazolyl, thienyl, or thiazolyl ring fused with a 5- or 6-membered heterocyclyl ring, wherein said 5- or 6-membered heterocyclyl ring comprising one or two heteroatoms selected from oxygen or nitrogen as ring member(s) and said 5- or 6-membered heterocyclyl ring is optionally substituted with one or two $C_{1-6}$alkyl or oxo, preferably two $C_{1-6}$alkyl, more preferably two methyl, most preferably two methyl on the same carbon atom. In some embodiments, $Cy^1$ is a 7- to 14-membered bicyclic heteroaryl which is a pyridinyl ring fused with a 5- or 6-membered heterocyclyl ring, wherein said 5- or 6-membered heterocyclyl ring comprising one or two heteroatoms selected from oxygen (O) or nitrogen (N) as ring member(s) and said 5- or 6-membered heterocyclyl ring is optionally substituted with one or two $C_{1-6}$alkyl or oxo, preferably two $C_{1-6}$alkyl, more preferably two methyl, most preferably two methyl on the same carbon atom. In some embodiments, $Cy^1$ is a 7- to 14-membered bicyclic heteroaryl which is a pyridinyl ring fused with a 5- or 6-membered heterocyclyl ring, wherein said 5- or 6-membered heterocyclyl ring comprising two oxygen atoms as ring member(s) and said 5- or 6-membered heterocyclyl ring is optionally substituted with one or two $C_{1-6}$alkyl, preferably two $C_{1-6}$alkyl, more preferably two methyl, most preferably two methyl on the same carbon atom. In some embodiments, $Cy^1$ is a 7- to 14-membered bicyclic heteroaryl which is a pyridinyl ring fused with 1,4-dioxane ring, wherein said 1,4-dioxane ring is optionally substituted with one or two $C_{1-6}$alkyl, preferably two $C_{1-6}$alkyl, more preferably two methyl, most preferably two methyl on the same carbon atom; any of the said alkyl or alkoxy is optionally enriched in deuterium. In some preferred embodiments, $Cy^1$ is

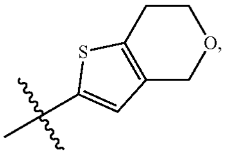,
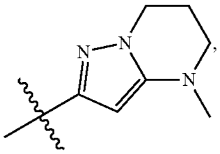,
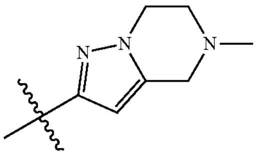,
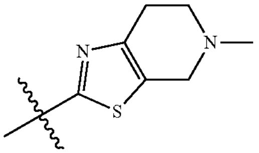,
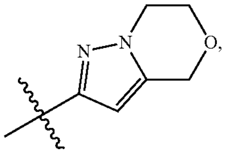,
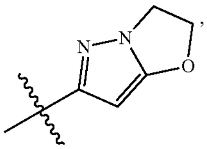,
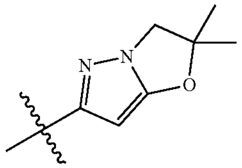,
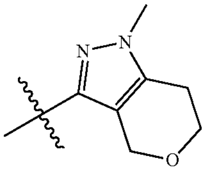,
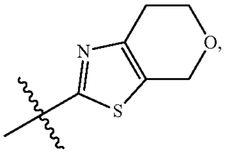,
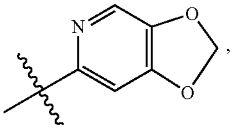,
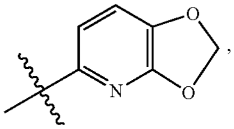,
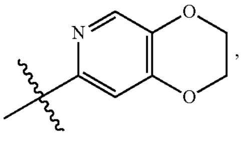,
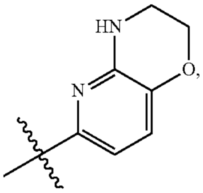,
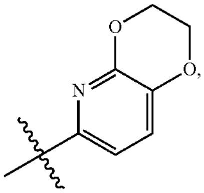,
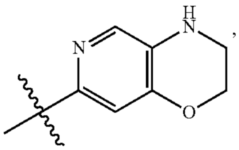,
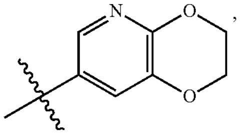,
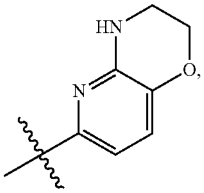,
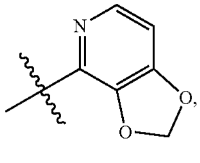,
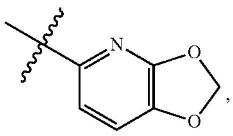, -continued
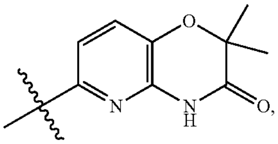
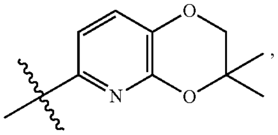
or
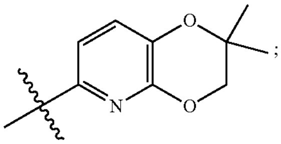
preferably
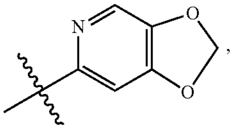
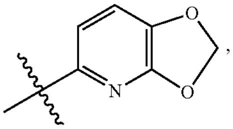
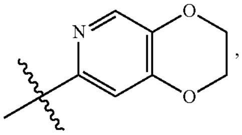
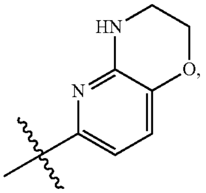
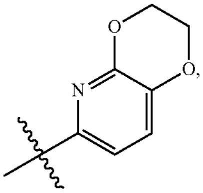
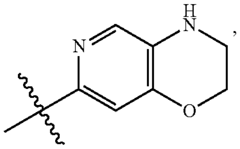
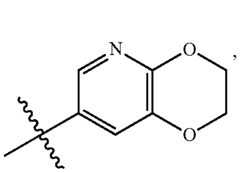
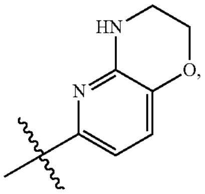
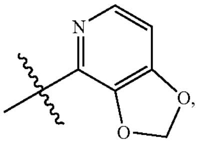
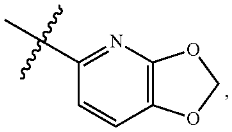
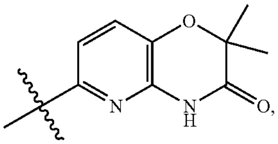
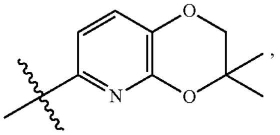
-continued
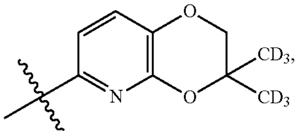
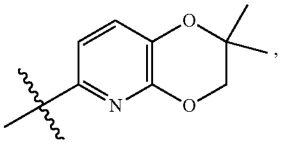
or
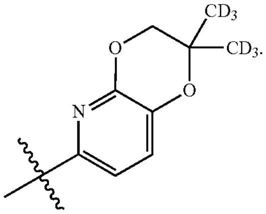
In some embodiments, $Cy^1$ is
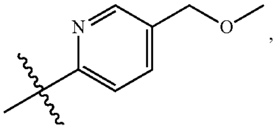
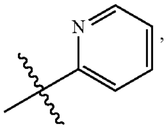
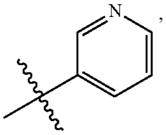
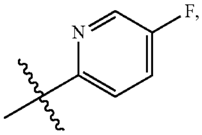
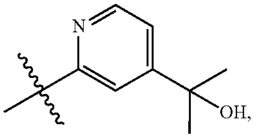
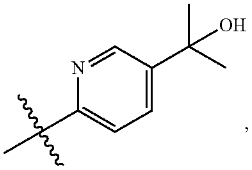
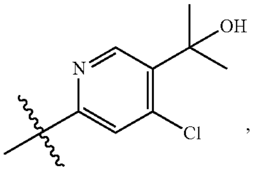
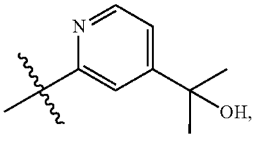
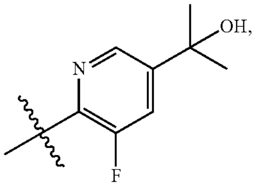
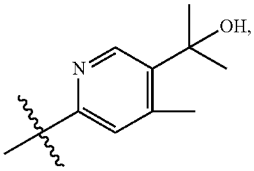
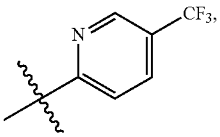
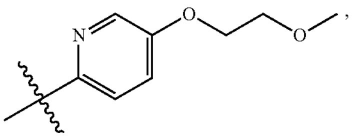

-continued
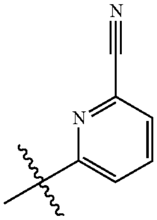,
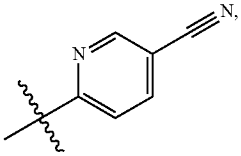,
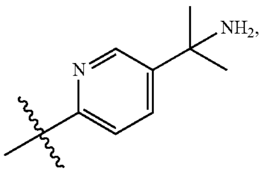,
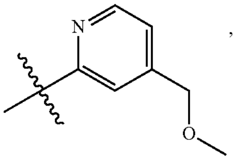,
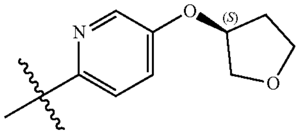,
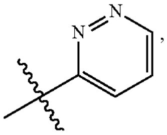,
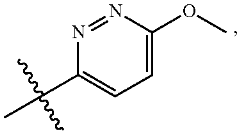,
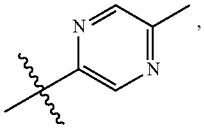,
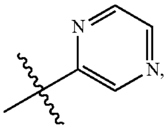, or
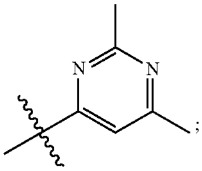;
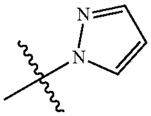,
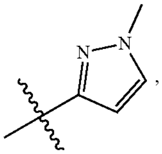,
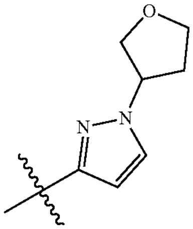,
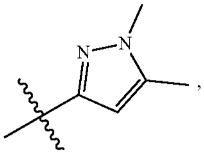,
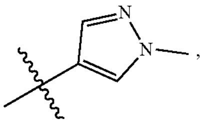,
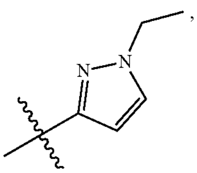,
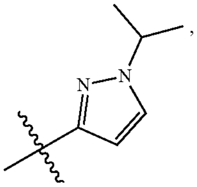,
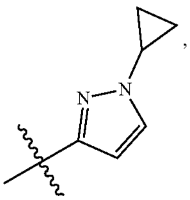,
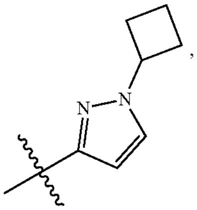,
-continued
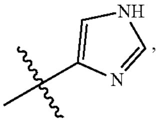,
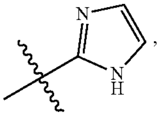,
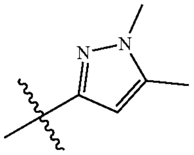;
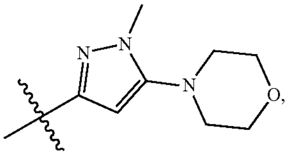,
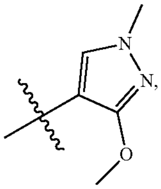,
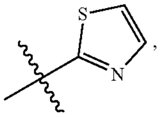,
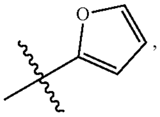,
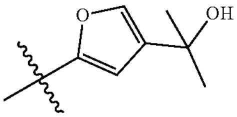,
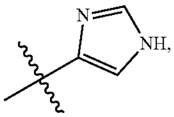,
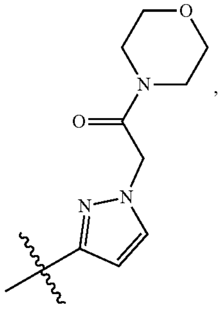,
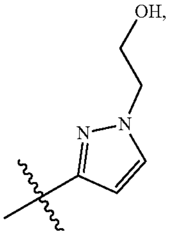,
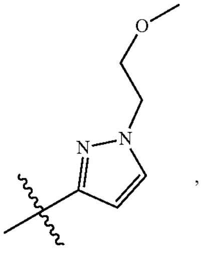, or
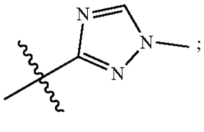;
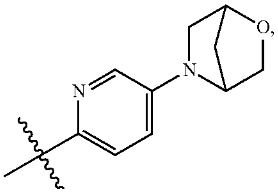,
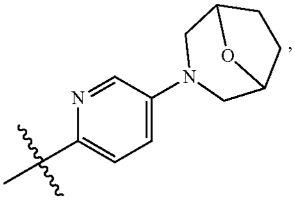, -continued
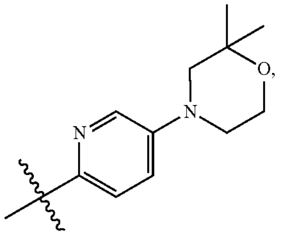
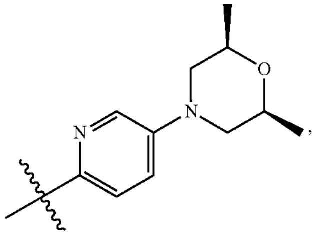
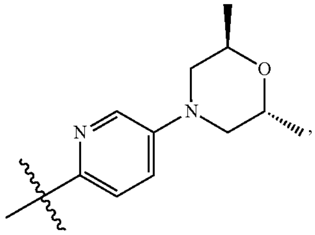
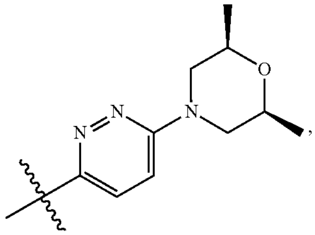
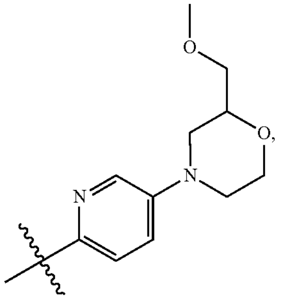
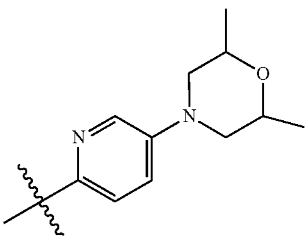
;
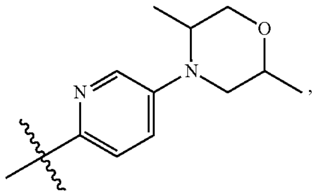
-continued
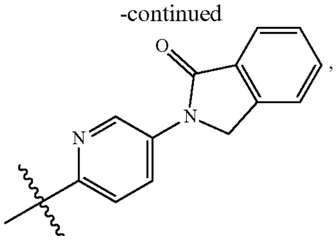
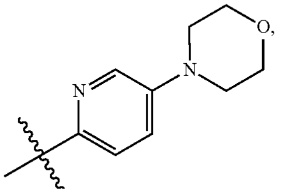
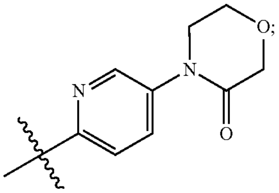
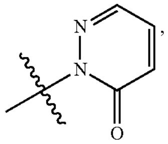
or
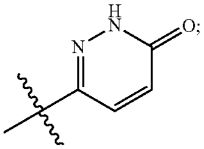
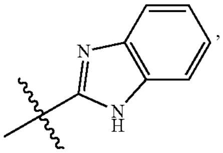
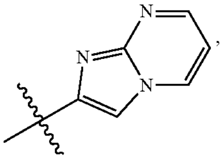
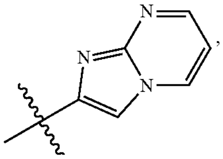
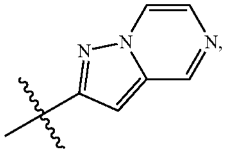
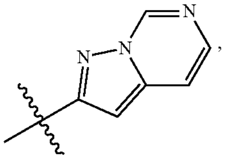
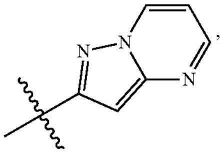
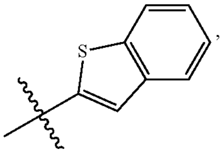
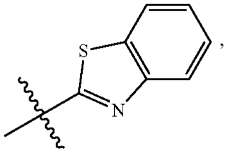
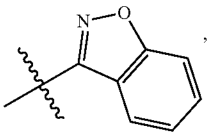
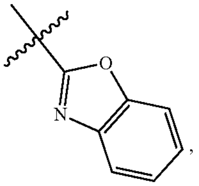
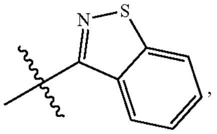
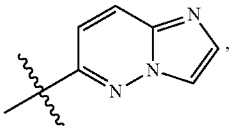
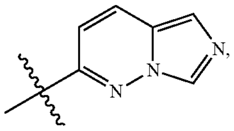

-continued
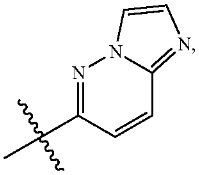,
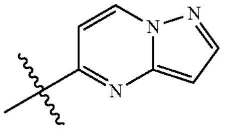,
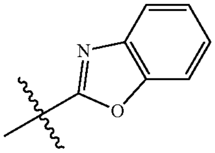
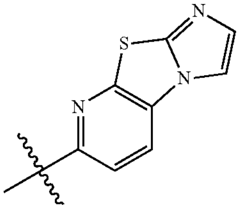,
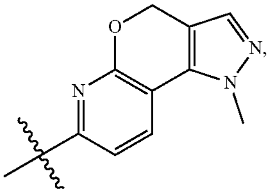, or
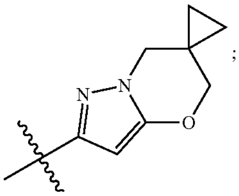;
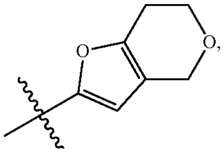,
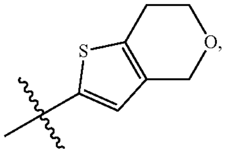,
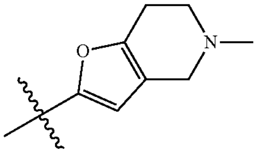,
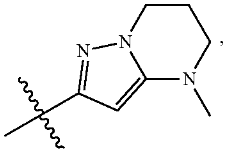,
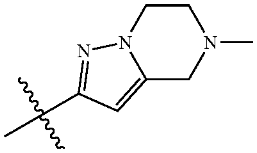,
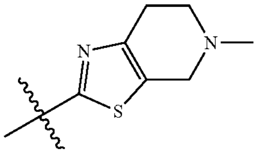,
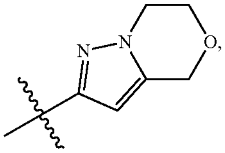,
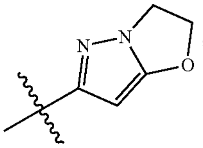,
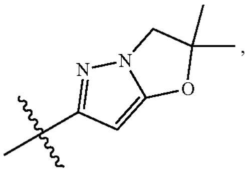,
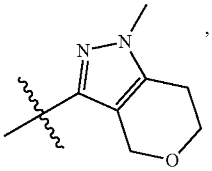,
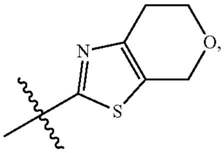,
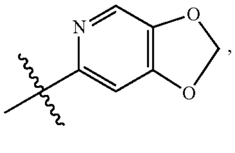,
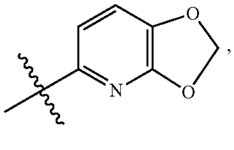,
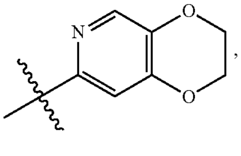,
-continued
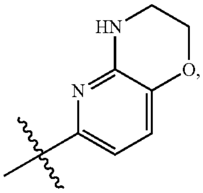,
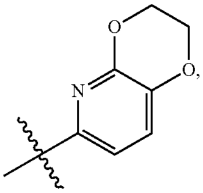,
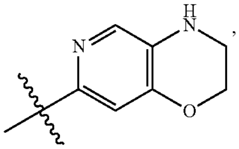,
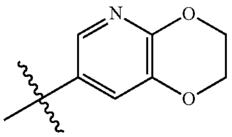,
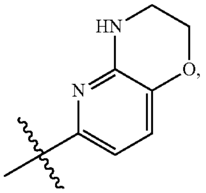,
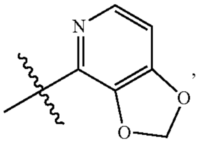,
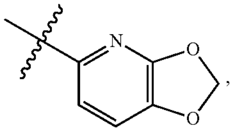,
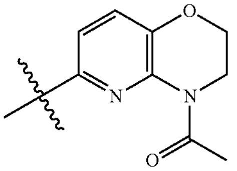,
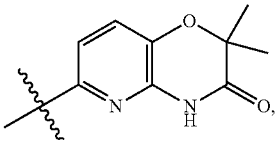,
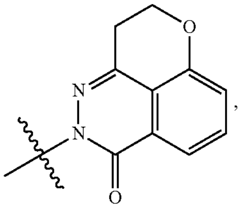,
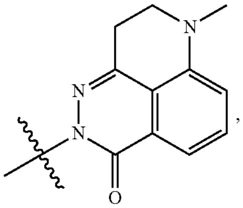,
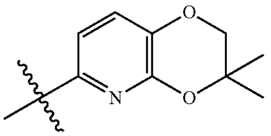,
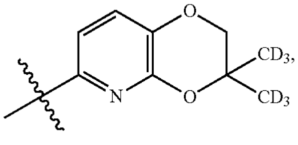,
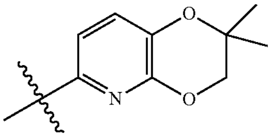,
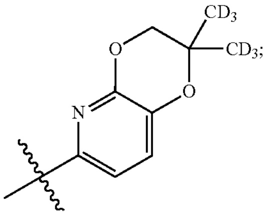;
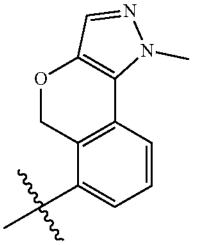, or -continued

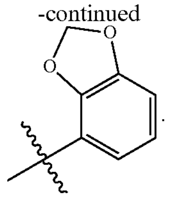

In one embodiment, disclosed herein is a compound of Formula (I-B):

(I-B)

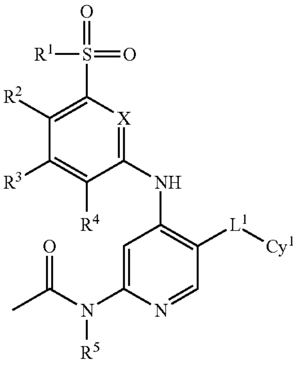

or a stereoisomer or a pharmaceutically acceptable salt thereof, wherein:

X is N or CH;

$L^1$ is a direct bond, $—(CR^aR^b)_q—$, —O—, —S—, —S(O)—, $—SO_2—$, —C(O)—, C(O)O—, —OC(O)—, $—NR^a—$, $—O—(CR^aR^b)_q$, $—S—(CR^aR^b))_q—$, $—S(O)R(CR^aR^b)_q—$, $—SO_2—(CR^aR^b)_q—$, $—C(O)—(CR^aR^b)_q—$, $C(O)O—(CR^aR^b)_q—$, $—OC(O)—(CR^aR^b)_q—$, $—NR^a—(CR^aR^b)_q—$, $—C(O)NR^a—$, $—NR^aC(O)—$, $—NR^aC(O)O—$, $—NR^aC(O)NR^b—$, $—SO_2NR^a—$, $—NR^aSO_2—$, $—NR^aS(O)_2NR^b—$, $—NR^aS(O)NR^b—$, $—C(O)NR^aSO_2—$, $—C(O)NR^aSO—$, or $—C(=NR^a)NR^b—$, wherein q is a number of 1 to 7, and;

$R^a$ and $R^b$ are independently hydrogen, $—C_{1-6}$alkyl, $—C_{2-6}$alkenyl, $—C_{2-6}$alkynyl, cycloalkyl, heterocyclyl, aryl, or heteroaryl;

$R^1$ is $—C_{1-6}$alkyl, -halo$C_{1-6}$alkyl, $—C_{1-6}$alkoxy, -halo$C_{1-6}$ alkoxyl, $—C_{3-6}$ cycloalkyl, aryl, or $—NR^cR^d$;

each of $R^2$, $R^3$, and $R^4$ is independently hydrogen, halogen, $—C_{1-6}$alkyl, $—C_{2-6}$alkenyl, $—C_{2-6}$alkynyl, $—C_{3-8}$ cycloalkyl, heterocyclyl (preferably, morpholin-4-yl, tetrahydrofuran-3-yl), aryl, heteroaryl, oxo, —CN, $—NO_2$, $—OR^e$, $—SO_2R^e$, $—COR^e$, $—CO_2R^e$, $—CONR^eR^f$, $—C(=NR^e)NR^fR^g$, $—NR^eR^f$, $—NR^eCOR^f$, $—NR^eCONR^fR^g$, $—NR^eCO_2R^f$, $—NR^eSONR^fR^g$, $—NR^eSO_2NR^fR^g$, or $—NR^eSO_2R^f$, wherein each of $—C_{1-6}$alkyl, $—C_{2-6}$alkenyl, $—C_{2-6}$alkynyl, $—C_{3-8}$cycloalkyl, heterocyclyl, aryl, or heteroaryl is independently and optionally substituted with at least one substituents selected from halogen, hydroxy-$C_{1-6}$ alkyl (preferably, hydroxymethyl), $—OR^h$, or $C_{1-6}$alkoxy-$C_{1-6}$alkyl-;

wherein $R^h$ is hydrogen, alkyl, or heterocyclyl, $R^e$, $R^f$, and $R^g$ are each independently hydrogen, $—C_{1-6}$ alkyl, $—C_{1-6}$alkoxy, $—C_{2-6}$alkenyl, $—C_{2-6}$alkynyl, cycloalkyl, heterocyclyl, aryl, or heteroaryl, wherein each of $—C_{1-6}$alkyl, $—C_{2-6}$alkenyl, $—C_{2-6}$alkynyl, cycloalkyl, heterocyclyl, aryl, or heteroaryl is optionally independently substituted with one to three substituents selected from halogen, hydroxy, cyano, $—C_{1-6}$alkoxy; $—C_{3-6}$cycloalkyl optionally substituted with halogen, hydroxy, or $C_{1-6}$alkoxy;

$R^5$ is hydrogen or $C_{1-6}$alkyl;

$Cy^1$ is 6- to 12-membered aryl or 5- to 14-membered heteroaryl, or 5- to 14-membered heterocyclyl, each of which is optionally substituted with at least one substituent $R^i$, $R^i$ is independently halogen, cyano, $—C_{1-6}$alkyl, $—C_{2-6}$ alkenyl, $—C_{2-6}$alkynyl, $—C_{3-6}$cycloalkyl, heterocyclyl, aryl, heteroaryl, oxo, —CN, $—NO_2$, $—OR^j$, $—SO_2R^j$, $—COR^j$, $—CO_2R^k$, $—CONR^jR^k$, $—C(=NR^j)NR^kR^l$, $—NR^jR^k$, $—NR^jCOR^k$, $—NR^jCONR^kR^l$, $—NR^jCO_2R^k$, $—NR^jSONR^kR^l$, $—NR^jSO_2NR^kR^l$, or $—NR^jSO_2R^k$, wherein each of said $—C_{1-6}$alkyl, $—C_{2-6}$alkenyl, $—C_{2-6}$ alkynyl, $—C_{3-8}$cycloalkyl, heterocyclyl, aryl, or heteroaryl is optionally substituted with halogen, $OR^m$, $C(O)R^m$, $—NR^mR^n$, $—C_{1-6}$alkyl, $C_{1-6}$alkoxy-, $C_{1-6}$alkoxy-$C_{1-6}$alkyl-, or oxo;

$R^j$, $R^k$, $R^l$, $R^m$, $R^n$ are each independently hydrogen, $—C_{1-6}$alkyl, $C_{1-6}$alkoxy-$C_{1-6}$alkyl-, $—C_{2-6}$alkenyl, $—C_{2-6}$alkynyl, cycloalkyl, heterocyclyl, aryl, or heteroaryl;

or ($R^1$ and $R^2$), or ($R^2$ and $R^3$), or ($R^3$ and $R^4$), together with the atoms to which they are attached, form a fused ring system, said fused ring system comprises 0-4 heteroatoms selected from oxygen, nitrogen or sulfur as ring member(s) and is optionally and independently substituted with halogen, $—C_{1-6}$alkyl, $—C_{1-6}$alkoxy, -halo$C_{1-6}$alkyl, -halo$C_{1-6}$alkoxy, or $—C_{3-6}$cycloalkyl;

any of the said alkyl or alkoxy can be optionally enriched in deuterium.

In some embodiments, disclosed here is a compound of Formula (I-C)

(I-C)

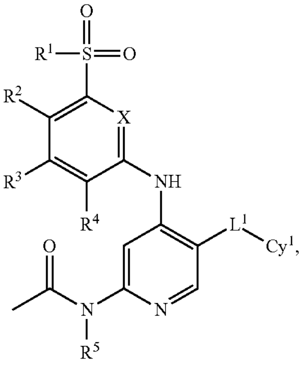

or a stereoisomer or a pharmaceutically acceptable salt thereof, wherein:

X is N or CH;

$L^1$ is a direct bond;

$R^1$ is $—C_{1-6}$alkyl, or -halo$C_{1-6}$alkyl;

each of $R^2$ and $R^4$ is independently hydrogen, halogen, $—C_{1-6}$alkyl or $—C_{1-6}$alkoxy;

$R^3$ is independently hydrogen, halogen, $—C_{1-6}$alkyl, $—C_{2-6}$alkenyl, $—C_{2-6}$alkynyl, $—C_{3-8}$cycloalkyl, heterocyclyl, aryl, heteroaryl, -oxo-, —CN, $—NO_2$, $—OR^e$, $—SO_2R^e$, $—COR^e$, $—CO_2R^e$, $—CONR^eR^f$, $—C(—NR^e)NR^fR^g$, $—NR^eR^f$, $—NR^eCOR^f$, $—NR^e$-

$CONR^fR^g$, $—NR^eCO_2R^f$, $—NR^eSONR^fR^g$, $—NR^eSO_2NR^fR^g$, or $—NR^eSO_2R^f$, wherein each of $—C_{1-6}$alkyl, $—C_{2-6}$alkenyl, $—C_{2-6}$alkynyl, $—C_{3-8}$cycloalkyl, heterocyclyl, aryl, or heteroaryl is independently and optionally substituted with at least one substituents selected from i) cyano, oxo, halogen, $—NH_2$, $—OR^h$, $—C(O)NR'''R''$;

ii) heterocyclyl optionally substituted with at least one substituent independently selected from cyano, -oxo, halogen, hydroxy, $—NR'''R''$, substituted or unsubstituted $—C_{1-6}$alkyl, substituted or unsubstituted $—C_{1-6}$ alkoxy or $—C(O)NR'''R''$; or, iii) $C_{1-6}$alkyl optionally substituted with halogen, $—C_{1-6}$ alkyl substituted with hydroxy (preferably, hydroxymethyl, hydroxyethyl), $—C_{1-6}$alkyl substituted with $—NH_2$, $—NH_2$ or $—C_{1-6}$alkyl substituted with $C_{1-6}$alkoxy;

wherein $R^h$ is hydrogen, hydroxy, alkyl, substituted with hydroxy, or heterocyclyl, $R^e$, $R^f$, and $R^g$ are each independently hydrogen, $—C_{1-6}$ alkyl, $—C_{1-6}$alkoxy, $—C_{2-6}$alkenyl, $—C_{2-6}$alkynyl, cycloalkyl, heterocyclyl, aryl, or heteroaryl, wherein each of $—C_{1-6}$alkyl, $—C_{2-6}$alkenyl, $—C_{2-6}$alkynyl, cycloalkyl, heterocyclyl, aryl, or heteroaryl is optionally independently substituted with one to three substituents selected from halogen, hydroxy, cyano, -oxo-, $—NR'''R''$, $—C_{1-6}$alkyl, $—C_{1-6}$alkoxy; $—C_{3-6}$cycloalkyl optionally substituted with halogen, hydroxy, or $C_{1-6}$alkoxy, $—C(O)NR'''R''$, or heterocyclyl;

$R^5$ is hydrogen or $C_{1-6}$alkyl;

$Cy^1$ is a 7- to 14-membered bicyclic or tricyclic heterocyclyl or heteroaryl having 1, 2, or 3 heteroatoms selected from oxygen (O), nitrogen (N) or sulfur (S) as ring member(s), which is optionally substituted with at least one substituent $R^i$, $R^i$ is independently halogen, cyano, $—C_{1-6}$alkyl, $—C_{2-6}$ alkenyl, $—C_{2-6}$alkynyl, $—C_{3-6}$cycloalkyl, heterocyclyl, aryl, heteroaryl, oxo, —CN, $—NO_2$, $—OR^j$, $—SO_2R^j$, $—COR^j$, $—CO_2R^k$, $—CONR^jR^k$, $—C(=NR^j)NR^kR^l$, $—NR^jR^k$, $—NR^jCOR^k$, $—NR^jCONR^kR^l$, $—NR^jCO_2R^k$, $—NR^jSONR^kR^l$, $—NR^jSO_2NR^kR^l$, or $—NR^jSO_2R^k$, wherein each of said $—C_{1-6}$alkyl, $—C_{2-6}$alkenyl, $—C_{2-6}$ alkynyl, $—C_{3-8}$cycloalkyl, heterocyclyl, aryl, or heteroaryl is optionally substituted with halogen, $OR'''$, $C(O)R'''$, $—NR'''R''$, $—C_{1-6}$alkyl, $C_{1-6}$alkoxy-, $C_{1-6}$alkyl substituted with $—C_{1-6}$alkoxy, or oxo;

$R^j$, $R^k$, $R^l$, $R'''$, $R''$ are each independently hydrogen, $—C_{1-6}$alkyl, $—C_{1-6}$alkyl substituted with $C_{1-6}$alkoxy, $—C_{2-6}$alkenyl, $—C_{2-6}$alkynyl, cycloalkyl, heterocyclyl, aryl, or heteroaryl;

or ($R^1$ and $R^2$), or ($R^2$ and $R^3$), or ($R^3$ and $R^4$), together with the atoms to which they are attached, form a fused ring system, said fused ring system comprises 0-4 heteroatoms selected from oxygen (O), nitrogen (N) or sulfur (S) as ring member(s) and is optionally and independently substituted with halogen, $—C_{1-6}$ alkyl, $—C_{1-6}$alkoxy, -halo$C_{1-6}$alkyl, -halo$C_{1-6}$alkoxy, or $—C_{3-6}$cycloalkyl; any of the said alkyl or alkoxy is optionally enriched in deuterium.

In some embodiments, $R^1$ is $—C_{1-3}$ alkyl, preferably methyl, ethyl, propyl, or isopropyl.

In some embodiments, $R^2$ and $R^4$ are each independently hydrogen, halogen, $—C_{1-3}$alkyl, or $—C_{1-3}$ alkoxy, preferably hydrogen, fluoro, methyl, methoxy, ethoxy, or isopropoxy.

In some embodiments, $R^3$ is hydrogen;

cyano;

halogen;

$—C_{1-4}$ alkyl optionally substituted with at least one substituent independently selected from halogen, 3- to 6-membered heterocyclyl or $—OR^h$, wherein 3- to 6-membered heterocyclyl comprises one or two heteroatoms selected from oxygen (O), nitrogen (N) or sulfur (O) as ring member(s), optionally substituted with at least one substituent independently selected from cyano, -oxo, halogen, hydroxy, $—NR'''R''$, $C_{1-6}$alkyl, $—C_{1-6}$alkoxy or $—C(O)NR'''R''$, wherein $—C_{1-6}$alkyl or $—C_{1-6}$alkoxy is substituted with at least one substitution independently selected from cyano, halogen, hydroxy, $—NH_2$, $—C_{1-6}$alkyl or $C_{1-6}$alkoxy; and $R^h$ is hydrogen, alkyl, or heterocyclyl;

$—C_{3-6}$cycloalkyl, optionally substituted with at least one substituent independently selected from cyano, -oxo, halogen, $—NR'''R''$, hydroxy, $—C_{1-6}$alkyl, $—C_{1-6}$alkoxy or $—C(O)NR'''R''$, wherein $—C_{1-6}$alkyl or $C_{1-6}$ alkoxy is substituted with at least one substitution independently selected from cyano, halogen, hydroxy, $—NH_2$, $—C_{1-6}$alkyl or $C_{1-6}$alkoxy;

heterocyclyl comprising one or two heteroatoms selected from oxygen (O), nitrogen (N) or sulfur (S) as ring member(s), optionally substituted with at least one substituent independently selected from cyano, -oxo-, halogen, hydroxy, $C_{1-6}$alkyl, alkoxy, $—NRR'''R''$, or $—C(O)NR'''R''$, and wherein $—C_{1-6}$alkyl or $C_{1-6}$alkoxy is substituted with at least one substitution independently selected from cyano, halogen, hydroxy, $—NH_2$, $—C_{1-6}$alkyl or $C_{1-6}$alkoxy;

$—OR^e$, wherein $R^e$ is $—C_{1-6}$alkyl, $—C_{3-6}$cycloalkyl, 3- to 6-membered heterocyclyl, or aryl, wherein i) $—C_{1-6}$alkyl is optionally substituted with cyano, -oxo-, halogen, hydroxy, $—NR'''R''$, $—C_{1-6}$alkoxy-, $—C_{3-6}$cycloalkyl optionally substituted with cyano, -oxo, halogen, hydroxy, $—NR'''R''$, $—C_{1-6}$alkyl, $C_{1-6}$alkoxy or $—C(O)NR'''R''$, 4- to 6-membered heterocyclyl optionally substituted with cyano, halogen, hydroxy, $C_{1-6}$alkyl or $C_{1-6}$alkoxy; and, ii) $—C_{3-6}$cycloalkyl or 3- to 6-membered heterocyclyl is optionally substituted with cyano, -oxo, halogen, hydroxy, $—NR'''R''$, $C_{1-6}$alkyl, $C_{1-6}$alkoxy or $—C(O)NR'''R''$, wherein $—C_{1-6}$alkyl or $C_{1-6}$alkoxy is substituted with at least one substitution independently selected from cyano, halogen, hydroxy, $—NH_2$, $—C_{1-6}$alkyl or $C_{1-6}$alkoxy;

$—C_{5-10}$aryl; or heteroaryl comprising one oxygen (O), nitrogen (N) or sulfur (S) heteroatom as ring member, optionally substituted with at least one substitution independently selected from cyano, -oxo, halogen, hydroxy, $—NR'''R''$, $—C_{1-6}$alkyl, $—C_{1-6}$alkoxy or $—C(O)NR'''R''$, wherein $—C_{1-6}$alkyl or $C_{1-6}$alkoxy is substituted with at least one substitution independently selected from cyano, halogen, hydroxy, $—NH_2$, $—C_{1-6}$ alkyl or $C_{1-6}$alkoxy;

and wherein $R'''$ and $R''$ are independently selected from hydrogen or $C_{1-3}$alkyl;

any of the said alkyl or alkoxy is optionally enriched in deuterium.

In some preferred embodiments, $R^3$ is heterocyclyl comprising one or two heteroatoms selected from oxygen (O), nitrogen (N) or sulfur (S) as ring member(s), optionally substituted with at least one substituent independently selected from cyano, -oxo-, halogen, hydroxy, $C_{1-6}$alkyl, alkoxy, —$NRR'''R''$, or —$C(O)NR'''R''$, and wherein —$C_{1-6}$ alkyl or $C_{1-6}$alkoxy is substituted with at least one substitution independently selected from cyano, halogen, hydroxy, —$NH_2$, —$C_{1-6}$alkyl or $C_{1-6}$alkoxy.

In some embodiments, $R^3$ is hydrogen;

cyano;

halogen;

—$C_{1-4}$ alkyl optionally substituted with at least one substituent independently selected from halogen, 3- to 6-membered heterocyclyl or —$OR^h$, wherein Said 3- to 6-membered heterocyclyl comprises one or two heteroatoms selected from oxygen (O), nitrogen (N) or sulfur (O) as ring member(s), optionally substituted with at least one substituent independently selected from cyano, -oxo, halogen, hydroxy, —$NR'''R''$, $C_{1-6}$alkyl, —$C_{1-6}$alkoxy or —$C(O)NR'''R''$, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy, and, $R^h$ is hydrogen, alkyl or heterocyclyl (preferably 3- to 6-membered heterocyclyl, e.g., tetrahydrofuranyl, thiazolidinyl);

—$C_{3-6}$cycloalkyl, optionally substituted with at least one substituent independently selected from cyano, -oxo, halogen, —$NR'''R''$, hydroxy, —$C_{1-6}$alkyl, —$C_{1-6}$ alkoxy or —$C(O)NR'''R''$, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

heterocyclyl, preferably 4- to 6-membered monocyclic saturated heterocyclyl, saturated mono-spiro heterocyclyl, saturated bicyclic fused heterocyclyl, or saturated bridged heterocyclyl, comprising one or two heteroatoms selected from oxygen (O), nitrogen (N) or sulfur (S) as ring member(s), more preferably morpholinyl, tetrahydrofuranyl, tetrahydropyranyl, pyrrolidinyl, 1,4-dioxanyl, piperidinyl or azetidinyl, optionally substituted with at least one substituent independently selected from cyano, -oxo, halogen, hydroxy, —$C_{1-6}$ alkyl, alkoxy, —$NR'''R''$, or —$C(O)NR'''R''$, and wherein —$C_{1-6}$alkyl or —$C_{1-6}$alkoxy is substituted with at least one substitution independently selected from cyano, halogen, hydroxy, —$NH_2$, —$C_{1-6}$alkyl or $C_{1-6}$alkoxy;

—$OR^e$, wherein $R^e$ is —$C_{1-6}$alkyl, —$C_{3-6}$cycloalkyl, 3- to 6-membered heterocyclyl (preferably 4- to 6-membered monocyclic saturated heterocyclyl comprising one oxygen heteroatom as ring member), or aryl, wherein i) —$C_{1-6}$alkyl is optionally substituted with cyano, -oxo-, halogen, hydroxy, —$NR'''R''$, —$C_{1-6}$alkoxy-, —$C_{3-6}$cycloalkyl optionally substituted with cyano, -oxo, halogen, hydroxy, —$NR'''R''$, —$C_{1-6}$alkyl, $C_{1-6}$alkoxy or —$C(O)NR'''R''$, 4- to 6-membered heterocyclyl optionally substituted with cyano, halogen, hydroxy, —$C_{1-6}$alkyl or —$C_{1-6}$alkoxy; and, ii) —$C_{3-6}$cycloalkyl or 3- to 6-membered heterocyclyl is optionally substituted with cyano, -oxo, halogen, hydroxy, $NR'''R''$, $C_{1-6}$alkyl, $C_{1-6}$alkoxy or —$C(O)NR'''R''$, wherein —$C_{1-6}$alkyl or $C_{1-6}$alkoxy is substituted with at least one substitution independently selected from cyano, halogen, hydroxy, —$NH_2$, —$C_{1-6}$ alkyl or $C_{1-6}$alkoxy;

—$C_{5-10}$aryl; or heteroaryl, preferably 5- to 6-membered heteroaryl comprising one oxygen (O), nitrogen (N) or sulfur (S) heteroatom as ring member, optionally substituted with at least one substitution independently selected from cyano, -oxo, halogen, hydroxy, —$NR'''R''$, —$C_{1-6}$alkyl, —$C_{1-6}$alkoxy or —$C(O)NR'''R''$, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

and wherein $R'''$ and $R''$ are independently selected from hydrogen or $C_{1-3}$alkyl.

In some preferred embodiments, $R^3$ is heterocyclyl, preferably 4- to 6-membered monocyclic saturated heterocyclyl, saturated mono-spiro heterocyclyl, saturated bicyclic fused heterocyclyl, or saturated bridged heterocyclyl, comprising one or two heteroatoms selected from oxygen (O), nitrogen (N) or sulfur (S) as ring member(s), more preferably morpholinyl, tetrahydrofuranyl, tetrahydropyranyl, pyrrolidinyl, 1,4-dioxanyl, piperidinyl or azetidinyl, optionally substituted with at least one substituent independently selected from cyano, -oxo, halogen, hydroxy, —$C_{1-6}$alkyl, alkoxy, —$NR'''R''$, or —$C(O)NR'''R''$, and wherein —$C_{1-6}$alkyl or —$C_{1-6}$alkoxy is substituted with at least one substitution independently selected from cyano, halogen, hydroxy, —$NH_2$, —$C_{1-6}$alkyl or $C_{1-6}$alkoxy.

In some embodiments, $R^3$ is hydrogen, cyano, halogen;

—$C_{1-4}$ alkyl optionally substituted with at least one substituent independently selected from halogen, 3- to 6-membered heterocyclyl or —$OR^h$, wherein Said 3- to 6-membered heterocyclyl is selected from morpholinyl, tetrahydrofuranyl, tetrahydropyranyl, pyrrolidinyl, 1,4-dioxanyl, piperidinyl, thiazolidinyl or azetidinyl, each of which is optionally substituted with at least one substituent independently selected from cyano, -oxo, halogen, hydroxy, —$NR'''R''$, $C_{1-6}$ alkyl, —$C_{1-6}$alkoxy or —$C(O)NR'''R''$, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy, and, $R^h$ is hydrogen, $C_{1-6}$alkyl or 3- to 6-membered heterocyclyl (e.g., tetrahydrofuranyl or thiazolidinyl);

—$C_{3-6}$cycloalkyl, optionally substituted with at least one substituent independently selected from cyano, -oxo, halogen, $NR'''R''$, hydroxy, —$C_{1-6}$alkyl, —$C_{1-6}$alkoxy or —$C(O)NR'''R''$, hydroxy, or $C_{1-6}$alkoxy, wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

heterocyclyl is selected from morpholinyl, tetrahydrofuranyl, tetrahydropyranyl, pyrrolidinyl, 1,4-dioxanyl, piperidinyl or azetidinyl, optionally substituted with at least one substituent independently selected from cyano, -oxo, halogen, hydroxy, $C_{1-6}$alkyl, alkoxy, —$NRR'''R''$, or —$C(O)NR'''R''$, and wherein —$C_{1-6}$ alkyl or —$C_{1-6}$alkoxy is substituted with at least one substitution independently selected from cyano, halogen, hydroxy, —$NH_2$, —$C_{1-6}$alkyl or —$C_{1-6}$alkoxy;

—$OR^e$, wherein $R^e$ is —$C_{1-6}$alkyl, —$C_{3-6}$cycloalkyl, 4- to 6-membered monocyclic saturated heterocyclyl comprising one oxygen heteroatom as ring member, or $C_{6-10}$aryl, wherein i) —$C_{1-6}$alkyl is optionally substituted with cyano, -oxo-, halogen, hydroxy, —$NR'''R''$, —$C_{1-6}$alkoxy-, —$C_{3-6}$cycloalkyl optionally substituted with cyano, -oxo, halogen, hydroxy, —$NR'''R''$, —$C_{1-6}$alkyl, —$C_{1-6}$alkoxy or —$C(O)NR'''R''$, 4- to 6-membered heterocyclyl optionally substituted with cyano, halogen, hydroxy, —$C_{1-6}$alkyl or —$C_{1-6}$ alkoxy; and, ii) —$C_{3-6}$cycloalkyl or 3- to 6-membered heterocyclyl is optionally substituted with cyano, -oxo, halogen, hydroxy, NR'''R'', $C_{1-6}$alkyl, $C_{1-6}$alkoxy or —C(O)NR'''R'', wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

—$C_{6-10}$aryl; or 5- to 6-membered heteroaryl selected from pyridinyl, pyridazinyl, pyrazinyl, thiazolyl or isoxazolyl, each of which is optionally substituted with at least one substitution independently selected from cyano, -oxo, halogen, hydroxy, —NR'''R'', —$C_{1-6}$alkyl, —$C_{1-6}$ alkoxy or —C(O)NR'''R'', wherein —$C_{1-6}$alkyl or $C_{1-6}$alkoxy is substituted with at least one substitution independently selected from cyano, halogen, hydroxy, —$NH_2$, —$C_{1-6}$alkyl or $C_{1-6}$alkoxy;

and wherein R''' and R'' are independently selected from hydrogen or —$C_{1-3}$alkyl.

In some preferred embodiments, $R^3$ is heterocyclyl is selected from morpholinyl, tetrahydrofuranyl, tetrahydropyranyl, pyrrolidinyl, 1,4-dioxanyl, piperidinyl or azetidinyl, optionally substituted with at least one substituent independently selected from cyano, -oxo, halogen, hydroxy, $C_{1-6}$alkyl, alkoxy, —NRR'''R'', or —C(O)NR'''R'', and wherein —$C_{1-6}$alkyl or —$C_{1-6}$alkoxy is substituted with at least one substitution independently selected from cyano, halogen, hydroxy, —$NH_2$, —$C_{1-6}$alkyl or —$C_{1-6}$alkoxy.

In some embodiments, $R^3$ is hydrogen, cyano, halogen;

—$C_{1-4}$ alkyl optionally substituted with at least one substituent independently selected from halogen, hydroxy, $C_{1-3}$alkoxy, thiazolidin-3-yl optionally substituted with at least one substituent independently selected from cyano, -oxo, halogen, hydroxy, —NR'''R'', or —$C_{1-3}$ alkyl;

—$C_{3-6}$cycloalkyl, optionally substituted with at least one substituent independently selected from cyano, -oxo, halogen, —NR'''R'', hydroxy, —$C_{1-6}$alkyl, or —$C_{1-6}$alkoxy, wherein —$C_{1-6}$alkyl or $C_{1-6}$alkoxy is substituted with at least one substitution independently selected from cyano, halogen, hydroxy, —$NH_2$, —$C_{1-6}$ alkyl or —$C_{1-3}$alkoxy;

heterocyclyl is selected from morpholinyl, tetrahydrofuranyl, tetrahydropyranyl, pyrrolidinyl, 1,4-dioxanyl, piperidinyl or azetidinyl, optionally substituted with at least one substituent independently selected from cyano, -oxo, halogen, hydroxy, $C_{1-6}$alkyl, alkoxy, —NR'''R'', or —C(O)NR'''R'', and wherein —$C_{1-6}$alkyl or $C_{1-6}$alkoxy is substituted with at least one substitution independently selected from cyano, halogen, hydroxy, —$NH_2$, —$C_{1-6}$alkyl or —$C_{1-6}$alkoxy;

—$OR^e$, wherein R is —$C_{1-6}$alkyl, —$C_{3-6}$cycloalkyl, 4- to 6-membered monocyclic saturated heterocyclyl comprising one oxygen heteroatom as ring member, or $C_{6-10}$aryl, wherein i) —$C_{1-6}$alkyl is optionally substituted with cyano, -oxo-, halogen, hydroxy, —NR'''R'', —$C_{1-6}$alkoxy-, —$C_{3-6}$cycloalkyl optionally substituted with cyano, -oxo, halogen, hydroxy, —NR'''R'', —$C_{1-6}$alkyl, —$C_{1-6}$alkoxy or —C(O)NR'''R'', 4- to 6-membered heterocyclyl optionally substituted with cyano, halogen, hydroxy, —$C_{1-6}$alkyl or —$C_{1-6}$alkoxy; and, ii) —$C_{3-6}$cycloalkyl or 3- to 6-membered heterocyclyl is optionally substituted with cyano, -oxo, halogen, hydroxy, —NR'''R'', —$C_{1-6}$alkyl, —$C_{1-6}$alkoxy or —C(O)NR'''R'', wherein —$C_{1-6}$alkyl or —$C_{1-6}$alkoxy is substituted with at least one substitution independently selected from cyano, halogen, hydroxy, —$NH_2$, —$C_{1-6}$alkyl or —$C_{1-6}$alkoxy;

—$C_{6-10}$aryl; or 5- to 6-membered heteroaryl selected from pyridinyl, pyridazinyl, pyrazinyl, thiazolyl or isoxazolyl, each of which is optionally substituted with at least one substitution independently selected from cyano, -oxo, halogen, hydroxy, —NR'''R'', —$C_{1-6}$alkyl, —$C_{1-6}$ alkoxy or —C(O)NR'''R'', wherein —$C_{1-6}$alkyl or —$C_{1-6}$alkoxy is substituted with at least one substitution independently selected from cyano, halogen, hydroxy, —$NH_2$, —$C_{1-6}$alkyl or —$C_{1-6}$alkoxy;

and wherein R''' and R'' are independently selected from hydrogen or —$C_{1-3}$alkyl.

In some preferred embodiments, $R^3$ is heterocyclyl is selected from morpholinyl, tetrahydrofuranyl, tetrahydropyranyl, pyrrolidinyl, 1,4-dioxanyl, piperidinyl or azetidinyl, optionally substituted with at least one substituent independently selected from cyano, -oxo, halogen, hydroxy, $C_{1-6}$alkyl, alkoxy, —NR'''R'', or —C(O)NR'''R'', and wherein —$C_{1-6}$alkyl or $C_{1-6}$alkoxy is substituted with at least one substitution independently selected from cyano, halogen, hydroxy, —$NH_2$, —$C_{1-6}$alkyl or —$C_{1-6}$alkoxy In some embodiments, $R^3$ is hydrogen, cyano, halogen;

methyl, ethyl, propyl or butyl, each of which optionally substituted with at least one substituent independently selected from halogen, hydroxy, methoxy, ethoxy, propoxy, or 2,4-dioxothiazolidin-3-yl;

cyclopropyl, cyclobutyl, cyclopentyl or cyclohexyl, each of which is optionally substituted with at least one substituent independently selected from cyano, -oxo, halogen, —NR'''R'', hydroxy, —$C_{1-3}$alkyl, or —$C_{1-3}$ alkoxy, wherein —$C_{1-3}$alkyl or $C_{1-3}$alkoxy is optionally substituted with at least one substitution independently selected from cyano, halogen, hydroxy, —$NH_2$, —$C_{1-3}$alkyl or —$C_{1-3}$alkoxy;

heterocyclyl is selected from morpholin-2-yl, morpholin-3-yl, morpholin-4-yl, tetrahydrofuran-2-yl, tetrahydrofuran-3-yl, tetrahydropyran-2-yl, tetrahydropyran-3-yl, tetrahydropyran-4-yl, pyrrolidine-1-yl, pyrrolidin-2-yl, pyrrolidin-3-yl, 1,4-dioxan-2-yl, piperidin-1-yl, piperidin-2-yl, piperidin-3-yl, piperidin-4-yl, azetidin-1-yl, azetidine-2-yl, azetidin-3-yl, 5-azaspiro[2.4]heptanyl, 3-azabicyclo[3.1.0]hexan-3-yl or 2-azabicyclo[3.1.0]hexan-2-yl, each of which is optionally substituted with at least one substituent independently selected from cyano, -oxo, halogen, hydroxy, —$C_{1-6}$alkyl, —$C_{1-6}$ alkoxy, —NR'''R'', or —C(O)NR'''R'', and wherein —$C_{1-6}$alkyl or $C_{1-6}$alkoxy is substituted with at least one substitution independently selected from cyano, halogen, hydroxy, —$NH_2$, —$C_{1-6}$alkyl or —$C_{1-6}$ alkoxy;

—$OR^e$, wherein $R^e$ is i) methyl, ethyl, propyl (iso-propyl), butyl, pentyl or hexyl, each of which is optionally substituted with deuterium, cyano, -oxo-, halogen, hydroxy, —NR'''R'', —$C_{1-3}$alkoxy-, —$C_{3-6}$cycloalkyl optionally substituted with cyano, -oxo, halogen, hydroxy, —NR'''R'', —$C_{1-3}$alkyl, —$C_{1-3}$alkoxy or —C(O)NR'''R'', or 4- to 6-membered heterocyclyl optionally substituted with cyano, halogen, hydroxy, —$C_{1-3}$alkyl or —$C_{1-3}$alkoxy; or, ii) cyclopropyl, cyclobutyl, cyclopentyl, cyclohexyl, morpholin-2-yl, morpholin-3-yl, morpholin-4-yl, tetrahydrofuran-2-yl, tetrahydrofuran-3-yl, tetrahydropyran-2-yl, tetrahydropyran-3-yl, tetrahydropyran-4-yl, pyrrolidin-1-yl, pyrrolidin-2-yl, pyrrolidin-3-yl, 1,4-dioxan-2-yl, piperidin-1-yl, piperidin-2-yl, piperidin-3-yl, piperidin-4-yl, azetidin-1-yl, azetidine-2-yl or azetidin-3-yl, each of which is optionally substituted with cyano, -oxo, halogen, hydroxy, —NR'''R'', —$C_{1-3}$alkyl, —$C_{1-3}$alkoxy or —C(O)NR'''R'', wherein —$C_{1-3}$alkyl or —$C_{1-3}$alkoxy is substituted with at least one substitution independently selected from cyano, halogen, hydroxy, —$NH_2$, —$C_{1-3}$alkyl or —$C_{1-3}$alkoxy;

—$C_{6-10}$aryl; or 5- to 6-membered heteroaryl selected from pyridin-1-yl, pyridin-2-yl, pyridin-3-yl, pyridin-4-yl, pyridazin-1-yl, pyridazin-2-yl, pyridazin-3-yl, pyridazin-4-yl, pyrazin-1-yl, pyrazin-2-yl, thiazol-2-yl, thiazol-3-yl, thiazol-4-yl, isoxazol-2-yl, isoxazol-3-yl or isoxazol-4-yl, each of which is optionally substituted with at least one substitution independently selected from cyano, -oxo, halogen, hydroxy, —NR'''R'', —$C_{1-6}$alkyl, —$C_{1-3}$ alkoxy or —C(O)NR'''R'', wherein —$C_{1-3}$alkyl or —$C_{1-3}$alkoxy is substituted with at least one substitution independently selected from cyano, halogen, hydroxy, —$NH_2$, —$C_{1-3}$alkyl or $C_{1-3}$alkoxy; and wherein R''' and R'' are independently selected from hydrogen or —$C_{1-3}$alkyl.

In some preferred embodiments, $R^3$ is heterocyclyl is selected from morpholin-2-yl, morpholin-3-yl, morpholin-4-yl, tetrahydrofuran-2-yl, tetrahydrofuran-3-yl, tetrahydropyran-2-yl, tetrahydropyran-3-yl, tetrahydropyran-4-yl, pyrrolidine-1-yl, pyrrolidin-2-yl, pyrrolidin-3-yl, 1,4-dioxan-2-yl, piperidin-1-yl, piperidin-2-yl, piperidin-3-yl, piperidin-4-yl, azetidin-1-yl, azetidine-2-yl, azetidin-3-yl, 5-azaspiro[2.4]heptanyl, 3-azabicyclo[3.1.0]hexan-3-yl or 2-azabicyclo[3.1.0]hexan-2-yl, each of which is optionally substituted with at least one substituent independently selected from cyano, -oxo, halogen, hydroxy, —$C_{1-6}$alkyl, —$C_{1-6}$alkoxy, —NR'''R'', or —C(O)NR'''R'', and wherein —$C_{1-6}$alkyl or $C_{1-6}$alkoxy is substituted with at least one substitution independently selected from cyano, halogen, hydroxy, —$NH_2$, —$C_{1-6}$alkyl or —$C_{1-6}$alkoxy In some embodiments, $R^3$ is Hydrogen;

Methyl, 1-methoxyethyl, 2-hydroxypropan-2-yl, 1-methoxyethyl, or (2,4-dioxothiazolidin-3-yl)methyl;

Isopropoxy, methoxy-d3, methoxy, ethoxy, difluoromethoxy, 2-methoxyethoxy, 2-methoxy-2-methylpropoxy, 2-hydroxy-2-methylpropoxy, cyclopropylmethoxy, (1,4-dioxan-2-yl)methoxy, (4-hydroxycyclohexyl)oxy, (cis-4-hydroxycyclohexyl)oxy, (trans-4-hydroxycyclohexyl)oxy, (4-methoxycyclohexyl)oxy, (cis-4-methoxycyclohexyl)oxy, (trans-4-methoxycyclohexyl)oxy, or (3-methyloxetan-3-yl)methoxy;

cyano 3-methoxycyclobutyl, (trans)-3-methoxycyclobutyl, (cis)-3-methoxycyclobutyl, 2,2-dichlorocyclopropyl, or 1-cyanocyclopropyl;

Morpholino, 3-methyl-morpholino, 3(R)-methyl-morpholino, 3(S)-methyl-morpholino;

tetrahydro-2H-pyran-4-yl, tetrahydro-2H-pyran-3-yl, (R)-tetrahydro-2H-pyran-3-yl, (S)-tetrahydro-2H-pyran-3-yl, 2,2,6,6-tetramethyltetrahydro-2H-pyran-4-yl, 3,3-dimethylmorpho;

3-methoxypyrrolidin-1-yl, 3(R)-methoxypyrrolidin-1-yl, 3(S)-methoxypyrrolidin-1-yl, 3-hydroxy-3-methylpyrrolidin-1-yl, 3-(2-hydroxyethoxy)pyrrolidin-1-yl, 3-(trifluoromethoxy)pyrrolidin-1-yl, 3(R)-(trifluoromethoxy)pyrrolidin-1-yl, 3(S)-(trifluoromethoxy)pyrrolidin-1-yl, 2-(aminocarbonyl)pyrrolidin-1-yl, 2(R)-(aminocarbonyl)pyrrolidin-1-yl, 2(S)-(aminocarbonyl)pyrrolidin-1-yl, 3-(methoxymethyl)pyrrolidin-1-yl, 3(R)-(methoxymethyl)pyrrolidin-1-yl, 3(S)-(methoxymethyl)pyrrolidin-1-yl, 3-cyano-4-hydroxypyrrolidin-1-yl, cis-3-cyano-4-hydroxypyrrolidin-1-yl, trans-3-cyano-4-hydroxypyrrolidin-1-yl, 3-cyano-4-methoxypyrrolidin-1-yl, cis-3-cyano-4-methoxypyrrolidin-1-yl, trans-3-cyano-4-methoxypyrrolidin-1-yl, 2-(methoxymethyl)pyrrolidin-1-yl, 2(R)-(methoxymethyl)pyrrolidin-1-yl, 2(S)-(methoxymethyl)pyrrolidin-1-yl, 3-methylpyrrolidin-1-yl, 3(R)-methylpyrrolidin-1-yl, 3(S)-methylpyrrolidin-1-yl, pyrrolidin-1-yl, 3-(cyanomethoxy)pyrrolidin-1-yl;

5-azaspiro[2.4]heptan-5-yl;

tetrahydrofuran-3-yl;

3-methoxyazetidin-1-yl, 3-hydroxy-3-methylazetidin-1-yl;

1,4-dioxan-2-yl;

4-aminotetrahydro-2H-pyran-4-yl, 4-(aminomethyl)tetrahydro-2H-pyran-4-yl, 4-methoxypiperidin-1-yl, 4-hydroxy-4-methylpiperidin-1-yl, 1-(2,2,2-trifluoroethyl)piperidin-4-yl, 3-methoxypiperidin-1-yl, 3(R)-methoxypiperidin-1-yl, 3(S)-methoxypiperidin-1-yl, 3-ethoxypiperidin-1-yl, 3(R)-ethoxypiperidin-1-yl, 3(S)-ethoxypiperidin-1-yl;

3-cyano-2-azabicyclo[3.1.0]hexan-2-yl, (3R)-3-cyano-2-azabicyclo[3.1.0]hexan-2-yl, (3S)-3-cyano-2-azabicyclo[3.1.0]hexan-2-yl, 3-azabicyclo[3.1.0]hexan-3-yl;

4-methylpyridin-3-yl, 5-methylpyridazin-4-yl, 5-methoxypyridazin-4-yl, 3,5-dimethylisoxazol-4-yl, 4-methoxypyridin-3-yl, 4-(2-hydroxypropan-2-yl)pyridin-3-yl, 6-cyanopyridin-3-yl, 4-cyanopyridin-3-yl, 2-cyanopyridin-3-yl, 3-methylpyrazin-2-yl, 5-cyanopyridazin-4-yl, 5-fluoropyridazin-4-yl, 4-fluoropyridin-3-yl, 4-isopropylpyridin-3-yl, 4-(1-hydroxyethyl)pyridin-3-yl, 4-(1-methoxyethyl)pyridin-3-yl, pyridin-2-yl, or thiazol-4-yl.

In some preferred embodiments, $R^3$ is

Morpholino, 3-methyl-morpholino, 3(R)-methyl-morpholino, 3(S)-methyl-morpholino;

tetrahydro-2H-pyran-4-yl, tetrahydro-2H-pyran-3-yl, (R)-tetrahydro-2H-pyran-3-yl, (S)-tetrahydro-2H-pyran-3-yl, 2,2,6,6-tetramethyltetrahydro-2H-pyran-4-yl;

3-methoxypyrrolidin-1-yl, 3(R)-methoxypyrrolidin-1-yl, 3(S)-methoxypyrrolidin-1-yl, 3-hydroxy-3-methylpyrrolidin-1-yl, 3-(2-hydroxyethoxy)pyrrolidin-1-yl, 3-(trifluoromethoxy)pyrrolidin-1-yl, 3(R)-(trifluoromethoxy)pyrrolidin-1-yl, 3(S)-(trifluoromethoxy)pyrrolidin-1-yl, 2-(aminocarbonyl)pyrrolidin-1-yl, 2(R)-(aminocarbonyl)pyrrolidin-1-yl, 2(S)-(aminocarbonyl)pyrrolidin-1-yl, 3-(methoxymethyl)pyrrolidin-1-yl, 3(R)-(methoxymethyl)pyrrolidin-1-yl, 3(S)-(methoxymethyl)pyrrolidin-1-yl, 3-cyano-4-hydroxypyrrolidin-1-yl, cis-3-cyano-4-hydroxypyrrolidin-1-yl, trans-3-cyano-4-hydroxypyrrolidin-1-yl, 3-cyano-4-methoxypyrrolidin-1-yl, cis-3-cyano-4-methoxypyrrolidin-1-yl, trans-3-cyano-4-methoxypyrrolidin-1-yl, 2-(methoxymethyl)pyrrolidin-1-yl, 2(R)-(methoxymethyl)pyrrolidin-1-yl, 2(S)-(methoxymethyl)pyrrolidin-1-yl, 3-methylpyrrolidin-1-yl, 3(R)-methylpyrrolidin-1-yl, 3(S)-methylpyrrolidin-1-yl, pyrrolidin-1-yl, 3-(cyanomethoxy)pyrrolidin-1-yl;

5-azaspiro[2.4]heptan-5-yl;

tetrahydrofuran-3-yl;

3-methoxyazetidin-1-yl, 3-hydroxy-3-methylazetidin-1-yl;

1,4-dioxan-2-yl;

4-aminotetrahydro-2H-pyran-4-yl, 4-(aminomethyl)tetrahydro-2H-pyran-4-yl, 4-methoxypiperidin-1-yl, 4-hydroxy-4-methylpiperidin-1-yl, 1-(2,2,2-trifluoroethyl)piperidin-4-yl, 3-methoxypiperidin-1-yl, 3(R)-methoxypiperidin-1-yl, 3(S)-methoxypiperidin-1-yl, 3-ethoxypiperidin-1-yl, 3(R)-ethoxypiperidin-1-yl, 3(S)-ethoxypiperidin-1-yl;

3-cyano-2-azabicyclo[3.1.0]hexan-2-yl, (3R)-3-cyano-2-azabicyclo[3.1.0]hexan-2-yl, (3S)-3-cyano-2-azabicyclo[3.1.0]hexan-2-yl, or 3-azabicyclo[3.1.0]hexan-3-yl.

In some further preferred embodiments, $R^3$ is morpholino, 3-methyl-morpholino, 3(R)-methyl-morpholino, or 3(S)-methyl-morpholino.

In some embodiments, ($R^1$ and $R^2$), or ($R^2$ and $R^3$), or ($R^3$ and $R^4$), together with the atoms to which they are attached, form a fused 5- to 7-membered ring system, said fused ring system comprises 0-2 oxygen heteroatoms as ring member(s) and is optionally and independently substituted with halogen, —$C_{1-6}$alkyl, —$C_{1-6}$alkoxy, -halo$C_{1-6}$alkyl, -halo$C_{1-6}$alkoxy, or —$C_{3-6}$cycloalkyl.

In some embodiments, $R^1$ and $R^2$, together with the atoms to which they are attached, form a fused ring system selected from

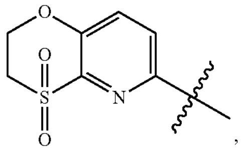
,
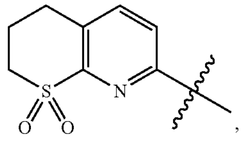
, or
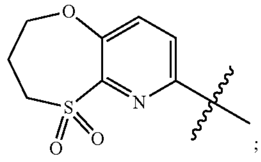
;

or $R^2$ and $R^3$, together with the atoms to which they are attached, form a fused ring system

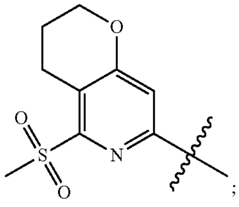 [SMILES: *c1cc2c(c(S(C)(=O)=O)n1)CCCO2]
;

$R^3$ and $R^4$, together with the atoms to which they are attached, form a fused ring system selected from

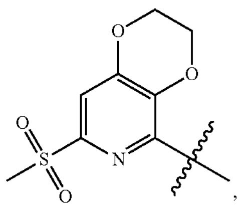
,
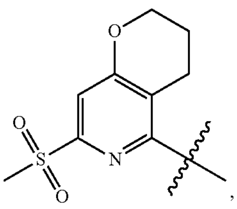
,
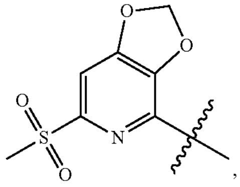
, or
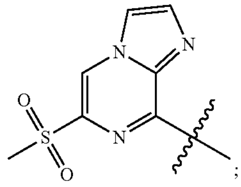
;

and wherein each of fused ring system is optionally and independently substituted with halogen, —$C_{1-6}$alkyl, —$C_{1-6}$alkoxy, -halo$C_{1-6}$alkyl, -halo$C_{1-6}$alkoxy, or —$C_{3-6}$cycloalkyl.

In some embodiments, $Cy^1$ is said 7- to 14-membered bicyclic or tricyclic heteroaryl comprising 1, 2, or 3 heteroatom(s) selected from oxygen, nitrogen or sulfur as ring member(s), preferably benzoimidazolyl, imidazopyrimidinyl, pyrazolopyrazinyl, pyrazolopyrimidinyl, benzothiophenyl, benzothiazolyl, benzoisoxazolyl, benzooxazolyl, benzoisothiazolyl, imidazopyridazinyl, imidazopyridazinyl; dihydro-4H-furo[3,2-c]pyranyl, 6,7-dihydro-4H-thieno[3,2-c]pyranyl, 2,3-dihydropyrazolo[5,1-b]oxazolyl, 4,5,6,7-tetrahydrofuro[3,2-c]pyridinyl, 1,3a,4,6,7,7a-hexahydropyrano[4,3-c]pyrazolyl, 4,5,6,7-tetrahydropyrazolo[1,5-a]pyrazinyl, 4,5,6,7-tetrahydropyrazolo[1,5-a]pyrimidinyl, 4,5,6,7-tetrahydropyrazolo[1,5-a]pyrazinyl, 4,5,6,7-tetrahydrothiazolo[5,4-c]pyridinyl, 4,5,6,7-tetrahydropyrazolo[1,5-a]pyrazinyl, 6,7-dihydro-4H-pyrazolo[5,1-c][1,4]oxazinyl, 2,3-dihydropyrazolo[5,1-b]oxazolyl, 2,3-dihydropyrazolo[5,1-b]oxazolyl, 1,3a,4,6,7,7a-hexahydropyrano[4,3-c]pyrazolyl, 6,7-dihydro-4H-pyrano[4,3-d]thiazolyl, [1,3]dioxolo[4,5-c]pyridinyl, 2,3-dihydro-[1,4]dioxino[2,3-c]pyridinyl, 3,4-dihydro-2H-pyrido[3,2-b][1,4]oxazinyl, 2,3-dihydro-[1,4]dioxino[2,3-b]pyridinyl, 2,3-dihydro-[1,4]dioxino[2,3-b]pyridin-6-yl, 3,4-dihydro-2H-pyrido[4,3-b][1,4]oxazinyl, or 2H-pyrido[3,2-b][1,4]oxazin-4 (3H)-yl, each of which is optionally substituted with halogen, —$C_{1-6}$alkyl, —$NH_2$, or —C(O)$R'''$, wherein $R'''$ is $C_{1-6}$alkyl; any of the said alkyl is optionally enriched in deuterium.

In some embodiments, $Cy^1$ is a 7- to 14-membered bicyclic heteroaryl which is a pyridinyl, pyrazolyl, thienyl, or thiazolyl ring fused with a 5- or 6-membered heterocyclyl ring, wherein said 5- or 6-membered heterocyclyl ring comprising one or two heteroatoms selected from oxygen or nitrogen as ring member(s) and said 5- or 6-membered heterocyclyl ring is optionally substituted with one or two $C_{1-6}$alkyl or oxo, preferably two $C_{1-6}$alkyl, more preferably two methyl, most preferably two methyl on the same carbon atom. In some embodiments, $Cy^1$ is a 7- to 14-membered bicyclic heteroaryl which is a pyridinyl ring fused with a 5- or 6-membered heterocyclyl ring, wherein said 5- or 6-membered heterocyclyl ring comprising one or two heteroatoms selected from oxygen or nitrogen as ring member(s) and said 5- or 6-membered heterocyclyl ring is optionally substituted with one or two $C_{1-6}$alkyl or oxo, preferably two $C_{1-6}$alkyl, more preferably two methyl, most preferably two methyl on the same carbon atom. In some embodiments, $Cy^1$ is a 7- to 14-membered bicyclic heteroaryl which is a pyridinyl ring fused with a 5- or 6-membered heterocyclyl ring, wherein said 5- or 6-membered heterocyclyl ring comprising two oxygen atoms as ring member(s) and said 5- or 6-membered heterocyclyl ring is optionally substituted with one or two $C_{1-6}$alkyl, preferably two $C_{1-6}$alkyl, more preferably two methyl, most preferably two methyl on the same carbon atom. In some embodiments, $Cy^1$ is a 7- to 14-membered bicyclic heteroaryl which is a pyridinyl ring fused with 1,4-dioxane ring, wherein said 1,4-dioxane ring is optionally substituted with one or two $C_{1-6}$alkyl, preferably two $C_{1-6}$alkyl, more preferably two methyl most preferably two methyl on the same carbon atom. In some preferred embodiments, $Cy^1$ is

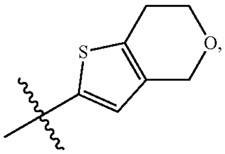 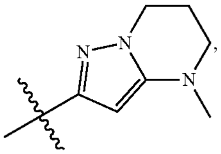
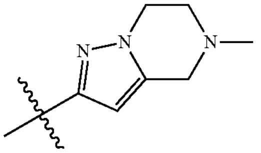
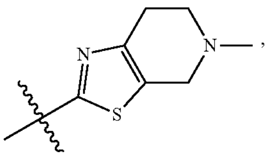 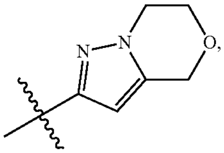
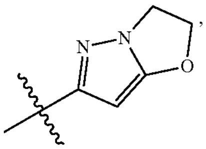 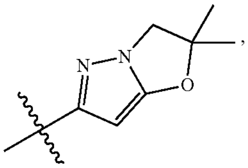
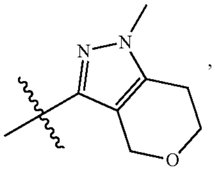 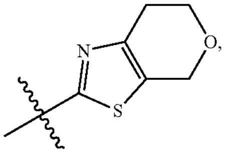
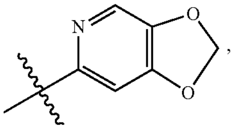 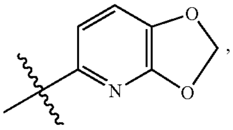
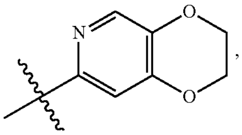 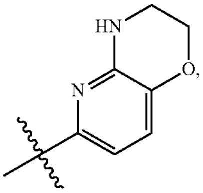
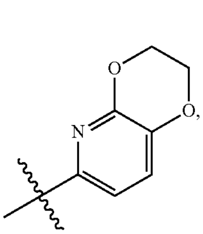 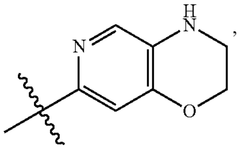
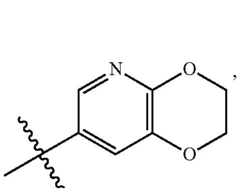 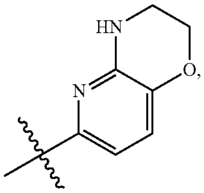
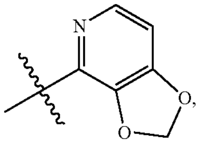 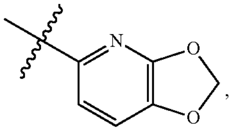
-continued
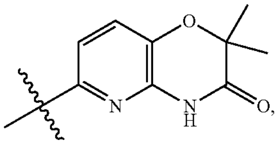
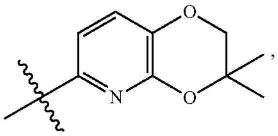 or
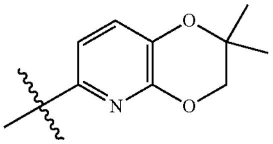;
preferably
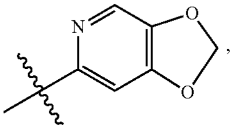 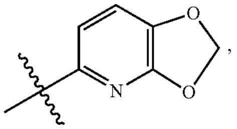
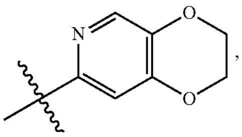 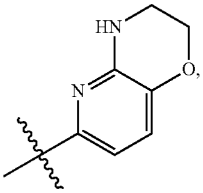
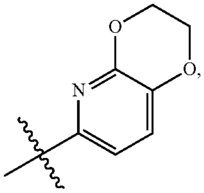 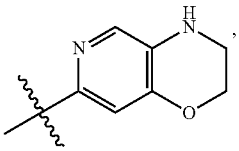
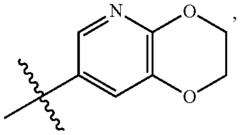 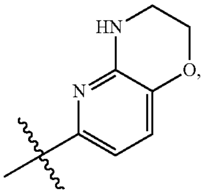
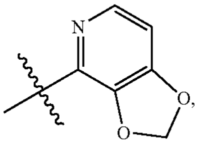 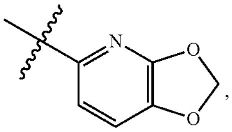
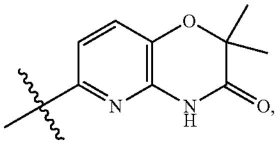
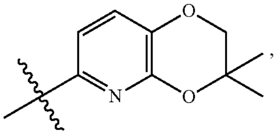 or -continued
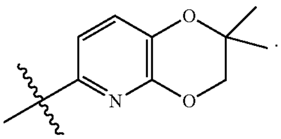
In some embodiments, Cy[1] is
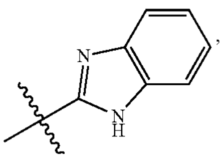
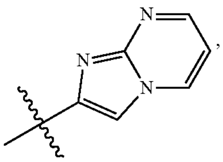
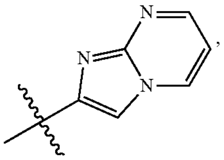
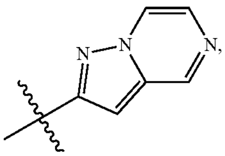
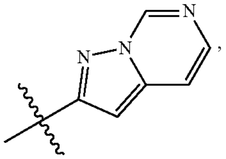
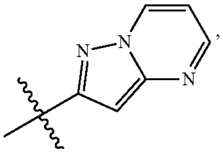
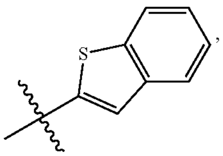
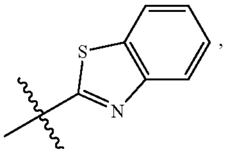
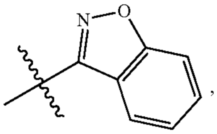
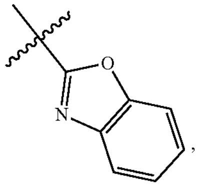
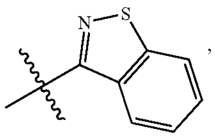
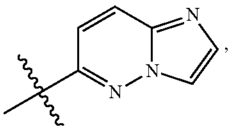
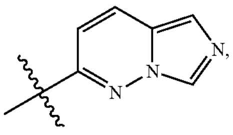
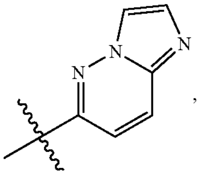
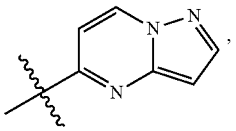
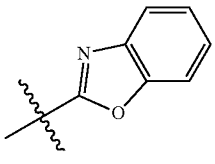
-continued
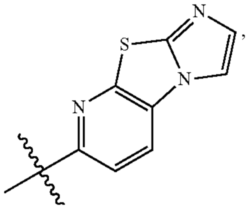
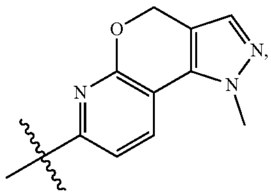
or
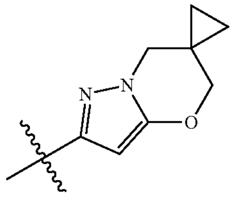
;
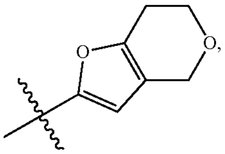
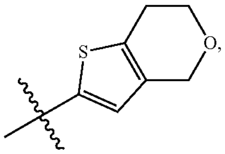
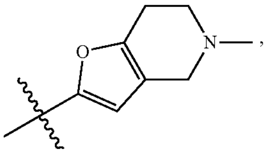
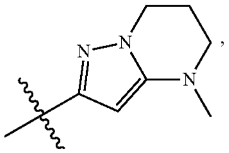
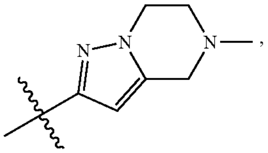
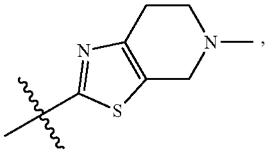
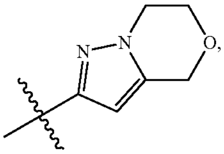
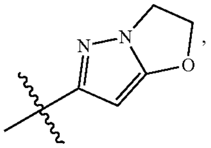
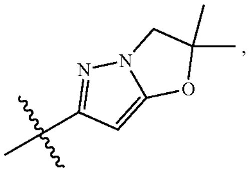
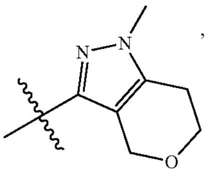
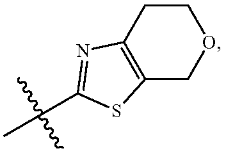
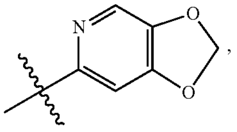
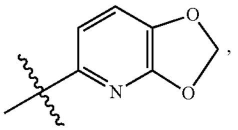
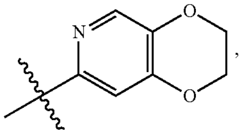
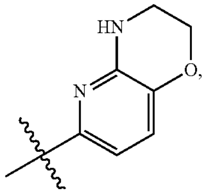
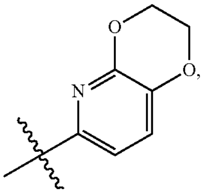

-continued

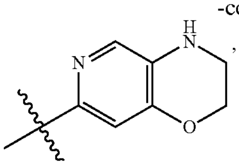,
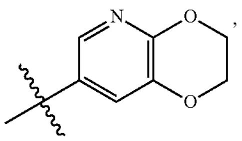,
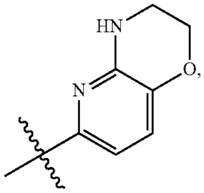,
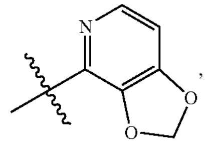,
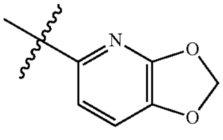,
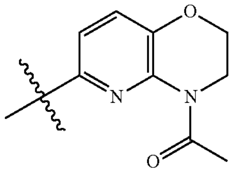,
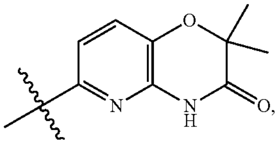,
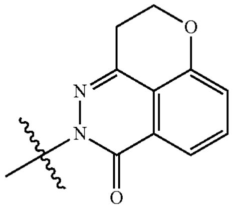,
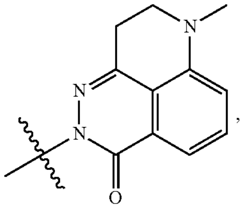,
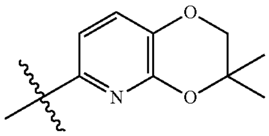,
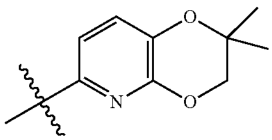;
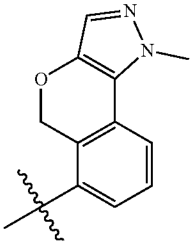, or
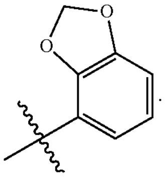 [SMILES: *c1cccc2c1OCO2].

In some embodiments, the compound is selected from the exemplified compounds in Examples.

In the second aspect, disclosed herein provides a pharmaceutical composition comprising one or more compounds in the present disclosure or a stereoisomer or pharmaceutically acceptable salt thereof, and a pharmaceutically acceptable excipient.

In the third aspect, disclosed herein provides a method for treating a disease associated with undesirable TYK2 activity (TYK2-related diseases), comprising administrating to a subject in need of such treatment a therapeutically effective amount of the compounds in the present disclosure or a stereoisomer or pharmaceutically acceptable salt thereof.

In one embodiment, the disease is inflammatory or autoimmune.

DETAILED DESCRIPTION OF THE DISCLOSURE

Definitions

The following terms have the indicated meanings throughout the specification:

As used herein, including the appended claims, the singular forms of words such as "a," "an," and "the," include their corresponding plural references unless the context clearly dictates otherwise.

The term "or" is used to mean, and is used interchangeably with, the term "and/or" unless the context clearly dictates otherwise.

The term "alkyl" refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. The alkyl group can be optionally enriched in deuterium, e.g., $—CD_3$, $—CD_2CD_3$ and the like.

The term "halogen" refers to fluoro (F), chloro (Cl), bromo (Br) and iodo (I).

The term "haloalkyl" refers to an alkyl group in which one or more hydrogen is/are replaced by one or more halogen atoms such as fluoro, chloro, bromo, and iodo. Examples of the haloalkyl include halo$C_{1-6}$alkyl, halo$C_{1-6}$alkyl or halo $C_{1-4}$alkyl, but not limited to $—CF_3$, $—CH_2Cl$, $—CH_2CF_3$, $—CCl_2$, $CF_3$, and the like.

The term "alkyloxy" or "alkoxy" refers to an alkyl group as defined above attached to the parent molecular moiety through an oxygen atom. Examples of an alkyloxy, e.g., $C_{1-6}$alkyloxy or $C_{1-4}$ alkyloxy include, but not limited to, methoxy, ethoxy, isopropoxy, propoxy, n-butoxy, tert-butoxy, pentoxy and hexoxy and the like.

The term "alkoxy-alkyl-" refers to an alkyl group as defined above further substituted with an alkoxy as defined above. Examples of an alkoxy-alkyl-, e.g., $C_{1-8}$alkoxy-$C_{1-8}$ alkyl- or $C_{1-6}$alkoxy-$C_{1-6}$alkyl-include, but not limited to, methoxymethyl, ethoxymethyl, ethoxyethyl, isopropoxymethyl, or propoxymethyl and the like.

The term "amino" refers to $—NH_2$. The term "alkylamino" refers to —NH(alkyl). The term "dialkylamino" refers to $—N(alkyl)_2$.

The term "alkenyl" herein refers to a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., C2-6 alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., C2-6 alkynyl, include, but not limited to ethynyl, 1-propynyl, 2-propynyl (propargyl), 1-butynyl, 2-butynyl, and 3-butynyl groups.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, Examples of the saturated monocyclic cycloalkyl group, e.g., $C_{3-6}$cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, preferably cyclohexenyl.

The term "cycloalkynyl" refers to non-aromatic cycloalkyl groups of from 5 to 10 carbon atoms having single or multiple rings and having at least one triple bond.

The term "deuterated" is used herein to modify a chemical structure or an organic group or radical, wherein one or more carbon-bound hydrogen(s) are replaced by one or more deuterium(s), e.g., "deuterated-alkyl", "deuterated-cycloalkyl", "deuterated-heterocycloalkyl", "deuterated-aryl", "deuterated-morpholinyl", and the like. For example, the term "deuterated-alkyl" defined above refers to an alkyl group as defined herein, wherein at least one hydrogen atom bound to carbon is replaced by a deuterium. In a deuterated alkyl group, at least one carbon atom is bound to a deuterium; and it is possible for a carbon atom to be bound to more than one deuterium; it is also possible that more than one carbon atom in the alkyl group is bound to a deuterium.

The term "aryl" used alone or in combination with other terms refers to a group selected from:

- 5- and 6-membered carbocyclic aromatic rings, e.g., phenyl;
- bicyclic ring systems such as 7 to 12 membered bicyclic ring systems, wherein at least one ring is carbocyclic and aromatic, e.g., naphthyl and indanyl; and,
- tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., C5-10 aryl). Examples of a monocyclic or bicyclic aromatic hydrocarbon ring include, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "heteroaryl" herein refers to a group selected from:

- 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
- 7- to 12-membered bicyclic rings comprising at least one heteroatom, for example, from 1 to 4, or, in some embodiments, from 1 to 3, or, in other embodiments, 1 or 2, heteroatoms, selected from nitrogen, oxygen or optionally oxidized sulfur as ring member(s), with the remaining ring atoms being carbon and wherein at least one ring is aromatic and at least one heteroatom is present in the aromatic ring; and
- 11- to 14-membered tricyclic rings comprising at least one heteroatom, for example, from 1 to 4, or in some embodiments, from 1 to 3, or, in other embodiments, 1 or 2, heteroatoms, selected from nitrogen, oxygen or optionally oxidized sulfur as ring member(s), with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

The term "optionally oxidized sulfur" used herein refers to S, SO or SO2.

The terms "aromatic heterocyclic ring" and "heteroaryl" are used interchangeably throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is an 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

Also, a "heteroaryl" which is further fused with a "Heterocyclyl" is defined as a "heteroaryl".

"Heterocyclyl," "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "monocyclic heterocyclyl" refers to monocyclic groups in which at least one ring member is a heteroatom selected from nitrogen, oxygen or optionally oxidized sulfur. A heterocycle may be saturated or partially saturated.

Exemplary monocyclic 4 to 9-membered heterocyclyl groups include, but not limited to, (as numbered from the linkage position assigned priority 1) pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl.

The term "spiro heterocyclyl" refers to a 5 to 20-membered polycyclic heterocyclyl with rings connected through one common carbon atom (called a spiro atom), comprising one or more heteroatoms selected from nitrogen, oxygen or optionally oxidized sulfur as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 12-membered. According to the number of common spiro atoms, a spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, and more preferably 4-membered/4-membered, 3-membered/5-membered, 4-membered/5-membered, 4-membered/6-membered, 5-membered/5-membered, or 5-membered/6-membered mono-spiro heterocyclyl.

The term "fused heterocyclic group" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but none of the rings has a completely conjugated pi-electron system. Preferably, a fused heterocyclyl is 6 to 14-membered, and more preferably 7 to 10-membered. According to the number of membered rings, a fused heterocyclyl is divided into bicyclic, tricyclic, tetracyclic, or polycyclic fused heterocyclyl, preferably refers to bicyclic or tricyclic fused heterocyclyl, and more preferably 5-membered/5-membered, or 5-membered/6-membered bicyclic fused heterocyclyl. Representative examples of fused heterocycles include, but not limited to, the following groups octahydrocyclopenta[c]pyrrole (e.g., octahydrocyclopenta[c]pyrrol-2-yl), octahydropyrrolo[3,4-c]pyrrolyl, octahydroisoindolyl, isoindolinyl (e.g., isoindoline-2-yl), octahydro-benzo[b][1,4]dioxin.

The term "bridged heterocyclyl" refers to a 5- to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2]octyl and 2-azabicyclo[3.3.2]decyl.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclohexyl or cyclobutyl group, substituents found on cyclohexyl or cyclobutyl ring may adopt cis and trans formations. Cis formation means that both substituents are found on the upper side of the 2 substituent placements on the carbon, while trans would mean that they were on opposing sides.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents [Eliel, E. and Wilen, S. *Stereochemistry of Organic Compounds*. New York: John Wiley & Sons, Inc., 1994; Lochmuller C. H., et al. "*Chromatographic resolution of enantiomers: Selective review.*" *J Chromatogr.*, 113 (3) (1975): pp. 283-302]. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer Irving W, Ed. *Drug Stereochemistry: Analytical Methods and Pharmacology*. New York: Marcel Dekker Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid Formulation such as tablets, powder, granule, capsules and the like, a liquid Formulation such as water or oil suspension or other liquid Formulation such as syrup, solution, suspension or the like; for parenteral administration, the pharmaceutical composition may be solution, water solution, oil suspension concentrate, lyophilized powder or the like. Preferably, the Formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All Formulations of the pharmaceutical composition disclosed herein can be produced by the conventional methods in the pharmaceutical field. For example, the active ingredient can be mixed with one or more excipients, then to make the desired Formulation. The "pharmaceutically acceptable excipient" refers to conventional pharmaceutical carriers suitable for the desired pharmaceutical Formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise," and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "Cn-m" indicates a range which includes the endpoints, wherein n and m are integers and indicate the number of carbons. Examples include C1-8, C1-6, and the like.

Unless specifically defined elsewhere in this document, all other technical and scientific terms used herein have the meaning commonly understood by one of ordinary skill in the art to which this invention belongs.

Example

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise.

Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using prepacked silica gel cartridges.

$^1H$ NMR spectra were recorded on a Varian instrument operating at 400 MHz. $^1H$ NMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). Compound names except the reagents were generated by ChemDraw version 12.0.

Abbreviations

AcOH Acetic acid
Aq Aqueous
Brine Saturated aqueous sodium chloride solution
Bn Benzyl
BnBr Benzyl Bromide
$(Boc)_2O$ di-tert-butyl dicarbonate
DMF N,N-Dimethylformamide
Dppf 1,1"-bis(diphenylphosphino)ferrocene
DBU 1,8-diazabicyclo[5.4.0]undec-7-ene
DIEA or DIPEA N-ethyl-N-isopropylpropan-2-amine
DMAP 4-N,N-dimethylaminopyridine
DMSO Dimethyl sulfoxide
EtOAc or EA EA
EtOH Ethanol
$Et_2O$ or ether Diethyl ether
$Et_3N$ Triethyl amine
HATU O-(7-Azabenzotriazol-1-yl)-N,N,N',N'-tetramethyluronium hexafluorophosphate
HPLC High-performance liquid chromatography
IPA 2-propanol
i-PrOH Isopropyl alcohol
ms or MS Mass spectrum
NaHMDS Sodium Hexamethylenedisilazane
PE petroleum ether PPA Polyphosphoric acid
p-TSA p-Toluenesulfonic acid
Rt Retention time
Rt or rt Room temperature
TBAF Tetra-butyl ammonium fluoride
TBSCl tert-Butyldimethylsilyl chloride
TFA Trifluoroacetic acid
THF tetrahydrofuran
TLC thin layer chromatography Example BB1: Synthesis of 2-bromo-4-(methoxymethyl)-6-(methylsulfonyl)pyridine

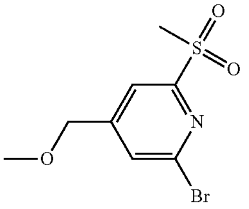

Step 1: 2,6-dibromo-4-(bromomethyl)pyridine

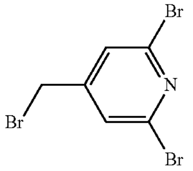

A mixture of 2,6-dibromo-4-methylpyridine (10.0 g, 39.85 mmol), $CCl_4$ (100 mL), AIBN (1.31 g, 7.98 mmol) and NBS (10.64 g, 59.78 mmol) was stirred for 15 h at 80° C. After cooled to room temperature, DCM (100 mL) was added and the resulting mixture was washed with $H_2O$ (150 mL×3). The mixture was dried over anhydrous $Na_2SO_4$ and concentrated under vacuum. The residue was purified by combi-flash (EA/PE=0-20%) give 2,6-dibromo-4-(bromomethyl)pyridine (10.0 g, 76%). LCMS (ESI) m/e $[M+1]^+$ 328.

Step 2: 2,6-dibromo-4-(methoxymethyl)pyridine

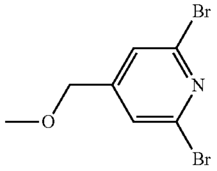

A mixture of 2,6-dibromo-4-(bromomethyl)pyridine (10.0 g, 30.32 mmol), MeOH (100 mL) and $K_2CO_3$ (8.38 g, 60.63 mmol) was stirred for 2 h at RT. Upon completion of the reaction, EA (200 mL) was added and the resulting mixture was washed with $H_2O$ (200 mL×3). The organic layer was dried over anhydrous $Na_2SO_4$ and concentrated under vacuum. The residue was purified by combi-flash (EA/PE=0-25%) to give 2,6-dibromo-4-(methoxymethyl)pyridine (2.00 g, 23%). LCMS (ESI) m/e $[M+1]^+$ 280.

Step 3: 2-bromo-4-(methoxymethyl)-6-(methylsulfanyl)pyridine

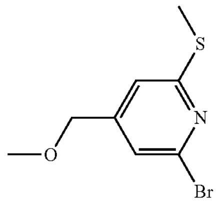

A mixture of 2,6-dibromo-4-(methoxymethyl)pyridine (2.00 g, 7.12 mmol), DMF (20 mL) and $NaSCH_3$ (0.50 g, 7.14 mmol) was stirred for 1 h at RT. Upon completion of the reaction, EA (100 mL) was added and the resulting mixture was washed with $H_2O$ (200 mL×3). The organic layer was dried over anhydrous $Na_2SO_4$ and concentrated under vacuum. The residue was purified by combi-flash (EA/PE=0-25%) to give 2-bromo-4-(methoxymethyl)-6-(methylsulfanyl)pyridine (1.40 g, 79%). LCMS (ESI) m/e $[M+1]^+$ 248.

Step 4: 2-bromo-6-methanesulfonyl-4-(methoxymethyl)pyridine

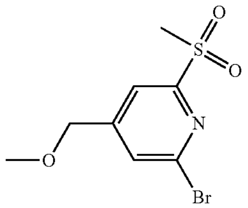

A mixture of 2-bromo-4-(methoxymethyl)-6-(methylsulfanyl)pyridine (1.40 g, 5.64 mmol), THF (10 mL), $H_2O$ (10.00 mL), $NaIO_4$ (2.41 g, 11.26 mmol) and $RuCl_3 \cdot H_2O$ (127.19 mg, 0.56 mmol) was stirred for 1 h at 0° C. Upon completion of the reaction, EA (100 mL) was added and the resulting mixture was washed with $H_2O$ (200 mL×3). The organic layer was dried over anhydrous $Na_2SO_4$, concentrated and purified by combi-flash (EA/PE=0-30%) give 2-bromo-6-methanesulfonyl-4-(methoxymethyl)pyridine (1.10 g, 69%). $^1H$ NMR (300 MHz, $CDCl_3$) δ 7.99 (s, 1H), 7.74 (s, 1H), 4.56 (s, 2H), 3.50 (s, 3H), 3.27 (s, 3H). LCMS (ESI) m/e $[M+1]^+$ 280.

Example BB2: Synthesis of 2-bromo-4-[2-[(tert-butyldimethylsilyl)oxy]ethoxy]-6-methanesulfonyl pyridine

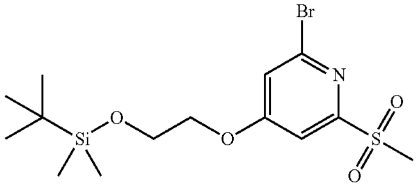 [SMILES: CC(C)(C)[Si](C)(C)OCCOc1cc(Br)nc(S(C)(=O)=O)c1]

Step 1: 2-bromo-6-(methylthio)pyridin-4-ol

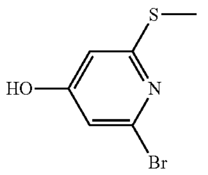

A mixture of 2, 6-dibromopyridin-4-ol (10.00 g, 39.542 mmol), DIEA (10.22 g, 0.079 mmol), Xantphos (0.23 g, 0.39 mmol), $NaSCH_3$ (2.93 g, 39.54 mmol) and $Pd_2(dba)_3$ (0.18 g, 0.20 mmol) in 1,4-dioxane (200 mL) was stirred overnight at 75° C. under nitrogen atmosphere. After cooled to room temperature, water was added and the resulting mixture was extracted with EA (100 mL×3). The combined organic layers were washed with water, dried over anhydrous $Na_2SO_4$. After filtration, the filtrate was concentrated under vacuum and the crude product 2-bromo-6-(methylthio)pyridin-4-ol was used directly for next step without further purification. LCMS (ESI) m/e $[M+1]^+$ 220.

Step 2: 2-bromo-6-methanesulfonylpyridin-4-ol

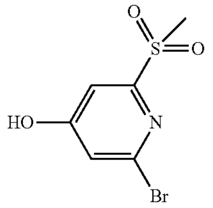

To a stirred solution of 2-bromo-6-(methylsulfanyl)pyridin-4-ol (6.00 g, 27.26 mmol) in $H_2O$ (100 mL)/THF (100 mL) was added $RuCl_3{\cdot}H_2O$ (0.18 g, 0.82 mmol) in water (30 mL) dropwise at 0° C., then $NaIO_4$ (11.66 g, 0.055 mmol) was added dropwise successively at 0° C. The resulting mixture was stirred for additional 30 mins at 0° C. Upon completion of the reaction, the resulting mixture was extracted with EA (100 mL×3). The combined organic layers were washed with water, dried over anhydrous $Na_2SO_4$. After filtration, the filtrate was concentrated under vacuum. The residue was purified by silica gel column chromatography (DCM/MeOH=12:1) to give 2-bromo-6-methanesulfonylpyridin-4-ol (3 g, 44%). LCMS (ESI) m/e $[M+1]^+$ 252.

Step 3: 2-bromo-4-[2-[(tert-butyldimethylsilyl)oxy]ethoxy]-6-methanesulfonylpyridine

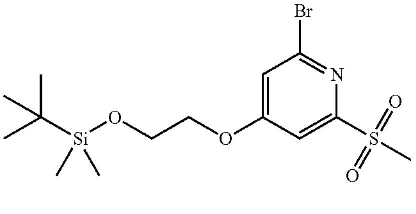 [SMILES: CC(C)(C)[Si](C)(C)OCCOc1cc(Br)nc(S(C)(=O)=O)c1]

A mixture of 2-bromo-6-methanesulfonylpyridin-4-ol (1.00 g, 3.97 mmol), $K_2CO_3$ (1.10 g, 79.59 mmol) and (2-bromoethoxy)(tert-butyl)dimethylsilane (1.90 g, 79.42 mmol) in DMF (20 mL) was stirred for 3 h at 60° C. After cooled to room temperature, water was added and the resulting mixture was extracted with EA (100 mL×3). The combined organic layers were washed with brine, dried over anhydrous $Na_2SO_4$. After filtration, the filtrate was concentrated under vacuum. The residue was purified by Prep-TLC (hexane/EA=5:1) to give the product (1.08 g, 68%). $^1H$ NMR (300 MHz, DMSO-$d_6$) δ 7.62 (s 1H), 7.54 (s 1H), 4.30-4.25 (m, 2H), 3.90-3.87 (m, 2H), 3.28 (s, 3H), 0.85 (s, 9H), 0.06 (s, 6H). LCMS (ESI) m/e $[M+1]^+$ 410.

Example BB3: Synthesis of 2-bromo-4-((2,2-dimethyl-1,3-dioxolan-4-yl)methoxy)-6-(methyl sulfonyl)pyridine

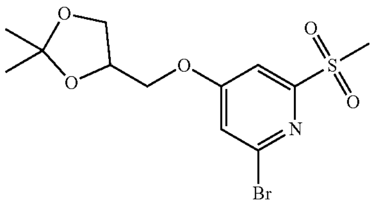

A mixture of 2-bromo-6-methanesulfonylpyridin-4-ol (200 mg, 0.79 mmol), $Cs_2CO_3$ (517.01 mg, 1.59 mmol) and (2,2-dimethyl-1,3-dioxolan-4-yl)methyl 4-methylbenzenesulfonate (272.62 mg, 0.95 mmol) in DMF (5 mL) was stirred for 3 h at 80° C. under nitrogen atmosphere. After cool to room temperature, water was added and the resulting mixture was extracted with EA (100 mL×3). The combined organic layers were washed with water, dried over anhydrous $Na_2SO_4$. After filtration, the filtrate was concentrated under vacuum. The residue was purified by Prep-TLC (PE/EA=5:1) to give 2-bromo-4-((2,2-dimethyl-1,3-dioxolan-4-yl)methoxy)-6-(methylsulfonyl)pyridine (260 mg, 89%). $^1H$ NMR (300 MHz, MeOD-$d_4$) δ 7.64 (s, 1H), 7.49 (s, 1H), 4.59-4.40 (m, 1H), 4.32-4.13 (m, 3H), 3.89 (d, J=8.6 Hz, 1H), 3.23 (s, 3H), 1.41 (s, 3H), 1.37 (s, 3H). LCMS (ESI) m/e $[M+1]^+$ 366.

Example BB4: Synthesis of 2-bromo-4-(2-((tert-butyldimethylsilyl)oxy)propoxy)-6-(methylsulfonyl)pyridine

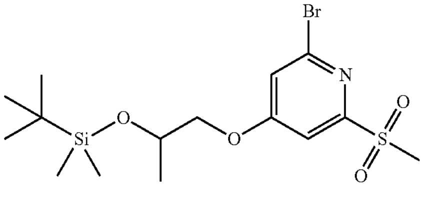 [SMILES: CC(COc1cc(Br)nc(S(C)(=O)=O)c1)O[Si](C)(C)C(C)(C)C]

Step 1: 1-((2-Bromo-6-(methylsulfonyl)pyridin-4-yl)oxy)propan-2-ol

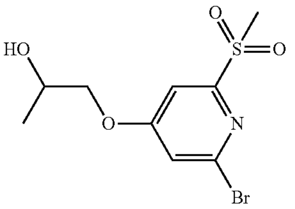 [SMILES: CC(O)COc1cc(Br)nc(S(C)(=O)=O)c1]

A mixture of 2-bromo-6-methanesulfonylpyridin-4-ol (500 mg, 1.98 mmol), 2-propanol-1-bromo (4.14 g, 29.75 mmol) and $K_2CO_3$ (548 mg, 3.97 mmol) in DMF (5 mL) was stirred for 12 h at 70° C. After cool to room temperature, water was added and the resulting mixture was extracted with EA (100 mL×3). The combined organic layers were washed with brine, dried over anhydrous $Na_2SO_4$. After filtration, the filtrate was concentrated to give the crude product 1-((2-Bromo-6-(methylsulfonyl)pyridin-4-yl)oxy) propan-2-ol was used for the next step directly without further purification. LCMS (ESI) m/e $[M+1]^+$ 310.

Step 2: 2-Bromo-4-(2-((tert-butyldimethylsilyl)oxy) propoxy)-6-(methylsulfonyl)pyridine

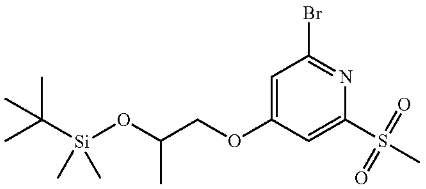 [SMILES: CC(COc1cc(Br)nc(S(C)(=O)=O)c1)O[Si](C)(C)C(C)(C)C]

A solution of 1-[(2-bromo-6-methanesulfonylpyridin-4-yl)oxy]propan-2-ol (600 mg, 1.93 mmol), TBSCl (437.4 mg, 2.90 mmol) and DIEA (500 mg, 3.87 mmol) in DCM (10 mL) was stirred for 12 h at RT. Upon completion of the reaction, the solvent was removed and the residue was purified by Prep-TLC (EA/PE=1:3) to give 2-bromo-4-[2-[(tert-butyldimethylsilyl)oxy]propoxy]-6-methanesulfonylpyridine (635 mg, 77%). $^1H$ NMR (300 MHz, DMSO-$d_6$) δ 7.61 (s, 1H), 7.52 (s, 1H), 4.24-4.05 (m, 1H), 3.35 (s, 3H), 3.28 (d, J=4.4 Hz, 2H), 1.25-1.20 (m, 3H), 0.82 (s, 9H), 0.08 (s, 6H). LCMS (ESI) m/e $[M+1]^+$ 425.

Example 1B1B5: Synthesis of 2-[(2-bromo-6-methanesulfonylpyridin-4-yl)oxy]acetonitrile

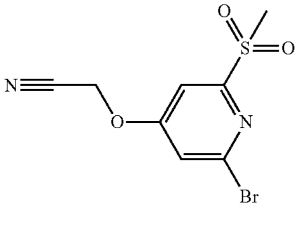

To a stirred solution of 2-bromo-6-methanesulfonylpyridin-4-ol (500 mg, 1.98 mmol) and 2-bromoacetonitrile (475 mg, 3.97 mmol) in DMF (10 mL) was added $K_2CO_3$ (548 mg, 3.97 mmol) in portions at room temperature, then the resulting mixture was stirred overnight at 80° C. After cooled to room temperature, water was added and the resulting mixture was extracted with EA (40 mL×3). The combined organic layers were washed with brine (3×30 mL), dried over anhydrous $Na_2SO_4$, concentrated and purified by Prep-TLC (PE/EA=3:1) to give 2-[(2-bromo-6-methanesulfonylpyridin-4-yl)oxy]acetonitrile (254.3 mg, 44%). $^1H$ NMR (300 MHz, MeOD-$d_4$) δ 7.73 (s, 1H), 7.63 (s, 1H), 5.27 (s, 2H), 3.27 (s, 3H). LCMS (ESI) m/e $[M+1]^+$ 291.

Example BB6: Synthesis of 2-bromo-4-isopropoxy-6-methanesulfonylpyridine

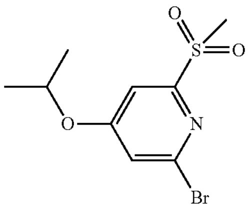

To a stirred solution of 2-bromo-6-methanesulfonylpyridin-4-ol (600 mg, 2.38 mmol) and 2-iodopropane (809 mg, 4.76 mmol) in DMF (10 mL) was added $K_2CO_3$ (658 mg, 4.76 mmol) in portions at room temperature. After cooled to room temperature, water was added and the resulting mixture was extracted with EA (40 mL×3). The combined organic layers were washed with brine (30 mL×3), dried over anhydrous $Na_2SO_4$. After filtration, the filtrate was concentrated under vacuum. The residue was purified by Prep-TLC (PE/EA=3:1) to give the product (570 mg, 82%). $^1H$ NMR (400 MHz, MeOD-$d_4$) δ 7.54 (s, 1H), 7.41 (s, 1H), 4.96-4.85 (m, 1H), 3.24 (s, 3H), 1.40 (d, J=6.1 Hz, 6H). LCMS (ESI) m/e $[M+1]^+$ 294.

Example BB7: Synthesis of 2-bromo-6-methanesulfonyl-4-[(trans)-3-[(tert-butyldimethylsilyl)oxy] cyclobutoxy]pyridine

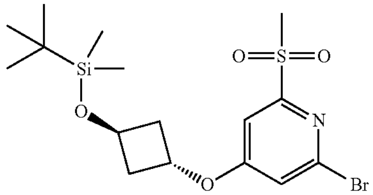 [SMILES: CC(C)(C)[Si](C)(C)O[C@H]1C[C@H](Oc2cc(Br)nc(S(C)(=O)=O)c2)C1]

A solution of 2-bromo-6-methanesulfonylpyridin-4-ol (2.00 g, 7.93 mmol), $PPh_3$ (3.12 g, 11.89 mmol), DIAD (2.41 g, 11.92 mmol) and trans-3-[(tert-butyldimethylsilyl)oxy] cyclobutan-1-ol (1.61 g, 7.95 mmol) in THF (100 mL) was stirred overnight at 50° C. After cooled to room temperature, water was added and the resulting mixture was extracted with EA (40 mL×3). The combined organic layers were washed with brine, dried over anhydrous $Na_2SO_4$. After filtration, the filtrate was concentrated under vacuum. The residue was purified by Prep-TLC (hexane/EA=5:1) to give the product (2.06 g, 60%). $^1$H NMR (300 MHz, MeOD-$d_4$) δ 7.48 (s, 1H), 7.29 (s, 1H), 5.03 (t, J=6.3 Hz, 1H), 4.70-4.52 (m, 1H), 3.23 (s, 3H), 2.59-2.37 (m, 4H), 0.92 (s, 9H), 0.08 (s, 6H). LCMS (ESI) m/e $[M+1]^+$ 436.

Example BB8: Synthesis of 2-bromo-6-methanesulfonylpyridine-4-carbonitrile

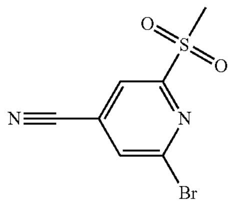

Step 1: 2-bromo-6-(methylsulfanyl)pyridine-4-carbonitrile

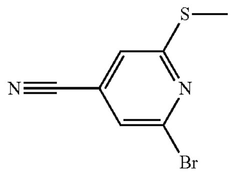

A mixture of 2,6-dibromopyridine-4-carbonitrile (4.00 g, 15.27 mmol), DMF (40 mL) and $CH_3SNa$ (1.28 g, 18.33 mmol) was stirred overnight at rt. Upon completion of the reaction, water was added and the resulting solution was extracted with EA (60 mL×3). The combined organic layer was washed with brine, dried over anhydrous $Na_2SO_4$. The solid were filtered out and the resulting mixture was concentrated under vacuum. The residue was purified by combi-flash (EA/PE=0-5%) to give the product (1.50 g, 43%). GCMS (ESI) [M] 228.

Step 2: 2-bromo-6-methanesulfonylpyridine-4-carbonitrile

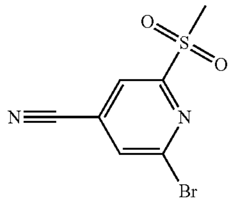

To a solution of 2-bromo-6-(methylsulfanyl)pyridine-4-carbonitrile (1.50 g, 6.55 mmol) in THF (15 mL) was added $NaIO_4$ (2.80 g, 13.10 mmol) in $H_2O$ (20 mL) in portions at 0° C., then to this was added $RuCl_3 \cdot H_2O$ (147.60 mg, 0.655 mmol) in $H_2O$ (10 mL) in portions at 0° C. The resulting solution was stirred for 2 h at RT. Upon completion of the reaction, the resulting solution was extracted with EA (60 mL×3) and the combined organic layer was washed with brine, dried over anhydrous $Na_2SO_4$. The solid was filtered out and the resulting mixture was concentrated under vacuum and the residue was purified by Prep-TLC (EA/PE=1:2) to give the product (1.06 g, 62%). $^1$H NMR (300 MHz, DMSO-$d_6$) δ 8.65 (s, 1H), 8.55 (s, 1H), 3.40 (s, 3H); GC-MS (ESI) [M] 260.

Example BB9: Synthesis of 2-bromo-6-methanesulfonyl-4-methoxypyridine

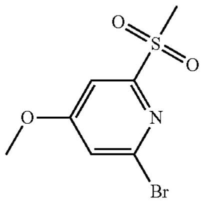

To a mixture of 2-bromo-6-methanesulfonylpyridin-4-ol (5.00 g, 19.84 mmol) and $K_2CO_3$ (5.49 g, 0.04 mmol) in DMF (100 mL) was added $CH_3I$ (4.20 g, 29.59 mmol) dropwise at 60° C. for 2 h. After cooled to rt, water was added and the resulting mixture was extracted with EA (150 mL×3). The combined organic layers were washed with brine, dried over anhydrous $Na_2SO_4$. After filtration, the filtrate was concentrated under vacuum. The residue was purified by combi-flash (EA/PE=25-35%) to give the product (4.00 g, 76%). $^1$H NMR (300 MHz, $CDCl_3$) δ 7.56 (s, 1H), 7.18 (s, 1H), 3.95 (s, 3H), 3.24 (s, 3H). LCMS (ESI) m/e $[M+1]^+$ 266.

Example BB10: Synthesis of 6-bromo-4-methylpyridine-2-sulfonamide

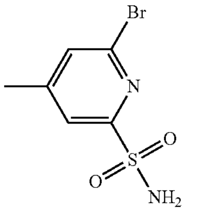

Step 1: 2-(benzylsulfanyl)-6-bromo-4-methylpyridine

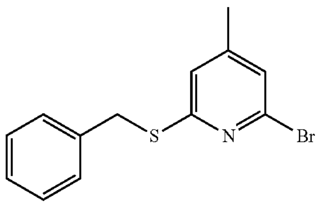 [SMILES: Cc1cc(Br)nc(SCc2ccccc2)c1]

A mixture of 2,6-dibromo-4-methylpyridine (2.00 g, 7.97 mmol), DMF (30 mL), benzyl mercaptan (1.09 g, 8.78 mmol) and $Cs_2CO_3$ (5.19 g, 15.93 mmol) was stirred for 2 h at RT. Upon completion of the reaction, EA (100 mL) was added and the resulting mixture was washed with water (100 mL×3). Then the mixture was dried over anhydrous $Na_2SO_4$ and concentrated under vacuum. The residue was purified by combi-flash (EA/PE=0-25%) give the product (2.30 g, 98%). LCMS (ESI) m/e $[M+1]^+$ 294.

Step 2: 6-bromo-4-methylpyridine-2-sulfonyl chloride

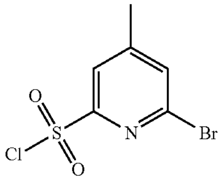

A mixture of 2-(benzylsulfanyl)-6-bromo-4-methylpyridine (2.30 g, 7.82 mmol), AcOH (36 mL), $H_2O$ (4 mL) and NCS (3.65 g, 27.33 mmol) was stirred for 1 h at RT. Upon completion of the reaction, EA (100 mL) was added and the resulting mixture was washed with water (100 mL×3). The mixture was dried over anhydrous $Na_2SO_4$ and concentrated under vacuum. The residue was purified by combi-flash (EA/PE=0-25%) give the product (2.00 g, 94%).

Step 3: 4-methylpyridine-2-sulfonamide

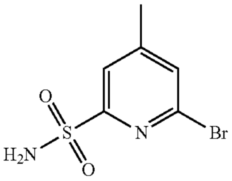

A solution of 6-bromo-4-methylpyridine-2-sulfonyl chloride (2.00 g, 7.39 mmol) in THF (20 mL) was added ammonium (10 mL, 33% wt) dropwise at 0° C. and was stirred for 1 h at RT. Upon completion of the reaction, EA (100 mL) was added and the resulting mixture was washed with water (100 mL×3). The mixture was dried over anhydrous $Na_2SO_4$ and concentrated. The residue was purified by combi-flash (EA/PE=0-50%) give the product (1.02 g, 55%). $^1H$ NMR (300 MHz, DMSO-$d_6$) δ 7.84 (s, 1H), 7.62 (s, 2H), 7.37 (s, 1H), 2.43 (s, 3H). LCMS (ESI) m/e $[M+1]^+$ 251.

Example BB11: Synthesis of 6-bromo-4-(2-methoxyethoxy)pyridine-2-sulfonamide

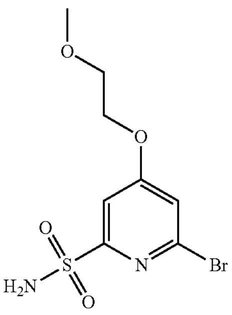 [SMILES: COCCOc1cc(Br)nc(S(N)(=O)=O)c1]

Step 1: 2,6-dibromo-4-(2-methoxyethoxy)pyridine

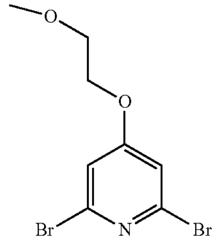

A mixture of 2, 6-dibromopyridin-4-ol (2.02 g, 7.90 mmol), 2-bromoethyl methyl ether (1.65 g, 11.86 mmol) and $K_2CO_3$ (2.19 g, 15.82 mmol) in DMF (10.00 mL) was stirred at 80° C. for 3 h. After cooled to RT, water was added and the resulting mixture was extracted with EA (150 mL×3). The combined organic layers were washed with brine, dried over anhydrous $Na_2SO_4$. After filtration, the filtrate was concentrated under vacuum to afford crude product. The crude product was used for the next step directly without further purification. LCMS (ESI) m/e $[M+1]^+$ 310.

Step 2: 6-bromo-4-(2-methoxyethoxy)pyridine-2-sulfonyl chloride

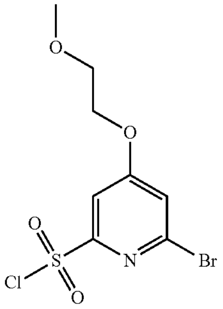 [SMILES: COCCOc1cc(Br)nc(S(=O)(=O)Cl)c1]

To a stirred solution of 2,6-dibromo-4-(2-methoxyethoxy) pyridine (1.90 g, 6.11 mmol) in THF (10 mL) was added i-PrMgCl (4.0 mL, 8.00 mmol, 2M) dropwise at 0° C. and the resulting mixture was stirred for 1 h at RT. under nitrogen atmosphere. $SO_2Cl_2$ (1.2 mL) in hexane (3 mL) was added dropwise at 0° C. and the resulting mixture was stirred for 1 h at rt under nitrogen atmosphere. Upon completion of the reaction, the reaction was quenched with cool water. The resulting mixture was concentrated under vacuum to afford crude product 6-bromo-4-(2-methoxyethoxy) pyridine-2-sulfonyl chloride (2.0 g). It was used directly for next step without purification.

Step 3: 6-bromo-4-(2-methoxyethoxy)pyridine-2-sulfonamide

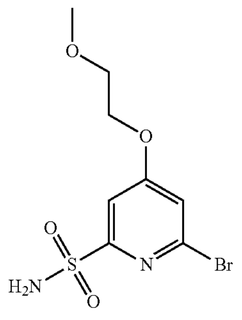 [SMILES: COCCOc1cc(Br)nc(S(N)(=O)=O)c1]

A mixture of 6-bromo-4-(2-methoxyethoxy) pyridine-2-sulfonyl chloride (1.80 g, 5.44 mmol) in $NH_3$/THF (0.5M, 33 mL) was stirred at 1 h at RT. Upon completion of the reaction, the solvent was removed under vacuum and the residue was purified by prep-HPLC (column: Phenomenex Gemini-NX; phase: A-$H_2O$; B-Acetonitrile, B %: 15%-25% in 15 min) to give the product (128 mg, 81%). $^1$H NMR (300 MHz, DMSO-$d_6$) δ 7.63 (s, 2H), 7.52 (s, 1H), 7.43 (s, 1H), 4.34-4.32 (m, 2H), 3.68-3.66 (m, 2H), 3.31 (s, 3H). LCMS (ESI) m/e $[M+1]^+$ 312.

Example BB12: Synthesis of 2-bromo-4-(difluoromethyl)-6-(methylsulfonyl)pyridine

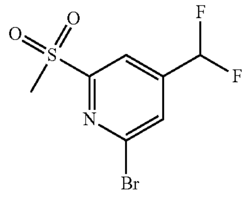

Step 1: (2,6-dibromopyridin-4-yl)methanol

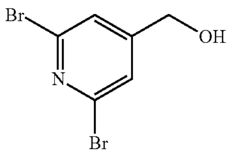

A solution of 2,6-dibromopyridine-4-carboxylic acid (2.00 g, 7.12 mmol) in THF (20 mL) was added $BH_3$·THF (14 mL, 14.00 mmol, 1 M in THF) dropwise and the resulting mixture was stirred for 48 h at RT. Upon completion of the reaction, water was added slowly to quench the reaction and the resulting mixture was extracted with EA (3×200 mL). The combined organic layers were dried over anhydrous $Na_2SO_4$. After filtration, the filtrate was concentrated under vacuum. The crude product was used directly for the next step without further purification. LCMS (ESI) m/e $[M+1]^+$ 266.

Step 2: 2,6-dibromoisonicotinaldehyde

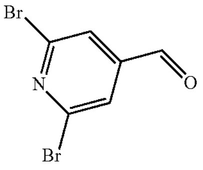

A solution of (2, 6-dibromopyridin-4-yl)methanol (1.50 g, 5.62 mmol) and DMP (3.58 g, 8.43 mmol) in DCM (15 mL) was stirred for 12 h at RT. Upon completion of the reaction, water was added and the resulting mixture was extracted with DCM (200 mL×3). The combined organic layers were dried over anhydrous $Na_2SO_4$. After filtration, the filtrate was concentrated under vacuum. The residue was purified by Prep-TLC (DCM/PE=1:1) to give the product (900 mg, 60%).

Step 3: 2,6-dibromo-4-(difluoromethyl)pyridine

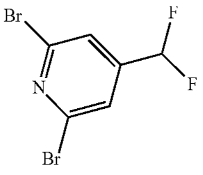 [SMILES: FC(F)c1cc(Br)nc(Br)c1]

To a stirred solution of 2,6-dibromopyridine-4-carbaldehyde (850 mg, 3.21 mmol) in DCM (8.5 mL) was added DAST (1.55 g, 9.63 mmol) dropwise at rt. The resulting mixture was stirred for additional 1 h at RT. Upon completion of the reaction, EtOH was added and the resulting mixture was concentrated under vacuum. The crude product was used directly for the next step without further purification. LCMS (ESI) m/e $[M+1]^+$ 286.

Step 4: 2-bromo-4-(difluoromethyl)-6-(methylthio)pyridine

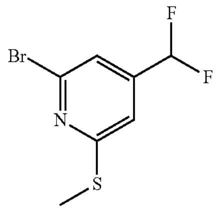

A solution of 2,6-dibromo-4-(difluoromethyl)pyridine (1.00 g, 3.49 mmol) and MeSNa (195 mg, 2.79 mmol) in DMF (10 mL) was stirred for 2 h at RT. Upon completion of the reaction, water was added and the resulting mixture was extracted with EA (100 mL×3). The combined organic layers were dried over anhydrous $Na_2SO_4$. After filtration, the filtrate was concentrated under vacuum. The crude product was used directly for the next step without further purification. LCMS (ESI) m/e $[M+1]^+$ 254.

Step 5: 2-bromo-4-(difluoromethyl)-6-(methylsulfonyl)pyridine

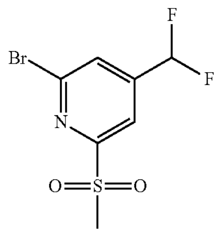

To a stirred solution of 2-bromo-4-(difluoromethyl)-6-(methylsulfanyl)pyridine (450 mg, 1.77 mmol) in $H_2O$ (5 mL) and THF (5 mL) was added $RuCl_3 \cdot H_2O$ (12 mg, 0.053 mmol) in water (2 mL) dropwise at 0° C. To the above mixture was added $NaIO_4$ (1515 mg, 7.08 mmol) dropwise at 0° C. The resulting mixture was stirred for additional 30 mins at 0° C. Upon completion of the reaction, the resulting mixture was extracted with EA (3×100 mL) and the combined organic layers were dried over anhydrous $Na_2SO_4$. After filtration, the filtrate was concentrated under vacuum. The residue was purified by Prep-TLC (EA/PE=1:4) to give the product (317 mg, 63%). $^1H$ NMR (300 MHz, DMSO-$d_6$) δ 8.28 (s, 1H), 8.21 (s, 1H), 7.40-7.05 (m, 1H), 3.37 (s, 3H). LCMS (ESI) m/e $[M+1]^+$ 286.

Example BB13: Synthesis of 2-bromo-6-methanesulfonyl-4-(oxetan-3-ylmethoxy)pyridine

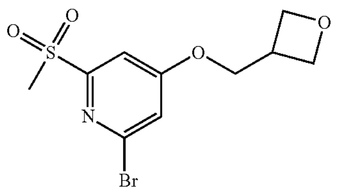 [SMILES: CS(=O)(=O)c1cc(OCC2COC2)cc(Br)n1]

A mixture of 2-bromo-6-methanesulfonylpyridin-4-ol (1.00 g, 3.97 mmol), $PPh_3$ (3.12 g, 11.89 mmol), DIAD (2.41 g, 11.92 mmol) and oxetan-3-ylmethanol (0.35 g, 3.97 mmol) in THF (20 mL) was stirred overnight at 50° C. After cooled to RT, water was added and the resulting mixture was extracted with EA (100 mL×3). The combined organic layers were washed with brine, dried over anhydrous $Na_2SO_4$. After filtration, the filtrate was concentrated under vacuum. The residue was purified by Prep-TLC (hexane/EA=5:1) to give the product (996 mg, 78%). $^1H$ NMR (300 MHz, DMSO-$d_6$) δ 7.65 (s, 1H), 7.58 (s, 1H), 4.71 (d, J=7.9 Hz, 2H), 4.52-4.37 (m, 4H), 3.49-3.37 (m, 1H), 2.54 (s, 3H). LCMS (ESI) m/e $[M+1]^+$ 322.

Example BB14: Synthesis of 2-bromo-6-methanesulfonyl-4-(oxetan-3-yloxy)pyridine

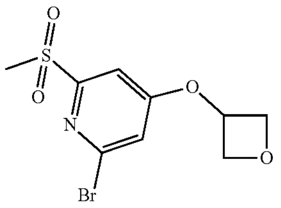 [SMILES: CS(=O)(=O)c1cc(OC2COC2)cc(Br)n1]

A solution of 2-bromo-6-methanesulfonylpyridin-4-ol (826 mg, 3.27 mmol), $PPh_3$ (3.12 g, 11.89 mmol), DIAD (2.41 g, 11.92 mmol)) and oxetan-3-ol (0.59 g, 7.93 mmol) in THF (20 mL) was stirred overnight at 50° C. After cooled to RT, water was added, and the resulting mixture was extracted with EA (50 mL×3). The combined organic layers were washed with brine, dried over anhydrous $Na_2SO_4$. After filtration, the filtrate was concentrated under vacuum. The residue was purified by Prep-TLC (hexane/EA=5:1) to give (899 mg, 89%) of the product. $^1H$ NMR (300 MHz, DMSO-$d_6$) δ 7.50 (s, 1H), 7.45 (s, 1H), 5.59-5.50 (m, 1H), 4.99-4.95 (m, 2H), 4.60-4.55 (m, 2H), 3.29 (s, 3H). LCMS (ESI) m/e $[M+1]^+$ 308.

Example BB15: Synthesis of 2-bromo-6-methanesulfonyl-4-(oxetan-3-ylmethoxy)pyridine

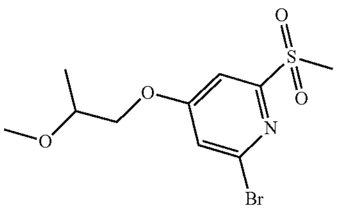

A solution of 2-bromo-6-methanesulfonylpyridin-4-ol (1.00 g, 3.97 mmol), $PPh_3$ (3.12 g, 11.89 mmol), DIAD (2.41 g, 11.92 mmol) and 2-methoxypropan-1-ol (0.44 g, 3.97 mmol) in THF (20 mL) was stirred overnight at 50° C. After cooled to RT, water was added and the resulting mixture was extracted with EA (100 mL×3). The combined organic layers were washed with brine, dried over anhydrous $Na_2SO_4$. After filtration, the filtrate was concentrated under vacuum. The residue was purified by Prep-TLC (hexane/EA=5:1) to give the product (900 mg, 70%) of the product. $^1H$ NMR (300 MHz, DMSO-$d_6$) δ 7.63 (s, 1H), 7.56 (s, 1H), 4.31-4.14 (m, 2H), 3.70-3.65 (m, 1H), 3.39 (m, 3H), 3.25 (m, 3H), 1.17-1.14 (m, 3H). LCMS (ESI) m/e $[M+1]^+$ 324.

Example BB16: Synthesis of 2-bromo-6-methanesulfonyl-3-methoxypyridine

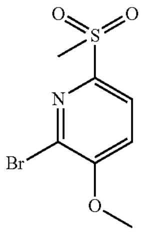

Step 1: 2-bromo-3-methoxy-6-(methylsulfanyl)pyridine

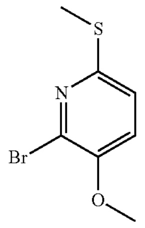

A mixture of 2-bromo-6-iodo-3-methoxypyridine (4.00 g, 12.74 mmol), (methylsulfanyl)sodium (0.80 g, 11.41 mmol), $Pd_2(dba)_3$ (0.58 g, 0.63 mmol), Xantphos (0.74 g, 1.27 mmol) in dioxane (64 mL) was stirred for 3 h at 75° C. under nitrogen atmosphere. After cooled to rt, water was added, and the resulting mixture was extracted with EA (200 mL×3). The combined organic layers were washed with brine, dried over anhydrous $Na_2SO_4$. After filtration, the filtrate was concentrated under vacuum and purified by combi-flash (EA/PE=0-4%) to give the product (1.72 g, 52%). LCMS (ESI, m/e) $[M+1]^+$ 234.

Step 2: 2-bromo-6-methanesulfonyl-3-methoxypyridine

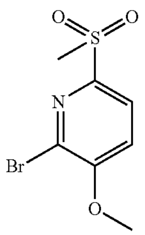

To a mixture of 2-bromo-3-methoxy-6-(methylsulfanyl) pyridine (1.72 g, 7.34 mmol) in THF (15 mL) were added $NaIO_4$ (4.73 g, 22.14 mmol) and $RuCl_3$ (0.05 g, 0.22 mmol) in $H_2O$ (15 mL) dropwise at 0° C. The resulting solution was stirred for 1 h at RT. Upon completion of the reaction, the resulting mixture was concentrated under vacuum. The residue was purified by combi-flash (EA/PE=0-39%) to give the product (1.78 g, 82%). $^1H$ NMR (300 MHz, DMSO-$d_6$) δ 8.06 (d, J=8.5 Hz, 1H), 7.75 (d, J=8.5 Hz, 1H), 4.01 (s, 3H), 3.24 (s, 3H). LCMS (ESI, m/e) $[M+1]^+$ 266.

Example BB17: Synthesis of 1-bromo-3-methanesulfonyl-5-(2-methoxyethoxy) benzene

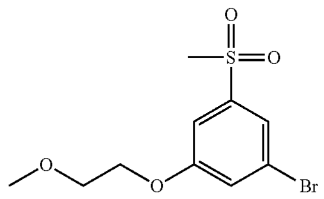 [SMILES: COCCOc1cc(Br)cc(S(C)(=O)=O)c1]

Step 1: 1,3-dibromo-5-(2-methoxyethoxy) benzene

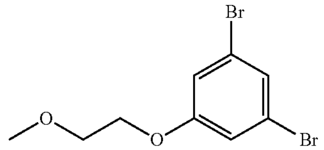

A mixture of 3,5-dibromophenol (11.00 g, 43.66 mmol), 2-bromoethyl methyl ether (15.17 g, 109.14 mmol) and $Cs_2CO_3$ (28.46 g, 87.33 mmol) in DMF (165 mL) was stirred for 4 h at 80° C. After cooled to RT, water was added then extracted with EA (500 mL×3). The combined organic layers were washed with brine, dried over anhydrous $Na_2SO_4$. After filtration, the filtrate was concentrated to give the crude product and used directly for the next step without further purification. LCMS (ESI, m/e) $[M+1]^+$ 311.

Step 2: 1-bromo-3-(2-methoxyethoxy)-5-(methylsulfanyl) benzene

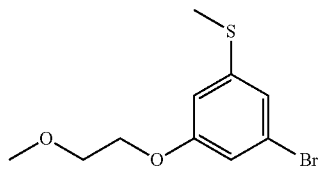

A mixture of 1,3-dibromo-5-(2-methoxyethoxy) benzene (15.00 g, 48.39 mmol), (methylsulfanyl)sodium (2.71 g, 38.67 mmol), $Pd_2(dba)_3$ (2.22 g, 2.42 mmol), Xantphos (2.80 g, 4.83 mmol) in dioxane (150 mL) was stirred overnight at 75° C. under nitrogen atmosphere. After cooled to RT, the resulting mixture was concentrated under vacuum. The residue was purified by combi-flash (EA/PE=0-1%) to give the product (5.71 g, 38%). LCMS (ESI, m/e) $[M+1]^+$ 277.

Step 3: 1-bromo-3-methanesulfonyl-5-(2-methoxyethoxy) benzene

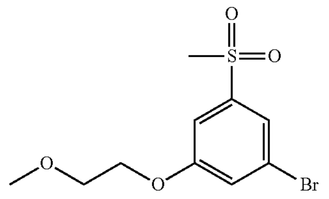 [SMILES: COCCOc1cc(Br)cc(S(C)(=O)=O)c1]

To a mixture of 1-bromo-3-(2-methoxyethoxy)-5-(methylsulfanyl) benzene (5.71 g, 20.60 mmol) in THF (60 mL) and $H_2O$ (30 mL) was added the solution of $NaIO_4$ (13.22 g, 61.81 mmol) in $H_2O$ (15 mL) in portions at 0° C. Then to the mixture was added the solution of $RuCl_3$ (0.14 g, 0.62 mmol) in $H_2O$ (15 mL) in portions at 0° C. The resulting solution was stirred for 1 h at RT. Upon completion of the reaction, the resulting solution was extracted with EA (50 mL×3). The solvent was removed under vacuum and the residue was purified by combi-flash (EA/PE=0-31%) to give the product (4.99 g, 71%). $^1H$ NMR (300 MHz, DMSO-$d_6$) δ 7.65 (s, 1H), 7.56 (s, 1H), 7.46 (s, 1H), 4.30-4.22 (m, 2H), 3.70-3.65 (m, 2H), 3.31 (s, 3H), 3.29 (s, 3H). LCMS (ESI, m/e) $[M+1]^+$ 309.

Example BB18: Synthesis of [2-(3-bromo-5-methanesulfonylphenoxy)ethoxy](tert-butyl)dimethylsilane

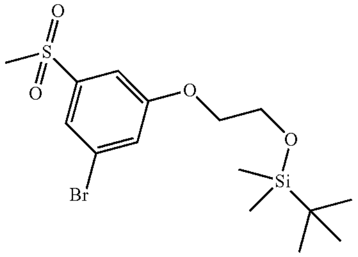 [SMILES: CC(C)(C)[Si](C)(C)OCCOc1cc(Br)cc(S(C)(=O)=O)c1]

Step 1: tert-butyl[2-(3,5-dibromophenoxy)ethoxy] dimethylsilane

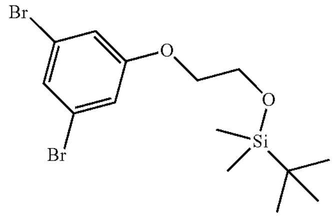 [SMILES: CC(C)(C)[Si](C)(C)OCCOc1cc(Br)cc(Br)c1]

A mixture of 3,5-dibromophenol (5.00 g, 19.85 mmol), (2-bromoethoxy)(tert-butyl)dimethyl silane (7.12 g, 29.77 mmol), $Cs_2CO_3$ (12.93 g, 39.69 mmol) in DMF (50 mL) was stirred for 2 h at 80° C. After cooled to RT, water was added and the resulting mixture was extracted with EA (80 mL×3).

The combined organic layers were washed with water, dried over anhydrous $Na_2SO_4$. After filtration, the filtrate was concentrated under vacuum. The residue was purified by combi-flash (EA/PE=0-20%) to give the product (5.00 g, 61%).

Step 2: [2-[3-bromo-5-(methylsulfanyl)phenoxy] ethoxy](tert-butyl)dimethylsilane

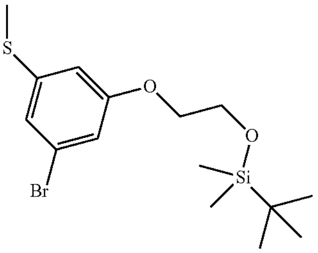 [SMILES: CSc1cc(Br)cc(OCCO[Si](C)(C)C(C)(C)C)c1]

A mixture of tert-butyl[2-(3,5-dibromophenoxy)ethoxy] dimethylsilane (5.00 g, 12.19 mmol), (methylsulfanyl)sodium (768 mg, 10.97 mmol), Xantphos (705 mg, 1.22 mmol), DIEA (3.15 g, 24.38 mmol), $Pd_2(dba)_3$ (558 mg, 0.61 mmol) and 1,4-dioxane (50 mL) was stirred overnight at 90° C. under nitrogen atmosphere. After cooled to RT, water was added, and the resulting mixture was extracted with EA (120 mL×3). The combined organic layers were washed with brine (50 mL×3), dried over anhydrous $Na_2SO_4$. After filtration, the filtrate was concentrated under vacuum. The residue was purified by combi-flash (EA/PE=0-10%) to give the product (2.80 g, 60%). LCMS (ESI, m/e) $[M+1]^+$ 377.

Step 3: [2-(3-bromo-5-methanesulfonylphenoxy) ethoxy](tert-butyl)dimethylsilane

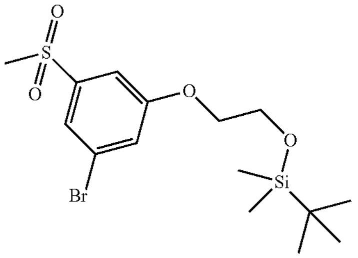 [SMILES: CC(C)(C)[Si](C)(C)OCCOc1cc(Br)cc(S(C)(=O)=O)c1]

To a stirred solution of [2-[3-bromo-5-(methylsulfanyl) phenoxy]ethoxy](tert-butyl)dimethylsilane (2.80 g, 7.41 mmol) in THF (30 mL) were added $RuCl_3 \cdot H_2O$ (50 mg, 0.22 mmol) and $NaIO_4$ (3.17 g, 14.84 mmol) in $H_2O$ (20 mL) at 0° C. and the resulting solution was stirred for 2 h at this temperature. Upon completion of the reaction, the reaction mixture was filtered and the filtrate was concentrated under vacuum. The residue was purified by combi-flash (EA/PE=0-30%) to give the product (1.07 g, 35%). $^1H$ NMR (300 MHz, DMSO-$d_6$) δ 7.64 (s, 1H), 7.57-7.52 (m, 1H), 7.44 (s, 1H), 4.20-4.15 (m, 2H), 3.96-3.90 (m, 2H), 3.29 (s, 3H), 0.86 (s, 9H), 0.07 (s, 6H). LCMS (ESI) m/e $[M+1]^+$ 409.

Example BB19: Synthesis of 1-bromo-3-isopropoxy-5-(methylsulfonyl)benzene

Step 1: 1,3-dibromo-5-isopropoxybenzene

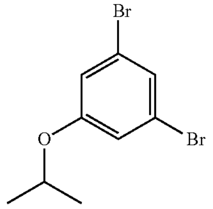

A mixture of 3,5-dibromophenol (10 g, 39.69 mmol), DMF (200 mL), 2-iodopropane (20.24 g, 119.06 mmol) and $K_2CO_3$ (10.97 g, 79.38 mmol) was stirred for 2 h at 80° C. After cooled to RT, EA (200 mL) was added and the resulting mixture was washed with $H_2O$ (200 mL×3). The mixture was dried over anhydrous $Na_2SO_4$ and concentrated under vacuum. The residue was purified by combi-flash (EA/PE=0-15%) give the product (7.6 g, 65%).

Step 2: 1-bromo-3-isopropoxy-5-(methylsulfanyl)benzene

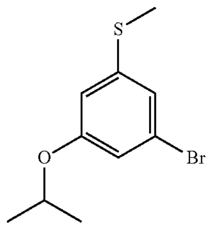

A mixture of 1,3-dibromo-5-isopropoxybenzene (7.60 g, 25.85 mmol), dioxane (100 mL), $Pd_2(dba)_3$ (1.18 g, 1.29 mmol), Xantphos (1.50 g, 2.59 mmol), MeSNa (1.81 g, 25.85 mmol) was stirred for 3 h at 75° C. After cooled to RT, EA (200 mL) was added and the resulting mixture was washed with $H_2O$ (200 mL×3). The mixture was dried over anhydrous $Na_2SO_4$ and concentrated under vacuum. The residue was purified by combi-flash (EA/PE=0-15%) give the product (7.1 g, crude). GCMS (ESI) m/e [M+1]260.

Step 3: 1-bromo-3-isopropoxy-5-(methylsulfonyl)benzene

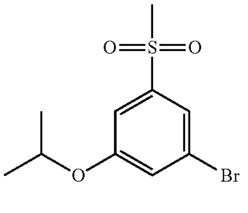

A mixture of 1-bromo-3-isopropoxy-5-(methylsulfanyl)benzene (7.10 g, 27.18 mmol), THF (60 mL), $H_2O$ (60 mL), $NaIO_4$ (23.26 g, 108.75 mmol) and $RuCl_3 \cdot H_2O$ (1.23 g, 5.46 mmol) was stirred for 1 h at 0° C. Upon completion of the reaction, the resulting solution was diluted with EA (200 mL). The resulting mixture was washed with $H_2O$ (100 mL×3). The mixture was dried over anhydrous $Na_2SO_4$ and concentrated. The residue was purified by combi-flash (EA/PE=0-25%) give the product (4.25 g, 53%). $^1H$ NMR (300 MHz, $CDCl_3$) δ 7.63 (s, 1H), 7.37 (s, 1H), 7.30 (s, 1H), 4.62 (q, J=6.1 Hz, 1H), 3.08 (s, 3H), 1.38 (d, J=6.0 Hz, 6H). GCMS (ESI) m/e [M] 292.

Example BB20: Synthesis of 1-bromo-3-methoxy-5-(methylsulfonyl)benzene

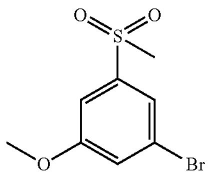

Step 1: (3-bromo-5-methoxyphenyl)(methyl)sulfane

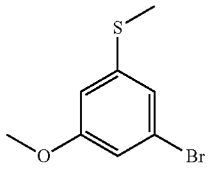

A mixture of 1,3-dibromo-5-methoxybenzene (9.00 g, 33.16 mmol), dioxane (100 mL), $NaSCH_3$ (3.19 g, 33.19 mmol), $Pd_2(dba)_3$ (1.52 g, 1.66 mmol) and Xantphos (1.92 g, 3.31 mmol) was stirred overnight at 75° C. under nitrogen atmosphere. After cooled to RT, the solvent was removed under vacuum and the residue was purified by combi-flash (EA/PE=0-10%) to give the product (3.2 g, 39%). GCMS (ESI) m/e [M] 232.

Step 2: 1-bromo-3-methoxy-5-(methylsulfonyl)benzene

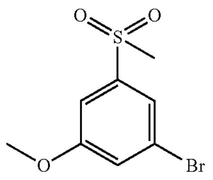

To a mixture of 1-bromo-3-methoxy-5-(methylsulfanyl)benzene (3.10 g, 12.63 mmol) and THF (30 mL)/$H_2O$ (30 mL) was added $NaIO_4$ (10.81 g, 50.54 mmol) in $H_2O$ (15 mL) in portions at 0° C., then $RuCl_3$ (0.14 g, 0.62 mmol) in $H_2O$ (15 mL) was added in portions successively at 0° C. The resulting solution was stirred for 1 h at RT. The resulting solution was diluted with $H_2O$ (50 mL), extracted with EA (30 mL×3), the organic layers were concentrated and purified by combi-flash (EA/PE=0-30%) to give the product (3.22 g, 91%). $^1$H NMR (300 MHz, DMSO-d6) δ 7.66 (s, 1H), 7.54 (s, 1H), 7.45 (s, 1H), 3.89 (s, 3H), 3.30 (s, 3H). GCMS (ESI) m/e [M] 264.

Example BB21: Synthesis of 1-bromo-3-methyl-5-(methylsulfonyl)benzene

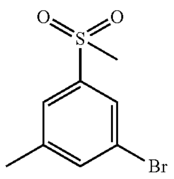

Step 1: (3-bromo-5-methylphenyl)(methyl)sulfane

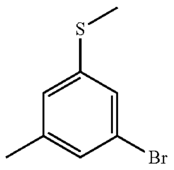

A mixture of 1,3-dibromo-5-methylbenzene (11.00 g, 43.13 mmol), dioxane (150 mL), $NaSCH_3$ (3.02 g, 43.14 mmol), $Pd_2(dba)_3$ (1.97 g, 2.15 mmol and Xantphos (2.50 g, 4.32 mmol) was stirred overnight at 75° C. under nitrogen atmosphere. After cooled to RT, the solvent was removed under vacuum and the residue was purified by combi-flash (EA/PE=0-8%) to give the product (4.40 g, 42%). GCMS (ESI) m/e [M] 216

Step 2: 1-bromo-3-methyl-5-(methylsulfonyl)benzene

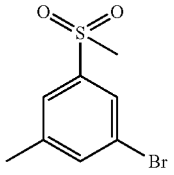

To a mixture of 1-bromo-3-methyl-5-(methylsulfanyl) benzene (4.30 g, 17.82 mmol) and THF (20 mL) was added $NaIO_4$ (15.25 g, 71.29 mmol) in $H_2O$ (10 mL) in portions at 0° C., then $RuCl_3$ (0.20 g, 0.89 mmol) in $H_2O$ (10 mL) was added in portions successively at 0° C. The resulting solution was stirred for 1 h at RT. Upon completion of the reaction, the resulting solution was diluted with 50 mL of $H_2O$, extracted with 3×30 mL of EA and the organic layers were combined and concentrated. The residue was purified by combi-flash (EA/PE=0-20%) to give the product (4.51 g, 96%). $^1$H NMR (300 MHz, DMSO-$d_6$) δ 7.91 (s, 1H), 7.84-7.72 (m, 2H), 3.28 (s, 3H), 2.46-2.40 (m, 3H). GCMS (ESI) m/e [M] 248.

Example BB22: Synthesis of 1-bromo-3-methanesulfonyl-5-(methoxymethyl)benzene

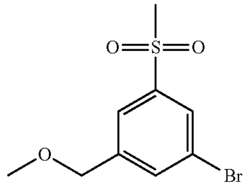

Step 1: 1,3-dibromo-5-(methoxymethyl)benzene

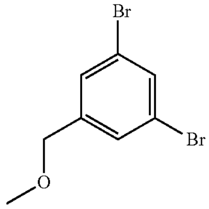

A mixture of 1,3-dibromo-5-(bromomethyl)benzene (7.00 g, 21.28 mmol), MeONa (5.75 g, 106.40 mmol) in MeOH (70 mL) and was stirred for 1 h at 70° C. After cooled to rt, the solvent was removed under vacuum and the residue was diluted with water. The resulting solution was extracted with EA (100 mL×3) and the combined organic layer was washed with brine. The organic layer was dried over anhydrous $Na_2SO_4$ and concentrated under vacuum. The residue was purified by combi-flash (EA/PE=0-5%) to give the product (5.00 g, 84%). GCMS (ESI) m/e [M] 280.

Step 2: 1-bromo-3-(methoxymethyl)-5-(methylsulfanyl)benzene

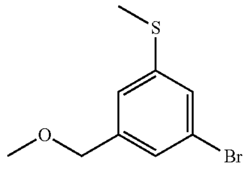

A mixture of 1,3-dibromo-5-(methoxymethyl)benzene (5.00 g, 17.86 mmol), DMF (50 mL) and $CH_3SNa$ (1.50 g, 21.43 mmol) was stirred overnight at RT. Upon completion of the reaction, water (20 mL) was added and the resulting solution was extracted with EA (100 mL×3). The combined organic layers were washed with brine and dried over anhydrous $Na_2SO_4$. The solids were filtered out and the resulting mixture was concentrated under vacuum. The residue was purified by combi-flash (EA/PE=0-2%) to give the product (3.50 g, 79%). GCMS (ESI) m/e [M] 246.

Step 3: 1-bromo-3-methanesulfonyl-5-(methoxymethyl)benzene

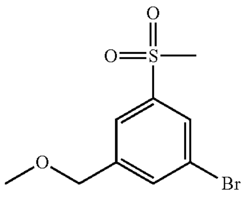

A mixture of 1-bromo-3-(methoxymethyl)-5-(methylsulfanyl)benzene (3.50 g, 14.16 mmol), $RuCl_3 \cdot H_2O$ (319.26 mg, 1.416 mmol) and $NaIO_4$ (6.06 g, 28.32 mmol) in THF (35 mL) and $H_2O$ (35 mL) was stirred for 2 h at RT. Upon completion of the reaction, the resulting solution was extracted with EA (100 mL×3) and the organic layers combined. The resulting mixture was washed with brine, dried over anhydrous $Na_2SO_4$. The resulting mixture was concentrated under vacuum and the residue was purified by combi-flash (EA/PE=0-10%) to give the product (2.21 g, 56%). $^1$H NMR (300 MHz, DMSO-$d_6$) δ 8.05 (s, 1H), 7.75 (s, 1H), 7.70 (s, 1H), 4.50 (s, 2H), 3.45 (s, 3H), 3.03 (s, 3H). GCMS (ESI) m/e [M] 278.

Example BB23: Synthesis of 1-bromo-3-(difluoromethyl)-5-methanesulfonylbenzene

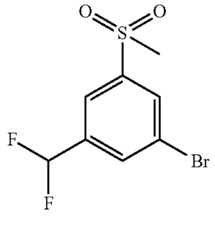

Step 1: 1-bromo-3-(difluoromethyl)-5-(methylsulfanyl)benzene

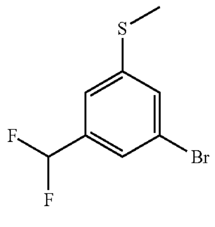

A mixture of 1,3-dibromo-5-(difluoromethyl)benzene (4.20 g, 14.69 mmol), (methylsulfanyl) sodium (927 mg, 13.22 mmol), DIEA (3.80 g, 29.38 mmol), Xantphos (849.97 mg, 1.47 mmol), $Pd_2(dba)_3$ (672.58 mg, 0.74 mmol) and 1,4-dioxane (50 mL) was stirred overnight at 80° C. under nitrogen atmosphere. After cooled to RT, the resulting mixture was extracted with EA (150 mL×3) and the combined organic layers were washed with brine, dried over anhydrous $Na_2SO_4$. After filtration, the filtrate was concentrated under vacuum. The residue was purified by combi-flash (EA/PE=0-10%) to give the product (2.60 g, 69%). GCMS (ESI) m/e [M] 252

Step 2: 1-bromo-3-(difluoromethyl)-5-methanesulfonylbenzene

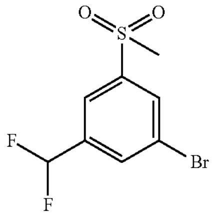

To a stirred solution of 1-bromo-3-(difluoromethyl)-5-(methylsulfanyl)benzene (2.60 g, 10.27 mmol) in THF (40 ml) and $H_2O$ (40 mL) were added $RuCl_3 \cdot H_2O$ (69.48 mg, 0.31 mmol) and $NaIO_4$ (4.39 g, 20.55 mmol) in portions at 0° C. The resulting mixture was stirred for 2 h at 0° C. Upon completion of the reaction, the resulting mixture was filtered out and the filtrate was concentrated under vacuum. The residue was purified by combi-flash (EA/PE=0-40%) to give the product (1.79 g, 61%). $^1$H NMR (300 MHz, DMSO-$d_6$) δ 8.31 (s, 1H), 8.19 (s, 1H), 8.13 (s, 1H), 7.20-7.10 (m, 1H), 3.37 (s, 3H).

Example BB24: Synthesis of 3-bromo-5-methanesulfonylbenzonitrile

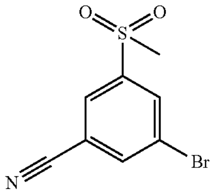

Step 1: 3-bromo-5-(methylsulfanyl)benzonitrile

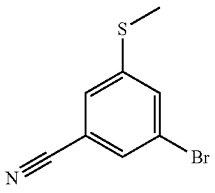

A mixture of 3,5-dibromobenzonitrile (10.00 g, 38.32 mmol), dioxane (160 mL), (methylsulfanyl) sodium (2.42 g, 34.53 mmol), $Pd_2(dba)_3$ (1.75 g, 1.91 mmol) and Xantphos (2.22 g, 3.83 mmol) was stirred overnight at 75° C. in an oil bath. After cooled to room temperature, the solvent was removed in vacuo and the residue was diluted with water (20 mL). The resulting solution was extracted with EA (100 mL×3) and the combined organic layers were washed with brine, dried over anhydrous sodium sulfate. The solvent was removed in vacuo and the residue was purified by combiflash (EA/PE=0-9%) to give the product (8.52 g, 88%). LCMS (ESI, m/e) $[M+1]^+$ 228.

Step 2: 3-bromo-5-methanesulfonylbenzonitrile

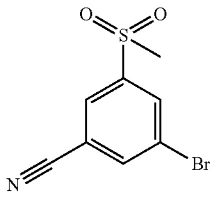

To a mixture of 3-bromo-5-(methylsulfanyl) benzonitrile (8.52 g, 37.35 mmol) and THF (75 mL) were added $NaIO_4$ (23.97 g, 112.06 mmol) in $H_2O$ (35 mL) and $RuCl_3$ (0.25 g, 1.12 mmol) in $H_2O$ (35 mL) dropwise with stirring at 0° C. The resulting solution was stirred for 1 h at RT. Upon completion of the reaction, the resulting solution was extracted with EA (100 mL×3) and then concentrated under vacuum. The residue was purified by combi-flash (EA/PE=0-38%) to give the product (4.40 g, 40%). $^1$H NMR (300 MHz, DMSO-$d_6$) δ 8.55 (s, 1H), 8.45-8.32 (m, 2H), 3.36 (s, 3H). LCMS (ESI, m/e) $[M+1]^+$ 260.

Example BB25: Synthesis of 1-bromo-3-methanesulfonyl-5-(trifluoromethoxy)benzene

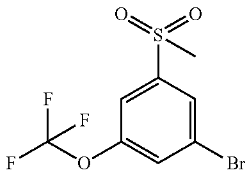 [SMILES: CS(=O)(=O)c1cc(Br)cc(OC(F)(F)F)c1]

Step 1: 1-bromo-3-(methylsulfanyl)-5-(trifluoromethoxy)benzene

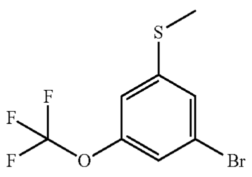

A mixture of 1,3-dibromo-5-(trifluoromethoxy)benzene (5.00 g, 15.63 mmol), 1,4-dioxane (50 mL), $CH_3SNa$ (984.67 mg, 14.07 mmol), $Pd_2(dba)_3$ (715.62 mg, 0.78 mmol) and XantPhos (904.37 mg, 1.56 mmol) was stirred for 2 h at 75° C. under nitrogen atmosphere. After cooled to room temperature, the solvent was removed and the residue was diluted with water. The resulting solution was extracted with of EA (150 mL) and the combined organic layers were washed with brine, dried over anhydrous sodium sulfate. The solvent was removed in vacuo and the residue was purified by combi-flash (EA/PE=0-5%) to give the product (3.00 g, 67%). GCMS (ESI) m/e [M] 286.

Step 2: 1-bromo-3-methanesulfonyl-5-(trifluoromethoxy)benzene

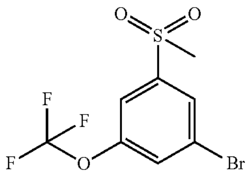

A mixture of 1-bromo-3-(methylsulfanyl)-5-(trifluoromethoxy)benzene (3.00 g, 10.45 mmol), $RuCl_3 \cdot H_2O$ (235.58 mg, 1.05 mmol), $NaIO_4$ (6.71 g, 31.35 mmol), $H_2O$ (30 mL) in THF (30 mL) was stirred for 2 h at RT. Upon completion of the reaction, the resulting solution was extracted with EA (100 mL×3) and the organic layers combined. The resulting mixture was washed with brine, dried over anhydrous $Na_2SO_4$. The resulting mixture was concentrated under vacuum and the residue was purified by combi-flash (EA/PE=0-15%) to give the product (2.31 g, 69%). $^1$H NMR (300 MHz, DMSO-$d_6$) δ 8.05 (s, 1H), 7.75 (s, 1H), 7.70 (s, 1H), 3.10 (s, 3H). GCMS (ESI) m/e [M] 318.

Example BB26: Synthesis of 2-bromo-4-[(2R)-2-[(tert-butyldimethylsilyl)oxy]propoxy]-6-methanesulfonylpyridine

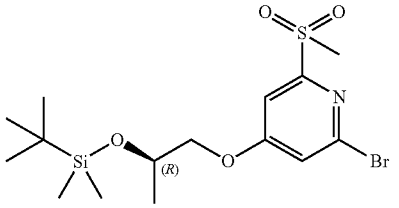

A mixture of 2-bromo-6-methanesulfonylpyridin-4-ol (1.00 g, 3.97 mmol), (2R)-2-[(tert-butyldimethylsilyl)oxy]propyl 4-methylbenzenesulfonate (2.73 g, 7.94 mmol) and $Cs_2CO_3$ (2.59 g, 7.90 mmol) in DMF (10 mL) was stirred at 100° C. overnight under nitrogen atmosphere. After cooled to room temperature, the solvent was removed and the residue was diluted with water. The resulting solution was extracted with EA (50 mL×3) and the combined organic layers were washed with brine, dried over anhydrous sodium sulfate. The solvent was removed in vacuo and the residue was purified by Prep-TLC (PE/EA=5:1) to give the product (644 mg, 82%). $^1$H NMR (300 MHz, $CDCl_3$) δ 7.55 (s, 1H), 7.18 (s, 1H), 4.26-4.11 (m, 1H), 4.03-3.89 (m, 2H), 3.24 (s, 3H), 1.24 (d, J=6.3 Hz, 3H), 0.88 (s, 9H), 0.11 (s, 3H), 0.08 (s, 3H). LCMS (ESI) m/e $[M+1]^+$ 424.

Example BB27: Synthesis of 7-bromo-2H,3H-[1,4]dioxino[2,3-c]pyridine

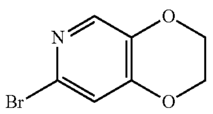 [SMILES: Brc1cc2c(cn1)OCCO2]

Step 1: 2-[(6-bromo-4-iodopyridin-3-yl) oxy] ethanol

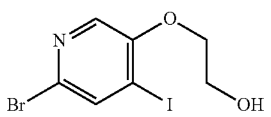 [SMILES: OCCOc1cnc(Br)cc1I]

To a mixture of 2-bromo-5-fluoro-4-iodopyridine (11.00 g, 36.43 mmol) in NMP (135 mL) were added ethylene glycol (10.81 g, 174.16 mmol) and t-BuOK (4.50 g, 40.08 mmol) in NMP (30 mL) dropwise at 0° C. The resulting solution was stirred for 1 h at 80° C. After cooled to room temperature, the solvent was removed in vacuo and the residue was diluted with water (300 mL). The resulting solution was extracted with EA (200 mL×3) and the combined organic layers were washed with brine, dried over anhydrous sodium sulfate. The solvent was removed in vacuo and the residue was purified by combi-flash (EA/PE=0-41%) to give the product (12.00 g, 86%). LCMS (ESI, m/e) $[M+1]^+$ 344.

Step 2: 7-bromo-2H,3H-[1,4]dioxino[2,3-c]pyridine

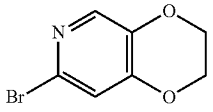 [SMILES: Brc1cc2c(cn1)OCCO2]

A mixture of 2-[(6-bromo-4-iodopyridin-3-yl) oxy] ethanol (12.00 g, 34.89 mmol), i-PrOH (180.00 mL), 3,4,7,8-tetramethyl-1,10-phenantholine (0.68 g, 2.88 mmol), CuI (0.41 g, 2.13 mmol) and t-BuOK (5.48 g, 48.85 mmol) was stirred for 1 h at 80° C. under nitrogen atmosphere. After cooled to room temperature, the solvent was removed in vacuo and the residue was diluted with water (20 mL). The resulting solution was extracted with EA (300 mL×3) and the combined organic layers were washed with brine, dried over anhydrous sodium sulfate. The solvent was removed in vacuo and the residue was purified by combi-flash (EA/PE=0-7%) to give the product (1.36 g, 16%). $^1H$ NMR (300 MHz, DMSO-$d_6$) δ 7.95 (s, 1H), 7.19 (s, 1H), 4.44-4.24 (m, 4H). LCMS (ESI, m/e) $[M+1]^+$ 216.

Example BB29: Synthesis of 2-bromo-4-chloro-6-(methylsulfonyl)pyridine

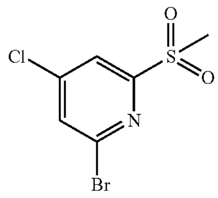

Step 1: 2-bromo-6-(methylthio)pyridin-4-amine

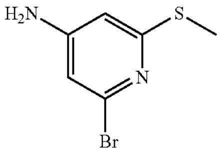

A mixture of 2,6-dibromopyridin-4-amine (5.00 g, 19.85 mmol), $Cs_2CO_3$ (9.70 g, 29.77 mmol) and MeSNa (1.53 g, 21.83 mmol) in DMSO (50 mL) was stirred for 12 h at 80° C. After cooled to room temperature, water was added and the resulting mixture was extracted with EA (500 mL×3). The combined organic layers were washed with brine, dried over anhydrous $Na_2SO_4$. After filtration, the filtrate was concentrated under vacuum and the residue was used in the next step directly without further purification. LCMS (ESI) m/e $[M+1]^+$ 219.

Step 2: 2-bromo-6-(methylsulfonyl)pyridin-4-amine

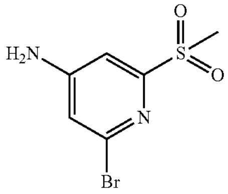

To a solution of 2-bromo-6-(methylsulfanyl)pyridin-4-amine (2.50 g, 11.41 mmol) in THF (25 mL) was added $RuCl_3 \cdot H_2O$ (77.17 mg, 0.34 mmol), $NaIO_4$ (9.76 g, 45.64 mmol) and $H_2O$ (25 mL) at 0° C. and the resulting mixture was stirred at room temperature for 1 h. Upon completion of the reaction, the resulting mixture was extracted with EA (300 mL×3). The combined organic layers were dried over anhydrous $Na_2SO_4$. After filtration, the filtrate was concentrated under vacuum. The residue was purified by combi-flash (EA/PE=1:1) to give the product (1.02 g, 35%). LCMS (ESI) m/e $[M+1]^+$ 251.

Step 3: 2-bromo-4-chloro-6-(methylsulfonyl)pyridine

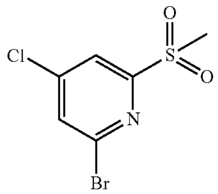

To a solution of 2-bromo-6-methanesulfonylpyridin-4-amine (800 mg, 3.18 mmol) in HCl (12M, 14.4 mL) was added $NaNO_2$ (1.10 g, 15.93 mmol) at 0° C. and the mixture was stirred for 1 h at this temperature. Upon completion of the reaction, the resulting mixture was extracted with EA (100 mL×3). The combined organic layers were dried over anhydrous $Na_2SO_4$. After filtration, the filtrate was concentrated under vacuum. The residue was purified by Prep-TLC (EA/PE=1:4) to give the product (468 mg, 54%). $^1$H NMR (300 MHz, DMSO-$d_6$) δ 8.33 (s, 1H), 8.17 (s, 1H), 3.33 (s, 3H). LCMS (ESI) m/e $[M+1]^+$ 270.

Example BB30: Synthesis of 1-bromo-3-fluoro-5-methanesulfonylbenzene

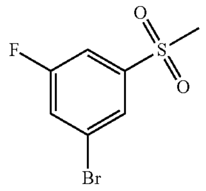

Step 1: 1-bromo-3-fluoro-5-(methylsulfanyl)benzene

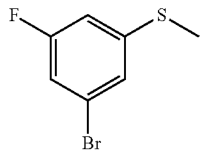

A mixture of 1-bromo-3,5-difluorobenzene (5.00 g, 25.91 mmol), (methylsulfanyl)sodium (1.82 g, 25.91 mmol) in DMF (50 mL) was stirred for 2 h at RT. Upon completion of the reaction, water was added and the resulting solution was extracted with EA (100 mL×3) and the organic layers combined. The resulting mixture was washed with brine, dried over anhydrous $Na_2SO_4$. The solid were filtered out and the resulting mixture was concentrated under vacuum. The residue was purified by combi-flash (EA/PE=0-2%) to give the product (4.80 g, 84%). GCMS (ESI) m/e [M] 220.

Step 2: 1-bromo-3-fluoro-5-methanesulfonylbenzene

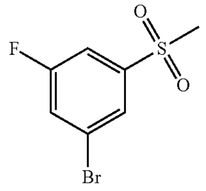

To a mixture of 1-bromo-3-fluoro-5-(methylsulfanyl)benzene (4.80 g, 21.71 mmol) and THF (50 mL)/$H_2O$ (50 mL) were added $RuCl_3 \cdot H_2O$ (489 mg, 2.17 mmol) and $NaIO_4$ (13.93 g, 65.13 mmol) in several batches at 0° C. The resulting solution was stirred for 2 h at RT. Upon completion of the reaction, water was added and the resulting solution was extracted with EA (100 mL×3) and the combined organic layers were washed with brine, dried over anhydrous sodium sulfate. The solvent was removed in vacuo and the residue was purified by combi-flash (EA/PE=0-15%) to give the product (4.60 g, 80%). $^1$H NMR (300 MHz, $CDCl_3$) δ 7.91 (s, 1H), 7.60-7.50 (m, 2H), 3.13 (s, 3H). GCMS (ESI) m/e [M] 252.

Example BB31: Synthesis of 1-bromo-3-chloro-5-(methylsulfonyl)benzene

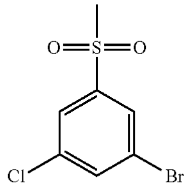

Step 1: 1-bromo-3-chloro-5-(methylsulfanyl)benzene

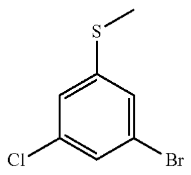

A mixture of 1,3-dibromo-5-chlorobenzene (10.00 g, 36.98 mmol), DMF (200 mL) and MeSNa (2.59 g, 37.00 mmol) was stirred for 1 h at RT. Upon completion of the reaction, the resulting solution was diluted with EA (200 mL) and the resulting mixture was washed with $H_2O$ (200 mL×3). The mixture was dried over anhydrous $Na_2SO_4$ and concentrated. The residue was purified by combi-flash (EA/PE=0-15%) give the product (7.6 g, 87%). GCMS (ESI) m/e [M] 236.

Step 2: 1-bromo-3-chloro-5-methanesulfonylbenzene

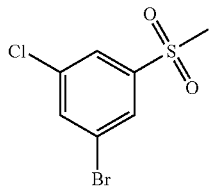

A mixture of 1-bromo-3-chloro-5-(methylsulfanyl)benzene (7.60 g, 31.99 mmol), THF (60 mL), $H_2O$ (60 mL), $NaIO_4$ (27.37 g, 127.96 mmol) and $RuCl_3 \cdot H_2O$ (1.44 g, 6.39 mmol) was stirred for 1 h at 0° C. Upon completion of the reaction, the resulting solution was diluted with EA (200 mL) and the resulting mixture was washed with $H_2O$ (200 mL×3). The mixture was dried over anhydrous $Na_2SO_4$ and concentrated. The residue was purified by combi-flash (EA/PE=0-30%) give the product (1.13 g, 13%). $^1$H NMR (400 MHz, $CDCl_3$) δ 7.91 (s, 1H), 7.81 (s, 1H), 7.73 (s, 1H), 3.02 (s, 3H). GCMS (ESI) m/e [M]268.

Example BB32: Synthesis of 1-bromo-3-cyclopropoxy-5-methanesulfonylbenzene

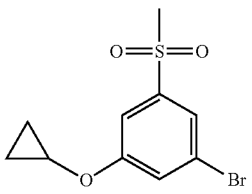

Step 1: 1,3-dibromo-5-cyclopropoxybenzene

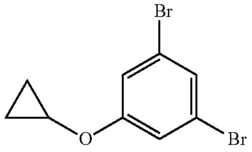 [SMILES: Brc1cc(Br)cc(OC2CC2)c1]

A mixture of 3,5-dibromophenol (5.00 g, 19.85 mmol), cyclopropyltrifluoro-lambda4-borane potassium (11.75 g, 79.40 mmol), $K_2CO_3$ (5.49 g, 39.70 mmol), 1,10-phenantholine (357.69 mg, 1.99 mmol) and $Cu(OAc)_2$ (360.5 mg, 1.985 mmol) in toluene (45 mL) and $H_2O$ (15 mL) was stirred for overnight at 70° C. under nitrogen atmosphere. After cooled to room temperature, water was added and the resulting solution was extracted with EA (200 mL×3) and the combined organic layers were washed with brine, dried over anhydrous $Na_2SO_4$. The solids were filtered out and the resulting mixture was concentrated under vacuum. The residue was purified by combi-flash (EA/PE=0-5%) to give the product (1.00 g, 17%). GCMS (ESI) m/e [M] 290.

Step 2: 1-bromo-3-cyclopropoxy-5-(methylsulfanyl)benzene

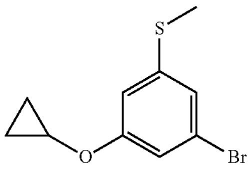

A mixture of 1,3-dibromo-5-cyclopropoxybenzene (1.00 g, 3.43 mmol), 1,4-dioxane (10 mL), $CH_3SNa$ (191.8 mg, 2.74 mmol), Xantphos (396.35 mg, 0.69 mmol) and $Pd_2(dba)_3$ (313.6 mg, 0.34 mmol) was stirred for 2 h at 75° C. under nitrogen atmosphere. After cooled to room temperature, the solvent was removed in vacuo and the residue was diluted with 40 mL of water. The resulting solution was extracted with EA (60 mL×3) and the combined organic layers were washed with brine, dried over anhydrous sodium sulfate. The solvent was removed in vacuo and the residue was purified by combi-flash (EA/PE=0-5%) to give the product (300 mg, 34%). GCMS (ESI) m/e [M] 258.

Step 3: 1-bromo-3-cyclopropoxy-5-methanesulfonylbenzene

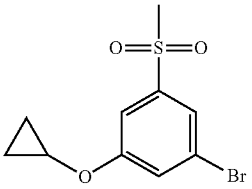

To a mixture of 1-bromo-3-cyclopropoxy-5-(methylsulfanyl)benzene (300 mg, 1.16 mmol) in THF (5 mL)/$H_2O$ (5 mL) were added $RuCl_3 \cdot H_2O$ (26 mg, 0.12 mmol) at 0° C. Then $NaIO_4$ (742.79 mg, 3.47 mmol) was added in several batches at 0° C. The resulting solution was stirred for 2 h at RT. Upon completion of the reaction, water was added and the resulting solution was extracted with EA (30 mL×3) and the organic layers combined. The resulting mixture was washed with brine, dried over anhydrous $Na_2SO_4$. The resulting mixture was concentrated under vacuum and the residue was purified by Prep-TLC (EA/PE=1:2) to give the product (165 mg, 49%). $^1H$ NMR (300 MHz, $CDCl_3$) δ 7.69 (s, 1H), 7.55 (s, 1H), 7.49 (s, 1H), 3.85-3.81 (m, 1H), 3.09 (s, 3H), 0.94-0.76 (m, 4H). GCMS (ESI) m/e [M] 290.

Example BB33: Synthesis of of 2-bromo-3-isopropoxy-6-methanesulfonylpyridine

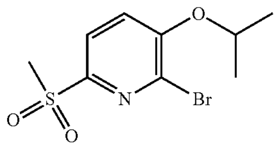

Step 1: 2-bromo-6-iodo-3-isopropoxypyridine

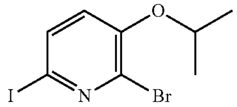

A mixture of 2-bromo-6-iodopyridin-3-ol (10.00 g, 33.34 mmol), DMF (150 mL), 2-iodopropane (13.04 g, 76.70 mmol) and $Cs_2CO_3$ (21.73 g, 66.69 mmol) was stirred for 3 h at 80° C. After cooled to room temperature, water was added and the resulting solution was extracted with EA (100 mL×3). The resulting mixture was concentrated under vacuum to give the product (11.08 g, 87%). LCMS (ESI, m/e) $[M+1]^+$ 342.

Step 2: 2-bromo-3-isopropoxy-6-(methylsulfanyl)pyridine

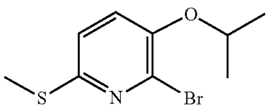

A mixture of 2-bromo-6-iodo-3-isopropoxypyridine (11.08 g, 32.40 mmol), 1,4-dioxane (166 mL), (methylsulfanyl)sodium (1.82 g, 25.97 mmol), $Pd_2(dba)_3$ (1.48 g, 1.62 mmol), Xantphos (1.87 g, 3.24 mmol) was stirred for 3 h at 75° C. nitrogen atmosphere. After cooled to room temperature, the solvent was removed in vacuo and the residue was diluted with water (20 mL). The resulting solution was extracted with EA (30 mL×3) and the combined organic layers were washed with brine, dried over anhydrous sodium sulfate. The solvent was removed in vacuo and the residue was purified by combi-flash (EA/PE=10:1) to give the product (8.00 g, 84%). LCMS (ESI, m/e) $[M+1]^+$ 262.

Step 3: 2-bromo-3-isopropoxy-6-methanesulfonylpyridine

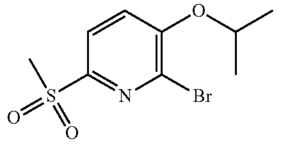

To a mixture of 2-bromo-3-isopropoxy-6-(methylsulfanyl)pyridine (5.00 g, 19.07 mmol) in THF (50.00 mL) was added $NaIO_4$ (12.24 g, 57.22 mmol) and $RuCl_3$ (0.13 g, 0.57 mmol) in $H_2O$ (30 mL) dropwise at 0° C. and the resulting solution was stirred for 1 h at RT. Upon completion of the reaction, the resulting solution was extracted EA (30 mL×3) and the combined organic layers were concentrated under vacuum. The residue was purified by combi-flash (EA/PE=0-24%) to give the product (3.10 g, 50%). $^1H$ NMR (300 MHz, DMSO-$d_6$) δ 8.02 (d, J=8.5 Hz, 1H), 7.79 (d, J=8.5 Hz, 1H), 4.95-4.91 (m, 1H), 3.25 (s, 3H), 1.37 (d, J=6.0 Hz, 6H). LCMS (ESI, m/e) $[M+1]^+$ 294.

Example BB34: Synthesis of 2-bromo-4-(cyclopropylmethoxy)-6-methanesulfonyl pyridine

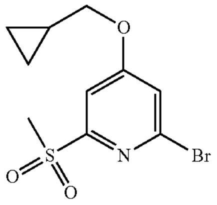 [SMILES: CS(=O)(=O)c1cc(OCC2CC2)cc(Br)n1]

A mixture of 2-bromo-6-methanesulfonylpyridin-4-ol (1.00 g, 3.97 mmol), $Cs_2CO_3$ (2.59 g, 7.94 mmol) and (bromomethyl)cyclopropane (0.80 g, 5.95 mmol) in DMF (10 mL) was stirred for 5 h at 80° C. under nitrogen atmosphere. After cooled to room temperature, the solvent was removed in vacuo and the residue was diluted with 50 mL of water. The resulting solution was extracted with EA (30 mL×3) and the combined organic layers were washed with brine, dried over anhydrous sodium sulfate. The solvent was removed in vacuo and the residue was purified by Prep-TLC (PE/EA=5:1) to give the product (793 mg, 65%). $^1H$ NMR (300 MHz, $CDCl_3$) δ 7.54 (s, 1H), 7.16 (s, 1H), 3.94 (d, J=7.1 Hz, 2H), 3.23 (s, 3H), 1.35-1.22 (m, 1H), 0.77-0.65 (m, 2H), 0.43-0.34 (m, 2H). LCMS (ESI) m/e $[M+1]^+$ 306.

Example BB35: Synthesis of 1-bromo-3-(cyclopropylmethoxy)-5-(methylsulfonyl) benzene

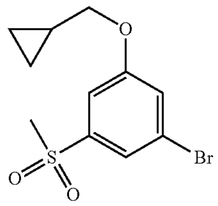 [SMILES: CS(=O)(=O)c1cc(Br)cc(OCC2CC2)c1]

Step 1: 1,3-dibromo-5-(cyclopropylmethoxy)benzene

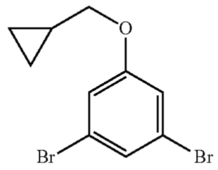 [SMILES: Brc1cc(Br)cc(OCC2CC2)c1]

A mixture of 3,5-dibromophenol (5.00 g, 19.85 mmol), DMF (50 mL), (bromomethyl)cyclopropane (8.04 g, 59.55 mmol) and $K_2CO_3$ (5.49 g, 39.72 mmol) was stirred for 2 h at 80° C. After cooled to room temperature, the solvent was removed in vacuo and the residue was diluted with water (100 mL). The resulting solution was extracted with EA (30 mL×3) and the combined organic layers were washed with brine, dried over anhydrous sodium sulfate. The solvent was removed in vacuo and the residue was purified by combi-flash (EA/PE=0-15%) give the product (2.80 g, 46%). GCMS (ESI) m/e $[M+1]^+$ 304.

Step 2: (3-bromo-5-(cyclopropylmethoxy)phenyl)(methyl)sulfane

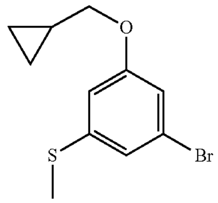

A mixture of 1,3-dibromo-5-(cyclopropylmethoxy)benzene (2.80 g, 9.15 mmol), 1,4-dioxane (20 mL), $Pd_2(dba)_3$ (418 mg, 0.46 mmol), Xantphos (529 mg, 0.915 mmol) and MeSNa (641 mg, 9.15 mmol) was stirred for 4 h at 80° C. After cooled to room temperature, the solvent was removed in vacuo and the residue was diluted with water (20 mL). The resulting solution was extracted with EA (30 mL×3) and the combined organic layers were washed with brine, dried over anhydrous sodium sulfate. The solvent was removed in vacuo and the residue was purified by combi-flash (EA/PE=0-15%) give the product (2.0 g, 80%). LCMS (ESI) m/e $[M+1]^+$ 272.

Step 3: 1-bromo-3-(cyclopropylmethoxy)-5-(methylsulfonyl)benzene

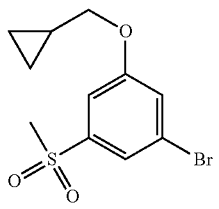 [SMILES: CS(=O)(=O)c1cc(Br)cc(OCC2CC2)c1]

A mixture of 1-bromo-3-(cyclopropylmethoxy)-5-(methylsulfanyl)benzene (2.00 g, 7.32 mmol), $NaIO_4$ (6.26 g, 29.27 mmol), $RuCl_3 \cdot H_2O$ (330 mg, 1.46 mmol) in THF (20 mL) and $H_2O$ (20 mL) was stirred for 1 h at 0° C. Upon completion of the reaction, EA (100 mL) was added and the resulting mixture was washed with water (100 mL×3). The mixture was dried over anhydrous $Na_2SO_4$ and concentrated. The residue was purified by combi-flash (EA/PE=0-20%) to give the product (1.07 g, 48%). $^1H$ NMR (300 MHz, DMSO-$d_6$) δ 7.61 (s, 1H), 7.52 (s, 1H), 7.42 (s, 1H), 3.96 (d, J=7.1 Hz, 2H), 3.28 (s, 3H), 1.30-1.13 (m, 1H), 0.63-0.53 (m, 2H), 0.39-0.30 (m, 2H).

Example BB36: Synthesis of 2-bromo-4-cyclobutoxy-6-(methylsulfonyl)pyridine

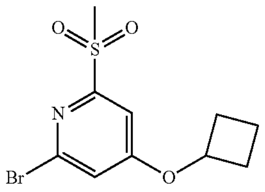 [SMILES: CS(=O)(=O)c1cc(OC2CCC2)cc(Br)n1]

A solution of 2-bromo-6-methanesulfonylpyridin-4-ol (700 mg, 2.78 mmol), bromocyclobutane (749 mg, 5.55 mmol) and $K_2CO_3$ (767 mg, 5.55 mmol) in DMF (7 mL) was stirred for 8 h at 80° C. After cooled to room temperature, water was added and the resulting mixture was extracted with EA (200 mL×3). The combined organic layers were washed with brine (200 mL×3), dried over anhydrous $Na_2SO_4$. After filtration, the filtrate was concentrated under vacuum. The residue was purified by Prep-TLC (EA/PE=1:3) to give the product (382 mg, 45%). $^1H$ NMR (300 MHz, DMSO-$d_6$) δ 7.49 (s, 1H), 7.41 (s, 1H), 5.07-4.95 (m, 1H), 3.28 (s, 3H), 2.51-2.41 (m, 1H), 2.16-2.02 (m, 2H), 1.83-1.80 (m, 1H), 1.74-1.58 (m, 1H). LCMS (ESI) m/e $[M+1]^+$ 306.

Example BB37: Synthesis of 2-bromo-4-(cyclopentyloxy)-6-methanesulfonylpyridine

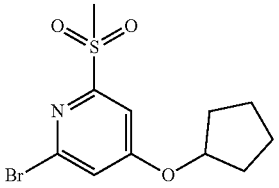 [SMILES: CS(=O)(=O)c1cc(OC2CCCC2)cc(Br)n1]

To a stirred solution of 2-bromo-6-methanesulfonylpyridin-4-ol (500 mg, 1.98 mmol), $PPh_3$ (780 mg, 2.97 mmol) and cyclopentanol (188 mg, 2.18 mmol) in THF (10 mL) was added DIAD (642 mg, 3.17 mmol) dropwise at 0° C. and the resulting mixture was stirred overnight at 50° C. After cooled to room temperature, the solvent was removed in vacuo and the residue was diluted with water (20 mL). The resulting solution was extracted with EA (30 mL×3) and the combined organic layers were washed with brine, dried over anhydrous sodium sulfate. The solvent was removed in vacuo and the residue was purified by Prep-TLC (PE/EA=5:1) to give the product (300 mg, 47%). $^1H$ NMR (300 MHz, DMSO-$d_6$) δ 7.53 (s, 1H), 7.46 (s, 1H), 5.14-5.10 (m, 1H), 3.27 (s, 3H), 2.04-1.89 (m, 3H), 1.82-1.51 (m, 5H). LCMS (ESI) m/e $[M+1]^+$ 320.

Example BB38: Synthesis of 2-bromo-6-methanesulfonyl-4-(oxolan-3-yloxy)pyridine

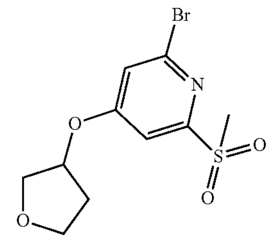 [SMILES: CS(=O)(=O)c1cc(OC2CCOC2)cc(Br)n1]

To a stirred solution of 2-bromo-6-methanesulfonylpyridin-4-ol (400 mg, 1.59 mmol) and 3-hydroxytetrahydrofuran (154 mg, 1.75 mmol) in THF were added $PPh_3$ (832 mg, 3.17 mmol) and DIAD (642 mg, 3.17 mmol) dropwise portions at 0° C. The resulting mixture was stirred overnight at RT. Upon completion of the reaction, water was added and the resulting mixture was extracted with EA (50 mL×3). The combined organic layers were washed with brine (30 mL×3), dried over anhydrous $Na_2SO_4$, concentrated under vacuum. The residue was purified by Prep-TLC (PE/EA=1:1) to give the product (250 mg, 47%). $^1H$ NMR (300 MHz, DMSO-$d_6$) δ 7.60 (s, 1H), 7.51 (s, 1H), 5.38-5.34 (m, 1H), 3.90-3.82 (m, 3H), 3.82-3.72 (m, 1H), 3.28 (s, 3H), 2.29-2.25 (m, 1H), 2.00-1.95 (m, 1H). LCMS (ESI) m/e [M+1] 322.

Example BB39: Synthesis of 2-bromo-4-(1-methoxyethyl)-6-(methylsulfonyl)pyridine

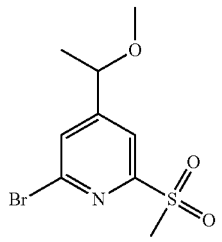

Step 1: 2,6-dibromo-N-methoxy-N-methylisonicotinamide

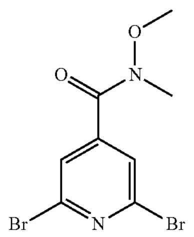

A mixture of 2,6-dibromoisonicotinic acid (9 g, 32.0 mmol) and CDI (5.7 g, 35.0 mmol) in DCM (100 mL) was stirred at 20° C. for 2 h, N,O-dimethylhydroxylamine hydrochloride (3.4 g, 35.0 mmol) was added and stirred at 20° C. for 12 h. The mixture was diluted with $H_2O$ (100 mL) and extracted with DCM (100 mL×3). The combined organic layers were dried over $Na_2SO_4$ and concentrated to give the product (7.3 g, 70%). $^1H$ NMR (400 MHz, $CDCl_3$) δ 7.68 (s, 2H), 3.58 (s, 3H), 3.37 (s, 3H). MS (ESI) m/e $[M+1]^+$ 324.

Step 2: 1-(2,6-dibromopyridin-4-yl)ethanone

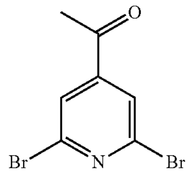

A mixture of 2,6-dibromo-N-methoxy-N-methylisonicotinamide (4.0 g, 12.3 mmol) in THF (40 mL) was added $MgBrCH_3$ (41 mL, 123 mmol, 3M) dropwise at 0° C. The mixture was stirred at 20° C. for 2 h. The mixture was diluted with $H_2O$ (50 ml) and extracted with EA (50 mL×3). The combined organic layers were dried over $Na_2SO_4$ and concentrated to give the product (3.2 g, 93%). $^1H$ NMR (400 MHz, $CDCl_3$) δ 7.87 (s, 2H), 2.61 (s, 3H). MS (ESI) m/e $[M+1]^+$ 278.

Step 3: 1-(2,6-dibromopyridin-4-yl)ethanol

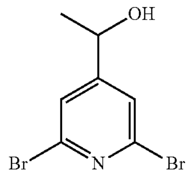

A solution of 1-(2,6-dibromopyridin-4-yl)ethanone (3.2 g, 11.5 mmol) in MeOH (30 mL) at 0° C., was added $NaBH_4$ (434 mg, 11.5 mmol). The mixture was stirred at 0° C. for 30 mins. The mixture was diluted with $H_2O$ (50 ml) and extracted with EA (50 mL×3). The combined organic layers were dried over $Na_2SO_4$ and concentrated to give the product (3.2 g, 99%). MS (ESI) m/e $[M+1]^+$ 282.

Step 4: 2,6-dibromo-4-(1-methoxyethyl)pyridine

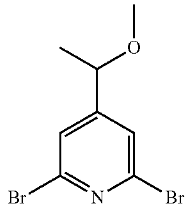

A solution of 1-(2,6-dibromopyridin-4-yl)ethanol (3.2 g, 11.4 mmol) in THF (50 mL) at 0° C., was added NaH (60% in mineral oil, 592 mg, 14.8 mmol). The mixture was stirred at 0° C. for 20 min. MeI (4.9 g, 34.2 mmol) was added and stirred at 20° C. for 2 h. The mixture was diluted with sat. $NH_4Cl$ (50 ml) and extracted with EA (50 mL×3). The combined organic layers were dried over $Na_2SO_4$ and concentrated to give the crude product (3.2 g, crude), used directly. MS (ESI) m/e $[M+1]^+$ 294.

Step 5: 2-bromo-4-(1-methoxyethyl)-6-(methylthio)pyridine

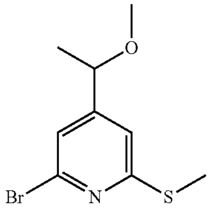

A solution of 2,6-dibromo-4-(1-methoxyethyl)pyridine (1.5 g, 5.1 mmol) in DMF (20 mL) at 20° C., was added $NaSCH_3$ (392 mg, 5.6 mmol). The mixture was stirred at 20° C. for 1 h. The mixture was diluted with brine (20 mL) and extracted with EA (20 mL×3). The combined organic layers were dried over $Na_2SO_4$ and concentrated to give the product (1.5 g, crude), used directly. MS (ESI) m/e $[M+1]^+$ 262.0.

Step 6: 2-bromo-4-(1-methoxyethyl)-6-(methylsulfonyl)pyridine

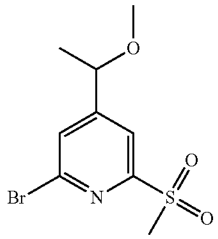

A mixture of 2-bromo-4-(1-methoxyethyl)-6-(methylthio) pyridine (1.5 g, 5.1 mmol) and oxone (12.5 g, 20.4 mmol) in MeOH (16 mL) and $H_2O$ (8 ml) was stirred at 20° C. for 12 h. The mixture was filtered, added brine (20 ml) and extracted with EA (20 mL×3). The combined organic layers were dried over $Na_2SO_4$ and concentrated. The crude was purified by column chromatography (PE/EA=20:1-3:1) to give the product (1.1 g, 65%). $^1$H NMR (400 MHz, $CDCl_3$) δ 7.97 (s, 1H), 7.70 (s, 1H), 4.39-4.35 (m, 1H), 3.33 (s, 3H), 3.28 (s, 3H), 1.45 (d, J=6.4 Hz, 3H). MS (ESI) m/e $[M+1]^+$ 294.

Example BB40: Synthesis of 2-bromo-4-[(2S)-butan-2-yloxy]-6-methanesulfonyl pyridine

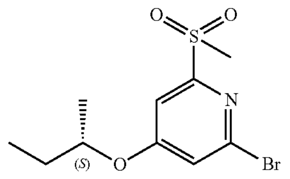

To a stirred solution of 2-bromo-6-methanesulfonylpyridin-4-ol (400 mg, 1.59 mmol), (S)-2-butanol (176 mg, 2.38 mmol) and $PPh_3$ (624 mg, 2.38 mmol) in THF (10 mL) was added DIAD (513 mg, 2.54 mmol) dropwise at 0° C. under air atmosphere. The resulting mixture was stirred overnight at 50° C. The resulting mixture was extracted with EA (100 mL×3). The combined organic layers were washed with brine (100 mL), dried over anhydrous $Na_2SO_4$. After filtration, the filtrate was concentrated and purified by silica gel column chromatography (PE/EA=8:1) to give 2-bromo-4-[(2S)-butan-2-yloxy]-6-methanesulfonylpyridine (358 mg, 73% yield). $^1$H NMR (400 MHz, DMSO-$d_6$) δ 7.58 (s, 1H), 7.48 (s, 1H), 4.86-4.71 (m, 1H), 3.27 (s, 3H), 1.77-1.52 (m, 2H), 1.27 (d, J=6.1 Hz, 3H), 0.91 (t, J=7.4 Hz, 3H). LCMS (ESI) m/e $[M+1]^+$ 308.

Example BB41: Synthesis of 2-bromo-4-(difluoromethoxy)-6-methanesulfonylpyridine

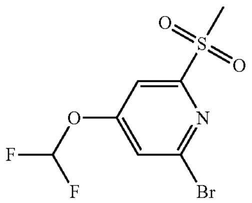

A mixture solution of KOH (1.11 g, 19.78 mmol), $CH_3CN$ (5 mL) and $H_2O$ (5 mL) was cooled to approximately −10° C. 2-bromo-6-methanesulfonylpyridin-4-ol (500 mg, 1.98 mmol) was added dropwise followed by diethyl bromodifluoromethylphosphonate (1.06 g, 3.97 mmol) over 15 mins. The mixture was allowed to warm to RT over 1 h. The mixture was poured into water and extracted with EA (50 mL×3), washed with brine and dried over $Na_2SO_4$. The residue was purified by Prep-TLC (EA/PE=1:10) to give 2-bromo-4-(difluoromethoxy)-6-methanesulfonyl pyridine (310 mg, 52% yield). $^1$H NMR (400 MHz, DMSO-$d_6$) δ 7.94 (t, J=1.8 Hz, 1H), 7.88-7.50 (m, 2H), 3.34 (s, 3H). LCMS (ESI) m/e $[M+1]^+$ 301.

Example BB42: Synthesis of 2-bromo-4-ethoxy-6-methanesulfonylpyridine

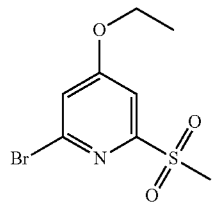

A mixture solution of 2-bromo-6-methanesulfonylpyridin-4-ol (3.50 g, 13.88 mmol), $Cs_2CO_3$ (9.10 g, 27.84 mmol) and ethyl iodide (3.26 g, 20.90 mmol) in DMF (40 mL) was stirred for 1 h at 80° C. The mixture was allowed to cool down to rt. The resulting mixture was extracted with EA (50 mL×3). The combined organic layers were washed with brine (50 mL×2), dried over anhydrous $Na_2SO_4$. After filtration, the filtrate was concentrated under reduced pressure. The residue was purified by combi-flash (EA/PE=20-25%) to give 2-bromo-4-ethoxy-6-methanesulfonylpyridine (3.05 g, 78% yield). 1H NMR (300 MHz, $CDCl_3$) δ 7.55 (d, J=2.2 Hz, 1H), 7.17 (d, J=2.2 Hz, 1H), 4.19 (m, 2H), 3.25 (s, 3H), 1.49 (t, J=7.0 Hz, 3H). LCMS (ESI) m/e $[M+1]^+$ 281.

Example BB43: Synthesis of [[(2R)-1-(3-bromo-5-methanesulfonylphenoxy)propan-2-yl]oxy](tert-butyl)dimethylsilane

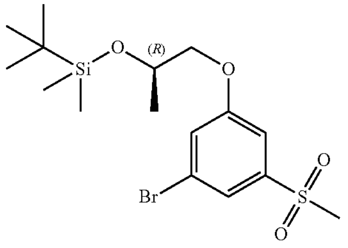

Step 1: (2R)-1-[(4-methylbenzenesulfonyl)oxy]propan-2-ol

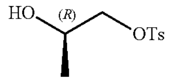

To a stirred solution of R-1, 2-propanediol (5.00 g, 65.71 mmol) in Py (50 mL) was added TsCl (13.78 g, 72.28 mmol) in portions at 0° C. The resulting mixture was stirred overnight at RT. The resulting mixture was extracted with EA (100 mL×3). The combined organic layers were washed with brine (100 mL×3), dried over anhydrous $Na_2SO_4$. After filtration, the filtrate was concentrated and purified by combi-flash (EA/PE=28-32%) to give (2R)-1-[(4-methylbenzenesulfonyl)oxy]propan-2-ol (10.0 g, 66% yield). LCMS (ESI) m/e $[M+1]^+$ 230.

Step 2: (2R)-2-[(tert-butyldimethylsilyl)oxy]propyl 4-methylbenzenesulfonate

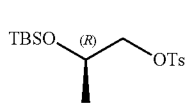

To a stirred mixture of (2R)-1-[(4-methylbenzenesulfonyl)oxy]propan-2-ol (10 g, 43.42 mmol), Imidazole (8.87 g, 130.28 mmol) in DCM (100 mL) was added TBSCl (19.64 g, 130.28 mmol) in portions at 0° C. The resulting mixture was stirred for 1 h at RT. The resulting mixture was concentrated under reduced pressure. The residue was purified by combi-flash (EA/PE=3-5%) to give the crude product (15.00 g, 100% yield). LCMS (ESI) m/e $[M+1]^+$ 344.

Step 3: tert-butyl([[(2R)-1-(3,5-dibromophenoxy) propan-2-yl]oxy])dimethylsilane

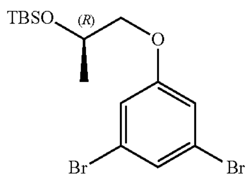

A mixture of 3,5-dibromophenol (2.0 g, 7.94 mmol) and (2R)-2-[(tert-butyldimethylsilyl)oxy]propyl 4-methylbenzenesulfonate (5.46 g, 15.85 mmol) and $Cs_2CO_3$ (5.17 g, 15.86 mmol) in DMF (20 mL) was stirred for one night at 100° C. The mixture was allowed to cool down to RT. The resulting mixture was extracted with EA (40 mL×3). The combined organic layers were washed with brine (40 mL×2), dried over anhydrous $Na_2SO_4$. After filtration, the filtrate was concentrated under reduced pressure. The residue was purified by combi-flash (EA/PE=3-5%) to give tert-butyl([[(2R)-1-(3,5-dibromophenoxy)propan-2-yl]oxy])dimeth ylsilane (1.90 g, 56% yield).

Step 4: [[(2R)-1-[3-bromo-5-(methylsulfanyl)phenoxy]propan-2-yl]oxy](tert-butyl) dimethylsilane

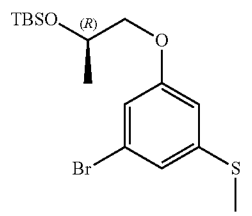

A mixture of tert-butyl([[(2R)-1-(3,5-dibromophenoxy) propan-2-yl]oxy])dimethylsilane (1.00 g, 2.36 mmol), (methylsulfanyl)sodium (166 mg, 2.37 mmol), DIEA (0.82 mL, 4.71 mmol), $Pd_2(dba)_3$ (108 mg, 0.12 mmol) and Xantphos (137 mg, 0.24 mmol) in dioxane (10 mL) was stirred for 4 h at 70° C. under $N_2$ atmosphere. The mixture was allowed to cool down to RT. The resulting mixture was extracted with EA (40 mL×3). The combined organic layers were washed with brine (30 mL×3), dried over anhydrous $Na_2SO_4$. After filtration, the filtrate was concentrated under reduced pressure. The residue was purified by Prep-TLC (PE/EA=20:1) to give [[(2R)-1-[3-bromo-5-(methylsulfanyl)phenoxy]propan-2-yl]oxy](tert-butyl)dimethylsilane (470 mg, 50% yield).

Step 5: [[(2R)-1-(3-bromo-5-methanesulfonylphenoxy)propan-2-yl]oxy](tert-butyl) dimethylsilane

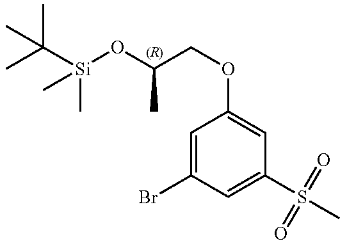

To a stirred solution of [[(2R)-1-[3-bromo-5-(methylsulfanyl]phenoxy]propan-2-yl]oxy](tert-butyl)dimethylsilane (470 mg, 1.20 mmol) in THF (30 mL) were added $RuCl_3 \cdot H_2O$ (7.5 mg, 0.04 mmol) and $NaIO_4$ (513.6 mg, 2.40 mmol) in $H_2O$ (20 mL) at 0° C. and the resulting solution was stirred for 1 h at 0° C. Then the mixture was extracted with EA (30 mL×3). The combined organic layers were washed with brine (30 mL×3), dried over $Na_2SO_4$. After filtration, the filtrate was concentrated and purified by Prep-TLC (PE/EA=10:1) to give [[(2R)-1-(3-bromo-5-methanesulfonyl phenoxy)propan-2-yl]oxy](tert-butyl)dimethylsilane (344.2 mg, 67% yield). $^1H$ NMR (400 MHz, $CDCl_3$) δ 7.66 (s, 1H), 7.38 (s, 1H), 7.33 (s, 1H), 4.23-4.15 (m, 1H), 3.96-3.81 (m, 2H), 3.08 (s, 3H), 1.29-1.23 (d, J=8.0 Hz, 3H), 0.91 (s, 9H), 0.10 (s, 6H). LCMS (ESI) m/e $[M+1]^+$ 422.

Example BB44: Synthesis of 2-bromo-6-(ethanesulfonyl)-4-isopropoxypyridine

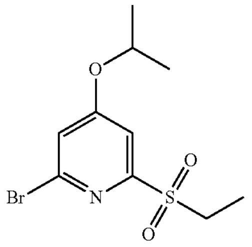 [SMILES: CCS(=O)(=O)c1cc(OC(C)C)cc(Br)n1]

Step 1: 2-bromo-6-(ethylsulfanyl)pyridin-4-ol

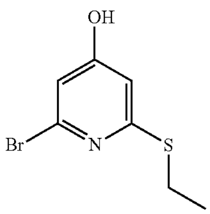

A stirred mixture of 2, 6-dibromopyridin-4-ol (5.00 g, 19.77 mmol), EtSNa (1.66 g, 19.77 mmol), $Pd_2(dba)_3$ (181 mg, 0.20 mmol), Xantphos (114.4 mg, 0.20 mmol) and DIEA (6.9 mL, 53.29 mmol) in dioxane (50 mL) was stirred for 3 h at 80° C. The mixture was allowed to cool down to RT. The resulting mixture was extracted with EA (50 mL×3). The combined organic layers were washed with brine (50 mL×2), dried over anhydrous $Na_2SO_4$. After filtration, the filtrate was concentrated under reduced pressure to give 2-bromo-6-(ethylsulfanyl)pyridin-4-ol as a crude product, and used in the next step directly without further purification. LCMS (ESI) m/e $[M+1]^+$ 234.

Step 2: 2-bromo-6-(ethanesulfonyl)pyridin-4-ol

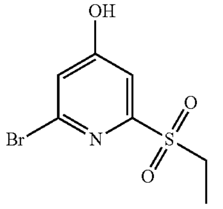

To a stirred mixture of 2-bromo-6-(ethylsulfanyl)pyridin-4-ol (5.00 g, 21.36 mmol) in THF was added $RuCl_3 \cdot H_2O$ (133 mg, 0.64 mmol) in water for a moment and $NaIO_4$ (9.14 g, 42.72 mmol) was added in THF and water in portions at 0° C. for 30 mins. The resulting mixture was extracted with EA (100 mL×3). The combined organic layers were washed with brine (2×50 mL), dried over anhydrous $Na_2SO_4$. After filtration, the filtrate was concentrated under reduced pressure. The residue was purified by combi-flash (EA/PE=28-32%) to 2-bromo-6-(ethanesulfonyl)pyridin-4-ol (2.00 g, 35% yield). LCMS (ESI) m/e $[M+1]^+$ 266.

Step 3: 2-bromo-6-(ethanesulfonyl)-4-isopropoxypyridine

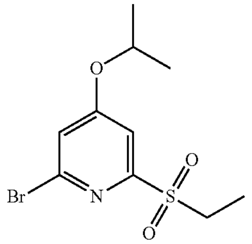 [SMILES: CCS(=O)(=O)c1cc(OC(C)C)cc(Br)n1]

A stirred solution of 2-bromo-6-(ethanesulfonyl)pyridin-4-ol (1.50 g, 5.64 mmol), $Cs_2CO_3$ (3.68 g. 11.27 mmol) and 2-iodopropane (1.44 g. 8.46 mmol) in dimethylformamide (10 mL) at 80° C. for 1 h. The mixture was allowed to cool down to rt. The resulting mixture was extracted with EA (40 mL×3). The combined organic layers were washed with brine (30 mL×2), dried over anhydrous $Na_2SO_4$. After filtration, the filtrate was concentrated under reduced pressure. The residue was purified by combi-flash (EA/PE=28-32%) to give 2-bromo-6-(ethanesulfonyl)-4-isopropoxypyridine (1.40 g, 78% yield). $^1H$ NMR (400 MHz, $CDCl_3$) δ 7.53 (s, 1H), 7.13 (s, 1H), 4.75-4.70 (m, 1H), 3.46-3.42 (m, 2H), 1.41 (d, J=6.1 Hz, 6H), 1.35-1.32 (m, 3H). LCMS (ESI) m/e $[M+1]^+$ 307.

Example BB45: Synthesis of [[(2S)-1-(3-bromo-5-methanesulfonylphenoxy)propan-2-yl]oxy](tert-butyl)dimethylsilane

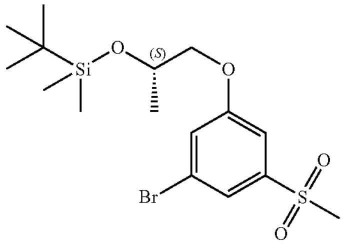

Step 1: (2S)-1-[(4-methylbenzenesulfonyl)oxy]propan-2-ol

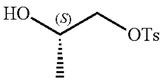

To a stirred solution of (S)-1, 2-propanediol (5.00 g, 65.71 mmol) in Py (50 mL) was added TsCl (13.78 g, 72.28 mmol) in portions at 0° C. The resulting mixture was stirred overnight at RT. The resulting mixture was extracted with EA (100 mL×3). The combined organic layers were washed with brine (100×3 mL), dried over anhydrous $Na_2SO_4$, concentrated under reduced pressure. The residue was purified by combi-flash (EA/PE=28-32%) to give (2S)-1-[(4-methylbenzenesulfonyl)oxy]propan-2-ol (10.00 g, 66% yield). LCMS (ESI) m/e $[M+1]^+$ 230.

Step 2: (2S)-2-[(tert-butyldimethylsilyl)oxy]propyl 4-methylbenzenesulfonate

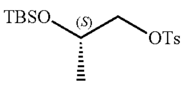

To a stirred mixture of (2S)-1-[(4-methylbenzenesulfonyl)oxy]propan-2-ol (10.00 g, 43.42 mmol), Imidazole (8.87 g, 130.28 mmol) and in DCM (100 mL) was added TBSCl (19.64 g, 130.28 mmol) in portions at 0° C. The resulting mixture was stirred for 1 h at RT. The mixture was concentrated and purified by combi-flash (EA/PE=3-5%) to give (2S)-2-[(tert-butyldimethylsilyl)oxy] propyl-4-methylbenzenesulfonate (15.00 g, 100% yield). LCMS (ESI) m/e $[M+1]^+$ 344.

Step 3: tert-butyl([[(2S)-1-(3,5-dibromophenoxy) propan-2-yl]oxy])dimethylsilane

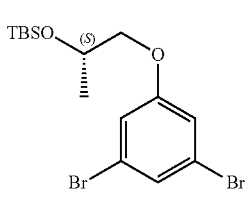

A mixture of 3, 5-dibromophenol (2.0 g, 7.94 mmol) and (2S)-2-[(tert-butyldimethylsilyl)oxy]propyl 4-methylbenzenesulfonate (5.46 g, 15.85 mmol) and $Cs_2CO_3$ (5.17 g, 15.86 mmol) in DMF (20 mL) was stirred overnight at 100° C. The mixture was allowed to cool down to RT. The resulting mixture was extracted with EA (40 mL×3). The combined organic layers were washed with brine (40 mL×2), dried over anhydrous $Na_2SO_4$. After filtration, the filtrate was concentrated and purified by combi-flash (EA/PE=3-5%) to give tert-butyl([[(2S)-1-(3,5-dibromophenoxy)propan-2-yl]oxy])dimethylsilane (1.90 g, 56% yield).

Step 4: [[(2S)-1-[3-bromo-5-(methylsulfanyl)phenoxy]propan-2-yl]oxy](tertbutyl)dimethylsilane

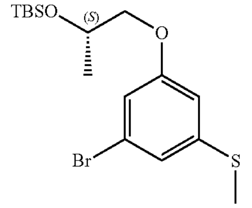

A mixture of tert-butyl([[(2S)-1-(3,5-dibromophenoxy) propan-2-yl]oxy])dimethylsilane (2.00 g, 4.72 mmol), (methylsulfanyl)sodium (332.00 mg, 4.74 mmol), DIEA (1.64 mL, 3.48 mmol), $Pd_2(dba)_3$ (216.00 mg, 0.24 mmol) and Xantphos (274.00 mg, 0.48 mmol) in dioxane (20 mL) was stirred for 4 h at 75° C. under $N_2$ atmosphere. The mixture was allowed to cool down to RT. The resulting mixture was extracted with EA (100 mL×3). The combined organic layers were washed with brine (100 mL×3), dried over anhydrous $Na_2SO_4$, concentrated to give the reside and purified by Prep-TLC (PE/EA=20:1) to give [[(2S)-1-[3-bromo-5-(methylsulfanyl)phenoxy]propan-2-yl]oxy](tert-butyl)dimethylsilane (940 mg, 50% yield).

Step 5: [[(2S)-1-(3-bromo-5-methanesulfonylphenoxy)propan-2-yl]oxy](tert-butyl)dimethylsilane

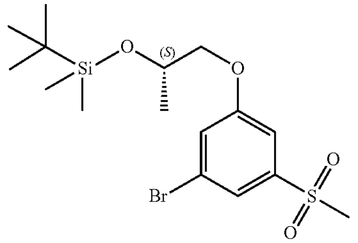

To a stirred solution of [[(2S)-1-[3-bromo-5-(methylsulfanyl)phenoxy]propan-2-yl]oxy](tert-butyl)dimethylsilane (940 mg, 2.40 mmol) in THF (10 mL) were added $RuCl_3H_2O$ (15 mg, 0.08 mmol) and $NaIO_4$ (1.03 g, 4.80 mmol) in $H_2O$ (10 mL) at 0° C. and the resulting solution was stirred for 1 h at 0° C. The resulting mixture was extracted with EA (100 mL×3). The combined organic layers were washed with brine (100 mL×3), dried over anhydrous $Na_2SO_4$, concentrated and purified by Prep-TLC (PE/EA=10:1) to give [[(2S)-1-(3-bromo-5-methanesulfonylphenoxy)propan-2-yl]oxy](tert-butyl)dimethyl silane (646.4 mg, 63% yield). $^1H$ NMR (400 MHz, $CDCl_3$) δ 7.58 (m, 1H), 7.34 (m, 1H), 7.31 (m, 1H), 4.24-4.12 (m, 1H), 3.89-3.72 (m, 2H), 3.06 (s, 3H), 1.29-1.23 (d, J=8.0 Hz, 3H), 0.91 (s, 9H), 0.10 (s, 6H). LCMS (ESI) m/e $[M+1]^+$ 422.

Example BB46: Synthesis of 2-bromo-4-isobutoxy-6-(methylsulfonyl)pyridine

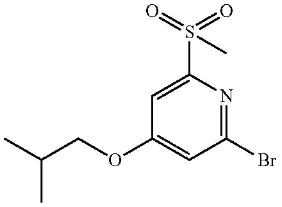 [SMILES: CC(C)COc1cc(Br)nc(S(C)(=O)=O)c1]

A solution of 2-bromo-6-methanesulfonylpyridin-4-ol (500 mg, 1.98 mmol), isobutyl bromide (815 mg, 5.95 mmol) and $K_2CO_3$ (548 mg, 3.97 mmol) in DMF (5 mL) was stirred for 2 h at 80° C. The resulting mixture was extracted with EA (100 mL×3). The combined organic layers were washed with brine (100 mL×2), dried over anhydrous $Na_2SO_4$. After filtration, the filtrate was concentrated under reduced pressure. The residue was purified by Prep-TLC (EA/PE=1:5) to give 2-bromo-4-isobutoxy-6-(methylsulfonyl)pyridine (547 mg, 89% yield). $^1H$ NMR (400 MHz, DMSO-$d_6$) δ 7.61 (s, 1H), 7.54 (s, 1H), 4.02 (d, J=6.5 Hz, 2H), 3.29 (s, 3H), 2.06-2.02 (m, 1H), 0.98 (d, J=6.7 Hz, 6H). LCMS (ESI) m/e $[M+1]^+$ 309.

Example BB48: Synthesis of 2-bromo-3-(difluoromethoxy)-6-(methylsulfonyl)pyridine

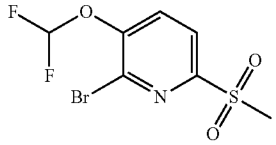

Step 1: 2-bromo-3-(difluoromethoxy)-6-iodopyridine

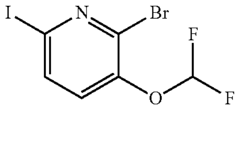 [SMILES: FC(F)Oc1ccc(I)nc1Br]

A solution of 2-bromo-6-iodopyridin-3-ol (5.00 g, 16.67 mmol), sodium 2-chloro-2,2-difluoroacetate (5.08 g, 33.34 mmol) and $Cs_2CO_3$ (10.86 g, 33.34 mmol) in DMF (50 mL) was stirred for 4 h at 80° C. The resulting mixture was extracted with EA (200 mL×3). The combined organic layers were washed with brine (200 mL×3), dried over anhydrous $Na_2SO_4$. After filtration, the filtrate was concentrated under reduced pressure to give the crude product 2-bromo-3-(difluoromethoxy)-6-iodopyridine (5.00 g) and used in the next step directly without further purification. LCMS (ESI) m/e $[M]^+$ 350.

Step 2: 2-bromo-3-(difluoromethoxy)-6-(methylsulfanyl)pyridine

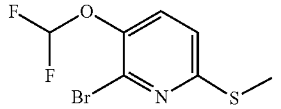

To a solution of 2-bromo-3-(difluoromethoxy)-6-iodopyridine (2.00 g, 5.72 mmol) and $CH_3SNa$ (320 mg, 4.57 mmol) in dioxane (20 mL) were added Xantphos (331 mg, 0.57 mmol) and $Pd_2(dba)_3$ (523 mg, 0.57 mmol). After stirring for 4 h at 70° C. under a nitrogen atmosphere, the resulting mixture was extracted with EA (200 mL×3). The combined organic layers were dried over anhydrous $Na_2SO_4$. After filtration, the filtrate was concentrated to give the crude product 2-bromo-3-(difluoromethoxy)-6-(methylsulfanyl)pyridine (2.0 g) and used in the next step directly without further purification. LCMS (ESI) m/e $[M]^+$ 270.

Step 3: 2-bromo-3-(difluoromethoxy)-6-methanesulfonylpyridine

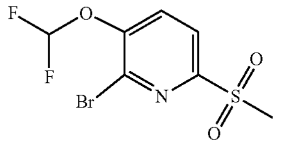

To a solution of 2-bromo-3-(difluoromethoxy)-6-(methylsulfanyl)pyridine (2.00 g, 7.41 mmol) in THF (20 mL) was added $RuCl_3 \cdot H_2O$ (50 mg, 0.22 mmol) at 0° C. $NaIO_4$ (6.34 g, 29.62 mmol) and $H_2O$ (20 mL) was added and the mixture was allowed to warm to RT and stirred for 1 h. The resulting mixture was extracted with EA (200 mL×3). The combined organic layers were washed with brine (200 mL×3), dried over anhydrous $Na_2SO_4$. After filtration, the filtrate was concentrated under reduced pressure. The residue was purified by Prep-TLC (EA/PE=1:3) to give 2-bromo-3-(difluoromethoxy)-6-methanesulfonylpyridine (556.8 mg, 25% yield). $^1H$ NMR (400 MHz, DMSO-$d_6$) δ 8.17 (d, J=8.4 Hz, 4H), 8.08-8.01 (m, 1H), 7.71-7.35 (m 1H), 3.32 (s, 3H). LCMS (ESI) m/e $[M]^+$ 301.

Example BB49: Synthesis of 5-bromo-7-methanesulfonyl-2H,3H-[1,4]dioxino[2,3-c]pyridine

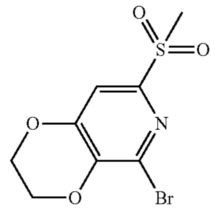

Step 1: 2-bromo-6-iodo-3-methoxypyridine

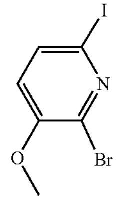

A mixture of 2-bromo-6-iodopyridin-3-ol (11.00 g, 36.68 mmol), $CH_3I$ (10.41 g, 73.34 mmol), $K_2CO_3$ (10.14 g, 73.35 mmol) in DMF (165 mL) was stirred for 1 h at RT. The resulting solution was added to $H_2O$ (200 mL) and extracted with EA (100 mL×3), The combined organic layers were washed with brine (200 mL×3), dried over anhydrous $Na_2SO_4$, concentrated to give the residue and purified by combi-flash (EA/PE=0-6%) to give 2-bromo-6-iodo-3-methoxypyridine (11.00 g, 85% yield). LCMS (ESI) m/e $[M+1]^+$ 314.

Step 2: 2-bromo-6-iodo-3-methoxypyridin-4-ol

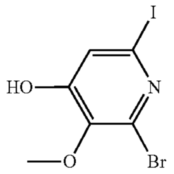

Into a 250-mL 3-necked round-bottom flask purged and maintained with an inert atmosphere of nitrogen, were placed 2-bromo-6-iodo-3-methoxypyridine (5.00 g, 15.92 mmol), THF (100 mL). This was followed by the addition of LDA (2.0 M, 9.6 mL, 19.11 mmol) dropwise with stirring at −78° C. The resulting solution was stirred for 1 h at −78° C. To the mixture was added trimethyl borate (2.48 g, 23.86 mmol) dropwise with stirring at −78° C. The resulting solution was stirred for 2 h at −78° C. To the mixture was added $H_2O_2$ (0.15 mL) dropwise with stirring at −60° C. The resulting solution was allowed to react, with stirring, for an additional 1 h at RT. The reaction was then quenched by the addition of $Na_2S_2O_3$. The resulting solution was extracted with EA (50 mL×3), dried over anhydrous $Na_2SO_4$, concentrated under reduced pressure to give the residue and purified by combi-flash (EA/PE=0-36%) to give 2-bromo-6-iodo-3-methoxypyridin-4-ol (1.92 g, 32% yield). LCMS (ESI) m/e $[M+1]^+$ 330.

Step 3: 2-bromo-6-iodopyridine-3,4-diol

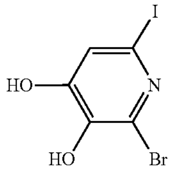

To a solution of 2-bromo-6-iodo-3-methoxypyridin-4-ol (1.92 g, 5.82 mmol) in DCM (35 mL) was followed by the addition of $BBr_3$ (4.37 g, 17.45 mmol) dropwise with stirring at 0° C. The resulting solution was stirred for 3 h at rt. The reaction was then quenched by the addition of MeOH (5 mL). The resulting mixture was concentrated under vacuum and purified by combi-flash (EA/PE=0-8%) to give 2-bromo-6-iodopyridine-3,4-diol (2.12 g crude). LCMS (ESI) m/e $[M+1]^+$ 316.

Step 4: 5-bromo-7-iodo-2H,3H-[1,4]dioxino[2,3-c] pyridine

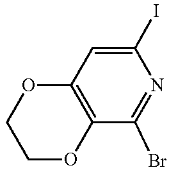 [SMILES: Brc1nc(I)cc2c1OCCO2]

A mixture of 2-bromo-6-iodopyridine-3,4-diol (2.12 g, 6.71 mmol), 1,2-dibromoethane (1.89 g, 10.06 mmol), $K_2CO_3$ (4.64 g, 33.55 mmol) in DMF (40 mL) was stirred for 2 h at 90° C. The resulting solution was added to $H_2O$ (100 mL) and extracted with EA (50 mL×3), dried over anhydrous $Na_2SO_4$, concentrated to give 5-bromo-7-iodo-2H,3H-[1,4]dioxino[2,3-c] pyridine (1.26 g, 49% yield). LCMS (ESI) m/e $[M+1]^+$ 342.

Step 5: 5-bromo-7-(methylsulfanyl)-2H,3H-[1,4] dioxino[2,3-c] pyridine

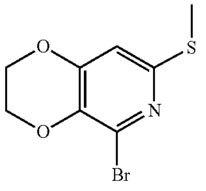

A mixture of 5-bromo-7-iodo-2H,3H-[1,4]dioxino[2,3-c] pyridine (1.26 g, 3.68 mmol), (methylsulfanyl)sodium (0.23 g, 3.28 mmol), $Pd_2(dba)_3$ (0.17 g, 0.18 mmol), Xantphos (0.21 g, 0.36 mmol) in dioxane (20 mL) was stirred for 3 h at 75° C. The resulting mixture was filtrated and filtrate was concentrated under vacuum. The residue was purified by combi-flash (EA/PE=0-5%) to give 5-bromo-7-(methylsulfanyl)-2H,3H-[1,4]dioxino[2,3-c] pyridine (492 mg, 45% yield). LCMS (ESI) m/e $[M+1]^+$ 262.

Step 6: 5-bromo-7-methanesulfonyl-2H,3H-[1,4] dioxino[2,3-c] pyridine

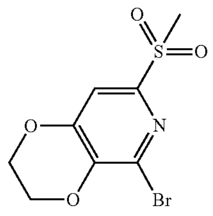

To a solution of 2-bromo-3-[(4-methoxyphenyl) methoxy]-6-(methylsulfanyl)pyridine (492.8 mg, 1.88 mmol) in THF (10 mL) was added $RuCl_3 \cdot H_2O$ (12.72 mg, 0.05 mmol) at 0° C. $NaIO_4$ (1206.4 mg, 5.64 mmol) in $H_2O$ (10 mL) was added at 0° C. The resulting solution was stirred for 1 h at RT. The resulting mixture was concentrated under vacuum. The residue was purified by combi-flash (EA/PE=0-25%) to give 5-bromo-7-methanesulfonyl-2H, 3H-[1,4]dioxino[2,3-c] pyridine (207.0 mg, 33%). $^1H$ NMR (400 MHz, DMSO-$d_6$) δ 7.56 (s, 1H), 4.54-4.48 (m, 4H), 3.23 (s, 3H). LCMS (ESI) m/e $[M+1]^+$ 294.

Example BB50: Synthesis of (R)-2-bromo-4-(2-methoxypropoxy)-6-(methylsulfonyl)pyridine

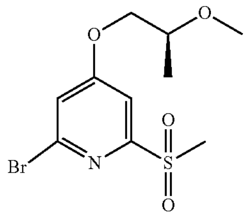 [SMILES: CO[C@@H](C)COc1cc(Br)nc(S(C)(=O)=O)c1]

Step 1: (R)-2-methoxypropyl 4-methylbenzenesulfonate

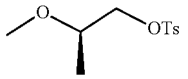 [SMILES: CO[C@H](C)COS(=O)(=O)c1ccc(C)cc1]

To a mixture of NaH (60% in mineral oil, 1.2 g, 30 mmol) in DMF (20 mL) was added 4-(R)-2-methoxypropan-1-ol (1.8 g, 20 mmol) at 0~ 5° C., after 30 mins, methylbenzenesulfonyl chloride (5.7 g, 30 mmol) was added to the mixture and stirred for 16 h at RT. The mixture was poured into water (50 mL), and extracted with EA (20 mL×3). The combined organic layers were dried over $Na_2SO_4$, concentrated under reduced pressure to give (R)-2-methoxypropyl 4-methylbenzenesulfonate (3.95 g, 82.3%). MS (ESI) m/e $[M+1]^+$ 245.

Step 2: (R)-2,6-dibromo-4-(2-methoxypropoxy)pyridine

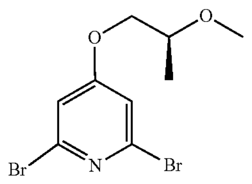

A mixture of (R)-2-methoxypropyl 4-methylbenzenesulfonate (3.95 g, 16.2 mmol), 2,6-dibromopyridin-4-ol (3.37 g, 13.5 mmol), $K_2CO_3$ (3.72 g, 27.0 mmol) in DMF (20 mL) was heated to 80° C. 16 h. The mixture was poured into water (50 mL), and extracted with EA (20 mL×3). The combined organic layers were dried over $Na_2SO_4$, concentrated under reduced pressure to give (R)-2,6-dibromo-4-(2-methoxypropoxy)pyridine (3.05 g, 71.3%). MS (ESI) m/e $[M+1]^+$ 325.

Step 3: (R)-2-bromo-4-(2-methoxypropoxy)-6-(methylthio)pyridine

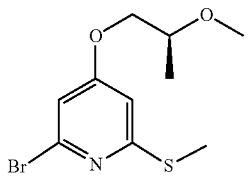

A mixture of (R)-2,6-dibromo-4-(2-methoxypropoxy)pyridine (3.0 g, 9.23 mmol), Sodium methyl mercaptan (wt: 20%, 7.9 g, 27.7 mmol) in DMF (20 mL) was stirred for 16 h at RT. The mixture was poured into water (50 mL), and extracted with EA (20 mL×3). The combined organic layers were dried over $Na_2SO_4$, concentrated under reduced pressure to give (R)-2-bromo-4-(2-methoxypropoxy)-6-(methylthio)pyridine (2.4 g, 88.9%). MS (ESI) m/e $[M+1]^+$ 292.

Step 4: (R)-2-bromo-4-(2-methoxypropoxy)-6-(methylsulfonyl)pyridine

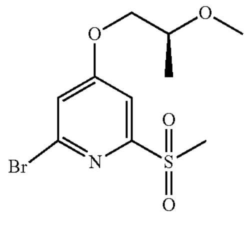 [SMILES: CO[C@@H](C)COc1cc(Br)nc(S(C)(=O)=O)c1]

A mixture of (R)-2-bromo-4-(2-methoxypropoxy)-6-(methylthio)pyridine (2.4 g, 8.22 mmol), 3-Chloroperbenzoic acid (2.12 g, 12.33 mmol) in DCM (30 mL) was stirred for 16 h at RT. The DCM was exchanged by EA (30 mL), then the organic layer was washed with the mixture solution $NaHCO_3$ (10 mL) and $Na_2S_2O_3$ (10 mL), dried over $Na_2SO_4$, concentrated to give the crude product and purification by column chromatograph on silica gel using EA/PE (1/2) as eluant to afford (R)-2-bromo-4-(2-methoxypropoxy)-6-(methylsulfonyl)pyridine (2.5 g, 93.6%). MS (ESI) m/e $[M+1]^+$ 324.

Example BB51: Synthesis of 6-bromo-3-methoxy-2-(methylsulfonyl)pyridine

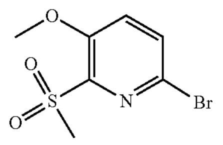

Step 1: 6-bromo-3-methoxy-2-(methylthio)pyridine

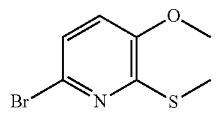

Into a 100-mL round-bottom flask, were placed 6-bromo-2-fluoro-3-methoxypyridine (1.00 g, 4.85 mmol), DMF (10 mL), $NaSCH_3$ (339.78 mg, 4.85 mmol). The resulting solution was stirred for 1 h at RT. The resulting solution was diluted with EA (100 mL). The resulting mixture was washed with $H_2O$ (100 mL×3). The mixture was dried over anhydrous sodium sulfate and concentrated. The residue was purified by combi-flash (EA/PE=0-15%) give the product (0.90 g, 79% yield). LCMS (ESI) m/e $[M+1]^+$ 234.

Step 2: 6-bromo-3-methoxy-2-(methylsulfonyl)pyridine

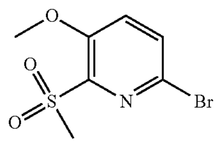

Into a 100-mL round-bottom flask purged and maintained with an inert atmosphere of nitrogen, were placed 6-bromo-3-methoxy-2-(methylsulfanyl)pyridine (1.00 g, 4.27 mmol), THF (10 mL), $H_2O$ (10 mL), $NaIO_4$ (3.65 g, 17.07 mmol), $RuCl_3 \cdot H_2O$ (192.59 mg, 0.85 mmol). The resulting solution was stirred for 1 h at 0° C. The resulting solution was diluted with EA (100 mL). The resulting mixture was washed with $H_2O$ (100 mL×3). The mixture was dried over anhydrous sodium sulfate and concentrated. The residue was purified by combi-flash (EA/PE=0-20%) give the product (705.30 mg, 62% yield). $^1H$ NMR (400 MHz, $CDCl_3$) δ 7.66 (d, J=8.7 Hz, 1H), 7.37 (d, J=8.7 Hz, 1H), 4.03 (s, 3H), 3.35 (s, 3H). LCMS (ESI) m/e $[M+1]^+$ 266.

Example BB52: Synthesis of 2-bromo-6-(methylsulfonyl)-4-phenylpyridine

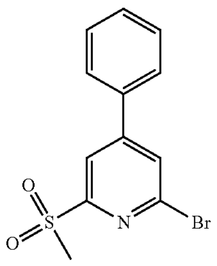 [SMILES: CS(=O)(=O)c1cc(-c2ccccc2)cc(Br)n1]

Step 1: Synthesis of 2,6-dibromo-4-phenylpyridine

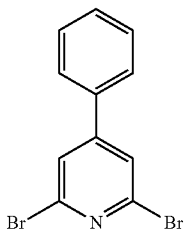 [SMILES: Brc1cc(-c2ccccc2)cc(Br)n1]

Into a 250 mL round-bottom flask purged and maintained with an inert atmosphere of nitrogen, were placed 2,6-dibromo-4-iodopyridine (5.20 g, 14.33 mmol), dioxane (30 mL), $H_2O$ (10 mL), phenyl boronic acid (1.75 g, 14.35 mmol), $Na_2CO_3$ (3.04 g, 28.68 mmol), $Pd(PPh_3)_4$ (1656.31 mg, 1.43 mmol). The resulting solution was stirred for 2 h at 90° C. The resulting solution was diluted with (100 mL). The resulting mixture was washed with $H_2O$ (100 mL×3). The mixture was dried over anhydrous sodium sulfate and concentrated. The residue was purified by combi-flash (EA/PE=0-15%) give the product (0.77 g, 17% yield). LCMS (ESI) m/e $[M+1]^+$ 312.

Step 2: 2,6-dibromo-4-phenylpyridine

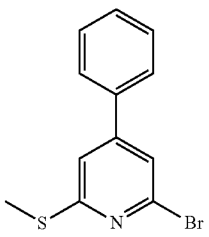

Into a 100 mL round-bottom flask, were placed 2,6-dibromo-4-phenylpyridine (770.00 mg, 2.460 mmol), DMF (10 mL, $NaSCH_3$ (172.21 mg, 2.46 mmol). The resulting solution was stirred for 1 h at rt. The resulting solution was diluted with EA (100 mL). The resulting mixture was washed with $H_2O$ (100 mL×3). The mixture was dried over anhydrous sodium sulfate and concentrated. The residue was purified by combi-flash (EA/PE=0-10%) give the product (0.43 g, 62% yield). LCMS (ESI) m/e $[M+1]^+$ 280.

Step 3: 2-bromo-6-(methylsulfonyl)-4-phenylpyridine

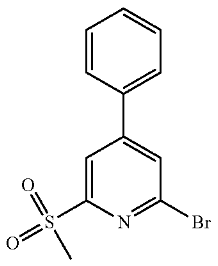 [SMILES: CS(=O)(=O)c1cc(-c2ccccc2)cc(Br)n1]

Into a 100 mL round-bottom flask purged and maintained with an inert atmosphere of nitrogen, were placed 2-bromo-6-(methylsulfanyl)-4-phenylpyridine (430.00 mg, 1.54 mmol), THF (10 mL), $H_2O$ (10 mL), $NaIO_4$ (1313.06 mg, 6.14 mmol), $RuCl_3 \cdot H_2O$ (69.20 mg, 0.31 mmol). The resulting solution was stirred for 1 h at 0° C. The resulting solution was diluted with EA (50 mL). The resulting mixture was washed with $H_2O$ (50 mL×3). The mixture was dried over anhydrous sodium sulfate and concentrated. The residue was purified by combi-flash (EA/PE=0-25%) give the product (386.50 mg, 80% yield). 1H NMR (400 MHz, DMSO-$d_6$) δ 8.37 (d, J=1.5 Hz, 1H), 8.29 (d, J=1.5 Hz, 1H), 8.01-7.92 (m, 2H), 7.63-7.54 (m, 3H), 3.37 (s, 3H). LCMS (ESI) m/e $[M+1]^+$ 312.

Example BB53: Synthesis of 2-bromo-4-methyl-6-(methylsulfonyl)pyridine

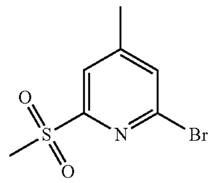

Step 1: 2-bromo-4-methyl-6-(methylthio)pyridine

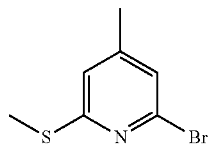

Into a 250-mL round-bottom flask, were placed 2,6-dibromo-4-methylpyridine (4.00 g, 15.62 mmol), DMF (50 mL), $NaSCH_3$ (0.98 g, 14.00 mmol). The resulting solution was stirred for 3 h at 25° C. The resulting solution was diluted with $H_2O$ (100 mL), extracted with 3×80 mL of EA (100 mL×3) and the organic layers were combined and concentrated. The residue was purified by combi-flash (EA/PE=0-20%) to give the product (3.3 g, 87% yield). LCMS (ESI, m/z) $[M+1]^+$ 218.

Step 2: 2-bromo-4-methyl-6-(methylsulfonyl)pyridine

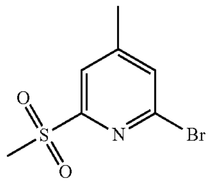

Into a 250-mL round-bottom flask, were placed 2-bromo-4-methyl-6-(methylsulfanyl)pyridine (3.30 g, 13.61 mmol), THF (30 mL), $H_2O$ (10 mL). This was followed by the addition of $NaIO_4$ (11.65 g, 0.05 mmol) in $H_2O$ (10 mL) in portions at 0° C. To the mixture was added $RuCl_3$ (0.31 g, 1.37 mmol) in $H_2O$ (10 mL) in portions at 0° C. The resulting solution was stirred for 1 h at 25° C. The resulting solution was diluted with $H_2O$, extracted with EA (100 mL×3) and the organic layers were combined and concentrated. The residue was purified by combi-flash (EA/PE=0-30%) to give the product (2.45 g, 65% yield). $^1$H NMR (300 MHz, DMSO-$d_6$) δ 7.97 (t, J=0.9 Hz, 1H), 7.92 (t, J=1.1 Hz, 1H), 3.30 (s, 3H), 2.47 (s, 3H). LCMS (ESI, m/z): $[M+H]^+$ 250.

Example BB54: Synthesis of 2-bromo-6-methanesulfonyl-4-phenoxypyridine

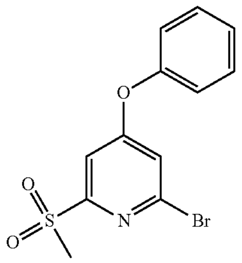 [SMILES: CS(=O)(=O)c1cc(Oc2ccccc2)cc(Br)n1]

Step 1: 2,6-dibromo-4-phenoxypyridine

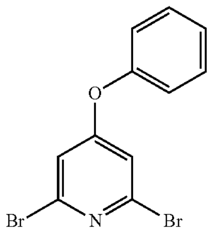 [SMILES: Brc1cc(Oc2ccccc2)cc(Br)n1]

Into a 250-mL round-bottom flask, were placed 2,6-dibromo-4-chloropyridine (4.80 g, 17.69 mmol), DMF (75 mL), phenol (1.50 g, 15.93 mmol), $Cs_2CO_3$ (11.53 g, 35.38 mmol). The resulting solution was stirred for 2 h at 90° C. in an oil bath. The resulting solution was extracted with EA (50 mL×3) concentrated. The residue was purified by prep-MPLC (column: C18 spherical 20-35 um, 100A, 330 g; phase: A-$H_2O$ (0.05% TFA); B-Acetonitrile, B %: 60%-70% in 40 min) to give the product (0.96 g, 14% yield). LCMS (ESI) m/e $[M+1]^+$ 330.

Step 2:2-bromo-6-(methylsulfanyl)-4-phenoxypyridine

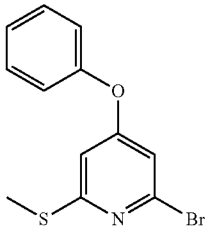 [SMILES: CSc1cc(Oc2ccccc2)cc(Br)n1]

Into a 50-mL round-bottom flask purged and maintained with an inert atmosphere of nitrogen, were placed 2,6-dibromo-4-phenoxypyridine (0.96 g, 2.91 mmol), dioxane (15 mL), (methylsulfanyl)sodium (0.18 g, 2.56 mmol), $Pd_2(dba)_3$ (0.13 g, 0.14 mmol), XantPhos (0.17 g, 0.29 mmol). The resulting solution was stirred for 3 h at 75° C. in an oil bath. The resulting mixture was concentrated under vacuum. The residue was purified by combi-flash (EA/PE=0-1%) to give the product (0.82 g, 85%). LCMS (ESI) m/e $[M+1]^+$ 296.

Step 3: 2-bromo-6-methanesulfonyl-4-phenoxypyridine

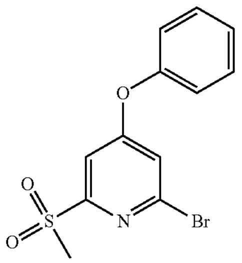 [SMILES: CS(=O)(=O)c1cc(Oc2ccccc2)cc(Br)n1]

Into a 25-mL round-bottom flask, were placed 2-bromo-6-(methylsulfanyl)-4-phenoxypyridine (0.82 g, 2.76 mmol), THF (7 mL). This was followed by the addition of $NaIO_4$ (1.78 g, 8.32 mmol) and $RuCl_3$ (0.020 g, 0.080 mmol) in $H_2O$ (7 mL) dropwise with stirring at 0° C. The resulting solution was stirred for 1 h at RT. The resulting mixture was concentrated under vacuum. The residue was purified by combi-flash (EA/PE=0-11%) to give the product (488.80 mg, 48% yield). $^1$H NMR (300 MHz, DMSO-$d_6$) δ 7.60-7.51 (m, 3H), 7.43-7.36 (m, 2H), 7.34-7.27 (m, 2H), 3.28 (s, 3H). LCMS (ESI) m/e $[M+1]^+$ 328.

Example BB55: Synthesis of 2-chloro-6-methanesulfonyl-4-(trifluoromethyl)pyridine

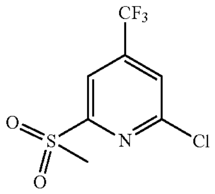

Step 1: 2-chloro-6-(methylsulfanyl)-4-(trifluoromethyl)pyridine

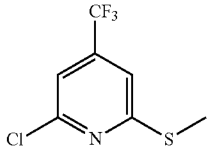

Into a 250-mL round-bottom flask, were placed 2,6-dichloro-4-(trifluoromethyl) pyridine (6.00 g, 27.78 mmol), DMF (90.00 mL), (methylsulfanyl)sodium (1.75 g, 24.97 mmol). The resulting solution was stirred for 1 h at RT. The resulting solution was extracted with 3×50 mL of EA concentrated. The residue was purified by combi-flash to give the product (2.56 g, 36% yield). GCMS (ESI) m/e [M] 227.

Step 2: 2-chloro-6-methanesulfonyl-4-(trifluoromethyl)pyridine

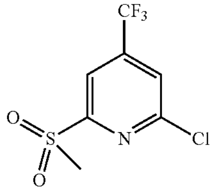

Into a 100-mL 3-necked round-bottom flask, were placed 2-chloro-6-(methylsulfanyl)-4-(trifluoromethyl) pyridine (2.56 g, 11.24 mmol), THF (20 mL). This was followed by the addition of $NaIO_4$ (7.22 g, 33.75 mmol) and $RuCl_3$ (0.08 g, 0.337 mmol) in $H_2O$ (20 mL) dropwise with stirring at 0° C. The resulting solution was stirred for 1 h at RT. The resulting mixture was concentrated under vacuum. The residue was purified by combi-flash (EA/PE=0-11%) to give the product (1.08 g, 33% yield). $^1H$ NMR (300 MHz, DMSO-$d_6$) δ 8.49-8.46 (m, 1H), 8.35-8.30 (m, 1H), 3.38 (s, 3H). LCMS (ESI) m/e $[M+1]^+$ 260.

Example BB56: Synthesis of 6-bromo-3-methyl-2-(methylsulfonyl)pyridine

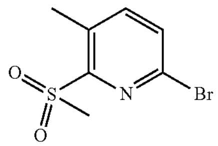

Step: 1:6-bromo-2-fluoro-3-methylpyridine

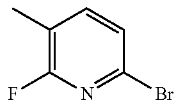

Into a 500-mL 3-necked round-bottom flask purged and maintained with an inert atmosphere of nitrogen, were placed 2-bromo-6-fluoropyridine (10.00 g, 56.82 mmol), THF (200 mL). This was followed by the addition of LDA (7.91 g, 73.87 mmol) dropwise with stirring at −78° C. in 15 mins. The resulting solution was stirred for 3 h at −78° C. in a liquid nitrogen bath. To this was added methyl iodide (8.87 g, 62.50 mmol) dropwise with stirring at −78° C. in 5 min. The resulting solution was allowed to react, with stirring, for an additional 1 h at RT. The reaction was then quenched by the addition of aq. $NH_4Cl$ (150 mL). The resulting solution was extracted with EA (100 mL×3). The resulting mixture was washed with $H_2O$. The resulting mixture was concentrated under vacuum. The residue was purified by combi-flash (PE/EA=0-10%) give the product (4.4 g, 40% yield). LCMS (ESI) m/e $[M+1]^+$ 190.

Step: 2: 6-bromo-3-methyl-2-(methylthio)pyridine

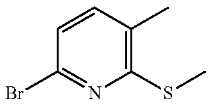

Into a 100-mL round-bottom flask, were placed 6-bromo-2-fluoro-3-methylpyridine (3.40 g, 17.89 mmol), DMF (40 mL), $NaSCH_3$ (1.00 g, 14.31 mmol). The resulting solution was stirred for 1.5 h at RT. The reaction was then quenched by the addition of aq. $NH_4Cl$ (50 mL). The resulting solution was extracted with EA (50 mL×3). The resulting mixture was washed with $H_2O$. The resulting mixture was concentrated under vacuum. The residue was purified by combi-flash (PE/EA=0-1%) give the product (2.9 g, 74% yield). LCMS (ESI) m/e $[M+1]^+$ 218.

Step: 3: 6-bromo-3-methyl-2-(methylsulfonyl)pyridine

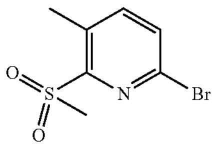

Into a 250-mL round-bottom flask, were placed 6-bromo-3-methyl-2-(methylsulfanyl)pyridine (2.90 g, 13.29 mmol), THF (30 mL). This were followed by the addition of $NaIO_4$ (8.53 g, 39.88 mmol), $H_2O$ (30 mL) and $RuCl_3$ (82.57 mg, 0.40 mmol), in portions at 0° C. in 5 min. The resulting solution was stirred for 1 h at RT. The resulting solution was extracted with 50 mL of EA. The resulting mixture was washed with $H_2O$ (25 mL×2). The resulting mixture was concentrated under vacuum. The residue was purified by combi-flash (PE/EA=0-13%) give the product (2.48 g, 75% yield). $^1H$ NMR (400 MHz, DMSO-$d_6$) δ 7.93-7.89 (m, 2H), 3.38 (s, 3H), 2.57 (s, 3H). LCMS (ESI) m/e $[M+1]^+$ 250.

Example BB57: Synthesis of 2-bromo-6-(methylsulfonyl)-4-(tetrahydro-2H-pyran-4-yl)pyridine

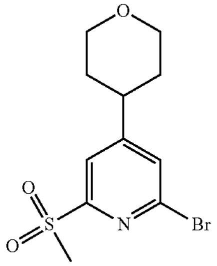 [SMILES: CS(=O)(=O)c1cc(C2CCOCC2)cc(Br)n1]

Step 1: Synthesis of 2,6-dibromo-4-iodopyridine

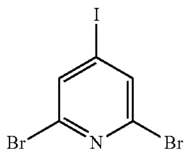

In a flame-dried and nitrogen-flushed 3-necked Schlenk tube equipped with a rubber septum and a magnetic stirring bar, 2,6-dibromopyridine (5.0 g, 21.11 mmol) was dissolved in dry THF (20 mL). The mixture was cooled to −30° C. Then 2,2,6,6-tetramethylpiperidinylmagnesium chloride lithium chloride complex (32 mL, 31.70 mmol, 1 M in THF) was added dropwise via a syringe and stirred for a further 30 min at that temperature. Then $I_2$ (5.9 g, 23.24 mmol) was added quickly to the mixture at −30° C. under the protection of nitrogen gas and stirred for 30 min at the same temperature. The reaction mixture was quenched by adding 30 mL of sat. $NH_4Cl$ followed by extraction with EtOAc, dryness over anhydrous $Na_2SO_4$ and concentration under reduced pressure. The residue was purified by silica gel column chromatography, eluted with EtOAc/PE (1/10, v/v) to afford the product (3.0 g, 39% yield). LCMS (ESI) m/e $[M+1]^+$ =362.

Step 2: Synthesis of 2,6-dibromo-4-(3,6-dihydro-2H-pyran-4-yl)pyridine

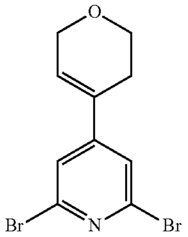 [SMILES: Brc1cc(C2=CCOCC2)cc(Br)n1]

Into a stirred solution of 2,6-dibromo-4-iodopyridine (2.0 g, 5.51 mmol) and 2-(3,6-dihydro-2H-pyran-4-yl)-4,4,5,5-tetramethyl-1,3,2-dioxaborolane (1.2 g, 5.71 mmol) in 1,4-dioxane (40 mL) and water (8 mL), were added Pd(dppf)$Cl_2$ (403 mg, 0.55 mmol) and $K_2CO_3$ (1.5 g, 10.85 mmol) at it under nitrogen atmosphere. The resulting mixture was stirred for 2 hours at 90° C. under nitrogen atmosphere. The resulting mixture was concentrated under reduced pressure. The resulting mixture was extracted with EtOAc (2×100 mL). The combined organic layers were washed with water (100 mL) and brine (100 mL) and then dried over anhydrous $Na_2SO_4$. After filtration, the filtrate was concentrated under reduced pressure. The residue was purified by silica gel column chromatography, eluted with EtOAc/PE (1/12, v/v) to give the product (1.2 g, 68% yield). LCMS (ESI) m/e [M+1]=318.

Step 3: Synthesis of 2,6-dibromo-4-(tetrahydro-2H-pyran-4-yl)pyridine

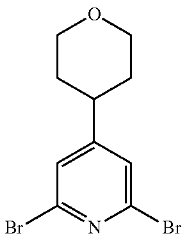 [SMILES: Brc1cc(C2CCOCC2)cc(Br)n1]

Into a solution of 2,6-dibromo-4-(3,6-dihydro-2H-pyran-4-yl)pyridine (1.0 g, 3.13 mmol) in EtOAc (30 mL) was added 5% Rh/C (200 mg, 5% wt). The mixture was stirred at room temperature overnight under hydrogen atmosphere. The resulting mixture was filtered, the filter cake was washed with EtOAc. The filtrate was concentrated under reduced pressure to afford the product (1.0 g, 100% yield). LCMS (ESI) m/e $[M+1]^+$=320.

Step 4: Synthesis of 2-bromo-6-(methylthio)-4-(tetrahydro-2H-pyran-4-yl)pyridine

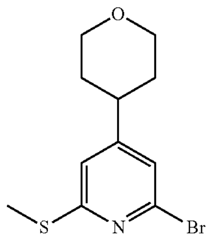

A solution of 2,6-dibromo-4-(tetrahydro-2H-pyran-4-yl) pyridine (1.0 g, 3.11 mmol) and Sodium thiomethoxide (195 mg, 2.79 mmol) in DMF (10 mL) was stirred overnight at room temperature. Water was added to the reaction mixture, and the resulting mixture was extracted with EtOAc. The combined organic layers were dried over anhydrous $Na_2SO_4$. After filtration, the filtrate was concentrated under reduced pressure. The residue was purified by silica gel column chromatography, eluted with EtOAc/PE (1/4, v/v) to give the product (550 mg, 61% yield) LCMS (ESI) m/e $[M+1]^+$=288.

Step 5: Synthesis of 2-bromo-6-(methylsulfonyl)-4-(tetrahydro-2H-pyran-4-yl)pyridine

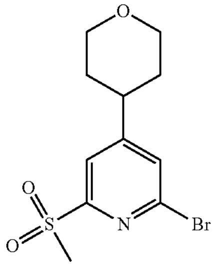 [SMILES: CS(=O)(=O)c1cc(C2CCOCC2)cc(Br)n1]

To a stirred solution of 2-bromo-6-(methylthio)-4-(tetrahydro-2H-pyran-4-yl)pyridine (550 mg, 1.91 mmol) in water (5 mL) and THF (5 mL) was added $RuCl_3 \cdot H_2O$ (12 mg, 0.05 mmol) in water (2 mL) dropwise at 0° C. To the above mixture was added $NaIO_4$ (1.5 g, 7.01 mmol) in water (10 mL) dropwise at 0° C. The resulting mixture was stirred for additional 30 min at 0° C. The resulting mixture was extracted with EtOAc. The combined organic layers were dried over anhydrous $Na_2SO_4$. After filtration, the filtrate was concentrated under reduced pressure. The residue was purified by Prep-TLC (EtOAc:PE=1:5) to give the product (361 mg, 59% yield). $^1$H NMR (300 MHz, DMSO-$d_6$) δ 7.97 (s, 1H), 7.95 (s, 1H), 3.97-3.94 (m, 2H), 3.44-3.39 (m, 2H), 3.33 (s, 3H), 3.08-3.00 (m, 1H), 1.78-1.69 (m, 4H). LCMS (ESI) m/e $[M+1]^+$=320.

Example BB58: Synthesis of 2-bromo-3,4-dimethoxy-6-(methylsulfonyl)pyridine

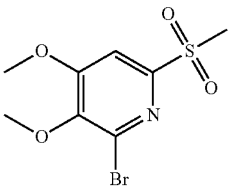

Step: 1:2-bromo-6-iodo-3,4-dimethoxypyridine

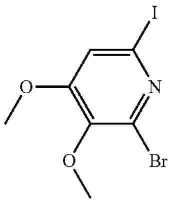

Into a 250-mL round-bottom flask, were placed 2-bromo-6-iodo-3-methoxypyridin-4-ol (2.95 g, 8.94 mmol), DMF (90 mL) and $K_2CO_3$ (2.47 g, 17.88 mmol). This was followed by the addition of $CH_3I$ (2.54 g, 17.88 mmol) at 0° C. in 5 mins. The resulting solution was stirred for 1 hr at rt. The reaction was then quenched by the addition of 40 mL of $NH_4Cl$ (aq). The resulting solution was extracted with of EtOAc (40 mL×2) and combined organic layer was washed with $H_2O$ and brine. The resulting mixture was concentrated under vacuum. The residue was purified by combi-flash (PE/EtOAc=0-11%) to give the product (2.6 g, 84.5% yield). LCMS (ESI) m/e $[M+1]^+$ 344.

Step: 2: 2-bromo-3,4-dimethoxy-6-(methylthio)pyridine

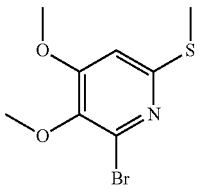

Into a 100-mL round-bottom flask purged and maintained with an inert atmosphere of nitrogen, were placed 2-bromo-6-iodo-3,4-dimethoxypyridine (2.60 g, 7.56 mmol), $Pd_2(dba)_3$ (346.1 mg, 0.38 mmol), Xant-phos (437.4 mg, 0.76 mmol) and dioxane (60 mL). This was followed by the addition of $CH_3SNa$ (529.6 mg, 7.56 mmol). The resulting solution was stirred overnight at 75° C. in an oil bath. The resulting mixture was concentrated under vacuum. The residue was purified by combi-flash (PE/EtOAc=0-6%) to give the product (1.64 g, 82%). LCMS (ESI) m/e $[M+1]^+$ 264.

Step: 3: 2-bromo-3,4-dimethoxy-6-(methylsulfonyl)pyridine

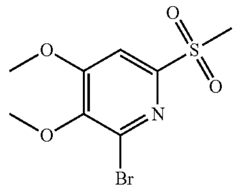

Into a 100-mL round-bottom flask, were placed 2-bromo-3,4-dimethoxy-6-(methylsulfanyl)pyridine (1.60 g, 6.06 mmol), $H_2O$ (35 mL), THF (35 mL). This was followed by the addition of $RuCl_3$ (126 mg, 0.61 mmol) at 0° C. in 2 min. To this was added $NaIO_4$ (3.89 g, 18.17 mmol) at 0° C. in 2 min. The resulting solution was stirred for 1 RT at rt. The reaction was then quenched by the addition of 50 mL of $NH_4Cl$ (aq). The resulting solution was extracted with EtOAc (80 mL) and the combined organic layer was washed with brine. The resulting mixture was concentrated under vacuum and the residue was purified by combi-flash (PE/EtOAc=0-18%) to give the product (354.5 mg, 19.8%). $^1H$ NMR (400 MHz, DMSO-$d_6$) δ 7.72 (s, 1H), 4.06 (s, 3H), 3.88 (s, 3H), 3.28 (s, 3H). LCMS (ESI) m/e $[M+1]^+$ 296.

Example BB59: Synthesis of 2-bromo-4-(methoxy-d3)-6-(methylsulfonyl)pyridine

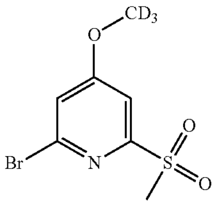

Step 1: 2,6-dibromo-4-(methoxy-d3)pyridine

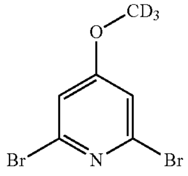

A mixture of 2,6-dibromopyridin-4-ol (2.4 g, 9.5 mmol), $CD_3I$ (1.4 g, 9.5 mmol), $K_2CO_3$ (3.9 g, 28.5 mmol) in DMF (30 mL) was stirred at 25° C. for 2 hr. Upon completion of the reaction, $H_2O$ (200 mL) was added and the resulting solution was extracted with EA (30 mL×3). The combined organic layers were dried over $Na_2SO_4$ and concentrated in vacuo to give the crude product (2.56 g, crude). MS(ESI) m/e $[M+1]^+$ 269.

Step 2: 2-bromo-4-(methoxy-d3)-6-(methylthio)pyridine

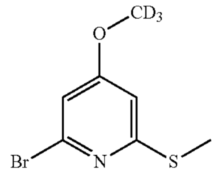

To a solution of 2,6-dibromo-4-(methoxy-d3)pyridine (2.56 g, 9.5 mmol) in DMF (30 ml) was added NaSMe (731 mg, 10.4 mmol) in one portion at 25° C. The mixture was stirred at 25° C. for 16 h. The mixture was poured into $H_2O$ (200 ml) and extracted with EA (30 mL×3). The combined organic layers were dried over $Na_2SO_4$ and concentrated to give crude product (2.4 g, crude). MS(ESI) m/e $[M+1]^+$ 237.

Step 3: 2-bromo-4-(methoxy-d3)-6-(methylsulfonyl)pyridine

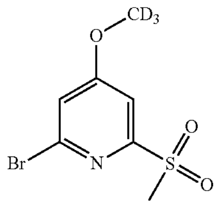 [SMILES: [2H]C([2H])([2H])Oc1cc(Br)nc(S(C)(=O)=O)c1]

To a solution of 2-bromo-4-(methoxy-d3)-6-(methylthio)pyridine (2.4 g, 10.1 mmol) in MeOH (40 ml)/$H_2O$ (20 ml) was added Oxone (12.4 g, 20.1 mmol) at 25° C. The mixture was stirred at RT for 2 hr. Upon completion of the reaction, the solid was filtered out and the filtrate was concentrated. The crude product was purified by silica gel column chromatography eluted with (PE/EtOAc 100:1 to 20:1) to give the product (1.3 g, 47% yield). $^1H$ NMR (400 MHz, $CDCl_3$) δ 7.57 (s, 1H), 7.18 (s, 1H), 3.25 (s, 3H). MS(ESI) m/e $[M+1]^+$ 269.

Example BB60: Synthesis of (R and S)-2-chloro-4-(1-methoxyethyl)-6-(methylsulfonyl)pyridine

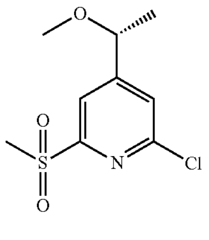

and

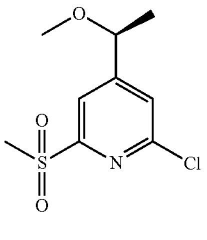

Step 1. Synthesis of 1-(2,6-dichloropyridin-4-yl)ethan-1-ol

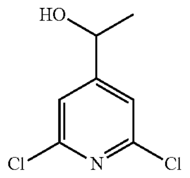

To a stirred solution of 2,6-dichloro-4-iodopyridine (10.00 g, 36.51 mmol) in THF (100 mL) was added n-BuLi in n-hexane (21.9 mL, 2.5 M, 54.77 mmol) dropwise at −78° C. under $N_2$ atmosphere. The resulting mixture was stirred for 1 h at −78° C. To the above mixture was added acetaldehyde (4.83 g, 0.11 mmol) dropwise over 15 min at −78° C. The resulting mixture was stirred for additional 1 h at −78° C. The reaction was quenched with sat. $NH_4Cl$ (aq.) at −78° C. The resulting mixture was extracted with EtOAc (2×300 mL). The combined organic layers were washed with brine (2×200 mL), dried over anhydrous $Na_2SO_4$. After filtration, the filtrate was concentrated under reduced pressure. The crude product (5.50 g, 78% yield) was used in the next step directly without further purification. LCMS (ESI) m/e [M+1]191.99.

Step 2. Synthesis of 2,6-dichloro-4-(1-methoxyethyl)pyridine

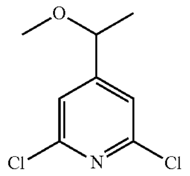

To a stirred solution of 1-(2,6-dichloropyridin-4-yl)ethanol (5.50 g, 28.64 mmol) and $CH_3I$ (6.10 g, 42.98 mmol) in THF (100 mL) were added NaH (1.37 g, 60% in mineral oil, 57.28 mmol) in portions at 0° C. The resulting mixture was stirred for 2 h at rt under $N_2$ atmosphere. The reaction was quenched with Water/Ice at 0° C. The resulting mixture was extracted with EtOAc (2×200 mL). The combined organic layers were washed with brine (1×200 mL), dried over anhydrous $Na_2SO_4$. After filtration, the filtrate was concentrated under reduced pressure. The crude product (5 g, crude) was used in the next step directly without further purification. LCMS (ESI) m/e $[M+1]^+$ 206.

Step 3. Synthesis of 2-chloro-4-(1-methoxyethyl)-6-(methylthio)pyridine

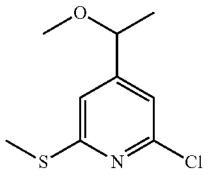

To a stirred solution of 2,6-dichloro-4-(1-methoxyethyl)pyridine (5.00 g, 24.26 mmol) in DMF (50 mL) was added MeSNa (2.55 g, 36.43 mmol) in portions at 0° C. The resulting mixture was stirred for 3 h at rt. The resulting mixture was extracted with EtOAc (2×200 mL). The combined organic layers were washed with brine (2×200 mL), dried over anhydrous $Na_2SO_4$. After filtration, the filtrate was concentrated under reduced pressure. The crude product (7 g, crude) was used in the next step directly without further purification. LCMS (ESI) m/e $[M+1]^+$ 218.

Step 4. Synthesis of 2-chloro-4-(1-methoxyethyl)-6-(methylsulfonyl)pyridine

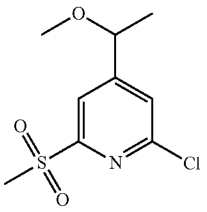

To a stirred solution of 2-chloro-4-(1-methoxyethyl)-6-(methylsulfanyl)pyridine (7.00 g, 32.15 mmol) and $RuCl_3 \cdot H_2O$ (0.22 g, 0.97 mmol) in THF (70 mL) and $H_2O$ (70 mL) were added $NaIO_4$ (13.75 g, 64.29 mmol) in portions at 0° C. and the resulting mixture was stirred at rt for 10 h. The resulting mixture was extracted with EtOAc (2×200 mL). The combined organic layers were washed with brine (2×200 mL), dried over anhydrous $Na_2SO_4$. After filtration, the filtrate was concentrated under reduced pressure. The residue was purified by combi-flash (PE/EtOAc=0-20%) to give the product (5 g, 62%). LCMS (ESI) m/e $[M+1]^+$ 250.

Step 5. Synthesis of (R and S)-2-chloro-4-(1-methoxyethyl)-6-(methylsulfonyl)pyridine

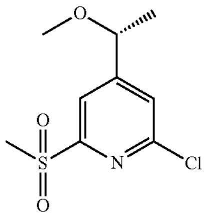

and

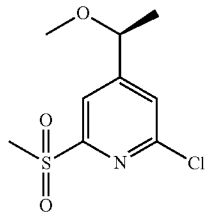

Racemic 2-chloro-4-(1-methoxyethyl)-6-(methylsulfonyl)pyridine) (3 g) was separated by chiral-HPLC with the following conditions (Column: CHIRAL ART Cellulose-SB, 5×25 cm, 5 um; Mobile Phase A: Hex (0.5% 2M $NH_3$-MeOH), Mobile Phase B: EtOH; Flow rate: 95 mL/min; Gradient: 20% B to 20% B in 15 min; 220 nm; RT1: 8.55 min; RT2: 9.50 min), the faster peak was collected and concentrated to give one pure isomer (1.32 g, 44% yield). For faster peak (retention time: 8.55 min): $^1H$ NMR (400 MHz, $CDCl_3$) δ 7.96 (dd, J=1.3 Hz, 1H), 7.56 (dd, J=1.3 Hz, 1H), 4.43-4.38 (m, 1H), 3.35 (s, 3H), 3.29 (s, 3H), 1.47 (d, J=6.6 Hz, 3H). LCMS (ESI) m/e $[M+1]^+$=249.85. The slower peak was collected and concentrated to afford the product (1.22 g, 41% yield). For slower peak (retention time:

9.50 min): $^1H$ NMR (400 MHz, $CDCl_3$) δ 7.96 (dd, J=1.2, Hz, 1H), 7.56 (dd, J=1.3 Hz, 1H), 4.46-4.36 (m, 1H), 3.35 (s, 3H), 3.29 (s, 3H), 1.47 (d, J=6.5 Hz, 3H). LCMS (ESI) m/e $[M+1]^+$ 250.

Example BB61: Synthesis of (S)-4-(2-chloro-6-(methylsulfonyl)pyridin-4-yl)-3-methylmorpholine

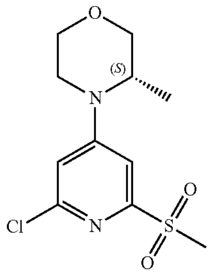

Step 1: Synthesis of (S)-4-(2,6-dichloropyridin-4-yl)-3-methylmorpholine

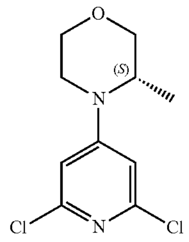

Into a 250 mL round-bottom flask purged and maintained with an inert atmosphere of nitrogen, were placed 2,6-dichloro-4-iodopyridine (5.00 g, 18.25 mmol), dioxane (100 mL), (3S)-3-methylmorpholine (1.85 g, 18.29 mmol), $Pd_2(dba)_3 \cdot CHCl_3$ (1.89 g, 1.82 mmol), XantPhos (2.11 g, 3.64 mmol) and $Cs_2CO_3$ (17.84 g, 54.75 mmol). The resulting solution was stirred for 3 hr at 110° C. in an oil bath. After cooling to room temperature, the reaction was concentrated. The residue was purified by combi-flash (EtOAc/PE=0-15%) to give the product (1.20 g, 24%). LCMS (ESI, m/z): $[M+H]^+$ 247.

Step 2: Synthesis of (S)-4-(2-chloro-6-(methylthio)pyridin-4-yl)-3-methylmorpholine

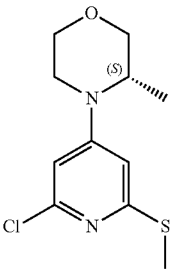

Into a 100 mL round-bottom flask, were placed (3S)-4-(2,6-dichloropyridin-4-yl)-3-methylmorpholine (1.90 g, 7.68 mmol), DMF (30 mL) and $CH_3SNa$ (1.08 g, 15.42 mmol). The resulting solution was stirred for 5 hr at 25° C. The resulting solution was diluted with 50 mL of $H_2O$, extracted with 3×30 mL of EtOAc and the organic layers were combined and concentrated. The residue was purified by combi-flash (EtOAc/PE=0-10%) to give the product (1.40 g, 63%). LCMS (ESI, m/z): $[M+H]^+$ 259.

Step 3: Synthesis of (S)-4-(2-chloro-6-(methylsulfonyl)pyridin-4-yl)-3-methylmorpholine

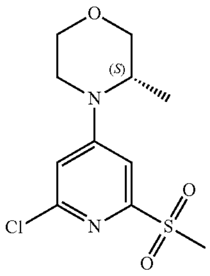

Into a 100 mL round-bottom flask, were placed (3S)-4-[2-chloro-6-(methylsulfanyl)pyridin-4-yl]-3-methylmorpholine (1.40 g, 5.41 mmol), THF (20 mL), $H_2O$ (20 mL), $NaIO_4$ (4.63 g, 21.64 mmol). To the mixture was added $RuCl_3 \cdot H_2O$ (0.12 g, 0.53 mmol) in portions at 0° C. The resulting solution was stirred for 3 hr at 25° C. The resulting solution was diluted with 50 mL of $H_2O$, extracted with 3×30 mL of ethyl acetate and the organic layers were combined and concentrated. The residue was purified by combi-flash (EtOAc/PE=0-45%) to give the product (1.30 g, 79%). $^1H$ NMR (300 MHz, DMSO-$d_6$) δ 7.31 (d, J=2.3 Hz, 1H), 7.11 (d, J=2.3 Hz, 1H), 4.17 (d, J=7.2 Hz, 1H), 4.02-3.90 (m, 1H), 3.81-3.58 (m, 3H), 3.58-3.45 (m, 1H), 3.24-3.15 (m, 4H), 1.18 (d, J=6.7 Hz, 3H). LCMS (ESI, m/z): $[M+H]^+$ 291.

Example BB62: Synthesis of (R)-4-(2-chloro-6-(methylsulfonyl)pyridin-4-yl)-3-methylmorpholine

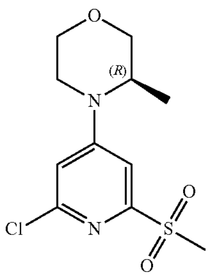

Step 1: Synthesis of (R)-4-(2,6-dichloropyridin-4-yl)-3-methylmorpholine

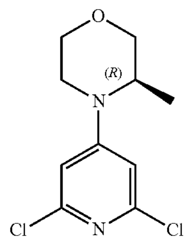

Into a 250 mL round-bottom flask purged and maintained with an inert atmosphere of nitrogen, were placed 2,6-dichloro-4-iodopyridine (2.50 g, 9.13 mmol), dioxane (50 mL), (3R)-3-methylmorpholine (0.97 g, 9.13 mmol), $Pd_2(dba)_3$-$CHCl_3$ (0.97 g, 0.91 mmol), XantPhos (1.06 g, 1.82 mmol), $Cs_2CO_3$ (8.92 g, 27.38 mmol). The resulting solution was stirred for 3 hr at 110° C. in an oil bath. After cooling to room temperature, the reaction was concentrated and the residue was purified by combi-flash (EtOAc/PE=0-15%) to give the product (1.9 g, 84%). LCMS (ESI, m/z): $[M+H]^+$ 247.

Step 2: Synthesis of (R)-4-(2-chloro-6-(methylthio)pyridin-4-yl)-3-methylmorpholine

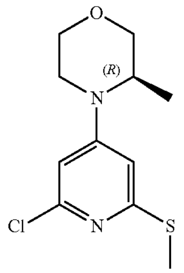

Into a 100 mL round-bottom flask, were placed (3R)-4-(2,6-dichloropyridin-4-yl)-3-methylmorpholine (1.90 g, 7.68 mmol), DMF (30 mL), $CH_3SNa$ (1.08 g, 15.42 mmol). The resulting solution was stirred for 5 h at 25° C. The resulting solution was diluted with 50 mL of $H_2O$, extracted with 3×30 mL of ethyl acetate and the organic layers were combined and concentrated. The residue was purified by combi-flash (EtOAc/PE=0-10%) to give the product (1.70 g, 86%). LCMS (ESI, m/z): $[M+H]^+$ 259.

Step 3: Synthesis of (R)-4-(2-chloro-6-(methylsulfonyl)pyridin-4-yl)-3-methylmorpholine

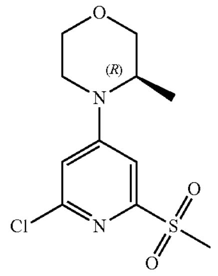

Into a 100 mL round-bottom flask, were placed (3R)-4-[2-chloro-6-(methylsulfanyl)pyridin-4-yl]-3-methylmorpholine (1.70 g, 6.59 mmol), THF (20 mL), $H_2O$ (20 mL), $NaIO_4$ (5.64 g, 26.36 mmol). To the mixture was added $RuCl_3$—$H_2O$ (0.17 g, 0.66 mmol) in portions at 0° C. The resulting solution was stirred for 3 h at 25° C. The resulting solution was diluted with 50 mL of $H_2O$, extracted with 3×30 mL of ethyl acetate and the organic layers were combined and concentrated. The residue was purified by combi-flash (EtOAc/PE=0-45%) to give the product (1.20 g, 63%). $^1H$ NMR (300 MHz, DMSO-$d_6$) δ 7.30 (d, J=2.3 Hz, 1H), 7.12 (d, J=2.3 Hz, 1H), 4.16 (d, J=7.2 Hz, 1H), 4.05-3.93 (m, 1H), 3.82-3.56 (m, 3H), 3.57-3.45 (m, 1H), 3.23-3.15 (m, 4H), 1.19 (d, J=6.7 Hz, 3H). LCMS (ESI, m/z): $[M+H]^+$ 291.

Example BB63: Synthesis of 2-chloro-6-methanesulfonyl-4-(3-methoxyazetidin-1-yl)pyridine

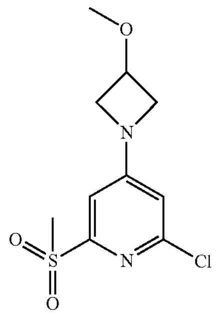 [SMILES: COC1CN(c2cc(Cl)nc(S(C)(=O)=O)c2)C1]

Step 1: Synthesis of 2,6-dichloro-4-(3-methoxyazetidin-1-yl)pyridine

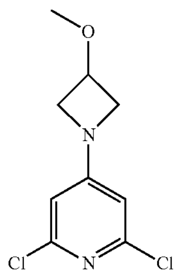

To a stirred mixture of 2,6-dichloro-4-iodopyridine (3.0 g, 10.95 mmol), 3-methoxyazetidine (1.15 g, 13.14 mmol), Xantphos (633.80 mg, 1.09 mmol) and $Cs_2CO_3$ (7.14 g, 21.91 mmol) in 1,4-dioxane (30 mL) was added $Pd_2(dba)_3$ (501.53 mg, 0.55 mmol) at rt. The resulting mixture was stirred for 2 h at 100° C. under $N_2$ atmosphere. The mixture was allowed to cool down to it. The resulting mixture was extracted with EtOAc (2×50 mL) and the combined organic layers were dried over anhydrous $Na_2SO_4$. The solid was removed by filtration and the filtrate was concentrated under reduced pressure. The residue was purified by combi-flash (EtOAc/PE=20%) to give the product (1.2 g, 47% yield). LCMS (ESI) m/e $[M+1]^+$=233.

Step 2: Synthesis of 2-chloro-4-(3-methoxyazetidin-1-yl)-6-(methylsulfanyl)pyridine

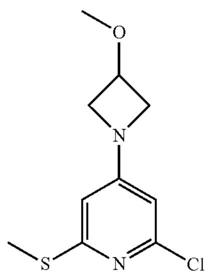

To a stirred solution of 2,6-dichloro-4-(3-methoxyazetidin-1-yl)pyridine (1.2 g, 5.15 mmol) in DMF (10 mL) was added $CH_3SNa$ (900.94 mg, 12.87 mmol) at 0° C. The resulting mixture was stirred for 2 h at rt. Upon completion of the reaction, water was added and the resulting mixture was extracted with EtOAc (2×50 mL). The combined organic layers were washed with water (2×50 mL), dried over anhydrous $Na_2SO_4$. After filtration, the filtrate was concentrated under reduced pressure to give the crude product (1.2 g). It was used in the next step directly without further purification. LCMS (ESI) m/e $[M+1]^+$=245.

Step 3: Synthesis of 2-chloro-6-methanesulfonyl-4-(3-methoxyazetidin-1-yl)pyridine

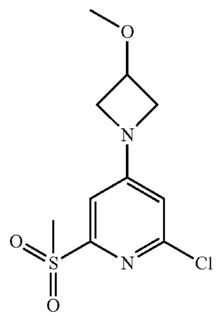 [SMILES: COC1CN(c2cc(Cl)nc(S(C)(=O)=O)c2)C1]

To a stirred solution of 2-chloro-4-(3-methoxyazetidin-1-yl)-6-(methylsulfanyl)pyridine (1.2 g, 4.90 mmol) and $RuCl_3·H_2O$ (33.16 mg, 0.15 mmol) in THF (10 mL) and $H_2O$ (10 mL) was added $NaIO_4$ (2.1 g, 9.81 mmol) at 0° C. the mixture was stirred for 1 h at rt. The resulting mixture was extracted with EtOAc (2×50 mL). The combined organic layers were dried over anhydrous $Na_2SO_4$. After filtration, the filtrate was concentrated under reduced pressure. The residue was purified by combi-flash (EtOAc/PE=50%) to give the product (806.4 mg, 59% yield). $^1H$ NMR (300 MHz, Chloroform-d) δ 6.96 (s, 1H), 6.35 (s, 1H), 4.48-4.37 (m, 1H), 4.30-4.20 (m, 2H), 3.99-3.90 (m, 2H), 3.38 (s, 3H), 3.21 (s, 3H). LCMS (ESI) m/e $[M+1]^+$=277.

Example BB64: Synthesis of 2-chloro-6-methanesulfonyl-4-(4-methoxypiperidin-1-yl)pyridine

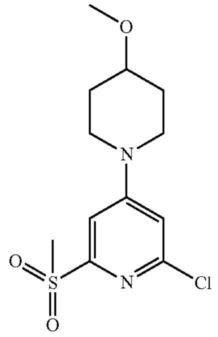 [SMILES: COC1CCN(c2cc(Cl)nc(S(C)(=O)=O)c2)CC1]

Step 1: Synthesis of 2,6-dichloro-4-(4-methoxypiperidin-1-yl)pyridine

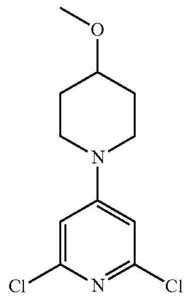 [SMILES: COC1CCN(c2cc(Cl)nc(Cl)c2)CC1]

To a stirred mixture of 2,6-dichloro-4-iodopyridine (3.0 g, 10.95 mmol), 4-methoxypiperidine (1.51 g, 13.14 mmol), Xantphos (633.80 mg, 1.09 mmol) and $Cs_2CO_3$ (7.14 g, 21.91 mmol) in 1,4-dioxane (30 mL) was added $Pd_2(dba)_3$ (501.53 mg, 0.55 mmol) at rt. The resulting mixture was stirred for 3 h at 100° C. under $N_2$ atmosphere. After cooled to rt, the resulting mixture was extracted with EtOAc (2×50 mL). The combined organic layers were dried over anhydrous $Na_2SO_4$. After filtration, the filtrate was concentrated under reduced pressure. The residue was purified by combi-flash (EtOAc/PE=25%) to give the product (1.3 g, 45% yield). LCMS (ESI) m/e $[M+1]^+$=261.

Step 2: Synthesis of 2-chloro-4-(4-methoxypiperidin-1-yl)-6-(methylsulfanyl)pyridine

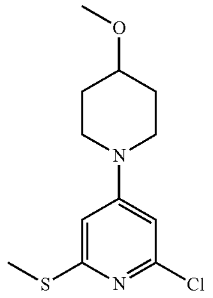 [SMILES: COC1CCN(c2cc(Cl)nc(SC)c2)CC1]

To a stirred solution of 2,6-dichloro-4-(4-methoxypiperidin-1-yl)pyridine (1.3 g, 4.98 mmol) in DMF (10 mL) was added $CH_3SNa$ (522.69 mg, 7.47 mmol) at 0° C. The resulting mixture was stirred for 2 h at rt. Water was added and the resulting mixture was extracted with EtOAc (2×50 mL). The combined organic layers were washed with water (2×50 mL), dried over anhydrous $Na_2SO_4$. After filtration, the filtrate was concentrated under reduced pressure to give the crude product. It was used in the next step directly without further purification. LCMS (ESI) m/e $[M+1]^+$=273.

Step 3: Synthesis of 2-chloro-6-methanesulfonyl-4-(4-methoxypiperidin-1-yl)pyridine

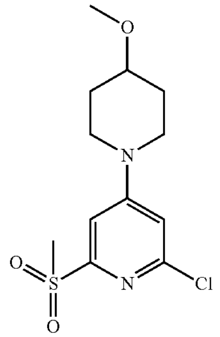 [SMILES: COC1CCN(c2cc(Cl)nc(S(C)(=O)=O)c2)CC1]

To a stirred solution of 2-chloro-4-(4-methoxypiperidin-1-yl)-6-(methylsulfanyl)pyridine (1.48 g, 5.42 mmol) and $RuCl_3 \cdot H_2O$ (36.69 mg, 0.16 mmol) in THF (15 mL) and $H_2O$ (15 mL) was added $NaIO_4$ (2.32 g, 10.85 mmol) at 0° C. The resulting mixture was stirred for 1 h at rt. Upon completion of the reaction, the resulting mixture was extracted with EtOAc (2×50 mL). The combined organic layers were dried over anhydrous $Na_2SO_4$. After filtration, the filtrate was concentrated under reduced pressure. The residue was purified by combi-flash (EtOAc/PE=50%) to give the product (613 mg, 37% yield). $^1H$ NMR (400 MHz, Chloroform-d) δ 7.36 (s, 1H), 6.75 (s, 1H), 3.70-3.62 (m, 2H), 3.59-3.50 (m, 1H), 3.40 (s, 3H), 3.40-3.31 (m, 2H), 3.22 (s, 3H), 1.98-1.88 (m, 2H), 1.84-1.69 (m, 2H). LCMS (ESI) m/e $[M+1]^+$=305.

Example BB65: Synthesis of 2-chloro-4-(1,4-dioxan-2-yl)-6-methanesulfonylpyridine, R or S 2-chloro-4-(1,4-dioxan-2-yl)-6-methanesulfonylpyridine

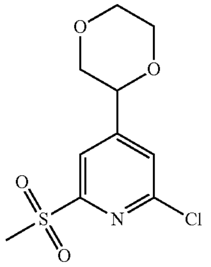

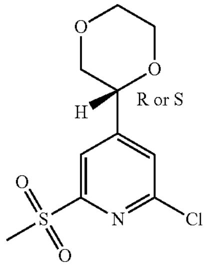

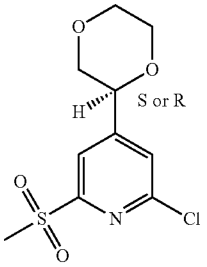

Step 1: Synthesis of 2,6-dichloro-4-ethenylpyridine

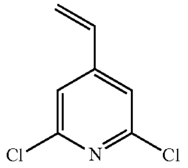

Into a 1000-mL round-bottom flask purged and maintained with an inert atmosphere of nitrogen, were placed 2,6-dichloro-4-iodopyridine (20.00 g, 73.02 mmol), dioxane (200 mL), $H_2O$ (100 mL), 2-ethenyl-4,4,5,5-tetramethyl-1,3,2-dioxaborolane (13.50 g, 87.65 mmol), $Pd(dppf)Cl_2$ (5.34 g, 7.30 mmol) and CsF (33.28 g, 219.07 mmol). The resulting solution was stirred for 2 h at 90° C. The resulting solution was extracted with EtOAc (200 mL×3). The resulting mixture was concentrated under vacuum. The residue was purified by combi-flash (EtOAc/PE=0.1%) to give the product (10.90 g, 86%). LCMS (ESI) m/e $[M+1]^+$=174.

Step 2: Synthesis of 1-(2,6-dichloropyridin-4-yl)ethane-1,2-diol

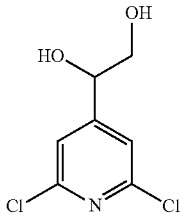 [SMILES: OCC(O)c1cc(Cl)nc(Cl)c1]

Into a 500-mL round-bottom flask, were placed 2,6-dichloro-4-ethenylpyridine (10.90 g, 62.63 mmol), acetone (110 mL), $H_2O$ (55 mL), NMO (8.07 g, 68.90 mmol) and $OSO_4$ (7.95 mL, 1 g/mL, 313.20 mmol). The resulting solution was stirred for 4 h at rt. The reaction was then quenched by the addition of 500 mg of florisil. The resulting solution was extracted with EtOAc (3×100 mL). The resulting mixture was concentrated under vacuum. The residue was purified by combi-flash (EtOAc/PE=32%) to give the product (3.20 g, 24.56%). LCMS (ESI) m/e $[M+1]^+$=208.

Step 3: Synthesis of 2,6-dichloro-4-(1,4-dioxan-2-yl) pyridine

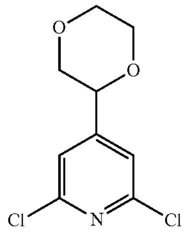 [SMILES: Clc1cc(C2COCCO2)cc(Cl)n1]

Into a 1000-mL round-bottom flask, were placed 1-(2,6-dichloropyridin-4-yl) ethane-1,2-diol (3.00 g, 14.42 mmol), ethylene dichloride (250 mL) and TBAB (1.29 g, 4.00 mmol). This was followed by the addition of NaOH (1 M aq., 50 mL) dropwise with stirring at 0° C. The resulting solution was stirred for 48 h at 35° C. in an oil bath. The resulting solution was extracted with EtOAc (3×150 mL). The resulting mixture was concentrated under vacuum. The residue was purified by combi-flash (EtOAc/PE=7.90%) to give the product (1.45 g, 43%). LCMS (ESI) m/e $[M+1]^+$ =234.

Step 4: Synthesis of 2-chloro-4-(1,4-dioxan-2-yl)-6-(methylsulfanyl)pyridine

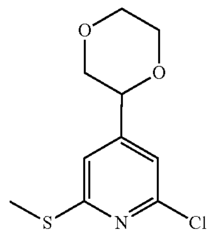

A mixture of 2,6-dichloro-4-(1,4-dioxan-2-yl) pyridine (1.45 g, 6.19 mmol), DMF (17 mL) and (methylsulfanyl) sodium (0.52 g, 7.42 mmol) was stirred for overnight at rt. Water was added and the resulting solution was extracted with EtOAc (3×50 mL). The resulting mixture was concentrated under vacuum. The residue was purified by combi-flash (EtOAc/PE=0.6%-5.3%) to give the product (1.48 g, 97%). LCMS (ESI) m/e $[M+1]^+$=246.

Step 5: Synthesis of 2-chloro-4-(1,4-dioxan-2-yl)-6-(methylsulfonyl)pyridine and (R or S)-2-chloro-4-(1,4-dioxan-2-yl)-6-(methylsulfonyl)pyridine

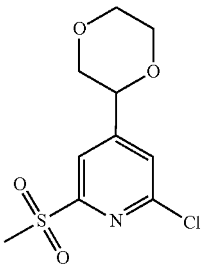

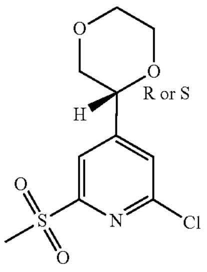

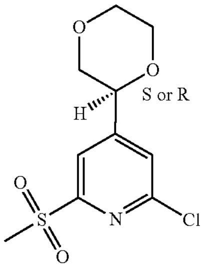

Into a 100-mL 3-necked round-bottom flask, were placed 2-chloro-4-(1,4-dioxan-2-yl)-6-(methylsulfanyl)pyridine (1.48 g, 6.02 mmol), THF (12 mL) and $H_2O$ (12 mL). This was followed by the addition of $NaIO_4$ (3.86 g, 18.06 mmol) in portions with stirring at 0° C. To this was added $RuCl_3H_2O$ (0.20 g, 0.90 mmol) with stirring at 0° C. The resulting solution was stirred for 1 h at rt. The resulting solution was extracted with EtOAc (3×50 mL) and the combined organic layer was concentrated under vacuum. The residue was purified by combi-flash (EtOAc/PE=15-22%) to give the racemic product (1.10 g). The racemic product was purified by Prep-SFC with the following conditions (Column: CHIRALPAK AD-3, 3.0×50 mm, 3 m; Mobile Phase B: MeOH (0.1% DEA); Flow rate: 2 mL/min; Gradient: isocratic 10% B; Wave Length: 220 nm) to give the product.

First peak (434.90 mg, 26.00%, $RT_1$: 0.959 min): $^1H$ NMR (300 MHz, DMSO-$d_6$) δ 8.06 (s, 1H), 7.90 (s, 1H), 4.86-4.83 (m, 1H), 4.15-3.92 (m, 2H), 3.87-3.73 (m, 2H), 3.61-3.59 (m, 1H), 3.33 (s, 4H). LCMS (ESI) m/e $[M+1]^+$= 278.

Second peak (413.3 mg, 24.71%, $RT_2$: 1.605 min): $^1H$ NMR (300 MHz, DMSO-$d_6$) δ 8.05 (s, 1H), 7.89 (s, 1H), 4.85-4.82 (m, J=9.9 Hz, 1H), 4.14-3.92 (m, 2H), 3.86-3.73 (m, 2H), 3.60-3.57 (m, 1H), 3.33-3.25 (m, 4H). LCMS (ESI) m/e $[M+1]^+$=278.

Example BB66: Synthesis of 1-(2-bromo-6-(methylsulfonyl)pyridin-4-yl)-4-methylpiperidin-4-ol

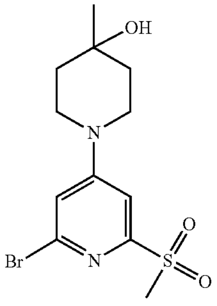

Step 1: 1-(2,6-dibromopyridin-4-yl)-4-methylpiperidin-4-ol

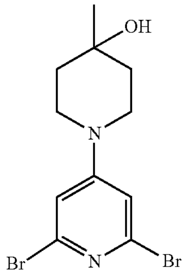

To a solution of 2,6-dibromo-4-nitropyridine (2.0 g, 7.1 mmol) in DMSO (30 mL) was added $K_2CO_3$ (2.0 g, 14.2 mmol) and 4-methylpiperidin-4-ol (899 mg, 7.8 mmol) at 0° C. under $N_2$. The mixture was stirred for 2 hr at 25° C. under $N_2$. The mixture was poured into water (20 mL) and extracted with EtOAc (30 mL, 20 mL). The combined organic phase was washed with brine (50 mL, 30 mL), dried over $Na_2SO_4$, filtered and concentrated to give the residue which was purified by column chromatography ($SiO_2$, PE/EA=100/1 to 0/1). Compound of 1-(2,6-dibromopyridin-4-yl)-4-methylpiperidin-4-ol to give the product (1.4 g, 56% yield) was obtained as a gray solid. LCMS (ESI) m/e $[M+1]^+$=350.8.

Step 2: 1-(2-bromo-6-(methylthio)pyridin-4-yl)-4-methylpiperidin-4-ol

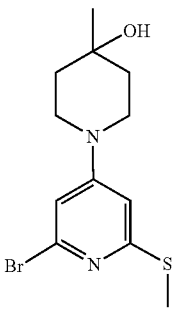 [SMILES: CSc1cc(N2CCC(C)(O)CC2)cc(Br)n1]

To a solution of 1-(2,6-dibromopyridin-4-yl)-4-methylpiperidin-4-ol (1.4 g, 4.0 mmol) in DMF (20 mL) was added sodium methanethiolate (336 mg, 4.8 mmol) at 0° C. under $N_2$. The reaction mixture was stirred for 3 hr at 25° C. under $N_2$. The mixture was poured into water (10 mL) and extracted with EtOAc (30 mL, 20 mL). The combined organic phase was washed with brine (30 mL, 20 mL), dried over $Na_2SO_4$, filtered and concentrated to give the residue. The crude product was purified by column chromatography ($SiO_2$, PE:EA=100/1 to 0/1). Compound of 1-(2-bromo-6-(methylthio)pyridin-4-yl)-4-methylpiperidin-4-ol (1.4 g, 95% yield) was obtained as a light yellow solid. LCMS (ESI) m/e $[M+1]^+$=319.

Step 3: 1-(2-bromo-6-(methylsulfonyl)pyridin-4-yl)-4-methylpiperidin-4-ol

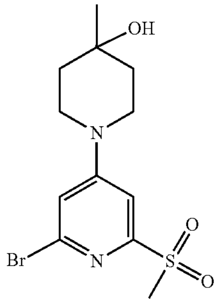 [SMILES: CC1(O)CCN(c2cc(Br)nc(S(C)(=O)=O)c2)CC1]

To a solution of 1-(2-bromo-6-(methylthio)pyridin-4-yl)-4-methylpiperidin-4-ol (1.1 g, 8.7 mmol) in $H_2O$/MeOH (1/1, 30 mL) was added oxone (4.3 g, 6.9 mmol) at 25° C. under $N_2$. The reaction mixture was stirred for 5 hr at 25° C. under $N_2$. The mixture was filtered to give the filtrate, which was poured into $Na_2SO_3$ aqueous solution (20 mL) and extracted with EtOAc (30 mL, 20 mL). The combined organic phase was washed with brine (10 mL), dried over $Na_2SO_4$, filtered and concentrated to give the residue. The crude was purified by column chromatography ($SiO_2$, PE:EA=100/1 to 0/1). Compound of 1-(2-bromo-6-(methylsulfonyl)pyridin-4-yl)-4-methylpiperidin-4-ol (412 mg, 34% yield) was obtained as a white solid. $^1$H NMR (DMSO) δ 7.30-7.31 (d, J=2.4, 1H) 7.21-7.22 (d, J=2.0, 1H) 4.48 (s, 1H) 3.5-3.7 (m, 2H) 3.31-3.34 (m, 2H) 3.21 (s, 3H) 1.51-1.52 (m, 4H) 1.14 (s, 3H). LCMS (ESI) m/e $[M+1]^+$=349.

Example BB67: Synthesis of 2-chloro-4-((trans)-3-methoxycyclobutyl)-6-(methylsulfonyl)pyridine and 2-chloro-4-(cis)-3-methoxycyclobutyl)-6-(methylsulfonyl)pyridine

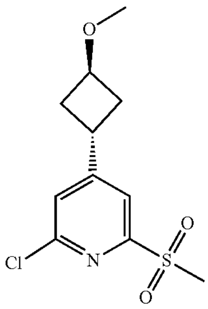

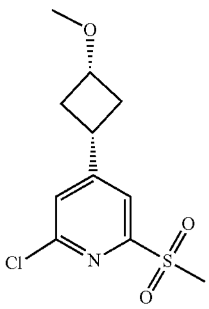

Step 1: Synthesis of 3-hydroxycyclobutane-1-carbonitrile

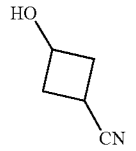

A solution of 3-oxocyclobutane-1-carbonitrile (5 g, 52.57 mmol) in MeOH was treated with $NaBH_4$ (2.98 g, 78.86 mmol) for 2 h at rt under nitrogen atmosphere. The reaction was quenched with water/ice at 0° C. The resulting mixture was extracted with EtOAc (3×80 mL). The combined organic layers were washed with water (3×50 mL), dried over anhydrous $Na_2SO_4$. After filtration, the filtrate was concentrated under reduced pressure. The crude product was used in the next step directly without further purification.

Step 2: Synthesis of 3-(benzyloxy)cyclobutane-1-carbonitrile

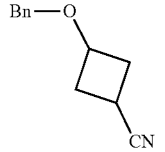 [SMILES: N#CC1CC(OCc2ccccc2)C1]

To a solution of 3-hydroxycyclobutane-1-carbonitrile (3.90 g, 40.15 mmol) in DMF (40 mL) was added NaH (2.01 g, 52.20 mmol, 60% wt) at 0° C. The mixture was stirred for 15 min. BnBr (8.24 g, 48.18 mmol) was added and the mixture was allowed to warm to rt and stirred at rt for 2 h. The resulting mixture was extracted with EtOAc (3×80 mL). The combined organic layers were washed with brine (3×40 mL), dried over anhydrous $Na_2SO_4$. After filtration, the filtrate was concentrated under reduced pressure. The residue was purified by combi-flash (EtOAc/PE=0-20%) to give the product (7.01 g, 93% yield). $^1$H NMR (400 MHz, Chloroform-d) δ 7.43-7.34 (m, 2H), 7.34 (m, 3H), 4.45 (s, 2H), 4.01 (m, 1H), 2.74-2.63 (m, 2H), 2.67-2.56 (m, 1H), 2.49-2.38 (m, 1H), 2.38 (m, 1H).

Step 3: Synthesis of 3-(benzyloxy)-1-(2,6-dichloropyridin-4-yl)cyclobutane-1-carbonitrile

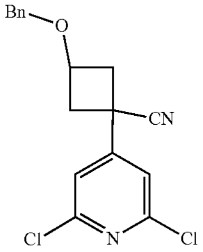 [SMILES: N#CC1(c2cc(Cl)nc(Cl)c2)CC(OCc2ccccc2)C1]

To a stirred mixture of 2,4,6-trichloropyridine (3 g, 16.44 mmol) and 3-(benzyloxy)cyclobutane-1-carbonitrile (3.08 g, 16.44 mmol) in THF (60 mL) was added LiHMDS (23.02 mL, 23.02 mmol, 1M in THF) dropwise portions at −10° C. under nitrogen atmosphere. The resulting mixture was stirred for 2 h at rt under nitrogen atmosphere. The reaction was quenched with water/ice at 0° C. and the resulting mixture was extracted with EtOAc (3×80 mL). The combined organic layers were washed with water (3×60 mL), dried over anhydrous $Na_2SO_4$. After filtration, the filtrate was concentrated under reduced pressure. The residue was purified by combi-flash (EtOAc/PE=0-20%) to give the product (4.5 g, 82% yield). LCMS (ESI) m/e $[M+1]^+$=333.

Step 4: Synthesis of 3-(benzyloxy)-1-(2,6-dichloropyridin-4-yl)cyclobutane-1-carboxylic acid

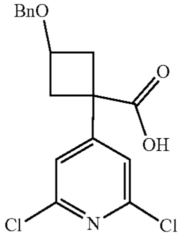 [SMILES: O=C(O)C1(c2cc(Cl)nc(Cl)c2)CC(OCc2ccccc2)C1]

A solution of 3-(benzyloxy)-1-(2,6-dichloropyridin-4-yl)cyclobutane-1-carbonitrile (4.50 g, 13.50 mmol) in $H_2O$ (50 mL) was treated with KOH (2.27 g, 40.51 mmol) for 2 h at 105° C. The resulting mixture was concentrated under reduced pressure. The crude product was used in the next step directly without further purification. LCMS (ESI) m/e $[M+1]^+$=352.

Step 5: Synthesis of 4-[3-(benzyloxy)cyclobutyl]-2,6-dichloropyridine

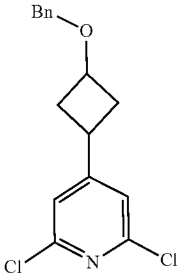 [SMILES: Clc1cc(C2CC(OCc3ccccc3)C2)cc(Cl)n1]

A solution of 3-(benzyloxy)-1-(2,6-dichloropyridin-4-yl)cyclobutane-1-carboxylic acid (4.50 g, 12.77 mmol) in pyridine (40 mL) was treated with Py-HCl (1.47 g, 12.77 mmol) for 2 h at 90° C. The resulting mixture was concentrated under reduced pressure. The resulting mixture was extracted with EtOAc (3×80 mL). The combined organic layers were washed with brine (3×50 mL), dried over anhydrous $Na_2SO_4$. After filtration, the filtrate was concentrated under reduced pressure. The residue was purified by combi-flash (EtOAc/PE=0-40%) to give the product (2.2 g, 55% yield). LCMS (ESI) m/e $[M+1]^+$=308.

Step 6: Synthesis of 3-(2,6-dichloropyridin-4-yl)cyclobutan-1-ol

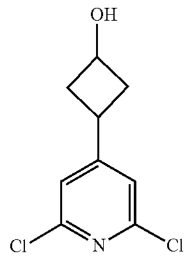 [SMILES: OC1CC(c2cc(Cl)nc(Cl)c2)C1]

A solution of 4-[3-(benzyloxy)cyclobutyl]-2,6-dichloropyridine (2.20 g, 7.13 mmol) in HCl (12 N) (20 mL) was stirred 2 h at 50° C. The resulting mixture was extracted with EtOAc (3×50 mL). The combined organic layers were washed with water (3×30 mL), dried over anhydrous $Na_2SO_4$. After filtration, the filtrate was concentrated under reduced pressure. The residue was purified by combi-flash (PE/EtOAc=50%) to give the product (880 mg, 56% yield). LCMS (ESI) m/e $[M+1]^+$=218.

Step 7: Synthesis of 2,6-dichloro-4-(3-methoxycyclobutyl)pyridine

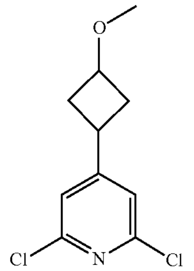

To a solution of 3-(2,6-dichloropyridin-4-yl)cyclobutan-1-ol (830 mg, 3.80 mmol) in DMF was added NaH (182 mg, 4.56 mmol, 60% wt) at 0° C. The mixture was stirred for 15 min at this temperature and then $CH_3I$ (810 mg, 5.70 mmol) was added and the mixture was allowed to warm to rt and stirred for 2 h. The reaction was quenched with water/ice at 0° C. The resulting mixture was extracted with EtOAc (3×30 mL). The combined organic layers were washed with water (3×20 mL), dried over anhydrous $Na_2SO_4$. After filtration, the filtrate was concentrated under reduced pressure. The residue was purified by Prep-TLC (PE/EtOAc=5:1) to give the product (520 mg, 58% yield). LCMS (ESI) m/e $[M+1]^+$=232.

Step 8: Synthesis of 2-chloro-4-(3-methoxycyclobutyl)-6-(methylsulfanyl)pyridine

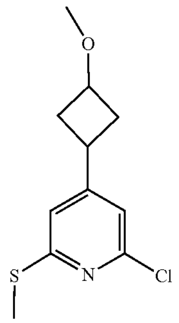

A mixture of 2,6-dichloro-4-(3-methoxycyclobutyl)pyridine (520 mg, 2.24 mmol) and (methylsulfanyl)sodium (235 mg, 3.36 mmol) in DMF (6 mL) was stirred for 2 h at rt. The resulting mixture was extracted with EtOAc (3×30 mL). The combined organic layers were washed with water (3×20 mL), dried over anhydrous $Na_2SO_4$. After filtration, the filtrate was concentrated under reduced pressure. The crude product was used in the next step directly without further purification. LCMS (ESI) m/e $[M+1]^+$=244.

Step 9: Synthesis of 2-chloro-6-methanesulfonyl-4-(3-methoxycyclobutyl)pyridine; 2-chloro-4-((trans)-3-methoxycyclobutyl)-6-(methylsulfonyl)pyridine; 2-chloro-4-((cis)-3-methoxycyclobutyl)-6-(methylsulfonyl)pyridine

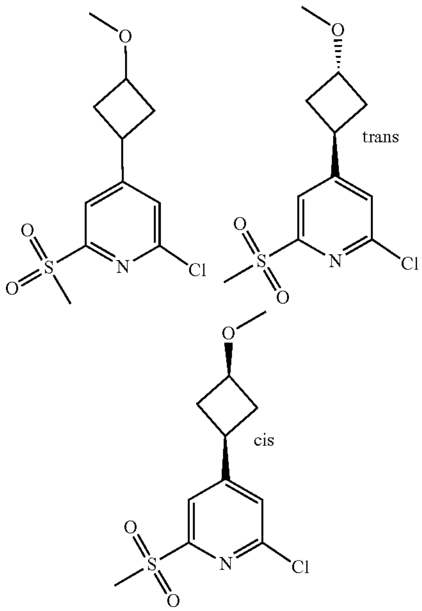

A solution of 2-chloro-4-(3-methoxycyclobutyl)-6-(methylsulfanyl)pyridine (520 mg, 2.13 mmol) in THF (10 mL) was treated with $NaIO_4$ (912.61 mg, 4.26 mmol) for 2 h at 0° C. under nitrogen atmosphere followed by the addition of $RuCl_3 \cdot H_2O$ (24.05 mg, 0.10 mmol) in $H_2O$ (5 mL) dropwise portions at 0° C. The resulting mixture was extracted with EtOAc (3×30 mL). The combined organic layers were washed with water (3×30 mL), dried over anhydrous $Na_2SO_4$. After filtration, the filtrate was concentrated under reduced pressure. The residue was purified by Prep-TLC (PE/EtOAc=3:1) to give the product (268 mg, 45% yield). $^1$H NMR (400 MHz, DMSO-$d_6$) δ 7.92-7.81 (s, 1H), 7.77 (s, 1H), 3.88 (tt, J=7.7, 6.6 Hz, 1H), 3.30 (s, 3H), 3.34-3.20 (m, 1H), 3.17 (s, 3H), 2.70 (m, 2H), 1.98 (m, 2H). LCMS (ESI) m/e $[M+1]^+$=276.

The racemic compound was separated by ACHIRAL-SFC (Column: DAICEL DCpak P4VP, 3×25 cm, 5 μm; Mobile Phase A: $CO_2$, Mobile Phase B: IPA (0.5% 2M $NH_3$-MeOH); Flow rate: 60 mL/min; Gradient: isocratic 15% B; Column Temperature: 35° C.; Back Pressure: 100 bar; Wave Length: 254 nm) to give the trans product (179 mg, $RT_1$: 4.78 min). $^1$H NMR (300 MHz, DMSO-$d_6$) δ 7.94-7.88 (m, 1H), 7.84 (s, 1H), 4.12-3.98 (m, 1H), 3.76 (p, J=7.9 Hz, 1H), 3.31 (s, 3H), 3.19 (s, 3H), 2.51-2.33 (m, 4H). LCMS (ESI) m/e $[M+1]^+$=276.

Cis product (1.31 g, $RT_2$: 5.28 min): $^1$H NMR (300 MHz, DMSO-$d_6$) δ 7.91-7.86 (m, 1H), 7.86-7.74 (m, 1H), 3.97-3.81 (m, 1H), 3.31 (s, 3H), 3.32-3.20 (m, 1H), 3.18 (s, 3H), 2.71 (m, 2H), 2.08-1.90 (m, 2H). LCMS (ESI) m/e $[M+1]^+$=276.

Example A1: Synthesis of N-(4-((3-(methylsulfonyl)phenyl)amino)-5-(pyridazin-3-yl)pyridin-2-yl)acetamide

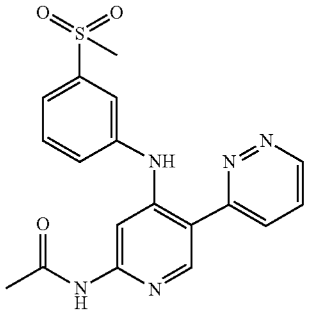 [SMILES: CC(=O)Nc1cc(Nc2cccc(S(C)(=O)=O)c2)c(-c2cccnn2)cn1]

Step 1: 4-chloro-5-(4,4,5,5-tetramethyl-1,3,2-dioxaborolan-2-yl)pyridin-2-amine

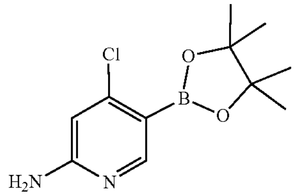 [SMILES: CC1(C)OB(c2cnc(N)cc2Cl)OC1(C)C]

A mixture of 5-bromo-4-chloropyridin-2-amine (1.0 g, 4.8 mmol), 4,4,4',4',5,5,5',5'-octamethyl-2,2'-bi(1,3,2-dioxaborolane) (1.3 g, 5.3 mmol), KOAc (1.4 g, 14.5 mmol) and $Pd(dppf)Cl_2$—$CH_2Cl_2$ (197 mg, 0.2 mmol) in 1,4-dioxane (20 mL) was stirred at 115° C. under $N_2$ for 6 h. After cooled to room temperature, the mixture was diluted with $H_2O$ (30 mL) and the resulting solution was extracted with EA (30 mL×3). The combined organic layers were dried over anhydrous $Na_2SO_4$ and concentrated under vacuum. The crude product was purified by silica gel column chromatography (PE/EA=1:1 to 0:1) to give 4-chloro-5-(4,4,5,5-tetramethyl-1,3,2-dioxaborolan-2-yl)pyridin-2-amine (1.5 g, crude). MS (ESI) m/e $[M+1]^+$ 173.

Step 2: 4-chloro-5-(pyridazin-3-yl)pyridin-2-amine

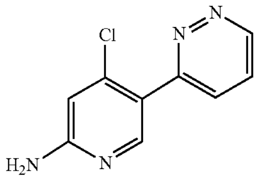 [SMILES: Nc1cc(Cl)c(-c2cccnn2)cn1]

A mixture of 4-chloro-5-(4,4,5,5-tetramethyl-1,3,2-dioxaborolan-2-yl)pyridin-2-amine (478 mg, 1.9 mmol), 3-bromopyridazine (100 mg, 0.6 mmol), $Na_2CO_3$ (133 mg, 1.3 mmol) and $Pd(dppf)Cl_2$ (44 mg, 0.06 mmol) in $CH_3CN$ (10 mL) and $H_2O$ (2 mL) was stirred at 120° C. for 10 mins in microwave reactor. After cooled to room temperature, the mixture was diluted with $H_2O$ (20 mL) and the resulting solution was extracted with EA (30 mL×3). The combined organic layers were dried over anhydrous $Na_2SO_4$ and concentrated under vacuum. The crude product was purified by silica gel column chromatography (PE/EA=1:1 to 0:1) to give 4-chloro-5-(pyridazin-3-yl)pyridin-2-amine (51 mg, 39.4%). MS (ESI) m/e $[M+1]^+$ 207.

Step 3: N-(4-chloro-5-(pyridazin-3-yl)pyridin-2-yl)acetamide

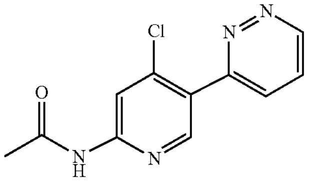 [SMILES: CC(=O)Nc1cc(Cl)c(-c2cccnn2)cn1]

To a solution of N-(4-chloro-5-(pyridazin-3-yl)pyridin-2-yl)acetamide (40 mg, 0.2 mmol) in pyridine (2 mL) was added acetyl chloride (17 mg, 0.2 mmol) dropwise at 0° C. Then the mixture was stirred at RT for 2 h. Upon completion of the reaction, the mixture was concentrate and the residue was diluted with water (5 mL), then the mixture was extracted with EA (10 mL×3) and citric acid (10 mL), dried over anhydrous $Na_2SO_4$, concentrated under vacuum to give N-(4-chloro-5-(pyridazin-3-yl)pyridin-2-yl)acetamide (45 mg, 93%). (ESI) m/e $[M+1]^+$ 249.

Step 4: N-(4-((3-(methylsulfonyl)phenyl)amino)-5-(pyridazin-3-yl)pyridin-2-yl)acetamide

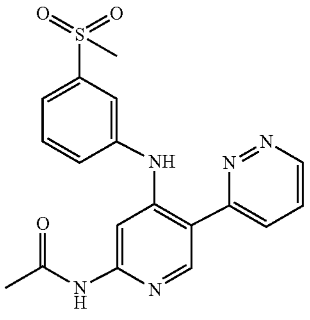 [SMILES: CC(=O)Nc1cc(Nc2cccc(S(C)(=O)=O)c2)c(-c2cccnn2)cn1]

A mixture of N-(4-chloro-5-(pyridazin-3-yl)pyridin-2-yl) acetamide (20.0 mg, 0.08 mmol), 3-(methylsulfonyl)aniline (27.0 mg, 0.16 mmol), $Cs_2CO_3$ (78 mg, 0.24 mmol), Xantphos (5 mg, 8 μmol) and $Pd_2(dba)_3$ (7 mg, 8 μmol) in 1,4-dioxane (2 mL) was stirred at 110° C. for 12 h under nitrogen atmosphere. After cooled to room temperature, the mixture was diluted with $H_2O$ (20 mL) and the resulting solution was extracted with EA (30 mL×3). The combined organic layers were dried over anhydrous $Na_2SO_4$ and concentrated under vacuum. The crude product was purified by Prep-HPLC (column: Phenomenex Gemini-NX 150×30 mm×5 um; phase: A-$H_2O$ (10 mM $NH_4HCO_3$); B-ACN; B %: 15%-35% in 20 min) to give N-(4-((3-(methylsulfonyl) phenyl)amino)-5-(pyridazin-3-yl)pyridin-2-yl)acetamide (1.8 mg, 6%). $^1H$ NMR (400 MHz, MeOD-$d_4$) δ 9.32 (d, J=4.4 Hz, 1H), 8.59 (s, 1H), 8.36 (d, J=8.8 Hz, 1H), 8.05 (s, 1H), 8.03-7.96 (m, 2H), 7.86-7.78 (m, 2H), 6.70 (s, 1H), 3.20 (s, 3H), 2.24 (s, 3H). MS (ESI) m/e $[M+1]^+$ 384.

Example A2: Synthesis of N-[4-[(3-methanesulfonylphenyl)amino]-5-(oxolan-2-yl)pyridin-2-yl]acetamide

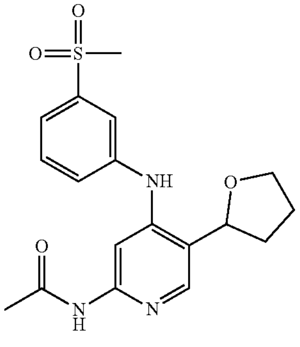 [SMILES: CC(=O)Nc1cc(Nc2cccc(S(C)(=O)=O)c2)c(C2CCCO2)cn1]

Step 1: 5-Bromo-2-chloro-N-(3-methanesulfonylphenyl)pyridin-4-amine

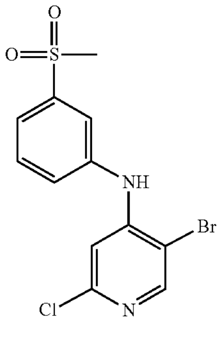 [SMILES: CS(=O)(=O)c1cccc(Nc2cc(Cl)ncc2Br)c1]

A mixture of 5-bromo-2-chloro-4-iodopyridine (3.00 g, 9.42 mmol), $Cs_2CO_3$ (6.14 g, 18.848 mmol), Xantphos (1.09 g, 1.88 mmol), 3-methanesulfonylaniline (1.77 g, 10.37 mmol), $Pd_2(dba)_3$ (0.86 g, 0.942 mmol) in 1,4-dioxane (30 mL) was stirred for overnight at 100° C. under nitrogen atmosphere. After cooled to room temperature, the mixture was diluted with $H_2O$ (20 mL) and the resulting solution was extracted with EA (80 mL×3). The resulting mixture was washed with brine (10 mL), dried over anhydrous sodium sulfate. The resulting mixture was concentrated under vacuum and the residue was purified by combi-flash (EA/PE=0-15%) to give 5-Bromo-2-chloro-N-(3-methanesulfonylphenyl)pyridin-4-amine (1.6 g, 46.95% yield). LCMS (ESI) m/e $[M+1]^+$ 362.

Step 2: 5-bromo-$N^2$-(4-methoxybenzyl)-$N^4$-(3-(methylsulfonyl)phenyl)pyridine-2,4-diamine

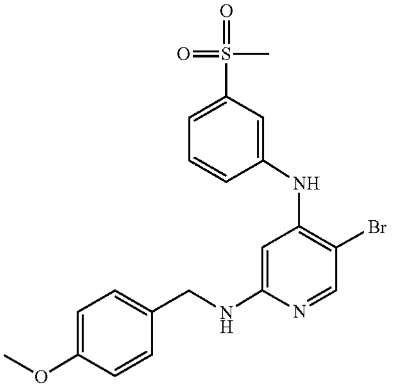 [SMILES: COc1ccc(CNc2cc(Nc3cccc(S(C)(=O)=O)c3)c(Br)cn2)cc1]

Into a 20-mL sealed tube, were placed 5-bromo-2-chloro-N-(3-methanesulfonylphenyl)pyridin-4-amine (1.5 g, 4.148 mmol) and $PMBNH_2$ (5 mL). The resulting solution was stirred overnight at 135° C. After cooled to room temperature, the residue was purified by prep-HPLC (column: Phenomenex Gemini-NX; phase: A-$H_2O$ (0.05% TFA); B-Acetonitrile, B %: 40%-60% in 20 min) to give 5-bromo-N2-(4-methoxybenzyl)-N4-(3-(methylsulfonyl)phenyl)pyridine-2,4-diamine (600 mg, 31%). LCMS (ESI) m/e $[M+1]^+$ 462.

Step 3: 5-(furan-2-yl)-$N^4$-(3-methanesulfonylphenyl)-$N^2$-[(4-methoxyphenyl)methyl]pyridine-2,4-diamine

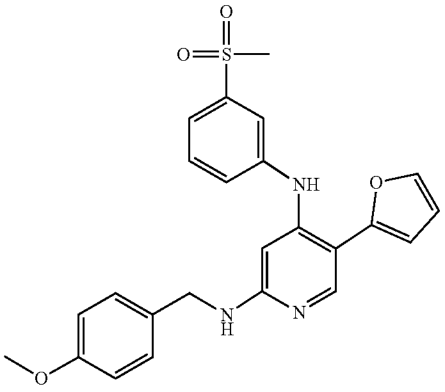 [SMILES: COc1ccc(CNc2cc(Nc3cccc(S(C)(=O)=O)c3)c(-c3ccco3)cn2)cc1]

A mixture of 5-bromo-N4-(3-methanesulfonylphenyl)-N2-[(4-methoxyphenyl)methyl]pyridine-2,4-diamine (420 mg, 0.91 mmol), $K_2CO_3$ (251 mg, 1.82 mmol), furan-2-ylboronic acid (152 mg, 1.36 mmol) and $Pd(PPh_3)_4$ (105 mg, 0.091 mmol) in 1,4-dioxane (4.00 mL) and $H_2O$ (0.80 mL) was stirred for 2 h at 100° C. under nitrogen atmosphere. After cooled to room temperature, the mixture was diluted with $H_2O$ (20 mL) and the resulting solution was extracted with EA (80 mL×3). The combined organic layer was washed with 100 mL of brine, dried over anhydrous sodium sulfate. The resulting mixture was concentrated under vacuum and the residue was purified by Prep-TLC (MeOH/DCM=1:15) to give 5-(furan-2-yl)-$N^4$-(3-methanesulfonylphenyl)-$N^2$-[(4-methoxyphenyl)methyl]pyri dine-2,4-diamine (270 mg, 66%). LCMS (ESI) m/e $[M+1]^+$ 450.

Step 4: $N^2$-(4-methoxybenzyl)-N4-(3-(methylsulfonyl)phenyl)-5-(tetrahydrofuran-2-yl)pyridine-2,4-diamine

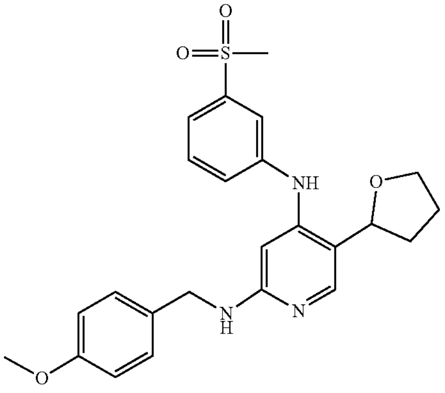 [SMILES: COc1ccc(CNc2cc(Nc3cccc(S(C)(=O)=O)c3)c(C3CCCO3)cn2)cc1]

Into a 20-mL pressure tank reactor were placed 5-(furan-2-yl)-N4-(3-methanesulfonylphenyl)-N2-[(4-methoxyphenyl)methyl]pyridine-2,4-diamine (270 mg, 0.60 mmol), i-PrOH (5 mL), hydrochloric acid (12 M, 0.05 mL) and $Pd(OH)_2/C$ (10%, 168 mg), the resulting solution was stirred overnight at 65° C. under hydrogen atmosphere (10 atm). After cooled to room temperature, the mixture was diluted with $H_2O$ (20 mL) and the resulting solution was extracted with EA (50 mL×3). The reaction mixture was cooled to rt with a water bath. The resulting solution was extracted with EA (50 mL×3) and the organic layers combined. The combined organic layers were washed with 100 mL of brine, dried over anhydrous sodium sulfate. The resulting mixture was concentrated under vacuum and the residue was purified by Prep-TLC (MeOH/DCM=1:12) to give $N^2$-(4-methoxybenzyl)-$N^4$-(3-(methylsulfonyl)phenyl)-5-(tetrahydrofuran-2-yl) pyridine-2,4-diamine (80 mg, 29%). LCMS (ESI) m/e $[M+1]^+$ 454.

Step 5: $N^4$-(3-(methylsulfonyl)phenyl)-5-(tetrahydrofuran-2-yl)pyridine-2,4-diamine

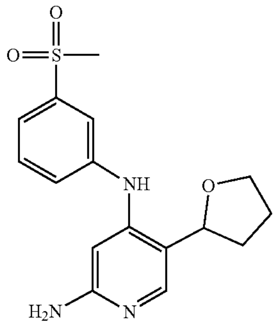 [SMILES: CS(=O)(=O)c1cccc(Nc2cc(N)ncc2C2CCCO2)c1]

A mixture of $N^4$-(3-methanesulfonylphenyl)-$N^2$-[(4-methoxyphenyl)methyl]-5-(oxolan-2-yl)pyridine-2,4-diamine (80 mg) and TFA (2 mL) was stirred for 1 h at 70° C. After cooled to room temperature, the solvent was removed in vacuo and the residue was purified by prep-HPLC (column: Phenomenex Gemini-NX; phase: A-$H_2O$ (0.05% TFA); B-Acetonitrile, B %: 13%-20% in 20 min) to give $N^4$-(3-(methylsulfonyl)phenyl)-5-(tetrahydrofuran-2-yl) pyridine-2,4-diamine (50 mg, 85%). LCMS (ESI) m/e $[M+1]^+$ 334.

Step 6: N-[4-[(3-methanesulfonylphenyl)amino]-5-(oxolan-2-yl)pyridin-2-yl]acetamide

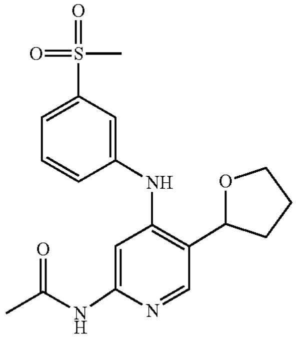 [SMILES: CC(=O)Nc1cc(Nc2cccc(S(C)(=O)=O)c2)c(C2CCCO2)cn1]

A mixture of N4-(3-methanesulfonylphenyl)-5-(oxolan-2-yl)-1,6-dihydropyridine-2,4-diamine (50 mg, 0.15 mmol), pyridine (1 mL) and acetic anhydride (12 mg, 0.12 mmol) was stirred for 1 h at 80° C. After cooled to room temperature, the solvent was removed in vacuo and the residue was diluted with 20 mL of water. The resulting solution was extracted with EA (30 mL×3) and the combined organic layers were washed with 50 mL of brine, dried over anhydrous sodium sulfate. The solvent was removed in vacuo and the residue was purified by prep-HPLC (column: Phenomenex Gemini-NX; phase: A-$H_2O$ (0.1% FA); B-Acetonitrile, B %: 35%-55% in 8 min) to give N-[4-[(3-methanesulfonylphenyl)amino]-5-(oxolan-2-yl)pyridin-2-yl]acetamide (1.8 mg, 3%). $^1H$ NMR (400 MHz, DMSO-$d_6$) δ 10.34 (s, 1H), 8.20 (d, J=6.7 Hz, 1H), 8.11 (s, 1H), 8.00 (s, 1H), 7.73 (s, 1H), 7.60 (d, J=8.9 Hz, 1H), 7.58-7.50 (m, 2H), 5.08-5.03 (m, 1H), 4.10-4.05 (m, 1H), 3.82-3.78 (m, 1H), 3.35 (s, 3H), 2.38-2.34 (m, 1H), 2.03 (s, 3H), 2.00-1.95 (m, 2H), 1.78-1.72 (m, 1H). MS (ES, m/z): $[M+H]^+$ 376.

Example A3: Synthesis of N-(5-(1H-imidazol-4-yl)-4-((6-(methylsulfonyl)pyridin-2-yl)amino)pyridin-2-yl)acetamide

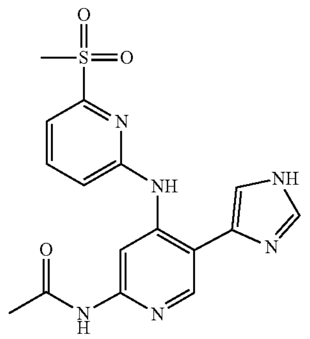 [SMILES: CC(=O)Nc1cc(Nc2cccc(S(C)(=O)=O)n2)c(-c2c[nH]cn2)cn1]

Step 1: 4-iodo-1-((2-(trimethylsilyl)ethoxy)methyl)-1H-imidazole and 5-iodo-1-((2-(trimethylsilyl)ethoxy)methyl)-1H-imidazole and 5-iodo-1-((2-(trimethylsilyl)ethoxy)methyl)-1H-imidazole

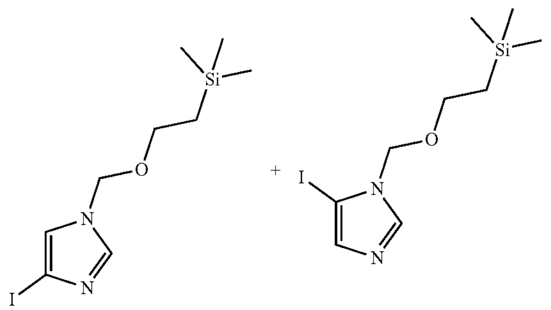

To a solution of 5-iodo-1H-imidazole (2 g, 10.3 mmol) in THF (15 mL) was added NaH (60% in mineral oil, 454 mg, 11.3 mmol) in portions at 0° C. The resulting mixture was stirred for 30 mins at 0° C. Then added a solution of (2-(chloromethoxy)ethyl)trimethylsilane (1.72 g, 10.8 mmol) in THF (5 mL) dropwise with stirring at 0° C. The reaction was warmed to room temperature with stirring for 1 h. The reaction was quenched by saturated $NH_4Cl$ at 0° C. and extracted with EA. The organic layer was washed with brine, dried over $Na_2SO_4$, concentrated to give the residue and purification by silica gel column with EA/DCM (1:1) to afford a mixture of 4-iodo-1-((2-(trimethylsilyl)ethoxy)methyl)-1H-imidazole and 5-iodo-1-((2-(trimethylsilyl)ethoxy)methyl)-1H-imidazole (2.66 g, 79.6%). MS (ESI) m/e $[M+1]^+$ 325.

Step 2: 2-chloro-5-(1-((2-(trimethylsilyl)ethoxy)methyl)-1H-imidazol-4-yl)pyridin-4-amine and 2-chloro-5-(1-((2-(trimethylsilyl)ethoxy)methyl)-1H-imidazol-5-yl)pyridin-4-amine

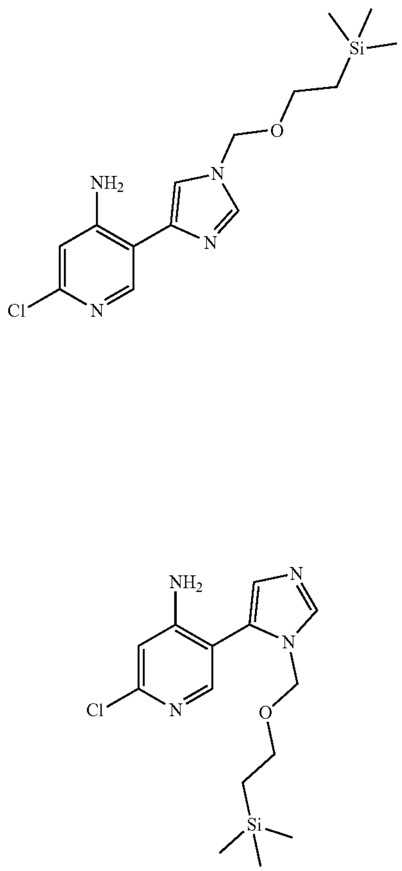

A mixture of 2-chloro-5-(1-((2-(trimethylsilyl)ethoxy)methyl)-1H-imidazol-4-yl)pyridin-4-amine and 2-chloro-5-(1-((2-(trimethylsilyl)ethoxy)methyl)-1H-imidazol-5-yl)pyridin-4-amine (966 mg, 4.98 mmol), 2-chloro-5-(4,4,5,5-tetramethyl-1,3,2-dioxaborolan-2-yl)pyridin-4-amine (1.39 g, 5.48 mmol), Pd(dppf)$Cl_2$ (182 mg, 0.25 mmol) and $K_2CO_3$ (1.37 g, 9.96 mmol) in 1,4-dioxane (18 mL) and $H_2O$ (3 mL) was charged with nitrogen and heated to 90° C. stirred for 1 h. The reaction was cooled to room temperature and diluted with EA, washed with brine, dried and concentrated. The residue was applied onto a silica gel column with EA/PE (1:2) to afford the product (862 mg, 89.2%). MS (ESI) m/e $[M+1]^+$ 325.

Step 3: N-(2-chloro-5-(1-((2-(trimethylsilyl)ethoxy)methyl)-1H-imidazol-4-yl)pyridin-4-yl)-6-(methylsulfonyl)pyridin-2-amine and N-(2-chloro-5-(1-((2-(trimethylsilyl)ethoxy)methyl)-1H-imidazol-5-yl)pyridin-4-yl)-6-(methylsulfonyl)pyridin-2-amine

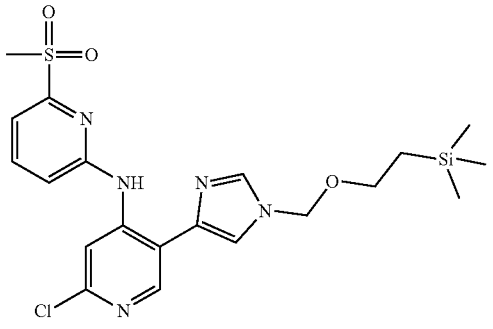

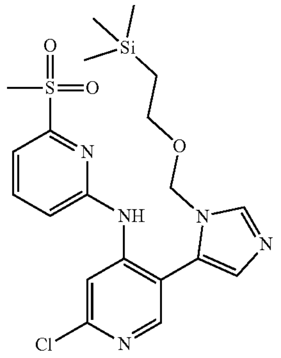

A mixture of 2-chloro-5-(1-((2-(trimethylsilyl)ethoxy)methyl)-1H-imidazol-4-yl)pyridin-4-amine and 2-chloro-5-(1-((2-(trimethylsilyl)ethoxy)methyl)-1H-imidazol-5-yl)pyridin-4-amine (412 mg, 1.27 mmol), 2-bromo-6-(methylsulfonyl)pyridine (358 mg, 1.5 mmol), $Pd_2dba_3$ (58 mg, 0.06 mmol), BINAP (118 mg, 0.19 mmol) and $Cs_2CO_3$ (829 mg, 2.5 mmol) in 1,4-dioxane (10 mL) was heated to 130° C. and stirred at this temperature for 3 h under nitrogen atmosphere. The reaction was cooled to room temperature, filtered and the filtration was concentrated under vacuum. The residue was applied onto Prep-TLC with DCM/MeOH (30:1) to afford the product (139 mg, 22.9%). MS (ESI) m/e $[M+1]^+$ 480.

Step 4: N-(4-((6-(methylsulfonyl)pyridin-2-yl)amino)-5-(1-((2-(trimethylsilyl)ethoxy)methyl)-1H-imidazol-4-yl)pyridin-2-yl)acetamide and N-(4-((6-(methylsulfonyl)pyridin-2-yl)amino)-5-(1-((2-(trimethylsilyl)ethoxy)methyl)-1H-imidazol-5-yl)pyridin-2-yl)acetamide

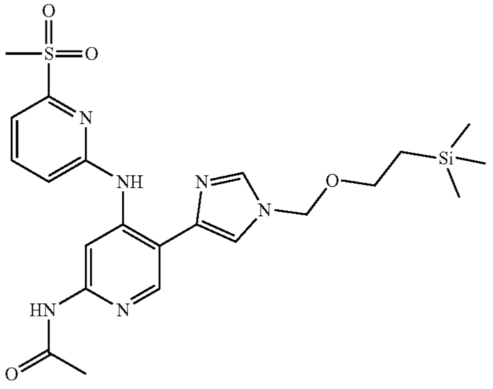

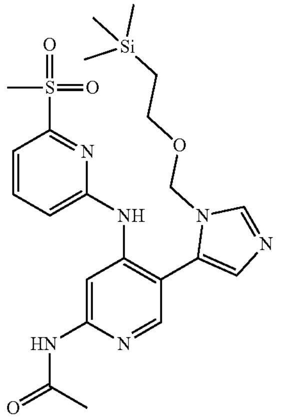

A mixture of N-(2-chloro-5-(1-((2-(trimethylsilyl)ethoxy)methyl)-1H-imidazol-4-yl)pyridin-4-yl)-6-(methylsulfonyl)pyridin-2-amine and N-(2-chloro-5-(1-((2-(trimethylsilyl)ethoxy)methyl)-1H-imidazol-5-yl)pyridin-4-yl)-6-(methylsulfonyl)pyridin-2-amine (139 mg, 0.29 mmol), acetamide (51 mg, 0.87 mmol), $Pd_2dba_3$ (26.6 mg, 0.03 mmol), Xantphos (50 mg, 0.09 mmol) and $Cs_2CO_3$ (189 mg, 0.58 mmol) in 1,4-dioxane (4 mL) was heated at 130° C. for 3 h under nitrogen atmosphere. The reaction was cooled to room temperature, filtered and the filtration was concentrated under vacuum. The residue was applied onto a silica gel column with DCM/MeOH (25:1) to afford the product (94 mg, 64.5%). MS (ESI) m/e $[M+1]^+$ 502.

Step 5: N-(5-(1H-imidazol-4-yl)-4-((6-(methylsulfonyl)pyridin-2-yl)amino)pyridin-2-yl)acetamide

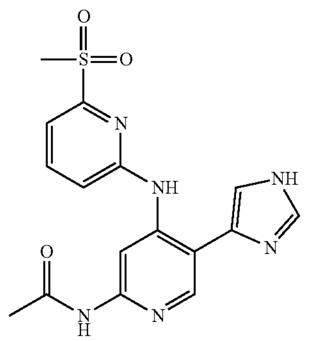 [SMILES: CC(=O)Nc1cc(Nc2cccc(S(C)(=O)=O)n2)c(-c2c[nH]cn2)cn1]

A solution of N-(4-((6-(methylsulfonyl)pyridin-2-yl)amino)-5-(1-((2-(trimethylsilyl)ethoxy)methyl)-1H-imidazol-4-yl)pyridin-2-yl)acetamide and N-(4-((6-(methylsulfonyl)pyridin-2-yl)amino)-5-(1-((2-(trimethylsilyl)ethoxy)methyl)-1H-imidazol-5-yl)pyridin-2-yl)acetamide (94 mg, 0.19 mmol) in TFA (5 mL) was heated to 50° C. stirred for 1 h. Then TFA was removed under vacuum and the residue was treated with $NH_3$ in MeOH (4 mL, 7M). The solvent was removed under vacuum and the residue was applied onto a $C^{18}$ column with $CH_3CN$/water to afford N-(5-(1H-imidazol-4-yl)-4-((6-(methylsulfonyl)pyridin-2-yl)amino)pyridin-2-yl)acetamide (31.04 mg, 43.9%). $^1H$ NMR (400 MHz, DMSO-$d_6$) δ 12.71 (s, 1H), 12.67 (s, 1H), 10.38 (s, 1H), 9.21 (s, 1H), 8.63 (s, 1H), 8.04-7.93 (m, 2H), 7.88 (s, 1H), 7.54 (d, J=8.2 Hz, 1H), 7.23 (d, J=8.2 Hz, 1H), 3.49 (s, 3H), 2.10 (s, 3H). MS (ESI) m/e $[M+1]^+$ 373.

Example A25: Synthesis of N-(4-((4-(cyclopropylmethoxy)-6-(methylsulfonyl)pyridin-2-yl)amino)-5-(6-methoxypyridazin-3-yl)pyridin-2-yl)acetamide

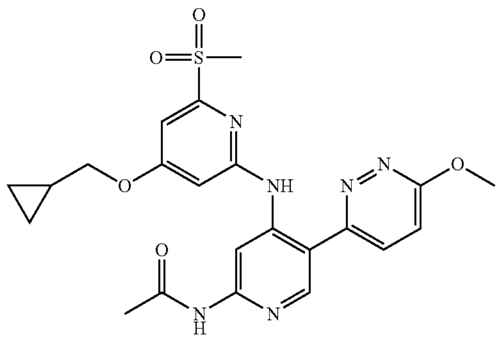 [SMILES: COc1ccc(-c2cnc(NC(C)=O)cc2Nc2cc(OCC3CC3)cc(S(C)(=O)=O)n2)nn1]

A mixture of N-(4-amino-5-(6-methoxypyridazin-3-yl)pyridin-2-yl)acetamide (50 mg, 0.19 mmol), 2-bromo-4-(cyclopropylmethoxy)-6-(methylsulfonyl)pyridine (71 mg, 0.23 mmol), $Pd_2(dba)_3$ (17 mg, 0.019 mmol), BINAP (12 mg, 0.019 mmol) and $Cs_2CO_3$ (186 mg, 0.57 mmol) in dioxane (5 mL) was stirred for 16 h at 120° C. under nitrogen atmosphere. After cooled to room temperature, the resulting mixture was filtered. The filtrate was concentrated under reduced pressure. The residue was purified by combi-flash (MeOH/DCM=0-10%) to give the product (0.84 mg, 22%). $^1H$ NMR (400 MHz, DMSO-$d_6$) δ 11.39 (s, 1H), 10.58 (s, 1H), 8.96 (s, 1H), 8.65 (s, 1H), 8.25 (d, J=8.0 Hz, 1H), 7.41 (d, J=8.0 Hz, 1H), 7.10 (s, 1H), 6.82 (s, 1H), 4.11 (s, 3H), 4.06-4.02 (m, 2H), 3.37 (s, 3H), 2.12 (s, 3H), 1.26-1.24 (m, 1H), 0.61-0.60 (m, 2H), 0.38-0.37 (m, 2H). MS (ESI) m/e $[M+1]^+$ 485.

Example A26: Synthesis of N-(4-((4-isopropoxy-6-(methylsulfonyl)pyridin-2-yl)amino)-5-(6-methoxypyridazin-3-yl)pyridin-2-yl)acetamide

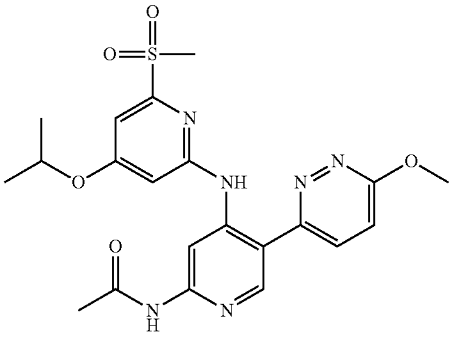 [SMILES: COc1ccc(-c2cnc(NC(C)=O)cc2Nc2cc(OC(C)C)cc(S(C)(=O)=O)n2)nn1]

A mixture of N-(4-amino-5-(6-methoxypyridazin-3-yl)pyridin-2-yl)acetamide (50 mg, 0.19 mmol), 2-bromo-4-isopropoxy-6-(methylsulfonyl)pyridine (67 mg, 0.23 mmol), $Pd_2(dba)_3$ (17 mg, 0.019 mmol), BINAP (12 mg, 0.019 mmol) and $Cs_2CO_3$ (186 mg, 0.57 mmol) in dioxane (5 mL) was stirred for 16 h at 120° C. under nitrogen atmosphere. The mixture was allowed to cool down to room temperature. The resulting mixture was filtered. The filtrate was concentrated under reduced pressure. The residue was purified by combi-flash (MeOH/DCM=0-10%) to give the product (4.20 mg, 4%). $^1H$ NMR (400 MHz, DMSO-$d_6$) δ 11.25 (s, 1H), 10.52 (s, 1H), 8.91 (s, 1H), 8.59 (s, 1H), 8.19 (d, J=8.0 Hz, 1H), 7.36 (d, J=8.0 Hz, 1H), 7.02 (s, 1H), 6.74 (s, 1H), 4.95-4.66 (m, 1H), 4.07 (s, 3H), 3.32 (s, 3H), 2.07 (s, 3H), 1.28 (d, J=4.0 Hz, 6H). MS (ESI) m/e $[M+1]^+$ 473.

The following Examples were prepared in a similar manner to the product Example A3:

| Example | Compound | Chemical Name | $^1$H NMR and LC/MS m/z (M + 1) |
|---|---|---|---|
| A4 | 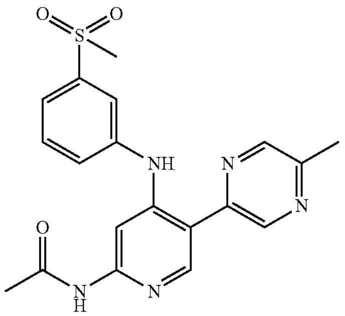 [SMILES: CC(=O)Nc1cc(Nc2cccc(S(C)(=O)=O)c2)c(-c2cnc(C)cn2)cn1] | N-(5-(5-methylpyrazin-2-yl)-4-((3-(methylsulfonyl)phenyl) amino)pyridin-2-yl)acetamide | $^1$H NMR (400 MHz, $CD_3OD$) δ: 9.00 (s, 1 H), 8.60 (s, 1 H), 8.58 (s, 1 H), 8.16 (s, 1 H), 7.88 (s, 1 H), 7.69-7.56 (m, 3 H), 3.20 (s, 3 H), 2.58 (s, 3 H), 2.12 (s, 3 H). MS (ESI) m/e $[M + 1]^+$ 398. |
| A5 | 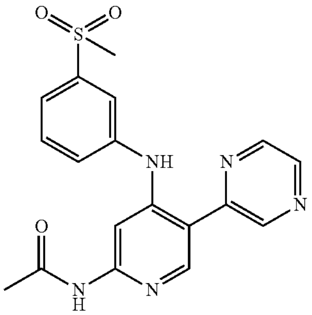 [SMILES: CC(=O)Nc1cc(Nc2cccc(S(C)(=O)=O)c2)c(-c2cnccn2)cn1] | N-(4-((3-(methylsulfonyl) phenyl)amino)-5-(pyrazin-2-yl)pyridin-2-yl)acetamide | $^1$H NMR (400 MHz, DMSO-$d_6$) δ 10.55 (s, 1H), 10.43 (s, 1H), 9.25 (s, 1H), 8.74-8.68 (m, 2H), 8.61 (s, 1H), 8.17 (s, 1H), 7.80 (s, 1H), 7.66-7.58 (m, 3H), 3.27 (s, 3H), 2.07 (s, 3H). MS (ESI) m/e $[M + 1]^+$ 384. |
| A6 | 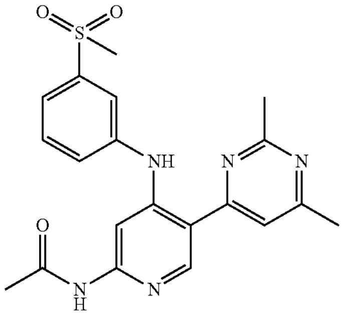 [SMILES: CC(=O)Nc1cc(Nc2cccc(S(C)(=O)=O)c2)c(-c2cc(C)nc(C)n2)cn1] | N-(5-(2,6-dimethylpyrimidin-4-yl)-4-((3-(methylsulfonyl)phenyl) amino)pyridin-2-yl)acetamide | $^1$H NMR (400 MHz, DMSO-$d_6$) δ 11.73 (s, 1H), 10.60 (s, 1H), 8.82 (s, 1H), 8.19 (s, 1H), 7.90-7.85 (m, 2H), 7.74-7.58 (m, 3H), 3.33 (s, 3H), 3.30 (s, 3H), 2.68 (s, 3H), 2.07 (s, 3H). MS (ESI) m/e $[M + 1]^+$ 412. |
| A7 | 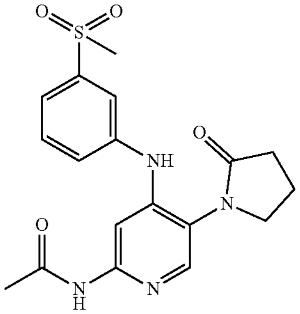 [SMILES: CC(=O)Nc1cc(Nc2cccc(S(C)(=O)=O)c2)c(N2CCCC2=O)cn1] | N-(4-((3-(methylsulfonyl)phenyl) amino)-5-(2-oxopyrrolidin-1-yl)pyridin-2-yl)acetamide | $^1$H NMR (300 MHz, DMSO-$d_6$) δ 10.40 (s, 1H), 8.45 (s, 1H), 8.05-8.00 (m, 2H), 7.75-7.70 (m, 1H), 7.68-7.47 (m, 3H), 3.65-3.60 (m, 2H), 2.45 (s, 3H), 2.10-2.05 (m, 2H), 2.06 (s, 3H). 2.05-2.00 (m, 2H), MS (ESI) m/e $[M + 1]^+$ 389. |
| A8 | 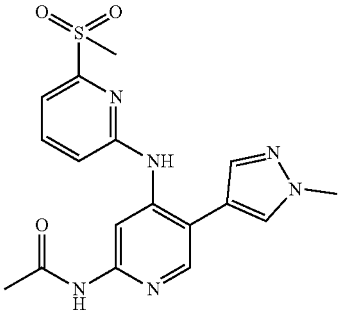 [SMILES: CC(=O)Nc1cc(Nc2cccc(S(C)(=O)=O)n2)c(-c2cnn(C)c2)cn1] | N-(5-(1-methyl-1H-pyrazol-4-yl)-4-((6-(methylsulfonyl) pyridin-2-yl)amino)pyridin-2-yl)acetamide | $^1$H NMR (400 MHz, DMSO-$d_6$) δ 10.42 (s, 1H), 8.91 (s, 1H), 8.71 (s, 1H), 8.21 (s, 1H), 8.02 (s, 1H), 7.95-7.85 (m, 1H), 7.69 (s, 1H), 7.50-7.40 (m, 1H), 7.35-7.25 (m, 1H), 3.86 (s, 3H), 3.28 (s, 3H), 2.06 (s, 3H). MS (ESI) m/e $[M + 1]^+$ 387. |

-continued

| Example | Compound | Chemical Name | $^1$H NMR and LC/MS m/z (M + 1) |
|---|---|---|---|
| A9 | 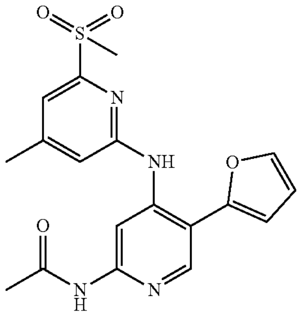 [SMILES: CC(=O)Nc1cc(Nc2cc(C)cc(S(C)(=O)=O)n2)c(-c2ccco2)cn1] | N-(5-(furan-2-yl)-4-((4-methyl-6-(methylsulfonyl)pyridin-2-yl)amino)pyridin-2-yl)acetamide | $^1$H NMR (400 MHz, DMSO-$d_6$) δ 10.52 (s, 1H), 9.06 (s, 1H), 8.74 (s, 1H), 8.44 (s, 1H), 7.77 (d, J = 0.7 Hz, 1H), 7.38-7.33 (m, 1H), 7.17-7.11 (m, 1H), 6.78 (d, J = 3.4 Hz, 1H), 6.61 (d, J = 3.4 Hz, 1H), 3.24 (s, 3H), 2.35 (s, 3H), 2.07 (s, 3H). MS (ESI) m/e [M + 1]$^+$ 387. |
| A10 | 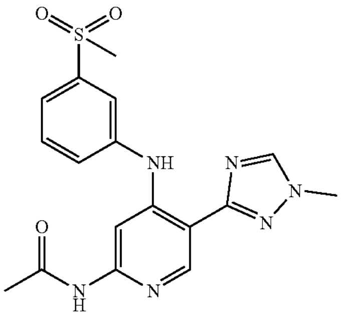 [SMILES: CC(=O)Nc1cc(Nc2cccc(S(C)(=O)=O)c2)c(-c2ncn(C)n2)cn1] | N-(5-(1-methyl-1H-1,2,4-triazol-3-yl)-4-((3-(methylsulfonyl)phenyl)amino)pyridin-2-yl)acetamide | $^1$H NMR (400 MHz, $CDCl_3$) δ = 10.16 (s, 1H), 8.98 (s, 1H), 8.25 (s, 1H), 8.12 (s, 2H), 7.97 (s, 1H), 7.71 (d, J = 7.2 Hz, 1H), 7.66-7.58 (m, 2H), 4.03 (s, 3H), 3.21 (s, 3H), 2.17 (s, 3H). MS (ESI) m/e [M + 1]$^+$ 387. |
| A11 | 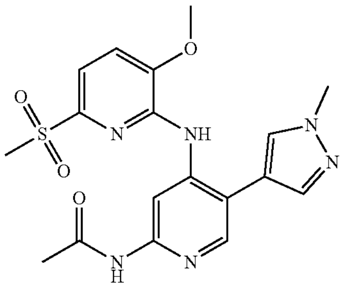 [SMILES: COc1ccc(S(C)(=O)=O)nc1Nc1cc(NC(C)=O)ncc1-c1cnn(C)c1] | N-(4-((3-methoxy-6-(methylsulfonyl)pyridin-2-yl)amino)-5-(1-methyl-1H-pyrazol-4-yl)pyridin-2-yl)acetamide | $^1$H NMR (400 MHz, DMSO-$d_6$) δ 10.45 (s, 1H), 9.25 (s, 1H), 8.19 (s, 1H), 8.15 (s, 1H), 8.12 (s, 1H), 7.77 (s, 1H), 7.58 (d, J = 8.2 Hz, 1H), 7.51 (d, J = 8.2 Hz, 1H), 3.95 (s, 3H), 3.92 (s, 3H), 3.43 (s, 3H), 2.11 (s, 3H). MS (ESI) m/e [M + 1]$^+$ 417. |
| A12 | 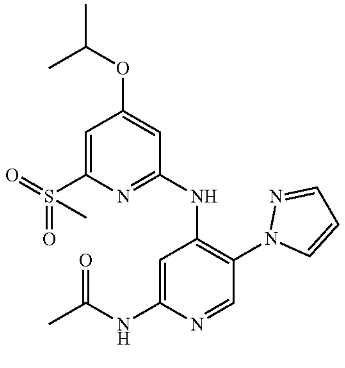 [SMILES: CC(=O)Nc1cc(Nc2cc(OC(C)C)cc(S(C)(=O)=O)n2)c(-n2cccn2)cn1] | N-(4-((4-isopropoxy-6-(methylsulfonyl)pyridin-2-yl)amino)-5-(1H-pyrazol-1-yl)pyridin-2-yl)acetamide | $^1$H NMR (400 MHz, DMSO-$d_6$) δ 10.59 (s, 1H), 9.65 (s, 1H), 9.02 (s, 1H), 8.34 (s, 1H), 8.30 (d, J = 2.4 Hz, 1H), 7.90 (s, 1H), 7.03 (d, J = 2.4 Hz, 1H), 6.85 (s, 1H), 6.70-6.60 (m, 1H), 4.81 (s, 1H), 3.37 (s, 3H), 2.11 (s, 3H), 1.31 (d, J = 6.0 Hz, 6H). MS (ESI) m/e [M + 1]$^+$ 431. |

-continued

| Example | Compound | Chemical Name | $^1$H NMR and LC/MS m/z (M + 1) |
|---|---|---|---|
| A13 | 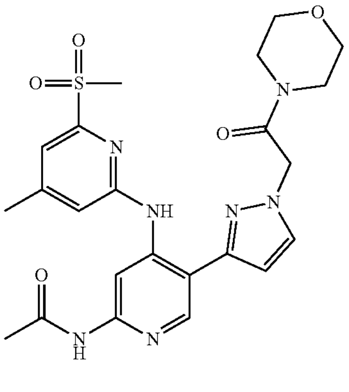 [SMILES: CC(=O)Nc1cc(Nc2cc(C)cc(S(C)(=O)=O)n2)c(-c2ccn(CC(=O)N3CCOCC3)n2)cn1] | N-(4-((4-methyl-6-(methylsulfonyl)pyridin-2-yl)amino)-5-(1-(2-morpholino-2-oxoethyl)-1H-pyrazol-3-yl)pyridin-2-yl)acetamide | $^1$H NMR (400 MHz, DMSO-$d_6$) δ 11.44 (s, 1H), 10.50 (s, 1H), 9.26 (s, 1H), 8.63 (s, 1H), 7.89 (d, J = 4.0 Hz, 1H), 7.46 (s, 1H), 7.16 (s, 1H), 6.93 (d, J = 4.0 Hz, 1H), 5.38 (s, 2H), 3.68-3.64 (m, 2H), 3.60-3.55 (m, 4H), 3.54-3.50 (m, 2H), 3.48 (s, 3H), 2.42 (s, 3H), 2.12 (s, 3H). MS (ESI) m/e [M + 1]$^+$ 514. |
| A14 | 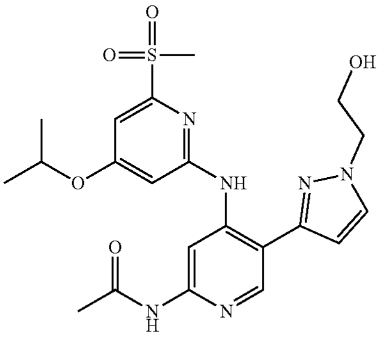 [SMILES: CC(=O)Nc1cc(Nc2cc(OC(C)C)cc(S(C)(=O)=O)n2)c(-c2ccn(CCO)n2)cn1] | N-(5-(1-(2-hydroxyethyl)-1H-pyrazol-3-yl)-4-((4-isopropoxy-6-(methylsulfonyl) pyridin-2-yl)amino)pyridin-2-yl)acetamide | $^1$H NMR (400 MHz, DMSO-$d_6$) δ 11.43 (s, 1H), 10.42 (s, 1H), 9.19 (s, 1H), 8.62 (s, 1H), 7.90 (d, J = 2.3 Hz, 1H), 7.06 (s, 1H), 6.91 (d, J = 2.3 Hz, 1H), 6.74 (s, 1H), 5.00 (s, 1H), 4.90-4.83 (m, 1H), 4.36-4.29 (m, 2H), 3.90-3.83 (m, 2H), 3.46 (s, 3H), 2.11 (s, 3H), 1.34 (d, J = 6.0 Hz, 6H). MS (ESI) m/e [M + 1]$^+$ 475. |
| A15 | 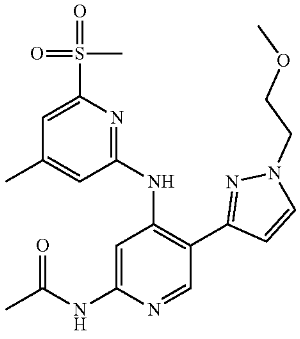 [SMILES: COCCn1ccc(-c2cnc(NC(C)=O)cc2Nc2cc(C)cc(S(C)(=O)=O)n2)n1] | N-(5-(1-(2-methoxyethyl)-1H-pyrazol-3-yl)-4-((4-methyl-6-(methylsulfonyl)pyridin-2-yl)amino)pyridin-2-yl)acetamide | $^1$H NMR (400 MHz, DMSO-$d_6$) δ 11.57 (s, 1H), 10.54 (s, 1H), 9.21 (s, 1H), 8.65 (s, 1H), 7.92 (d, J = 4.1 Hz, 1H), 7.47 (s, 1H), 7.17 (s, 1H), 6.95 (d, J = 4.1 Hz, 1H), 4.49-4.45 (m, 2H), 3.80-3.75 (m, 2H), 3.47 (s, 3H), 3.28 (s, 3H), 2.45 (s, 3H), 2.12 (s, 3H). MS (ESI) m/e [M + 1]$^+$ 445. |
| A16 | 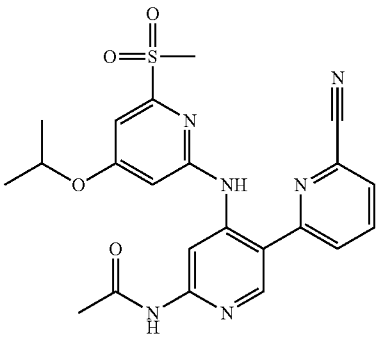 [SMILES: CC(=O)Nc1cc(Nc2cc(OC(C)C)cc(S(C)(=O)=O)n2)c(-c2cccc(C#N)n2)cn1] | N-(6-cyano-4'-((4-isopropoxy-6-(methylsulfonyl)pyridin-2-yl)amino)-[2,3'-bipyridin]-6'-yl)acetamide | $^1$H NMR (400 MHz, DMSO-$d_6$) δ 11.03 (s, 1H), 10.61 (s, IH), 9.04 (s, 1H), 8.68 (s, 1H), 8.28 (d, J = 8.4 Hz, 1H), 8.20-8.15 (m, 1H), 8.04 (d, J = 8.4 Hz, 1H), 7.16-7.04 (m, 1H), 6.75-6.70 (m, 1H), 4.80-4.46 (m, 1H), 3.39 (s, 3H), 2.13 (s, 3H), 1.34 (d, J = 5.9 Hz, 6H). MS (ESI) m/e [M + 1]$^+$ 467. |

-continued

| Example | Compound | Chemical Name | $^1$H NMR and LC/MS m/z (M + 1) |
|---|---|---|---|
| A17 | 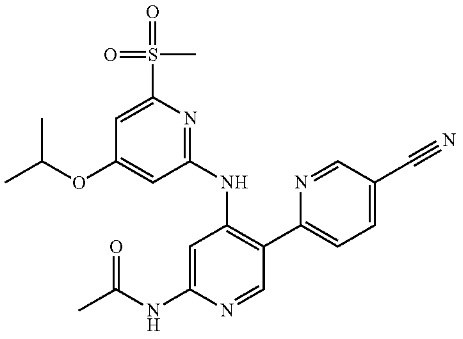 [SMILES: CC(=O)Nc1cc(Nc2cc(OC(C)C)cc(S(C)(=O)=O)n2)c(-c2ccc(C#N)cn2)cn1] | N-(5-cyano-4'-((4-isopropoxy-6-(methylsulfonyl) pyridin-2-yl)amino)-[2,3'-bipyridin]-6'-yl)acetamide | $^1$H NMR (400 MHz, DMSO-$d_6$) δ 11.92 (s, 1H), 10.57 (s, 1H), 9.18 (s, 1H), 9.10 (s, 1H), 8.77 (s, 1H), 8.39 (d, J = 8.6 Hz, 1H), 8.22 (d, J = 8.6 Hz, 1H), 7.04 (s, 1H), 6.84 (s, 1H), 4.89-4.83 (m, 1H), 3.37 (s, 3H), 2.08 (s, 3H), 1.29 (d, J = 5.9 Hz, 6H). MS (ESI) m/e [M + 1]$^+$ 467. |
| A18 | 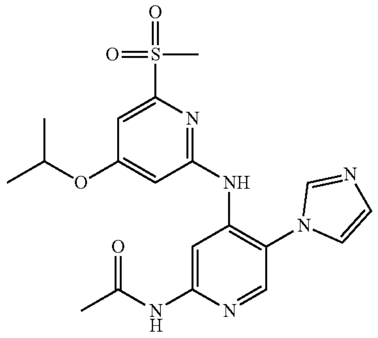 [SMILES: CC(=O)Nc1cc(Nc2cc(OC(C)C)cc(S(C)(=O)=O)n2)c(-n2ccnc2)cn1] | N-(5-(1H-imidazol-1-yl)-4-((4-isopropoxy-6-(methylsulfonyl)pyridin-2-yl)amino)pyridin-2-yl)acetamide | $^1$H NMR (400 MHz, DMSO-$d_6$) δ 10.59 (s, 1H), 8.91 (s, 1H), 8.83 (s, 1H), 8.13 (s, 1H), 7.94 (d, J = 1.9 Hz, 1H), 7.42 (s, 1H), 7.14 (s, 1H), 7.00 (d, J = 1.9 Hz, 1H), 6.86 (s, 1H), 4.73-4.67 (m, 1H), 3.33 (s, 3H), 2.10 (s, 3H), 1.30 (d, J = 6.0 Hz, 6H). MS (ESI) m/e [M + 1]$^+$ 431. |
| A19 | 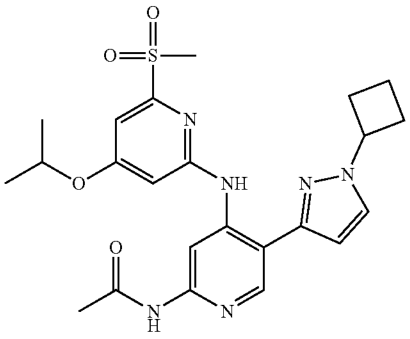 [SMILES: CC(=O)Nc1cc(Nc2cc(OC(C)C)cc(S(C)(=O)=O)n2)c(-c2ccn(C3CCC3)n2)cn1] | N-(5-(1-cyclobutyl-1H-pyrazol-3-yl)-4-((4-isopropoxy-6-(methylsulfonyl)pyridin-2-yl)amino)pyridin-2-yl)acetamide | $^1$H NMR (400 MHz, DMSO-$d_6$) δ 11.49 (s, 1H), 10.50 (s, 1H), 9.12 (s, 1H), 8.66 (s, 1H), 8.00 (d, J = 2.2 Hz, 1H), 7.07 (s, 1H), 6.95 (d, J = 2.2 Hz, 1H), 6.72 (s, 1H), 5.07-4.96 (m, 1H), 4.95-4.79 (m, 1H), 3.45 (s, 5H), 2.71-2.53 (m, 2H), 2.50-2.42 (m, 3H), 2.12 (s, 3H), 1.91-1.81 (m, 2H), 1.35 (d, J = 5.9 Hz, 6H). MS (ESI) m/e [M + 1]$^+$ 485. |
| A20 | 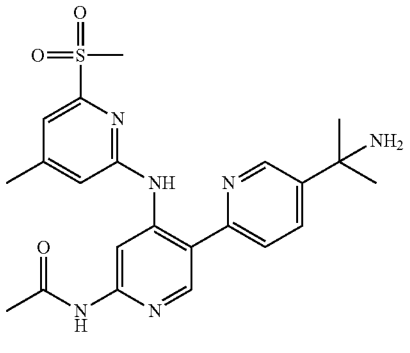 [SMILES: CC(=O)Nc1cc(Nc2cc(C)cc(S(C)(=O)=O)n2)c(-c2ccc(C(C)(C)N)cn2)cn1] | N-(5-(2-aminopropan-2-yl)-4'-((4-methyl-6-(methylsulfonyl)pyridin-2-yl)amino)-[2,3'-bipyridin]-6'-yl)acetamide | $^1$H NMR (400 MHz, DMSO-$d_6$) δ 12.88 (s, 1H), 10.54 (s, 1H), 9.23 (s, 1H), 8.99-8.95 (m, 1H), 8.85 (s, 1H), 8.45-8.40 (m, 2H), 8.26-8.18 (m, 2H), 7.46 (s, 1H), 7.24 (s, 1H), 3.45 (s, 3H), 2.44 (s, 3H), 2.13 (s, 3H), 1.73 (s, 6H). MS (ESI) m/e [M + 1]$^+$ 455. |

-continued

| Example | Compound | Chemical Name | $^1$H NMR and LC/MS m/z (M + 1) |
|---|---|---|---|
| A21 | 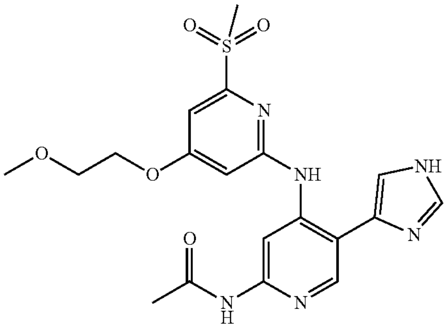 [SMILES: COCCOc1cc(Nc2cc(NC(C)=O)ncc2-c2c[nH]cn2)nc(S(C)(=O)=O)c1] | N-(5-(1H-imidazol-4-yl)-4-((4-(2-methoxyethoxy)-6-(methylsulfonyl)pyridin-2-yl)amino)pyridin-2-yl)acetamide | MS (ESI) m/e [M + 1]$^+$ 447. |
| A22 | 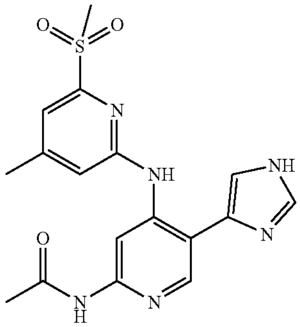 [SMILES: CC(=O)Nc1cc(Nc2cc(C)cc(S(C)(=O)=O)n2)c(-c2c[nH]cn2)cn1] | N-(5-(1H-imidazol-4-yl)-4-((4-methyl-6-(methylsulfonyl)pyridin-2-yl)amino)pyridin-2-yl)acetamide | MS (ESI) m/e [M + 1]$^+$ 387. |
| A23 | 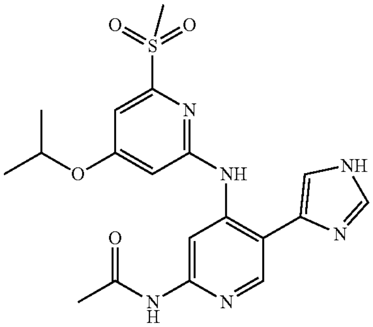 [SMILES: CC(=O)Nc1cc(Nc2cc(OC(C)C)cc(S(C)(=O)=O)n2)c(-c2c[nH]cn2)cn1] | N-(5-(1H-imidazol-4-yl)-4-((4-isopropoxy-6-(methylsulfonyl)pyridin-2-yl)amino)pyridin-2-yl)acetamide | MS (ESI) m/e [M + 1]$^+$ 431. |
| A24 | 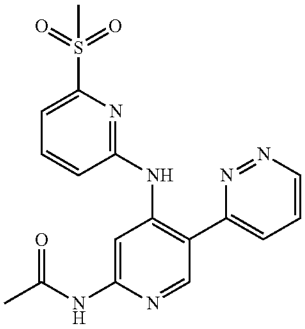 [SMILES: CC(=O)Nc1cc(Nc2cccc(S(C)(=O)=O)n2)c(-c2cccnn2)cn1] | N-(4-((6-(methylsulfonyl)pyridin-2-yl)amino)-5-(pyridazin-3-yl)pyridin-2-yl)acetamide | Molecular Weight: 384 |

-continued

| Example | Compound | Chemical Name | $^1$H NMR and LC/MS m/z (M + 1) |
|---|---|---|---|
| A27 | 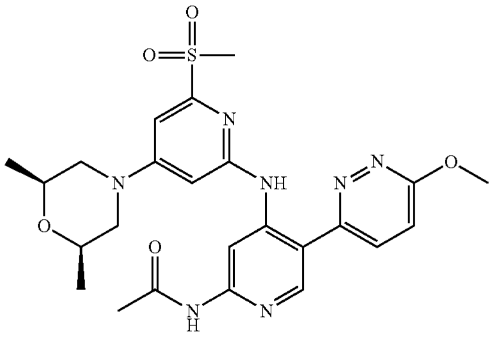 | N-(4-((4-((2S,6R)-2,6-dimethylmorpholino)-6-(methylsulfonyl)pyridin-2-yl)amino)-5-(6-methoxypyridazin-3-yl)pyridin-2-yl)acetamide | Molecular Weight: 528 |
| A28 | 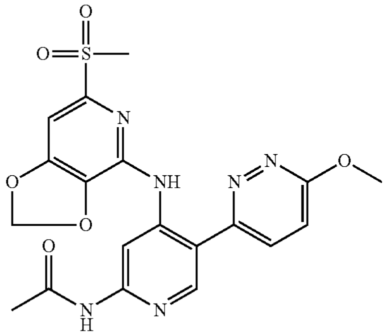 [SMILES: COc1ccc(-c2cnc(NC(C)=O)cc2Nc2nc(S(C)(=O)=O)cc3c2OCO3)nn1] | N-(5-(6-methoxypyridazin-3-yl)-4-((6-(methylsulfonyl)-[1,3]dioxolo[4,5-c]pyridin-4-yl)amino)pyridin-2-yl)acetamide | Molecular Weight: 459 |
| A29 | 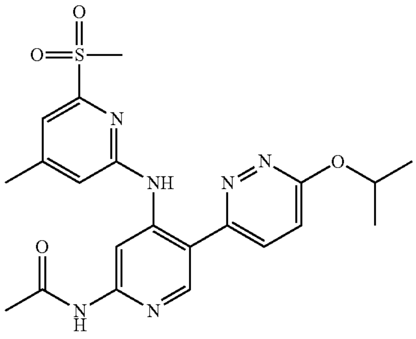 [SMILES: CC(=O)Nc1cc(Nc2cc(C)cc(S(C)(=O)=O)n2)c(-c2ccc(OC(C)C)nn2)cn1] | N-(5-(6-isopropoxypyridazin-3-yl)-4-((4-methyl-6-(methylsulfonyl)pyridin-2-yl)amino)pyridin-2-yl)acetamide | Molecular Weight:457 |
| A30 | 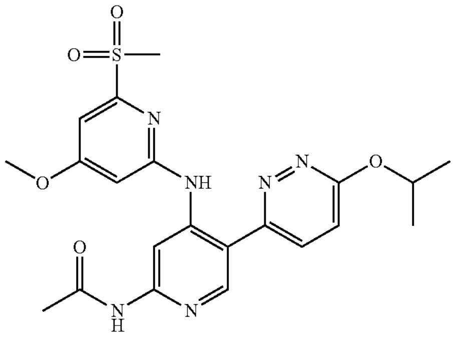 [SMILES: COc1cc(Nc2cc(NC(C)=O)ncc2-c2ccc(OC(C)C)nn2)nc(S(C)(=O)=O)c1] | N-(5-(6-isopropoxypyridazin-3-yl)-4-((4-methoxy-6-(methylsulfonyl)pyridin-2-yl)amino)pyridin-2-yl)acetamide | Molecular Weight: 473 |

-continued

| Example | Compound | Chemical Name | $^1$H NMR and LC/MS m/z (M + 1) |
| --- | --- | --- | --- |
| A31 | 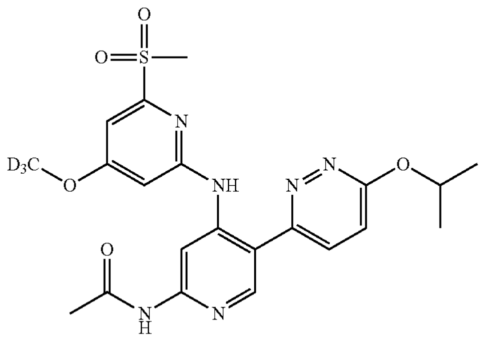 [SMILES: [2H]C([2H])([2H])Oc1cc(Nc2cc(NC(C)=O)ncc2-c2ccc(OC(C)C)nn2)nc(S(C)(=O)=O)c1] | N-(5-(6-isopropoxypyridazin-3-yl)-4-(4-(methoxy-d3)-6-(methylsulfonyl)pyridin-2-ylamino)pyridin-2-yl)acetamide | Molecular Weight: 476 |

Example B1: Synthesis of N-(4'-((3-(methylsulfonyl)phenyl)amino)-[2,3'-bipyridin]-6'-yl)acetamide

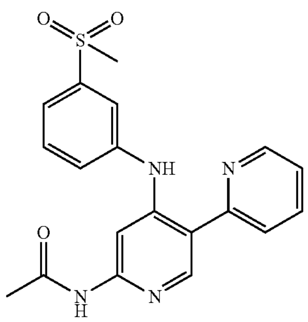 [SMILES: CC(=O)Nc1cc(Nc2cccc(S(C)(=O)=O)c2)c(-c2ccccn2)cn1]

Step 1: tert-butyl (5-bromo-2-chloropyridin-4-yl)carbamate

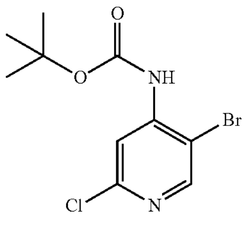 [SMILES: CC(C)(C)OC(=O)Nc1cc(Cl)ncc1Br]

To a mixture of 5-bromo-2-chloropyridin-4-amine (30 g, 144.6 mmol), DMAP (1.8 g, 14.4 mmol), TEA (43.9 g, 434.0 mmol) in DCM (300 mL) was added $Boc_2O$ (38.0 g, 173.0 mmol) dropwise at room temperature and the resulting mixture was stirred at this temperature for 12 h. Upon completion of the reaction, the solvent was removed in vacuo and the residue was purified by silica gel column chromatography (PE/EA=20:1 to 5:1) to give tert-butyl (5-bromo-2-chloropyridin-4-yl)carbamate (40.0 g, 90.2% yield). $^1$H NMR (400 MHz, $CDCl_3$) δ 8.35 (s, 1H), 8.25 (s, 1H), 7.19 (s, 1H), 1.56 (s, 9H). MS (ESI) m/e $[M+1]^+$ 307.

Step 2: tert-butyl (6'-chloro-[2,3'-bipyridin]-4'-yl)carbamate

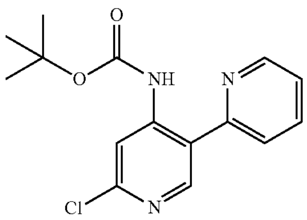 [SMILES: CC(C)(C)OC(=O)Nc1cc(Cl)ncc1-c1ccccn1]

A mixture of tert-butyl (5-bromo-2-chloropyridin-4-yl)carbamate (5.0 g, 16.3 mmol), 2-bromopyridine (2.8 g, 17.9 mmol), $Pd(PPh_3)_2Cl_2$ (1.1 g, 1.6 mmol), $Pd(PPh_3)_4$ (1.9 g, 1.6 mmol) and $Sn_2Me_6$ (8.0 g, 24.0 mmol) in dioxane (50 mL) was stirred at 110° C. for 12 h under nitrogen atmosphere. After cooled to room temperature, the mixture was diluted with KF—$H_2O$ (50 mL) and extracted with EA (50 mL×3). The combined organic layers were dried over anhydrous $Na_2SO_4$ and concentrated under vacuum. The residue was purified by silica gel column chromatography (PE/EA=20:1 to 10:1) to give tert-butyl (6'-chloro-[2,3'-bipyridin]-4'-yl)carbamate (880 mg, 18.0%). MS (ESI) m/e $[M+1]^+$ 306.

Step 3: tert-butyl (6'-acetamido-[2,3'-bipyridin]-4'-yl)carbamate

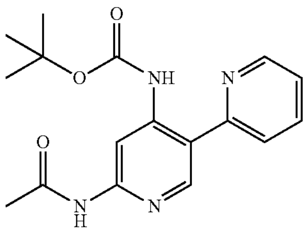 [SMILES: CC(=O)Nc1cc(NC(=O)OC(C)(C)C)c(-c2ccccn2)cn1]

A mixture of tert-butyl (6'-chloro-[2,3'-bipyridin]-4'-yl)carbamate (2.0 g, 6.5 mmol), acetamide (773 mg, 13.1 mmol), $Cs_2CO_3$ (6.3 g, 19.5 mmol), Xant-Phos (753 mg, 1.3 mmol) and $Pd_2(dba)_3$ (595 mg, 0.65 mmol) in dioxane (20 mL) was stirred at 110° C. for 12 h under nitrogen atmosphere. After cooled to room temperature, the solvent was removed in vacuo and the residue was diluted with water (20 mL). The resulting solution was extracted with EA (30 mL×3) and the combined organic layers were washed with 50 mL of brine, dried over anhydrous sodium sulfate. The solvent was removed in vacuo and the residue was purified by silica gel column chromatography (PE/EA=3:1 to 1:1) to give tert-butyl (6'-acetamido-[2,3'-bipyridin]-4'-yl)carbamate (1.3 g, 61.0%). $^1H$ NMR (400 MHz, DMSO-$d_6$) δ 12.02 (s, 1H), 10.50 (s, 1H), 8.98 (s, 1H), 8.73 (s, 1H), 8.68-8.63 (m, 1H), 8.10-8.05 (m, 1H), 7.98 (m, 1H), 7.45-7.40 (m, 1H), 2.11 (s, 3H), 1.50-1.47 (m, 9H). MS (ESI) m/e $[M+1]^+$ 329.

Step 4: N-(4'-amino-[2,3'-bipyridin]-6'-yl)acetamide

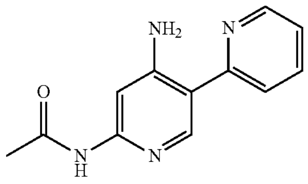 [SMILES: CC(=O)Nc1cc(N)c(-c2ccccn2)cn1]

A mixture of tert-butyl (6'-acetamido-[2,3'-bipyridin]-4'-yl)carbamate (4.0 g, 12.2 mmol) in TFA (20 mL) and DCM (20 mL) was stirred at room temperature for 3 h. Upon completion of the reaction, the solvent was removed in vacuo and the residue diluted with water. $NaHCO_3$ (40 mL) was added to adjust the pH value to 9 and the resulting solution was extracted with EA (40 mL×3). The combined organic layers were dried over anhydrous $Na_2SO_4$ and concentrated in vacuo to give N-(4'-amino-[2,3'-bipyridin]-6'-yl)acetamide (2.7 g, 97.1%). $^1H$ NMR (400 MHz, DMSO-$d_6$) δ 10.35 (s, 1H), 8.60 (d, J=4.9 Hz, 1H), 8.42 (s, 1H), 7.90-7.86 (m, 2H), 7.38 (s, 1H), 6.88 (s, 2H), 7.33-7.28 (m, 1H), 2.09 (s, 3H). MS (ESI) m/e $[M+1]^+$ 229.

Step 5: N-(4'-((3-(methylsulfonyl)phenyl)amino)-[2,3'-bipyridin]-6'-yl)acetamide

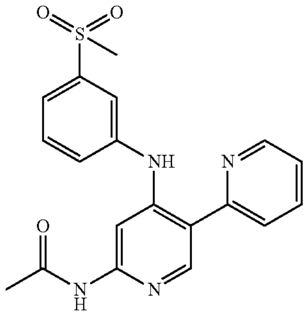 [SMILES: CC(=O)Nc1cc(Nc2cccc(S(C)(=O)=O)c2)c(-c2ccccn2)cn1]

A mixture of N-(4'-amino-[2,3'-bipyridin]-6'-yl)acetamide (120 mg, 0.53 mmol), 1-bromo-3-(methyl sulfonyl) benzene (120 mg, 0.5 mmol), $Pd_2dba_3$ (80 mg, 0.09 mmol), Xant-Phos (60 mg, 0.1 mmol) and $Cs_2CO_3$ (300 mg, 0.92 mmol) in dioxane (6 mL) was stirred at 130° C. under $N_2$ in a sealed tube for 3 h. The reaction mixture was filtered and the solid was washed with EA (10 mL). The filtrate was concentrated and the residue was purified by prep-TLC (DCM/MeOH=20:1) to give N-(4'-((3-(methylsulfonyl)phenyl)amino)-[2,3'-bipyridin]-6'-yl)acetamide (24 mg, 12%). $^1H$ NMR (400 MHz, DMSO-$d_6$) δ 11.52 (s, 1H), 10.50 (s, 1H), 8.74-8.66 (m, 2H), 8.18 (s, 1H), 8.07 (d, J=8.2 Hz, 1H), 7.99-7.90 (m, 1H), 7.83 (s, 1H), 7.67-7.57 (m, 3H), 7.45-7.37 (m, 1H), 3.29 (s, 3H), 2.07 (s, 3H). MS (ESI) m/e $[M+1]^+$ 383.

The following Examples were prepared in a similar manner to the product Example B1:

| Example | Compound | Chemical Name | $^1H$ NMR and LC /MS m/z (M + 1) |
|---|---|---|---|
| B2 | 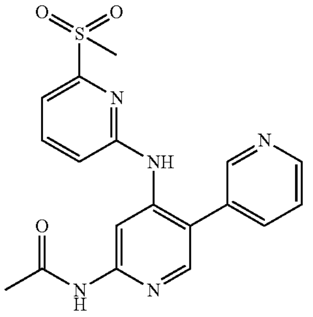 [SMILES: CC(=O)Nc1cc(Nc2cccc(S(C)(=O)=O)n2)c(-c2cccnc2)cn1] | N-(4-((6-(methylsulfonyl)pyridin-2-yl)amino)-[3,3'-bipyridin]-6-yl)acetamide | $^1H$ NMR (400 MHz, DMSO-$d_6$) δ 10.54 (s, 1H), 9.09 (s, 1H), 8.77 (s, 1H), 8.64 (s, 1H), 8.57 - 8.55 (m, 1H), 8.19 - 8.17 (m, 1H), 7.88 - 7.84 (m, 2H), 7.42 (d, J = 8.0 Hz, 2H), 7.17 (d, J = 8 Hz, 1H), 3.28 (s, 3H), 2.08 (s, 3H). MS (ESI) m/e $[M + 1]^+$ 384. |
| B3 | 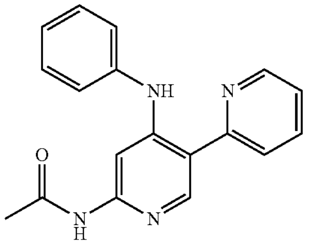 | N-(4'-(phenylamino)-[2,3'-bipyridin]-6'-yl)acetamide | $^1H$ NMR (400 MHz, DMSO-$d_6$) δ 11.41 (s, 1H), 10.36 (s, 1H), 8.75 - 8.65 (m, 1H), 8.65 (s, 1H), 8.10 - 8.05 (m, 2H), 8.00 - 7.90 (m, 1H), 7.42 - 7.34 (m, 2H), 7.31 (s, 2H), 7.29 (s, 1H), 7.15 - 7.10 (m, 1H), 2.05 (s, 3H). MS (ESI) m/e $[M + 1]^+$ 383. |

-continued

| Example | Compound | Chemical Name | $^1$H NMR and LC /MS m/z (M + 1) |
|---|---|---|---|
| B4 | 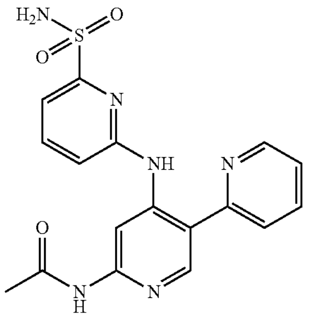 [SMILES: CC(=O)Nc1cc(Nc2cccc(S(N)(=O)=O)n2)c(-c2ccccn2)cn1] | N-(4'-((6-sulfamoylpyridin-2-yl)amino)-[2,3'-bipyridin]-6'-yl)acetamide | $^1$H NMR (400 MHz, DMSO-$d_6$) δ 13.09 (s, 1H), 10.74 (s, 1H), 9.70 (s, 1H), 8.85 - 8.80 (m, 2H), 8.20 - 8.15 (m, 1H), 8.01 -7.91 (m, 2H), 7.50 - 7.45 (m, 2H), 7.38 (s, 1H), 7.35 (s, 2H), 2.18 (s, 3H). MS (ESI) m/e $[M + 1]^+$ 385. |
| B5 | 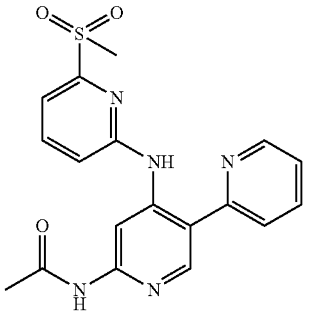 [SMILES: CC(=O)Nc1cc(Nc2cccc(S(C)(=O)=O)n2)c(-c2ccccn2)cn1] | N-(4'-((6-(methylsulfonyl)pyridin-2-yl)amino)-[2,3'-bipyridin]-6'-yl)acetamide | $^1$H NMR (400 MHz, DMSO-$d_6$) δ 12.97 (s, 1H), 10.57 (s, 1H), 9.24 (s, 1H), 8.90 - 8.80 (m, 2H), 8.27 (s, 1H), 8.15 - 8.10 (m, 1H), 8.05 - 7.95 (m, 2H), 7.60 - 7.50 (m, 1H), 7.48 - 7.35 (m, 2H), 3.47 (s, 3H), 2.13 (s, 3H). MS (ESI) m/e $[M + 1]^+$ 384. |
| B6 | 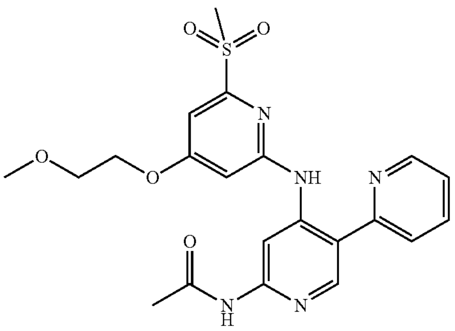 [SMILES: COCCOc1cc(Nc2cc(NC(C)=O)ncc2-c2ccccn2)nc(S(C)(=O)=O)c1] | N-(4'-((4-(2-methoxyethoxy)-6-(methylsulfonyl)pyridin-2-yl)amino)-[2,3'-bipyridin]-6'-yl)acetamide | $^1$H NMR (400 MHz, DMSO-$d_6$) δ 12.71 (s, 1H), 10.54 (s, 1H), 9.15 (s, 1H), 8.82 (d, J = 3.6 Hz, 1H), 8.77 (s, 1H), 8.11 (d, J = 7.8 Hz, 1H), 7.99 (t, J = 7.7 Hz, 1H), 7.50 - 7.42 (m, 1H), 7.11 (s, 1H), 6.91 (s, 1H), 4.38 - 4.30 (m, 2H), 3.74 - 3.66 (m, 2H), 3.44 (s, 3H), 3.32 (s, 3H), 2.12 (s, 3H). MS (ESI) m/e $[M + 1]^+$ 458. |
| B7 | 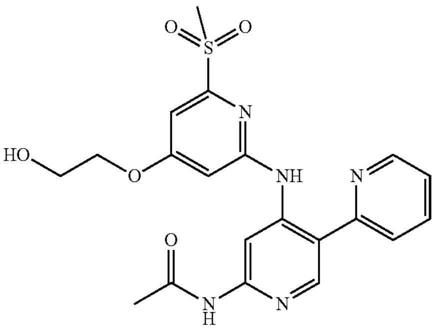 [SMILES: CC(=O)Nc1cc(Nc2cc(OCCO)cc(S(C)(=O)=O)n2)c(-c2ccccn2)cn1] | N-(4'-((4-(2-hydroxyethoxy)-6-(methylsulfonyl)pyridin-2-yl)amino)-[2,3'-bipyridin]-6'-yl)acetamide | $^1$H NMR (400 MHz, DMSO-$d_6$) δ 12.67 (s, 1H), 10.54 (s, 1H), 9.15 (s, 1H), 8.82 - 8.81 (m, 1H), 8.76 (s, 1H), 8.10 (d, J = 7.9 Hz, 1H), 7.99 (t, J = 7.3 Hz, 1H), 7.48 - 7.42 (m, 1H), 7.11 (s, 1H), 6.90 (s, 1H), 5.02 - 4.95 (m, 1H), 4.26 - 4.19 (m, 2H), 3.79 - 3.72 (m, 2H), 3.44 (s, 3H), 2.12 (s, 3H). MS (ESI) m/e $[M + 1]^+$ 444. |

-continued

| Example | Compound | Chemical Name | $^1$H NMR and LC /MS m/z (M + 1) |
|---|---|---|---|
| B8 | 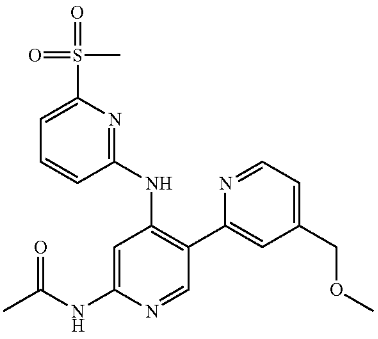 [SMILES: COCc1ccnc(-c2cnc(NC(C)=O)cc2Nc2cccc(S(C)(=O)=O)n2)c1] | N-(4-(methoxymethyl)-4'-((6-(methylsulfonyl)pyridin-2-yl)amino)-[2,3'-bipyridin]-6'-yl)acetamide | $^1$H NMR (400 MHz, DMSO-$d_6$) δ 12.94 (s, 1H), 10.58 (s, 1H), 9.22 (s, 1H), 8.76 - 8.72 (m, 2H), 7.99 - 7.95 (m, 2H), 7.55 - 7.53 (m, 1H), 7.46 - 7.30 (m, 2H), 4.55 (s, 2H), 3.45 (s, 3H), 3.36 (s, 3H), 2.11 (s, 3H). MS (ESI) m/e $[M + 1]^+$ 428. |
| B9 | 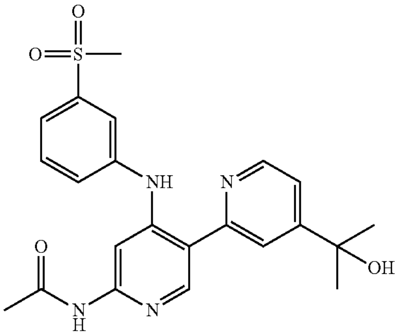 [SMILES: CC(=O)Nc1cc(Nc2cccc(S(C)(=O)=O)c2)c(-c2cc(C(C)(C)O)ccn2)cn1] | N-(4-(2-hydroxypropan-2-yl)-4'-((3-(methylsulfonyl)phenyl)amino)-[2,3'-bipyridin]-6'-yl)acetamide | $^1$H NMR (400 MHz, DMSO-$d_6$) δ 11.52 (s, 1H), 10.53 (s, 1H), 8.69 (s, 1H), 8.63 (d, J = 4.5 Hz, 1H), 8.18 (s, 1H), 8.03 (s, 1H), 7.81 (s, 1H), 7.63 - 7.58 (m, 3H), 7.48, (d, J = 4.5 Hz, 1H), 5.36 (s, 1H), 3.28 (s, 3H), 2.07 (s, 3H), 1.48 (s, 6H). MS (ESI) m/e $[M + 1]^+$ 441. |
| B10 | 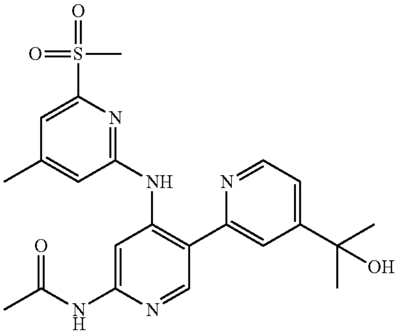 [SMILES: CC(=O)Nc1cc(Nc2cc(C)cc(S(C)(=O)=O)n2)c(-c2cc(C(C)(C)O)ccn2)cn1] | N-(4-(2-hydroxypropan-2-yl)-4'-((4-methyl-6-(methylsulfonyl)pyridin-2-yl)amino)-[2,3'-bipyridin]-6'-yl)acetamide | $^1$H NMR (400 MHz, DMSO-$d_6$) δ 12.89 (s, 1H), 10.56 (s, 1H), 9.24 (s, 1H), 8.78 (s, 1H), 8.72 (d, J = 4.5 Hz, 1H), 8.08 (s, 1H), 7.54 (d, J = 4.5 Hz, 1H), 7.43 (s, 1H), 7.22 (s, 1H), 5.39 (s, 1H), 3.45 (s, 3H), 2.42 (s, 3H), 2.13 (s, 3H), 1.50 (s, 6H). MS (ESI) m/e $[M + 1]^+$ 456. |
| B11 | 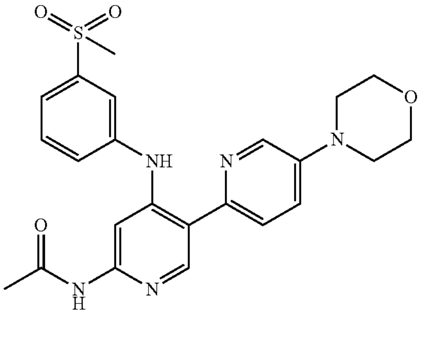 [SMILES: CC(=O)Nc1cc(Nc2cccc(S(C)(=O)=O)c2)c(-c2ccc(N3CCOCC3)cn2)cn1] | N-(4'-((3-(methylsulfonyl)phenyl)amino)-5-morpholino-[2,3'-bipyridin]-6'-yl)acetamide | $^1$H NMR (400 MHz, DMSO-$d_6$) δ 11.61 (s, 1H), 10.50 (s, 1H), 8.61 (s, 1H), 8.42 (s, 1H), 8.16 - 8.03 (m, 1H), 7.93 (d, J = 9.0 Hz, 1H), 7.80 (s, 1H), 7.69 - 7.51 (m, 4H), 3.81 - 3.73 (m, 4H), 3.29 (s, 3H), 3.27 - 3.22 (m, 4H), 2.07 (s, 3H). MS (ESI) m/e $[M + 1]^+$ 468. |

-continued

| Example | Compound | Chemical Name | $^1$H NMR and LC /MS m/z (M + 1) |
|---|---|---|---|
| B12 | 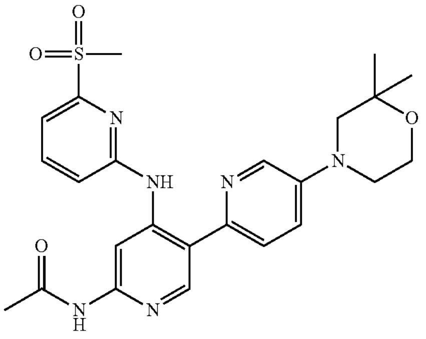 [SMILES: CC(=O)Nc1cc(Nc2cccc(S(C)(=O)=O)n2)c(-c2ccc(N3CCOC(C)(C)C3)cn2)cn1] | N-(5-(2,2-dimethylmorpholino)-4'-((6-(methylsulfonyl)pyridin-2-yl)amino)-[2,3'-bipyridin]-6'-yl)acetamide | $^1$H NMR (400 MHz, DMSO-$d_6$) δ 13.16 (s, 1H), 10.49 (s, 1H), 9.19 (s, 1H), 8.69 (s, 1H), 8.47 (s, 1H), 8.19 - 7.85 (m, 2H), 7.52 (d, J = 7.4 Hz, 2H), 7.35 (d, J = 8.4 Hz, 1H), 3.78 (d, J = 3.5 Hz, 2H), 3.46 (s, 3H), 3.22 (s, 2H), 3.12 (s, 2H), 2.09 (s, 3H), 1.23 (s, 6H). MS (ESI) m/e [M + 1]$^+$ 497. |
| B13 | 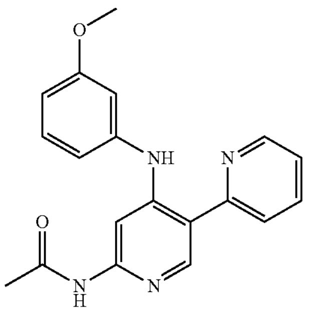 [SMILES: COc1cccc(Nc2cc(NC(C)=O)ncc2-c2ccccn2)c1] | N-(4'-((3-methoxyphenyl)amino)-[2,3'-bipyridin]-6'-yl)acetamide | $^1$H NMR (400 MHz, DMSO-$d_6$) δ 11.44 (s, 1H), 10.40 (s, 1H), 8.70 - 8.69 (m, 1H), 8.65 (s, 1H), 8.15 (s, 1H), 8.06 (d, J = 8.1 Hz, 1H), 7.95 (d, J = 7.5 Hz, 1H), 7.42 - 7.37 (m, 1H), 7.28 (t, J = 8.0 Hz, 1H), 6.91 (s, 1H), 6.85 (d, J = 7.5 Hz, 1H), 6.68 (d, J = 7.6 Hz, 1H), 3.78 (s, 3H), 2.06 (s, 3H). MS (ESI) m/e [M + 1]$^+$ 335. |
| B14 | 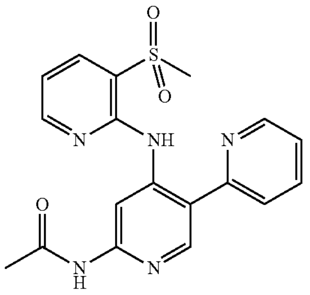 [SMILES: CC(=O)Nc1cc(Nc2ncccc2S(C)(=O)=O)c(-c2ccccn2)cn1] | N-(4'-((3-(methylsulfonyl)pyridin-2-yl)amino)-[2,3'-bipyridin]-6'-yl)acetamide | $^1$H NMR (400 MHz, DMSO-$d_6$) δ 12.51 (s, 1H), 10.50 (s, 1H), 9.11 (s, 1H), 8.73 (s, 1H), 8.69 - 8.66 (m, 1H), 8.55 - 8.52 (m, 1H), 8.23 (d, J = 7.1 Hz, 1H), 8.04 (d, J = 7.6 Hz, 1H), 8.05 - 7.95 (m, 1H), 7.44 - 7.39 (m, 1H), 7.26 - 7.20 (m, 1H), 3.36 (s, 3H), 2.10 (s, 3H). MS (ESI) m/e [M + 1]$^+$ 384. |
| B15 | 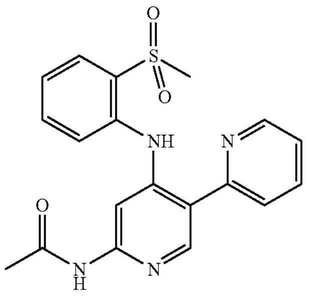 [SMILES: CC(=O)Nc1cc(Nc2ccccc2S(C)(=O)=O)c(-c2ccccn2)cn1] | N-(4'-((2-(methylsulfonyl)phenyl)amino)-[2,3'-bipyridin]-6'-yl)acetamide | $^1$H NMR (400 MHz, DMSO-$d_6$) δ 12.14 (s, 1H), 10.52 (s, 1H), 8.77 (s, 1H), 8.60 - 8.59 (m, 1H), 8.21 (s, 1H), 8.09 (d, J = 8.4 Hz, 1H), 7.98 - 7.93 (m, 2H), 7.73 - 7.65 (m, 2H), 7.42 - 7.36 (m, 1H), 7.33 - 7.27 (m, 1H), 3.24 (s, 3H), 2.06 (s, 3H). MS (ESI) m/e [M + 1]$^+$ 383. |

-continued

| Example | Compound | Chemical Name | $^1$H NMR and LC /MS m/z (M + 1) |
|---|---|---|---|
| B16 | 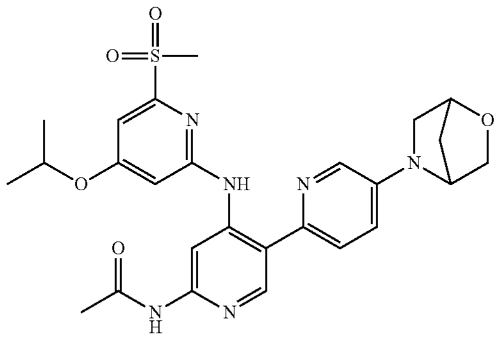 [SMILES: CC(=O)Nc1cc(Nc2cc(OC(C)C)cc(S(C)(=O)=O)n2)c(-c2ccc(N3CC4CC3CO4)cn2)cn1] | N-(5-(2-oxa-5-azabicyclo[2.2.1]heptan-5-yl)-4'-((4-isopropoxy-6-(methylsulfonyl)pyridin-2-yl)amino)-[2,3'-bipyridin]-6'-yl)acetamide | $^1$H NMR (400 MHz, DMSO-$d_6$) δ 12.76 (s, 1H), 10.41 (s, 1H), 9.09 (s, 1H), 8.64 (s, 1H), 8.25 (s, 1H), 7.91 (d, J = 8.0 Hz, 1H), 7.25 (d, J = 8.0 Hz, 1H), 7.07 (s, 1H), 6.79 (s, 1H), 4.94 - 4.91 (m, 1H), 4.75 - 4.70 (m, 2H), 3.81 - 3.79 (m, 1H), 3.71 - 3.70 (m, 1H), 3.60 - 3.58 (m, 1H), 3.44 (s, 3H), 3.14 - 3.11 (m, 1H), 2.11 (s, 3H), 1.98 - 1.90 (m, 2H), 1.33 (d, J = 8.0 Hz, 6H). MS (ESI) m/e $[M + 1]^+$ 539. |
| B17 | 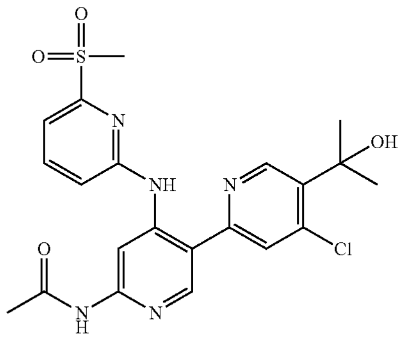 [SMILES: CC(=O)Nc1cc(Nc2cccc(S(C)(=O)=O)n2)c(-c2cc(Cl)c(C(C)(C)O)cn2)cn1] | N-(4-chloro-5-(2-hydroxypropan-2-yl)-4'-((6-(methylsulfonyl)pyridin-2-yl)amino)-[2,3'-bipyridin]-6'-yl)acetamide | $^1$H NMR (400 MHz, DMSO-$d_6$) δ 12.77 (s, 1H), 10.61 (s, 1H), 9.23 (s, 1H), 9.11 (s, 1H), 8.85 (s, 1H), 8.21 (s, 1H), 7.99 (t, J = 7.9 Hz, 1H), 7.57 (d, J = 7.3 Hz, 1H), 7.48 (d, J = 8.3 Hz, 1H), 5.63 (s, 1H), 3.47 (s, 3H), 2.13 (s, 3H), 1.66 (s, 6H). MS (ESI) m/e $[M + 1]^+$ 476. |
| B18 | 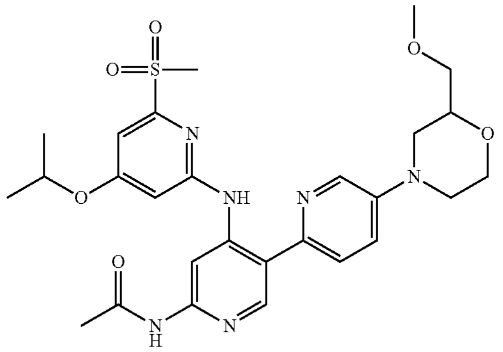 [SMILES: COCC1CN(c2ccc(-c3cnc(NC(C)=O)cc3Nc3cc(OC(C)C)cc(S(C)(=O)=O)n3)nc2)CCO1] | N-(4'-((4-isopropoxy-6-(methylsulfonyl)pyridin-2-yl)amino)-5-(2-(methoxymethyl)morpholino)-[2,3'-bipyridin]-6'-yl)acetamide | $^1$H NMR (400 MHz, DMSO-$d_6$) δ 12.79 (s, 1H), 10.44 (s, 1H), 9.12 (s, 1H), 8.68 (s, 1H), 8.53 (s, 1H), 7.96 (d, J = 8.0 Hz, 1H), 7.56 (d, J = 8.0 Hz, 1H), 7.07 (s, 1H), 6.82 (s, 1H), 5.03 - 4.77 (m, 1H), 4.01 - 3.98 (m, 1H), 3.82 - 3.61 (m, 4H), 3.46 - 3.44 (m, 5H), 3.32 (s, 3H), 2.86 - 2.80 (m, 1H), 2.65 - 2.59 (m, 1H), 2.11 (s, 3H), 1.33 (d, J = 8.0 Hz, 6H). MS (ESI) m/e $[M + 1]^+$ 571. |
| B19 | 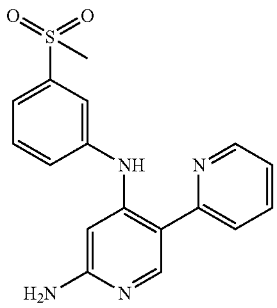 [SMILES: CS(=O)(=O)c1cccc(Nc2cc(N)ncc2-c2ccccn2)c1] | N4'-(3-(methylsulfonyl)phenyl)-[2,3'-bipyridine]-4',6'-diamine | MS (ESI) m/e $[M + 1]^+$ 341. |

-continued

| Example | Compound | Chemical Name | $^1$H NMR and LC /MS m/z (M + 1) |
|---|---|---|---|
| B20 | 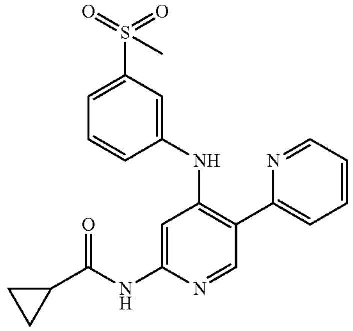 [SMILES: CS(=O)(=O)c1cccc(Nc2cc(NC(=O)C3CC3)ncc2-c2ccccn2)c1] | N-(4'-((3-(methylsulfonyl)phenyl)amino)-[2,3'-bipyridin]-6'-yl)cyclopropanecarboxamide | MS (ESI) m/e $[M + 1]^+$ 409. |
| B21 | 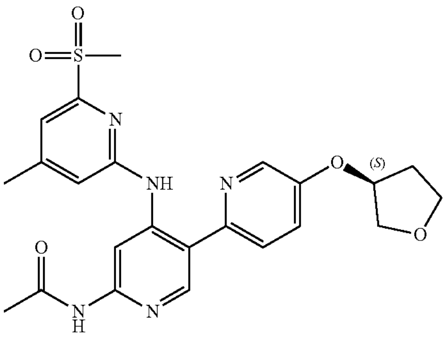 | (S)-N-(4'-((4-methyl-6-(methylsulfonyl)pyridin-2-yl)amino)-5-((tetrahydrofuran-3-yl)oxy)-[2,3'-bipyridin]-6'-yl)acetamide | $^1$H NMR (400 MHz, DMSO-$d_6$) δ 12.61 (s, 1H), 10.58 (s, 1H), 9.15 (s, 1H), 8.53 (s, 1H), 8.04 (d, J = 7.2 Hz, 1H), 7.61 (s, 1H), 7.55 - 7.45 (m, 2H), 7.24 (s, 1H), 5.23 - 5.20 (m, 1H), 3.92 - 3.88 (m, 3H), 3.85 - 3.80 (m, 1H), 3.47 (s, 3H), 2.42 (s, 3H), 2.35 - 2.30 (m, 1H), 2.12 (s, 3H), 2.10 - 2.05 (m, 1H). MS (ESI) m/e $[M + 1]^+$ 484. |
| B22 | 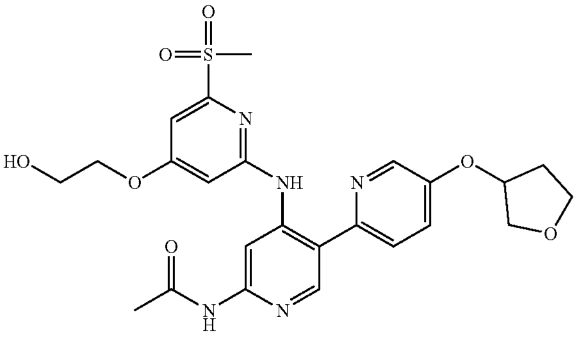 [SMILES: CC(=O)Nc1cc(Nc2cc(OCCO)cc(S(C)(=O)=O)n2)c(-c2ccc(OC3CCOC3)cn2)cn1] | N-(4'-((4-(2-hydroxyethoxy)-6-(methylsulfonyl)pyridin-2-yl)amino)-5-((tetrahydrofuran-3-yl)oxy)-[2,3'-bipyridin]-6'-yl)acetamide | $^1$H NMR (400 MHz, DMSO-$d_6$) δ 12.35 (s, 1H), 10.50 (s, 1H), 9.13 (s, 1H), 8.68 (s, 1H), 8.53 (s, 1H), 8.02 (d, J = 8.0 Hz, 1H), 7.60 (d, J = 8.0 Hz, 1H), 7.10 (s, 1H), 6.87 (s, 1H), 5.23 - 5.20 (m, 1H), 4.98 (s, 1H), 4.25 - 4.22 (m, 2H), 3.95 - 3.75 (m, 6H), 3.43 (s, 3H), 2.33 - 2.28 (m, 1H), 2.12 (s, 3H), 2.08 - 2.05 (m, 1H). MS (ESI) m/e $[M + 1]^+$ 530. |
| B23 | 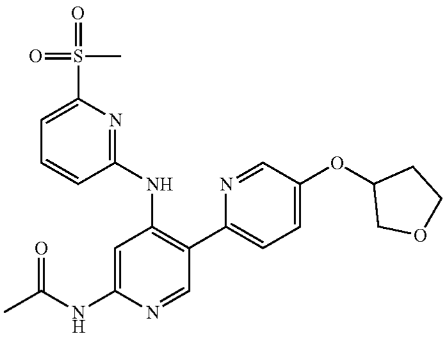 [SMILES: CC(=O)Nc1cc(Nc2cccc(S(C)(=O)=O)n2)c(-c2ccc(OC3CCOC3)cn2)cn1] | N-(4'-((6-(methylsulfonyl)pyridin-2-yl)amino)-5-((tetrahydrofuran-3-yl)oxy)-[2,3'-bipyridin]-6'-yl)acetamide | $^1$H NMR (400 MHz, DMSO-$d_6$) δ 12.64 (s, 1H), 10.51 (s, 1H), 9.21 (s, 1H), 8.72 (s, 1H), 8.51 (s, 1H), 8.07 (d, J = 7.4 Hz, 1H), 7.99 (t, J = 7.9 Hz, 1H), 7.61 (d, J = 8.8 Hz, 1H), 7.55 (d, J = 7.4 Hz, 1H), 7.40 (d, J = 8.3 Hz, 1H), 5.23 - 5.20 (m, 1H), 3.92 - 3.88 (m, 3H), 3.85 - 3.80 (m, 1H), 3.47 (s, 3H), 2.35 - 2.30 (m, 1H), 2.12 (s, 3H), 2.10 - 2.05 (m, 1H). MS (ESI) m/e $[M + 1]^+$ 470. |

-continued

| Example | Compound | Chemical Name | ¹H NMR and LC /MS m/z (M + 1) |
|---|---|---|---|
| B24 | 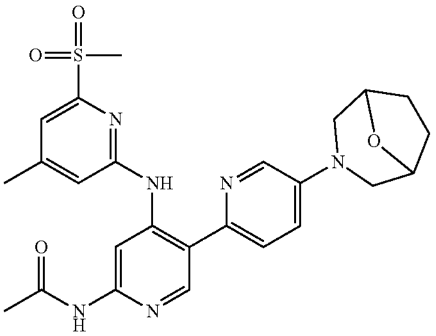 [SMILES: CC(=O)Nc1cc(Nc2cc(C)cc(S(C)(=O)=O)n2)c(-c2ccc(N3CC4CCC(C3)O4)cn2)cn1] | N-(5-(8-oxa-3-azabicyclo[3.2.1]octan-3-yl)-4'-((4-methyl-6-(methylsulfonyl)pyridin-2-yl)amino)-[2,3'-bipyridin]-6'-yl)acetamide | MS (ESI) m/e $[M + 1]^+$ 509. |
| B25 | 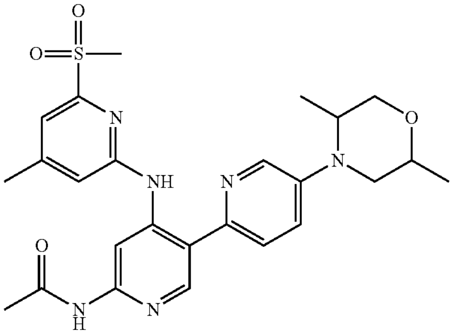 [SMILES: CC(=O)Nc1cc(Nc2cc(C)cc(S(C)(=O)=O)n2)c(-c2ccc(N3CC(C)OCC3C)cn2)cn1] | N-(5-(2,5-dimethylmorpholino)-4'-((4-methyl-6-(methylsulfonyl)pyridin-2-yl)amino)-[2,3'-bipyridin]-6'-yl)acetamid | MS (ESI) m/e $[M + 1]^+$ 511. |

Example C1: Synthesis of N-(5-(cis-2,6-dimethylmorpholino)-4'-((4-methyl-6-(methylsulfonyl)pyridin-2-yl)amino)-[2,3'-bipyridin]-6'-yl)acetamide

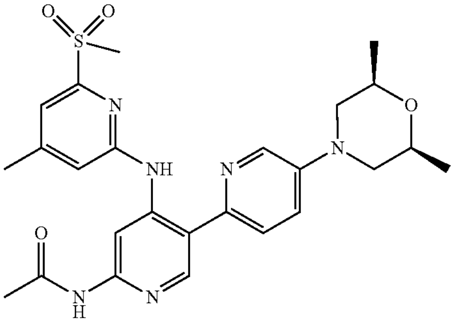 [SMILES: CC(=O)Nc1cc(Nc2cc(C)cc(S(C)(=O)=O)n2)c(-c2ccc(N3C[C@@H](C)O[C@@H](C)C3)cn2)cn1]

Step 1: (cis)-4-(6-bromopyridin-3-yl)-2,6-dimethylmorpholine

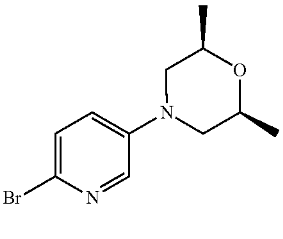

A mixture of 2-bromo-5-iodopyridine (20 g, 70.4 mmol), (Cis)-2,6-dimethylmorpholine (8.9 g, 77.5 mmol, 1.1 eq), $Pd_2(dba)_3$ (3.22 g, 3.52 mmol, 0.05 eq), Xant-Phos (2 g, 3.52 mmol, 0.05 eq) and t-BuONa (13.5 g, 140.8 mmol, 2 eq) in toluene (300 mL) was stirred at 80° C. under $N_2$ for 2 hrs. The reaction mixture was cooled, filtered and the filtrate was concentrated and the residue was purified by column chromatography (PE:EA=20: 1-10:1) to give the product (16 g, 84%) as a brown solid. MS (ESI) m/e $[M+1]^+$=271.

Step 2: 6'-chloro-5-(Cis-2,6-dimethylmorpholino)-[2,3'-bipyridin]-4'-amine

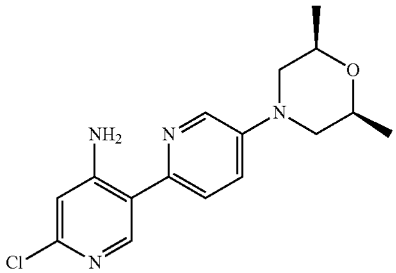 [SMILES: C[C@@H]1CN(c2ccc(-c3cnc(Cl)cc3N)nc2)C[C@H](C)O1]

To a solution of cis-4-(6-bromopyridin-3-yl)-2,6-dimethylmorpholine (13.6 g, 50.4 mmol) in dioxane/$H_2O$ (400 mL/100 mL) were added 2-chloro-5-(4,4,5,5-tetramethyl-1,3,2-dioxaborolan-2-yl)pyridin-4-amine (15.4, 60.4 mmol), $Pd(dppf)Cl_2$ (3.7 g, 5.04 mmol) and $K_2CO_3$ (10.4 g, 75.6 mmol), the resulting mixture was stirred at 100° C. for 2 h under nitrogen atmosphere. After cooled to room temperature, the solvent was removed in vacuo and the residue was diluted with water (500 mL). The resulting solution was extracted with EA (500 mL×3) and the combined organic layers were washed with brine, dried over anhydrous sodium sulfate. The solvent was removed in vacuo and the residue was purified by combi-flash (MeOH/DCM=0-5%) to give 6'-chloro-5-(Cis-2,6-dimethylmorpholino)-[2,3'-bipyridin]-4'-amine (18 g, crude). MS (ESI) m/e $[M+1]^+$ 319.

Step 3: N-(4'-amino-5-(Cis-2,6-dimethylmorpholino)-[2,3'-bipyridin]-6'-yl)acetamide

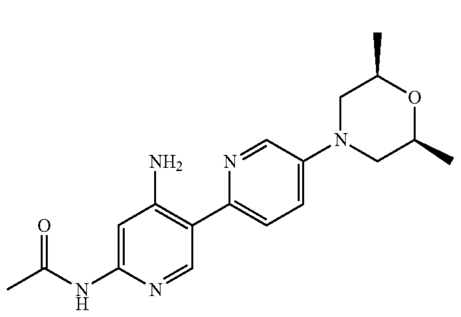 [SMILES: CC(=O)Nc1cc(N)c(-c2ccc(N3C[C@@H](C)O[C@@H](C)C3)cn2)cn1]

To a solution of 6'-chloro-5-(cis-2,6-dimethylmorpholino)-[2,3'-bipyridin]-4'-amine (18 g, 56.6 mmol) in 1,4-dioxane (250 mL) were added acetamide (16.7 g, 283 mmol), $Pd_2(dba)_3$ (5.2 g, 5.7 mmol), XantPhos (6.6 g, 11.4 mmol) and $Cs_2CO_3$ (37.2 g, 114 mmol), the resulting mixture was stirred at 130° C. for 4 h under nitrogen atmosphere. After cooled to room temperature, the solvent was removed in vacuo and the residue was diluted with water (20 mL). The resulting solution was extracted with EA (30 mL×3) and the combined organic layers were washed with brine, dried over anhydrous sodium sulfate. The solvent was removed in vacuo and the residue was purified by combi-flash (MeOH/DCM=0-7%) to give N-(4'-amino-5-(cis-2,6-dimethylmorpholino)-[2,3'-bipyridin]-6'-yl)acetamide (12.54 g, 65% yield). MS (ESI) m/e $[M+1]^+$ 342.

Step 4: N-(5-(Cis-2,6-dimethylmorpholino)-4'-((4-methyl-6-(methylsulfonyl)pyridin-2-yl)amino)-[2,3'-bipyridin]-6'-yl)acetamide

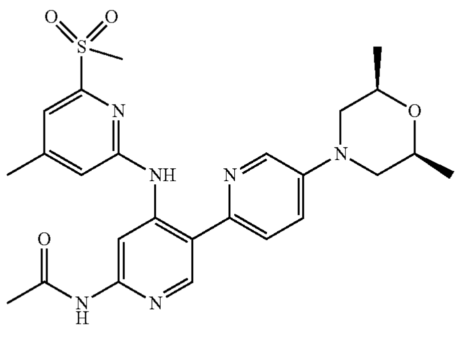

To a mixture of N-(4'-amino-5-(Cis-2,6-dimethylmorpholino)-[2,3'-bipyridin]-6'-yl)acetamide (50 mg, 0.17 mmol), 2-bromo-4-methyl-6-(methylsulfonyl)pyridine (52 mg, 0.21 mmol), $Pd_2dba_3$ (16 mg, 0.017 mmol), BINAP (11 mg, 0.017 mmol) and $Cs_2CO_3$ (111 mg, 0.34 mmol) in dioxane (10 mL) was stirred at 130° C. for 4 h. The mixture was filtrated and the filtrate as concentrated to give the residue and purified by Prep-TLC (MeOH/DCM=1:20) to afford N-(5-(Cis-2,6-dimethylmorpholino)-4'-((4-methyl-6-(methylsulfonyl)pyridin-2-yl)amino)-[2,3'-bipyridin]-6'-yl) acetamide (38 mg, 510% yield). $^1H$ NMR (400 MHz, DMSO-$d_6$) δ 13.13 (s, 1H), 10.45 (s, 1H), 9.23 (s, 1H), 8.72 (s, 1H), 8.51 (s, 1H), 8.00 (d, J=8.7 Hz, 1H), 7.58 (d, J=8.7 Hz, 1H), 7.42 (s, 1H), 7.20 (s, 1H), 3.80-3.74 (m, 4H), 3.46 (s, 3H), 2.45-2.40 (m, 2H), 2.35 (s, 3H), 2.11 (s, 3H), 1.20 (d, J=6.0 Hz, 6H). MS (ESI) m/e $[M+1]^+$ 511.

Example C9: Synthesis of N-(5-(cis-2,6-dimethylmorpholino)-4'-((4-methoxy-6-(methylsulfonyl)pyridin-2-yl)amino)-[2,3'-bipyridin]-6'-yl)acetamide

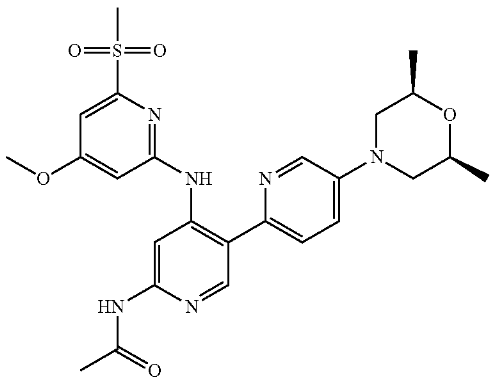

A mixture of N-(4'-amino-5-(cis-2,6-dimethylmorpholino)-[2,3'-bipyridin]-6'-yl)acetamide (1.20 g, 3.52 mmol), 2-bromo-4-methoxy-6-(methylsulfonyl)pyridine (1.15 g, 4.22 mmol), $Pd_2(dba)_3$ (320 mg, 0.35 mmol), BINAP (218 mg, 0.35 mmol) and $Cs_2CO_3$ (2.28 g, 7.04 mmol) in 1,4-Dioxane (50 mL) was stirred at 130° C. for 4 hr under nitrogen atmosphere. The reaction mixture was filtered out and the filtrate was concentrated, the residue was purified by combi-flash (MeOH/DCM=7:93) to give the crude product as brown oil, then slurry with ACN (50 mL) at RT for 30 min to give the solid by filtration and dried in vacuum drying oven to give the product (1.3 g, 70% yield). $^1H$ NMR (400 MHz, DMSO-$d_6$) δ 12.83 (s, 1H), 10.46 (s, 1H), 9.11 (s, 1H), 8.69 (s, 1H), 8.50 (s, 1H), 7.96 (d, J=9.1 Hz, 1H), 7.57 (d, J=9.1 Hz, 1H), 7.11 (s, 1H), 6.84 (s, 1H), 3.97 (s, 3H), 3.79-3.73 (m, 4H), 3.44 (s, 3H), 2.40 (t, J=11.0 Hz, 2H), 2.11 (s, 3H), 1.19 (d, J=6.0 Hz, 6H). MS (ESI) m/e $[M+1]^+$ 527.

Example C17: Synthesis of N-(5-((cis)-2,6-dimethylmorpholino)-4'-((4-(methoxy-d3)-6-(methylsulfonyl)pyridin-2-yl)amino)-[2,3'-bipyridin]-6'-yl)acetamide

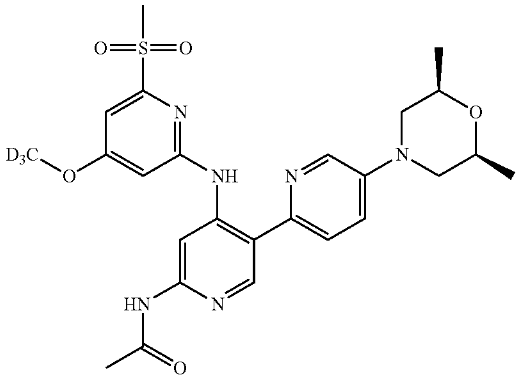 [SMILES: [2H]C([2H])([2H])Oc1cc(Nc2cc(NC(C)=O)ncc2-c2ccc(N3C[C@@H](C)O[C@@H](C)C3)cn2)nc(S(C)(=O)=O)c1]

A mixture of N-(4'-amino-5-(cis-2,6-dimethylmorpholino)-[2,3'-bipyridin]-6'-yl)acetamide (2.1 g, 6.16 mmol), 2-bromo-4-(methoxy-d3)-6-(methylsulfonyl)pyridine (2.0 g, 7.39 mmol), $Pd_2(dba)_3$ (568 mg, 0.62 mmol), BINAP (386 mg, 0.62 mmol) and $Cs_2CO_3$ (4.02 g, 12.32 mmol) in 1,4-dioxane (75 mL) was stirred at 130° C. for 4 h under $N_2$. The solid was filtered out and the filtrate was concentrated, the residue was purified by Prep-TLC (MeOH/DCM=1:20) to give the product (2.03 g, 62% yield). $^1H$ NMR (400 MHz, DMSO-$d_6$) δ 12.82 (s, 1H), 10.46 (s, 1H), 9.11 (s, 1H), 8.69 (s, 1H), 8.50 (s, 1H), 7.96 (d, J=9.1 Hz, 1H), 7.55 (s, 1H), 7.11 (s, 1H), 6.84 (s, 1H), 3.79-3.76 (m, 4H), 3.44 (s, 3H), 2.43-2.37 (m, 2H), 2.11 (s, 3H), 1.19 (d, J=5.3 Hz, 6H). MS (ESI) m/e $[M+1]^+$ 530.

Example C18: Synthesis of N-(5-(cis-2,6-dimethylmorpholino)-4'-((4-(1-methoxyethyl)-6-(methylsulfonyl)pyridin-2-yl)amino)-[2,3'-bipyridin]-6'-yl)acetamide

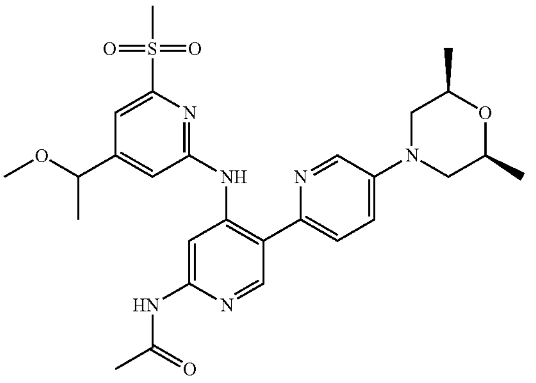

A mixture of N-(4'-amino-5-(cis-2,6-dimethylmorpholino)-[2,3'-bipyridin]-6'-yl)acetamide (60 mg, 0.17 mmol), 2-bromo-4-(1-methoxyethyl)-6-(methylsulfonyl)pyridine (62 mg, 0.21 mmol), $Pd_2dba_3$ (16 mg, 0.02 mmol), BINAP (11 mg, 0.02 mmol) and $Cs_2CO_3$ (111 mg, 0.34 mmol) in 1,4-dioxane (10 mL) was stirred at 130° C. for 4 h under nitrogen atmosphere. The solid was filtered out and the filtrate was concentrated, the residue was purified by Prep-TLC (MeOH/DCM=1:20) to give the product (40.56 mg, 42% yield) as a yellow solid. $^1H$ NMR (400 MHz, DMSO-$d_6$) δ 12.99 (s, 1H), 10.46 (s, 1H), 9.21 (s, 1H), 8.71 (s, 1H), 8.49 (s, 1H), 7.98 (d, J=9.0 Hz, 1H), 7.57 (d, J=9.2 Hz, 1H), 7.48 (s, 1H), 7.25 (s, 1H), 4.50-4.49 (m, 1H), 3.77-3.74 (m, 4H), 3.48 (s, 3H), 3.23 (s, 3H), 2.41 (t, J=11.1 Hz, 2H), 2.11 (s, 3H), 1.39 (d, J=6.5 Hz, 3H), 1.20 (d, J=6.0 Hz, 6H). MS (ESI) m/e $[M+1]^+$=555.

Example C19: Synthesis of N-(5-((cis)-2,6-dimethylmorpholino)-4'-((4-((R or S)-1-methoxyethyl)-6-(methylsulfonyl)pyridin-2-yl)amino)-[2,3'-bipyridin]-6'-yl)acetamide

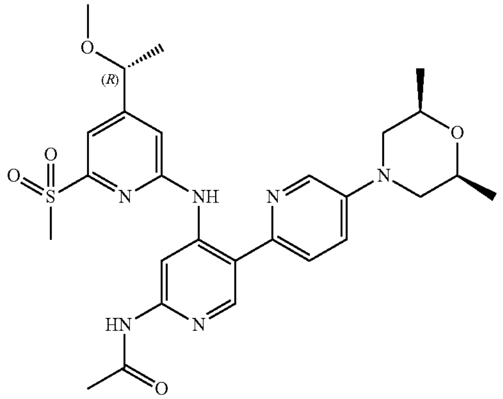

or

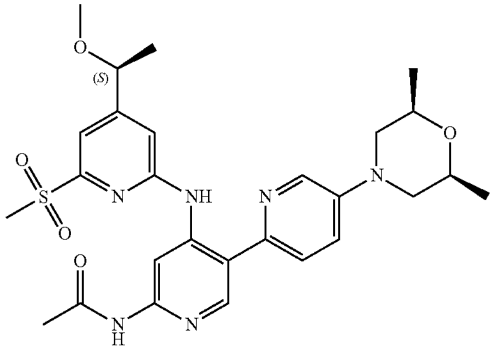

A mixture of N-(4'-amino-5-((cis)-2,6-dimethylmorpholino)-[2,3'-bipyridin]-6'-yl)acetamide (50 mg, 0.147 mmol), (R or S) 2-bromo-4-(1-methoxyethyl)-6-(methylsulfonyl)pyridine (44 mg, 0.176 mmol) (faster peak from example BB60, step 5), $Pd_2(dba)_3$ (13 mg, 0.0147 mmol), BINAP (18 mg, 0.0294 mmol) and $Cs_2CO_3$ (72 mg, 0.221 mmol) in 1,4-dioxane (6 mL) was stirred at 130° C. for 4 hr under nitrogen atmosphere. The reaction was cooled to room temperature, filtered and the filtration was concentrated under vacuum. The residue was purified with Prep-TLC (DCM/MeOH=20:1) to afford the product (33 mg, 40%). $^1H$ NMR (400 MHz, DMSO-$d_6$) δ 13.01 (s, 1H), 10.49 (s, 1H), 9.21 (s, 1H), 8.71 (s, 1H), 8.50 (s, 1H), 7.99 (d, J=8.9 Hz, 1H), 7.58 (d, J=8.9 Hz, 1H), 7.49 (s, 1H), 7.26 (s, 1H), 4.53-4.43 (m, 1H), 3.84-3.70 (m, 4H), 3.49 (s, 3H), 3.23 (s, 3H), 2.41 (t, J=10.9 Hz, 2H), 2.12 (s, 3H), 1.39 (d, J=5.9 Hz, 3H), 1.20 (d, J=5.4 Hz, 6H). MS (ESI) m/e $[M+1]^+$ 555.

Example C20: Synthesis of N-(5-((cis)-2,6-dimethylmorpholino)-4'-((4-((R or S)-1-methoxyethyl)-6-(methylsulfonyl)pyridin-2-yl)amino)-[2,3'-bipyridin]-6'-yl)acetamide

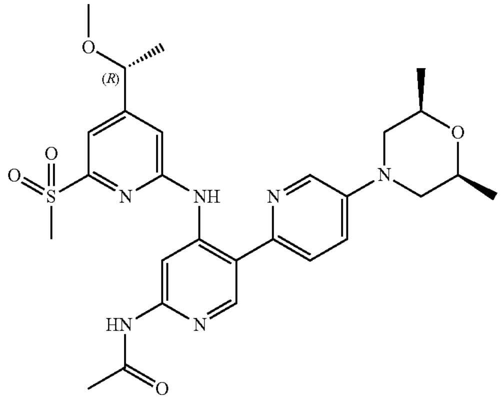

or

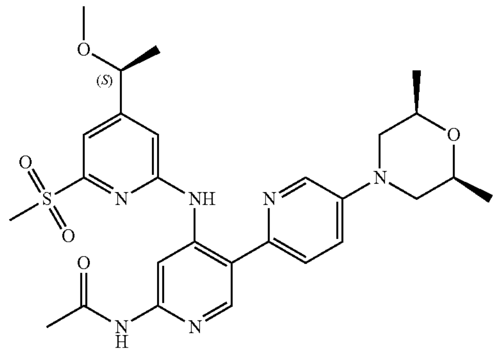

A solution of N-(4'-amino-5-(cis-2,6-dimethylmorpholino)-[2,3'-bipyridin]-6'-yl)acetamide (60 mg, 0.18 mmol), (S or R)-2-bromo-4-(1-methoxyethyl)-6-(methylsulfonyl)pyridine (slower peak from example BB60, step 5) (62 mg, 0.21 mmol), $Pd_2(dba)_3$ (33 mg, 0.036 mmol), Xantphos (41.7 mg, 0.072 mmol) and $Cs_2CO_3$ (117.4 mg, 0.36 mmol) in dioxane (3 mL) was stirred at 130° C. for 4 hr under nitrogen atmosphere. The reaction was cooled to room temperature, filtered and the filtration was concentrated under vacuum. The residue was purified with Prep-TLC (DCM/MeOH=15:1) to afford the product (35.83 mg, 35.89%). $^1$H NMR (400 MHz, DMSO-$d_6$) δ 13.00 (s, 1H), 10.47 (s, 1H), 9.22 (s, 1H), 8.71 (s, 1H), 8.50 (s, 1H), 7.99 (d, J=9.0 Hz, 1H), 7.58 (d, J=9.0 Hz, 1H), 7.48 (s, 1H), 7.26 (s, 1H), 4.53-4.45 (m, 1H), 3.84-3.67 (m, 4H), 3.49 (s, 3H), 3.23 (s, 3H), 2.41 (t, J=11.1 Hz, 2H), 2.11 (s, 3H), 1.39 (d, J=6.3 Hz, 3H), 1.20 (d, J=6.0 Hz, 6H). MS (ESI) m/e $[M+1]^+$ 555.

Example C21: Synthesis of N-(5-(cis-2,6-dimethylmorpholino)-4'-((6-(methylsulfonyl)-4-(tetrahydro-2H-pyran-4-yl)pyridin-2-yl)amino)-[2,3'-bipyridin]-6'-yl)acetamide

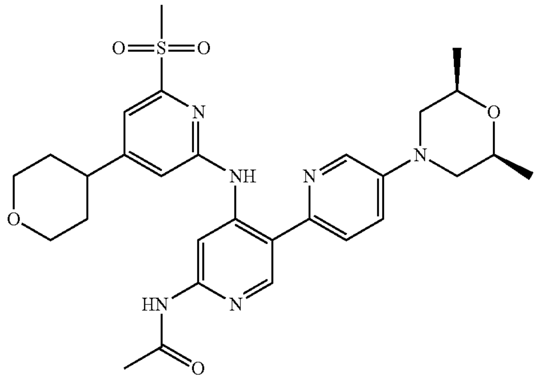 [SMILES: CC(=O)Nc1cc(Nc2cc(C3CCOCC3)cc(S(C)(=O)=O)n2)c(-c2ccc(N3C[C@@H](C)O[C@@H](C)C3)cn2)cn1]

A mixture of N-(4'-amino-5-(cis-2,6-dimethylmorpholino)-[2,3'-bipyridin]-6'-yl)acetamide (60 mg, 0.17 mmol), 2-bromo-6-(methylsulfonyl)-4-(tetrahydro-2H-pyran-4-yl)pyridine (66 mg, 0.21 mmol), $Pd_2(dba)_3$ (16 mg, 0.02 mmol), BINAP (11 mg, 0.02 mmol) and $Cs_2CO_3$ (111 mg, 0.34 mmol) in 1,4-dioxane (10 mL) was stirred at 130° C. for 4 hr under $N_2$. The reaction mixture was filtered out and the filtrate was concentrated, the residue was purified by Prep-TLC (MeOH/DCM=1:20) to give the product (47.27 mg, 46% yield). $^1$H NMR (400 MHz, DMSO-$d_6$) 12.97 (s, 1H), 10.46 (s, 1H), 9.20 (s, 1H), 8.70 (s, 1H), 8.52 (s, 1H), 7.98 (d, J=8.7 Hz, 1H), 7.57 (d, J=8.7 Hz, 1H), 7.46 (s, 1H), 7.21 (s, 1H), 3.98 (d, J=10.2 Hz, 2H), 3.83-3.70 (m, 4H), 3.47-3.42 (m, 5H), 3.02-2.95 (m, 1H), 2.41 (t, J=11.0 Hz, 2H), 2.11 (s, 3H), 1.76-1.74 (m, 4H), 1.20 (d, J=6.1 Hz, 6H). MS (ESI) m/e $[M+1]^+$ 581.

Example C22: Synthesis of N-(5-(cis-2,6-dimethylmorpholino)-4'-((6-(methylsulfonyl)pyrazin-2-yl)amino)-[2,3'-bipyridin]-6'-yl)acetamide

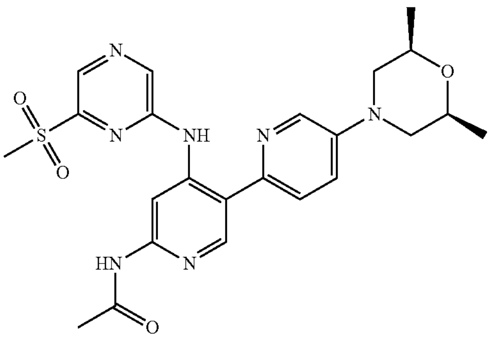

A mixture of N-(4'-amino-5-(cis-2,6-dimethylmorpholino)-[2,3'-bipyridin]-6'-yl)acetamide (60 mg, 0.17 mmol), 2-bromo-6-(methylsulfonyl)pyrazine (49 mg, 0.21 mmol), $Pd_2(dba)_3$ (16 mg, 0.02 mmol), BINAP (11 mg, 0.02 mmol) and $Cs_2CO_3$ (111 mg, 0.34 mmol) in 1,4-Dioxane (10 mL) was stirred at 130° C. for 4 hr under $N_2$ atmosphere. The reaction mixture was filtered out and the filtrate was concentrated, the residue was purified by Prep-TLC (MeOH/DCM=1:20) to give the product (27.37 mg, 31% yield). $^1$H NMR (400 MHz, DMSO-$d_6$) δ 14.00 (s, 1H), 10.50 (s, 1H), 9.29 (s, 1H), 8.78-8.75 (m, 2H), 8.55-8.50 (m, 2H), 8.00 (s, 1H), 7.55 (s, 1H), 3.75-3.69 (m, 4H), 3.53 (s, 3H), 2.37 (t, J=11.0 Hz, 2H), 2.08 (s, 3H), 1.15 (d, J=6.1 Hz, 6H). MS (ESI) m/e [M+1]$^+$ 498.

Example C23: Synthesis of compound N-(5-(cis-2,6-dimethylmorpholino)-4'-((4-((S)-3-methylmorpholino)-6-(methylsulfon-yl)pyridin-2-yl)amino)-[2,3'-bipyridin]-6'-yl)ace-tamide

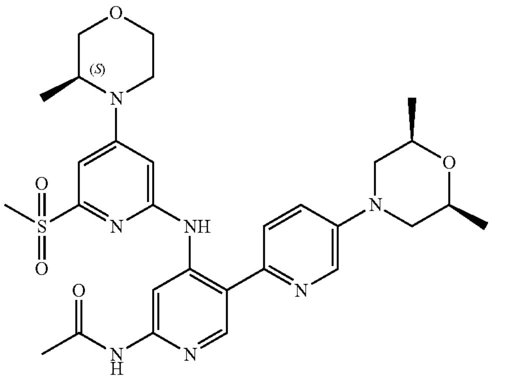

N-(4'-amino-5-(cis-2,6-dimethylmorpholino)-[2,3'-bipyridin]-6'-yl)aceta-mide (50 mg, 0.15 mmol), (S)-4-(2-chloro-6-(methylsulfonyl)pyridin-4-yl)-3-methyl-morpholine (47 mg, 0.16 mmol), $Pd_2dba_3$ (13.4 mg, 0.02 mmol), BINAP (18.3 mg, 0.03 mmol) and $Cs_2CO_3$ (72 mg, 0.22 mmol) were added into 1,4-dioxane (10 mL). The resulting mixture was degassed with nitrogen and stirred at 130° C. for 2 hr. After cooled to room temperature, the solid was filtered out. The filtration was concentrated under vacuum. The residue was purified with Prep-TLC (DCM/MeOH=20/1) to give product (63.39 mg, yield: 72.7%). $^1$H NMR (400 MHz, DMSO-$d_6$) δ 12.28 (s, 1H), 10.41 (s, 1H), 9.00 (s, 1H), 8.62 (s, 1H), 8.46 (s, 1H), 7.93 (d, J=8.5 Hz, 1H), 7.55 (d, J=8.5 Hz, 1H), 7.05 (s, 1H), 6.53 (s, 1H), 4.15-4.12 (m, 1H), 3.97 (d, J=12.0 Hz, 1H), 3.88-3.57 (m, 7H), 3.52 (t, J=11.6 Hz, 1H), 3.38 (s, 3H), 3.17 (t, J=11.6 Hz, 1H), 2.39 (t, J=11.0 Hz, 2H), 2.10 (s, 3H), 1.27-1.07 (m, 9H). MS (ESI) m/e [M+1]$^+$ 596.

Example C24: Synthesis of compound N-(5-(cis-2,6-dimethylmorpholino)-4'-((4-((R)-3-methylmorpholino)-6-(methylsulfon-yl)pyridin-2-yl)amino)-[2,3'-bipyridin]-6'-yl)ace-tamide

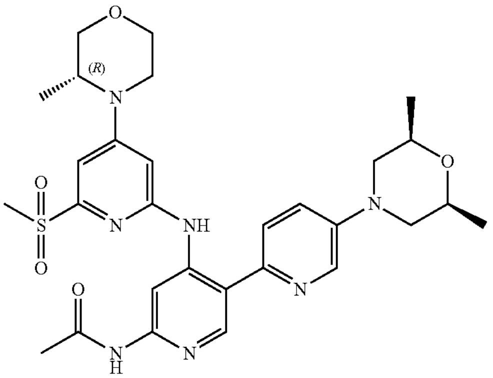

N-(4'-amino-5-(cis-2,6-dimethylmorpholino)-[2,3'-bipyridin]-6'-yl)aceta-mide (50 mg, 0.15 mmol), (R)-4-(2-chloro-6-(methylsulfonyl)pyridin-4-yl)-3-methyl-morpholine (47 mg, 0.16 mmol), $Pd_2dba_3$ (13.4 mg, 0.02 mmol), BINAP (18.3 mg, 0.03 mmol) and $Cs_2CO_3$ (72 mg, 0.22 mmol) were added into 1,4-dioxane (10 mL). The resulting mixture was degassed with nitrogen and stirred at 130° C. for 2 hr. After cooled to room temperature, the solid was filtered out. The filtration was concentrated under vacuum. The residue was purified with Prep-TLC (DCM/MeOH=20/1) to give the product (53.8 mg, yield: 61.7). $^1$H NMR (400 MHz, DMSO-$d_6$) δ 12.27 (s, 1H), 10.40 (s, 1H), 8.99 (s, 1H), 8.62 (s, 1H), 8.46 (s, 8H), 7.92 (d, J=8.6 Hz, 1H), 7.55 (d, J=8.6 Hz, 1H), 7.04 (s, 1H), 6.52 (s, 1H), 4.15-4.12 (m, 1H), 3.96 (d, J=10.4 Hz, 1H), 3.78-3.71 (m, 5H), 3.67-3.59 (m, 2H), 3.52 (t, J=11.4 Hz, 1H), 3.37 (s, 3H), 3.16 (t, J=11.4 Hz, 1H), 2.39 (t, J=11.1 Hz, 2H), 2.09 (s, 3H), 1.24-1.08 (in, 9H). MS (ESI) m/e [M+1](596.

The following Examples were prepared in a similar manner to the product Example C1:

| Example | Compound | Chemical Name | $^1$H NMR and LC /MS m/z (M + 1) |
|---|---|---|---|
| C2 | 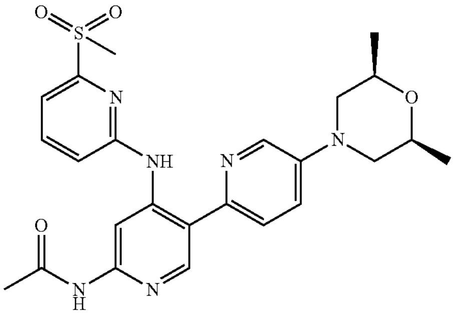 [SMILES: CC(=O)Nc1cc(Nc2cccc(S(C)(=O)=O)n2)c(-c2ccc(N3C[C@@H](C)O[C@@H](C)C3)cn2)cn1] | N-(5-((cis)-2,6-dimethylmorpholino)-4'-((6-(methylsulfonyl)pyridin-2-yl)amino)-[2,3'-bipyridin]-6'-yl)acetamide | $^1$H NMR (400 MHz, DMSO-$d_6$) δ 13.23 (s, 1H), 10.48 (s, 1H), 9.20 (s, 1H), 8.71 (s, 1H), 8.48 (d, J = 2.9 Hz, 1H), 7.97-7.94 (m, 2H), 7.57 - 7.52 (m, 2H), 7.36 (d, J = 8.4 Hz, 1H), 3.78 - 3.70 (m, 4H), 3.46 (s, 3H), 2.38 (t, J = 11.1 Hz, 2H), 2.10 (s, 3H), 1.17 (d, J = 6.2 Hz, 6H). MS (ESI) m/e [M + 1]$^+$ 497. |

-continued

| Example | Compound | Chemical Name | $^1$H NMR and LC /MS m/z (M + 1) |
|---|---|---|---|
| C3 | 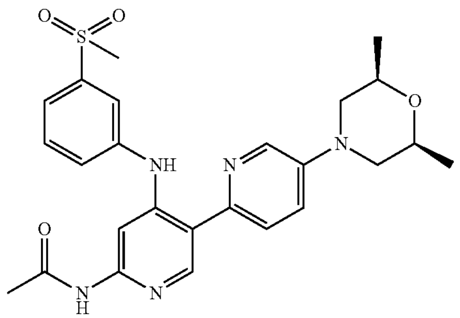 [SMILES: CC(=O)Nc1cc(Nc2cccc(S(C)(=O)=O)c2)c(-c2ccc(N3C[C@@H](C)O[C@@H](C)C3)cn2)cn1] | N-(5-((cis)-2,6-dimethylmorpholino)-4'-((3-(methylsulfonyl)phenyl)amino)-[2,3'-bipyridin]-6'-yl)acetamide | $^1$H NMR (400 MHz, DMSO-$d_6$) δ 11.65 (s, 1H), 10.44 (s, 1H), 8.62 (s, 1H), 8.41 (s, 1H), 8.18 (s, 1H), 7.93 (d, J = 9.1 Hz, 1H), 7.79 (s, 1H), 7.68-7.50 (m, 4H), 3.78 - 3.72 (m, 4H), 3.29 (s, 3H), 2.37 (t, J = 11.0 Hz, 2H), 2.06 (s, 3H), 1.17 (d, J = 5.8 Hz, 6H). MS (ESI) m/e [M + 1]$^+$ 496. |
| C4 | 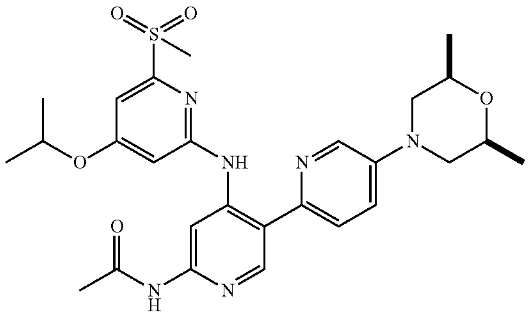 [SMILES: CC(=O)Nc1cc(Nc2cc(OC(C)C)cc(S(C)(=O)=O)n2)c(-c2ccc(N3C[C@@H](C)O[C@@H](C)C3)cn2)cn1] | N-(5-((cis)-2,6-dimethylmorpholino)-4'-((4-isopropoxy-6-(methylsulfonyl)pyridin-2-yl)amino)-[2,3'-bipyridin]-6'-yl)acetamide | $^1$H NMR (400 MHz, DMSO-$d_6$) δ 12.80 (s, 1H), 10.44 (s, 1H), 9.11 (s, 1H), 8.68 (s, 1H), 8.51 (s, 1H), 7.96 (d, J = 9.2 Hz, 1H), 7.56 (d, J = 6.3 Hz, 1H), 7.08 (s, 1H), 6.80 (s, 1H), 4.95 - 4.92 (m, 1H), 3.79 - 3.73 (m, 4H), 3.44 (s, 3H), 2.40 (t, J = 10.9 Hz, 2H), 2.11 (s, 3H), 1.33 (d, J = 5.9 Hz, 6H), 1.19 (d, J = 5.9 Hz, 6H). MS (ESI) m/e [M + 1]$^+$ 555. |
| C5 | 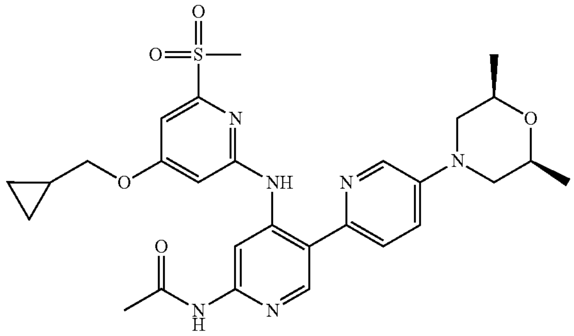 [SMILES: CC(=O)Nc1cc(Nc2cc(OCC3CC3)cc(S(C)(=O)=O)n2)c(-c2ccc(N3C[C@@H](C)O[C@@H](C)C3)cn2)cn1] | N-(4'-((4-(cyclopropylmethoxy)-6-(methylsulfonyl)pyridin-2-yl)amino)-5-((cis)-2,6-dimethylmorpholino)-[2,3'-bipyridin]-6'-yl)acetamide | $^1$H NMR (400 MHz, DMSO-$d_6$) δ 12.83 (s, 1H), 10.44 (s, 1H), 9.11 (s, 1H), 8.68 (s, 1H), 8.52 (s, 1H), 7.96 (d, J = 8.7 Hz, 1H), 7.56 (d, J = 8.7 Hz, 1H), 7.10 (s, 1H), 6.82 (s, 1H), 4.10 - 4.05 (m, 2H), 3.83 - 3.65 (m, 4H), 3.44 (s, 3H), 2.45 - 2.35 (m, 2H), 2.11 (s, 3H), 1.28 - 1.22 (m, 1H), 1.19 (d, J = 4.7 Hz, 6H), 0.65 - 0.60 (m, 2H), 0.40 - 0.35 (m, 2H). MS (ESI) m/e [M + 1]$^+$ 567. |
| C6 | 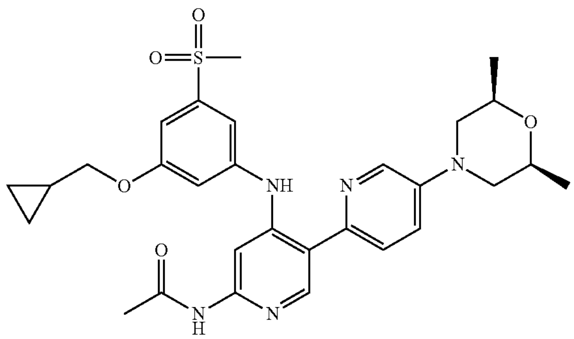 [SMILES: CC(=O)Nc1cc(Nc2cc(OCC3CC3)cc(S(C)(=O)=O)c2)c(-c2ccc(N3C[C@@H](C)O[C@@H](C)C3)cn2)cn1] | N-(4'-((3-(cyclopropylmethoxy)-5-(methylsulfonyl)phenyl)amino)-5-((cis)-2,6-dimethylmorpholino)-[2,3'-bipyridin]-6'-yl)acetamide | $^1$H NMR (400 MHz, DMSO-$d_6$) δ 11.64 (s, 1H), 10.43 (s, 1H), 8.61 (s, 1H), 8.41 (s, 1H), 8.20 (s, 1H), 7.91 (d, J = 9.0 Hz, 1H), 7.53 (d, J = 9.0 Hz, 1H), 7.34 (s, 1H), 7.15 (s, 1H), 7.06 (s, 1H), 3.99 - 3.96 (m, 2H), 3.77 - 3.74 (m, 4H), 3.27 (s, 3H), 2.40 - 2.35 (m, 2H), 2.07 (s, 3H), 1.26 - 1.22 (m, 1H), 1.17 (d, J = 6.0 Hz, 6H), 0.62 - 0.58 (m, 2H), 0.38 - 0.32 (m, 2H). MS (ESI) m/e [M + 1]$^+$ 566. |

-continued

| Example | Compound | Chemical Name | $^1$H NMR and LC /MS m/z (M + 1) |
|---|---|---|---|
| C7 | 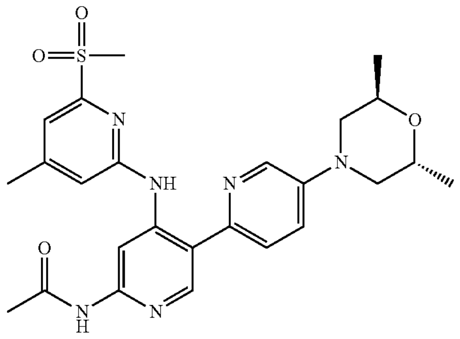 | N-(5-((trans)-2,6-dimethylmorpholino)-4'-((4-methyl-6-(methylsulfonyl)pyridin-2-yl)amino)-[2,3'-bipyridin]-6'-yl)acetamide | $^1$H NMR (400 MHz, DMSO-$d_6$) δ 13.09 (s, 1H), 10.47 (s, 1H), 9.21 (s, 1H), 8.70 (s, 1H), 8.49 (s, 1H), 7.98 (d, J = 8.9 Hz, 1H), 7.55 (d, J = 8.9 Hz, 1H), 7.42 (s, 1H), 7.20 (s, 1H), 4.11 (d, J = 2.6 Hz, 2H), 3.46 (s, 3H), 3.40 - 3.35 (m, 2H), 3.06 - 3.02 (m, 2H), 2.43 (s, 3H), 2.12 (s, 3H), 1.24 (d, J = 5.8 Hz, 6H). MS (ESI) m/e [M + 1]$^+$ 567. |
| C8 | 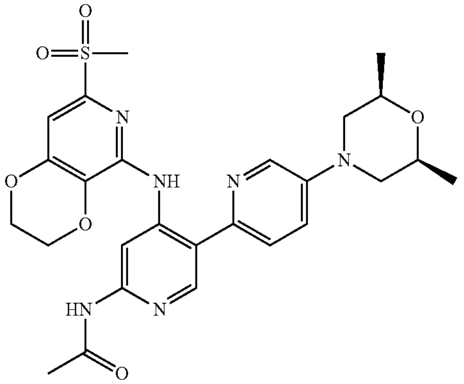 [SMILES: CC(=O)Nc1cc(Nc2nc(S(C)(=O)=O)cc3c2OCCO3)c(-c2ccc(N3C[C@@H](C)O[C@@H](C)C3)cn2)cn1] | N-(5-(Cis-2,6-dimethylmorpholino)-4'-((7-(methylsulfonyl)-2,3-dihydro-[1,4]dioxino[2,3-c]pyridin-5-yl)amino)-[2,3'-bipyridin]-6'-yl)acetamide | $^1$H NMR (400 MHz, DMSO-$d_6$) δ 13.26 (s, 1H), 10.44 (s, 1H), 9.39 (s, 1H), 8.70 (s, 1H), 8.37 (s, 1H), 7.97 (d, J = 9.0 Hz, 1H), 7.56 (d, J = 9.0 Hz, 1H), 7.13 (s, 1H), 4.66 - 4.63 (m, 2H), 4.50 - 4.45 (m, 2H), 3.82 - 3.74 (m, 4H), 3.46 (s, 3H), 2.45 - 2.40 (m, 2H), 2.12 (s, 3H), 1.19 (d, J = 6.0 Hz, 6H). MS (ESI) m/e [M + 1]$^+$ 555. |
| C9 | 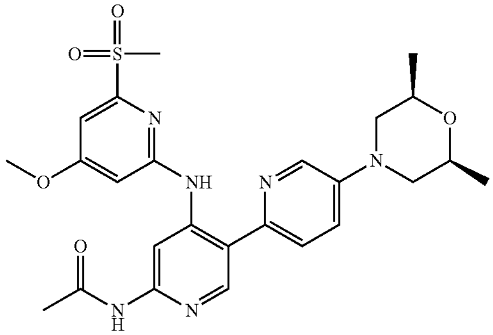 | N-(5-((cis)-2,6-dimethylmorpholino)-4'-((4-methoxy-6-(methylsulfonyl)pyridin-2-yl)amino)-[2,3'-bipyridin]-6'-yl)acetamide | MS (ESI) m/e [M + 1]$^+$ 527. |
| C10 | 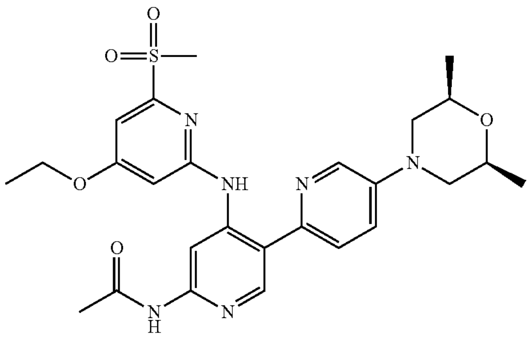 [SMILES: CCOc1cc(Nc2cc(NC(C)=O)ncc2-c2ccc(N3C[C@@H](C)O[C@@H](C)C3)cn2)nc(S(C)(=O)=O)c1] | N-(5-((cis)-2,6-dimethylmorpholino)-4'-((4-ethoxy-6-(methylsulfonyl)pyridin-2-yl)amino)-[2,3'-bipyridin]-6'-yl)acetamide | MS (ESI) m/e [M + 1]$^+$ 541. |

-continued

| Example | Compound | Chemical Name | $^1$H NMR and LC /MS m/z (M + 1) |
|---|---|---|---|
| C11 | 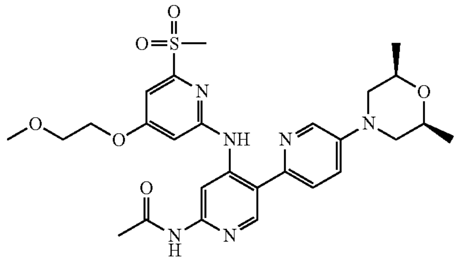 | N-(5-((cis)-2,6-dimethylmorpholino)-4'-((4-(2-methoxyethoxy)-6-(methylsulfonyl)pyridin-2-yl)amino)-[2,3'-bipyridin]-6'-yl)acetamide | MS (ESI) m/e $[M + 1]^+$ 571. |
| C12 | 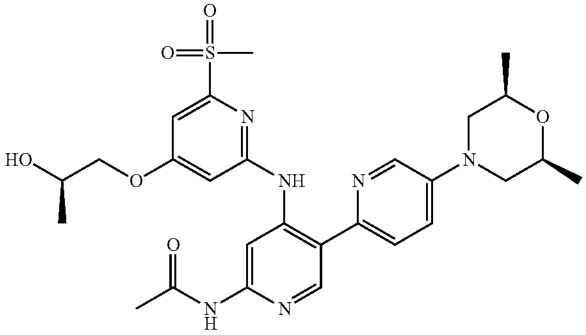 [SMILES: CC(=O)Nc1cc(Nc2cc(OC[C@@H](C)O)cc(S(C)(=O)=O)n2)c(-c2ccc(N3C[C@@H](C)O[C@@H](C)C3)cn2)cn1] | N-(5-((cis)-2,6-dimethylmorpholino)-4'-((4-((R)-2-hydroxypropoxy)-6-(methylsulfonyl)pyridin-2-yl)amino)-[2,3'-bipyridin]-6'-yl)acetamide | MS (ESI) m/e $[M + 1]^+$ 571. |
| C13 | 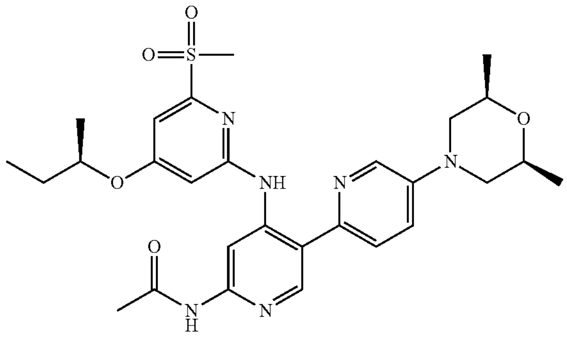 [SMILES: CC[C@@H](C)Oc1cc(Nc2cc(NC(C)=O)ncc2-c2ccc(N3C[C@@H](C)O[C@@H](C)C3)cn2)nc(S(C)(=O)=O)c1] | N-(4'-((4-((R)-sec-butoxy)-6-(methylsulfonyl)pyridin-2-yl)amino)-5-((cis)-2,6-dimethylmorpholino)-[2,3'-bipyridin]-6'-yl)acetamide Molecular Weight: 568.69 | MS (ESI) m/e $[M + 1]^+$ 569. |
| C14 | 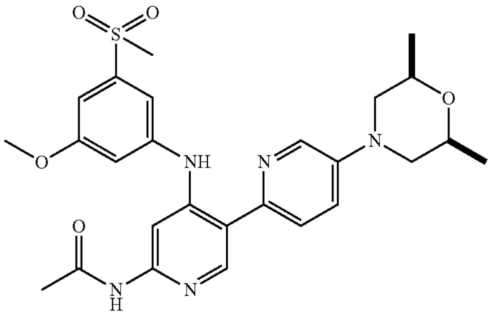 | N-(5-((cis)-2,6-dimethylmorpholino)-4'-((3-methoxy-5-(methylsulfonyl)phenyl)amino)-[2,3'-bipyridin]-6'-yl)acetamide Molecular Weight: 525.62 | MS (ESI) m/e $[M + 1]^+$ 526. |
| C15 | 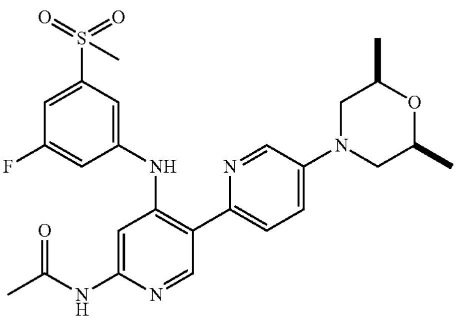 [SMILES: CC(=O)Nc1cc(Nc2cc(F)cc(S(C)(=O)=O)c2)c(-c2ccc(N3C[C@@H](C)O[C@@H](C)C3)cn2)cn1] | N-(5-((cis)-2,6-dimethylmorpholino)-4'-((3-fluoro-5-(methylsulfonyl)phenyl)amino)-[2,3'-bipyridin]-6'-yl)acetamide | MS (ESI) m/e $[M + 1]^+$ 514. |

-continued

| Example | Compound | Chemical Name | $^1$H NMR and LC /MS m/z (M + 1) |
|---|---|---|---|
| C16 | 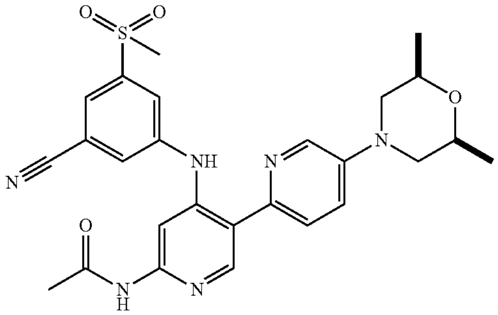 [SMILES: CC(=O)Nc1cc(Nc2cc(C#N)cc(S(C)(=O)=O)c2)c(-c2ccc(N3C[C@@H](C)O[C@@H](C)C3)cn2)cn1] | N-(4'-((3-cyano-5-(methylsulfonyl)phenyl)amino)-5-((cis)-2,6-dimethylmorpholino)-[2,3'-bipyridin]-6'-yl)acetamide | MS (ESI) m/e $[M + 1]^+$ 521. |
| C25 | 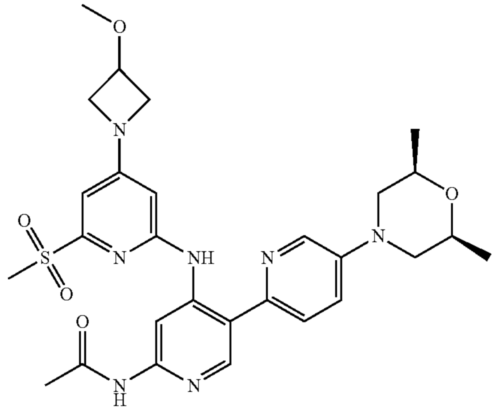 | N-(5-(cis-2,6-dimethyl-morpholino)-4'-((4-(3-methoxy-azetidin-1-yl)-6-(methylsulfonyl)pyridin -2-yl)amino)-[2,3'-bipyridin]-6'-yl)acetamide | 1H NMR (400 MHz, DMSO-d6) δ 12.39 (s, 1H), 10.49 (s, 1H), 9.04 (s, 1H), 8.70 (s, 1H), 8.53 (s, 1H), 8.00 (d, J = 8.0 Hz, 1H), 7.62 (d, J = 8.0 Hz, 1H), 6.70 (s, 1H), 6.20 (s, 1H), 4.45 - 4.42 (m, 1H), 4.32 - 4.30 (m, 2H), 3.97 - 3.95 (m, 2H), 3.86 - 3.80 (m, 4H), 3.43 (s, 3H), 3.34 (s, 3H), 2.49 - 2.44 (m, 2H), 2.17 (s, 3H), 1.26 - 1.23 (m, 6H). MS (ESI) m/e [M + 1]+ 582. |

Example D1: Synthesis of N-(5-(2-methoxyethoxy)-4'-((6-(methylsulfonyl)pyridin-2-yl)amino)-[2,3'-bipyridin]-6'-yl)acetamide

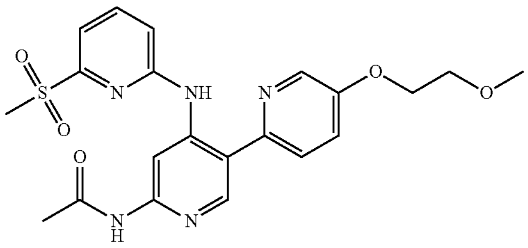

Step 1: 2-bromo-5-(2-methoxyethoxy)pyridine

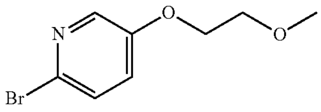

To a solution of 6-bromopyridin-3-ol (5 g, 28.7 mmol) in THF (50 mL) was added NaH (60% in mineral oil, 1.7 g, 43.1 mmol) one portions at 0° C. and the resulting mixture was stirred at this temperature for 15 mins, then 1-bromo-2-methoxyethane (8 g, 57.5 mmol) was added dropwise at 0° C. and the mixture was stirred at room temperature for 16 h. Upon completion of the reaction, the reaction mixture was poured into $H_2O$ (200 mL) and the resulting mixture was extracted with EA (40 mL×3). The combined organic layers were dried over $Na_2SO_4$ and concentrated under vacuum. The residue was purified by silica gel column chromatography (PE/EA=20:1 to 5:1) to give 2-bromo-5-(2-methoxyethoxy)pyridine (4.8 g, 72%). MS (ESI) m/e $[M+1]^+$ 232.

Step 2: tert-butyl (6'-chloro-5-(2-methoxyethoxy)-[2,3'-bipyridin]-4'-yl)carbamate

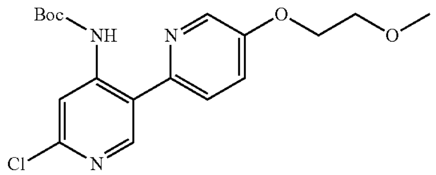 [SMILES: COCCOc1ccc(-c2cnc(Cl)cc2NC(=O)OC(C)(C)C)nc1]

A mixture of 2-bromo-5-(2-methoxyethoxy)pyridine (2.5 g, 10.7 mmol), tert-butyl (5-bromo-2-chloropyridin-4-yl) carbamate (3.6 g, 11.8 mmol), $Sn_2Me_6$ (5.2 g, 16.1 mmol), $Pd(PPh_3)_4$ (1.2 g, 1.08 mmol) and $Pd(PPh_3)_2Cl_2$ (756.1 mg, 1.1 mmol) in 1,4-dioxane (30 mL) was stirred at 110° C. for 16 h under nitrogen atmosphere. After cooled to room temperature, the solvent was removed in vacuo and the residue was diluted with 20 mL of water. The resulting solution was extracted with EA (40 mL×3) and the combined organic layers were washed with brine (50 mL), dried over anhydrous sodium sulfate. The solvent was removed in vacuo and the residue was purified by silica gel column chromatography (PE/EA=50:1 to 0:1) to give tert-butyl (6'-chloro-5-(2-methoxyethoxy)-[2,3'-bipyridin]-4'-yl)carbamate (1.2 g, 29%). $^1$H NMR (400 MHz, $CDCl_3$) δ 11.43 (s, 1H), 8.40 (s, 1H), 8.31-8.25 (m, 2H), 7.57 (d, J=8.8 Hz, 1H), 7.33-7.27 (m, 1H), 4.19-4.12 (m, 2H), 3.77-3.60 (m, 2H), 3.36 (s, 3H), 1.42 (s, 9H). MS (ESI) m/e $[M+1]^+$ 380.

Step 3: tert-butyl (6'-acetamido-5-(2-methoxyethoxy)-[2,3'-bipyridin]-4'-yl)carbamate

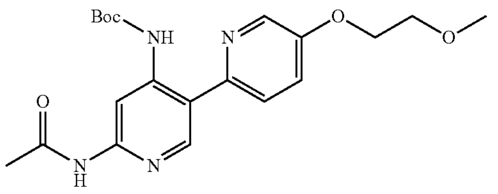 [SMILES: COCCOc1ccc(-c2cnc(NC(C)=O)cc2NC(=O)OC(C)(C)C)nc1]

To a solution of tert-butyl (6'-chloro-5-(2-methoxyethoxy)-[2,3'-bipyridin]-4'-yl)carbamate (0.8 g, 2.1 mmol) in 1,4-dioxane (10 mL) were added acetamide (149 mg, 2.5 mmol), $Cs_2CO_3$ (1.3 g, 4.2 mmol), XantPhos (243 mg, 0.42 mmol) and $Pd_2(dba)_3$ (192.86 mg, 0.21 mmol), the resulting mixture was stirred at 110° C. for 16 h under nitrogen atmosphere. After cooled to room temperature, the solvent was removed in vacuo and the residue was diluted with 10 mL of water. The resulting solution was extracted with EA (10 mL×3) and the combined organic layers were washed with brine (50 mL), dried over anhydrous sodium sulfate. The solvent was removed in vacuo and the residue was purified by silica gel column chromatography (PE/EA=50:1 to 0:1) to give tert-butyl (6'-acetamido-5-(2-methoxyethoxy)-[2,3'-bipyridin]-4'-yl)carbamate (0.5 g, 58%). MS (ESI) m/e $[M+1]^+$ 403.

Step 4: N-(4'-amino-5-(2-methoxyethoxy)-[2,3'-bipyridin]-6'-yl)acetamide

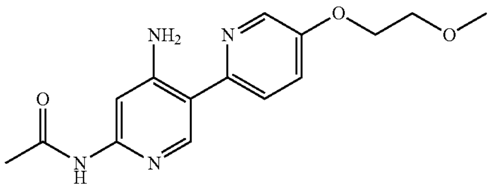 [SMILES: COCCOc1ccc(-c2cnc(NC(C)=O)cc2N)nc1]

To a mixture of tert-butyl (6'-acetamido-5-(2-methoxyethoxy)-[2,3'-bipyridin]-4'-yl)carbamate (0.5 g, 1.2 mmol) in DCM (8 mL) was added TFA (2 mL) and the resulting solution was stirred at room temperature for 3 h. Upon completion of the reaction, the solvent was removed in vacuo and the residue was diluted with water, then aq. $NaHCO_3$ (50%) was added to adjust the pH value to 10. The resulting mixture was extracted with EA (10 mL×3). The combined organic layers were dried over $Na_2SO_4$ and concentrated to give N-(4'-amino-5-(2-methoxyethoxy)-[2,3'-bipyridin]-6'-yl)acetamide (275 mg, 73%). $^1$H NMR (400 MHz, DMSO-$d_6$) δ 10.09 (s, 1H), 8.37-8.29 (m, 2H), 7.82 (d, J=9.0 Hz, 1H), 7.50-7.45 (m, 2H), 7.44-7.34 (m, 2H), 4.25-4.18 (m, 2H), 3.70-3.65 (m, 2H), 3.31 (s, 3H), 2.06 (s, 3H). MS(ESI) m/e $[M+1]^+$ 303.

Step 5: N-(5-(2-methoxyethoxy)-4'-((6-(methylsulfonyl)pyridin-2-yl)amino)-[2,3'-bipyridin]-6'-yl) acetamide

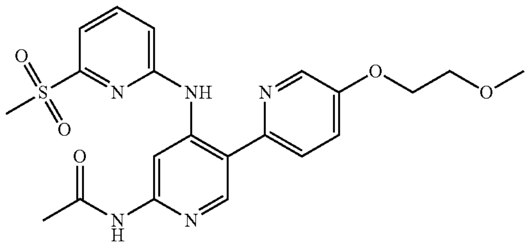

A solution of N-(T-amino-5-(2-methoxyethoxy)-[2,3'-bipyridin]-6'-yl)acetamide (50 mg, 0.17 mmol), 2-bromo-6-(methylsulfonyl)pyridine (60 mg, 0.26 mmol), $Pd(dba)_3$ (16 mg, 0.017 mmol), BINAP (10 mg, 0.017 mmol), $CsCO_3$ (110 mg, 0.34 mmol) in 10 ml dioxane was stirred at 120° C. in sealed tube for 2 h, the solution was concentrated and purified by Prep-TLC to give N-(5-(2-methoxyethoxy)-4'-((6-(methylsulfonyl)pyridin-2-yl)amino)-[2,3'-bipyridin]-6'-yl)acetamide (10 mg). $^1$H NMR (400 MHz, DMSO-$d_6$) δ 12.66 (s, 1H), 10.50 (s, 1H), 919 (s, 1H), 8.70 (s, 1H), 8.55-8.51 (m, 1H), 8.05-7.95 (s, 2H), 7.62-7.59 (m, 1H), 7.54-7.52 (m, 1H), 7.38-7.35 (m, 1H), 4.27-4.25 (m, 2H), 3.71-3.68 (m, 2H), 3.45 (s, 3H), 3.31 (s, 3H), 2.10 (s, 3H). MS (ESI) m/e $[M+1]^+$ 458.

The following Examples were prepared in a similar manner to the product Example D1:

| Example | Compound | Chemical Name | $^1$H NMR and LC /MS m/z (M + 1) |
|---|---|---|---|
| D2 | 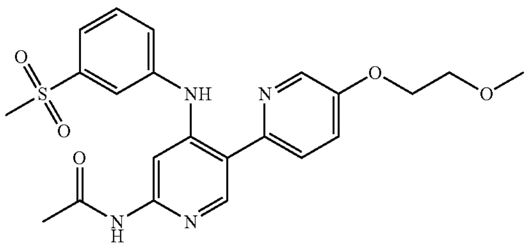 | N-(5-(2-methoxyethoxy)-4'-((3-(methylsulfonyl)phenyl)amino)-[2,3'-bipyridin]-6'-yl)acetamide | $^1$H NMR (400 MHz, DMSO-$d_6$) δ 11.21 (s, 1H), 10.48 (s, 1H), 8.60 (s, 1H), 8.44 (s, 1H), 8.15 (s, 1H), 7.99 (d, J = 9.1 Hz, 1H), 7.81 (s, 1H), 7.61-7.58 (m, 4H), 4.25 - 4.24 (m, 2H), 3.70 - 3.69 (m, 2H), 3.32 (s, 3H), 3.29 (s, 3H), 2.07 (s, 3H). MS (ESI) m/e $[M + 1]^+$ 457. |

-continued

| Example | Compound | Chemical Name | $^1$H NMR and LC /MS m/z (M + 1) |
|---|---|---|---|
| D3 | 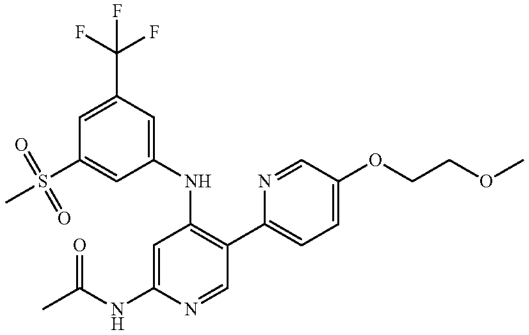 | N-(5-(2-methoxyethoxy)-4'-((3-(methylsulfonyl)-5-(trifluoromethyl)phenyl)amino)-[2,3'-bipyridin]-6'-yl)acetamide | $^1$H NMR (400 MHz, DMSO-$d_6$) δ 11.17 (s, 1H), 10.53 (s, 1H), 8.61 (s, 1H), 8.45 (s, 1H), 8.21 (s, 1H), 8.06 (s, 1H), 7.94 (d, J = 8.2 Hz, 2H), 7.76 (s, 1H), 7.57 (d, J = 8.9 Hz, 1H), 4.25 - 4.20 (m, 2H), 3.70 - 3.68 (m, 2H), 3.38 (s, 3H), 3.32 (s, 3H), 2.08 (s, 3H). MS (ESI) m/e [M + 1]$^+$ 525. |
| D4 | 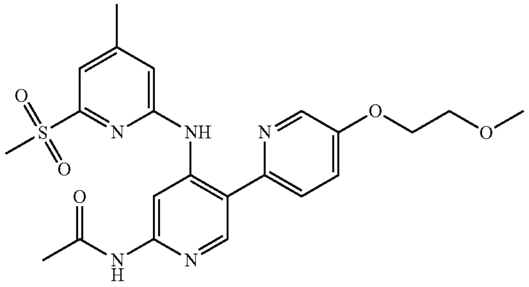 | N-(5-(2-methoxyethoxy)-4'-((4-methyl-6-(methylsulfonyl)pyridin-2-yl)amino)-[2,3'-bipyridin]-6'-yl)acetamide | $^1$H NMR (400 MHz, DMSO-$d_6$) δ 12.67 (s, 1H), 10.54 (s, 1H), 9.20 (s, 1H), 8.71 (s, 1H), 8.56 (s, 1H), 8.06 (d, J = 8.8 Hz, 1H), 7.64 (d, J = 8.9 Hz, 1H), 7.44 (s, 1H), 7.24 (d, J = 10.3 Hz, 2H), 4.29 - 4.22 (m, 2H), 3.72 - 3.70 (m, 2H), 3.46 (s, 3H), 3.34 (s, 3H), 2.42 (s, 3H), 2.12 (s, 3H). MS (ESI) m/e [M + 1]$^+$ 472. |
| D5 | 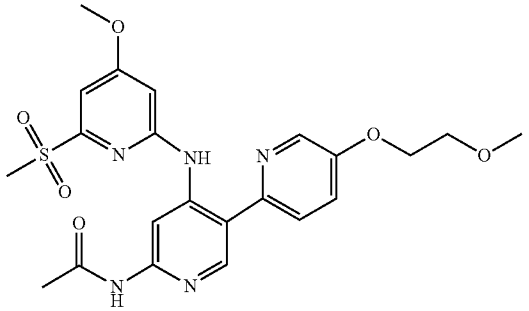 | N-(4'-((4-methoxy-6-(methylsulfonyl)pyridin-2-yl)amino)-5-(2-methoxyethoxy)-[2,3'-bipyridin]-6'-yl)acetamide | $^1$H NMR (400 MHz, DMSO-$d_6$) δ 12.39 (s, 1H), 10.51 (s, 1H), 9.12 (s, 1H), 8.68 (s, 1H), 8.56 (s, 1H), 8.03 (d, J = 8.6 Hz, 1H), 7.63 (d, J = 8.7 Hz, 1H), 7.10 (s, 1H), 6.87 (s, 1H), 4.28 - 4.25 (m, 2H), 3.96 (s, 3H), 3.75 - 3.70 (m, 2H), 3.44 (s, 3H), 3.34 (s, 3H), 2.12 (s, 3H). MS (ESI) m/e [M + 1]$^+$ 488. |
| D6 | 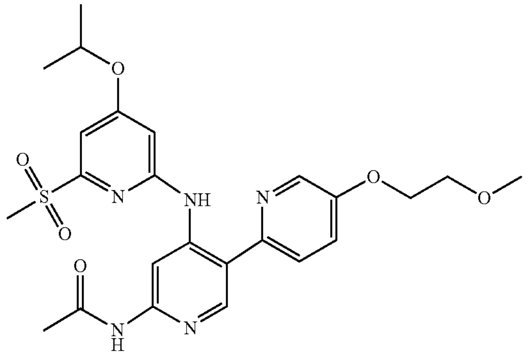 | N-(4'-((4-isopropoxy-6-(methylsulfonyl)pyridin-2-yl)amino)-5-(2-methoxyethoxy)-[2,3'-bipyridin]-6'-yl)acetamide | $^1$H NMR (400 MHz, DMSO-$d_6$) δ 12.36 (s, 1H), 10.50 (s, 1H), 9.12 (s, 1H), 8.67 (s, 1H), 8.56 (s, 1H), 8.03 (d, J = 9.1 Hz, 1H), 7.62 (d, J = 9.2 Hz, 1H), 7.06 (s, 1H), 6.83 (s, 1H), 4.95 - 4.91 (m, 1H), 4.30 - 4.25 (m, 2H), 3.75 - 3.71 (m, 2H), 3.43 (s, 3H), 3.34 (s, 3H), 2.11 (s, 3H), 1.33 (d, J = 5.4 Hz, 6H). MS (ESI) m/e [M + 1]$^+$ 516. |
| D7 | 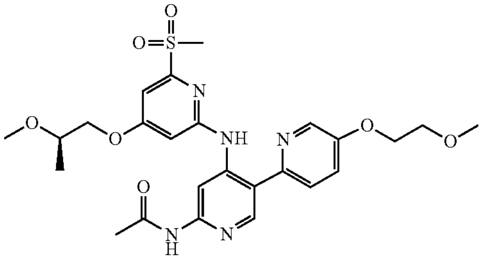 | (R)-N-(5-(2-methoxyethoxy)-4'-((4-(2-methoxypropoxy)-6-(methylsulfonyl)pyridin-2-yl)amino)-[2,3'-bipyridin]-6'-yl)acetamide | $^1$H NMR (400 MHz, DMSO-$d_6$) δ 12.41 (s, 1H), 10.52 (s, 1H), 9.12 (s, 1H), 8.68 (s, 1H), 8.57 (s, 1H), 8.03 (d, J = 8.8 Hz, 1H), 7.63 (d, J = 8.8 Hz, 1H), 7.11 (s, 1H), 6.88 (s, 1H), 4.30 - 4.25 (m, 2H), 4.20 - 4.15 (m, 2H), 3.72 (s, 3H), 3.44 (s, 3H), 3.35 - 3.28 (m, 6H), 2.12 (s, 3H), 1.19 (d, J = 5.6 Hz, 3H). MS (ESI) m/e [M + 1]$^+$ 546. |

-continued

| Example | Compound | Chemical Name | $^1$H NMR and LC /MS m/z (M + 1) |
|---|---|---|---|
| D8 | 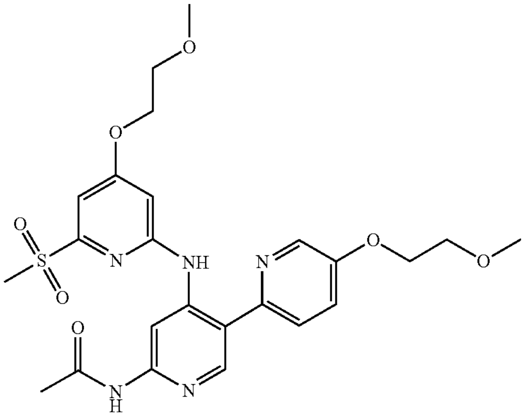 | N-(5-(2-methoxyethoxy)-4'-((4-(2-methoxyethoxy)-6-(methylsulfonyl)pyridin-2-yl)amino)-[2,3'-bipyridin]-6'-yl)acetamide | $^1$H NMR (400 MHz, DMSO-$d_6$) δ 12.45 (s, 1H), 10.49 (s, 1H), 9.13 (s, 1H), 8.68 (s, 1H), 8.56 (s, 1H), 8.03 (d, J = 8.9 Hz, 1H), 7.62 (d, J = 8.9 Hz, 1H), 7.11 (s, 1H), 6.87 (s, 1H), 4.33 - 4.28 (m, 4H), 3.75 - 3.70 (m, 4H), 3.44 (s, 3H), 3.33 (s, 3H), 3.32 (s, 3H), 2.12 (s, 3H). MS (ESI) m/e $[M + 1]^+$ 532. |
| D9 | 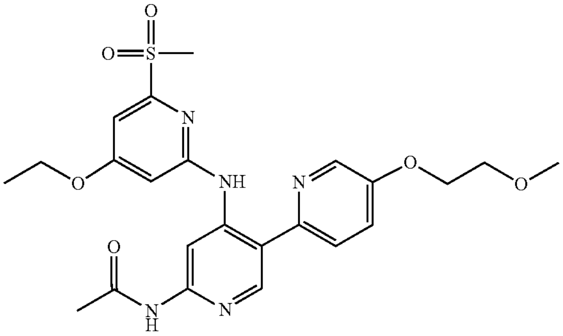 [SMILES: CCOc1cc(Nc2cc(NC(C)=O)ncc2-c2ccc(OCCOC)cn2)nc(S(C)(=O)=O)c1] | N-(4'-((4-ethoxy-6-(methylsulfonyl)pyridin-2-yl)amino)-5-(2-methoxyethoxy)-[2,3'-bipyridin]-6'-yl)acetamide | $^1$H NMR (400 MHz, DMSO-$d_6$) δ 12.38 (s, 1H), 10.48 (s, 1H), 9.11 (s, 1H), 8.67 (s, 1H), 8.56 (s, 1H), 8.03 (d, J = 8.8 Hz, 1H), 7.62 (d, J = 8.8 Hz, 1H), 7.08 (s, 1H), 6.84 (s, 1H), 4.28 - 4.24 (m, 4H), 3.75 - 3.70 (m, 2H), 3.43 (s, 3H), 3.34 (s, 3H), 2.11 (s, 3H), 1.38 (t, J = 6.5 Hz, 3H). MS (ESI) m/e $[M + 1]^+$ 502. |
| D10 | 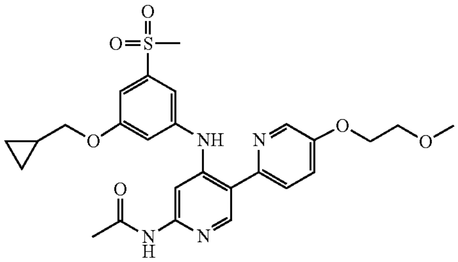 [SMILES: COCCOc1ccc(-c2cnc(NC(C)=O)cc2Nc2cc(OCC3CC3)cc(S(C)(=O)=O)c2)nc1] | N-(4'-((3-(cyclopropylmethoxy)-5-(methylsulfonyl)phenyl)amino)-5-(2-methoxyethoxy)-[2,3'-bipyridin]-6'-yl)acetamide | $^1$H NMR (400 MHz, DMSO-$d_6$) δ 11.18 (s, 1H), 10.45 (s, 1H), 8.59 (s, 1H), 8.45 (s, 1H), 8.18 (s, 1H), 7.95 (d, J = 8.4 Hz, 1H), 7.58 (d, J = 8.4 Hz, 1H), 7.35 (s, 1H), 7.16 (s, 1H), 7.06 (s, 1H), 4.25 - 4.20 (m, 2H), 3.95 - 3.93 (m, 2H), 3.70 - 3.65 (m, 2H), 3.27 (s, 3H), 2.07 (s, 3H), 1.25 - 1.20 (m, 1H), 0.60 - 0.55 (m, 2H), 0.35 - 0.30 (m, 2H). MS (ESI) m/e $[M + 1]^+$ 527. |
| D11 | 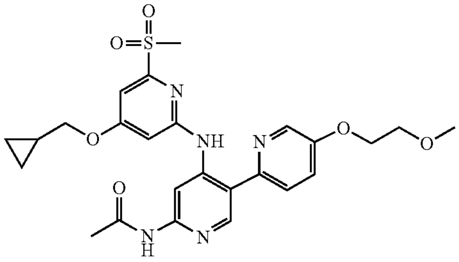 [SMILES: COCCOc1ccc(-c2cnc(NC(C)=O)cc2Nc2cc(OCC3CC3)cc(S(C)(=O)=O)n2)nc1] | N-(4'-((4-(cyclopropylmethoxy)-6-(methylsulfonyl)pyridin-2-yl)amino)-5-(2-methoxyethoxy)-[2,3'-bipyridin]-6'-yl)acetamide | MS (ESI) m/e $[M + 1]^+$ 528. |

Example E1: Synthesis of N-(5-(methoxymethyl)-4'-((3-(methylsulfonyl) phenyl)amino)-[2,3'-bipyridin]-6'-yl)acetamide

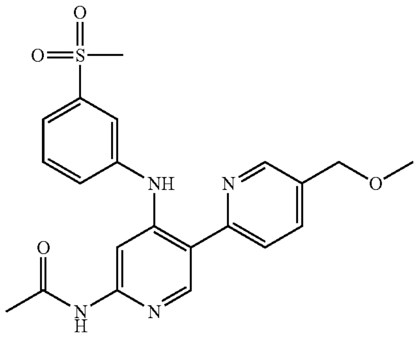 [SMILES: COCc1ccc(-c2cnc(NC(C)=O)cc2Nc2cccc(S(C)(=O)=O)c2)nc1]

Step 1: 2-bromo-5-(methoxymethyl)pyridine

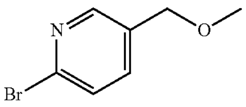

A solution of 2-bromo-5-(bromomethyl) pyridine (10 g, 39.85 mmol), NaOMe (9.6 mL, 51.8 mmol) in MeOH (150 mL) was stirred at RT overnight. The solvent was removed in vacuo and the residue was extracted between EA and $H_2O$. The organic layer was dried over $Na_2SO_4$. The organic layer was filtered, and the filtrate was concentrated under reduced pressure. The crude product was purified by silica gel column chromatography (PE/EA=5:1) to give the desired product 2-bromo-5-(methoxymethyl) pyridine (7.8 g, 96.9% yield). MS (ESI) m/e $[M+1]^+$ 202.

Step 2: tert-butyl (6'-chloro-5-(methoxymethyl)-[2, 3'-bipyridin]-6$^{4}$'-yl) carbamate

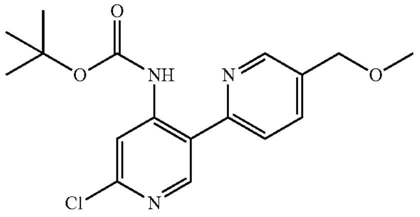 [SMILES: COCc1ccc(-c2cnc(Cl)cc2NC(=O)OC(C)(C)C)nc1]

A mixture of 2-bromo-5-(methoxymethyl)pyridine (3 g, 14.84 mmol), $Sn_2Me_6$ (5.4 g, 16.48 mmol) and $Pd(PPh_3)_4$ (1.9 g, 1.65 mmol) in dioxane (50 mL) was stirred at 100° C. under $N_2$ overnight. The mixture was cooled to RT and then tert-butyl (5-bromo-2-chloropyridin-4-yl)carbamate (4.8 g, 15.6 mmol) and $Pd(PPh_3)_2Cl_2$ (1.2 g, 1.75 mmol) in dioxane (40 mL) was added under $N_2$. The mixture was stirred at 100° C. for 10 h under nitrogen atmosphere. After cooled to room temperature, the mixture was diluted with KF—$H_2O$ (50 mL) and extracted with EA (100 mL×2). The combined organic layers were dried over anhydrous $Na_2SO_4$ and concentrated under vacuum. The residue was purified by silica gel column chromatography (PE/EA=10:1 to 5:1) to give tert-butyl (6'-chloro-5-(methoxymethyl)-[2,3'-bipyridin]-4'-yl)carbamate (930 mg, 17.9%). MS (ESI) m/e $[M+1]^+$ 250.

Step 3: N-(4'-amino-5-(methoxymethyl)-[2,3'-bipyridin]-6'-yl) acetamide TFA salt

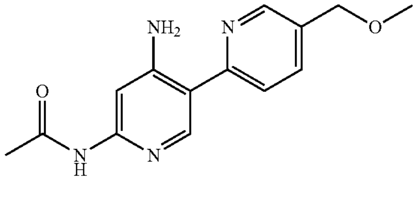 [SMILES: COCc1ccc(-c2cnc(NC(C)=O)cc2N)nc1]

A solution of tert-butyl (6'-chloro-5-(methoxymethyl)-[2, 3'-bipyridin]-4'-yl) carbamate (580 mg, 1.56 mmol) in DCM (4 mL) was added TFA (2 mL). The mixture was stirred at RT for 5 h. The solvent was removed, and the crude was used in the next step without further purification (400 mg, TFA salt). MS (ESI) m/e $[M+1]^+$ 273.

Step 4: N-(5-(methoxymethyl)-4'-((3-(methylsulfonyl)phenyl)amino)-[2,3'-bipyridin]-6'-yl)acetamide

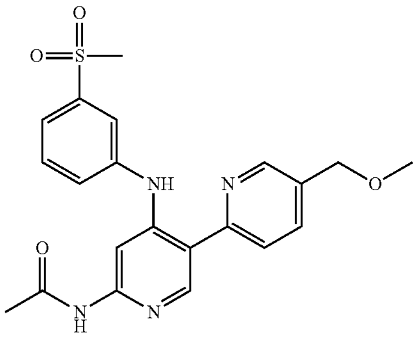 [SMILES: COCc1ccc(-c2cnc(NC(C)=O)cc2Nc2cccc(S(C)(=O)=O)c2)nc1]

05761 A solution of N-(4'-amino-5-(methoxymethyl)-[2, 3'-bipyridin]-6'-yl) acetamide TFA salt (100 mg, 0.27 mmol), 1-bromo-3-(methylsulfonyl)benzene (174 mg, 0.74 mmol), $Cs_2CO_3$ (479.8 mg, 1.47 mmol), Xant-phos Pd G3 (70.2 mg, 0.074 mmol) and Xant-phos (85.2 mg, 0.15 mmol) in dioxane (3 mL) was stirred at 130'° C. under $N_2$ overnight. The mixture was filtered and the filtrate as concentrated to give the crude residue which was purified by Prep-TLC (MeOH/DCM=1:10) to afford N-(5-(Cis-2,6-dimethylmorpholino)-4'-((4-methyl-6-(methylsulfonyl)pyridin-2-yl) amino)-[2,3'-bipyridin]-6'-yl)acetamide (45.9 mg, 39.9% yield). $^1H$ NMR (400 MHz, DMSO-d6) δ11.48 (s, 1H), 10.50 (s, 1H), 8.68 (d, J=7.9 Hz, 2H), 8.19 (s, 1H), 8.06 (d, J=8.4 Hz, 1H), 7.89 (d, J=8.4 Hz, 1H), 7.83 (s, 1H), 7.64 (s, 2H), 7.62-7.58 (m, 1H), 4.51 (s, 2H), 3.28 (s, 3H), 2.07 (s, 3H). MS (ESI) m/e $[M+1]^+$ 427.

| Example | Compound | Chemical Name | $^1$H NMR and LC /MS m/z (M + 1) |
|---|---|---|---|
| E2 | 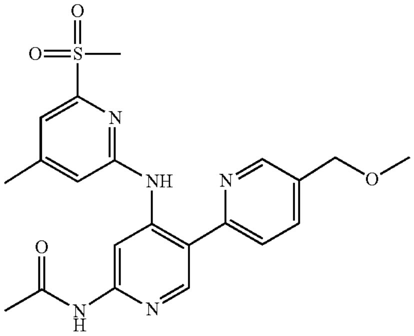 | N-(5-(methoxymethyl)-4'-((4-methyl-6-(methylsulfonyl)pyridin-2-yl)amino)-[2,3'-bipyridin]-6'-yl)acetamide | $^1$H NMR (400 MHz, DMSO-d$_6$) δ 12.94 (s, 1H), 10.54 (s, 1H), 9.25 (s, 1H), 8.85 - 8.75 (m, 2H), 8.12 (d, J = 8.4 Hz, 1H), 7.94 (d, J = 8.4 Hz, 1H), 7.44 (s, 1H), 7.27 (s, 1H), 4.55 (s, 2H), 3.46 (s, 3H), 3.37 (s, 3H), 2.42 (s, 3H), 2.12 (s, 3H). MS (ESI) m/e [M + 1]$^+$ 442. |
| E3 | 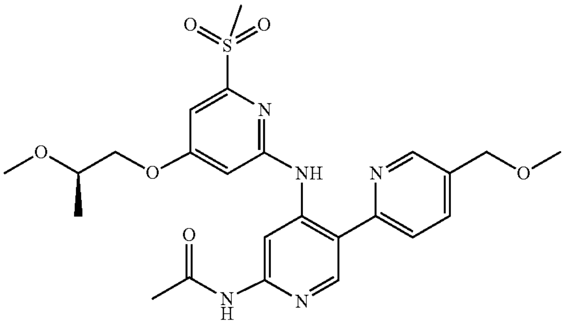 | (R)-N-(5-(methoxymethyl)-4'-((4-(2-methoxypropoxy)-6-(methylsulfonyl)pyridin-2-yl)amino)-[2,3'-bipyridin]-6'-yl)acetamide | $^1$H NMR (400 MHz, DMSO-d$_6$) δ 12.69 (s, 1H), 10.55 (s, 1H), 9.16 (s, 1H), 8.80 (s, 1H), 8.77 (s, 1H), 8.11 (d, J = 8.5 Hz, 1H), 7.93 (d, J = 8.5 Hz, 1H), 7.11 (s, 1H), 6.93 (s, 1H), 4.54 (s, 2H), 4.25 - 4.12 (m, 2H), 3.71 (s, 1H), 3.44 (s, 3H), 3.37 (s, 3H), 2.12 (s, 3H), 1.20 (d, J = 6.2 Hz, 3H). MS (ESI) m/e [M + 1]$^+$ 516. |
| E4 | 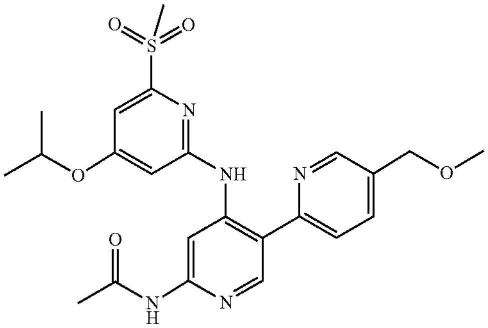 [SMILES: COCc1ccc(-c2cnc(NC(C)=O)cc2Nc2cc(OC(C)C)cc(S(C)(=O)=O)n2)nc1] | N-(4'-((4-isopropoxy-6-(methylsulfonyl)pyridin-2-yl)amino)-5-(methoxymethyl)-[2,3'-bipyridin]-6'-yl)acetamide | $^1$H NMR (400 MHz, DMSO-d$_6$) δ 12.62 (s, 1H), 10.54 (s, 1H), 9.14 (s, 1H), δ 8.79 (s, 1H), 8.77 (s, 1H), 8.10 (d, J = 8.4 Hz, 1H), 7.92 (d, J = 8.4 Hz, 1H), 7.06 (s, 1H), 6.88 (s, 1H), 5.01 - 4.83 (m, 1H), 4.54 (s, 2H), 3.43 (s, 3H), 3.37 (s, 3H), 2.12 (s, 3H), 1.33 (d, J = 5.9 Hz, 6H). MS (ESI) m/e [M + 1]$^+$ 486. |
| E5 | 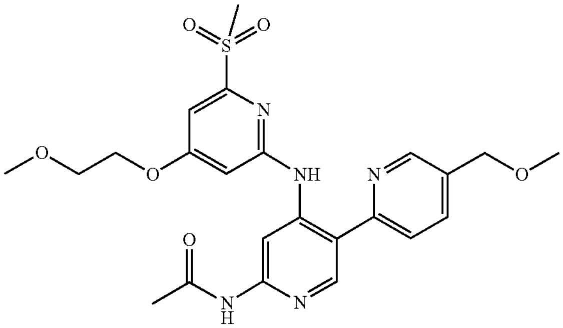 | N-(4'-((4-(2-methoxyethoxy)-6-(methylsulfonyl)pyridin-2-yl)amino)-5-(methoxymethyl)-[2,3'-bipyridin]-6'-yl)acetamide | 1H NMR (400 MHz, DMSO- d$_6$) δ 12.74 (s, 1H), 10.55 (s, 1H), 9.17 (s, 1H), 8.80 (s, 1H), 8.75 (s, 1H), 8.11 (d, J = 8.1 Hz, 1H), 7.92 (d, J = 8.1 Hz, 1H), 7.11 (s, 1H), 6.92 (s, 1H), 4.54 (s, 2H), 4.40 - 4.30 (m, 2H), 3.75 - 3.65 (m, 2H), 3.44 (s, 3H), 3.37 (s, 3H), 3.32 (s, 3H), 2.12 (s, 3H). MS (ESI) m/e [M + 1]$^+$ 502. |

-continued

| Example | Compound | Chemical Name | $^1$H NMR and LC /MS m/z (M + 1) |
|---|---|---|---|
| E6 | 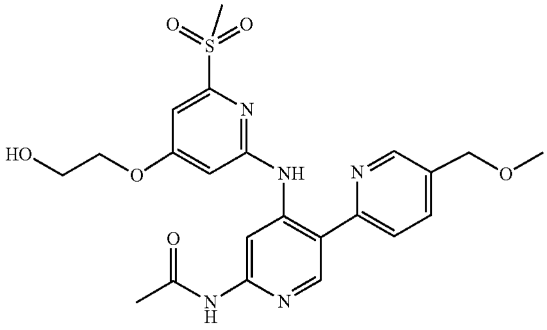 [SMILES: COCc1ccc(-c2cnc(NC(C)=O)cc2Nc2cc(OCCO)cc(S(C)(=O)=O)n2)nc1] | N-(4'-((4-(2-hydroxyethoxy)-6-(methylsulfonyl)pyridin-2-yl)amino)-5-(methoxymethyl)-[2,3'-bipyridin]-6'-yl)acetamide | $^1$H NMR (400 MHz, DMSO-$d_6$) δ 12.69 (s, 1H), 10.54 (s, 1H), 9.17 (s, 1H), 8.80 (s, 1H), 8.78 (s, 1H), 8.11 (d, J = 8.0 Hz, 1H), 7.92 (d, J = 8.0 Hz, 1H), 7.10 (s, 1H), 6.91 (s, 1H), 4.98 (s, 1H), 4.54 (s, 2H), 4.30 - 4.20 (m, 2H), 3.80 - 3.70 (m, 2H), 3.44 (s, 3H), 3.37 (s, 3H), 2.12 (s, 3H). MS (ESI) m/e [M + 1]$^+$ 488. |
| E7 | 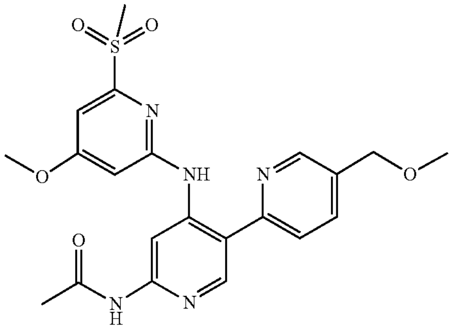 | N-(4'-((4-methoxy-6-(methylsulfonyl)pyridin-2-yl)amino)-5-(methoxymethyl)-[2,3'-bipyridin]-6'-yl)acetamide | $^1$H NMR (400 MHz, DMSO-$d_6$) δ 12.68 (s, 1H), 10.55 (s, 1H), 9.15 (s, 1H), 8.78 (s, 1H), 8.72 (s, 1H), 8.11 (d, J = 8.4 Hz, 1H), 7.93 (d, J = 8.4 Hz, 1H), 7.11 (s, 1H), 6.92 (s, 1H), 4.54 (s, 2H), 3.96 (s, 3H), 3.44 (s, 3H), 3.37 (s, 3H), 2.12 (s, 3H). MS (ESI) m/e [M + 1]$^+$ 458. |
| E8 | 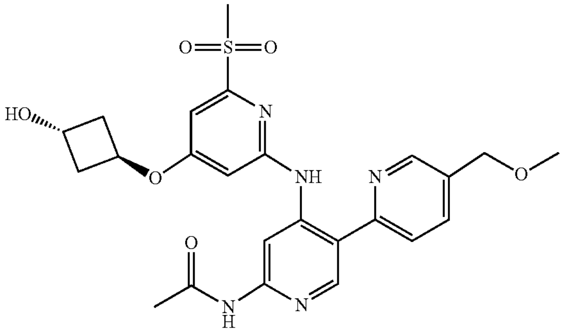 [SMILES: COCc1ccc(-c2cnc(NC(C)=O)cc2Nc2cc(O[C@H]3C[C@H](O)C3)cc(S(C)(=O)=O)n2)nc1] | N-(4'-((4-((1r,3r)-3-hydroxycyclobutoxy)-6-(methylsulfonyl)pyridin-2-yl)amino)-5-(methoxymethyl)-[2,3'-bipyridin]-6'-yl)acetamide | $^1$H NMR (400 MHz, DMSO-$d_6$) δ = 12.56 (s, 1H), 10.54 (s, 1H), 9.12 (s, 1H), 8.76 (s, 2H), 8.09 (d, J = 8.1 Hz, 1H), 7.92 (d, J = 8.4 Hz, 1H), 6.99 (s, 1H), 6.73 (s, 1H), 5.28 (d, J = 5.4 Hz, 1H), 5.12 - 5.06 (m, 1H), 4.54 (s, 2H), 4.42 - 4.36 (m, 1H), 3.42 (s, 3H), 3.37 (s, 3H), 2.39 - 2.35 (m, 4H), 2.12 (s, 3H). MS (ESI) m/e [M + 1]$^+$ 514. |
| E9 | 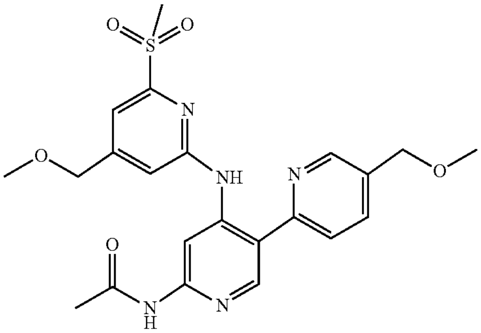 | N-(5-(methoxymethyl)-4'-((4-(methoxymethyl)-6-(methylsulfonyl)pyridin-2-yl)amino)-[2,3'-bipyridin]-6'-yl)acetamide | $^1$H NMR (400 MHz, DMSO-$d_6$) δ 12.89 (s, 1H), 10.56 (s, 1H), 9.26 (s, 1H), δ 8.79 (s, 1H), 8.77 (s, 1H), 8.12 (d, J = 8.3 Hz, 1H), 7.93 (d, J = 8.3 Hz, 1H), 7.50 (s, 1H), 7.31 (s, 1H), δ 4.56 (s, 2H), 4.55 (s, 2H), 3.48 (s, 3H), 3.39 (s, 2H), 3.37 (s, 2H), 2.13 (s, 3H). MS (ESI) m/e [M + 1]$^+$ 472. |

Example F1: Synthesis of N-(4'-((4-methyl-6-(methylsulfonyl)pyridin-2-yl)amino)-5-(trifluoromethyl)-[2,3'-bipyridin]-6'-yl)acetamide

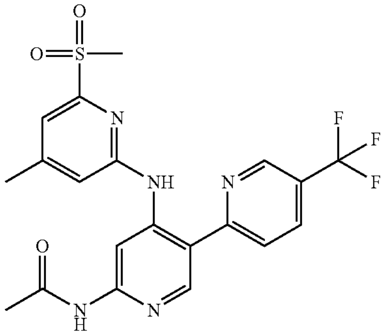 [SMILES: CC(=O)Nc1cc(Nc2cc(C)cc(S(C)(=O)=O)n2)c(-c2ccc(C(F)(F)F)cn2)cn1]

A mixture of N-(4'-amino-5-(trifluoromethyl)-[2,3'-bipyridin]-6'-yl)acetamide (100 mg, 0.34 mmol), 2-bromo-4-methyl-6-(methylsulfonyl)pyridine (100 mg, 0.4 mmol), $Pd_2dba_3$ (27 mg, 0.03 mmol), BINAP (18 mg, 0.03 mmol) and $Cs_2CO_3$ (208 mg, 0.64 mmol) in dioxane (6 mL) was stirred at 130° C. under $N_2$ in a sealed tube for 4 h. The reaction mixture was filtered and the solid was washed with EA (10 mL). The filtrate was concentrated and the residue was purified by prep-TLC (DCM/MeOH=20:1) to give N-(4'-((4-methyl-6-(methyl sulfonyl)pyridin-2-yl)amino)-5-(trifluoromethyl)-[2,3'-bipyridin]-6'-yl)acetamide (37 mg, 23%). $^1$H NMR (400 MHz, DMSO-$d_6$) δ 12.42 (s, 1H), 10.61 (s, 1H), 9.26 (s, 1H), 9.20 (s, 1H), 8.84 (s, 1H), 8.32-8.30 (m, 2H), 7.44 (s, 1H), 7.31 (s, 1H), 3.44 (s, 3H), 2.41 (s, 3H), 2.11 (s, 3H). MS (ESI) m/e $[M+1]^+$ 466.

Example F17: Synthesis of N-(5-fluoro-4'-((4-methyl-6-(methylsulfonyl)pyridin-2-yl)amino)-[2,3'-bipyridin]-6'-yl)acetamide

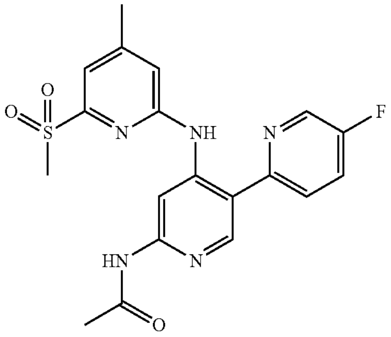 [SMILES: CC(=O)Nc1cc(Nc2cc(C)cc(S(C)(=O)=O)n2)c(-c2ccc(F)cn2)cn1]

A mixture of N-(4'-amino-5-fluoro-[2,3'-bipyridin]-6'-yl) acetamide (800 mg, 3.25 mmol), 2-bromo-4-methyl-6-(methylsulfonyl)pyridine (976 mg, 3.9 mmol), $Pd_2(dba)_3$ (297 mg, 0.325 mmol), BINAP (405 mg, 0.65 mmol) and $Cs_2CO_3$ (1.59 g, 4.875 mmol) in 1,4-dioxane (14 mL) was stirred 130° C. for 3 hr under $N_2$ atmosphere. The reaction was cooled to room temperature, filtered and the filtration was concentrated under vacuum. The residue was purified by silica gel column chromatography (DCM/MeOH=100:1) to afford the product (600 mg, 44%). $^1$H NMR (400 MHz, DMSO-$d_6$) δ 12.06 (s, 1H), 10.53 (s, 1H), 9.20 (s, 1H), 8.80 (s, 1H), 8.71 (s, 1H), 8.16 (d, J=7.3 Hz, 1H), 7.95 (d, J=7.3 Hz, 1H), 7.44 (s, 1H), 7.23 (s, 1H), 3.44 (s, 3H), 2.41 (s, 3H), 2.12 (s, 3H). MS (ESI) m/e $[M+1]^+$ 416.

Example F22: Synthesis of N-(5-fluoro-4'-((4-methoxy-6-(methylsulfonyl)pyridin-2-yl)amino)-[2,3'-bipyridin]-6'-yl)acetamide

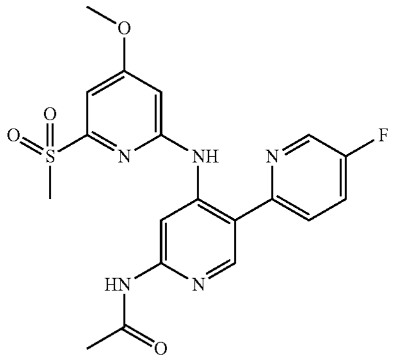 [SMILES: COc1cc(Nc2cc(NC(C)=O)ncc2-c2ccc(F)cn2)nc(S(C)(=O)=O)c1]

Step 1: 6'-chloro-5-fluoro-[2,3'-bipyridin]-4'-amine

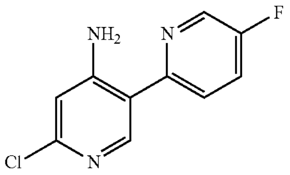 [SMILES: Nc1cc(Cl)ncc1-c1ccc(F)cn1]

A mixture of 2-bromo-5-fluoropyridine (1.6 g, 9.09 mmol), 2-chloro-5-(4,4,5,5-tetramethyl-1,3,2-dioxaborolan-2-yl)pyridin-4-amine (2.54 g, 10 mmol), $Pd(dppf)Cl_2$ (664 mg, 0.909 mmol) and $K_2CO_3$ (1.88 g, 13.64 mmol) in 1,4-dioxane (50 mL) and $H_2O$ (5 mL) was stirred at 100° C. for 2 hr. The reaction was cooled to room temperature and diluted with EA, washed with brine, dried and concentrated. The residue was purified by silica gel column chromatography (EA/PE=1:3) to give the product (1.9 g). MS (ESI) m/e $[M+1]^+$ 224.

Step 2: N-(4'-amino-5-fluoro-[2,3'-bipyridin]-6'-yl) acetamide

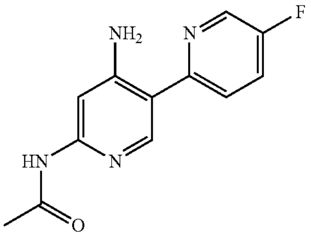 [SMILES: CC(=O)Nc1cc(N)c(-c2ccc(F)cn2)cn1]

A mixture 6'-chloro-5-fluoro-[2,3'-bipyridin]-4'-amine (1.4 g, 6.25 mmol), acetamide (2.21 g, 37.5 mmol), $Pd_2(dba)_3$ (572 mg, 0.625 mmol), Xantphos (724 mg, 1.25 mmol) and $Cs_2CO_3$ (4.08 g, 12.5 mmol) in 1,4-dioxane (20 mL) was degassed with nitrogen and heated to 130° C. in a sealed tube stirring overnight. The reaction was cooled to room temperature and concentrated under vacuum. The residue was purified by silica gel column chromatography (DCM/MeOH=50:1) to give the product (1.4 g, crude). MS (ESI) m/e $[M+1]^+$ 247.

Step 3: N-(5-fluoro-4'-((4-methoxy-6-(methylsulfonyl)pyridin-2-yl)amino)-[2,3'-bipyridin]-6'-yl)acetamide

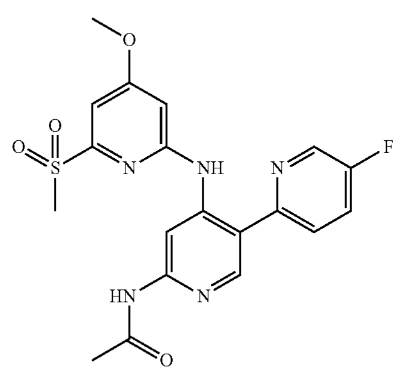 [SMILES: COc1cc(Nc2cc(NC(C)=O)ncc2-c2ccc(F)cn2)nc(S(C)(=O)=O)c1]

A mixture of N-(4'-amino-5-fluoro-[2,3'-bipyridin]-6'-yl) acetamide (1.5 g, 6.07 mmol), 2-bromo-4-methoxy-6-(methylsulfonyl)pyridine (1.78 g, 6.68 mmol), $Pd_2(dba)_3$ (555 mg, 0.607 mmol), BINAP (765 mg, 1.214 mmol) and $Cs_2CO_3$ (3.96 g, 12.14 mmol) in 1,4-dioxane (30 mL) was degassed with nitrogen and heated to 130° C. in a sealed tube stirring for 3 hr. The reaction was cooled to room temperature, filtered and the filtration was concentrated under vacuum. The residue was purification by column flash on silica gel eluted with DCM/MeOH (100:1) to afford the desired product as a light yellow solid. It was then washed with 10 mL of MeCN to give the product (27 mg, 30%). $^1H$ NMR (400 MHz, DMSO-$d_6$) δ 11.82 (s, 1H), 10.54 (s, 1H), 9.10 (s, 1H), 8.81 (s, 1H), 8.68 (s, 1H), 8.20-8.06 (m, 1H), 7.95-7.90 (m, 1H), 7.11 (s, 1H), 6.90 (s, 1H), 3.95 (s, 3H), 3.42 (s, 3H), 2.12 (s, 3H). MS (ESI) m/e $[M+1]^+$ 432.

Example F23: Synthesis of N-(4'-((3,4-dimethoxy-6-(methylsulfonyl)pyridin-2-yl)amino)-5-fluoro-[2,3'-bipyridin]-6'-yl)acetamide

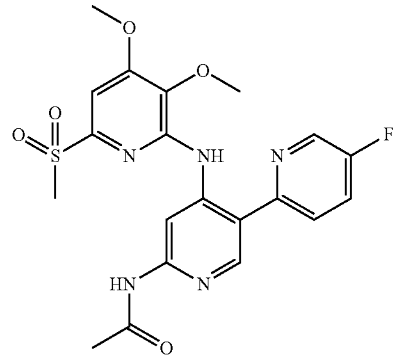 [SMILES: COc1cc(S(C)(=O)=O)nc(Nc2cc(NC(C)=O)ncc2-c2ccc(F)cn2)c1OC]

A mixture of N-(4'-amino-5-fluoro-[2,3'-bipyridin]-6'-yl) acetamide (40 mg, 0.163 mmol), 2-bromo-3,4-dimethoxy-6-(methylsulfonyl)pyridine (53 mg, 0.179 mmol), $Pd_2(dba)_3$ (15 mg, 0.0163 mmol), BINAP (20 mg, 0.0326 mmol) and $Cs_2CO_3$ (106 mg, 0.326 mmol) in 1,4-dioxane (6 mL) was degassed with nitrogen and heated to 130° C. in a sealed tube stirring for 4 hr. The reaction was cooled to room temperature, filtered and the filtration was concentrated under vacuum. The residue was applied onto Prep-TLC with (DCM/MeOH=20:1) to afford the product (40 mg, 30%). $^1H$ NMR (400 MHz, DMSO-$d_6$) δ 12.64 (s, 1H), 10.53 (s, 1H), 9.40 (s, 1H), 8.82 (s, 1H), 8.75 (s, 1H), 8.21 (d, J=4.8 Hz, 1H), 7.99 (d, J=6.4 Hz, 1H), 7.38 (s, 1H), 4.02 (s, 3H), 3.97 (s, 3H), 3.50 (s, 3H), 2.13 (s, 3H). MS (ESI) m/e $[M+1]^+$ 462.

Example F24: Synthesis of N-(5-fluoro-4'-((4-(methoxy-d3)-6-(methylsulfonyl)pyridine-2-yl) amino)-[2,3'-bipyridin]-6'-yl)acetamide

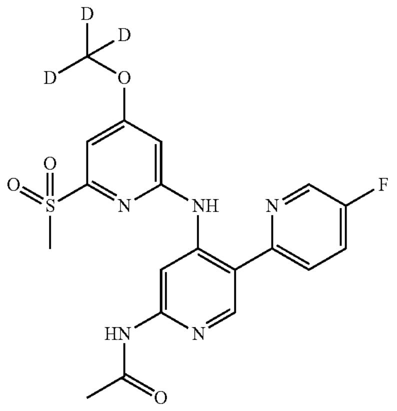 [SMILES: [2H]C([2H])([2H])Oc1cc(Nc2cc(NC(C)=O)ncc2-c2ccc(F)cn2)nc(S(C)(=O)=O)c1]

A mixture of N-(4'-amino-5-fluoro-[2,3'-bipyridin]-6'-yl) acetamide 40 mg, 0.163 mmol), 2-bromo-4-(methoxy-d3)-6-(methylsulfonyl)pyridine (48 mg, 0.179 mmol), $Pd_2(dba)_3$ (15 mg, 0.0163 mmol), BINAP (20 mg, 0.0326 mmol) and $Cs_2CO_3$ (132 mg, 0.326 mmol) in 1,4-dioxane (6 mL) was degassed with nitrogen and heated to 130° C. in a sealed tube stirring for 3 hr. The reaction was cooled to room temperature, filtered and the filtration was concentrated under vacuum. The residue was applied onto Prep-TLC (DCM/MeOH=20:1) to afford the product (30 mg, 30%). $^1H$ NMR (400 MHz, DMSO-$d_6$) δ 11.81 (s, 1H), 10.54 (s, 1H), 9.10 (s, 1H), 8.81 (s, 1H), 8.68 (s, 1H), 8.13 (d, J=7.5 Hz, 1H), 7.94 (d, J=7.5 Hz, 1H), 7.11 (s, 1H), 6.89 (s, 1H), 3.42 (s, 3H), 2.12 (s, 3H). MS (ESI) m/e $[M+1]^+$ 435.

Example F25: Synthesis of N-(4'-((4-cyclopropyl-6-(methylsulfonyl)pyridin-2-yl)amino)-5-fluoro-[2,3'-bipyridin]-6'-yl)acetamide

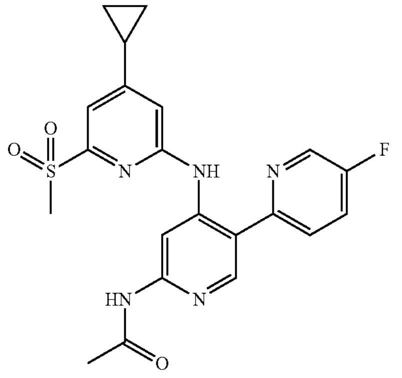 [SMILES: CC(=O)Nc1cc(Nc2cc(C3CC3)cc(S(C)(=O)=O)n2)c(-c2ccc(F)cn2)cn1]

A mixture of N-(4'-amino-5-fluoro-[2,3'-bipyridin]-6'-yl) acetamide (50 mg, 0.203 mmol), 2-chloro-4-cyclopropyl-6-(methylsulfonyl)pyridine (57 mg, 0.244 mmol), $Pd_2(dba)_3$ (19 mg, 0.0203 mmol), BINAP (25 mg, 0.0406 mmol) and $Cs_2CO_3$ (132 mg, 0.406 mmol) in 1,4-dioxane (6 mL) was degassed with nitrogen and heated to 130° C. in a sealed tube stirring for 4 hr. The reaction was cooled to room temperature, filtered and the filtration was concentrated under vacuum. The residue was applied onto Prep-TLC with (DCM/MeOH=20:1) to afford the product (23 mg, 25%). $^1$H NMR (400 MHz, DMSO-$d_6$) δ 11.84 (s, 11), 10.49 (s, 1H), 9.06 (s, 1H), 8.77 (s, 1H), 8.64 (s, 1H), 8.10-8.08 (m, 8H), 7.95-7.90 (m, 1H), 7.22 (s, 1H), 7.02 (s, 1H), 3.37 (s, 3H), 2.07 (s, 4H), 1.96-1.94 (m, 1H), 1.12-1.05 (m, 2H), 0.95-0.88 (m, 2H). MS (ESI) m/e $[M+]^+$ 442.

| Example | Compound | Chemical Name | $^1$H NMRand LC /MS m/z (M + 1) |
|---|---|---|---|
| F2 | 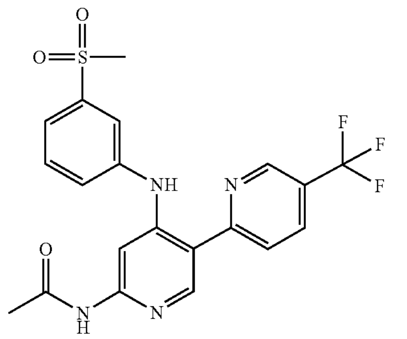 [SMILES: CC(=O)Nc1cc(Nc2cccc(S(C)(=O)=O)c2)c(-c2ccc(C(F)(F)F)cn2)cn1] | N-(4'-((3-(methylsulfonyl)phenyl)amino)-5-(trifluoromethyl)-[2,3'-bipyridin]-6'-yl)acetamide | $^1$H NMR (400 MHz, DMSO-$d_6$) δ 10.99 (s, 1H), 10.56 (s, 1H), 9.07 (s, 1H), 8.72 (s, 1H), 8.28 (s, 1H), 8.25 (s, 1H), 8.16 (s, 1H), 7.81 (s, 1H), 7.65 -7.61 (m, 3H), 3.26 (s, 3H), 2.05 (s, 3H). MS (ESI) m/e $[M + 1]^+$ 451. |
| F3 | 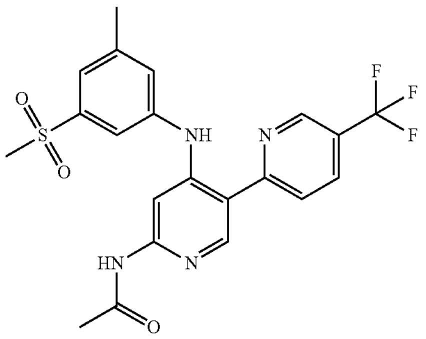 [SMILES: CC(=O)Nc1cc(Nc2cc(C)cc(S(C)(=O)=O)c2)c(-c2ccc(C(F)(F)F)cn2)cn1] | N-(4'-((3-methyl-5-(methylsulfonyl)phenyl)amino)-5-(trifluoromethyl)-[2,3'-bipyridin]-6'-yl)acetamide | $^1$H NMR (400 MHz, DMSO-$d_6$) δ 11.02 (s, 1H), 10.56 (s, 1H), 9.09 (s, 1H), 8.74 (s, 1H), 8.41 - 8.12 (m, 3H), 7.64 (s, 1H), 7.46 (s, 2H), 3.26 (s, 3H), 2.41 (s, 3H), 2.08 (s, 3H). MS (ESI) m/e $[M + 1]^+$ 465. |
| F4 | 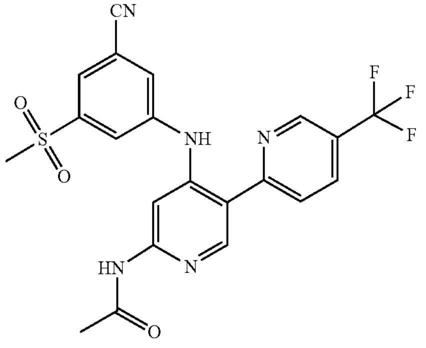 [SMILES: CC(=O)Nc1cc(Nc2cc(C#N)cc(S(C)(=O)=O)c2)c(-c2ccc(C(F)(F)F)cn2)cn1] | N-(4'-((3-cyano-5-(methylsulfonyl)phenyl)amino)-5-(trifluoromethyl)-[2,3'-bipyridin]-6'-yl)acetamide | $^1$H NMR (400 MHz, DMSO-$d_6$) δ 11.06 (s, 1H), 10.67 (s, 1H), 9.08 (s, 1H), 8.75 (s, 1H), 8.31 (s, 1H), 8.21 (s, 2H), 8.07 (s, 2H), 7.98 (s, 1H), 2.10 (s, 3H). MS (ESI) m/e $[M + 1]^+$ 476. |

-continued

| Example | Compound | Chemical Name | $^1$H NMRand LC /MS m/z (M + 1) |
|---|---|---|---|
| F5 | 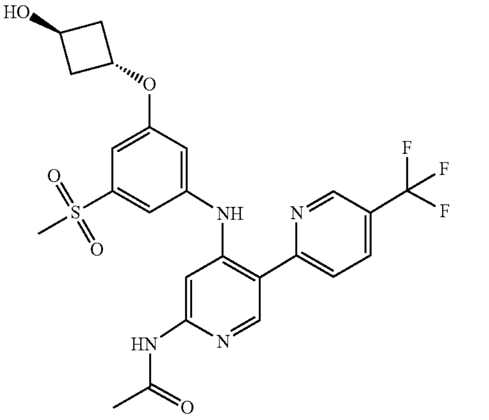 [SMILES: CC(=O)Nc1cc(Nc2cc(O[C@H]3C[C@H](O)C3)cc(S(C)(=O)=O)c2)c(-c2ccc(C(F)(F)F)cn2)cn1] | N-(4'-((3-((trans)-3-hydroxycyclobutoxy)-5-(methylsulfonyl)phenyl)amino)-5-(trifluoromethyl)-[2,3'-bipyridin]-6'-yl)acetamide | $^1$H NMR (400 MHz, DMSO-$d_6$) δ 10.92 (s, 1H), 10.56 (s, 1H), 9.09 (s, 1H), 8.72 (s, 1H), 8.29 - 8.20 (m, 3H), 7.40 (s, 1H), 7.03 (s, 1H), 6.98 (s, 1H), 5.25 - 5.19 (m, 1H), 4.95 - 4.90 (m, 1H), 4.37 - 4.32 (m, 1H), 3.27 (s, 3H), 2.35 - 2.30 (m, 4H), 2.08 (s, 3H). MS (ESI) m/e $[M + 1]^+$ 537. |
| F6 | 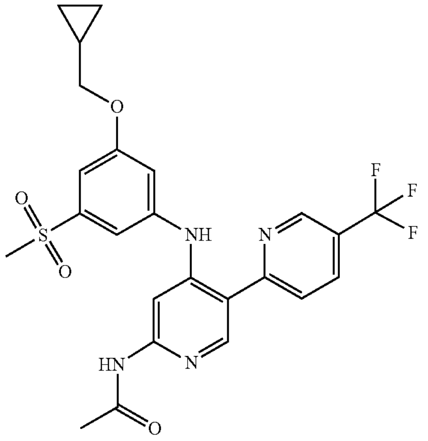 [SMILES: CC(=O)Nc1cc(Nc2cc(OCC3CC3)cc(S(C)(=O)=O)c2)c(-c2ccc(C(F)(F)F)cn2)cn1] | N-(4'-((3-(cyclopropylmethoxy)-5-(methylsulfonyl)phenyl)amino)-5-(trifluoromethyl)-[2,3'-bipyridin]-6'-yl)acetamide | $^1$H NMR (400 MHz, DMSO-$d_6$) δ 11.01 (s, 1H), 10.56 (s, 1H), 9.10 (s, 1H), 8.73 (s, 1H), 8.32 - 8.22 (m, 3H), 7.39 (s, 1H), 7.19 (s, 1H), 7.10 (s, 1H), 3.95 (d, J = 6.6 Hz, 2H), 3.27 (s, 3H), 2.08 (s, 3H), 1.30 - 1.24 (m, 1H), 0.59 - 0.58 (m, 2H), 0.35 - 0.30 (m, 2H). MS (ESI) m/e $[M + 1]^+$ 521. |
| F7 | 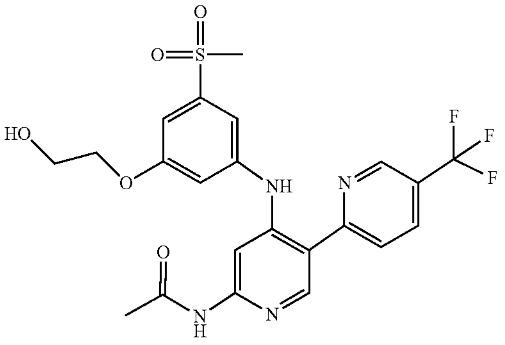 [SMILES: CC(=O)Nc1cc(Nc2cc(OCCO)cc(S(C)(=O)=O)c2)c(-c2ccc(C(F)(F)F)cn2)cn1] | N-(4'-((3-(2-hydroxyethoxy)-5-(methylsulfonyl)phenyl)amino)-5-(trifluoromethyl)-[2,3'-bipyridin]-6'-yl)acetamide | $^1$H NMR (400 MHz, DMSO-$d_6$) δ 11.00 (s, 1H), 10.57 (s, 1H), 9.10 (s, 1H), 8.74 (s, 1H), 8.30 - 8.26 (m, 3H), 7.41 (s, 1H), 7.21 (s, 1H), 7.12 (s, 1H), 4.93 (s, 1H), 4.11 (s, 2H), 3.74 (s, 2H), 3.28 (s, 3H), 2.09 (s, 3H). MS (ESI) m/e $[M + 1]^+$ 511. |
| F8 | 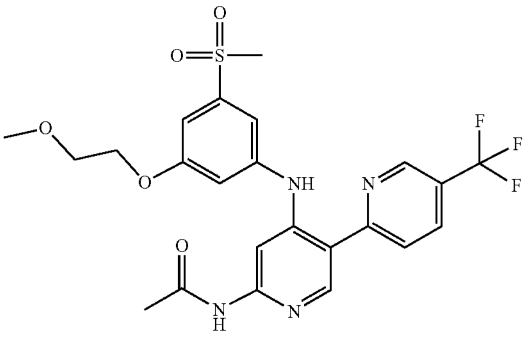 [SMILES: COCCOc1cc(Nc2cc(NC(C)=O)ncc2-c2ccc(C(F)(F)F)cn2)cc(S(C)(=O)=O)c1] | N-(4'-((3-(2-methoxyethoxy)-5-(methylsulfonyl)phenyl)amino)-5-(trifluoromethyl)-[2,3'-bipyridin]-6'-yl)acetamide | $^1$H NMR (400 MHz, DMSO-$d_6$) δ 11.02 (s, 1H), 10.58 (s, 1H), 9.10 (s, 1H), 8.74 (s, 1H), 8.34 - 8.21 (m, 3H), 7.41 (s, 1H), 7.22 (s, 1H), 7.12 (s, 1H), 4.23 (s, 2H), 3.69 (s, 2H), 3.28 (s, 3H), 2.09 (s, 3H). MS (ESI) m/e $[M + 1]^+$ 525. |

-continued

| Example | Compound | Chemical Name | $^1$H NMRand LC /MS m/z (M + 1) |
|---|---|---|---|
| F9 | 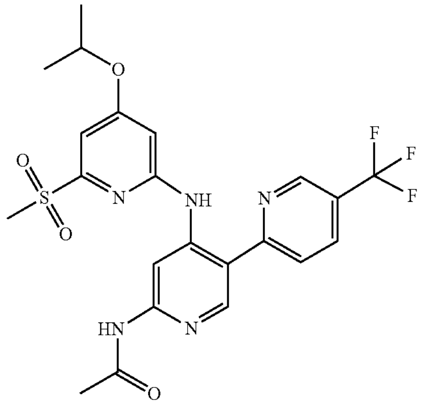 [SMILES: CC(=O)Nc1cc(Nc2cc(OC(C)C)cc(S(C)(=O)=O)n2)c(-c2ccc(C(F)(F)F)cn2)cn1] | N-(4'-((4-isopropoxy-6-(methylsulfonyl)pyridin-2-yl)amino)-5-(trifluoromethyl)-[2,3'-bipyridin]-6'-yl)acetamide | $^1$H NMR (400 MHz, DMSO-$d_6$) δ 12.13 (s, 1H), 10.62 (s, 1H), 9.20 - 9.15 (m, 2H), 8.83 (s, 1H), 8.40 - 8.23 (m, 2H), 7.09 (s, 1H), 6.93 (s, 1H), 4.92 (s, 1H), 3.43 (s, 3H), 2.13 (s, 3H), 1.33 (d, J = 5.0 Hz, 6H). MS (ESI) m/e $[M + 1]^+$ 510. |
| F10 | 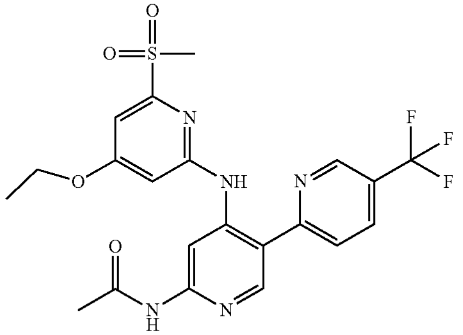 [SMILES: CCOc1cc(Nc2cc(NC(C)=O)ncc2-c2ccc(C(F)(F)F)cn2)nc(S(C)(=O)=O)c1] | N-(4'-((4-ethoxy-6-(methylsulfonyl)pyridin-2-yl)amino)-5-(trifluoromethyl)-[2,3'-bipyridin]-6'-yl)acetamide | $^1$H NMR (400 MHz, DMSO-$d_6$) δ 12.21 (s, 1H), 10.62 (s, 1H), 9.22 (s, 1H), 9.19 (s, 1H), 8.83 (s, 1H), 8.35 - 8.32 (m, 2H), 7.11 (s, 1H), 6.94 (s, 1H), 4.28 - 4.24 (m, 2H), 3.44 (s, 3H), 2.13 (s, 3H), 1.40 - 1.38 (m, 3H). MS (ESI) m/e $[M + 1]^+$ 496. |
| F11 | 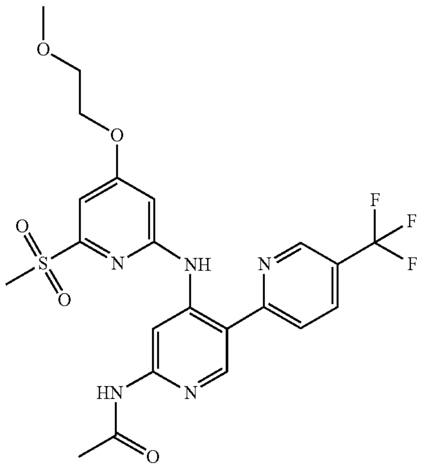 [SMILES: COCCOc1cc(Nc2cc(NC(C)=O)ncc2-c2ccc(C(F)(F)F)cn2)nc(S(C)(=O)=O)c1] | N-(4'-((4-(2-methoxyethoxy)-6-(methylsulfonyl)pyridin-2-yl)amino)-5-(trifluoromethyl)-[2,3'-bipyridin]-6'-yl)acetamidecarboxamide | $^1$H NMR (400 MHz, DMSO-$d_6$) δ 12.27 (s, 1H), 10.63 (s, 1H), 9.25 - 9.20 (m, 2H), 8.85 (s, 1H), 8.34 (d, J = 9.4 Hz, 2H), 7.14 (s, 1H), 6.98 (s, 1H), 4.34 (s, 2H), 3.71 (s, 2H), 3.44 (s, 3H), 2.13 (s, 3H). MS (ESI) m/e $[M + 1]^+$ 526. |
| F12 | 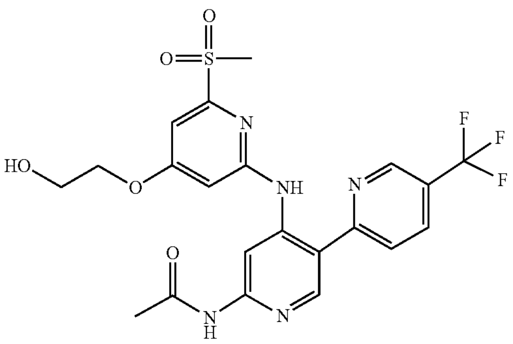 [SMILES: CC(=O)Nc1cc(Nc2cc(OCCO)cc(S(C)(=O)=O)n2)c(-c2ccc(C(F)(F)F)cn2)cn1] | N-(4'-((4-(2-hydroxyethoxy)-6-(methylsulfonyl)pyridin-2-yl)amino)-5-(trifluoromethyl)-[2,3'-bipyridin]-6'-yl)acetamide | $^1$H NMR (400 MHz, DMSO-d6) δ 12.19 (s, 1H), 10.62 (s, 1H), 9.25 - 9.20 (m, 2H), 8.83 (s, 1H), 8.42 - 8.24 (m, 2H), 7.13 (s, 1H), 6.96 (s, 1H), 4.98 (s, 1H), 4.22 (s, 2H), 3.77 (s, 2H), 3.44 (s, 3H), 2.13 (s, 3H). MS (ESI) m/e $[M + 1]^+$ 512. |

-continued

| Example | Compound | Chemical Name | $^1$H NMRand LC /MS m/z (M + 1) |
|---|---|---|---|
| F13 | 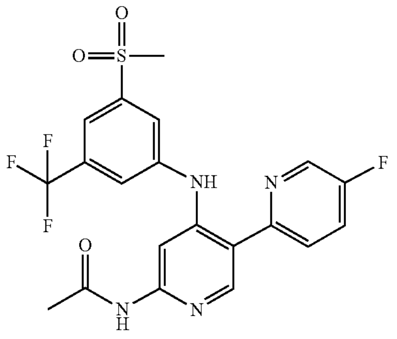 | N-(5-fluoro-4'-((3-(methylsulfonyl)-5-(trifluoromethyl)phenyl)amino)-[2,3'-bipyridin]-6'-yl)acetamide | $^1$H NMR (400 MHz, DMSO-$d_6$) δ 10.68 (s, 1H), 10.58 (s, 1H), 8.71 (s, 1H), 8.60 (s, 1H), 8.21 (s, 1H), 8.05 (s, 2H), 7.99 - 7.90 (m, 2H), 7.77 (s, 1H), 3.37 (s, 3H), 2.09 (s, 3H). MS (ESI) m/e $[M + 1]^+$ 460. |
| F14 | 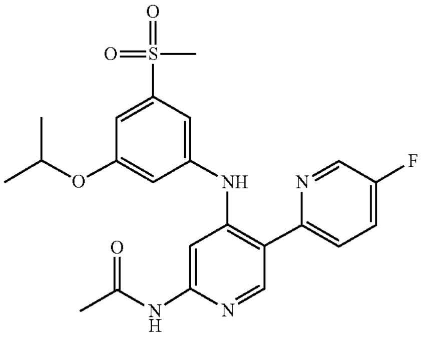 [SMILES: CC(=O)Nc1cc(Nc2cc(OC(C)C)cc(S(C)(=O)=O)c2)c(-c2ccc(F)cn2)cn1] | N-(5-fluoro-4'-((3-isopropoxy-5-(methylsulfonyl)phenyl)amino)-[2,3'-bipyridin]-6'-yl)acetamide | $^1$H NMR (400 MHz, DMSO-$d_6$) δ 10.69 (s, 1H), 10.49 (s, 1H), 8.71 (s, 1H), 8.60 (s, 1H), 8.18 (s, 1H), 8.07 (d, J = 7.2 Hz, 1H), 7.90 (d, J = 7.2 Hz, 1H), 7.35 (s, 1H), 7.11 (s, 1H), 7.05 (s, 1H), 4.73 (s, 1H), 3.27 (s, 3H), 2.07 (s, 3H), 1.30 (d, J = 5.1 Hz, 6H). MS (ESI) m/e $[M + 1]^+$ 459. |
| F15 | 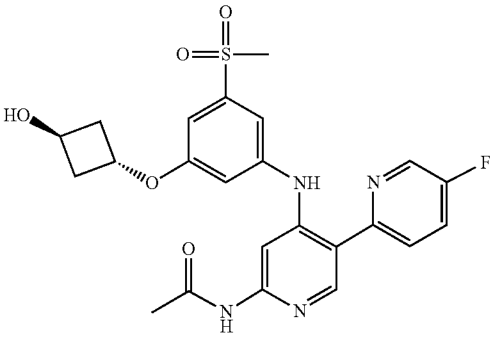 [SMILES: CC(=O)Nc1cc(Nc2cc(O[C@H]3C[C@H](O)C3)cc(S(C)(=O)=O)c2)c(-c2ccc(F)cn2)cn1] | N-(5-fluoro-4'-((3-((trans)-3-hydroxycyclobutoxy)-5-(methylsulfonyl)phenyl)amino)-[2,3'-bipyridin]-6'-yl)acetamide | $^1$H NMR (400 MHz, DMSO-$d_6$) δ 10.64 (s, 1H), 10.49 (s, 1H), 8.71 (s, 1H), 8.59 (s, 1H), 8.18 (s, 1H), 8.07 (d, J = 7.2 Hz, 1H), 7.89 (d, J = 7.2 Hz, 1H), 7.37 (s, 1H), 7.00 (s, 1H), 6.95 (s, 1H), 5.20 (s, 1H), 4.94 - 4.90 (m, 1H), 4.37 - 4.32 (m, 1H), 3.26 (s, 3H), 2.35 - 2.30 (m, 4H), 2.08 (s, 3H). MS (ESI) m/e $[M + 1]^+$ 487. |
| F16 | 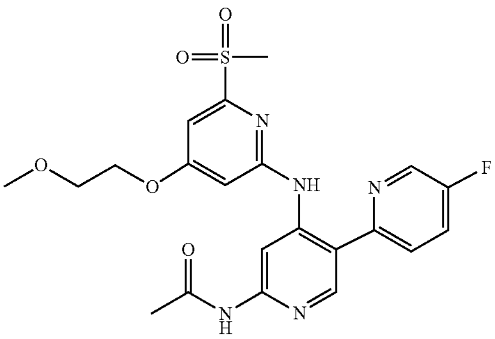 [SMILES: COCCOc1cc(Nc2cc(NC(C)=O)ncc2-c2ccc(F)cn2)nc(S(C)(=O)=O)c1] | N-(5-fluoro-4'-((4-(2-methoxyethoxy)-6-(methylsulfonyl)pyridin-2-yl)amino)-[2,3'-bipyridin]-6'-yl)acetamide | $^1$H NMR (400 MHz, DMSO-$d_6$) δ 11.91 (s, 1H), 10.55 (s, 1H), 9.12 (s, 1H), 8.81 (s, 1H), 8.70 (s, 1H), 8.18 - 8.10 (m, 1H), 7.99 - 7.90 (m, 1H), 7.11 (s, 1H), 6.90 (s, 1H), 4.36 - 4.28 (m, 2H), 3.74 - 3.66 (m, 2H), 3.42 (s, 3H), 3.32 (s, 3H), 2.12 (s, 3H). MS (ESI) m/e $[M + 1]^+$ 476. |

-continued

| Example | Compound | Chemical Name | $^1$H NMRand LC /MS m/z (M + 1) |
|---|---|---|---|
| F18 | 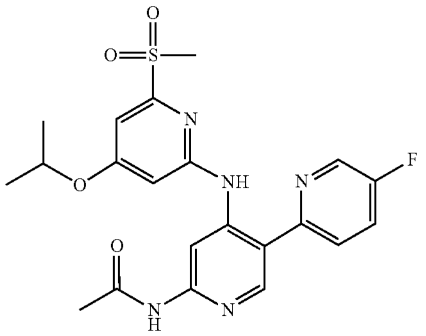 [SMILES: CC(=O)Nc1cc(Nc2cc(OC(C)C)cc(S(C)(=O)=O)n2)c(-c2ccc(F)cn2)cn1] | N-(5-fluoro-4'-((4-isopropoxy-6-(methylsulfonyl)pyridin-2-yl)amino)-[2,3'-bipyridin]-6'-yl)acetamide | $^1$H NMR (400 MHz, DMSO-$d_6$) δ 11.79 (s, 1H), 10.53 (s, 1H), 9.10 (s, 1H), 8.82 (s, 1H), 8.68 (s, 1H), 8.12 - 7.94 (m, 2H), 7.06 (s, 1H), 6.86 (s, 1H), 4.90 - 4.88 (m, 1H), 3.42 (s, 3H), 2.12 (s, 3H), 1.33 (d, J = 5.2 Hz, 6H). MS (ESI) m/e $[M + 1]^+$ 460. |
| F19 | 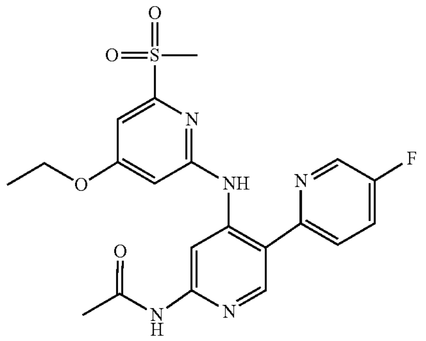 [SMILES: CCOc1cc(Nc2cc(NC(C)=O)ncc2-c2ccc(F)cn2)nc(S(C)(=O)=O)c1] | N-(4'-((4-ethoxy-6-(methylsulfonyl)pyridin-2-yl)amino)-5-fluoro-[2,3'-bipyridin]-6'-yl)acetamide | $^1$H NMR (400 MHz, DMSO-$d_6$) δ 11.85 (s, 1H), 10.55 (s, 1H), 9.12 (s, 1H), 8.82 (s, 1H), 8.69 (s, 1H), 8.13 -7.95 (m, 2H), 7.08 (s, 1H), 6.87 (s, 1H), 4.26 - 4.23 (m, 2H), 3.42 (s, 3H), 2.12 (s, 3H), 1.37 (t, J = 6.3 Hz , 3H). MS (ESI) m/e $[M + 1]^+$ 446. |
| F20 | 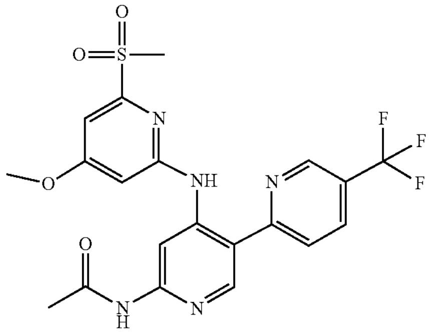 [SMILES: COc1cc(Nc2cc(NC(C)=O)ncc2-c2ccc(C(F)(F)F)cn2)nc(S(C)(=O)=O)c1] | N-(4'-((4-methoxy-6-(methylsulfonyl)pyridin-2-yl)amino)-5-(trifluoromethyl)-[2,3'-bipyridin]-6'-yl)acetamide | $^1$H NMR (400 MHz, DMSO-$d_6$) δ 12.16 (s, 1H), 10.61 (s, 1H), 9.21(s, 1H), 9.17 (s, 1H), 8.83 (s, 1H), 8.36 - 8.29 (m, 2H), 7.13 (s, 1H), 6.95 (s, 1H), 3.96 (s, 3H), 3.43 (s, 3H), 2.13 (s, 3H). MS (ESI) m/e $[M + 1]^+$ 482. |
| F21 | 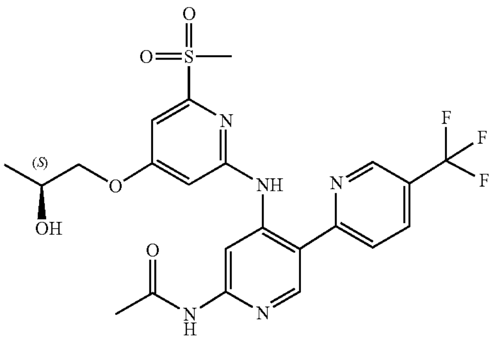 | (S)-N-(4'-((4-(2-hydroxypropoxy)-6-(methylsulfonyl)pyridin-2-yl)amino)-5-(trifluoromethyl)-[2,3'-bipyridin]-6'-yl)acetamide | $^1$H NMR (400 MHz, DMSO-$d_6$) δ 12.10 (s, 1H), 10.60 (s, 1H), 9.22 (s, 1H), 9.18 (s, 1H), 8.82 (s, 1H), 8.35 (d, J = 8.3 Hz, 1H), 8.30 (d, J = 8.3 Hz, 1H), 7.15 - 7.13 (m, 1H), 6.99 - 6.95 (m, 1H), 4.98 (s, 1H), 4.05 - 4.00 (m, 2H), 3.43 (s, 3H), 2.13 (s, 3H), 1.99 - 1.95 (m, 1H), 1.20 - 1.15 (m, 3H). MS (ESI) m/e $[M + 1]^+$ 526. |

Example G1: Synthesis of N-(4'-((3-(methylsulfonyl)phenyl)amino)-5-(3-oxomorpholino)-[2,3'-bipyridin]-6'-yl)acetamide

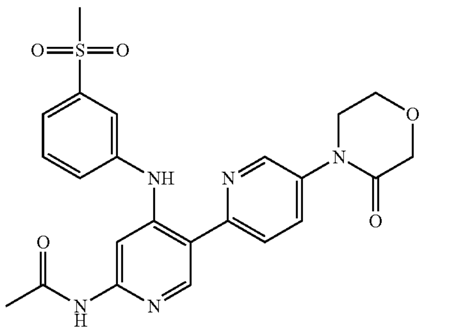 [SMILES: CC(=O)Nc1cc(Nc2cccc(S(C)(=O)=O)c2)c(-c2ccc(N3CCOCC3=O)cn2)cn1]

Step 1: 2-(2-chloroethoxy)acetyl chloride

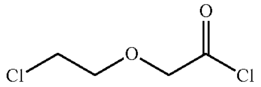

A mixture of 2-(2-chloroethoxy)acetic acid (1.0 g, 7.2 mmol) and DMF (0.1 mL) in $SOCl_2$ (20 mL) was heated at 70° C. for 3 h. After cooled to room temperature, the solvent was removed in vacuo to give 2-(2-chloroethoxy)acetyl chloride (1.1 g, crude).

Step 2: N-(6-bromopyridin-3-yl)-2-(2-chloroethoxy) acetamide

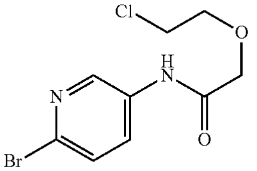

To a mixture of 2-(2-chloroethoxy)acetyl chloride (1.1 g, 7.0 mmol) in THF (20 mL) was added 6-bromopyridin-3-amine (1.2 g, 7.0 mmol) and $Et_3N$ (2.1 g, 21.0 mmol) and the resulting mixture was stirred at room temperature for 12 h. Upon completion of the reaction, the solvent was removed in vacuo and the residue was purified by silica gel column chromatography (PE/EA=2:1 to 1:1) to give N-(6-bromopyridin-3-yl)-2-(2-chloroethoxy)acetamide (1.5 g, 72.8%). $^1$H NMR (400 MHz, $CDCl_3$) δ 8.59 (s, 1H), 8.48 (s, 1H), 8.11 (d, J=8.4 Hz, 1H), 7.47 (d, J=8.4 Hz, 1H), 4.18 (s, 2H), 3.94-3.89 (m, 2H), 3.80-3.76 (m, 2H). MS (ESI) m/e $[M+1]^+$ 293.

Step 3: 4-(6-bromopyridin-3-yl)morpholin-3-one

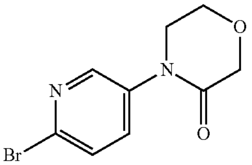 [SMILES: O=C1COCCN1c1ccc(Br)nc1]

To a solution of N-(6-bromopyridin-3-yl)-2-(2-chloroethoxy)acetamide (1.5 g, 5.1 mmol) in DMF (20 mL) was added NaH (60% in mineral oil, 307 mg, 7.7 mmol) portionwise at 0° C. Then the mixture was stirred at room temperature for 2 h. Upon completion of the reaction, water was added and the resulting mixture was extracted with EA (50 mL×3). The combined organic layers were concentrated under vacuum to give 4-(6-bromopyridin-3-yl)morpholin-3-one (1.1 g, 84.6%). $^1$H NMR (400 MHz, $CDCl_3$) δ 8.35-8.30 (m, 1H), 7.61 (s, 1H), 7.49-7.42 (m, 1H), 4.28 (s, 2H), 4.02-3.97 (m, 1H), 4.02-3.97 (m, 1H), 3.76-3.71 (m, 1H), 3.76-3.71 (m, 1H). MS (ESI) m/e $[M+1]^+$ 412.

Step 4: 4-(6'-amino-4'-chloro-[2,3'-bipyridin]-5-yl) morpholin-3-one

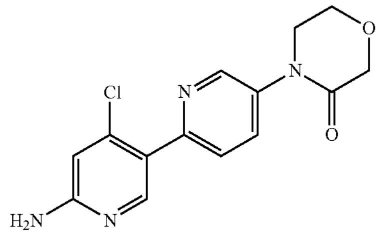 [SMILES: Nc1cc(Cl)c(-c2ccc(N3CCOCC3=O)cn2)cn1]

A mixture of 4-(6-bromopyridin-3-yl)morpholin-3-one (200 mg, 673.4 umol), 4-chloro-5-(4,4,5,5-tetramethyl-1,3,2-dioxaborolan-2-yl)pyridin-2-amine (340 mg, 1.4 mmol), Pd(dppf)$Cl_2$ (49 mg, 67.3 umol), and $Na_2CO_3$ (142 mg, 1.4 mmol) in ACN (10 mL)/$H_2O$ (2 mL) was heated at 120° C. under microwave irradiation for 20 mins under nitrogen atmosphere. After cooled to room temperature, the solvent was removed in vacuo and the residue was purified by silica gel column chromatography (EA/MeOH=100:1 to 30:1) to give 4-(6'-amino-4'-chloro-[2,3'-bipyridin]-5-yl)morpholin-3-one (120 mg, 58.5%). MS (ESI) m/e $[M+1]^+$ 305.

Step 5: N-(4'-chloro-5-(3-oxomorpholino)-[2,3'-bipyridin]-6'-yl)acetamide

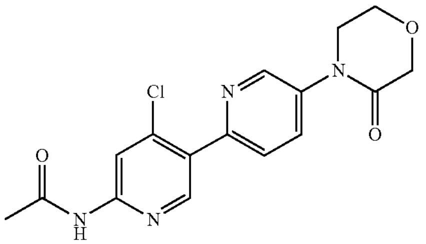 [SMILES: CC(=O)Nc1cc(Cl)c(-c2ccc(N3CCOCC3=O)cn2)cn1]

To a mixture of 4-(6'-amino-4'-chloro-[2,3'-bipyridin]-5-yl)morpholin-3-one (340 mg, 1.1 mmol) in pyridine (10 mL) was added AcCl (105 mg, 1.3 mmol) dropwise at 0° C. Then the mixture was stirred at room temperature for 12 h. Upon completion of the reaction, water (0.2 mL) was added and the solvent was removed in vacuo. The residue was purified by silica gel column chromatography (EA/MeOH=100:1 to 30:1) to give N-(4'-chloro-5-(3-oxomorpholino)-[2,3'-bipyridin]-6'-yl)acetamide (150 mg, 39%). $^1$H NMR (400 MHz, DMSO-$d_6$) δ 10.97 (s, 1H), 8.88 (s, 1H), 8.61 (s, 1H), 8.37 (s, 1H), 8.08 (d, J=8.4 Hz, 1H), 7.89 (d, J=8.4 Hz, 1H), 4.34 (s, 2H), 4.13-4.05 (m, 2H), 3.97-3.89 (m, 2H), 2.21 (s, 3H). MS (ESI) m/e [M+1]$^+$ 347.

Step 6: N-(4'-((3-(methylsulfonyl)phenyl)amino)-5-(3-oxomorpholino)-[2,3'-bipyridin]-6'-yl)acetamide

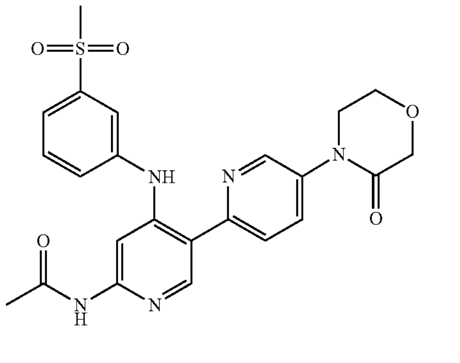 [SMILES: CC(=O)Nc1cc(Nc2cccc(S(C)(=O)=O)c2)c(-c2ccc(N3CCOCC3=O)cn2)cn1]

A mixture of N-(4'-chloro-5-(3-oxomorpholino)-[2,3'-bipyridin]-6'-yl)acetamide (150 mg, 432 umol), 3-(methylsulfonyl)aniline (147 mg, 865 umol), $Pd_2(dba)_3$ (39 mg, 43 umol), Xant-Phos (25 mg, 43 umol), and $Cs_2CO_3$ (421 mg, 1.3 mmol) in dioxane (5 mL) was heated at 110° C. for 12 h under nitrogen atmosphere. After cooled to room temperature, the solvent was removed in vacuo and the residue was purified by neutral prep-HPLC (column: Phenomenex Gemini-NX 150×30 mm×5 um; phase: A-$H_2O$ (10 mM $NH_4HCO_3$); B-ACN; B %: 10%-40% in 20 min) to give N-(4'-((3-(methylsulfonyl)phenyl)amino)-5-(3-oxomorpholino)-[2,3'-bipyridin]-6'-yl)acetamide (5.6 mg, 2.7%). $^1$H NMR (400 MHz, DMSO-$d_6$) δ 11.31 (s, 1H), 10.52 (s, 1H), 8.84 (s, 1H), 8.71 (s, 1H), 8.20 (s, 1H), 8.13 (d, J=8.0 Hz, 1H), 8.05 (d, J=8.0 Hz, 1H), 7.84 (s, 1H), 7.69-7.64 (m, 2H), 7.63-7.58 (m, 1H), 4.29 (s, 2H), 4.08-4.01 (m, 2H), 3.91-3.84 (m, 2H), 3.30 (s, 3H), 2.09 (s, 3H). MS (ESI) m/e [M+1]$^+$ 482.

Example G2: Synthesis of N-(4'-((6-(methylsulfonyl)pyridin-2-yl)amino)-5-(3-oxomorpholino)-[2,3'-bipyridin]-6'-yl)acetamide

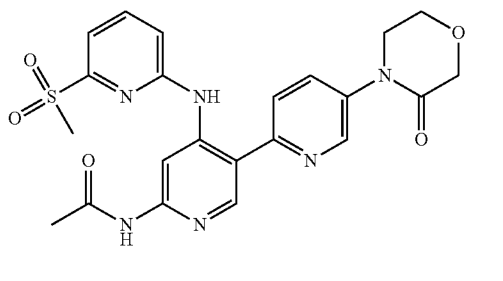 [SMILES: CC(=O)Nc1cc(Nc2cccc(S(C)(=O)=O)n2)c(-c2ccc(N3CCOCC3=O)cn2)cn1]

Step 1: tert-butyl (6'-chloro-5-(3-oxomorpholino)-[2,3'-bipyridin]-4'-yl)carbamate

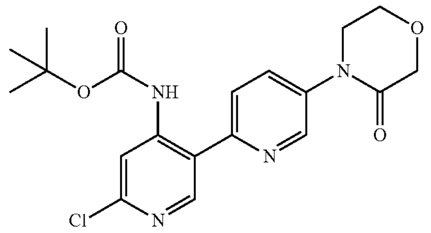 [SMILES: CC(C)(C)OC(=O)Nc1cc(Cl)ncc1-c1ccc(N2CCOCC2=O)cn1]

A mixture of tert-butyl (5-bromo-2-chloropyridin-4-yl) carbamate (3.0 g, 9.8 mmol), 4-(6-bromopyridin-3-yl)morpholin-3-one (2.9 g, 9.8 mmol), $Pd(PPh_3)_2Cl_2$ (688 mg, 977 umol), $Pd(PPh_3)_4$ (1.1 g, 977 umol), and $Sn_2Me_6$ (4.8 g, 14.7 mmol) in 1,4-dioxane (30 mL) was heated at 100° C. under nitrogen atmosphere for 12 h. After cooled to room temperature, the mixture was quenched with 10% KF solution (100 mL) and extracted with EA (100 mL×3). The combined organic layer was washed with brine (100 mL), dried over $Na_2SO_4$, and concentrated under vacuum. The residue was purified by silica gel column chromatography (PE/EA=1:1 to 1:2) to give tert-butyl (6'-chloro-5-(3-oxomorpholino)-[2,3'-bipyridin]-4'-yl)carbamate (1.1 g, 28%). $^1$H NMR (400 MHz, DMSO-$d_6$) δ 11.96 (s, 1H), 8.87 (s, 1H), 8.86-8.83 (m, 1H), 8.28 (s, 1H), 8.24-8.18 (m, 1H), 8.17-8.10 (m, 1H), 4.29 (s, 2H), 4.08-3.99 (m, 2H), 3.93-3.86 (m, 2H), 1.50 (s, 9H). MS (ESL) m/e [M+1]$^+$ 405.

Step 2: tert-butyl (6'-acetamido-5-(3-oxomorpholino)-[2,3'-bipyridin]-4'-yl)carbamate

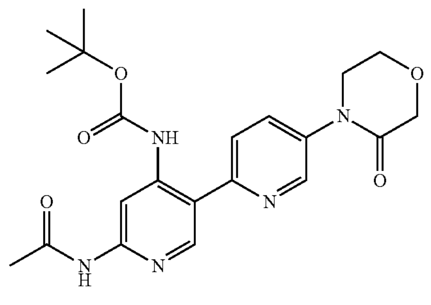 [SMILES: CC(=O)Nc1cc(NC(=O)OC(C)(C)C)c(-c2ccc(N3CCOCC3=O)cn2)cn1]

A mixture of tert-butyl (6'-chloro-5-(3-oxomorpholino)-[2,3'-bipyridin]-4'-yl)carbamate (500 mg, 1.2 mmol), acetamide (146 mg, 2.5 mmol), $Pd_2(dba)_3$ (113 mg, 123 umol), Xantphos (72 mg, 124 umol) and $Cs_2CO_3$ (808 mg, 2.5 mmol) in 1,4-dioxane (10 mL) was heated at 110° C. under nitrogen atmosphere for 12 h. After cooled to room temperature, the mixture was filtered and the filtrate was concentrated. The residue was purified by silica gel column chromatography (EA/MeOH=100:1 to 30:1) to give tert-butyl (6'-acetamido-5-(3-oxomorpholino)-[2,3'-bipyridin]-4'-yl)carbamate (300 mg, 57%). MS (ESI) m/e [M+1]$^+$ 428.

Step 3: N-(4'-amino-5-(3-oxomorpholino)-[2,3'-bipyridin]-6'-yl)acetamide

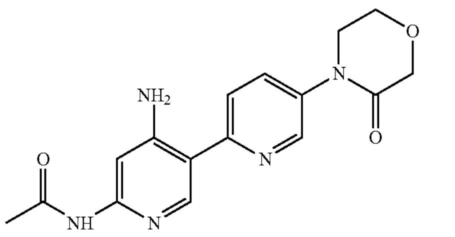 [SMILES: CC(=O)Nc1cc(N)c(-c2ccc(N3CCOCC3=O)cn2)cn1]

A mixture of tert-butyl (6'-acetamido-5-(3-oxomorpholino)-[2,3'-bipyridin]-4'-yl)carbamate (300 mg, 703 umol) in HCl/EA (20 mL, v:v=1:9) was stirred at room temperature for 2 h. Upon completion of the reaction, the solvent was removed in vacuo and the residue was purified by prep-HPLC [column: Phenomenex Gemini-NX C18 75×30 mm×3 um; liquid phase: [A-10 mM $NH_4HCO_3$ in $H_2O$; B-ACN]B %: 5%-45%, 8 min] to give N-(4'-amino-5-(3-oxomorpholino)-[2,3'-bipyridin]-6'-yl)acetamide (98 mg, 43%). $^1H$ NMR (400 MHz, DMSO-$d_6$) δ 10.11 (s, 1H), 8.63 (s, 1H), 8.41 (s, 1H), 7.96-7.86 (m, 2H), 7.55-7.45 (m, 3H), 4.22 (s, 2H), 3.99-3.95 (m, 2H), 3.82-3.78 (m, 2H), 2.03 (s, 3H). MS (ESI) m/e $[M+1]^+$ 328.

Step 4: N-(4'-((6-(methylsulfonyl)pyridin-2-yl)amino)-5-(3-oxomorpholino)-[2,3'-bipyridin]-6'-yl)acetamide

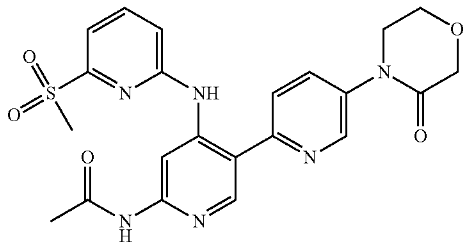 [SMILES: CC(=O)Nc1cc(Nc2cccc(S(C)(=O)=O)n2)c(-c2ccc(N3CCOCC3=O)cn2)cn1]

A mixture of N-(4',5-diamino-[2,3'-bipyridin]-6'-yl)acetamide (98 mg, 0.40 mmol), 2-bromo-6-(methylsulfonyl)pyridine (96 mg, 0.41 mmol), $Pd_2(dba)_3$ (18 mg, 0.02 mmol), BINAP (23 mg, 0.04 mmol) and $K_3PO_4$ (174 mg, 0.82 mmol) in 1,4-dioxane (10 mL) was heated to 100° C. for 4 h under nitrogen atmosphere. After cooled to room temperature, the mixture was filtrated and the filtrate was concentrated under vacuum. The residue was purified by Prep-TLC (MeOH/DCM=1/15) to afford N-(4'-((6-(methylsulfonyl)pyridin-2-yl)amino)-5-(3-oxomorpholino)-[2,3'-bipyridin]-6'-yl)acetamide (15 mg, 7.6). $^1H$ NMR (400 MHz, DMSO-$d_6$) δ 12.70 (s, 1H), 10.56 (s, 1H), 9.20 (s, 1H), 8.93-8.83 (m, 1H), 8.79 (s, 1H), 8.17 (d, J=8.4 Hz, 1H), 8.06 (d, J=8.4 Hz, 1H), 8.02-7.95 (m, 1H), 7.54 (s, 1H), 7.45-7.41 (i, 1H), 4.27 (s, 2H), 4.05-4.00 (m, 2H), 3.90-3.82 (m, 2H), 3.45 (s, 3H), 2.11 (s, 3H). MS (ESI) m/e $[M+1]^+$ 483.

The following Examples were prepared in a similar manner to the product Examples G2:

| Example | Compound | Chemical Name | $^1H$ NMR and LC /MS m/z (M + 1) |
|---|---|---|---|
| G3 | 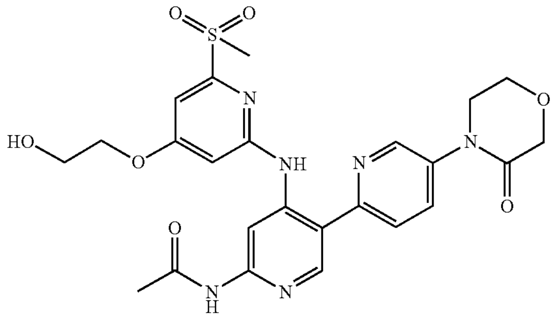 [SMILES: CC(=O)Nc1cc(Nc2cc(OCCO)cc(S(C)(=O)=O)n2)c(-c2ccc(N3CCOCC3=O)cn2)cn1] | N-(4'-((4-(2-hydroxyethoxy)-6-(methylsulfonyl)pyridin-2-yl)amino)-5-(3-oxomorpholino)-[2,3'-bipyridin]-6'-yl)acetamide | $^1H$ NMR (400 MHz, DMSO-$d_6$) δ 12.49 (s, 1H), 10.53 (s, 1H), 9.13 (s, 1H), 8.90 (s, 1H), 8.75 (s, 1H), 8.13 (d, J = 8.6 Hz, 1H), 8.05 (d, J = 8.6 Hz, 1H), 7.08 (s, 1H), 6.87 (s, 1H), 5.02 (s, 1H), 4.27 (s, 2H), 4.25 - 4.15 (m, 2H), 4.05 - 4.00 (m, 2H), 3.90 - 3.82 (m, 2H), 3.80 - 3.70 (m, 2H), 3.41 (s, 3H), 2.10 (s, 3H). MS (ESI) m/e $[M + 1]^+$ 543. |
| G4 | 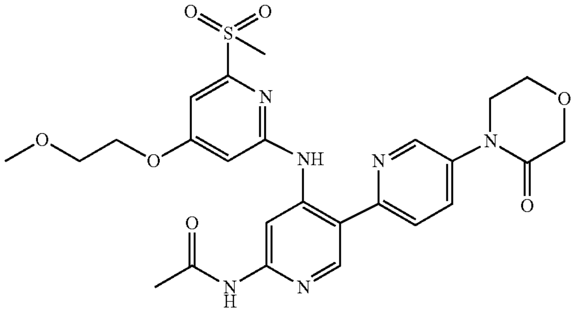 [SMILES: COCCOc1cc(Nc2cc(NC(C)=O)ncc2-c2ccc(N3CCOCC3=O)cn2)nc(S(C)(=O)=O)c1] | N-(4'-((4-(2-methoxyethoxy)-6-(methylsulfonyl)pyridin-2-yl)amino)-5-(3-oxomorpholino)-[2,3'-bipyridin]-6'-yl)acetamide | $^1H$ NMR (400 MHz, DMSO-$d_6$) δ 12.54 (s, 1H), 10.55 (s, 1H), 9.14 (s, 1H), 8.93 - 8.90 (m, 1H), 8.77 (s, 1H), 8.20 - 8.15 (m, 1H), 8.10 - 8.00 (m, 1H), 7.09 (s, 1H), 6.91 (s, 1H), 4.35 - 4.30 (m, 2H), 4.27 (s, 2H), 4.05 - 3.97 (m, 2H), 3.90 - 3.80 (m, 2H), 3.70 - 3.60 (m, 2H), 3.42 (s, 3H), 3.35 (s, 3H), 2.10 (s, 3H). MS (ESI) m/e $[M + 1]^+$ 557. |

Example H1: Synthesis of N-(5-(2-hydroxypropan-2-yl)-4'-((3-(methylsulfonyl)phenyl)amino)-[2,3'-bipyridin]-6'-yl)acetamide

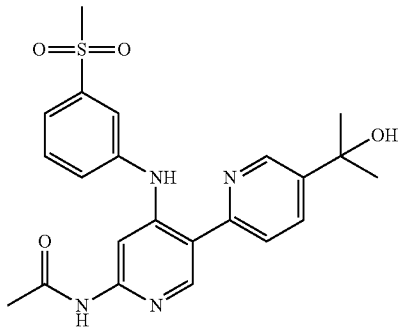 [SMILES: CC(=O)Nc1cc(Nc2cccc(S(C)(=O)=O)c2)c(-c2ccc(C(C)(C)O)cn2)cn1]

Step 1: tert-butyl (6'-chloro-5-(2-hydroxypropan-2-yl)-[2,3'-bipyridin]-4'-yl)carbamate

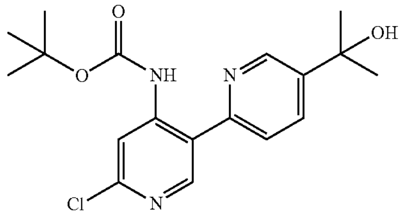 [SMILES: CC(C)(C)OC(=O)Nc1cc(Cl)ncc1-c1ccc(C(C)(C)O)cn1]

A mixture of tert-butyl (5-bromo-2-chloropyridin-4-yl) carbamate (650 mg, 2.1 mmol), 2-(6-bromopyridin-3-yl) propan-2-ol (525 mg, 2.4 mmol), $Sn_2Me_6$ (1.0 g, 3.1 mmol), $Pd(PPh_3)_4$ (244.2 mg, 211.3 umol) and $Pd(PPh_3)_2Cl_2$ in 1,4-dioxane (10 mL) was heated to 105° C. for 12 h under nitrogen atmosphere. After cooled to room temperature, the mixture was washed with KF (5 mL) and filtered. The organic layer was concentrated under vacuum and the residue was purified by silica gel column chromatography (PE/EA=10:1) to give tert-butyl (6'-chloro-5-(2-hydroxy-propan-2-yl)-[2,3'-bipyridin]-4'-yl)carbamate (0.4 g, 52%). $^1H$ NMR (400 MHz, $CDCl_3$) δ 11.93 (s, 1H), 8.82 (s, 1H), 8.59 (s, 1H), 8.45 (s, 1H), 7.97 (d, J=8.4 Hz, 1H), 7.74 (d, J=8.4 Hz, 1H) 1.68 (s, 6H), 1.56 (s, 9H). MS (ESI) m/e $[M+1]^+$ 364.

Step 2: tert-butyl (6'-acetamido-5-(2-hydroxypropan-2-yl)-[2,3-bipyridin]-4'-yl)carbamate

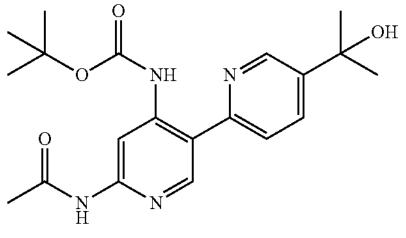 [SMILES: CC(=O)Nc1cc(NC(=O)OC(C)(C)C)c(-c2ccc(C(C)(C)O)cn2)cn1]

A mixture of tert-butyl (6'-chloro-5-(2-hydroxypropan-2-yl)-[2,3'-bipyridin]-4'-yl)carbamate (0.3 g, 824 umol), acetamide (97 mg, 1.6 mmol), $Cs_2CO_3$ (841 mg, 2.4 mmol), Xantphos (95 mg, 165 umol), $Pd_2(dba)_3$ (151 mg, 165 umol) in 1,4-dioxane (50 mL) was gradually warmed up to 90° C. and stirred at this temperature for 12 h under nitrogen atmosphere. After cooled to room temperature, the solution was filtered and concentrated under vacuum. The residue was purified by silica gel column chromatography (PE/EA=1/1 to 0/1) to give tert-butyl (6'-acetamido-5-(2-hydroxypropan-2-yl)-[2,3'-bipyridin]-4'-yl)carbamate (0.22 g, 69%). $^1H$ NMR (400 MHz, $CDCl_3$) δ 11.81 (s, 1H), 9.15 (s, 1H), 8.79 (s, 1H), 8.50 (s, 1H), 7.94 (d, J=8.4 Hz, 2H), 7.72-7.68 (m, 1H), 2.23 (s, 3H), 1.67 (s, 6H), 1.66-1.69 (m, 1H), 1.56 (s, 9H). MS (ESI) m/e $[M+1]^+$ 387.

Step 3: N-(4'-amino-5-(2-hydroxypropan-2-yl)-[2,3'-bipyridin]-6'-yl)acetamide

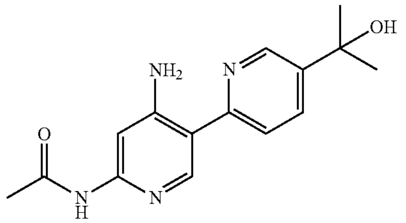 [SMILES: CC(=O)Nc1cc(N)c(-c2ccc(C(C)(C)O)cn2)cn1]

A mixture of tert-butyl (6'-acetamido-5-(2-hydroxypropan-2-yl)-[2,3'-bipyridin]-4'-yl)carbamate (150 mg, 388 umol) in TFA (1 mL) and DCM (2 mL) was stirred at 15° C. for 2 h under nitrogen atmosphere. Upon completion of the reaction, the solvent was removed in vacuo to give N-(4'-amino-5-(2-hydroxypropan-2-yl)-[2,3'-bipyridin]-6'-yl)acetamide (0.1 g, crude). It was used directly for next step without further purification. MS (ESI) m/e $[M+1]^+$ 287.

Step 4: N-(5-(2-hydroxypropan-2-yl)-4'-((3-(methylsulfonyl)phenyl)amino)-[2,3'-bipyridin]-6'-yl)acetamide

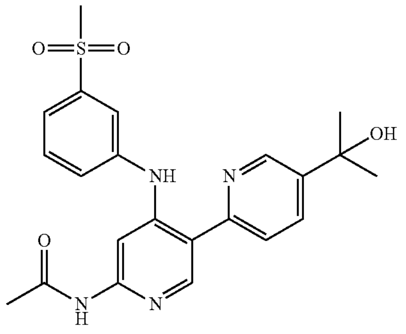 [SMILES: CC(=O)Nc1cc(Nc2cccc(S(C)(=O)=O)c2)c(-c2ccc(C(C)(C)O)cn2)cn1]

A mixture of N-(4'-amino-5-(2-hydroxypropan-2-yl)-[2,3'-bipyridin]-6'-yl)acetamide (0.1 g, 349 umol), 1-bromo-3-

(methylsulfonyl)benzene (246 mg, 1.1 mmol), $Cs_2CO_3$ (358 mg, 1.1 mmol), Xantphos (20 mg, 35 umol), $Pd_2(dba)_3$ (35 mg, 35 umol) in 1,4-dioxane (5 mL) was gradually warmed up to 110° C. and stirred at this temperature for 12 h under nitrogen atmosphere. After cooled to room temperature, the solution was filtered and the filtrate was concentrated under vacuum. The residue was purified by Prep-HPLC (column: Phenomenex Gemini-NX 150×30 mm×5 um; phase: A-$H_2O$ (10 mM $NH_4HCO_3$); B-ACN; B %: 10%-40% in 20 min) to give N-(5-(2-hydroxypropan-2-yl)-4'-((3-(methylsulfonyl)phenyl)amino)-[2,3'-bipyridin]-6'-yl)acetamide (11 mg, 7.1%). $^1H$ NMR (400 MHz, DMSO-$d_6$) δ 11.66 (s, 1H), 10.47 (s, 1H), 8.81 (s, 1H), 8.69 (s, 1H), 8.18 (s, 1H), 8.00 (s, 2H), 7.82 (s, 1H), 7.66-7.62 (m, 2H), 7.60-7.55 (m, 1H), 5.29 (s, 1H), 3.28 (s, 3H), 2.07 (s, 3H), 1.50 (s, 6H). MS (ESI) m/e $[M+1]^+$ 441.

Example H2: Synthesis of N-(5-(2-hydroxypropan-2-yl)-4'-((4-isopropoxy-6-(methylsulfonyl)pyridin-2-yl)amino)-[2,3'-bipyridin]-6'-yl)acetamide

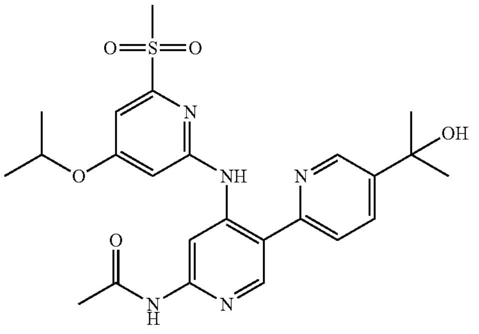 [SMILES: CC(=O)Nc1cc(Nc2cc(OC(C)C)cc(S(C)(=O)=O)n2)c(-c2ccc(C(C)(C)O)cn2)cn1]

A mixture of N-(4'-amino-5-(2-hydroxypropan-2-yl)-[2,3'-bipyridin]-6'-yl)acetamide (400 mg, 1.40 mmol), 2-bromo-4-isopropoxy-6-(methylsulfonyl)pyridine (492 mg, 1.68 mmol), $Pd_2(dba)_3$ (128 mg, 0.14 mmol), BINAP (88 mg, 0.14 mmol) and $Cs_2CO_3$ (1.368 g, 4.20 mmol) in dioxane (20 mL) was stirred for 4 h at 130° C. under nitrogen atmosphere. The mixture was allowed to cool down to room temperature. The resulting mixture was filtered. The filtrate was concentrated under reduced pressure. The residue was purified by combi-flash (MeOH/DCM=0-10%) to give the crude product. The crude product was suspended in acetonitrile to give N-(5-(2-hydroxypropan-2-yl)-4'-((4-isopropoxy-6-(methylsulfonyl)pyridin-2-yl)amino)-[2,3'-bipyridin]-6'-yl)acetamide (272.5 mg, 39.0%). $^1H$ NMR (400 MHz, DMSO-$d_6$) δ 12.82 (s, 1H), 10.50 (s, 1H), 9.11 (s, 1H), 8.90 (s, 1H), 8.75 (s, 1H), 8.05-7.99 (m, 2H), 7.05 (s, 1H), 6.86 (s, 1H), 5.33 (s, 1H), 4.98-4.81 (m, 1H), 3.41 (s, 3H), 2.10 (s, 3H), 1.50 (s, 6H), 1.31 (d, J=4.0 Hz, 6H). MS (ESI) m/e $[M+1]^+$ 500.

Example H3: Synthesis of N-(5-(2-hydroxypropan-2-yl)-4'-((3-(methylsulfonyl)-5-(trifluoro methyl)phenyl)amino)-[2,3'-bipyridin]-6'-yl)acetamide

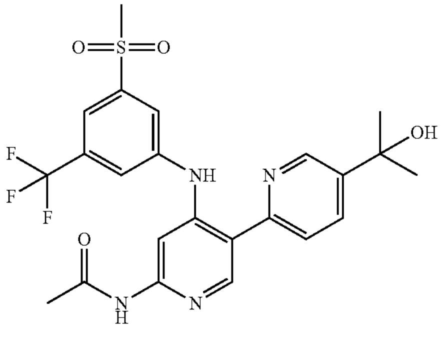 [SMILES: CC(=O)Nc1cc(Nc2cc(C(F)(F)F)cc(S(C)(=O)=O)c2)c(-c2ccc(C(C)(C)O)cn2)cn1]

A mixture of N-(4'-amino-5-(2-hydroxypropan-2-yl)-[2,3'-bipyridin]-6'-yl)acetamide (100 mg, 0.35 mmol), 1-bromo-3-(methylsulfonyl)-5-(trifluoromethyl)benzene (127 mg, 0.42 mmol), $Pd_2(dba)_3$ (32 mg, 0.035 mmol), BINAP (22 mg, 0.035 mmol) and $Cs_2CO_3$ (342 mg, 1.05 mmol) in dioxane (10 mL) was stirred for 16 h at 120° C. under nitrogen atmosphere. The mixture was allowed to cool down to room temperature. The resulting mixture was filtered. The filtrate was concentrated under reduced pressure. The residue was purified by combi-flash (MeOH/DCM=0-10%) to give the crude product. The crude product was suspended in acetonitrile to give N-(5-(2-hydroxypropan-2-yl)-4'-((3-(methylsulfonyl)-5-(trifluoromethyl)phenyl)amino)-[2,3'-bipyridin]-6'-yl)acetamide (18.77 mg, 10.5%). $^1H$ NMR (400 MHz, DMSO-$d_6$) δ 11.66 (s, 1H), 10.50 (s, 1H), 8.76 (s, 1H), 8.64 (s, 1H), 8.17 (s, 1H), 8.03 (s, 1H), 7.92-7.90 (m, 3H), 7.71 (s, 1H), 5.26 (s, 1H), 3.24 (s, 3H), 2.02 (s, 3H), 1.43 (s, 6H). MS (ESI) m/e $[M+1]^+$ 509.

Example H43: Synthesis of N-(5-(2-hydroxypropan-2-yl)-4'-((3-isopropoxy-5-(methylsulfonyl)phenyl)amino)-[2,3'-bipyridin]-6'-yl)acetamide

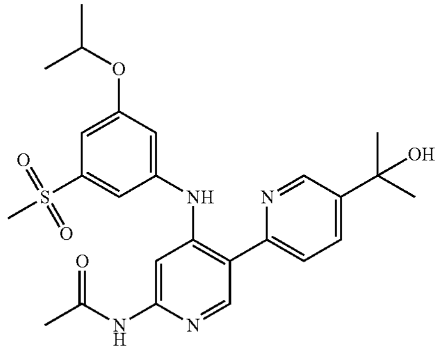 [SMILES: CC(=O)Nc1cc(Nc2cc(OC(C)C)cc(S(C)(=O)=O)c2)c(-c2ccc(C(C)(C)O)cn2)cn1]

A solution of N-(4'-amino-5-(2-hydroxypropan-2-yl)-[2,3'-bipyridin]-6'-yl)acetamide (860 mg, 3 mmol), 1-bromo-3-isopropoxy-5-(methylsulfonyl)benzene (1.1 g, 3.6 mmol), $Pd_2(dba)_3$ (274.7 mg, 0.3 mmol), Xant-phos (347.2 mg, 0.6 mmol) and $Cs_2CO_3$ (1.96 g, 6 mmol) in dioxane (20 mL) was stirred at 130° C. for 5 hr. The mixture was cooled to RT then filtered. The filtrate was concentrated under reduced pressure to give the crude product and purified by silica gel column chromatography (DCM/MeOH=15:1) to give the desired product (937.6 mg, 62.67%). $^1$H NMR (400 MHz, DMSO-d6) δ711.63 (s, 1H), 10.47 (s, 1H), 8.82 (s, 1H), 8.68 (s, 1H), 8.20 (s, 1H), 8.00 (s, 2H), 7.37 (s, 1H), 7.15 (s, 1H), 7.05 (s, 1H), 5.30 (s, 1H), 4.84-4.69 (in, H), 3.32 (s, 3H), 3.28 (s, 3H), 2.08 (s, 3H), 1.50 (s, 6H), 1.31 (d, J=5.9 Hz, 6H). MS (ESI) m/e $[M+1]^+$ 499.

The following Examples were prepared in a similar manner to the product Example H1:

| Example | Compound | Chemical Name | $^1$H NMR and LC /MS m/z (M + 1) |
|---|---|---|---|
| H4 | 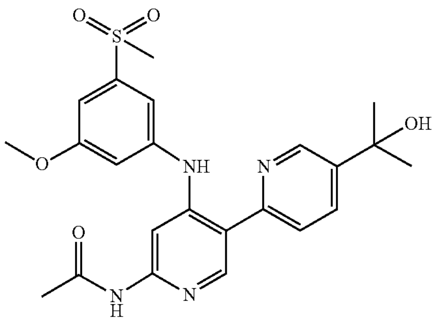 [SMILES: COc1cc(Nc2cc(NC(C)=O)ncc2-c2ccc(C(C)(C)O)cn2)cc(S(C)(=O)=O)c1] | N-(5-(2-hydroxypropan-2-yl)-4'-((3-methoxy-5-(methylsulfonyl)phenyl)amino)-[2,3'-bipyridin]-6'-yl)acetamide | $^1$H NMR (400 MHz, DMSO-$d_6$) δ 11.66 (s, 1H), 10.48 (s, 1H), 8.80 (s, 1H), 8.67 (s, 1H), 8.22 (s, 1H), 8.04 - 7.92 (m, 2H), 7.36 (s, 1H), 7.22 - 7.21 (m, 1H), 7.07 (s, 1H), 5.30 (s, 1H), 3.86 (s, 3H), 3.27 (s, 3H), 2.06 (s, 3H), 1.48 (s, 6H). MS (ESI) m/e $[M + 1]^+$ 471. |
| H5 | 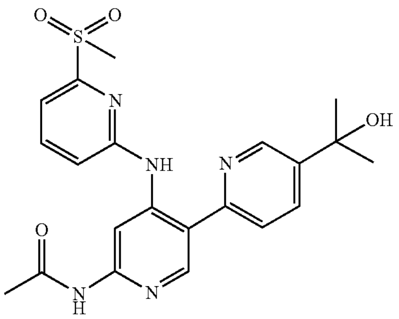 [SMILES: CC(=O)Nc1cc(Nc2cccc(S(C)(=O)=O)n2)c(-c2ccc(C(C)(C)O)cn2)cn1] | N-(5-(2-hydroxypropan-2-yl)-4'-((6-(methylsulfonyl)pyridin-2-yl)amino)-[2,3'-bipyridin]-6'-yl)acetamide | $^1$H NMR (400 MHz, DMSO-$d_6$) δ 13.17 (s, 1H), 10.52 (s, 1H), 9.23 (s, 1H), 8.89 (s, 1H), 8.79 (s, 1H), 8.05 - 8.00 (m, 3H), 7.54 (d, J = 7.3 Hz, 1H), 7.42 (d, J = 8.4 Hz, 1H), 5.32 (s, 1H), 3.46 (s, 3H), 2.11 (s, 3H), 1.50 (s, 6H) MS (ESI) m/e $[M + 1]^+$ 442. |
| H6 | 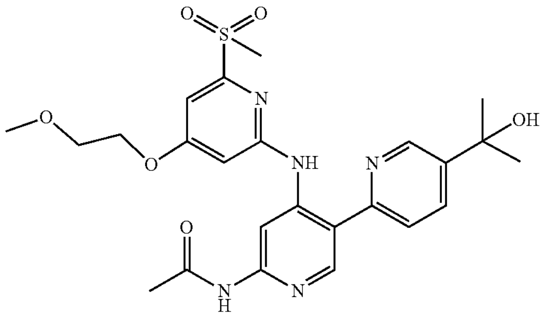 [SMILES: COCCOc1cc(Nc2cc(NC(C)=O)ncc2-c2ccc(C(C)(C)O)cn2)nc(S(C)(=O)=O)c1] | N-(5-(2-hydroxypropan-2-yl)-4'-((4-(2-methoxyethoxy)-6-(methylsulfonyl)pyridin-2-yl)amino)-[2,3'-bipyridin]-6'-yl)acetamide | $^1$H NMR (400 MHz, DMSO-$d_6$) δ 12.94 (s, 1H), 10.52 (s, 1H), 9.15 (s, 1H), 8.93 (s, 1H), 8.78 (s, 1H), 8.05 - 8.00 (m, 2H), 7.12 (s, 1H), 6.93 (s, 1H), 5.34 (s, 1H), 4.40 - 4.36 (m, 2H), 3.71 - 3.62 (m, 2H), 3.44 (s, 3H), 2.12 (s, 3H), 1.52 (s, 6H). MS (ESI) m/e $[M + 1]^+$ 516. |
| H7 | 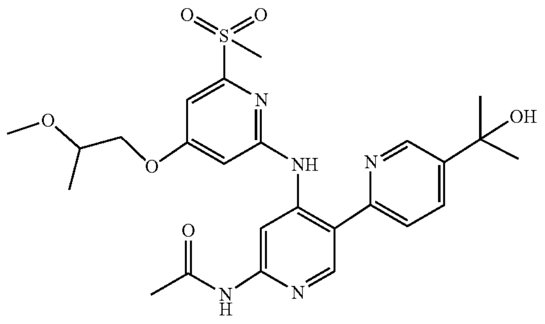 [SMILES: COC(C)COc1cc(Nc2cc(NC(C)=O)ncc2-c2ccc(C(C)(C)O)cn2)nc(S(C)(=O)=O)c1] | N-(5-(2-hydroxypropan-2-yl)-4'-((4-(2-methoxypropoxy)-6-(methylsulfonyl)pyridin-2-yl)amino)-[2,3'-bipyridin]-6'-yl)acetamide | $^1$H NMR (400 MHz, DMSO-$d_6$) δ 12.87 (s, 1H), 10.50 (s, 1H), 9.13 (s, 1H), 8.91 (s, 1H), 8.75 (s, 1H), 8.05 - 7.99 (m, 2H), 7.10 (s, 1H), 6.91 (s, 1H), 5.35 (s, 1H), 4.22 - 4.12 (m, 2H), 3.76 - 3.61 (m, 1H), 3.42 (s, 3H), 3.30 (s, 3H), 2.10 (s, 3H), 1.50 (s, 6H), 1.18 (d, J = 6.3 Hz, 3H). MS (ESI) m/e $[M + 1]^+$ 530. |

-continued

| Example | Compound | Chemical Name | $^1$H NMR and LC /MS m/z (M + 1) |
|---|---|---|---|
| H8 | 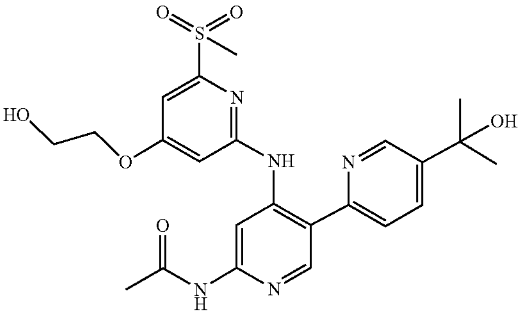 [SMILES: CC(=O)Nc1cc(Nc2cc(OCCO)cc(S(C)(=O)=O)n2)c(-c2ccc(C(C)(C)O)cn2)cn1] | N-(4'-((4-(2-hydroxyethoxy)-6-(methylsulfonyl)pyridin-2-yl)amino)-5-(2-hydroxypropan-2-yl)-[2,3'-bipyridin]-6'-yl)acetamide | $^1$H NMR (400 MHz, DMSO-$d_6$) δ 12.89 (s, 1H), 10.51 (s, 1H), 9.14 (s, 1H), 8.97 - 8.84 (m, 1H), 8.76 (s, 1H), 8.04 - 7.99 (m, 2H), 7.09 (s, 1H), 6.89 (s, 1H), 5.33 (s, 1H), 4.97 - 4.92 (m, 1H), 4.31 - 4.12 (m, 2H), 3.76 - 3.72 (m, 2H), 3.42 (s, 3H), 2.10 (s, 3H), 1.50 (s, 6H). MS (ESI) m/e [M + 1]$^+$ 502. |
| H9 | 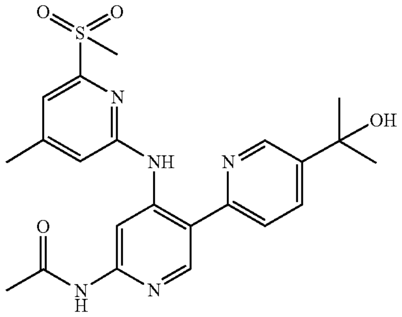 [SMILES: CC(=O)Nc1cc(Nc2cc(C)cc(S(C)(=O)=O)n2)c(-c2ccc(C(C)(C)O)cn2)cn1] | N-(5-(2-hydroxypropan-2-yl)-4'-((4-methyl-6-(methylsulfonyl)pyridin-2-yl)amino)-[2,3'-bipyridin]-6'-yl)acetamide | $^1$H NMR (400 MHz, DMSO-$d_6$) δ 13.18 (s, 1H), 10.51 (s, 1H), 9.27 (s, 1H), 8.93 (s, 1H), 8.80 (s, 1H), 8.11 - 8.03 (m, 2H), 7.44 (s, 1H), 7.27 (s, 1H), 5.36 (s, 1H), 3.47 (s, 3H), 2.43 (s, 3H), 2.13 (s, 3H), 1.53 (s, 6H). MS (ESI) m/e [M + 1]$^+$ 456. |
| H10 | 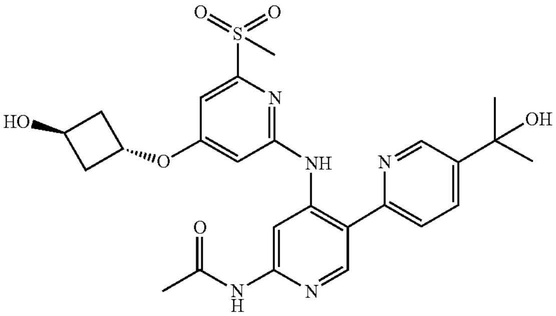 [SMILES: CC(=O)Nc1cc(Nc2cc(O[C@H]3C[C@H](O)C3)cc(S(C)(=O)=O)n2)c(-c2ccc(C(C)(C)O)cn2)cn1] | N-(4'-((4-((trans)-3-hydroxycyclobutoxy)-6-(methylsulfonyl)pyridin-2-yl)amino)-5-(2-hydroxypropan-2-yl)-[2,3'-bipyridin]-6'-yl)acetamide | $^1$H NMR (400 MHz, DMSO-$d_6$) δ 12.77 (s, 1H), 10.49 (s, 1H), 9.09 (s, 1H), 8.89 (s, 1H), 8.74 (s, 1H), 8.02 (s, 2H), 6.97 (s, 1H), 6.72 (s, 1H), 5.32 - 5.27 (m, 2H), 5.07 (s, 1H), 4.38 (s, 1H), 3.41 (s, 3H), 2.35 (s, 4H), 2.10 (s, 3H), 1.50 (s, 6H). MS (ESI) m/e [M + 1]$^+$ 528. |
| H11 | 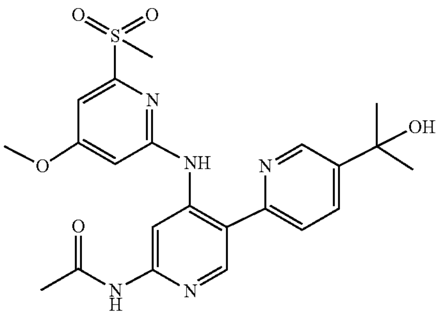 [SMILES: COc1cc(Nc2cc(NC(C)=O)ncc2-c2ccc(C(C)(C)O)cn2)nc(S(C)(=O)=O)c1] | N-(5-(2-hydroxypropan-2-yl)-4'-((4-methoxy-6-(methylsulfonyl)pyridin-2-yl)amino)-[2,3'-bipyridin]-6'-yl)acetamide | $^1$H NMR (400 MHz, DMSO-$d_6$) δ 12.87 (s, 1H), 10.52 (s, 1H), 9.14 (s, 1H), 8.92 (s, 1H), 8.77 (s, 1H), 8.05 - 8.00 (m, 2H), 7.12 (s, 1H), 6.92 (s, 1H), 5.34 (s, 1H), 3.97 (s, 3H), 3.44 (s, 3H), 2.12 (s, 3H), 1.52 (s, 6H). MS (ESI) m/e [M + 1]$^+$ 472. |

-continued

| Example | Compound | Chemical Name | $^1$H NMR and LC /MS m/z (M + 1) |
|---|---|---|---|
| H12 | 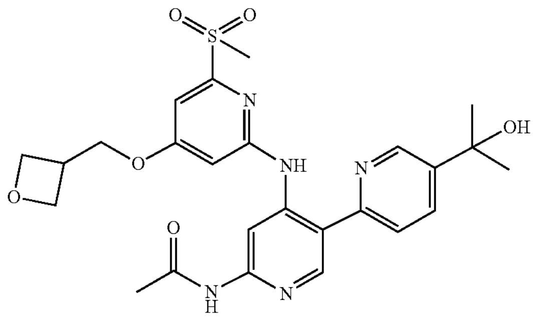 [SMILES: CC(=O)Nc1cc(Nc2cc(OCC3COC3)cc(S(C)(=O)=O)n2)c(-c2ccc(C(C)(C)O)cn2)cn1] | N-(5-(2-hydroxypropan-2-yl)-4'-((6-(methylsulfonyl)-4-(oxetan-3-ylmethoxy)pyridin-2-yl)amino)-[2,3'-bipyridin]-6'-yl)acetamide | $^1$H NMR (400 MHz, DMSO-$d_6$) δ 12.91 (s, 1H), 10.51 (s, 1H), 9.14 (s, 1H), 8.92 (s, 1H), 8.76 (s, 1H), 8.06 - 7.99 (m, 2H), 7.12 (s, 1H), 6.93 (s, 1H), 5.34 (s, 1H), 4.73 - 4.69 (m, 2H), 4.46 - 4.43 (m, 4H), 3.43 (s, 3H), 3.40 - 3.38 (m, 1H) 2.10 (s, 3H), 1.50 (s, 6H). MS (ESI) m/e $[M + 1]^+$ 528. |
| H13 | 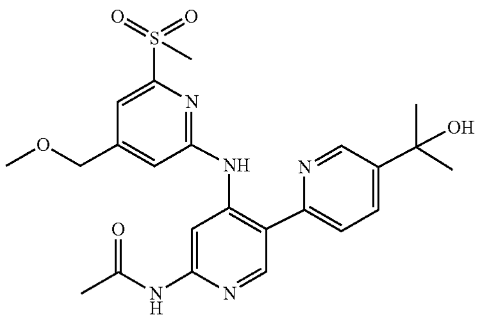 [SMILES: COCc1cc(Nc2cc(NC(C)=O)ncc2-c2ccc(C(C)(C)O)cn2)nc(S(C)(=O)=O)c1] | N-(5-(2-hydroxypropan-2-yl)-4'-((4-(methoxymethyl)-6-(methylsulfonyl)pyridin-2-yl)amino)-[2,3'-bipyridin]-6'-yl)acetamide | $^1$H NMR (400 MHz, DMSO-$d_6$) δ 13.07 (s, 1H), 10.47 (s, 1H), 9.20 (s, 1H), 8.84 (s, 1H), 8.74 (s, 1H), 7.82 - 7.75 (m, 2H), 7.43 (s, 1H), 7.24 (s, 1H), 5.31 (s, 1H), 4.50 (s, 2H), 3.42 (s, 3H), 3.35 (s, 3H), 2.06 (s, 3H), 1.45 (s, 6H). MS (ESI) m/e $[M + 1]^+$ 486. |
| H14 | 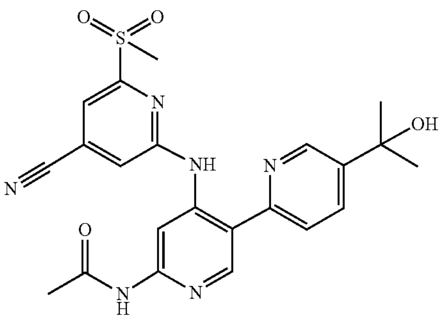 [SMILES: CC(=O)Nc1cc(Nc2cc(C#N)cc(S(C)(=O)=O)n2)c(-c2ccc(C(C)(C)O)cn2)cn1] | N-(4'-((4-cyano-6-(methylsulfonyl)pyridin-2-yl)amino)-5-(2-hydroxypropan-2-yl)-[2,3'-bipyridin]-6'-yl)acetamide | $^1$H NMR (400 MHz, DMSO-$d_6$) δ 13.81 (s, 1H), 10.60 (s, 1H), 9.26 (s, 1H), 8.96 (s, 1H), 8.86 (s, 1H), 8.12 (s, 1H), 8.10 (s, 1H), 8.07 (s, 1H), 8.03 (d, J = 8.0 Hz, 1H), 7.9 (d, J = 8.0 Hz, 1H), 5.36 (s, 1H), 3.52 (s, 3H), 2.11 (s, 3H), 1.51 (s, 6H). MS (ESI) m/e $[M + 1]^+$ 467. |
| H15 | 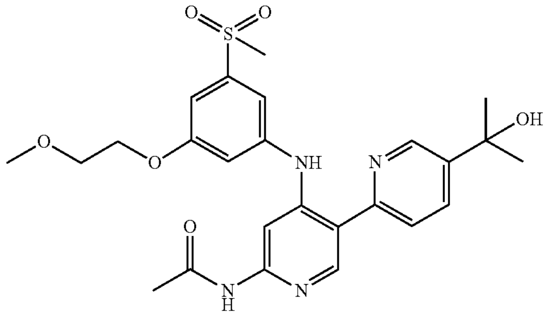 [SMILES: COCCOc1cc(Nc2cc(NC(C)=O)ncc2-c2ccc(C(C)(C)O)cn2)cc(S(C)(=O)=O)c1] | N-(5-(2-hydroxypropan-2-yl)-4'-((3-(2-methoxyethoxy)-5-(methylsulfonyl)phenyl)amino)-[2,3'-bipyridin]-6'-yl)acetamide | $^1$H NMR (400 MHz, DMSO-$d_6$) δ 11.68 (s, 1H), 10.49 (s, 1H), 8.82 (s, 1H), 8.69 (s, 1H), 8.22 (s, 1H), 8.05 - 8.00 (m, 2H), 7.39 (s, 1H), 7.22 (s, 1H), 7.09 (s, 1H), 5.31 (s, 1H), 4.28 - 4.24 (m, 2H), 3.68 - 3.62 (m, 2H), 3.28 (s, 3H), 2.08 (s, 3H), 1.50 (s, 6H). MS (ESI) m/e $[M + 1]^+$ 515. |

-continued

| Example | Compound | Chemical Name | $^1$H NMR and LC /MS m/z (M + 1) |
|---|---|---|---|
| H16 | 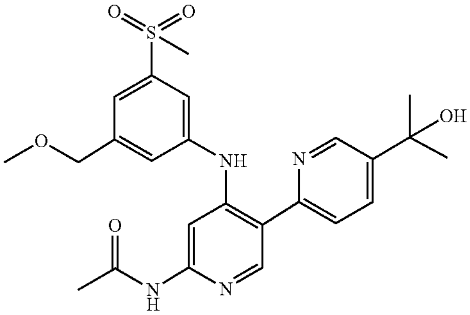 [SMILES: COCc1cc(Nc2cc(NC(C)=O)ncc2-c2ccc(C(C)(C)O)cn2)cc(S(C)(=O)=O)c1] | N-(5-(2-hydroxypropan-2-yl)-4'-((3-(methoxymethyl)-5-(methylsulfonyl)phenyl)amino)-[2,3'-bipyridin]-6'-yl)acetamide | $^1$H NMR (400 MHz, DMSO-$d_6$) δ 11.67 (s, 1H), 10.49 (s, 1H), 8.81 (s, 1H), 8.69 (s, 1H), 8.19 (s, 1H), 8.05 - 8.00 (m, 2H), 7.76 (s, 1H), 7.54 (d, J = 8.1 Hz, 2H), 5.31 (s, 1H), 4.52 (s, 2H), 3.36 (s, 3H), 3.29 (s, 3H), 2.08 (s, 3H), 1.50 (s, 6H). MS (ESI) m/e [M + 1]$^+$ 485. |
| H17 | 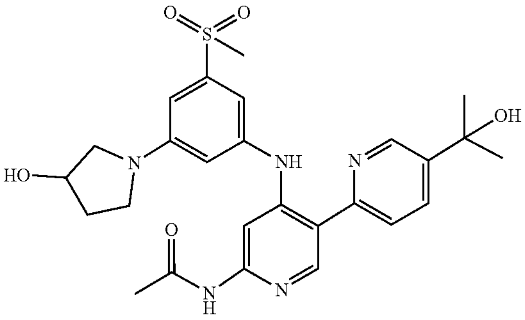 [SMILES: CC(=O)Nc1cc(Nc2cc(N3CCC(O)C3)cc(S(C)(=O)=O)c2)c(-c2ccc(C(C)(C)O)cn2)cn1] | N-(5-(2-hydroxypropan-2-yl)-4'-((3-(3-hydroxypyrrolidin-1-yl)-5-(methylsulfonyl)phenyl)amino)-[2,3'-bipyridin]-6'-yl)acetamide | $^1$H NMR (400 MHz, DMSO-$d_6$) δ 11.61 (s, 1H), 10.47 (s, 1H), 8.82 (s, 1H), 8.65 (s, 1H), 8.19 (s, 1H), 8.05 - 8.00 (m, 2H), 6.98 (s, 1H), 6.69 (d, J = 18.3 Hz, 2H), 5.31 (s, 1H), 5.02 (s, 1H), 4.42 (s, 1H), 3.53 - 3.49 (m, 1H), 3.45 - 3.40 (m, 2H), 3.24 (s, 3H), 3.17 (d, J = 10.0 Hz, 1H), 2.08 (s, 4H), 1.96 - 1.93 (m, 1H), 1.50 (s, 6H). MS (ESI) m/e [M + 1]$^+$ 526. |
| H18 | 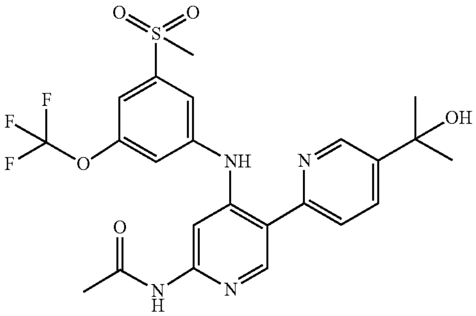 [SMILES: CC(=O)Nc1cc(Nc2cc(OC(F)(F)F)cc(S(C)(=O)=O)c2)c(-c2ccc(C(C)(C)O)cn2)cn1] | N-(5-(2-hydroxypropan-2-yl)-4'-((3-(methylsulfonyl)-5-(trifluoromethoxy)phenyl)amino)-[2,3'-bipyridin]-6'-yl)acetamide | $^1$H NMR (400 MHz, DMSO-$d_6$) δ 11.72 (s, 1H), 10.56 (s, 1H), 8.83 (s, 1H), 8.71 (s, 1H), 8.23 (s, 1H), 8.05 - 8.00 (m, 2H), 7.86 (s, 1H), 7.66 (s, 1H), 7.45 (s, 1H), 5.32 (s, 1H), 3.31 (s, 3H), 2.09 (s, 3H), 1.50 (s, 6H). MS (ESI) m/e [M + 1]$^+$ 525. |
| H19 | 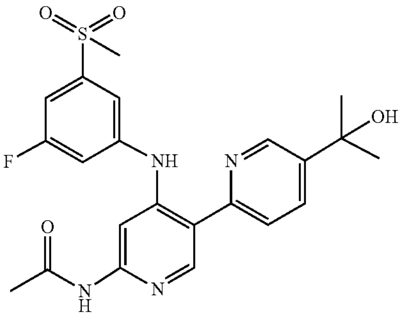 [SMILES: CC(=O)Nc1cc(Nc2cc(F)cc(S(C)(=O)=O)c2)c(-c2ccc(C(C)(C)O)cn2)cn1] | N-(4'-((3-fluoro-5-(methylsulfonyl)phenyl)amino)-5-(2-hydroxypropan-2-yl)-[2,3'-bipyridin]-6'-yl)acetamide | $^1$H NMR (400 MHz, DMSO-$d_6$) δ 11.74 (s, 1H), 10.54 (s, 1H), 8.82 (s, 1H), 8.71 (s, 1H), 8.24 (s, 1H), 8.05 - 7.99 (m, 2H), 7.67 (s, 1H), 7.55 - 7.50 (m, 1H), 7.40 - 7.36 (m, 1H), 5.31 (s, 1H), 3.34 (s, 3H), 2.09 (s, 3H), 1.50 (s, 6H). MS (ESI) m/e [M + 1]$^+$ 459. |

-continued

| Example | Compound | Chemical Name | $^1$H NMR and LC /MS m/z (M + 1) |
|---|---|---|---|
| H20 | 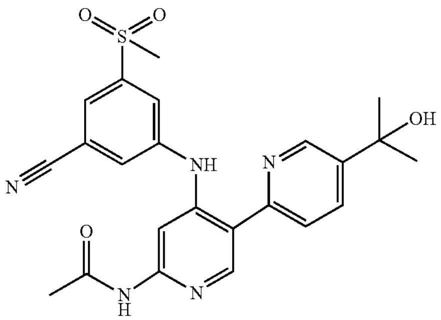 [SMILES: CC(=O)Nc1cc(Nc2cc(C#N)cc(S(C)(=O)=O)c2)c(-c2ccc(C(C)(C)O)cn2)cn1] | N-(4'-((3-cyano-5-(methylsulfonyl)phenyl)amino)-5-(2-hydroxypropan-2-yl)-[2,3'-bipyridin]-6'-yl)acetamide | $^1$H NMR (400 MHz, DMSO-$d_6$) δ 11.79 (s, 1H), 10.57 (s, 1H), 8.82 (s, 1H), 8.72 (s, 1H), 8.21 (s, 1H), 8.09 - 8.05 (m, 2H), 7.99 - 7.95 (m, 2H), 7.94 (s, 1H), 5.30 (s, 1H), 3.36 (s, 3H), 2.10 (s, 3H), 1.50 (s, 6H). MS (ESI) m/e $[M + 1]^+$ 466. |
| H21 | 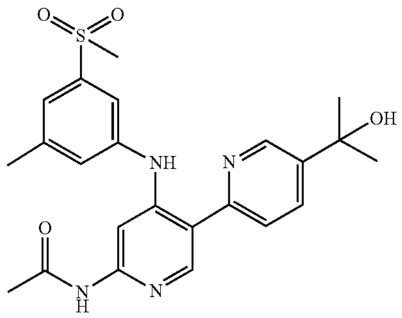 [SMILES: CC(=O)Nc1cc(Nc2cc(C)cc(S(C)(=O)=O)c2)c(-c2ccc(C(C)(C)O)cn2)cn1] | N-(5-(2-hydroxypropan-2-yl)-4'-((3-methyl-5-(methylsulfonyl)phenyl)amino)-[2,3'-bipyridin]-6'-yl)acetamide | $^1$H NMR (400 MHz, DMSO-$d_6$) δ 11.66 (s, 1H), 10.47 (s, 1H), 8.81 (s, 1H), 8.68 (s, 1H), 8.18 (s, 1H), 8.00 - 7.95 (m, 2H), 7.64 (s, 1H), 7.47 (s, 1H), 7.42 (s, 1H), 5.30 (s, 1H), 3.27 (s, 3H), 2.42 (s, 3H), 2.08 (s, 3H), 1.50 (s, 6H). MS (ESI) m/e $[M + 1]^+$ 455. |
| H22 | 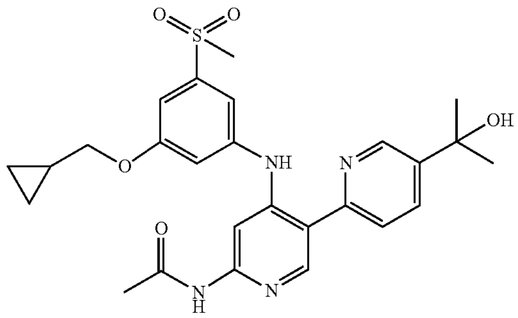 [SMILES: CC(=O)Nc1cc(Nc2cc(OCC3CC3)cc(S(C)(=O)=O)c2)c(-c2ccc(C(C)(C)O)cn2)cn1] | N-(4'-((3-(cyclopropylmethoxy)-5-(methylsulfonyl)phenyl)amino)-5-(2-hydroxypropan-2-yl)-[2,3'-bipyridin]-6'-yl)acetamide | $^1$H NMR (400 MHz, DMSO-$d_6$) δ 11.66 (s, 1H), 10.48 (s, 1H), 8.82 (s, 1H), 8.69 (s, 1H), 8.22 (s, 1H), 8.00 - 7.94 (m, 2H), 7.38 (s, 1H), 7.20 (s, 1H), 7.07 (s, 1H), 5.30 (s, 1H), 4.00 - 3.95 (m, 2H), 3.32 (s, 3H), 2.08 (s, 3H), 1.50 (s, 6H), 1.29 - 1.25 (m, 1H), 0.65 - 0.59 (m, 2H), 0.36 - 0.31 (m, 2H). MS (ESI) m/e $[M + 1]^+$ 511. |
| H23 | 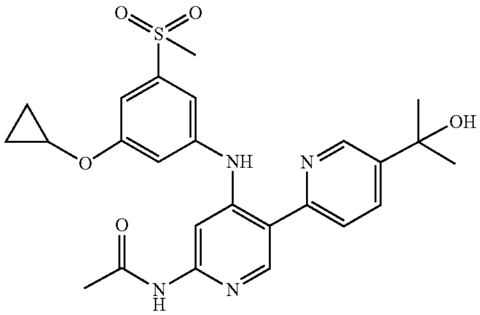 [SMILES: CC(=O)Nc1cc(Nc2cc(OC3CC3)cc(S(C)(=O)=O)c2)c(-c2ccc(C(C)(C)O)cn2)cn1] | N-(4'-((3-cyclopropoxy-5-(methylsulfonyl)phenyl)amino)-5-(2-hydroxypropan-2-yl)-[2,3'-bipyridin]-6'-yl)acetamide | $^1$H NMR (400 MHz, DMSO-$d_6$) δ 11.66 (s, 1H), 10.48 (s, 1H), 8.82 (s, 1H), 8.69 (s, 1H), 8.23 (s, 1H), 8.05 - 7.99 (m, 2H), 7.42 (s, 1H), 7.33 (s, 1H), 7.19 (s, 1H), 5.30 (s, 1H), 4.06 - 4.00 (m, 1H), 3.29 (s, 3H), 2.08 (s, 3H), 1.50 (s, 6H), 0.86 - 0.67 (m, 4H). MS (ESI) m/e $[M + 1]^+$ 497. |

-continued

| Example | Compound | Chemical Name | $^1$H NMR and LC /MS m/z (M + 1) |
|---|---|---|---|
| H24 | 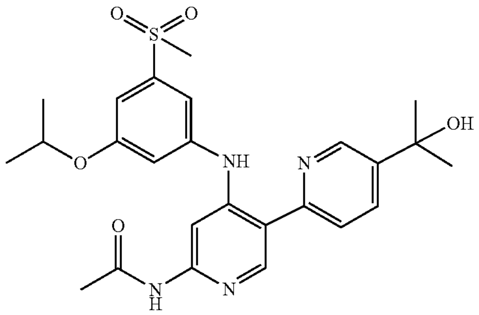 [SMILES: CC(=O)Nc1cc(Nc2cc(OC(C)C)cc(S(C)(=O)=O)c2)c(-c2ccc(C(C)(C)O)cn2)cn1] | N-(5-(2-hydroxypropan-2-yl)-4'-((3-isopropoxy-5-(methylsulfonyl)phenyl)amino)-[2,3'-bipyridin]-6'-yl)acetamide | $^1$H NMR (400 MHz, DMSO-$d_6$) δ 11.62 (s, 1H), 10.47 (s, 1H), 8.82 (s, 1H), 8.68 (s, 1H), 8.19 (s, 1H), 8.00 - 7.95 (m, 2H), 7.37 (s, 1H), 7.15 (s, 1H), 7.05 (s, 1H), 5.30 (s, 1H), 4.87 - 4.65 (m, 1H), 3.28 (s, 3H), 2.08 (s, 3H), 1.50 (s, 6H), 1.31 (d, J = 4.0 Hz, 6H). MS (ESI) m/e $[M + 1]^+$ 499 |
| H25 | 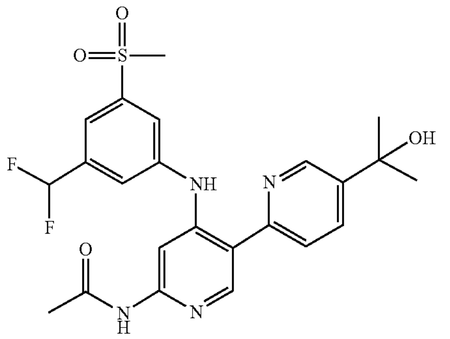 [SMILES: CC(=O)Nc1cc(Nc2cc(C(F)F)cc(S(C)(=O)=O)c2)c(-c2ccc(C(C)(C)O)cn2)cn1] | N-(4'-((3-(difluoromethyl)-5-(methylsulfonyl)phenyl)amino)-5-(2-hydroxypropan-2-yl)-[2,3'-bipyridin]-6'-yl)acetamide | $^1$H NMR (400 MHz, DMSO-$d_6$) δ 11.71 (s, 1H), 10.52 (s, 1H), 8.82 (s, 1H), 8.71 (s, 1H), 8.22 (s, 1H), 8.00 - 7.95 (m, 3H), 7.82 (s, 1H), 7.72 (s, 1H), 7.28 - 7.00 (m, 1H), 5.30 (s, 1H), 3.35 (s, 3H), 2.08 (s, 3H), 1.50 (s, 6H). MS (ESI) m/e $[M + 1]^+$ 491 |
| H26 | 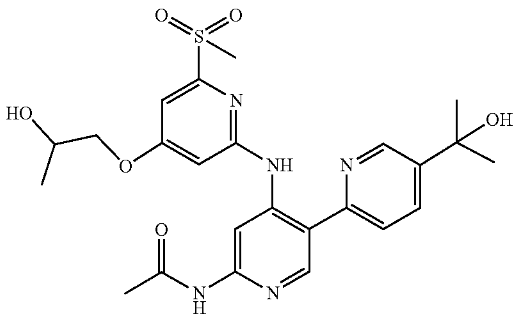 [SMILES: CC(=O)Nc1cc(Nc2cc(OCC(C)O)cc(S(C)(=O)=O)n2)c(-c2ccc(C(C)(C)O)cn2)cn1] | N-(5-(2-hydroxypropan-2-yl)-4'-((4-(2-hydroxypropoxy)-6-(methylsulfonyl)pyridin-2-yl)amino)-[2,3'-bipyridin]-6'-yl)acetamide | $^1$H NMR (400 MHz, DMSO-$d_6$) δ 12.83 (s, 1H), 10.51 (s, 1H), 9.14 (s, 1H), 8.92 (s, 1H), 8.77 (s, 1H), 8.04 - 8.02 (m, 2H), 7.12 (s, 1H), 6.91 (s, 1H), 5.34 (s, 1H), 5.10 (s, 1H), 4.99 - 4.92 (s, 1H), 4.06 - 4.02 (m, 2H), 3.43 (s, 3H), 2.12 (s, 3H), 1.52 (s, 6H), 1.27 - 1.17 (m, 3H). MS (ESI) m/e $[M + 1]^+$ 516. |
| H27 | 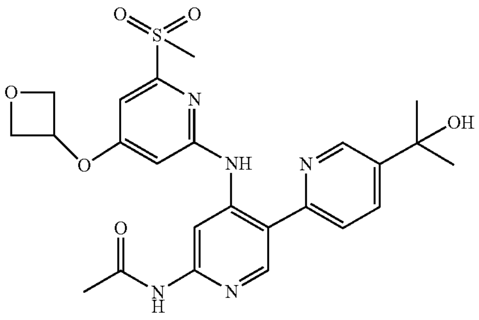 [SMILES: CC(=O)Nc1cc(Nc2cc(OC3COC3)cc(S(C)(=O)=O)n2)c(-c2ccc(C(C)(C)O)cn2)cn1] | N-(5-(2-hydroxypropan-2-yl)-4'-((6-(methylsulfonyl)-4-(oxetan-3-yloxy)pyridin-2-yl)amino)-[2,3'-bipyridin]-6'-yl)acetamide | $^1$H NMR (400 MHz, DMSO-$d_6$) δ 12.90 (s, 1H), 10.53 (s, 1H), 9.11 (s, 1H), 8.93 (s, 1H), 8.78 (s, 1H), 8.07 - 8.02 (m, 2H), 7.01 (s, 1H), 6.70 (s, 1H), 5.59 (s, 1H), 5.36 (s, 1H), 4.99 - 4.91 (m, 2H ), 4.66 - 4.61 (m, 2H), 3.44 (s, 3H), 2.12 (s, 3H), 1.53 (s, 6H). MS (ESI) m/e $[M + 1]^+$ 514. |

-continued

| Example | Compound | Chemical Name | $^1$H NMR and LC /MS m/z (M + 1) |
|---|---|---|---|
| H28 | 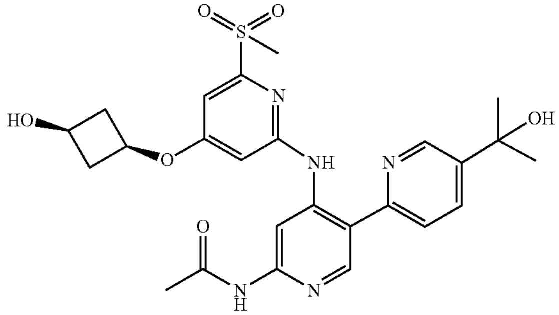 [SMILES: CC(=O)Nc1cc(Nc2cc(O[C@H]3C[C@@H](O)C3)cc(S(C)(=O)=O)n2)c(-c2ccc(C(C)(C)O)cn2)cn1] | N-(4'-((4-(cis-3-hydroxycyclobutoxy)-6-(methylsulfonyl)pyridin-2-yl)amino)-5-(2-hydroxypropan-2-yl)-[2,3'-bipyridin]-6'-yl)acetamide | $^1$H NMR (400 MHz, DMSO-$d_6$) δ 12.83 (s, 1H), 10.53 (s, 1H), 9.10 (s, 1H), 8.92 (s, 1H), 8.77 (s, 1H), 8.07 - 8.04 (m, 2H), 7.02 (s, 1H), 6.79 (s, 1H), 5.45 - 5.27 (m, 2H), 4.67 - 4.45 (m, 1H), 3.90 - 3.88 (m, 1H), 3.43 (s, 3H), 2.87 - 2.82 (m, 2H), 2.12 (s, 3H), 1.98 - 1.92 (m, 2H), 1.52 (s, 6H). MS (ESI) m/e $[M + 1]^+$ 528. |
| H29 | 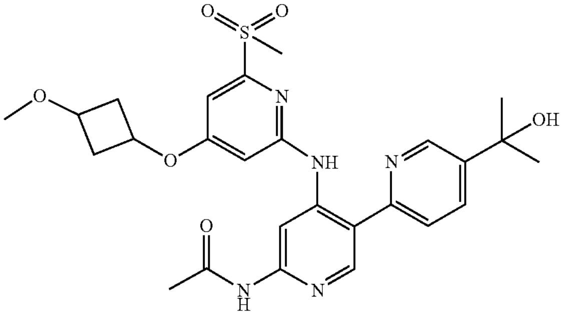 [SMILES: COC1CC(Oc2cc(Nc3cc(NC(C)=O)ncc3-c3ccc(C(C)(C)O)cn3)nc(S(C)(=O)=O)c2)C1] | N-(5-(2-hydroxypropan-2-yl)-4'-((4-(3-methoxycyclobutoxy)-6-(methylsulfonyl)pyridin-2-yl)amino)-[2,3'-bipyridin]-6'-yl)acetamide | $^1$H NMR (400 MHz, DMSO-$d_6$) δ 12.81 (s, 1H), 10.52 (s, 1H), 9.11 (s, 1H), 8.92 (s, 1H), 8.77 (s, 1H), 8.04 - 8.01 (m, 2H), 7.04 - 7.00 (m, 1H), 6.80 - 6.76 (m, 1H), 5.35 (s, 1H), 5.10 (s, 1H), 4.10 (s, 1H), 3.43 (s, 3H), 3.18 (s, 3H), 2.46 (m, 2H), 2.42 - 2.31 (m, 2H), 2.12 (s, 3H), 1.52 (s, 6H). MS (ESI) m/e $[M + 1]^+$ 542. |
| H30 | 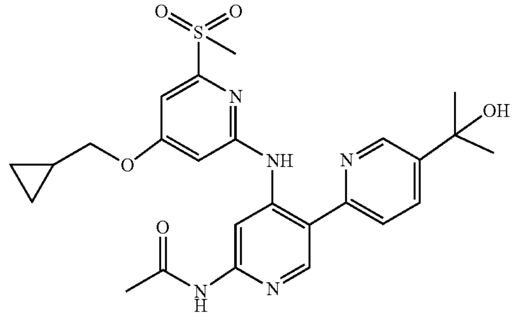 [SMILES: CC(=O)Nc1cc(Nc2cc(OCC3CC3)cc(S(C)(=O)=O)n2)c(-c2ccc(C(C)(C)O)cn2)cn1] | N-(4'-((4-(cyclopropylmethoxy)-6-(methylsulfonyl)pyridin-2-yl)amino)-5-(2-hydroxypropan-2-yl)-[2,3'-bipyridin]-6'-yl)acetamide | $^1$H NMR (400 MHz, DMSO-$d_6$) δ 12.87 (s, 1H), 10.52 (s, 1H), 9.14 (s, 1H), 8.94 (s, 1H), 8.78 (s, 1H), 8.08 - 8.05 (m, 2H), 7.15 - 7.10 (m, 1H), 6.91 (s, 1H), 5.35 (s, 1H), 4.08 (d, J = 8.0 Hz, 2H), 3.44 (s, 3H), 2.13 (s, 3H), 1.54 (s, 6H), 1.25 - 1.22 (m, 1H), 0.65 - 0.62 (m, 2H), 0.41 - 0.38 (m, 2H). MS (ESI) m/e $[M + 1]^+$ 512. |
| H31 | 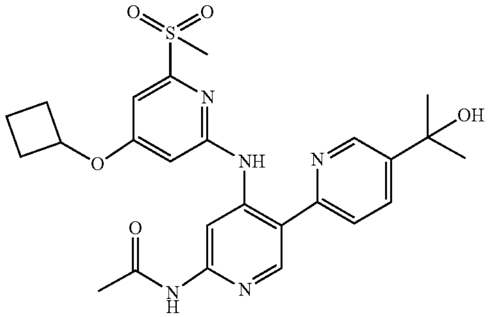 [SMILES: CC(=O)Nc1cc(Nc2cc(OC3CCC3)cc(S(C)(=O)=O)n2)c(-c2ccc(C(C)(C)O)cn2)cn1] | N-(4'-((4-cyclobutoxy-6-(methylsulfonyl)pyridin-2-yl)amino)-5-(2-hydroxypropan-2-yl)-[2,3'-bipyridin]-6'-yl)acetamide | $^1$H NMR (400 MHz, DMSO-$d_6$) δ 12.80 (s, 1H), 10.51 (s, 1H), 9.10 (s, 1H), 8.91 (s, 1H), 8.77 (s, 1H), 8.08 - 8.02 (m, 2H), 7.02 (s, 1H), 6.78 (s, 1H), 5.34 (s, 1H), 4.99 - 4.92 (m, 1H), 3.43 (s, 3H), 2.49 - 2.42 (m, 2H), 2.16 - 2.11 (m, 5H), 1.85 - 1.80 (m, 1H), 1.75 - 1.69 (m, 1H), 1.52 (s, 6H). MS (ESI) m/e $[M + 1]^+$ 512. |
| H32 | 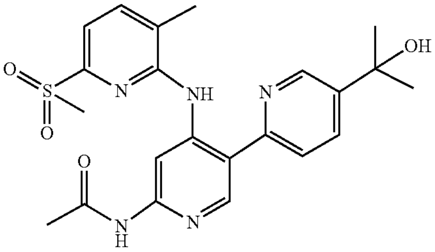 [SMILES: CC(=O)Nc1cc(Nc2nc(S(C)(=O)=O)ccc2C)c(-c2ccc(C(C)(C)O)cn2)cn1] | N-(5-(2-hydroxypropan-2-yl)-4'-((3-methyl-6-(methylsulfonyl)pyridin-2-yl)amino)-[2,3'-bipyridin]-6'-yl)acetamide | $^1$H NMR (400 MHz, DMSO-$d_6$) δ 13.14 (s, 1H), 10.52 (s, 1H), 9.35 (s, 1H), 8.86 (s, 1H), 8.82 (s, 1H), 8.14 (d, J = 8.0 Hz, 1H), 8.05 (d, J = 8.0 Hz, 1H), 7.90 (d, J = 8.0 Hz, 1H), 7.52 (d, J = 8.0 Hz, 1H), 5.36 (s, 1H), 3.45 (s, 3H), 2.53 (s, 3H), 2.13 (s, 3H), 1.52 (s, 6H). MS (ESI) m/e $[M + 1]^+$ 456. |

-continued

| Example | Compound | Chemical Name | $^1$H NMR and LC /MS m/z (M + 1) |
|---|---|---|---|
| H33 | 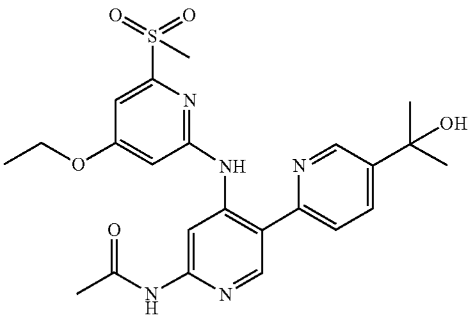 [SMILES: CCOc1cc(Nc2cc(NC(C)=O)ncc2-c2ccc(C(C)(C)O)cn2)nc(S(C)(=O)=O)c1] | N-(4'-((4-ethoxy-6-(methylsulfonyl)pyridin-2-yl)amino)-5-(2-hydroxypropan-2-yl)-[2,3'-bipyridin]-6'-yl)acetamide | $^1$H NMR (400 MHz, DMSO-$d_6$) δ 12.88 (s, 1H), 10.50 (s, 1H), 9.14 (s, 1H), 8.92 (s, 1H), 8.77 (s, 1H), 8.12 - 7.94 (m, 2H), 7.09 (s, 1H), 6.88 - 6.85 (m, 1H), 5.34 (s, 1H), 4.29 - 4.24 (m, 2H), 3.43 (s, 3H), 2.12 (s, 3H), 1.52 (s, 6H), 1.40 - 1.36 (m, 3H). MS (ESI) m/e $[M + 1]^+$ 486. |
| H34 | 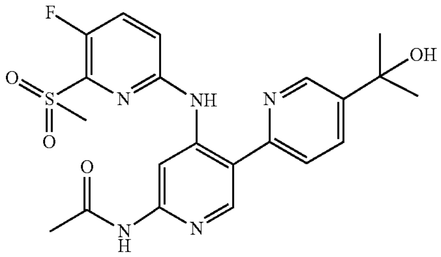 [SMILES: CC(=O)Nc1cc(Nc2ccc(F)c(S(C)(=O)=O)n2)c(-c2ccc(C(C)(C)O)cn2)cn1] | N-(4'-((5-fluoro-6-(methylsulfonyl)pyridin-2-yl)amino)-5-(2-hydroxypropan-2-yl)-[2,3'-bipyridin]-6'-yl)acetamide | $^1$H NMR (400 MHz, DMSO-$d_6$) δ 12.96 (s, 1H), 10.53 (s, 1H), 8.96 (s, 1H), 8.88 (s, 1H), 8.78 (s, 1H), 8.07 - 7.96 (m, 3H), 7.56 - 7.52 (m, 1H), 5.33 (s, 1H), 3.51 (s, 3H), 2.12 (s, 3H), 1.51 (s, 6H). MS (ESI) m/e $[M + 1]^+$ 460. |
| H35 | 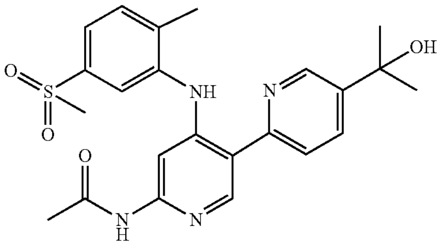 [SMILES: CC(=O)Nc1cc(Nc2cc(S(C)(=O)=O)ccc2C)c(-c2ccc(C(C)(C)O)cn2)cn1] | N-(5-(2-hydroxypropan-2-yl)-4'-((2-methyl-5-(methylsulfonyl)phenyl)amino)-[2,3'-bipyridin]-6'-yl)acetamide | $^1$H NMR (400 MHz, DMSO-$d_6$) δ 11.86 (s, 1H), 10.46 (s, 1H), 8.79 - 8.74 (m, 2H), 8.12 - 7.96 (m, 3H), 7.89 (s, 1H), 7.69 - 7.43 (m, 2H), 5.30 (s, 1H), 3.27 (s, 3H), 2.45 (s, 3H), 2.06 (s, 3H), 1.50 (s, 6H). MS (ESI) m/e $[M + 1]^+$ 455. |
| H36 | 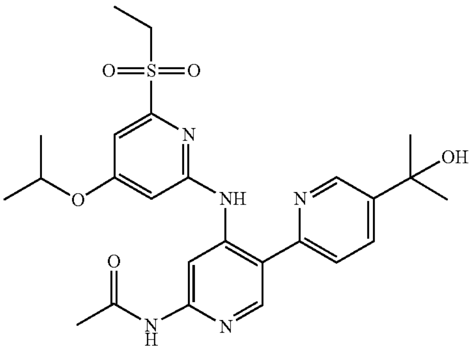 [SMILES: CCS(=O)(=O)c1cc(OC(C)C)cc(Nc2cc(NC(C)=O)ncc2-c2ccc(C(C)(C)O)cn2)n1] | N-(4'-((6-(ethylsulfonyl)-4-isopropoxypyridin-2-yl)amino)-5-(2-hydroxypropan-2-yl)-[2,3'-bipyridin]-6'-yl)acetamide | $^1$H NMR (400 MHz, DMSO-$d_6$) δ 12.76 (s, 1H), 10.48 (s, 1H), 9.04 (s, 1H), 8.92 (s, 1H), 8.76 (s, 1H), 8.06 - 8.03 (m, 2H), 7.07 (s, 1H), 6.88 (s, 1H), 5.33 (s, 1H), 5.04 - 4.82 (m, 1H), 3.69 - 3.64 (m, 2H), 2.12 (s, 3H), 1.52 (s, 6H), 1.34 (d, J = 4.0 Hz, 6H), 1.19 - 1.16 (m, 3H). MS (ESI) m/e $[M + 1]^+$ 514. |

-continued

| Example | Compound | Chemical Name | $^1$H NMR and LC /MS m/z (M + 1) |
|---|---|---|---|
| H37 | 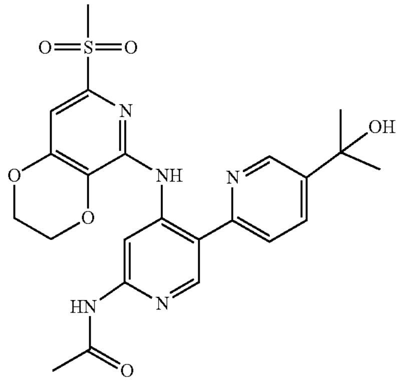 [SMILES: CC(=O)Nc1cc(Nc2nc(S(C)(=O)=O)cc3c2OCCO3)c(-c2ccc(C(C)(C)O)cn2)cn1] | N-(5-(2-hydroxypropan-2-yl)-4'-((7-(methylsulfonyl)-2,3-dihydro-[1,4]dioxino[2,3-c]pyridin-5-yl)amino)-[2,3'-bipyridin]-6'-yl)acetamide | $^1$H NMR (400 MHz, DMSO-$d_6$) δ 13.40 (s, 1H), 10.50 (s, 1H), 9.42 (s, 1H), 8.81 - 8.80 (m, 2H), 8.10 - 8.03 (m, 2H), 7.15 (s, 1H), 5.34 (s, 1H), 4.62 - 4.51 (m, 4H), 3.46 (s, 3H), 2.13 (s, 3H), 1.53 (s, 6H). MS (ESI) m/e [M + 1]$^+$ 500.4 |
| H38 | 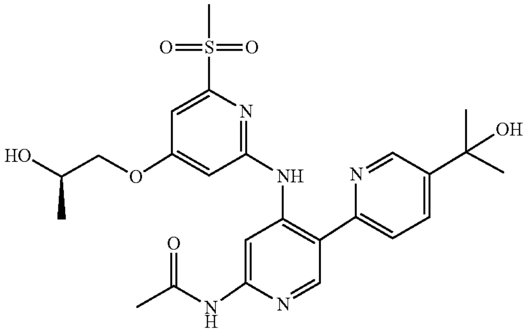 [SMILES: CC(=O)Nc1cc(Nc2cc(OC[C@@H](C)O)cc(S(C)(=O)=O)n2)c(-c2ccc(C(C)(C)O)cn2)cn1] | (R)-N-(5-(2-hydroxypropan-2-yl)-4'-((4-(2-hydroxypropoxy)-6-(methylsulfonyl)pyridin-2-yl)amino)-[2,3'-bipyridin]-6'-yl)acetamide | MS (ESI) m/e [M + 1]$^+$ 516. |
| H39 | 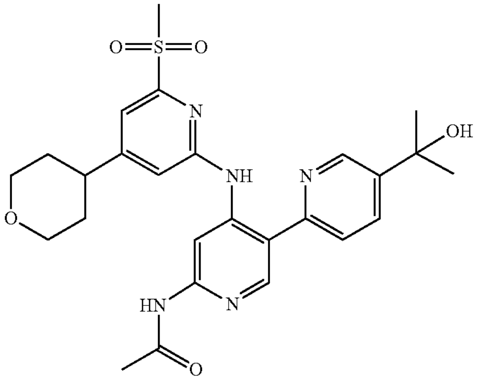 [SMILES: CC(=O)Nc1cc(Nc2cc(C3CCOCC3)cc(S(C)(=O)=O)n2)c(-c2ccc(C(C)(C)O)cn2)cn1] | N-(5-(2-hydroxypropan-2-yl)-4'-((6-(methylsulfonyl)-4-(tetrahydro-2H-pyran-4-yl)pyridin-2-yl)amino)-[2,3'-bipyridin]-6'-yl)acetamide | MS (ESI) m/e [M + 1]$^+$ 526. |
| H40 | 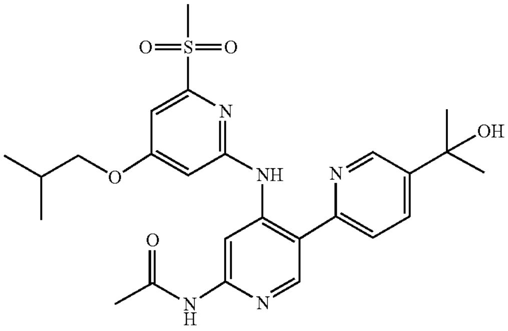 [SMILES: CC(=O)Nc1cc(Nc2cc(OCC(C)C)cc(S(C)(=O)=O)n2)c(-c2ccc(C(C)(C)O)cn2)cn1] | N-(5-(2-hydroxypropan-2-yl)-4'-((4-isobutoxy-6-(methylsulfonyl)pyridin-2-yl)amino)-[2,3'-bipyridin]-6'-yl)acetamide | MS (ESI) m/e [M + 1]$^+$ 514. |

-continued

| Example | Compound | Chemical Name | $^1$H NMR and LC /MS m/z (M + 1) |
|---|---|---|---|
| H41 | 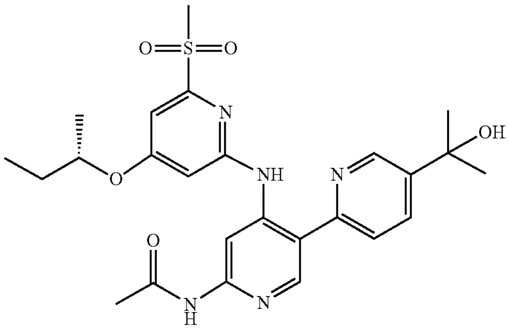 [SMILES: CC[C@H](C)Oc1cc(Nc2cc(NC(C)=O)ncc2-c2ccc(C(C)(C)O)cn2)nc(S(C)(=O)=O)c1] | (S)-N-(4'-((4-(sec-butoxy)-6-(methylsulfonyl)pyridin-2-yl)amino)-5-(2-hydroxypropan-2-yl)-[2,3'-bipyridin]-6'-yl)acetamide | MS (ESI) m/e [M + 1]$^+$ 514. |
| H42 | 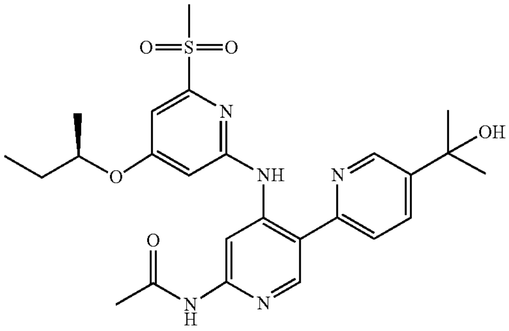 [SMILES: CC[C@@H](C)Oc1cc(Nc2cc(NC(C)=O)ncc2-c2ccc(C(C)(C)O)cn2)nc(S(C)(=O)=O)c1] | (R)-N-(4'-((4-(sec-butoxy)-6-(methylsulfonyl)pyridin-2-yl)amino)-5-(2-hydroxypropan-2-yl)-[2,3'-bipyridin]-6'-yl)acetamide | MS (ESI) m/e [M + 1]$^+$ 514. |

Example J1: Synthesis of N-(5-(1-methyl-1H-pyrazol-3-yl)-4-((4-methyl-6-(methylsulfonyl)pyridin-2-yl)amino)pyridin-2-yl)acetamide

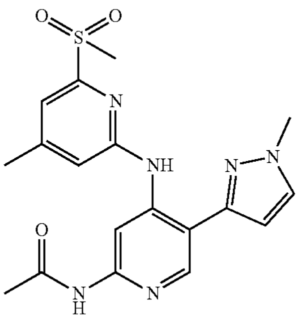 [SMILES: CC(=O)Nc1cc(Nc2cc(C)cc(S(C)(=O)=O)n2)c(-c2ccn(C)n2)cn1]

Step 1: 1-methyl-3-(4,4,5,5-tetramethyl-1,3,2-dioxaborolan-2-yl)-1H-pyrazole

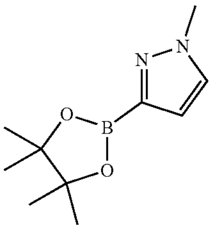

A mixture of 3-bromo-1-methyl-1H-pyrazole (4.1 g, 25.5 mmol), 4,4,4',4',5,5,5',5'-octamethyl-2,2'-bi(1,3,2-dioxaborolane) (9.7 g, 38.2 mmol), KOAc (10.0 g, 102.0 mmol) and Pd(dppf)$Cl_2$—$CH_2Cl_2$ (2.0 g, 2.5 mmol) in 1,4-dioxane (50 mL) was stirred at 95° C. under nitrogen atmosphere for 6 h. After cooled to room temperature, the solvent was removed in vacuo and the residue was diluted with 20 mL of water. The resulting solution was extracted with EA (30 mL×3) and the combined organic layers were washed with brine (50 mL), dried over anhydrous sodium sulfate. The solvent was removed in vacuo and the residue was purified by silica gel column chromatography (PE/EA=3:1 to 0:1) to give 1-methyl-3-(4,4,5,5-tetramethyl-1,3,2-dioxaborolan-2-yl)-1H-pyrazole (3.6 g, 68%). MS (ESI) m/e [M+1]$^+$ 127.

Step 2: tert-butyl (2-chloro-5-(1-methyl-1H-pyrazol-3-yl)pyridin-4-yl)carbamate

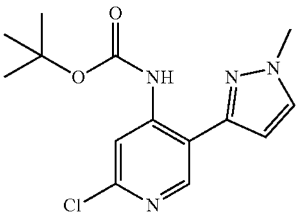 [SMILES: Cn1ccc(-c2cnc(Cl)cc2NC(=O)OC(C)(C)C)n1]

A mixture of tert-butyl (5-bromo-2-chloropyridin-4-yl) carbamate (3.5 g, 7.5 mmol), 1-methyl-3-(4,4,5,5-tetramethyl-1,3,2-dioxaborolan-2-yl)-1H-pyrazole (2.3 g, 11.0 mmol), $K_3PO_4$ (7.2 g, 3.3 mmol) and Pd(dppf)$Cl_2$ (805 mg, 1.1 mmol) in dioxane (50 mL) and $H_2O$ (5 mL) was stirred at 100° C. for 12 h under nitrogen atmosphere. After cooled to room temperature, the solvent was removed in vacuo and the residue was diluted with 20 mL of water. The resulting solution was extracted with EA (30 mL×3) and the combined organic layers were washed with 50 mL of brine, dried over anhydrous sodium sulfate. The solvent was removed in vacuo and the residue was purified by silica gel column chromatography (PE/EA=10:1 to 3:1) to give tert-butyl (2-chloro-5-(1-methyl-1H-pyrazol-3-yl)pyridin-4-yl)carbamate (2.9 g, 82%). MS (ESI) m/e $[M+1]^+$ 309.

Step 3: tert-butyl (2-acetamido-5-A1-methyl-1H-pyrazol-3-yl)pyridin-4-yl)carbamate

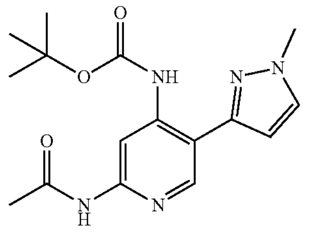 [SMILES: CC(=O)Nc1cc(NC(=O)OC(C)(C)C)c(-c2ccn(C)n2)cn1]

A mixture of tert-butyl (2-chloro-5-(1-methyl-1H-pyrazol-3-yl)pyridin-4-yl)carbamate (3.2 g, 10.3 mmol), acetamide (1.2 g, 20.7 mmol), $Cs_2CO_3$ (10.1 g, 31.0 mmol), Xant-phos (1.2 g, 2.1 mmol) and $Pd_2(dba)_3$ (916 mg, 1.0 mmol) in 1,4-dioxane (50 mL) was stirred at 110° C. for 12 h under nitrogen atmosphere. After cooled to room temperature, the solvent was removed in vacuo and the residue was diluted with 20 mL of water. The resulting solution was extracted with EA (30 mL×3) and the combined organic layers were washed with brine (50 mL), dried over anhydrous sodium sulfate. The solvent was removed in vacuo and the residue was purified by silica gel column chromatography (PE/EA=1:1 to 0:1) to give tert-butyl (2-acetamido-5-(1-methyl-1H-pyrazol-3-yl)pyridin-4-yl)carbamate (1.3 g, 38%). $^1H$ NMR (400 MHz, $CDCl_3$) δ 10.70 (s, 1H), 9.13 (s, 1H), 8.41 (s, 1H), 8.08 (s, 1H), 7.43 (d, J=2.4 Hz, 1H), 6.59 (d, J=2.4 Hz, 1H), 3.98 (s, 3H), 2.21 (s, 3H), 1.57 (s, 9H). MS (ESI) m/e $[M+1]^+$ 332.

Step 4: N-(4-amino-5-(1-methyl-1H-pyrazol-3-yl) pyridin-2-yl)acetamide

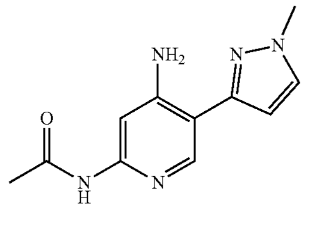 [SMILES: CC(=O)Nc1cc(N)c(-c2ccn(C)n2)cn1]

A mixture of tert-butyl (2-acetamido-5-(1-methyl-1H-pyrazol-3-yl)pyridin-4-yl)carbamate (1.3 g, 3.9 mmol) in TFA (5 mL) and DCM (5 mL) was stirred at 20° C. for 3 h. Upon completion of the reaction, the solvent was removed in vacuo and the residue was diluted with water, then sat. $NaHCO_3$ was added to adjust the pH value to 9. The resulting mixture was extracted with EA (30 mL×3) and the combined organic layers were dried over $Na_2SO_4$. The solvent was removed to give N-(4-amino-5-(1-methyl-1H-pyrazol-3-yl)pyridin-2-yl)acetamide (810 mg, crude). MS (ESI) m/e $[M+1]^+$ 232.

Step 5: N-(5-(1-methyl-1H-pyrazol-3-yl)-4-((4-methyl-6-(methylsulfonyl)pyridin-2-yl)amino)pyridin-2-yl)acetamide

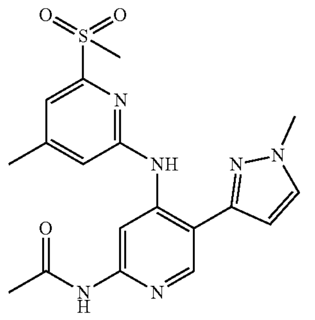 [SMILES: CC(=O)Nc1cc(Nc2cc(C)cc(S(C)(=O)=O)n2)c(-c2ccn(C)n2)cn1]

A mixture of N-(4-amino-5-(1-methyl-1H-pyrazol-3-yl) pyridin-2-yl)acetamide (70 mg, 0.3 mmol), 2-bromo-4-methyl-6-(methylsulfonyl)pyridine (91 mg, 0.36 mmol), $Pd_2dba_3$ (28 mg, 0.03 mmol), BINAP (19 mg, 0.03 mmol) and $Cs_2CO_3$ (196 mg, 0.6 mmol) in dioxane (5 mL) was stirred at 125° C. under $N_2$ in a sealed tube for 6 h. The reaction mixture was filtered and the solid was washed with EA (10 mL). The filtration was concentrated and the residue was purified by Prep-TLC (DCM/MeOH=20:1) to give the N-(5-(1-methyl-1H-pyrazol-3-yl)-4-((4-methyl-6-(methylsulfonyl)pyridin-2-yl)amino)pyridin-2-yl)acetamide (35 mg, 29%). $^1H$ NMR (400 MHz, DMSO-$d_6$) δ 11.47 (s, 1H), 10.43 (s, 1H), 9.27 (s, 1H), 8.64 (s, 1H), 7.90-7.85 (m, 1H), 7.45 (s, 1H), 7.18 (s, 1H), 6.95-6.90 (m, 1H), 4.04 (s, 3H), 3.48 (s, 3H), 2.44 (s, 3H), 2.11 (s, 3H). MS (ESI) m/e $[M+1]^+$ 401.

Example J2: Synthesis of N-(4-((4-isopropoxy-6-(methylsulfonyl)pyridin-2-yl)amino)-5-(1-methyl-1H-pyrazol-3-yl)pyridin-2-yl)acetamide

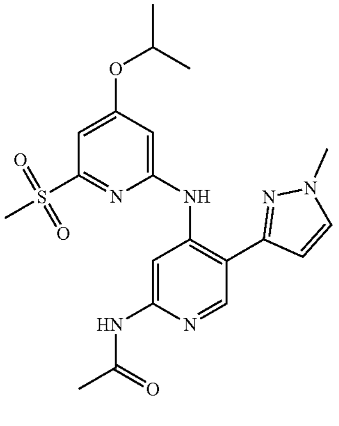 [SMILES: CC(=O)Nc1cc(Nc2cc(OC(C)C)cc(S(C)(=O)=O)n2)c(-c2ccn(C)n2)cn1]

A mixture of N-(4-amino-5-(1-methyl-1H-pyrazol-3-yl) pyridin-2-yl)acetamide (600 mg, 2.6 mmol), 2-bromo-4-isopropoxy-6-(methylsulfonyl)pyridine (916 mg, 3.1 mmol), $Pd_2dba_3$ (238 mg, 0.26 mmol), BINAP (162 mg, 0.26 mmol) and $K_2CO_3$ (718 mg, 5.2 mmol) in dioxane (20 mL) was stirred at 125° C. under $N_2$ in a sealed tube for 4 h. The reaction mixture was filtered and the solid was washed with EA (10 mL). The filtrate was concentrated and the residue was purified by column chromatography (DCM/MeOH=100:1-50:1) then combi-flash (($CH_3CN/H_2O$, 0.1%

HCOOH)=0-100%)) to give N-(4-((4-isopropoxy-6-(methyl sulfonyl)pyridin-2-yl)amino)-5-(1-methyl-1H-pyrazol-3-yl) pyridin-2-yl)acetamide (720 mg, 62%). $^1$H NMR (400 MHz, DMSO-$d_6$) δ 10.40 (s, 1H), 10.24 (s, 1H), 8.56 (s, 1H), 8.14 (s, 1H), 7.89-7.84 (m, 1H), 7.38 (s, 1H), 7.14 (s, 1H), 7.09 (s, 1H), 6.87-6.82 (m, 1H), 4.81-4.71 (m, 1H), 3.96 (s, 3H), 3.29 (s, 3H), 2.06 (s, 3H), 1.31 (d, J=5.9 Hz, 6H). MS (ESI) m/e [M+1]$^+$ 444.

Example J3: Synthesis of N-(4-((4-(cyclopropyl-methoxy)-6-(methylsulfonyl)pyridin-2-yl)amino)-5-(1-methyl-1H-pyrazol-3-yl)pyridin-2-yl)acetamide

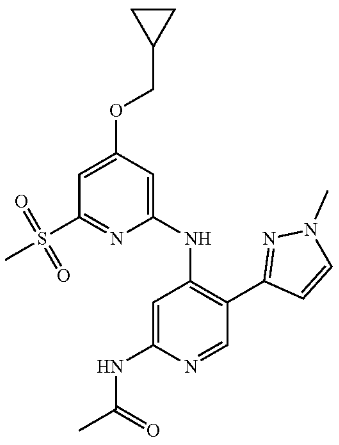 [SMILES: CC(=O)Nc1cc(Nc2cc(OCC3CC3)cc(S(C)(=O)=O)n2)c(-c2ccn(C)n2)cn1]

A mixture of N-(4-amino-5-(1-methyl-1H-pyrazol-3-yl) pyridin-2-yl)acetamide (300 mg, 1.3 mmol), 2-bromo-4-(cyclopropylmethoxy)-6-(methylsulfonyl)pyridine (477 mg, 1.56 mmol), $Pd_2dba_3$ (120 mg, 0.13 mmol), BINAP (80 mg, 0.13 mmol) and $K_2CO_3$ (360 mg, 2.6 mmol) in dioxane (20 mL) was stirred at 125° C. under $N_2$ in a sealed tube for 4 h. The reaction mixture was filtered and the solid was washed with EA (10 mL). The filtrate was concentrated and the residue was purified by column chromatography (DCM/MeOH=200:1-70:1) and the impure product was washed with $CH_3CN$ (5 mL) to give N-(4-((4-(cyclopropyl-methoxy)-6-(methylsulfonyl)pyridine-2-yl)amino)-5-(1-methyl-H-pyrazol-3-yl)pyridin-2-yl)acetamide (380 mg, 640). $^1$H NMR (400 MHz, DMSO-$d_6$) δ 10.48 (s, 1H), 10.30 (s, 1H), 8.55 (s, 1H), 8.10 (s, 1H), 7.86 (d, J=2.1 Hz, 1H), 7.39 (s, 1H), 7.20 (s, 10), 7.13 (s, 1H), 6.87 (d, J=2.1 Hz, 1H), 3.96-3.94 (N, 5H), 3.29 (s, 3H), 2.07 (s, 3H), 1.24-1.22 (s, 1H), 0.65-0.59 (m, 2H), 0.35-0.34 (in, 2H). MS (ESI) m/e [M+1]$^+$ 456.

The following Examples were prepared in a similar manner to the product Example J1:

| Example | Compound | Chemical Name | $^1$H NMR and LC/MS m/z (M + 1) |
|---|---|---|---|
| J4 | 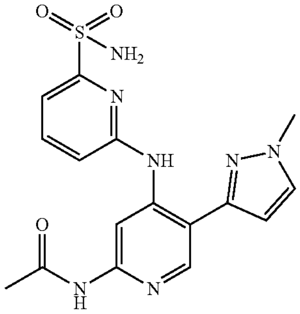 [SMILES: CC(=O)Nc1cc(Nc2cccc(S(N)(=O)=O)n2)c(-c2ccn(C)n2)cn1] | N-(5-(1-methyl-1H-pyrazol-3-yl)-4-((6-sulfamoylpyridin-2-yl)amino)pyridin-2-yl)acetamide | $^1$H NMR (400 MHz, DMSO-$d_6$) δ 11.61 (s, 1H), 10.66 (s, 1H), 9.75 (s, 1H), 8.67 (s, 1H), 8.05-7.88 (m, 2H), 7.47 (d, J = 6.4 Hz, 1H), 7.40-7.33 (m, 2H), 7.30 (d, J = 6.4 Hz, 1H), 6.97-6.92 (m, 1H), 4.04 (s, 3H), 2.16 (s, 3H). MS (ESI) m/e [M + 1]$^+$ 388. |
| J5 | 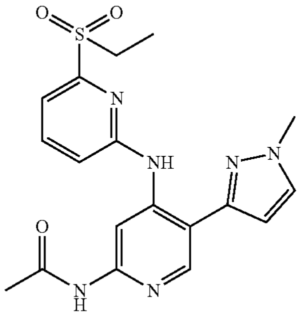 [SMILES: CCS(=O)(=O)c1cccc(Nc2cc(NC(C)=O)ncc2-c2ccn(C)n2)n1] | N-(4-((6-(ethylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.53 (s, 1H), 10.44 (s, 1H), 9.18 (s, 1H), 8.64 (s, 1H), 8.04-7.94 (m, 1H), 7.88-7.87 (m, 1H), 7.60-7.50 (m, 1H), 7.36 (d, J = 7.3 Hz, 1H), 6.95-6.91 (m, 1H), 4.00 (s, 3H), 3.73 (q, J = 7.3 Hz, 2H), 2.09 (s, 3H), 1.16 (t, J = 7.3 Hz, 3H). MS (ESI) m/e [M + 1]$^+$ 401. |

-continued

| Example | Compound | Chemical Name | $^1$H NMR and LC/MS m/z (M + 1) |
|---|---|---|---|
| J6 | 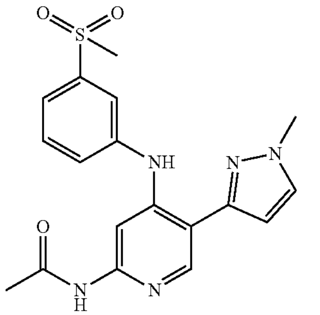 | N-(5-(1-methyl-1H-pyrazol-3-yl)-4-((3-(methylsulfonyl)phenyl) amino)pyridin-2-yl)acetamide | $^1$H NMR (400 MHz, DMSO-$d_6$) δ 10.41 (s, 1H), 10.28 (s, 1H), 8.56 (s, 1H), 8.14 (s, 1H), 7.86-7.80 (m, 2H), 7.62-7.50 (m, 3H), 6.87 (s, 1H), 3.94 (s, 3H), 3.29 (s, 3H), 2.04 (s, 3H). MS (ESI) m/e [M + 1]$^+$ 386. |
| J7 | 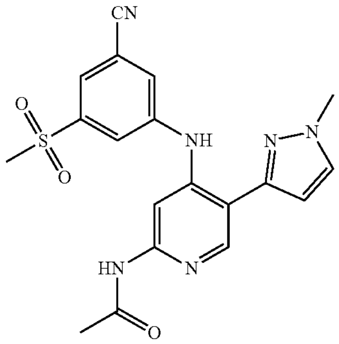 | N-(4-((3-cyano-5-(methylsulfonyl)phenyl) amino)-5-(1-methyl-1H-pyrazol-3-yl)pyridin-2-yl)acetamide | $^1$H NMR (400 MHz, DMSO-$d_6$) δ 10.49 (s, 1H), 10.36 (s, 1H), 8.59 (s, 1H), 8.16 (s, 1H), 8.08 (s, 1H), 8.07 (s, 1H), 7.97-7.92 (m, 1H), 7.83 (d, J = 2.4 Hz, 1H), 6.85 (d, J = 2.4 Hz, 1H), 3.94 (s, 3H), 3.35 (s, 3H), 2.05 (s, 3H). MS (ESI) m/e [M + 1]$^+$ 411. |
| J8 | 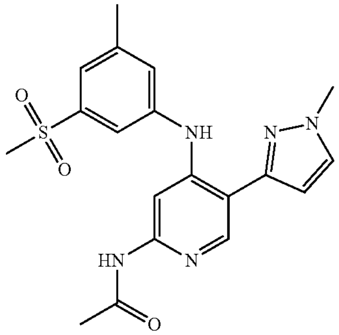 | N-(5-(1-methyl-1H-pyrazol-3-yl)-4-((3-methyl-5-(methylsulfonyl)phenyl) amino)pyridin-2-yl)acetamide | $^1$H NMR (400 MHz, DMSO-$d_6$) δ 10.38 (s, 1H), 10.22 (s, 1H), 8.55 (s, 1H), 8.13 (s, 1H), 7.83 (d, J = 2.4 Hz, 1H), 7.63 (s, 1H), 7.44 (s, 2H), 6.86 (d, J = 2.4 Hz, 1H), 3.94 (s, 3H), 3.26 (s, 3H), 2.41 (s, 3H), 2.03 (s, 3H). MS (ESI) m/e [M + 1]$^+$ 400. |
| J9 | 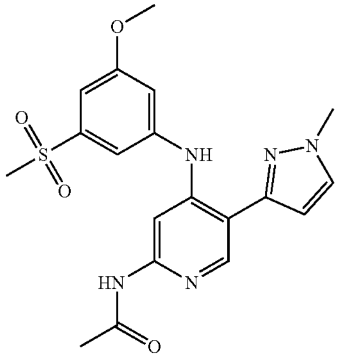 | N-(4-((3-methoxy-5-(methylsulfonyl)phenyl) amino)-5-(1-methyl-1H-pyrazol-3-yl)pyridin-2-yl)acetamide | $^1$H NMR (400 MHz, DMSO-$d_6$) δ 10.42 (s, 1H), 10.26 (s, 1H), 8.55 (s, 1H), 8.18 (s, 1H), 7.84 (d, J = 2.4 Hz, 1H), 7.38-7.32 (m, 1H), 7.25-7.21 (m, 1H), 7.15-7.10 (m, 1H), 6.86 (d, J = 2.4 Hz, 1H), 3.94 (s, 3H), 3.87 (s, 3H), 3.28 (s, 3H), 2.04 (s, 3H). MS (ESI) m/e [M + 1]$^+$ 416. |

-continued

| Example | Compound | Chemical Name | $^1$H NMR and LC/MS m/z (M + 1) |
|---|---|---|---|
| J10 | 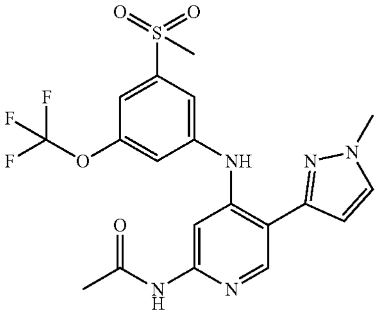 [SMILES: CC(=O)Nc1cc(Nc2cc(OC(F)(F)F)cc(S(C)(=O)=O)c2)c(-c2ccn(C)n2)cn1] | N-(5-(1-methyl-1H-pyrazol-3-yl)-4-((3-(methylsulfonyl)-5-(trifluoromethoxy)phenyl)amino)pyridin-2-yl)acetamide | $^1$H NMR (400 MHz, DMSO-$d_6$) δ 10.49 (s, 1H), 10.34 (s, 1H), 8.60 (s, 1H), 8.21 (s, 1H), 7.86-7.85 (m, 2H), 7.66 (s, 1H), 7.48 (s, 1H), 6.86-6.85 (m, 1H), 3.96 (s, 3H), 3.38 (s, 3H), 2.07 (s, 3H). MS (ESI) m/e [M + 1]$^+$ 470. |
| J11 | 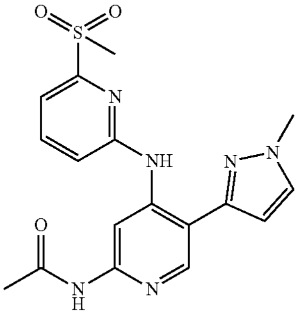 [SMILES: CC(=O)Nc1cc(Nc2cccc(S(C)(=O)=O)n2)c(-c2ccn(C)n2)cn1] | N-(5-(1-methyl-1H-pyrazol-3-yl)-4-((6-(methylsulfonyl)pyridin-2-yl)amino)pyridin-2-yl)actamide | $^1$H NMR (400 MHz, $CDCl_3$) δ 11.43 (s, 1H), 9.35 (s, 1H), 8.48 (s, 1H), 7.99 (s, 2H), 7.85-7.78 (m, 1H), 7.66 (d, J = 7.6 Hz, 1H), 7.47 (d, J = 2.4 Hz, 1H), 7.10 (d, J = 8.4 Hz, 1H), 6.66 (d, J = 2.4 Hz, 1H), 4.04 (s, 3H), 3.51 (s, 3H), 2.22 (s, 3H). MS (ESI) m/e [M + 1]$^+$ 387. |
| J12 | 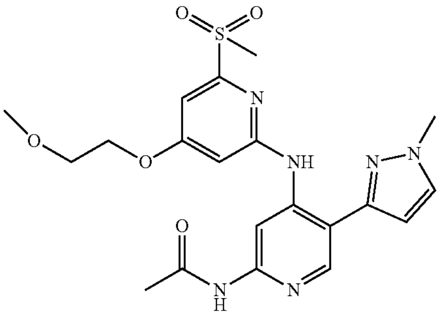 | N-(4-((4-(2-methoxyethoxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.33 (s, 1H), 10.43 (s, 1H), 9.18 (s, 1H), 8.63 (s, 1H), 7.89-7.84 (m, 1H), 7.14 (s, 1H), 6.95-6.91 (m, 1H), 6.83 (s, 1H), 4.39-4.32 (m, 2H), 4.03 (s, 3H), 3.74-3.68 (m, 2H), 3.46 (s, 3H), 2.10 (s, 3H). MS (ESI) m/e [M + 1]$^+$ 461. |
| J13 | 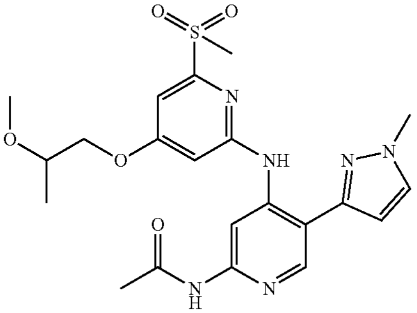 [SMILES: COC(C)COc1cc(Nc2cc(NC(C)=O)ncc2-c2ccn(C)n2)nc(S(C)(=O)=O)c1] | N-(4-((4-(2-methoxypropoxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.29 (s, 1H), 10.43 (s, 1H), 9.16 (s, 1H), 8.61 (s, 1H), 7.87-7.82 (m, 1H), 7.12 (s, 1H), 6.90-6.85 (m, 1H), 6.82 (s, 1H), 4.24-4.15 (m, 2H), 4.00 (s, 3H), 3.73-3.66 (m, 1H), 3.44 (s, 3H), 2.08 (s, 3H), 1.19-1.15 (m, 3H). MS (ESI) m/e [M + 1]$^+$ 475. |

-continued

| Example | Compound | Chemical Name | $^{1}$H NMR and LC/MS m/z (M + 1) |
|---|---|---|---|
| J14 | 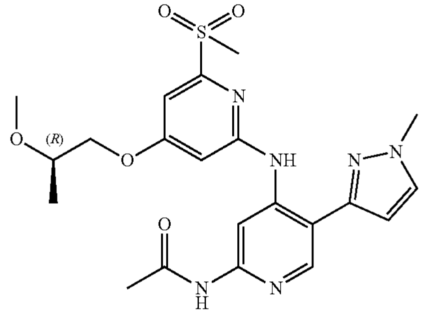 | (R)-N-(4-((4-(2-methoxypropoxy)-6-(methylsulfonyl)pyridin-2-yl)amino)-5-(1-methyl-1H-pyrazol-3-yl)pyridin-2-yl)acetamide | $^{1}$H NMR (400 MHz, DMSO-$d_6$) δ 11.31 (s, 1H), 10.45 (s, 1H), 9.17 (s, 1H), 8.63 (s, 1H), 7.90-7.82 (m, 1H), 7.15 (s, 1H), 6.96-6.91 (m, 1H), 6.85 (s, 1H), 4.27-4.13 (m, 2H), 4.03 (s, 3H), 3.78-3.68 (m, 1H), 3.46 (s, 3H), 3.35 (s, 3H), 2.11 (s, 3H), 1.20 (d, J = 6.2 Hz, 3H). MS (ESI) m/e $[M + 1]^+$ 475. |
| J15 | 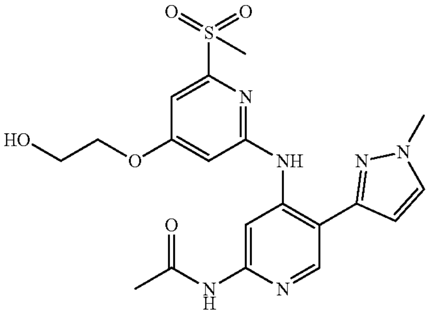 [SMILES: CC(=O)Nc1cc(Nc2cc(OCCO)cc(S(C)(=O)=O)n2)c(-c2ccn(C)n2)cn1] | N-(4-((4-(2-hydroxyethoxy)-6-(methylsulfonyl)pyridin-2-yl)amino)-5-(1-methyl-1H-pyrazol-3-yl)pyridin-2-yl)acetamide | 1H NMR (400 MHz, DMSO-d6) δ 11.33 (s, 1H), 10.44 (s, 1H), 9.19 (s, 1H), 8.63 (s, 1H), 7.90-7.86 (m, 1H), 7.14 (s, 1H), 6.95-6.92 (m, 1H), 6.82 (s, 1H), 5.03-4.97 (m, 1H), 4.28-4.20 (m, 2H), 4.03 (s, 3H), 3.80-3.72 (m, 2H), 3.46 (s, 3H), 2.10 (s, 3H). MS (ESI) m/e $[M + 1]^+$ 447. |
| J16 | 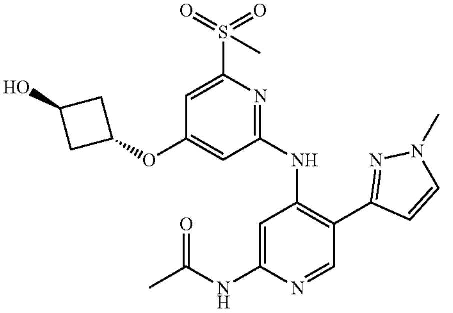 [SMILES: CC(=O)Nc1cc(Nc2cc(O[C@H]3C[C@H](O)C3)cc(S(C)(=O)=O)n2)c(-c2ccn(C)n2)cn1] | N-(4-((4-((trans)-3-hydroxycyclobutoxy)-6-(methylsulfonyl)pyridin-2-yl)amino)-5-(1-methyl-1H-pyrazol-3-yl)pyridin-2-yl)acetamde | $^{1}$H NMR (400 MHz, DMSO-$d_6$) δ 11.34 (s, 1H), 10.44 (s, 1H), 9.17 (s, 1H), 8.63 (s, 1H), 7.98-7.91 (m, 1H), 7.01 (s, 1H), 6.96-6.91 (m, 1H), 6.63 (s, 1H), 5.32-5.26 (m, 1H), 5.12-5.04 (m, 1H), 4.45-4.35 (m, 1H), 4.02 (s, 3H), 3.46 (s, 3H), 2.46-2.30 (m, 4H), 2.10 (s, 3H). MS (ESI) m/e $[M + 1]^+$ 473. |
| J17 | 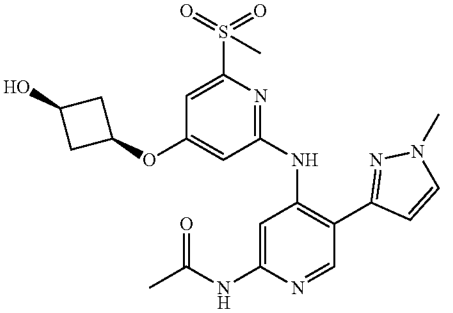 [SMILES: CC(=O)Nc1cc(Nc2cc(O[C@H]3C[C@@H](O)C3)cc(S(C)(=O)=O)n2)c(-c2ccn(C)n2)cn1] | N-(4-((4-((cis)-3-hydroxycyclobutoxy)-6-(methylsulfonyl)pyridin-2-yl)amino)-5-(1-methyl-1H-pyrazol-3-yl)pyridin-2-yl)acetamide | $^{1}$H NMR (400 MHz, DMSO-$d_6$) δ 11.34 (s, 1H), 10.43 (s, 1H), 9.15 (s, 1H), 8.62 (s, 1H), 7.88 (d, J = 2.4 Hz, 1H), 7.02 (s, 1H), 6.91 (d, J = 2.4 Hz, 1H), 6.67 (s, 1H), 5.29 (d, J = 6.8 Hz, 1H), 4.68-4.43 (m, 1H), 4.00 (s, 3H), 3.89-3.82 (m, 1H), 3.44 (s, 3H), 2.90-2.79 (m, 2H), 2.08 (s, 3H), 2.00-1.92 (m, 2H). MS (ESI) m/e $[M + 1]^+$ 473. |

-continued

| Example | Compound | Chemical Name | $^1H$ NMR and LC/MS m/z (M + 1) |
|---|---|---|---|
| J18 | 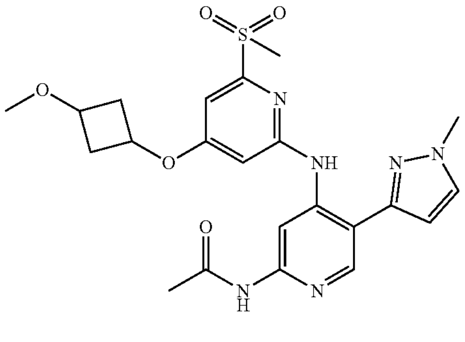 | N-(4-((4-(3-methoxycyclobutoxy)-6-(methylsulfonyl)pyridin-2-yl)amino)-5-(1-methyl-1H-pyrazol-3-yl)pyridin-2-yl)acetamide | $^1H$ NMR (400 MHz, DMSO-$d_6$) δ 11.33 (s, 1H), 10.45 (s, 1H), 9.16 (s, 1H), 8.63 (s, 1H), 7.92-7.89 (m, 1H), 7.02 (s, 1H), 6.95-6.91 (m, 1H), 6.65 (s, 1H), 5.13-5.05 (m, 1H), 4.15-4.07 (m, 1H), 4.02 (s, 3H), 3.46 (s, 3H), 3.18 (s, 3H), 2.48-2.34 (m, 4H), 2.10 (s, 3H). MS (ESI) m/e [M + 1]$^+$ 487. |
| J19 | 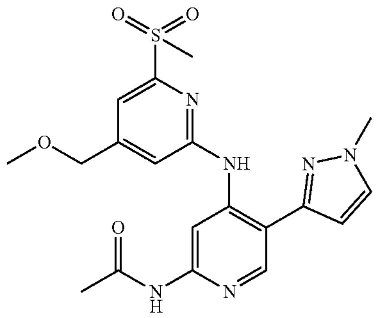 | N-(4-((4-(methoxymethyl)-6-(methylsulfonyl)pyridin-2-yl)amino)-5-(1-methyl-1H-pyrazol-3-yl)pyridin-2-yl)acetamide | $^1H$ NMR (400 MHz, DMSO-$d_6$) δ 11.52 (s, 1H), 10.46 (s, 1H), 9.28 (s, 1H), 8.66 (s, 1H), 7.95-7.90 (m, 1H), 7.52 (s, 1H), 7.23 (s, 1H), 6.98-6.94 (m, 1H), 4.59 (s, 2H), 4.03 (s, 3H), 3.50 (s, 3H), 3.40 (s, 3H), 2.11 (s, 3H). MS (ESI) m/e [M + 1]$^+$ 431. |
| J20 | 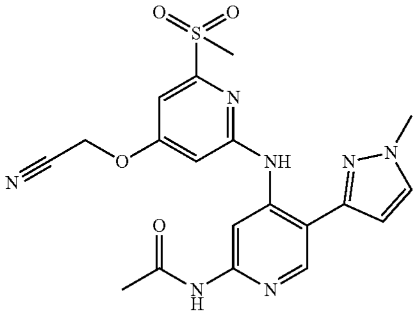 [SMILES: CC(=O)Nc1cc(Nc2cc(OCC#N)cc(S(C)(=O)=O)n2)c(-c2ccn(C)n2)cn1] | N-(4-((4-(cyanomethoxy)-6-(methylsulfonyl)pyridin-2-yl)amino)-5-(1-methyl-1H-pyrazol-3-yl)pyridin-2-yl)acetamide | $^1H$ NMR (400 MHz, DMSO-$d_6$) δ 11.51 (s, 1H), 10.46 (s, 1H), 9.21 (s, 1H), 8.66 (s, 1H), 7.90-7.85 (m, 1H), 7.27 (s, 1H), 6.95-6.90 (m, 2H), 5.46 (s, 2H), 4.04 (s, 3H), 3.50 (s, 3H), 2.11 (s, 3H). MS (ESI) m/e [M + 1]$^+$ 442. |
| J21 | 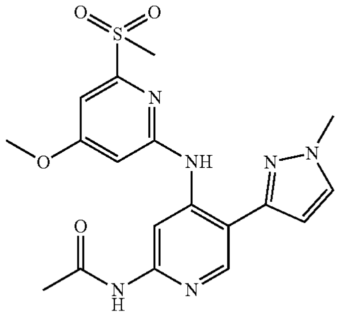 | N-(4-((4-methoxy-6-(methylsulfonyl)pyridin-2-yl)amino)-5-(1-methyl-1H-pyrazol-3-yl)pyridin-2-yl)acetamide | $^1H$ NMR (400 MHz, DMSO-$d_6$) δ 11.35 (s, 1H), 10.45 (s, 1H), 9.18 (s, 1H), 8.64 (s, 1H), 7.93-7.89 (m, 1H), 7.14 (s, 1H), 6.96-6.92 (m, 1H), 6.83 (s, 1H), 4.03 (s, 3H), 3.97 (s, 3H), 3.46 (s, 3H), 2.11 (s, 3H). MS (ESI) m/e [M + 1]$^+$ 417. |

-continued

| Example | Compound | Chemical Name | $^1$H NMR and LC/MS m/z (M + 1) |
|---|---|---|---|
| J22 | 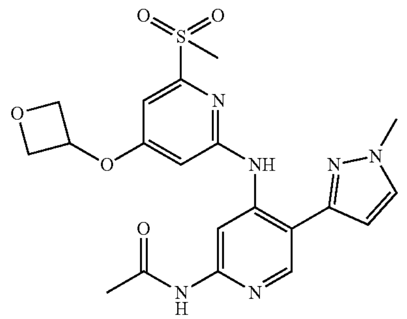 [SMILES: CC(=O)Nc1cc(Nc2cc(OC3COC3)cc(S(C)(=O)=O)n2)c(-c2ccn(C)n2)cn1] | N-(5-(1-methyl-1H-pyrazol-3-yl)-4-((6-(methylsulfonyl)-4-(oxetan-3-yloxy)pyridin-2-yl)amino)pyridin-2-yl)acetamide | $^1$H NMR (400 MHz, DMSO-$d_6$) δ 11.38 (s, 1H), 10.46 (s, 1H), 9.17 (s, 1H), 8.64 (s, 1H), 7.93-7.89 (m, 1H), 7.03 (s, 1H), 6.95-6.90 (m, 1H), 6.59 (s, 1H), 5.62-5.54 (m, 1H), 5.05-4.94 (m, 2H), 4.67-4.60 (m, 2H), 4.03 (s, 3H), 3.47 (s, 3H), 2.11 (s, 3H). MS (ESI) m/e [M + 1]$^+$ 459. |
| J23 | 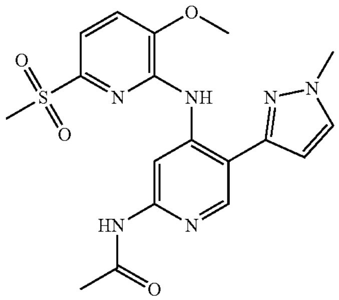 | N-(4-((3-methoxy-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.90 (s, 1H), 10.41 (s, 1H), 9.49 (s, 1H), 8.64 (s, 1H), 7.89-7.86 (m, 1H), 7.60-7.56 (m, 1H), 7.54-7.50 (m, 1H), 6.92-6.89 (m, 1H), 4.08 (s, 3H), 3.99 (s, 3H), 3.45 (s, 3H), 2.09 (s, 3H). MS (ESI) m/e [M + 1]$^+$ 417. |
| J24 | 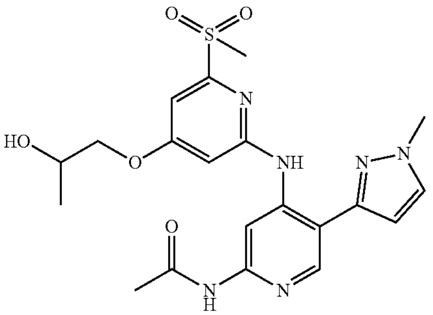 [SMILES: CC(=O)Nc1cc(Nc2cc(OCC(C)O)cc(S(C)(=O)=O)n2)c(-c2ccn(C)n2)cn1] | N-(4-((4-(2-hydroxypropoxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.30 (s, 1H), 10.44 (s, 1H), 9.18 (s, 1H), 8.63 (s, 1H), 7.94-7.89 (m, 1H), 7.14 (s, 1H), 6.95-6.91 (m, 1H), 6.82 (s, 1H), 5.04-4.98 (m, 1H), 4.12-3.96 (m, 5H), 3.46 (s, 3H), 2.11 (s, 3H), 1.22-1.12 (m, 2H). MS (ESI) m/e [M + 1]$^+$ 461. |
| J25 | 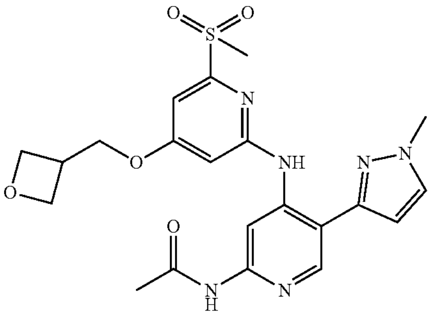 [SMILES: CC(=O)Nc1cc(Nc2cc(OCC3COC3)cc(S(C)(=O)=O)n2)c(-c2ccn(C)n2)cn1] | N-(5-(1-methyl-1H-pyrazol-3-yl)-4-((6-(methylsulfonyl)-4-(oxetan-3-ylmethoxy)pyridin-2-yl)amino)pyridin-2-yl)acetamide | $^1$H NMR (400 MHz, DMSO-$d_6$) δ 11.30 (s, 1H), 10.43 (s, 1H), 9.17 (s, 1H), 8.62 (s, 1H), 7.88 (d, J = 2.4 Hz, 1H), 7.15 (s, 1H), 6.91 (d, J = 2.4 Hz, 1H), 6.83 (s, 1H), 4.72-4.69 (m, 2H), 4.45-4.42 (m, 4H), 4.01 (s, 3H), 3.49-3.42 (m, 4H), 2.08 (s, 3H). MS (ESI) m/e [M + 1]$^+$ 473. |
| J26 | 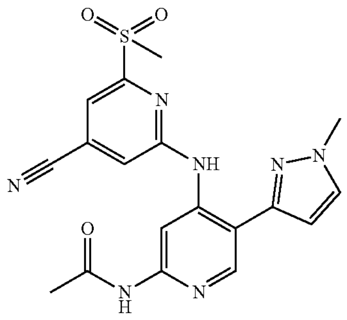 [SMILES: CC(=O)Nc1cc(Nc2cc(C#N)cc(S(C)(=O)=O)n2)c(-c2ccn(C)n2)cn1] | N-(4-((4-cyano-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.80 (s, 1H), 10.53 (s, 1H), 9.28 (s, 1H), 8.70 (s, 1H), 7.96 (s, 1H), 7.95-7.90 (m, 1H), 7.84 (s, 1H), 6.99-6.95 (m, 1H), 4.07 (s, 3H), 3.54 (s, 3H), 2.12 (s, 3H). MS (ESI) m/e [M + 1]$^+$ 412. |

-continued

| Example | Compound | Chemical Name | $^1$H NMR and LC/MS m/z (M + 1) |
|---|---|---|---|
| J27 | 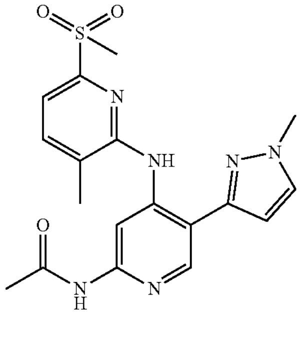 [SMILES: CC(=O)Nc1cc(Nc2nc(S(C)(=O)=O)ccc2C)c(-c2ccn(C)n2)cn1] | N-(5-(1-methyl-1H-pyrazol-3-yl)-4-((3-methyl-6-(methylsulfonyl)pyridin-2-yl)amino)pyridin-2-yl)acetamide | $^1$H NMR (400 MHz, DMOS-$d_6$) δ 11.29 (s, 1H), 10.45 (s, 1H), 9.40 (s, 1H), 8.71 (s, 1H), 7.92-7.89 (m, 2H), 7.54 (d, J = 7.5 Hz, 1H), 6.98-6.97 (m, 1H), 3.98 (s, 3H), 3.47 (s, 3H), 2.56 (s, 3H), 2.11 (s, 3H). MS (ESI) m/e [M + 1]$^+$ 401. |
| J28 | 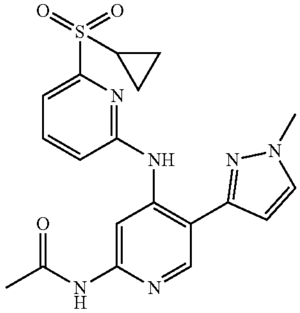 [SMILES: CC(=O)Nc1cc(Nc2cccc(S(=O)(=O)C3CC3)n2)c(-c2ccn(C)n2)cn1] | N-(4-((6-(cyclopropylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.50 (s, 1H), 10.44 (s, 1H), 9.18 (s, 1H), 8.66 (s, 1H), 8.05-7.95 (m, 1H), 7.90-7.89 (m, 1H), 7.49 (d, J = 7.2 Hz, 1H), 7.38 (d, J = 7.2 Hz, 1H), 6.95-6.90 (m, 1H), 4.02 (s, 3H), 3.70-3.65 (m, 1H), 2.09 (s, 3H), 1.15-1.05 (m, 4H). MS (ESI) m/e [M + 1]$^+$ 413. |
| J29 | 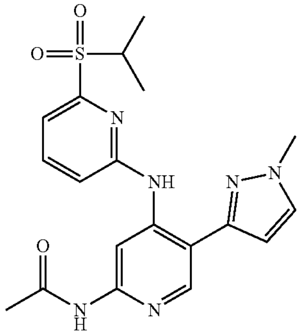 [SMILES: CC(=O)Nc1cc(Nc2cccc(S(=O)(=O)C(C)C)n2)c(-c2ccn(C)n2)cn1] | N-(4-((6-(isopropylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.52 (s, 1H), 10.44 (s, 1H), 9.17 (s, 1H), 8.66 (s, 1H), 8.01 (t, J = 7.6 Hz, 1H), 7.90 (d, J = 2.1 Hz, 1H), 7.58 (d, J = 8.1 Hz, 1H), 7.38 (d, J = 8.5 Hz, 1H), 6.94 (d, J = 2.1 Hz, 1H), 4.51-4.35 (m, 1H), 4.02 (s, 3H), 2.11 (s, 3H), 1.22 (d, J = 6.2 Hz, 6H). MS (ESI) m/e [M + 1]$^+$ 415. |
| J30 | 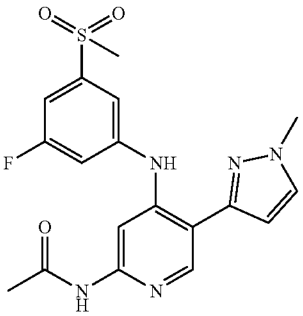 [SMILES: CC(=O)Nc1cc(Nc2cc(F)cc(S(C)(=O)=O)c2)c(-c2ccn(C)n2)cn1] | N-(4-((3-fluoro-5-(methylsulfonyl)phenyl)amino)-5-(1-methyl-1H-pyrazol-3-yl)pyridin-2-yl)acetamide | $^1$H NMR (400 MHz, DMSO-$d_6$) δ 10.47 (s, 1H), 10.35 (s, 1H), 8.60 (s, 1H), 8.21 (s, 1H), 7.86 (s, 1H), 7.69 (s, 1H), 7.55 (d, J = 4.6 Hz, 1H), 7.40 (s, 1H), 6.87 (d, J = 4.6 Hz, 1H), 3.96 (s, 3H), 3.34 (s, 3H), 2.07 (s, 3H). MS (ESI) m/e [M + 1]$^+$ 404. |

-continued

| Example | Compound | Chemical Name | $^1$H NMR and LC/MS m/z (M + 1) |
|---|---|---|---|
| J31 | 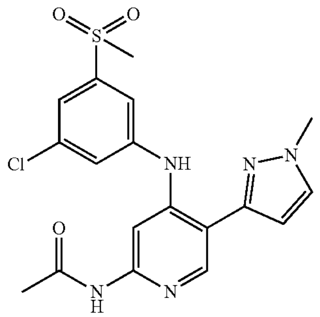 [SMILES: CC(=O)Nc1cc(Nc2cc(Cl)cc(S(C)(=O)=O)c2)c(-c2ccn(C)n2)cn1] | N-(4-((3-chloro-5-(methylsulfonyl)phenyl)amino)-5-(1-methyl-1H-pyrazol-3-yl)pyridin-2-yl)acetamide | $^1$H NMR (400 MHz, DMSO-$d_6$) δ 10.47 (s, 1H), 10.30 (s, 1H), 8.59 (s, 1H), 8.17 (s, 1H), 7.85-7.84 (m, 1H), 7.79 (s, 1H), 7.73 (s, 1H), 7.59 (s, 1H), 6.88-6.85 (m, 1H), 3.96 (s, 3H), 3.35 (s, 3H), 2.07 (s, 3H). MS (ESI) m/e $[M + 1]^+$ 420. |
| J32 | 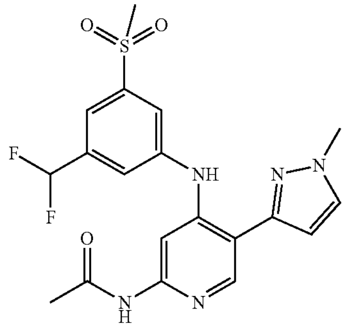 [SMILES: CC(=O)Nc1cc(Nc2cc(C(F)F)cc(S(C)(=O)=O)c2)c(-c2ccn(C)n2)cn1] | N-(4-((3-(difluoromethyl)-5-(methylsulfonyl)phenyl)amino)-5-(1-methyl-1H-pyrazol-3-yl)pyridin-2-yl)acetamide | $^1$H NMR (400 MHz, DMSO-$d_6$) δ 10.48 (s, 1H), 10.34 (s, 1H), 8.60 (s, 1H), 8.17 (s, 1H), 8.00 (s, 1H), 7.86-7.83 (m, 1H), 7.76 (s, 1H), 7.17 (s, 1H), 6.88-6.82 (m, 1H), 3.96 (s, 3H), 3.36 (s, 3H), 2.06 (s, 3H). MS (ESI) m/e $[M + 1]^+$ 436. |
| J33 | 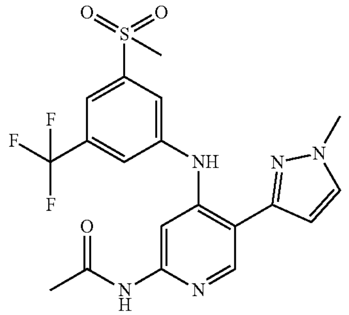 [SMILES: CC(=O)Nc1cc(Nc2cc(C(F)(F)F)cc(S(C)(=O)=O)c2)c(-c2ccn(C)n2)cn1] | N-(5-(1-methyl-1H-pyrazol-3-yl)-4-((3-(methylsulfonyl)-5-(trifluoromethyl)phenyl)amino)pyridin-2-yl)acetamide | $^1$H NMR (400 MHz, DMSO-$d_6$) δ 10.48 (s, 1H), 10.34 (s, 1H), 8.60 (s, 1H), 8.20 (s, 1H), 8.10 (s, 1H), 7.99 (s, 1H), 7.87-7.84 (m, 1H), 7.82 (s, 1H), 6.89-6.85 (m, 1H), 3.96 (s, 3H), 3.40 (s, 3H), 2.07 (s, 3H). MS (ESI) m/e $[M + 1]^+$ 454. |
| J34 | 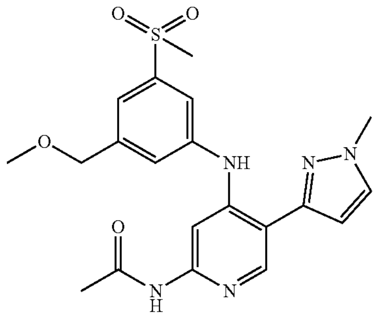 | N-(4-((3-(methoxymethyl)-5-(methylsulfonyl)phenyl)amino)-5-(1-methyl-1H-pyrazol-3-yl)pyridin-2-yl)acetamide | $^1$H NMR (400 MHz, DMSO-$d_6$) δ 10.43 (s, 1H), 10.28 (s, 1H), 8.57 (s, 1H), 8.13 (s, 1H), 7.89-7.85 (m, 1H), 7.77 (s, 1H), 7.58 (s, 1H), 7.55 (s, 1H), 6.89-6.87 (m, 1H), 4.54 (s, 2H), 3.96 (s, 3H), 3.36 (s, 3H), 3.30 (s, 3H), 2.06 (s, 3H). MS (ESI) m/e $[M + 1]^+$ 430. |

-continued

| Example | Compound | Chemical Name | $^1$H NMR and LC/MS m/z (M + 1) |
|---|---|---|---|
| J35 | 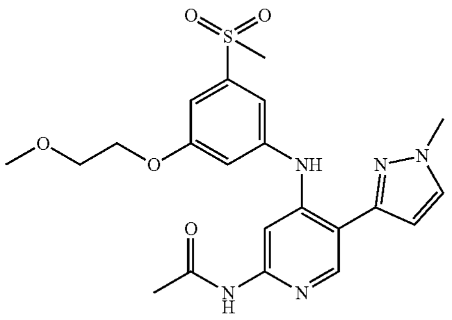 | N-(4-((3-(2-methoxyethoxy)-5-(methylsulfonyl)phenyl)amino)-5-(1-methyl-1H-pyrazol-3-yl)pyridin-2-yl)acetamide | $^1$H NMR (400 MHz, DMSO-$d_6$) δ 10.43 (s, 1H), 10.27 (s, 1H), 8.57 (s, 1H), 8.17 (s, 1H), 7.88-7.85 (m, 1H), 7.41 (s, 1H), 7.22 (s, 1H), 7.14 (s, 1H), 6.88-6.84 (m, 1H), 4.27-4.21 (m, 2H), 3.96 (s, 3H), 3.72-3.66 (m, 2H), 3.29 (s, 3H), 2.06 (s, 3H). MS (ESI) m/e $[M + 1]^+$ 460. |
| J36 | 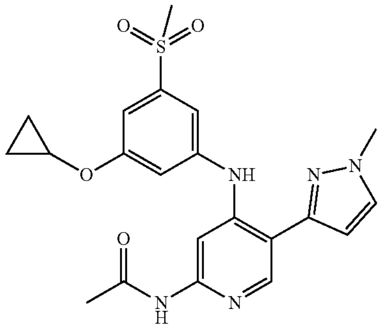 [SMILES: CC(=O)Nc1cc(Nc2cc(OC3CC3)cc(S(C)(=O)=O)c2)c(-c2ccn(C)n2)cn1] | N-(4-((3-cyclopropoxy-5-(methylsulfonyl)phenyl)amino)-5-(1-methyl-1H-pyrazol-3-yl)pyridin-2-yl)acetamide | $^1$H NMR (400 MHz, DMSO-$d_6$) δ 10.42 (s, 1H), 10.29 (s, 1H), 8.57 (s, 1H), 8.19 (s, 1H), 7.90-7.80 (m, 1H), 7.44 (s, 1H), 7.32 (s, 1H), 7.24 (s, 1H), 6.90-6.80 (m, 1H), 4.05-4.00 (m, 1H), 3.96 (s, 3H), 3.30 (s, 3H), 2.06 (s, 3H), 0.82-0.80 (m, 2H), 0.73-0.71 (m, 2H). MS (ESI) m/e $[M + 1]^+$ 442. |
| J37 | 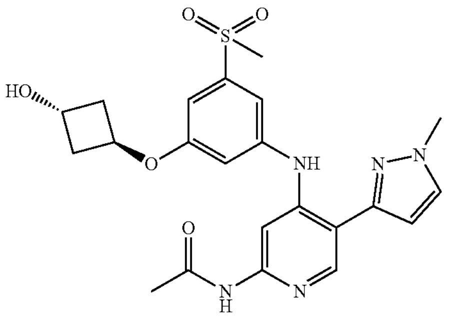 [SMILES: CC(=O)Nc1cc(Nc2cc(O[C@H]3C[C@H](O)C3)cc(S(C)(=O)=O)c2)c(-c2ccn(C)n2)cn1] | N-(4-((3-((trans)-3-hydroxycyclobutoxy)-5-(methylsulfonyl)phenyl)amino)-5-(1-methyl-1H-pyrazol-3-yl)pyridin-2-yl)acetamide | $^1$H NMR (400 MHz, DMSO-$d_6$) δ 10.40 (s, 1H), 10.23 (s, 1H), 8.57 (s, 1H), 8.17 (s, 1H), 7.85 (d, J = 2.1 Hz, 1H), 7.41 (s, 1H), 7.03 (s, 1H), 6.99 (s, 1H), 6.87 (d, J = 2.1 Hz, 1H), 5.25 (s, 1H), 4.99-4.96 (m, 1H), 4.40-4.35 (m, 1H), 3.96 (s, 3H), 3.29 (s, 3H), 2.40-2.30 (m, 4H), 2.06 (s, 3H). MS (ESI) m/e $[M + 1]^+$ 472. |
| J38 | 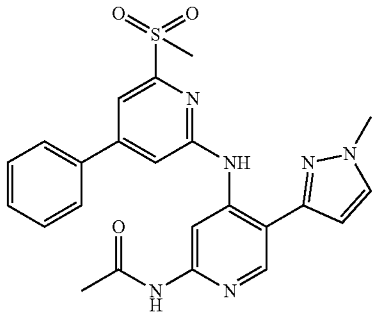 [SMILES: CC(=O)Nc1cc(Nc2cc(-c3ccccc3)cc(S(C)(=O)=O)n2)c(-c2ccn(C)n2)cn1] | N-(5-(1-methyl-1H-pyrazol-3-yl)-4-((6-(methylsulfonyl)-4-phenylpyridin-2-yl)amino)pyridin-2-yl)acetamide | $^1$H NMR (400 MHz, DMSO-$d_6$) δ 11.54 (s, 1H), 10.47 (s, 1H), 9.28 (s, 1H), 8.67 (s, 1H), 7.94-7.88 (m, 3H), 7.79 (s, 1H), 7.66-7.52 (m, 4H), 6.95-6.94 (m, 1H), 4.04 (s, 3H), 3.53 (s, 3H), 2.13 (s, 3H). MS (ESI) m/e $[M + 1]^+$ 463. |

-continued

| Example | Compound | Chemical Name | $^1$H NMR and LC/MS m/z (M + 1) |
|---|---|---|---|
| J39 | 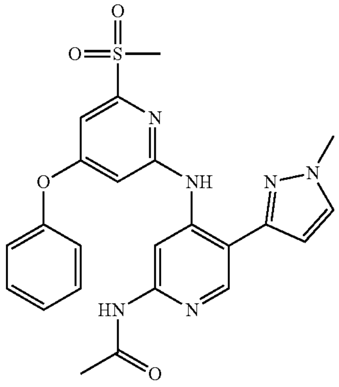 [SMILES: CC(=O)Nc1cc(Nc2cc(Oc3ccccc3)cc(S(C)(=O)=O)n2)c(-c2ccn(C)n2)cn1] | N-(5-(1-methyl-1H-pyrazol-3-yl)-4-((6-(methylsulfonyl)-4-phenoxypyridin-2-yl)amino)pyridin-2-yl)acetamide | $^1$H NMR (400 MHz, DMSO-$d_6$) δ 11.43 (s, 1H), 10.46 (s, 1H), 9.21 (s, 1H), 8.64 (s, 1H), 7.88-7.87 (m, 1H), 7.60-7.50 (m, 2H), 7.40-7.30 (m, 1H), 7.35-7.30 (m, 2H), 6.96-6.90 (m, 1H), 6.92 (s, 1H), 6.81 (s, 1H), 3.93 (s, 3H), 3.48 (s, 3H), 2.11 (s, 3H). MS (ESI) m/e $[M + 1]^+$ 479. |
| J40 | 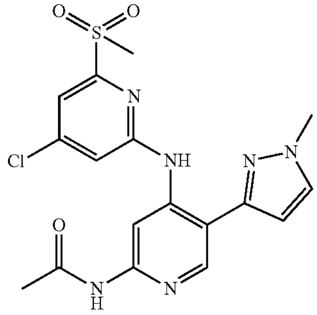 [SMILES: CC(=O)Nc1cc(Nc2cc(Cl)cc(S(C)(=O)=O)n2)c(-c2ccn(C)n2)cn1] | N-(4-((4-chloro-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.53 (s, 1H), 10.49 (s, 1H), 9.23 (s, 1H), 8.67 (s, 1H), 7.92-7.89 (m, 1H), 7.55 (s, 2H), 6.95-6.92 (m, 1H), 4.04 (s, 3H), 3.52 (s, 3H), 2.11 (s, 3H). MS (ESI) m/e $[M + 1]^+$ 421. |
| J41 | 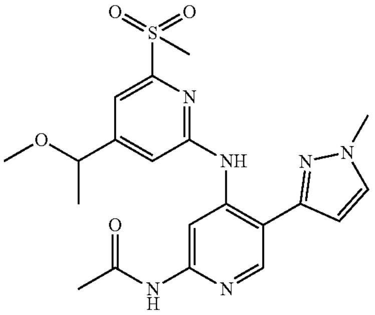 | N-(4-((4-(1-methoxyethyl)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.49 (s, 1H), 10.46 (s, 1H), 9.26 (s, 1H), 8.66 (s, 1H), 7.95-7.90 (m, 1H), 7.51 (s, 1H), 7.24 (s, 1H), 6.96-6.93 (m, 1H), 4.59-4.45 (m, 1H), 4.04 (s, 3H), 3.50 (s, 3H), 3.25 (s, 3H), 2.11 (s, 3H), 1.39 (d, J = 6.4 Hz, 3H). MS (ESI) m/e $[M + 1]^+$ 445. |
| J42 | 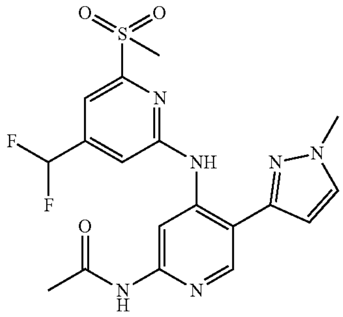 [SMILES: CC(=O)Nc1cc(Nc2cc(C(F)F)cc(S(C)(=O)=O)n2)c(-c2ccn(C)n2)cn1] | N-(4-((4-(difluoromethyl)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.66 (s, 1H), 10.50 (s, 1H), 9.29 (s, 1H), 8.68 (s, 1H), 7.95-7.90 (m, 1H), 7.64 (s, 1H), 7.52 (s, 1H), 7.25-7.15 (m, 1H), 6.94-6.91 (m, 1H), 4.04 (s, 3H), 3.54 (s, 3H), 2.12 (s, 3H). MS (ESI) m/e $[M + 1]^+$ 437. |

-continued

| Example | Compound | Chemical Name | $^1$H NMR and LC/MS m/z (M + 1) |
|---|---|---|---|
| J43 | 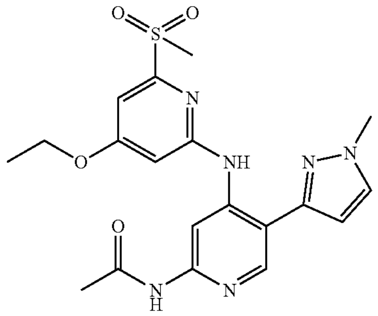 [SMILES: CCOc1cc(Nc2cc(NC(C)=O)ncc2-c2ccn(C)n2)nc(S(C)(=O)=O)c1] | N-(4-((4-ethoxy-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.31 (s, 1H), 10.42 (s, 1H), 9.17 (s, 1H), 8.63 (s, 1H), 7.89 (s, 1H), 7.11 (d, J = 2.3 Hz, 1H), 6.92 (d, J = 2.3 Hz, 1H), 6.79 (s, 1H), 4.27 (d, J = 7.0 Hz, 2H), 4.02 (s, 3H), 3.46 (s, 3H), 2.10 (s, 3H), 1.38 (t, J = 6.9 Hz, 3H). MS (ESI) m/e $[M + 1]^+$ 431. |
| J44 | 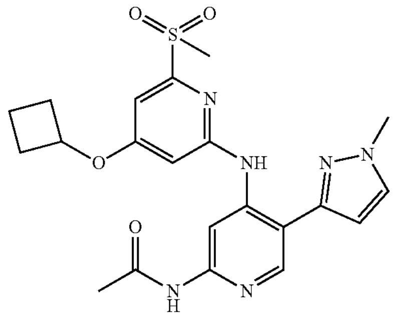 [SMILES: CC(=O)Nc1cc(Nc2cc(OC3CCC3)cc(S(C)(=O)=O)n2)c(-c2ccn(C)n2)cn1] | N-(4-((4-cyclobutoxy-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.34 (s, 1H), 10.43 (s, 1H), 9.17 (s, 1H), 8.63 (s, 1H), 7.90 (d, J = 2.4 Hz, 1H), 7.03 (s, 1H), 6.92 (d, J = 2.4 Hz, 1H), 6.68 (s, 1H), 5.00-4.96 (m, 1H), 4.02 (s, 3H), 3.46 (s, 3H), 2.16-2.10 (m, 5H), 1.85-1.83 (m, 1H), 1.74-1.69 (m, 1H). MS (ESI) m/e $[M + 1]^+$ 457. |
| J45 | 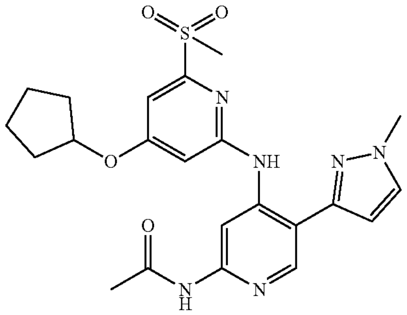 [SMILES: CC(=O)Nc1cc(Nc2cc(OC3CCCC3)cc(S(C)(=O)=O)n2)c(-c2ccn(C)n2)cn1] | N-(4-((4-(cyclopentyloxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.32 (s, 1H), 10.43 (s, 1H), 9.17 (s, 1H), 8.63 (s, 1H), 7.89-7.85 (m, 1H), 7.07 (s, 1H), 6.95-6.91 (m, 1H), 6.75 (s, 1H), 5.13-5.07 (m, 1H), 4.02 (s, 3H), 3.46 (s, 3H), 2.10 (s, 3H), 2.05-1.93 (m, 2H), 1.87-1.52 (m, 6H). MS (ESI) m/e $[M + 1]^+$ 471. |
| J46 | 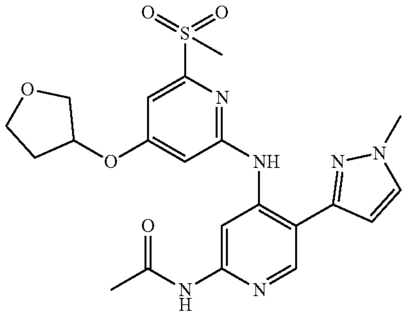 [SMILES: CC(=O)Nc1cc(Nc2cc(OC3CCOC3)cc(S(C)(=O)=O)n2)c(-c2ccn(C)n2)cn1] | N-(5-(1-methyl-1H-pyrazol-3-yl)-4-((6-(methylsulfonyl)-4-((tetrahydrofuran-3-yl)oxy)pyridin-2-yl)amino)pyridin-2-yl)acetamide | $^1$H NMR (400 MHz, DMSO-$d_6$) δ 11.35 (s, 1H), 10.44 (s, 1H), 9.17 (s, 1H), 8.64 (s, 1H), 7.89-7.85 (m, 1H), 7.10 (s, 1H), 6.96-6.91 (m, 1H), 6.79 (s, 1H), 5.36-5.31 (m, 1H), 4.02 (s, 3H), 3.94-3.83 (m, 3H), 3.82-3.74 (m, 1H), 3.46 (s, 3H), 2.36-2.25 (m, 1H), 2.10 (s, 3H), 2.08-2.00 (m, 1H). MS (ESI) m/e $[M + 1]^+$ 473. |

-continued

| Example | Compound | Chemical Name | $^1$H NMR and LC/MS m/z (M + 1) |
|---|---|---|---|
| J47 | 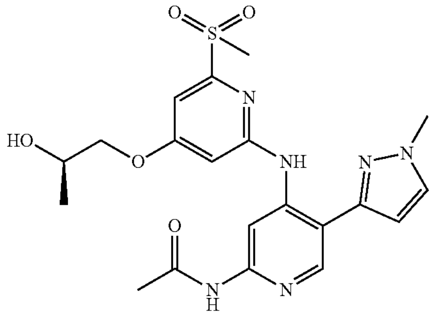 [SMILES: CC(=O)Nc1cc(Nc2cc(OC[C@@H](C)O)cc(S(C)(=O)=O)n2)c(-c2ccn(C)n2)cn1] | (R)-N-(4-((4-(2-hydroxypropoxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.29 (s, 1H), 10.44 (s, 1H), 9.17 (s, 1H), 8.63 (s, 1H), 7.90-7.85 (m, 1H), 7.14 (s, 1H), 6.95-6.91 (m, 1H), 6.82 (s, 1H), 5.04-4.95 (m, 1H), 4.12-3.92 (m, 5H), 3.46 (s, 3H), 2.11 (s, 3H), 1.17 (d, J = 5.9 Hz, 3H). MS (ESI) m/e $[M + 1]^+$ 461. |
| J48 | 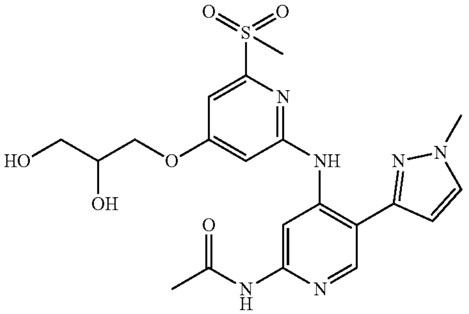 [SMILES: CC(=O)Nc1cc(Nc2cc(OCC(O)CO)cc(S(C)(=O)=O)n2)c(-c2ccn(C)n2)cn1] | N-(4-((4-(2,3-dihydroxypropoxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.32 (s, 1H), 10.44 (s, 1H), 9.19 (s, 1H), 8.63 (s, 1H), 7.89-7.86 (m, 1H), 7.15 (s, 1H), 6.95-6.91 (m, 1H), 6.83 (s, 1H), 5.16-4.97 (m, 1H), 4.84-4.64 (m, 1H), 4.30-4.22 (m, 1H), 4.12-4.02 (m, 1H), 4.02 (s, 3H), 3.87-3.80 (m, 1H), 3.49-3.43 (m, 5H), 2.11 (s, 3H). MS (ESI) m/e $[M + 1]^+$ 477. |
| J49 | 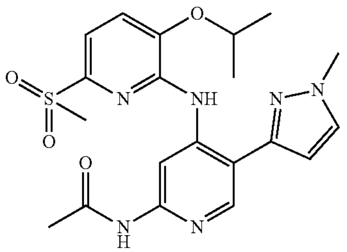 [SMILES: CC(=O)Nc1cc(Nc2nc(S(C)(=O)=O)ccc2OC(C)C)c(-c2ccn(C)n2)cn1] | N-(4-((3-isopropoxy-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 10.97 (s, 1H), 10.38 (s, 1H), 9.25 (s, 1H), 8.58 (s, 1H), 7.86-7.83 (m, 1H), 7.54-7.50 (m, 2H), 6.89-6.85 (m, 1H), 4.94-4.86 (m, 1H), 3.96 (s, 3H), 3.36 (s, 3H), 2.05 (s, 3H), 1.40 (d, J = 6.0 Hz, 6H). MS (ESI) m/e $[M + 1]^+$ 445. |
| J50 | 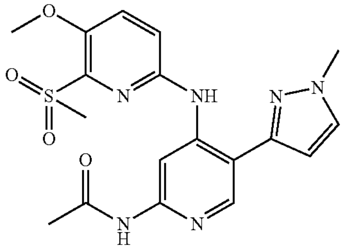 [SMILES: COc1ccc(Nc2cc(NC(C)=O)ncc2-c2ccn(C)n2)nc1S(C)(=O)=O] | N-(4-((5-methoxy-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.03 (s, 1H), 10.41 (s, 1H), 8.69 (s, 1H), 8.59 (s, 1H), 7.90 (d, J = 2.8 Hz, 1H), 7.80 (d, J = 6.4 Hz, 1H), 7.48-7.45 (d, J = 6.4 Hz, 1H), 6.90 (d, J = 2.8 Hz, 1H), 3.99 (s, 3H), 3.93 (s, 3H), 3.39 (s, 3H), 2.08 (s, 3H). MS (ESI) m/e $[M + 1]^+$ 417. |
| J51 | 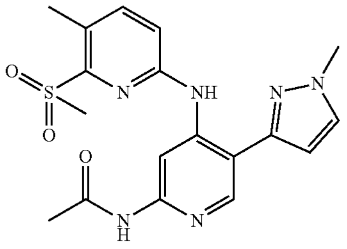 [SMILES: CC(=O)Nc1cc(Nc2ccc(C)c(S(C)(=O)=O)n2)c(-c2ccn(C)n2)cn1] | N-(5-(1-methyl-1H-pyrazol-3-yl)-4-((5-methyl-6-(methylsulfonyl)pyridin-2-yl)amino)pyridin-2-yl)acetamide | $^1$H NMR (400 MHz, DMSO-$d_6$) δ 11.24 (s, 1H), 10.42 (s, 1H), 8.91 (s, 1H), 8.63 (s, 1H), 7.88 (s, 1H), 7.84 (d, J = 8.3 Hz, 1H), 7.31 (d, J = 8.3 Hz, 1H), 6.91 (d, J = 2.1 Hz, 1H), 4.00 (s, 3H), 3.47 (s, 3H), 2.53 (s, 3H), 2.09 (s, 3H). MS (ESI) m/e $[M + 1]^+$ 401. |

-continued

| Example | Compound | Chemical Name | $^1H$ NMR and LC/MS m/z (M + 1) |
|---|---|---|---|
| J52 | 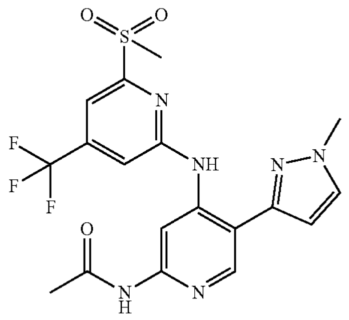 [SMILES: CC(=O)Nc1cc(Nc2cc(C(F)(F)F)cc(S(C)(=O)=O)n2)c(-c2ccn(C)n2)cn1] | N-(5-(1-methyl-1H-pyrazol-3-yl)-4-((6-(methylsulfonyl)-4-(trifluoromethyl)pyridin-2-yl)amino)pyridin-2-yl)acetamide | $^1H$ NMR (400 MHz, DMSO-$d_6$) δ 11.61 (s, 1H), 10.52 (s, 1H), 9.24 (s, 1H), 8.68 (s, 1H), 7.90-7.85 (m, 1H), 7.73 (s, 1H), 7.67 (s, 1H), 6.95-6.91 (m, 1H), 4.03 (s, 3H), 3.55 (s, 3H), 2.12 (s, 3H). MS (ESI) m/e $[M + 1]^+$ 455. |
| J53 | 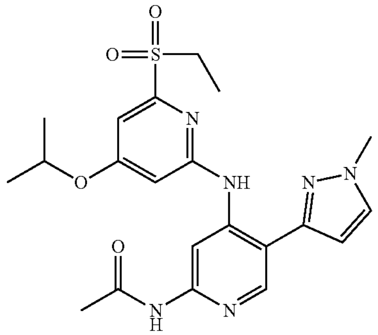 [SMILES: CCS(=O)(=O)c1cc(OC(C)C)cc(Nc2cc(NC(C)=O)ncc2-c2ccn(C)n2)n1] | N-(4-((6-(ethylsulfonyl)-4-isopropoxypyridin-2-yl)amino)-5-(1-methyl-1H-pyrazol-3-yl)pyridin-2-yl)acetamide | $^1H$ NMR (400 MHz, DMSO-$d_6$) δ 11.19 (s, 1H), 10.36 (s, 1H), 9.03 (s, 1H), 8.58 (s, 1H), 7.86-7.83 (m, 1H), 7.05 (s, 1H), 6.88-6.85 (m, 1H), 6.74 (s, 1H), 4.95-4.82 (m, 1H), 3.97 (s, 3H), 3.68-3.62 (m, 2H), 2.06 (s, 3H), 1.30 (d, J = 5.9 Hz, 6H), 1.13 (t, J = 7.3 Hz, 3H). MS (ESI) m/e $[M + 1]^+$ 459. |
| J54 | 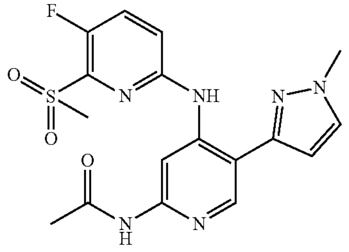 [SMILES: CC(=O)Nc1cc(Nc2ccc(F)c(S(C)(=O)=O)n2)c(-c2ccn(C)n2)cn1] | N-(4-((5-fluoro-6-(methylsulfonyl)pyridin-2-yl)amino)-5-(1-methyl-1H-pyrazol-3-yl)pyridin-2-yl)acetamide | $^1H$ NMR (400 MHz, DMSO-$d_6$) δ 11.34 (s, 1H), 10.39 (s, 1H), 8.94 (s, 1H), 8.60 (s, 1H), 7.95 (d, J = 9.4 Hz, 1H), 7.84-7.81 (m, 1H), 7.43 (d, J = 9.4 Hz, 1H), 6.87-6.82 (m, 1H), 3.96 (s, 3H), 3.49 (s, 3H), 2.05 (s, 3H). MS (ESI) m/e $[M + 1]^+$ 405. |
| J55 | 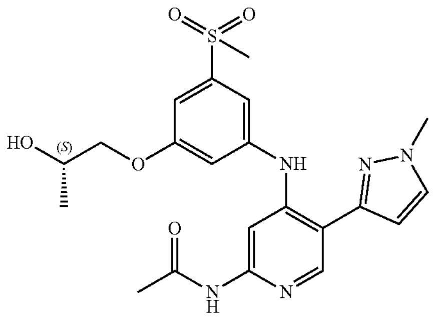 | (S)-N-(4-((3-(2-hydroxypropoxy)-5-(methylsulfonyl)phenyl)amino)-5-(1-methyl-1H-pyrazol-3-yl)pyridin-2-yl)acetamide | $^1H$ NMR (400 MHz, DMSO-$d_6$) δ 10.40 (s, 1H), 10.23 (s, 1H), 8.57 (s, 1H), 8.19 (s, 1H), 7.85-7.81 (m, 1H), 7.40 (s, 1H), 7.20 (s, 1H), 7.13 (s, 1H), 6.87-6.81 (m, 1H), 4.92 (s, 1H), 4.02-3.92 (m, 6H), 3.29 (s, 3H), 2.06 (s, 3H), 1.16 (d, J = 5.7 Hz, 3H). MS (ESI) m/e $[M + 1]^+$ 460. |
| J56 | 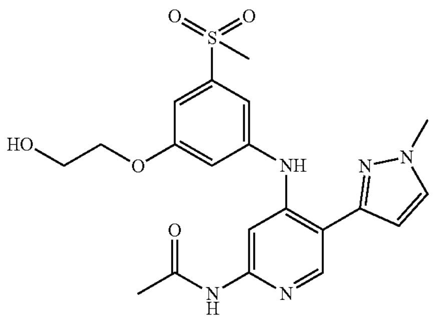 [SMILES: CC(=O)Nc1cc(Nc2cc(OCCO)cc(S(C)(=O)=O)c2)c(-c2ccn(C)n2)cn1] | N-(4-((3-(2-hydroxyethoxy)-5-(methylsulfonyl)phenyl)amino)-5-(1-methyl-1H-pyrazol-3-yl)pyridin-2-yl)acetamide | $^1H$ NMR (400 MHz, DMSO-$d_6$) δ 10.40 (s, 1H), 10.25 (s, 1H), 8.57 (s, 1H), 8.18 (s, 1H), 7.85-7.80 (m, 1H), 7.40 (s, 1H), 7.20 (s, 1H), 7.13 (s, 1H), 6.87-6.82 (m, 1H), 4.92 (s, 1H), 4.17-4.09 (m, 2H), 3.96 (s, 3H), 3.78-3.71 (m, 2H), 3.29 (s, 3H), 2.06 (s, 3H). MS (ESI) m/e $[M + 1]^+$ 446. |

-continued

| Example | Compound | Chemical Name | $^1$H NMR and LC/MS m/z (M + 1) |
|---|---|---|---|
| J57 | 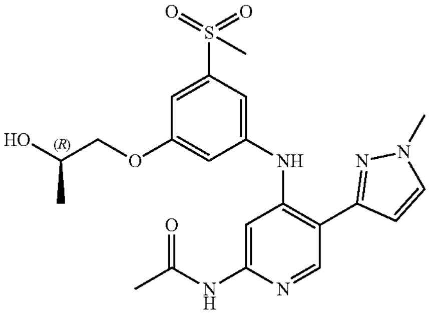 | (R)-N-(4-((3-(2-hydroxypropoxy)-5-(methylsulfonyl)phenyl)amino)-5-(1-methyl-1H-pyrazol-3-yl)pyridin-2-yl)acetamide | $^1$H NMR (400 MHz, DMSO-$d_6$) δ 10.40 (s, 1H), 10.23 (s, 1H), 8.57 (s, 1H), 8.19 (s, 1H), 7.85-7.80 (m, 1H), 7.40 (s, 1H), 7.20 (s, 1H), 7.13 (s, 1H), 6.87-6.82 (m, 1H), 4.92 (s, 1H), 4.02-3.92 (m, 6H), 3.29 (s, 3H), 2.06 (s, 3H), 1.16 (d, J = 5.7 Hz, 3H). MS (ESI) m/e [M + 1]$^+$ 460. |
| J58 | 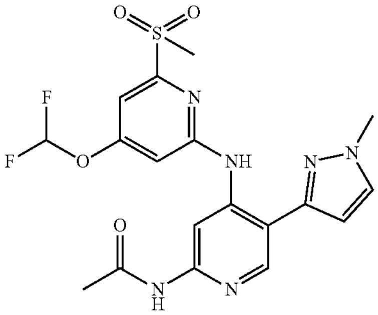 [SMILES: CC(=O)Nc1cc(Nc2cc(OC(F)F)cc(S(C)(=O)=O)n2)c(-c2ccn(C)n2)cn1] | N-(4-((4-(difluoromethoxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.51 (s, 1H), 10.47 (s, 1H), 9.22 (s, 1H), 8.66 (s, 1H), 7.90 (d, J = 2.8 Hz, 1H), 7.70-7.65 (m, 1H), 7.35 (s, 1H), 7.10 (s, 1H), 6.93 (d, J = 2.8 Hz, 1H), 4.03 (s, 3H), 3.52 (s, 3H), 2.11 (s, 3H). MS (ESI) m/e [M + 1]$^+$ 453. |
| J59 | 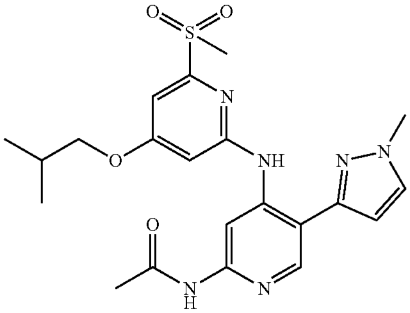 [SMILES: CC(=O)Nc1cc(Nc2cc(OCC(C)C)cc(S(C)(=O)=O)n2)c(-c2ccn(C)n2)cn1] | N-(4-((4-isobutoxy-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.26 (s, 1H), 10.42 (s, 1H), 9.16 (s, 1H), 8.62 (s, 1H), 7.89 (d, J = 2.2 Hz, 1H), 7.12 (s, 1H), 6.91 (d, J = 2.2 Hz, 1H), 6.82 (s, 1H), 4.03 (s, 3H), 4.05-4.00 (m, 2H), 3.45 (s, 3H), 2.10 (s, 3H), 2.09-2.03 (m, 1H), 1.01 (d, J = 6.7 Hz, 6H). MS (ESI) m/z [M + 1]$^+$ 459. |
| J60 | 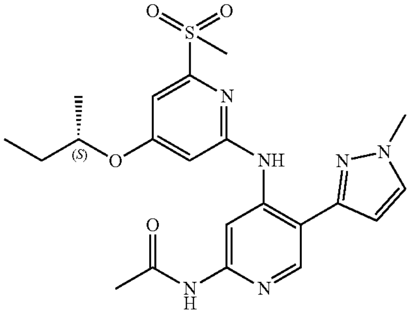 | (S)-N-(4-((4-(sec-butoxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.28 (s, 1H), 10.63-10.60 (m, 0H), 10.42 (s, 1H), 9.16 (s, 1H), 8.62 (s, 1H), 7.89 (d, J = 2.3 Hz, 1H), 7.09-7.05 (m, 1H), 6.91 (d, J = 2.3 Hz, 1H), 6.78 (s, 1H), 4.75-4.67 (m, 1H), 4.02 (s, 3H), 3.46 (s, 3H), 2.10 (s, 3H), 1.78-1.61 (m, 2H), 1.31 (d, J = 6.0 Hz, 3H), 0.95 (t, J = 7.5 Hz, 3H). MS (ESI) m/e [M + 1]$^+$ 459. |

-continued

| Example | Compound | Chemical Name | $^1$H NMR and LC/MS m/z (M + 1) |
|---|---|---|---|
| J61 | 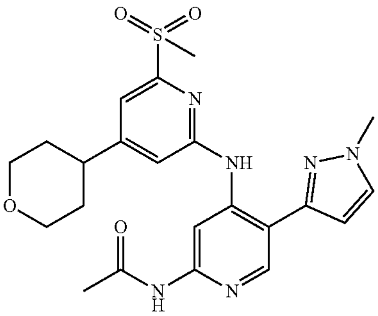 [SMILES: CC(=O)Nc1cc(Nc2cc(C3CCOCC3)cc(S(C)(=O)=O)n2)c(-c2ccn(C)n2)cn1] | N-(5-(1-methyl-1H-pyrazol-3-yl)-4-((6-(methylsulfonyl)-4-(tetrahydro-2H-pyran-4-yl)pyridin-2-yl)amino)pyridin-2-yl)acetamide | $^1$H NMR (400 MHz, DMSO-$d_6$) δ 11.44 (s, 1H), 10.43 (s, 1H), 9.24 (s, 1H), 8.64 (s, 1H), 7.90 (d, J = 2.3 Hz, 1H), 7.48 (s, 1H), 7.18 (s, 1H), 6.93 (d, J = 2.3 Hz, 1H), 4.05 (s, 3H), 3.99-3.96 (m, 2H), 3.50-3.41 (m, 5H), 3.08-2.93 (m, 1H), 2.11 (s, 3H), 1.81-1.71 (m, 4H). MS (ESI) m/e $[M + 1]^+$ 471. |
| J62 | 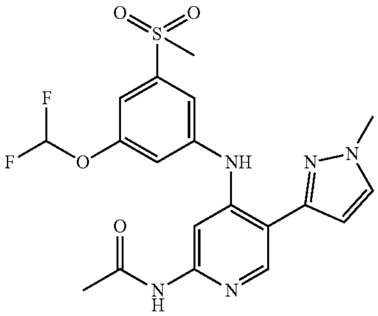 [SMILES: CC(=O)Nc1cc(Nc2cc(OC(F)F)cc(S(C)(=O)=O)c2)c(-c2ccn(C)n2)cn1] | N-(4-((3-(difluoromethoxy)-5-(methylsulfonyl)phenyl) amino)-5-(1-methyl-1H-pyrazol-3-yl)pyridin-2-yl)acetamide | $^1$H NMR (400 MHz, DMSO-$d_6$) δ 10.46 (s, 1H), 10.31 (s, 1H), 8.59 (s, 1H), 8.20 (s, 1H), 7.85 (d, J = 2.2 Hz, 1H), 7.71 (s, 1H), 7.46 (s, 1H), 7.45-7.42 (m, 1H), 7.34 (s, 1H), 6.87 (d, J = 2.2 Hz, 1H), 3.96 (s, 3H), 3.34 (s, 3H), 2.07 (s, 3H). MS (ESI) m/e $[M + 1]^+$ 452. |
| J63 | 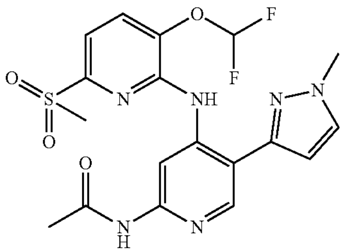 | N-(4-((3-(difluoromethoxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.79 (s, 1H), 10.48 (s, 1H), 9.45 (s, 1H), 8.70 (s, 1H), 7.90 (d, J = 2.1 Hz, 1H), 7.87 (d, J = 8.0 Hz, 1H), 7.65 (d, J = 8.0 Hz, 1H), 7.59-7.56 (m, 1H), 6.96 (d, J = 2.1 Hz, 1H), 3.97 (s, 3H), 3.51 (s, 3H), 2.12 (s, 3H). MS (ESI) m/e $[M + 1]^+$ 453. |
| J64 | 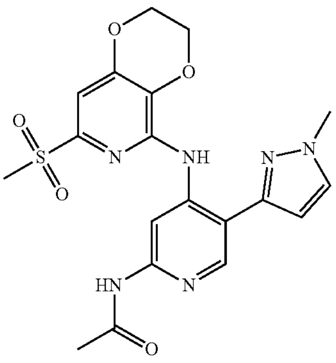 | N-(5-(1-methyl-1H-pyrazol-3-yl)-4-((7-(methylsulfonyl)-2,3-dihydro-[1,4]dioxino[2,3-c]pyridin-5-yl)amino)pyridin-2-yl)acetamide | $^1$H NMR (400 MHz, DMSO-$d_6$) δ 11.83 (s, 1H), 10.41 (s, 1H), 9.45 (s, 1H), 8.65 (s, 1H), 7.89-7.85 (m, 1H), 7.16 (s, 1H), 6.95-6.90 (m, 1H), 4.63-4.59 (m, 2H), 4.53-4.48 (m, 2H), 3.99 (s, 3H), 3.47 (s, 3H), 2.11 (s, 3H). MS (ESI) m/e $[M + 1]^+$ 445. |

-continued

| Example | Compound | Chemical Name | $^1$H NMR and LC/MS m/z (M + 1) |
|---|---|---|---|
| J65 | 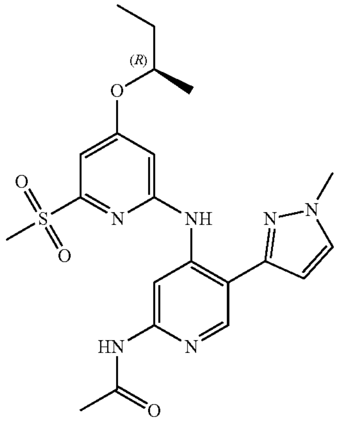 | (R)-N-(4-((4-(sec-butoxy)-6-(methylsulfonyl)pyridin-2-yl)amino)-5-(1-methyl-1H-pyrazol-3-yl)pyridin-2-yl)acetamide | $^1$H NMR (400 MHz, DMSO-$d_6$) δ 11.28 (s, 1H), 10.42 (s, 1H), 9.17 (s, 1H), 8.63 (s, 1H), 7.89 (d, J = 2.2 Hz, 1H), 7.09-7.05 (m, 1H), 6.92 (d, J = 2.2 Hz, 1H), 6.78 (s, 1H), 4.74-4.66 (m, 1H), 4.02 (s, 3H), 3.46 (s, 3H), 2.10 (s, 3H), 1.77-1.60 (m, 2H), 1.31 (d, J = 6.0 Hz, 3H), 0.95 (t, J = 7.4 Hz, 3H). MS (ESI) m/e [M + 1]$^+$ 459. |

Example M1: Synthesis of N-(5-(1-cyclopropyl-1H-pyrazol-3-yl)-4-((6-(methylsulfonyl)pyridin-2-yl)amino)pyridin-2-yl)acetamide

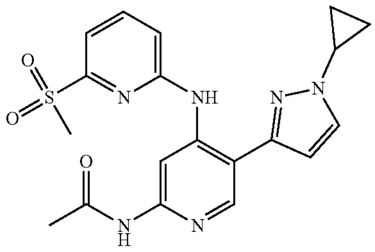 [SMILES: CC(=O)Nc1cc(Nc2cccc(S(C)(=O)=O)n2)c(-c2ccn(C3CC3)n2)cn1]

Step 1: 3-bromo-1-cyclopropyl-1H-pyrazole

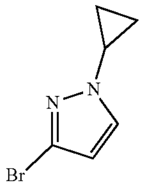

A mixture of Copper (II) acetate anhydrous (8.2 g, 41 mmol) and 2,2'bipyridyl (6.4 g, 41 mmol) in DCE (80 mL) was warmed to 50° C. and stirred for 10 min before adding to a mixture of 3-bromo-1H-pyrazole (6 g, 41 mmol), cyclopropylboronic acid (3.5 g, 41 mmol) and $Na_2CO_3$ (9.6 g, 90 mmol) in DCE (120 mL). The reaction mixture was stirred at 70° C. under $O_2$ atmosphere ($O_2$ balloon) for 2 d. The solvent was removed and the residue was dissolved in EA (300 mL) and washed with $NH_4Cl$ solution (300 mL×2) and brine (50 mL). The organic layer was dried over with $Na_2SO_4$ and filtered. The filtrate was concentrated and the residue was purified by column chromatography (PE/EA=10: 1-5:1) to give 3-bromo-1-cyclopropyl-1H-pyrazole (5.5 g, impure). MS (ESI) m/e [M+1]$^+$ 187.

Step 2: tert-butyl (2-chloro-5-(1-cyclopropyl-1H-pyrazol-3-yl)pyridin-4-yl)carbamate

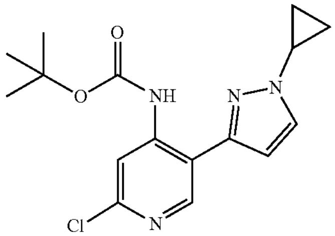 [SMILES: CC(C)(C)OC(=O)Nc1cc(Cl)ncc1-c1ccn(C2CC2)n1]

A mixture of 3-bromo-1-cyclopropyl-1H-pyrazole (5 g, 26.7 mmol), 4,4,4',4',5,5,5',5'-octamethyl-2,2'-bi(1,3,2-dioxaborolane) (1.34 g, 12 mmol), $Pd(PPh_3)_2Cl_2$ (702 mg, 1 mmol) and KOAc (5.2 g, 53.4 mmol) in dioxane (100 mL) was stirred at 120° C. under $N_2$ for 6 hrs. The reaction mixture was cooled to 90° C. and tert-butyl (5-bromo-2-chloropyridin-4-yl)carbamate (4.9 g, 16 mmol), $K_2CO_3$ (7.37 g, 53.4 mmol) and $H_2O$ (20 mL) and the mixture was stirred at 100° C. for 2 h. The reaction mixture was cooled and diluted with EA (200 mL) and washed with $H_2O$ (200 mL) and brine (200 mL). The organic layer was dried over with $Na_2SO_4$ and filtered. The filtrate was concentrated and the residue was purified by column chromatography (PE/EA=10: 1-2:1) to give tert-butyl (2-chloro-5-(1-cyclopropyl-1H-pyrazol-3-yl)pyridin-4-yl)carbamate (4.5 g, 84%). MS (ESI) m/e [M+1]$^+$ 335.

Step 3: tert-butyl (2-acetamido-5-(1-cyclopropyl-1H-pyrazol-3-yl)pyridin-4-yl)carbamate

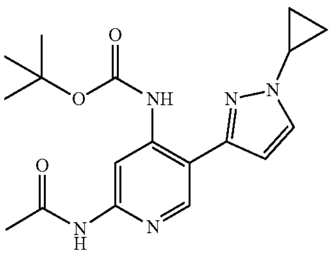 [SMILES: CC(=O)Nc1cc(NC(=O)OC(C)(C)C)c(-c2ccn(C3CC3)n2)cn1]

A mixture of tert-butyl (2-chloro-5-(1-cyclopropyl-1H-pyrazol-3-yl)pyridin-4-yl)carbamate (500 mg, 1.5 mmol), acetamide (177 mg, 3 mmol), $Pd_2dba_3$ (137 mg, 0.15 mmol), Xant-Phos (87 mg, 0.15 mmol) and $Cs_2CO_3$ (978 mg, 3 mmol) in dioxane (20 mL) was stirred at 130° C. under $N_2$ in a sealed tube for 4 hs. The reaction mixture was filtered and the solid was washed with EA (10 mL). The filtrate was concentrated and the residue was purified by column chromatography (DCM/MeOH=70:1 to 40:1) to give tert-butyl (2-acetamido-5-(1-cyclopropyl-1H-pyrazol-3-yl)pyridin-4-yl)carbamate (400 mg, 75%). MS (ESI) m/e $[M+1]^+$ 358.

Step 4: N-(4-amino-5-(1-cyclopropyl-1H-pyrazol-3-yl)pyridin-2-yl)acetamide

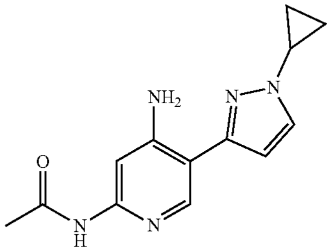 [SMILES: CC(=O)Nc1cc(N)c(-c2ccn(C3CC3)n2)cn1]

A solution of tert-butyl (2-acetamido-5-(1-cyclopropyl-1H-pyrazol-3-yl)pyridin-4-yl)carbamate (400 mg, 1.12 mmol) in TFA/DCM (14 mL, 1:3) was stirred at rt for 4 hs. The solvent evaporated and the residue was diluted with EA (20 mL) and washed with $NaHCO_3$ solution (10 mL) and brine (10 mL). The organic layer was dried over with $Na_2SO_4$ and filtered. The filtrate was concentrated to give the crude product N-(4-amino-5-(1-cyclopropyl-1H-pyrazol-3-yl)pyridin-2-yl)acetamide (300 mg). MS (ESI) m/e $[M+1]^+$ 258.

Step 5: N-(5-(1-cyclopropyl-1H-pyrazol-3-yl)-4-((6-(methylsulfonyl)pyridin-2-yl)amino)pyridin-2-yl) acetamide

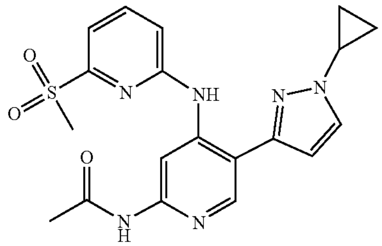 [SMILES: CC(=O)Nc1cc(Nc2cccc(S(C)(=O)=O)n2)c(-c2ccn(C3CC3)n2)cn1]

A mixture of N-(4-amino-5-(1-cyclopropyl-1H-pyrazol-3-yl)pyridin-2-yl)acetamide (60 mg, 0.23 mmol), 2-bromo-6-(methylsulfonyl)pyridine (66 mg, 0.28 mmol), $Pd_2dba_3$ (18 mg, 0.02 mmol), BINAP (12 mg, 0.02 mmol) and $K_2CO_3$ (60 mg, 0.46 mmol) in dioxane (5 mL) was stirred at 130° C. under $N_2$ in a sealed tube for 4 h. The reaction mixture was filtered and the solid was washed with EA (10 mL). The filtrate was concentrated and the residue was purified by prep-TLC (DCM:MeOH=20:1) twice to give N-(5-(1-cyclopropyl-1H-pyrazol-3-yl)-4-((6-(methylsulfonyl)pyridin-2-yl)amino)pyridin-2-yl)acetamide (43 mg, 45%). $^1H$ NMR (400 MHz, DMSO-$d_6$) δ 11.47 (s, 1H), 10.46 (s, 1H), 9.23 (s, 1H), 8.64 (s, 1H), 8.05-8.00 (m, 1H), 7.98 (d, J=2.4 Hz, 1H), 7.56 (d, J=8.3 Hz, 1H), 7.21 (d, J=8.3 Hz, 1H), 6.93 (d, J=2.4 Hz, 1H), 3.96-3.86 (m, 1H), 3.48 (s, 3H), 2.09 (s, 3H), 1.20-1.16 (m, 2H), 1.08-1.04 (m, 2H). MS (ESI) m/e $[M+1]^+$ 413.

The following Examples were prepared in a similar manner to the product Example M1:

| Example | Compound | Chemical Name | $^1H$ NMR and LC/MS m/z (M + 1) |
|---|---|---|---|
| M2 | 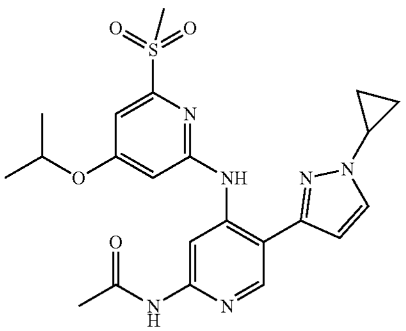 [SMILES: CC(=O)Nc1cc(Nc2cc(OC(C)C)cc(S(C)(=O)=O)n2)c(-c2ccn(C3CC3)n2)cn1] | N-(5-(1-cyclopropyl-1H-pyrazol-3-yl)-4-((4-isopropoxy-6-(methylsulfonyl)pyridin-2-yl)amino)pyridin-2-yl)acetamide | $^1H$ NMR (400 MHz, DMSO-d6) δ 11.34 (s, 1H), 10.46 (s, 1H), 9.14 (s, 1H), 8.64 (s, 1H), 8.02 (d, J = 2.4 Hz, 1H), 7.06 (s, 1H), 6.94 (d, J = 2.4 Hz, 1H), 6.67 (s, 1H), 4.88-4.82 (m, 1H), 3.96-3.92 (m, 1H), 3.46 (s, 3H), 2.11 (s, 3H), 1.36 (d, J = 5.2 Hz, 6H), 1.25-1.21 (m, 2H), 1.07-1.05 (m, 2H). MS (ESI) m/e $[M + H]^+$ 471. |

-continued

| Example | Compound | Chemical Name | $^1H$ NMR and LC/MS m/z (M + 1) |
|---|---|---|---|
| M3 | 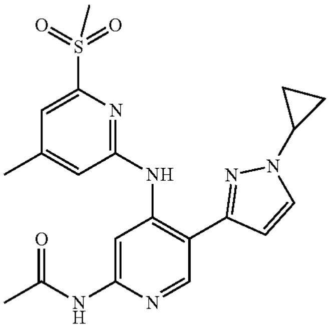 [SMILES: CC(=O)Nc1cc(Nc2cc(C)cc(S(C)(=O)=O)n2)c(-c2ccn(C3CC3)n2)cn1] | N-(5-(1-cyclopropyl-1H-pyrazol-3-yl)-4-((4-methyl-6-(methylsulfonyl)pyridin-2-yl)amino)pyridin-2-yl)acetamide | $^1H$ NMR (400 MHz, DMSO-$d_6$) δ 11.40 (s, 1H), 10.46 (s, 1H), 9.22 (s, 1H), 8.65 (s, 1H), 8.00 (d, J = 2.4 Hz, 1H), 7.47 (s, 1H), 7.05 (s, 1H), 6.95 (d, J = 2.4 Hz, 1H), 3.95-3.92 (m, 1H), 3.47 (s, 3H), 2.45 (s, 3H), 2.11 (s, 3H), 1.20-1.15 (m, 2H), 1.09-1.05 (m, 2H). MS (ESI) m/e $[M + 1]^+$ 427. |
| M4 | 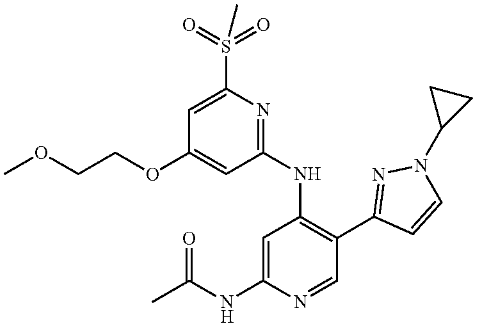 [SMILES: COCCOc1cc(Nc2cc(NC(C)=O)ncc2-c2ccn(C3CC3)n2)nc(S(C)(=O)=O)c1] | N-(5-(1-cyclopropyl-1H-pyrazol-3-yl)-4-((4-(2-methoxyethoxy)-6-(methylsulfonyl)pyridin-2-yl)amino)pyridin-2-yl)acetamide | $^1H$ NMR (400 MHz, DMSO-$d_6$) δ 11.33 (s, 1H), 10.47 (s, 1H), 9.12 (s, 1H), 8.64 (s, 1H), 8.00 (d, J = 2.4 Hz, 1H), 7.14 (s, 1H), 6.94 (d, J = 2.4 Hz, 1H), 6.73 (s, 1H), 4.35-4.33 (m, 2H), 3.93-3.90 (m, 1H), 3.75-3.71 (m, 2H), 3.46 (s, 3H), 3.34 (s, 3H), 2.11 (s, 3H), 1.25-1.20 (m, 2H), 1.07-1.02 (m, 2H). MS (ESI) m/e $[M + 1]^+$ 487. |
| M5 | 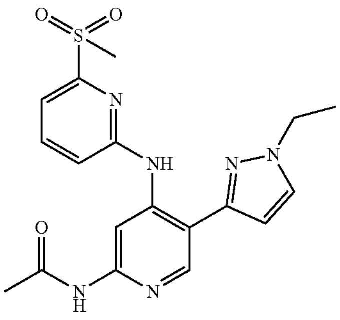 [SMILES: CCn1ccc(-c2cnc(NC(C)=O)cc2Nc2cccc(S(C)(=O)=O)n2)n1] | N-(5-(1-ethyl-1H-pyrazol-3-yl)-4-((6-(methylsulfonyl)pyridin-2-yl)amino)pyridin-2-yl)acetamide | $^1H$ NMR (400 MHz, DMSO-$d_6$) δ 11.61 (s, 1H), 10.45 (s, 1H), 9.26 (s, 1H), 8.70-8.60 (m, 1H), 8.10-8.00 (m, 1H), 7.94 (s, 1H), 7.58-7.49 (m, 1H), 7.35-7.25 (m, 1H), 7.00-6.90 (m, 1H), 4.31 (q, J = 7.3 Hz, 2H), 3.48 (s, 3H), 2.09 (s, 3H), 1.48 (t, J = 7.3 Hz, 3H). MS (ESI) m/e $[M + 1]^+$ 401. |
| M6 | 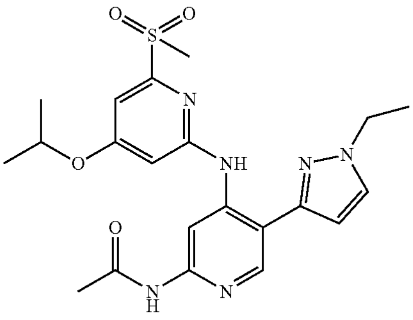 [SMILES: CCn1ccc(-c2cnc(NC(C)=O)cc2Nc2cc(OC(C)C)cc(S(C)(=O)=O)n2)n1] | N-(5-(1-ethyl-1H-pyrazol-3-yl)-4-((4-isopropoxy-6-(methylsulfonyl)pyridin-2-yl)amino)pyridin-2-yl)acetamide | $^1H$ NMR (400 MHz, DMSO-$d_6$) δ 11.41 (s, 1H), 10.44 (s, 1H), 9.16 (s, 1H), 8.64 (s, 1H), 8.00-7.90 (m, 1H), 7.10-6.95 (m, 1H), 6.93 (s, 1H), 6.73 (s, 1H), 4.95-4.87 (m, 1H), 4.35-4.27 (m, 2H), 3.46 (s, 3H), 2.11 (s, 3H), 1.50 (t, J = 7.2 Hz, 3H), 1.35 (d, J = 5.9 Hz, 6H). MS (ESI) m/e $[M + 1]^+$ 459. |

-continued

| Example | Compound | Chemical Name | $^1$H NMR and LC/MS m/z (M + 1) |
|---|---|---|---|
| M7 | 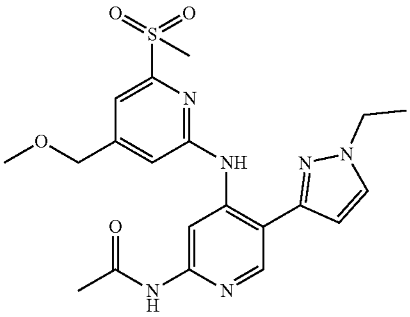 [SMILES: CCn1ccc(-c2cnc(NC(C)=O)cc2Nc2cc(COC)cc(S(C)(=O)=O)n2)n1] | N-(5-(1-ethyl-1H-pyrazol-3-yl)-4-((4-(methoxymethyl)-6-(methylsulfonyl)pyridin-2-yl)amino)pyridin-2-yl)acetamide | $^1$H NMR (400 MHz, DMSO-$d_6$) δ 11.62 (s, 1H), 10.46 (s, 1H), 9.28 (s, 1H), 8.67 (s, 1H), 8.05-7.95 (m, 1H), 7.51 (s, 1H), 7.18 (s, 1H), 7.05-6.95 (m, 1H), 4.59 (s, 2H), 4.36-4.28 (m, 2H), 3.50 (s, 3H), 3.40 (s, 3H), 2.11 (s, 3H), 1.51 (t, J = 7.3 Hz, 3H). MS (ESI) m/e [M + 1]$^+$ 445. |
| M8 | 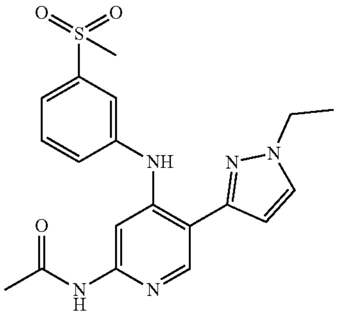 [SMILES: CCn1ccc(-c2cnc(NC(C)=O)cc2Nc2cccc(S(C)(=O)=O)c2)n1] | N-(5-(1-ethyl-1H-pyrazol-3-yl)-4-((3-(methylsulfonyl)phenyl)amino)pyridin-2-yl)acetamide | $^1$H NMR (400 MHz, DMSO-$d_6$) δ 10.41 (s, 1H), 10.40 (s, 1H), 8.58 (s, 1H), 8.19 (s, 1H), 7.98-7.87 (m, 1H), 7.84 (s, 1H), 7.72-7.58 (m, 3H), 6.95-6.85 (m, 1H), 4.29-4.21 (m, 2H), 3.30 (s, 3H), 2.06 (s, 3H), 1.45 (t, J = 7.3 Hz, 3H). MS (ESI) m/e [M + 1]$^+$ 400. |
| M9 | 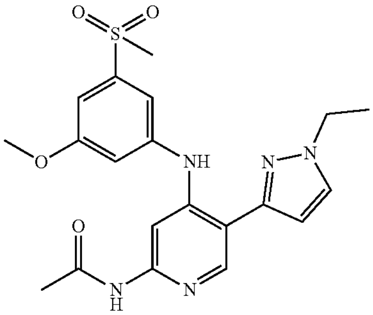 [SMILES: CCn1ccc(-c2cnc(NC(C)=O)cc2Nc2cc(OC)cc(S(C)(=O)=O)c2)n1] | N-(5-(1-ethyl-1H-pyrazol-3-yl)-4-((3-methoxy-5-(methylsulfonyl)phenyl)amino)pyridin-2-yl)acetamide | $^1$H NMR (400 MHz, DMSO-$d_6$) δ 10.41 (s, 1H), 10.39 (s, 1H), 8.58 (s, 1H), 8.23 (s, 1H), 7.90 (d, J = 2.1 Hz, 1H), 7.39 (s, 1H), 7.22 (s, 1H), 7.12 (s, 1H), 6.88 (d, J = 2.1 Hz, 1H), 4.26 (q, J = 7.2 Hz, 2H), 3.89 (s, 3H), 3.29 (s, 3H), 2.07 (s, 3H), 1.45 (t, J = 7.2 Hz, 3H). MS (ESI) m/e [M + 1]$^+$ 430. |
| M10 | 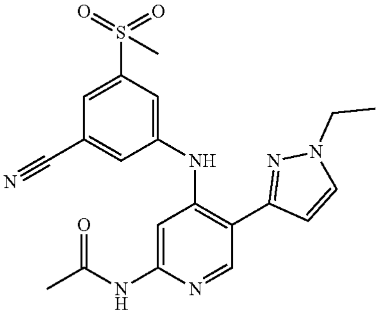 [SMILES: CCn1ccc(-c2cnc(NC(C)=O)cc2Nc2cc(C#N)cc(S(C)(=O)=O)c2)n1] | N-(4-((3-cyano-5-(methylsulfonyl)phenyl)amino)-5-(1-ethyl-1H-pyrazol-3-yl)pyridin-2-yl)acetamide | $^1$H NMR (400 MHz, DMSO-$d_6$) δ 10.50 (s, 1H), 10.44 (s, 1H), 9.12 (s, 1H), 8.62 (s, 1H), 8.18 (s, 1H), 8.08 (s, 1H), 7.97 (d, J = 2.2 Hz, 1H), 7.90 (s, 1H), 6.87 (d, J = 2.2 Hz, 1H), 4.26 (q, J = 7.3 Hz, 2H), 3.37 (s, 3H), 2.08 (s, 3H), 1.44 (t, J = 7.3 Hz, 3H). MS (ESI) m/e [M + 1]$^+$ 425. |

-continued

| Example | Compound | Chemical Name | $^1$H NMR and LC/MS m/z (M + 1) |
|---|---|---|---|
| M11 | 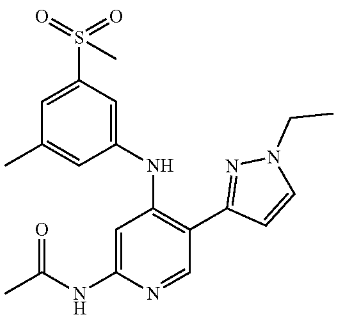 [SMILES: CCn1ccc(-c2cnc(NC(C)=O)cc2Nc2cc(C)cc(S(C)(=O)=O)c2)n1] | N-(5-(1-ethyl-1H-pyrazol-3-yl)-4-((3-methyl-5-(methylsulfonyl)phenyl)amino)pyridin-2-yl)acetamide | $^1$H NMR (400 MHz, DMSO-$d_6$) δ 10.38 (s, 1H), 10.33 (s, 1H), 8.57 (s, 1H), 8.17 (s, 1H), 7.90 (d, J = 2.1 Hz, 1H), 7.64 (s, 1H), 7.45 (s, 2H), 6.88 (d, J = 2.1 Hz, 1H), 4.25 (q, J = 7.2 Hz, 2H), 3.28 (s, 3H), 2.43 (s, 3H), 2.06 (s, 3H), 1.45 (t, J = 7.2 Hz, 3H). MS (ESI) m/e [M + 1]$^+$ 414. |
| M12 | 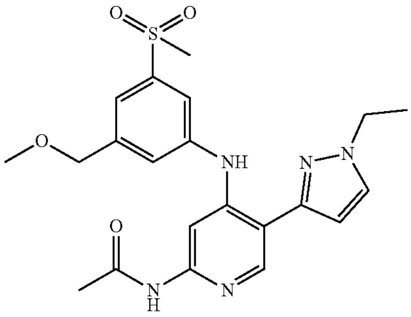 [SMILES: CCn1ccc(-c2cnc(NC(C)=O)cc2Nc2cc(COC)cc(S(C)(=O)=O)c2)n1] | N-(5-(1-ethyl-1H-pyrazol-3-yl)-4-((3-(methoxymethyl)-5-(methylsulfonyl)phenyl)amino)pyridin-2-yl)acetamide | $^1$H NMR (400 MHz, DMSO-$d_6$) δ 10.40 (s, 1H), 10.37 (s, 1H), 8.58 (s, 1H), 8.17 (s, 1H), 7.90 (d, J = 2.2 Hz, 1H), 7.77 (s, 1H), 7.56 (s, 1H), 7.53 (s, 1H), 6.88 (d, J = 2.2 Hz, 1H), 4.54 (s, 2H), 4.25 (q, J = 7.3 Hz, 2H), 3.36 (s, 3H), 3.30 (s, 3H), 2.06 (s, 3H), 1.45 (t, J = 7.2 Hz, 3H). MS (ESI) m/e [M + 1]$^+$ 444. |
| M13 | 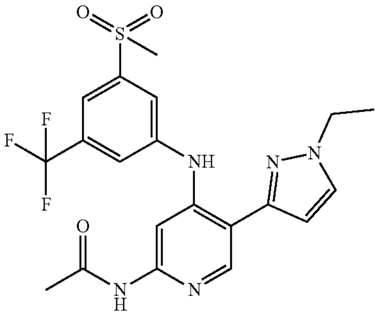 [SMILES: CCn1ccc(-c2cnc(NC(C)=O)cc2Nc2cc(C(F)(F)F)cc(S(C)(=O)=O)c2)n1] | N-(5-(1-ethyl-1H-pyrazol-3-yl)-4-((3-(methylsulfonyl)-5-(trifluoromethyl)phenyl)amino)pyridin-2-yl)acetamide | $^1$H NMR (400 MHz, DMSO-$d_6$) δ 10.48 (s, 1H), 10.44 (s, 1H), 8.61 (s, 1H), 8.21 (s, 1H), 8.07 (s, 1H), 7.97 (s, 1H), 7.90 (d, J = 2.2 Hz, 1H), 7.80 (s, 1H), 6.86 (d, J = 2.2 Hz, 1H), 4.25 (q, J = 7.3 Hz, 2H), 3.39 (s, 3H), 2.07 (s, 3H), 1.43 (t, J = 7.2 Hz, 3H). MS (ESI) m/e [M + 1]$^+$ 468. |
| M14 | 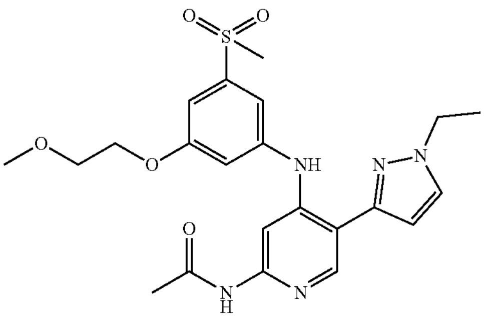 [SMILES: CCn1ccc(-c2cnc(NC(C)=O)cc2Nc2cc(OCCOC)cc(S(C)(=O)=O)c2)n1] | N-(5-(1-ethyl-1H-pyrazol-3-yl)-4-((3-(2-methoxyethoxy)-5-(methylsulfonyl)phenyl)amino)pyridin-2-yl)acetamide | $^1$H NMR (400 MHz, DMSO-$d_6$) δ 10.41 (s, 1H), 10.37 (s, 1H), 8.58 (s, 1H), 8.21 (s, 1H), 7.90 (d, J = 2.2 Hz, 1H), 7.40 (s, 1H), 7.20 (s, 1H), 7.13 (s, 1H), 6.88 (d, J = 2.2, 1H), 4.29-4.24 (m, 4H), 3.69 (s, 2H), 3.32 (s, 3H), 3.29 (s, 3H), 2.06 (s, 3H), 1.45 (t, J = 7.3 Hz, 3H). MS (ESI) m/e [M + 1]$^+$ 474. |

-continued

| Example | Compound | Chemical Name | $^1$H NMR and LC/MS m/z (M + 1) |
|---|---|---|---|
| M15 | 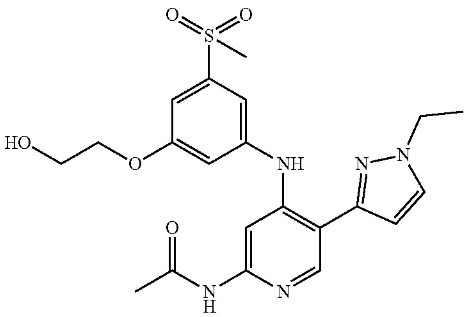 [SMILES: CCn1ccc(-c2cnc(NC(C)=O)cc2Nc2cc(OCCO)cc(S(C)(=O)=O)c2)n1] | N-(5-(1-ethyl-1H-pyrazol-3-yl)-4-((3-(2-hydroxyethoxy)-5-(methylsulfonyl)phenyl) amino)pyridin-2-yl)acetamide | $^1$H NMR (400 MHz, DMSO-$d_6$) δ 10.47 (s, 1H), 10.31 (s, 1H), 8.57 (s, 1H), 7.91 (s, 1H), 7.41 (s, 1H), 7.20 (s, 1H), 7.19 (s, 1H), 6.89 (d, J = 2.4 Hz, 1H), 6.69 (d, J = 2.4 Hz, 1H), 4.26 (q, J = 7.4 Hz, 2H), 4.30-4.20 (m, 2H), 3.80-3.70 (m, 2H), 3.29 (s, 3H), 2.08 (s, 3H), 1.45 (t, J = 7.4 Hz, 3H). MS (ESI) m/e [M + 1]$^+$ 460. |
| M16 | 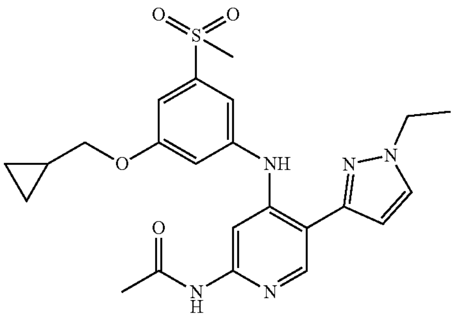 [SMILES: CCn1ccc(-c2cnc(NC(C)=O)cc2Nc2cc(OCC3CC3)cc(S(C)(=O)=O)c2)n1] | N-(4-((3-(cyclopropylmethoxy)-5-(methylsulfonyl)phenyl) amino)-5-(1-ethyl-1H-pyrazol-3-yl)pyridin-2-yl)acetamide | 1H NMR (400 MHz, DMSO-$d_6$) δ 10.40 (s, 1H), 10.36 (s, 1H), 8.58 (s, 1H), 8.20 (s, 1H), 7.90 (d, J = 2.2 Hz, 1H), 7.37 (s, 1H), 7.18 (s, 1H), 7.10 (s, 1H), 6.88 (d, J = 2.2 Hz, 1H), 4.30-4.25 (m, 2H), 3.96 (d, J = 6.9 Hz, 2H), 3.28 (s, 3H), 2.06 (s, 3H), 1.45 (t, J = 7.2 Hz, 3H), 1.30-1.23 (m, 1H), 0.62-0.54 (m, 2H), 0.41-0.31 (m, 2H). MS (ESI) m/e [M + 1]$^+$ 470. |
| M17 | 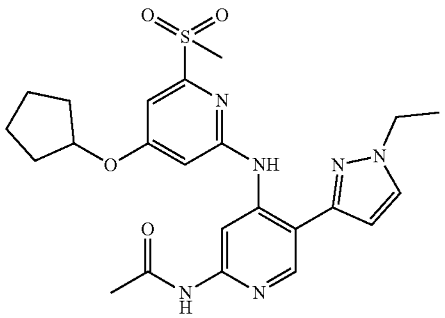 [SMILES: CCn1ccc(-c2cnc(NC(C)=O)cc2Nc2cc(OC3CCCC3)cc(S(C)(=O)=O)n2)n1] | N-(4-((4-(cyclopentyloxy)-6-(methylsulfonyl)pyridin-2-yl)amino)-5-(1-ethyl-1H-pyrazol-3-yl)pyridin-2-yl)acetamide | $^1$H NMR (400 MHz, DMSO-$d_6$) δ 11.43 (s, 1H), 10.43 (s, 1H), 9.16 (s, 1H), 8.64 (s, 1H), 7.94 (s, 1H), 7.05 (s, 1H), 6.92 (d, J = 2.4 Hz, 1H), 6.70 (d, J = 2.4 Hz, 1H), 5.13-5.05 (m, 1H), 4.38-4.22 (m, 2H), 3.45 (s, 3H), 2.10 (s, 3H), 2.03-1.94 (m, 2H), 1.89-1.68 (m, 4H), 1.67-1.62 (m, 2H), 1.50 (t, J = 7.2 Hz, 3H). MS (ESI) m/e [M + 1]$^+$ 485. |
| M18 | 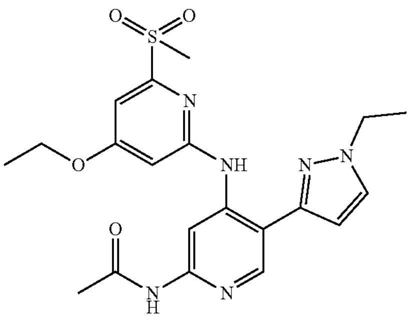 [SMILES: CCOc1cc(Nc2cc(NC(C)=O)ncc2-c2ccn(CC)n2)nc(S(C)(=O)=O)c1] | N-(4-((4-ethoxy-6-(methylsulfonyl)pyridin-2-yl)amino)-5-(1-ethyl-1H-pyrazol-3-y)pyridin-2-yl)acetamide | $^1$H NMR (400 MHz, DMSO-$d_6$) δ 11.42 (s, 1H), 10.45 (s, 1H), 9.16 (s, 1H), 8.64 (s, 1H), 7.95 (d, J = 2.2 Hz, 1H), 7.10 (d, J = 1.8 Hz, 1H), 6.93 (d, J = 2.2 Hz, 1H), 6.75 (s, 1H), 4.32-4.30 (m, 2H), 4.29-4.23 (m, 2H), 3.46 (s, 3H), 2.11 (s, 3H), 1.50 (t, J = 7.2 Hz, 3H), 1.38 (t, J = 6.9 Hz, 3H). MS (ESI) m/e [M + 1]$^+$ 445. |

-continued

| Example | Compound | Chemical Name | $^{1}$H NMR and LC/MS m/z (M + 1) |
|---|---|---|---|
| M19 | 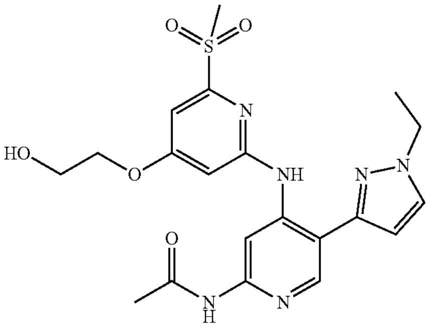 [SMILES: CCn1ccc(-c2cnc(NC(C)=O)cc2Nc2cc(OCCO)cc(S(C)(=O)=O)n2)n1] | N-(5-(1-ethyl-1H-pyrazol-3-yl)-4-((4-(2-hydroxyethoxy)-6-(methylsulfonyl)pyridin-2-yl)amino)pyridin-2-yl)acetamide | $^{1}$H NMR (400 MHz, DMSO-$d_6$) δ 11.41 (s, 1H), 10.44 (s, 1H), 9.16 (s, 1H), 8.64 (s, 1H), 7.95 (s, 1H), 7.13 (s, 1H), 6.93 (d, J = 2.8 Hz, 1H), 6.77 (d, J = 2.8 Hz, 1H), 4.99 (t, 1H), 4.36-4.28 (m, 2H), 4.30-4.20 (m, 2H), 3.80-3.70 (m, 2H), 3.46 (s, 3H), 2.11 (s, 3H), 1.50 (t, J = 7.3 Hz, 3H). MS (ESI) m/e $[M + 1]^+$ 461. |
| M20 | 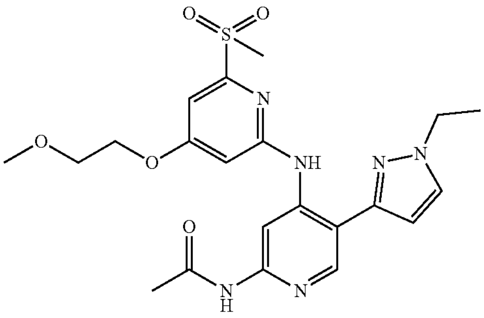 [SMILES: CCn1ccc(-c2cnc(NC(C)=O)cc2Nc2cc(OCCOC)cc(S(C)(=O)=O)n2)n1] | N-(5-(1-ethyl-1H-pyrazol-3-yl)-4-((4-(2-methoxyethoxy)-6-(methylsulfonyl)pyridin-2-yl)amino)pyridin-2-yl)acetamide | $^{1}$H NMR (400 MHz, DMSO-$d_6$) δ 11.46 (s, 1H), 10.60 (s, 1H), 9.10 (s, 1H), 8.64 (s, 1H), 7.96 (d, J = 2.2 Hz, 1H), 7.16 (s, 1H), 6.93 (s, 1H), 6.81 (d, J = 2.2 Hz, 1H), 4.37-4.31 (m, 4H), 3.75-3.71 (m, 2H), 3.45 (s, 3H), 3.32 (s, 3H), 2.12 (s, 3H), 1.50 (t, J = 7.2 Hz, 3H). MS (ESI) m/e $[M + 1]^+$ 475. |
| M21 | 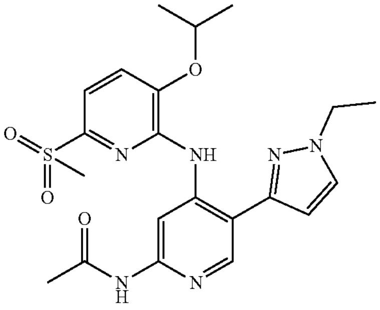 [SMILES: CCn1ccc(-c2cnc(NC(C)=O)cc2Nc2nc(S(C)(=O)=O)ccc2OC(C)C)n1] | N-(5-(1-ethyl-1H-pyrazol-3-yl)-4-((3-isopropoxy-6-(methylsulfonyl)pyridin-2-yl)amino)pyridin-2-yl)acetamide | $^{1}$H NMR (400 MHz, DMSO-$d_6$) δ 10.97 (s, 1H), 10.43 (s, 1H), 9.24 (s, 1H), 8.63 (s, 1H), 7.95 (d, J = 8.4 Hz, 1H), 7.60 (d, J = 8.4 Hz, 1H), 6.90 (d, J = 2.3 Hz, 1H), 6.70 (d, J = 2.3 Hz, 1H), 4.99-4.86 (m, 1H), 4.39-4.23 (m, 2H), 3.39 (s, 3H), 2.10 (s, 3H), 1.49-1.45 (m, 6H), 1.45-1.40 (m, 3H). MS (ESI) m/e $[M + 1]^+$ 459. |
| M22 | 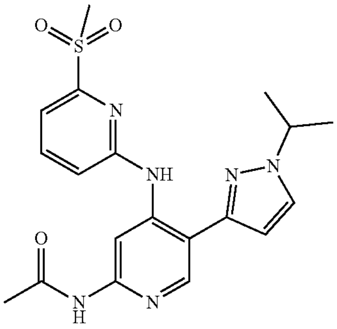 [SMILES: CC(=O)Nc1cc(Nc2cccc(S(C)(=O)=O)n2)c(-c2ccn(C(C)C)n2)cn1] | N-(5-(1-isopropyl-1H-pyrazol-3-yl)-4-((6-(methylsulfonyl)pyridin-2-yl)amino)pyridin-2-yl)acetamide | $^{1}$H NMR (400 MHz, DMSO-$d_6$) δ 11.65 (s, 1H), 10.46 (s, 1H), 9.26 (s, 1H), 8.68 (s, 1H), 8.04-7.99 (m, 2H), 7.58 (d, J = 7.0 Hz, 1H), 7.27 (d, J = 8.3 Hz, 1H), 6.95 (s, 1H), 4.72-4.69 (m, 1H), 3.49 (s, 3H), 2.12 (s, 3H), 1.54 (d, J = 6.6 Hz, 6H). MS (ESI) m/e $[M + 1]^+$ 415. |

-continued

| Example | Compound | Chemical Name | $^1$H NMR and LC/MS m/z (M + 1) |
|---|---|---|---|
| M23 | 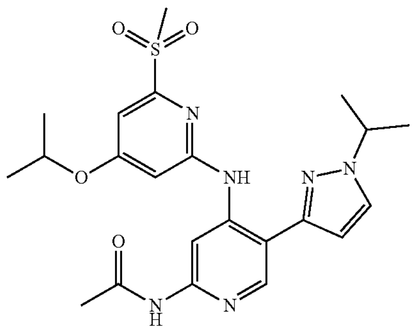 [SMILES: CC(=O)Nc1cc(Nc2cc(OC(C)C)cc(S(C)(=O)=O)n2)c(-c2ccn(C(C)C)n2)cn1] | N-(4-((4-isopropoxy-6-(methylsulfonyl)pyridin-2-yl)amino)-5-(1-isopropyl-1H-pyrazol-3-yl)pyridin-2-yl)acetamide | $^1$H NMR (400 MHz, DMSO-$d_6$) δ 11.52 (s, 1H), 10.49 (s, 1H), 9.13 (s, 1H), 8.65 (s, 1H), 7.98 (d, J = 2.3 Hz, 1H), 7.07 (s, 1H), 6.93 (d, J = 2.3 Hz, 1H), 6.68 (s, 1H), 4.89-4.82 (m, 1H), 4.69-4.62 (m, 1H), 3.46 (s, 3H), 2.11 (s, 3H), 1.54 (d, J = 6.6 Hz, 6H), 1.35 (d, J = 5.8 Hz, 6H). MS (ESI) m/e [M + 1]$^+$ 473. |
| M24 | 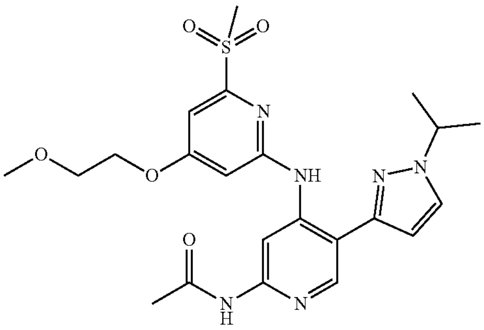 [SMILES: COCCOc1cc(Nc2cc(NC(C)=O)ncc2-c2ccn(C(C)C)n2)nc(S(C)(=O)=O)c1] | N-(5-(1-isopropyl-1H-pyrazol-3-yl)-4-((4-(2-methoxyethoxy)-6-(methylsulfonyl)pyridin-2-yl)amino)pyridin-2-yl)acetamide | $^1$H NMR (400 MHz, DMSO-$d_6$) δ 11.49 (s, 1H), 10.48 (s, 1H), 9.12 (s, 1H), 8.65 (s, 1H), 7.99 (d, J = 2.5 Hz, 1H), 7.14 (s, 1H), 6.94 (d, J = 2.5 Hz, 1H), 6.75 (s, 1H), 4.75-4.70 (m, 1H), 4.38-4.33 (m, 2H), 3.75-3.70 (m, 2H), 3.45 (s, 3H), 3.32 (s, 3H), 2.11 (s, 3H), 1.54 (d, J = 6.5 Hz, 6H). MS (ESI) m/e [M + H]$^+$ 489. |
| M25 | 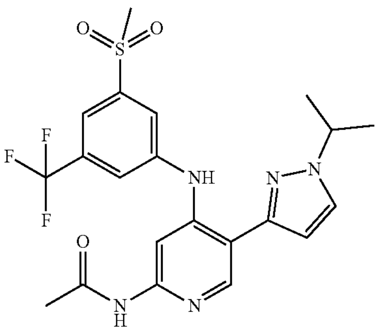 [SMILES: CC(=O)Nc1cc(Nc2cc(C(F)(F)F)cc(S(C)(=O)=O)c2)c(-c2ccn(C(C)C)n2)cn1] | N-(5-(1-isopropyl-1H-pyrazol-3-yl)-4-((3-(methylsulfonyl)-5-(trifluoromethyl)phenyl)amino)pyridin-2-yl)acetamide | $^1$H NMR (400 MHz, DMSO-$d_6$) δ 10.58 (s, 1H), 10.52 (s, 1H), 8.63 (s, 1H), 8.23 (s, 1H), 8.06 (s, 1H), 7.95 (s, 1H), 7.90 (d, J = 2.5 Hz, 1H), 7.81 (s, 1H), 6.88 (d, J = 2.5 Hz, 1H), 4.65-4.61 (m, 1H), 3.39 (s, 3H), 2.08 (s, 3H), 1.48 (d, J = 6.5 Hz, 6H). MS (ESI) m/e [M + 1]$^+$ 482. |
| M26 | 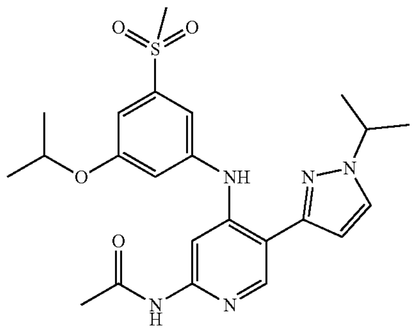 [SMILES: CC(=O)Nc1cc(Nc2cc(OC(C)C)cc(S(C)(=O)=O)c2)c(-c2ccn(C(C)C)n2)cn1] | N-(4-((3-isopropoxy-5-(methylsulfonyl)phenyl)amino)-5-(1-isopropyl-1H-pyrazol-3-yl)pyridin-2-yl)acetamide | $^1$H NMR (400 MHz, DMSO-$d_6$) δ 10.53 (s, 1H), 10.48 (s, 1H), 8.58 (s, 1H), 8.13 (s, 1H), 7.95 (d, J = 2.5 Hz, 1H), 7.39 (s, 1H), 7.14 (s, 1H), 7.10 (s, 1H), 6.89 (d, J = 2.5 Hz, 1H), 4.78-4.75 (m, 1H), 4.65-4.61 (m, 1H), 3.29 (s, 3H), 2.08 (s, 3H), 1.49 (d, J = 6.6 Hz, 6H), 1.32 (d, J = 5.9 Hz, 6H). MS (ESI) m/e [M + 1]$^+$ 473. |

-continued

| Example | Compound | Chemical Name | $^1$H NMR and LC/MS m/z (M + 1) |
|---|---|---|---|
| M27 | 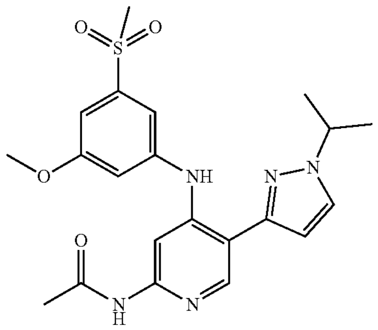 [SMILES: COc1cc(Nc2cc(NC(C)=O)ncc2-c2ccn(C(C)C)n2)cc(S(C)(=O)=O)c1] | N-(5-(1-isopropyl-1H-pyrazol-3-yl)-4-((3-methoxy-5-(methylsulfonyl)phenyl)amino)pyridin-2-yl)acetamide | $^1$H NMR (400 MHz, DMSO-$d_6$) δ 10.58 (s, 1H), 10.49 (s, 1H), 8.58 (s, 1H), 8.16 (s, 1H), 7.95 (d, J = 2.2 Hz, 1H), 7.39 (s, 1H), 7.23 (s, 1H), 7.14 (s, 1H), 6.89 (d, J = 2.2 Hz, 1H), 4.65-4.62 (m, 1H), 3.89 (s, 3H), 3.29 (s, 3H), 2.08 (s, 3H), 1.49 (d, J = 6.6 Hz, 6H). MS (ESI) m/e $[M + 1]^+$ 444. |
| M28 | 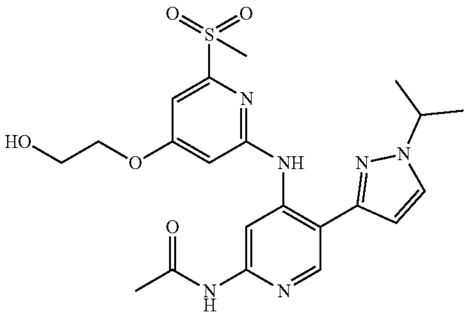 [SMILES: CC(=O)Nc1cc(Nc2cc(OCCO)cc(S(C)(=O)=O)n2)c(-c2ccn(C(C)C)n2)cn1] | N-(4-((4-(2-hydroxyethoxy)-6-(methylsulfonyl)pyridin-2-yl)amino)-5-(1-isopropyl-1H-pyrazol-3-yl)pyridin-2-yl)acetamide | $^1$H NMR (400 MHz, DMSO-$d_6$) δ 10.54 (s, 1H), 10.38 (s, 1H), 8.58 (s, 1H), 7.90-7.80 (m, 1H), 7.40 (s, 1H), 7.19 (s, 1H), 7.14 (s, 1H), 6.95-6.88 (m, 1H), 4.95 (s, 1H), 4.70-4.60 (m, 1H), 4.20-4.15 (m, 2H), 3.80-3.70 (m, 2H), 3.29 (s, 3H), 2.08 (s, 3H), 1.49 (d, J = 6.5 Hz, 6H). MS (ESI) m/e $[M + 1]^+$ 475. |
| M29 | 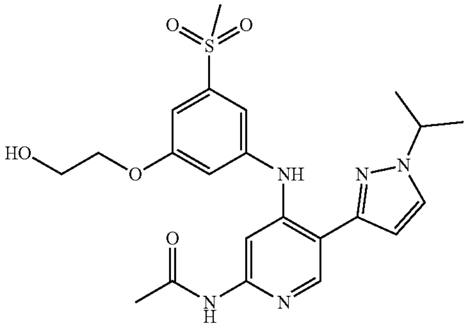 [SMILES: CC(=O)Nc1cc(Nc2cc(OCCO)cc(S(C)(=O)=O)c2)c(-c2ccn(C(C)C)n2)cn1] | N-(4-((3-(2-hydroxyethoxy)-5-(methylsulfonyl)phenyl)amino)-5-(1-isopropyl-1H-pyrazol-3-yl)pyridin-2-yl)acetamide | $^1$H NMR (400 MHz, DMSO-$d_6$) δ 10.54 (s, 1H), 10.38 (s, 1H), 8.58 (s, 1H), 8.25-8.20 (m, 1H), 7.95 (s, 1H), 7.40 (s, 1H), 7.19-7.14 (m, 2H), 6.89 (s, 1H), 5.02-4.83 (m, 1H), 4.65-4.63 (m, 1H), 4.13-4.10 (m, 2H), 3.76-3.74 (m, 2H), 3.29 (s, 3H), 2.08 (s, 3H), 1.49 (d, J = 6.5 Hz, 6H). MS (ESI) m/e $[M + 1]^+$ 474. |
| M30 | 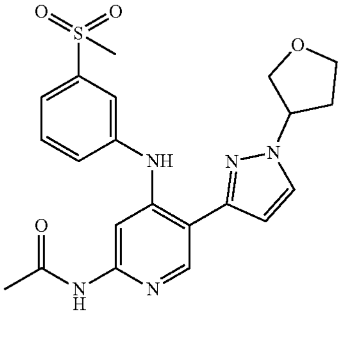 [SMILES: CC(=O)Nc1cc(Nc2cccc(S(C)(=O)=O)c2)c(-c2ccn(C3CCOC3)n2)cn1] | N-(4-((3-(methylsulfonyl)phenyl)amino)-5-(1-(tetrahydrofuran-3-yl)-1H-pyrazol-3-yl)pyridin-2-yl)acetamide | MS (ESI): m/e $[M + 1]^+$ 442. |

-continued

| Example | Compound | Chemical Name | $^1$H NMR and LC/MS m/z (M + 1) |
|---|---|---|---|
| M31 | 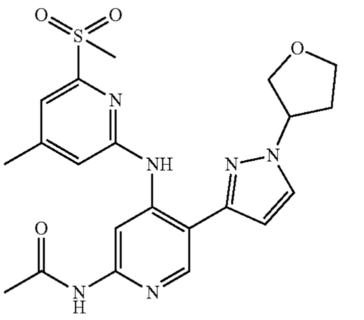 [SMILES: CC(=O)Nc1cc(Nc2cc(C)cc(S(C)(=O)=O)n2)c(-c2ccn(C3CCOC3)n2)cn1] | N-(4-((4-methyl-6-(methylsulfonyl)pyridin-2-yl)amino)-5-(1-(tetrahydrofuran-3-yl)-1H-pyrazol-3-yl)pyridin-2-yl)acetamide | MS (ESI) m/e $[M + 1]^+$ 457. |
| M32 | 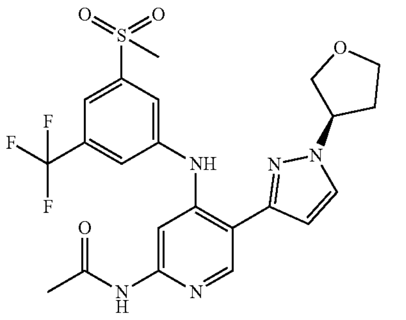 [SMILES: CC(=O)Nc1cc(Nc2cc(C(F)(F)F)cc(S(C)(=O)=O)c2)c(-c2ccn([C@@H]3CCOC3)n2)cn1] | (R)-N-(4-((3-(methylsulfonyl)-5-(trifluoromethyl)phenyl)amino)-5-(1-(tetrahydrofuran-3-yl)-1H-pyrazol-3-yl)pyridin-2-yl)acetamide | MS (ESI) m/e $[M + 1]^+$ 510. |
| M33 | 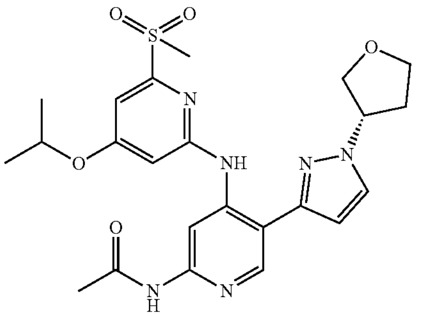 [SMILES: CC(=O)Nc1cc(Nc2cc(OC(C)C)cc(S(C)(=O)=O)n2)c(-c2ccn([C@H]3CCOC3)n2)cn1] | (S)-N-(4-((4-isopropoxy-6-(methylsulfonyl)pyridin-2-yl)amino)-5-(1-(tetrahydrofuran-3-yl)-1H-pyrazol-3-yl)pyridin-2-yl)acetamide | MS (ESI) m/e $[M + 1]^+$ 501. |
| M34 | 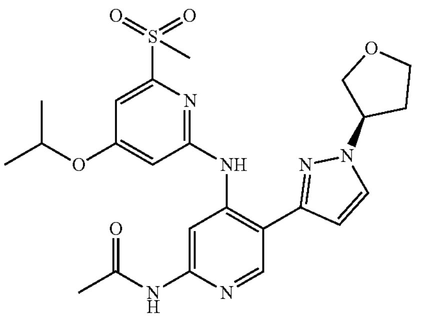 [SMILES: CC(=O)Nc1cc(Nc2cc(OC(C)C)cc(S(C)(=O)=O)n2)c(-c2ccn([C@@H]3CCOC3)n2)cn1] | (R)-N-(4-((4-isopropoxy-6-(methylsulfonyl)pyridin-2-yl)amino)-5-(1-(tetrahydrofuran-3-yl)-1H-pyrazol-3-yl)pyridin-2-yl)acetamide Molecular Weight: 501 | MS (ESI) m/e $[M + 1]^+$ 502. |

-continued

| Example | Compound | Chemical Name | $^1$H NMR and LC/MS m/z (M + 1) |
|---|---|---|---|
| M35 | 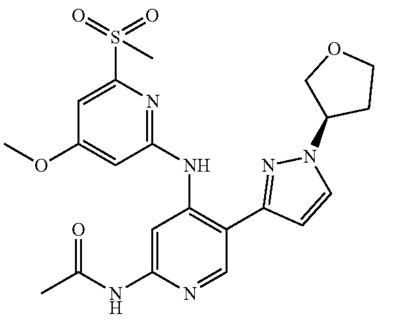 [SMILES: COc1cc(Nc2cc(NC(C)=O)ncc2-c2ccn([C@@H]3CCOC3)n2)nc(S(C)(=O)=O)c1] | (R)-N-(4-((4-methoxy-6-(methylsulfonyl)pyridin-2-yl)amino)-5-(1-(tetrahydrofuran-3-yl)-1H-pyrazol-3-yl)pyridin-2-yl)acetamide | MS (ESI) m/e $[M + 1]^+$ 473. |

Example N1: Synthesis of N-(5-(1,5-dimethyl-1H-pyrazol-3-yl)-4-((6-(methylsulfonyl)pyridin-2-yl)amino)pyridin-2-yl)acetamide

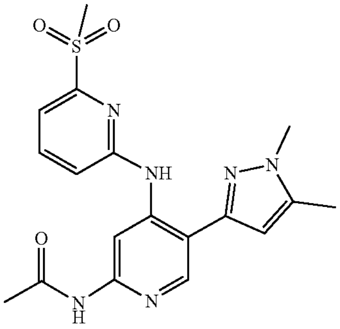 [SMILES: CC(=O)Nc1cc(Nc2cccc(S(C)(=O)=O)n2)c(-c2cc(C)n(C)n2)cn1]

Step 1: tert-butyl (2-chloro-5-(1,5-dimethyl-1H-pyrazol-3-yl)pyridin-4-yl)carbamate

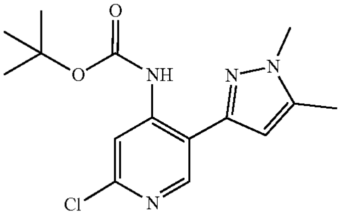 [SMILES: Cc1cc(-c2cnc(Cl)cc2NC(=O)OC(C)(C)C)nn1C]

A mixture of tert-butyl (5-bromo-2-chloropyridin-4-yl) carbamate (5.0 g, 16.3 mmol), 1,5-dimethyl-3-(4,4,5,5-tetramethyl-1,3,2-dioxaborolan-2-yl)-1H-pyrazole (3.58 g, 16.28 mmol), $Pd(PPh_3)_2Cl_2$ (595 mg, 0.81 mmol), $H_2O$ (1.0 mL) in dioxane (100 mL) was stirred at 100° C. for 4 h under nitrogen atmosphere. After cooled to room temperature, the mixture was filtrated and the filtration was concentrated under vacuum to give the residue, then purified by silica gel column chromatography using EA/PE (0-20%) to give tert-butyl (2-chloro-5-(1,5-dimethyl-1H-pyrazol-3-yl)pyridin-4-yl)carbamate (3.5 g, 67.3%). MS (ESI) m/e $[M+1]^+$ 323.

Step 2: tert-butyl (2-acetamido-5-(1,5-dimethyl-1H-pyrazol-3-yl)pyridin-4-yl)carbamate

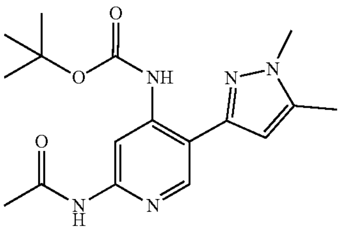 [SMILES: CC(=O)Nc1cc(NC(=O)OC(C)(C)C)c(-c2cc(C)n(C)n2)cn1]

A mixture of tert-butyl (2-chloro-5-(1,5-dimethyl-1H-pyrazol-3-yl)pyridin-4-yl)carbamate (3.0 g, 9.23 mmol), acetamide (1.08 g, 18.5 mmol), $Cs_2CO_3$ (6.0 g, 18.5 mmol), Xant-Phos (1.06 g, 1.85 mmol) and $Pd_2(dba)_3$ (875 mg, 0.0.92 mmol) in dioxane (100 mL) was stirred at 110° C. for 12 h under nitrogen atmosphere. After cooled to room temperature, the solvent was removed in vacuo and the residue was diluted with 20 mL of water. The resulting solution was extracted with EA (30 mL×3) and the combined organic layers were washed with 50 mL of brine, dried over anhydrous sodium sulfate. The solvent was removed in vacuo and the residue was purified by silica gel column chromatography using PE/EA (20-50%) to give tert-butyl (2-acetamido-5-(1,5-dimethyl-1H-pyrazol-3-yl)pyridin-4-yl)carbamate (2.2 g, 69.2%). MS (ESI) m/e $[M+1]^+$ 345.

Step 3: N-(4-amino-5-(1,5-dimethyl-1H-pyrazol-3-yl)pyridin-2-yl)acetamide

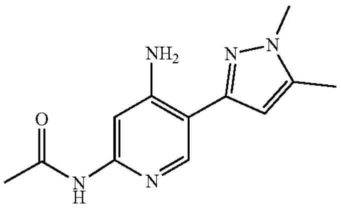 [SMILES: CC(=O)Nc1cc(N)c(-c2cc(C)n(C)n2)cn1]

A mixture of tert-butyl (2-acetamido-5-(1,5-dimethyl-1H-pyrazol-3-yl)pyridin-4-yl)carbamate (2.2 g, 6.38 mmol) in TFA (20 mL) and DCM (10 mL) was stirred at room temperature for 16 h. Upon completion of the reaction, the solvent was removed in vacuo and the residue diluted with water. $NaHCO_3$ (40 mL) was added to adjust the pH value to 9 and the resulting solution was extracted with EA (10 mL×3). The combined organic layers were dried over anhydrous $Na_2SO_4$ and concentrated in vacuo to give N-(4-amino-5-(1,5-dimethyl-1H-pyrazol-3-yl)pyridin-2-yl)acetamide (1.2 g, 76.9%). MS (ESI) m/e $[M+1]^+$ 246.

Step 4: N-(5-(1,5-dimethyl-1H-pyrazol-3-yl)-4-((6-(methylsulfonyl)pyridin-2-yl)amino)pyridin-2-yl) acetamide

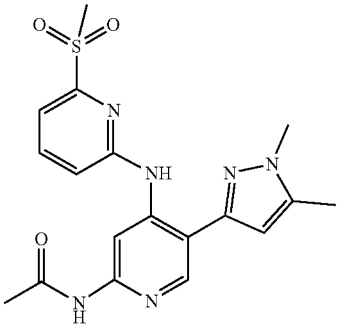 [SMILES: CC(=O)Nc1cc(Nc2cccc(S(C)(=O)=O)n2)c(-c2cc(C)n(C)n2)cn1]

A mixture of N-(4-amino-5-(1,5-dimethyl-1H-pyrazol-3-yl)pyridin-2-yl)acetamide (50 mg, 0.20 mmol), 2-bromo-6-(methylsulfonyl)pyridine (58 mg, 0.24 mmol), $Pd_2(dba)_3$ (19 mg, 0.020 mmol), BINAP (13 mg, 0.020 mmol) and $Cs_2CO_3$ (200 mg, 0.61 mmol) in dioxane (5 mL) was stirred for 16 h at 120° C. under nitrogen atmosphere. The mixture was allowed to cool down to room temperature. The resulting mixture was filtered. The filtrate was concentrated under reduced pressure. The residue was purified by combi-flash (MeOH/DCM=0-10%) to give the crude product. The crude product was suspended in acetonitrile to give N-(5-(1,5-dimethyl-NH-pyrazol-3-yl)-4-((6-(methylsulfonyl)pyridin-2-yl)amino)pyridin-2-yl)acetamide (7.66 mg, 9.6%) $^1H$ NMR (400 MHz, DMSO-$d_6$) δ 11.66 (s, 1H), 10.42 (s, 1H), 9.26 (s, 1H), 8.57 (s, 1H), 8.07-7.89 (i, 1H), 7.55 (d, J=7.2 Hz, 1H), 7.36 (d, J=8.4 Hz, 1H), 6.71 (s, 1H), 3.89 (s, 3H), 3.48 (s, 3H), 2.32 (s, 3H), 2.09 (s, 3H). MS (ESI) m/e $[M+1]^+$ 401.

The following Examples were prepared in a similar manner to the product Example N1:

| Example | Compound | Chemical Name | $^1H$ NMR and LC/MS m/z (M + 1) |
|---|---|---|---|
| N2 | 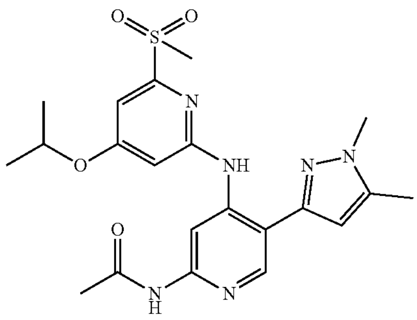 [SMILES: CC(=O)Nc1cc(Nc2cc(OC(C)C)cc(S(C)(=O)=O)n2)c(-c2cc(C)n(C)n2)cn1] | N-(5-(1,5-dimethyl-1H-pyrazol-3-yl)-4-((4-isopropoxy-6-(methylsulfonyl)pyridin-2-yl)amino)pyridin-2-yl)acetamide | $^1H$ NMR (400 MHz, DMSO-$d_6$) δ 11.39 (s, 1H), 10.43 (s, 1H), 9.15 (s, 1H), 8.56 (s, 1H), 7.08 (s, 1H), 6.77 (s, 1H), 6.71 (s, 1H), 4.95-4.90 (m, 1H), 3.90 (s, 3H), 3.46 (s, 3H), 2.33 (s, 3H), 2.10 (s, 3H), 1.34 (d, J = 5.7 Hz, 6H). MS (ESI) m/e $[M + 1]^+$ 459. |
| N3 | 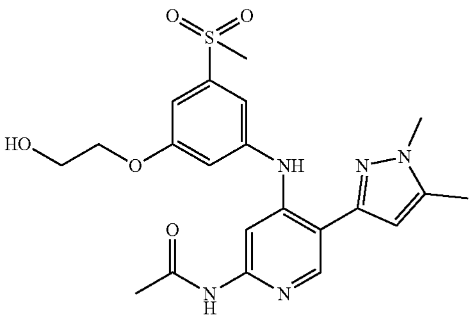 [SMILES: CC(=O)Nc1cc(Nc2cc(OCCO)cc(S(C)(=O)=O)c2)c(-c2cc(C)n(C)n2)cn1] | N-(5-(1,5-dimethyl-1H-pyrazol-3-yl)-4-((3-(2-hydroxyethoxy)-5-(methylsulfonyl)phenyl)amino)pyridin-2-yl)acetamide | $^1H$ NMR (400 MHz, DMSO-$d_6$) δ 10.51 (s, 1H), 10.39 (s, 1H), 8.49 (s, 1H), 8.10 (s, 1H), 7.41 (s, 1H), 7.22 (s, H), 7.14 (s, H), 6.66 (s, 1H), 4.95 (s, 1H), 4.20-4.10 (m, 2H), 3.84 (s, 3H), 3.80-3.70 (m, 2H), 3.30 (s, 3H), 2.32 (s, 3H), 2.07 (s, 3H). MS (ESI) m/e $[M + 1]^+$ 460. |

-continued

| Example | Compound | Chemical Name | $^1$H NMR and LC/MS m/z (M + 1) |
|---|---|---|---|
| N4 | 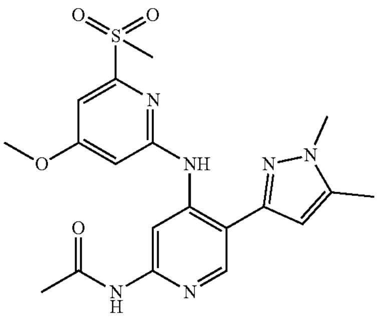 | N-(5-(1,5-dimethyl-1H-pyrazol-3-yl)-4-((4-methoxy-6-(methylsulfonyl)pyridin--2-yl)amino)pyridin-2-yl)acetamide | $^1$H NMR (400 MHz, DMSO-$d_6$) δ 11.49 (s, 1H), 10.46 (s, 1H), 9.22 (s, 1H), 8.61 (s, 1H), 7.18 (s, 1H), 6.85 (s, 1H), 6.76 (s, 1H), 4.02 (s, 3H), 3.96 (s, 3H), 3.52 (s, 3H), 2.39 (s, 3H), 2.16 (s, 3H). MS (ESI) m/e [M + 1]$^+$ 431. |
| N5 | 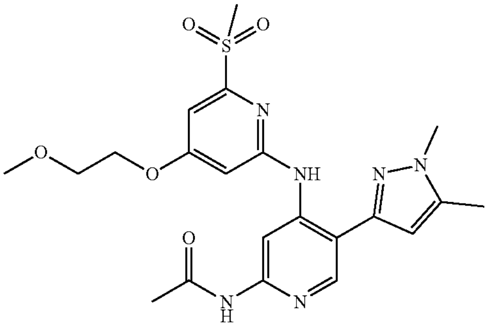 | N-(5-(1,5-dimethyl-1H-pyrazol-3-yl)-4-((4-(2-methoxyethoxy)-6-(methylsulfonyl)pyridin-2-yl)amino)pyridin-2-yl)acetamide | $^1$H NMR (400 MHz, DMSO-$d_6$) δ 11.48 (s, 1H), 10.46 (s, 1H), 9.23 (s, 1H), 8.61 (s, 1H), 7.19 (s, 1H), 6.86 (s, 1H), 6.76 (s, 1H), 4.45-4.40 (m, 2H), 3.97 (s, 3H), 3.80-3.75 (m, 2H), 3.63 (s, 3H), 3.52 (s, 3H), 2.39 (s, 3H), 2.16 (s, 3H). MS (ESI) m/e [M + 1]$^+$ 475. |
| N6 | 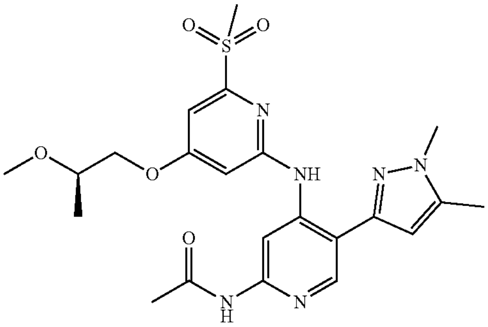 | (R)-N-(5-(1,5-dimethyl-1H-pyrazol-3-yl)-4-((4-(2-methoxypropoxy)-6-(methylsulfonyl)pyridin-2-yl)amino)pyridin-2-yl)acetamide | $^1$H NMR (400 MHz, DMSO-$d_6$) δ 11.40 (s, 1H), 10.42 (s, 1H), 9.17 (s, 1H), 8.56 (s, 1H), 7.14 (s, 1H), 6.83 (s, 1H), 6.71 (s, 1H), 4.27-4.13 (m, 2H), 3.91 (s, 3H), 3.72-3.71 (m, 1H), 3.46 (s, 3H), 3.34 (s, 3H), 2.34 (s, 3H), 2.10 (s, 3H), 1.20 (d, J = 6.2 Hz, 3H). MS (ESI) m/e [M + 1]$^+$ 489. |
| N7 | 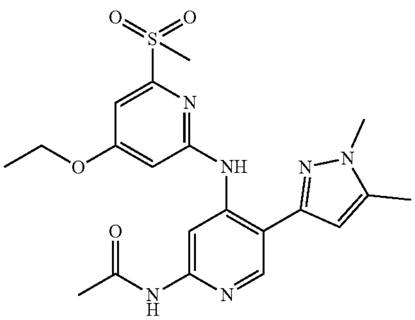 [SMILES: CCOc1cc(Nc2cc(NC(C)=O)ncc2-c2cc(C)n(C)n2)nc(S(C)(=O)=O)c1] | N-(5-(1,5-dimethyl-1H-pyrazol-3-yl)-4-((4-ethoxy-6-(methylsulfonyl)pyridin-2-yl)amino)pyridin-2-yl)acetamide | $^1$H NMR (400 MHz, DMSO-$d_6$) δ 11.41 (s, 1H), 10.39 (s, 1H), 9.16 (s, 1H), 8.55 (s, 1H), 7.15 (s, 1H), 6.77 (s, 1H), 6.70 (s, 1H), 4.27 (q, J = 6.9 Hz, 2H), 3.57 (s, 3H), 3.46 (s, 3H), 2.33 (s, 3H), 2.10 (s, 3H), 1.38 (t, J = 6.9 Hz, 3H). MS (ESI) m/e [M + 1]$^+$ 445. |

Example O1: Synthesis of N-(5-(1-methyl-5-morpholino-1H-pyrazol-3-yl)-4-((6-(methylsulfonyl)pyridin-2-yl)amino)pyridin-2-yl)acetamide

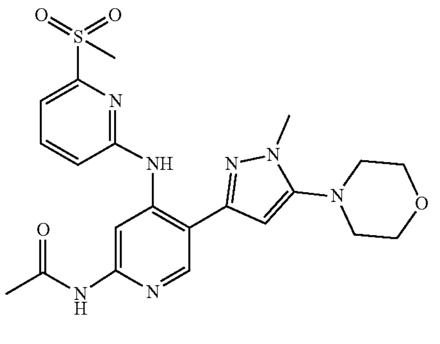 [SMILES: CC(=O)Nc1cc(Nc2cccc(S(C)(=O)=O)n2)c(-c2cc(N3CCOCC3)n(C)n2)cn1]

Step 1: ethyl 3,5-dibromo-1H-pyrazole-4-carboxylate

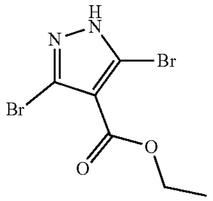

To a solution of ethyl 1H-pyrazole-4-carboxylate (10.0 g, 71.4 mmol) in EtOH (200 mL) was added NaOAc (41.0 g, 500 mmol) in $H_2O$ (300 mL) and then added $Br_2$ (45.6 g, 285 mmol) at 0° C. and the resulting mixture was stirred for 5 h at room temperature under nitrogen atmosphere. Upon completion of the reaction, the mixture was poured into water (100 mL) and extracted with EA (300 mL×2). The combined organic layer was washed with brine, dried over anhydrous $Na_2SO_4$, filtered and concentrated to give the residue, and purified by silica gel column chromatography (PE/EA=100/1 to 0/1) to give ethyl 3,5-dibromo-1H-pyrazole-4-carboxylate (10.0 g, 47% yield). MS(ESI) m/e $[M+1]^+$ 298.

Step 2: ethyl 3,5-dibromo-1-methyl-1H-pyrazole-4-carboxylate

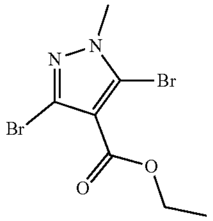

To a solution of ethyl 3,5-dibromo-1H-pyrazole-4-carboxylate (10.0 g, 33.6 mmol) in THF (100 mL) was added NaH (60% in mineral oil, 2.0 g, 50 mmol) at 0° C. and the resulting mixture was stirred at this temperature for 30 min, then Mel (5.7 g, 40.0 mmol) was added at 0° C. and the resulting mixture was stirred for 6 h at room temperature under nitrogen atmosphere. Upon completion of the reaction, the mixture was poured into water (50 mL) and the resulting mixture was extracted with EA (60 mL×2). The combined organic phase was washed with brine, dried over $Na_2SO_4$, concentrated under vacuum. The residue was purified by silica gel column chromatography (PE/EA=50/1 to 0/1) to give ethyl 3,5-dibromo-1-methyl-1H-pyrazole-4-carboxylate (5.1 g, 51%). MS(ESI) m/e $[M+1]^+$ 312.

Step 3: ethyl 3-bromo-1-methyl-5-morpholino-1H-pyrazole-4-carboxylate

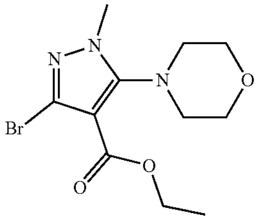 [SMILES: CCOC(=O)c1c(Br)nn(C)c1N1CCOCC1]

To a solution of ethyl 3,5-dibromo-1-methyl-1H-pyrazole-4-carboxylate (4.0 g, 12.8 mmol) in NMP (50 mL) were added morpholine (1.7 g, 19.2 mmol) and $K_2CO_3$ (4.4 g, 32.0 mmol), the resulting mixture was heated to 130° C. stirred for 25 h under nitrogen atmosphere. After cooled to room temperature, the solvent was removed and the residue was diluted with water (20 mL) then extracted with EA (30 mL×3), the combined organic layers were washed with brine (50 mL), dried over anhydrous sodium sulfate. The solvent was removed and the residue was purified by silica gel column chromatography (PE/EA=100/1 to 0/1) to give ethyl 3-bromo-1-methyl-5-morpholino-1H-pyrazole-4-carboxylate (2.5 g, 62%). $^1H$ NMR ($CDCl_3$) δ 4.40-4.35 (m, 2H), 3.79-3.75 (m, 4H), 3.73 (s, 3H), 3.15-3.10 (m, 4H), 1.40 (t, J=7.0 Hz, 3H). MS(ESI) m/e $[M+1]^+$ 318.

Step 4: 4-(3-bromo-1-methyl-1H-pyrazol-5-yl)morpholine

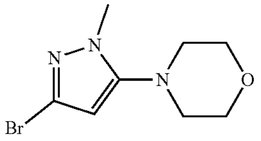

To a solution of ethyl 3-bromo-1-methyl-5-morpholino-1H-pyrazole-4-carboxylate (2.5 g, 7.9 mmol) in EtOH (20 mL) was added NaOH (1.0 g, 25.1 mmol) in water (15 mL) and the resulting mixture was stirred for 3 h at 70° C. under nitrogen atmosphere. Upon completion of the reaction, the reaction mixture was cooled down to 0° C. and $H_2SO_4$ (6.2 g, 62.8 mmol) was added, then the mixture was stirred for another 5 h at 70° C. under nitrogen atmosphere. After cooled to room temperature, the mixture was poured into water (10 mL) and sat $Na_2CO_3$ water solution was added to adjust the pH value to 8, the resulting mixture was extracted with EA (30 mL×2). The combined organic layer was washed with brine, dried over $Na_2SO_4$, concentrated under vacuum. The residue was purified by silica gel column chromatography (PE/EA=50/1 to 0/1) to give 4-(3-bromo-1-methyl-1H-pyrazol-5-yl)morpholine (1.2 mg, 62%). MS(ESI) m/e $[M+1]^+$ 246.

Step 5: (1-methyl-5-morpholino-1H-pyrazol-3-yl)boronic acid

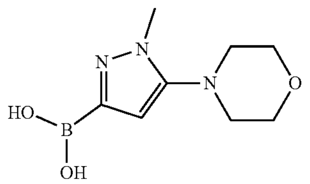

To a solution of 4-(3-bromo-1-methyl-1H-pyrazol-5-yl) morpholine (1.1 g, 4.47 mmol) in 1,4-dioxane (10 mL) was added $Pin_2B_2$ (1.7 g, 6.7 mmol), $Pd(dppf)Cl_2 \cdot CH_2Cl_2$ (365 mg, 450 umol) and AcOK (1.7 g, 17.9 mmol), the resulting mixture was heated up to 100° C. and stirred at this temperature for 5 h. After cooled to room temperature, the solvent was removed in vacuo and the residue was diluted with 20 mL of water. The resulting solution was extracted with 3×50 mL of EA and the combined organic layers were washed with 50 mL of brine, dried over anhydrous sodium sulfate. The solvent was removed in vacuo to give the crude product (1-methyl-5-morpholino-1H-pyrazol-3-yl)boronic acid and used directly for next step without purification. Ms (ESI) m/e $[M+1]^+$ 212.

Step 6: tert-butyl (2-chloro-5-(1-methyl-5-morpholino-1H-pyrazol-3-yl)pyridin-4-yl)carbamate

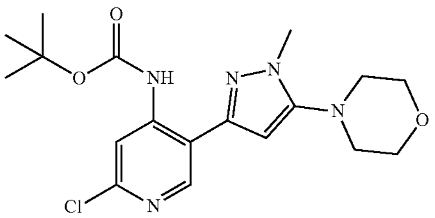 [SMILES: Cn1nc(-c2cnc(Cl)cc2NC(=O)OC(C)(C)C)cc1N1CCOCC1]

To a solution of tert-butyl (5-bromo-2-chloropyridin-4-yl)carbamate (1.5 g, 4.9 mmol) in 1,4-dioxane (10 mL) were added (1-methyl-5-morpholino-1H-pyrazol-3-yl)boronic acid (1.0 g, 4.9 mmol), $Pd(dppf)Cl_2$ (358.0 mg, 490 umol) and $K_3PO_4$ (4.1 g, 19.5 mmol), the resulting mixture was heated up to 100° C. and stirred for 12 h at this temperature under nitrogen atmosphere. After cooled to room temperature, the solvent was removed in vacuo and the residue was diluted with 20 mL of water. The resulting solution was extracted with 3×30 mL of EA and the combined organic layers were washed with 50 mL of brine, dried over anhydrous sodium sulfate. The solvent was removed in vacuo and the residue was purified by silica gel column chromatography (PE/EA=100/1 to 0/1) to give tert-butyl (2-chloro-5-(1-methyl-5-morpholino-1H-pyrazol-3-yl)pyridin-4-yl)carbamate (1.0 g, 52%). $^1H$ NMR ($CDCl_3$) δ 10.95 (s, 1H) 8.46 (s, 1H) 8.38 (s, 1H) 6.19 (s, 1H) 3.89-3.85 (m, 4H) 3.81 (s, 3H) 3.02-2.96 (m, 4H) 1.56 (s, 9H). MS(ESI) m/e $[M+1]^+$ 394.

Step 7: tert-butyl (2-acetamido-5-(1-methyl-5-morpholino-1H-pyrazol-3-yl)pyridin-4-yl)carbamate

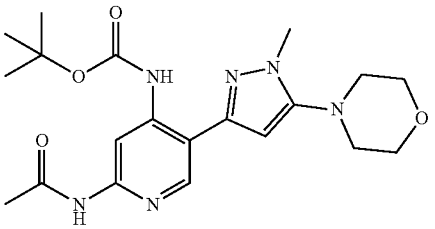 [SMILES: CC(=O)Nc1cc(NC(=O)OC(C)(C)C)c(-c2cc(N3CCOCC3)n(C)n2)cn1]

To a solution of tert-butyl (2-chloro-5-(1-methyl-5-morpholino-1H-pyrazol-3-yl)pyridin-4-yl)carbamate (1.0 g, 2.5 mmol) in 1,4-dioxane (30 mL) was added acetamide (450.0 mg, 7.6 mmol), $Pd_2(dba)_3$ (228.0 mg, 250.0 umol), Xantphos (144.0 mg, 250.0 umol) and $Cs_2CO_3$ (2.5 g, 7.6 mmol). The resulting mixture was heated up to 110° C. and stirred for 10 h at this temperature under nitrogen atmosphere. After cooled to room temperature, the solvent was removed in vacuo and the residue was diluted with 20 mL of water. The resulting solution was extracted with 3×20 mL of EA and the combined organic layers were washed with 50 mL of brine, dried over anhydrous sodium sulfate. The solvent was removed in vacuo and the residue was purified by silica gel column chromatography (PE/EA=100/1 to 0/1) to give tert-butyl (2-acetamido-5-(1-methyl-5-morpholino-1H-pyrazol-3-yl)pyridin-4-yl)carbamate (750 mg, 70% yield). MS(ESI) m/e $[M+1]^+$ 417.

Step 8: N-(4-amino-5-(1-methyl-5-morpholino-1H-pyrazol-3-yl)pyridin-2-yl)acetamide

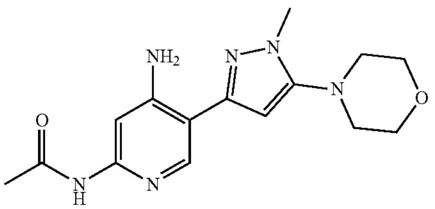

To a solution of tert-butyl (2-acetamido-5-(1-methyl-5-morpholino-1H-pyrazol-3-yl)pyridin-4-yl)carbamate (750 mg, 1.8 mmol) in DCM (2 mL) was added TFA (2 mL) and the resulting mixture was stirred at 40° C. for 5 h. After cooled to room temperature, the solvent was removed in vacuo and the residue was diluted with 20 mL of water. Then aqueous $Na_2CO_3$ was added to adjust the pH value to 8 and the resulting mixture was extracted with EA (10 mL×3). The combined organic layer was washed with brine (5 mL), dried over $Na_2SO_4$, filtered and concentrated under vacuum. The residue was purified by silica gel column chromatography (PE:EA=100/1 to 0/1) to give N-(4-amino-5-(1-methyl-5-morpholino-1H-pyrazol-3-yl)pyridin-2-yl)acetamide (480 mg, 80% yield). $^1H$ NMR (DMSO-$d_6$) δ 10.06 (s, 1H), 8.25 (s, 1H), 7.45 (s, 1H), 7.13 (s, 2H), 6.38 (s, 1H), 3.78-3.73 (m, 4H), 3.68 (s, 3H), 2.95-2.90 (m, 4H), 2.04 (s, 3H). MS(ESI) m/e $[M+1]^+$ 317.

Step 9: N-(5-(1-methyl-5-morpholino-1H-pyrazol-3-yl)-4-((6-(methylsulfonyl)pyridin-2-yl)amino)pyridin-2-yl)acetamide

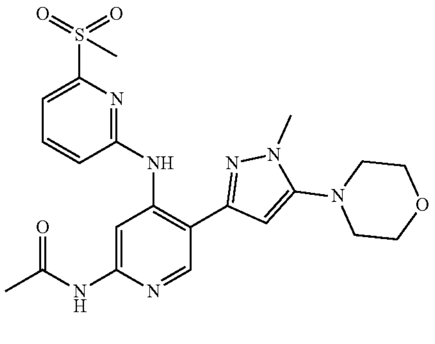 [SMILES: CC(=O)Nc1cc(Nc2cccc(S(C)(=O)=O)n2)c(-c2cc(N3CCOCC3)n(C)n2)cn1]

To a mixture of N-(4-amino-5-(1-methyl-5-morpholino-1H-pyrazol-3-yl)pyridin-2-yl)acetamide (100 mg, 0.32 mmol), 2-bromo-6-(methylsulfonyl)pyridine (90 mg, 0.38 mmol), $Pd_2dba_3$ (30 mg, 0.032 mmol), BINAP (40 mg, 0.064 mmol) and $Cs_2CO_3$ (205 mg, 0.64 mmol) in dioxane (10 mL) was stirred at 100° C. for 4 h. The mixture was filtrated and the filtrate as concentrated to give the residue and purified by Prep-TLC (MeOH/DCM=1:15) to afford N-(5-(1-methyl-5-morpholino-0H-pyrazol-3-yl)-4-((6-(methylsulfonyl)pyri dine-2-yl)amino)pyridin-2-yl)acetamide (75 mg, 52.8% yield). $^1H$ NMR (400 MHz, DMSO-$d_6$) δ 11.71 (s, HH), 10.47 (s, 1H), 9.28 (s, 1H), 863 (s, 1H), 8.05-8.001 (m, 1H), 7.57 (d, J=7.5 Hz, 1H), 7.36 (d, J=8.6 Hz, 1H), 6.63 (s, 1H), 3.84 (s, 3H), 3.79-3.77 (m, 4H), 3.50 (s, 3H), 2.99-2.96 (m, 4H), 2.11 (s, 3H). MS (ESI) m/e $[M+1]^+$ 472.

The following Examples were prepared in a similar manner to the product Example O1:

| Example | Compound | Chemical Name | $^1H$ NMR and LC/MS m/z (M + 1) |
|---|---|---|---|
| O2 | 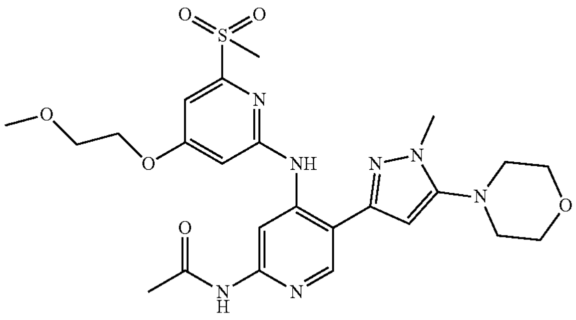 [SMILES: COCCOc1cc(Nc2cc(NC(C)=O)ncc2-c2cc(N3CCOCC3)n(C)n2)nc(S(C)(=O)=O)c1] | N-(4-((4-(2-methoxyethoxy)-6-(methylsulfonyl)pyridin-2-yl)amino)-5-(1-methyl-5-morpholino-1H-pyrazol-3-yl)pyridin-2-yl)acetamide | $^1H$ NMR (400 MHz, DMSO-$d_6$) δ 11.46 (s, 1H), 10.45 (s, 1H), 9.18 (s, 1H), 8.60 (s, 1H), 7.14 (s, 1H), 6.80 (s, 1H), 6.61 (s, 1H), 4.35-4.33 (m, 2H), 3.84 (s, 3H), 3.77-3.75 (m, 4H), 3.71-3.69 (m, 2H), 3.46 (s, 3H), 3.34 (s, 3H), 2.96-2.94 (m, 4H), 2.10 (s, 3H). MS (ESI) m/e $[M + 1]^+$ 546. |
| O3 | 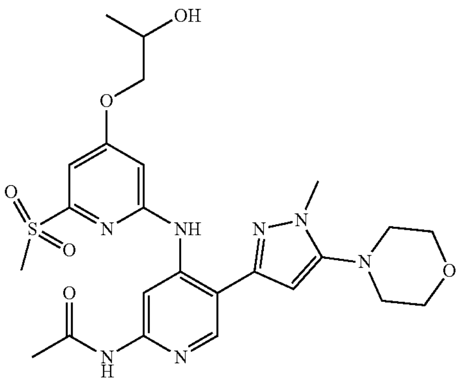 [SMILES: CC(=O)Nc1cc(Nc2cc(OCC(C)O)cc(S(C)(=O)=O)n2)c(-c2cc(N3CCOCC3)n(C)n2)cn1] | N-(4-((4-(2-hydroxypropoxy)-6-(methylsulfonyl)pyridin-2-yl)amino)-5-(1-methyl-5-morpholino-1H-pyrazol-3-yl)pyridin-2-yl)acetamide | $^1H$ NMR (400 MHz, DMSO-$d_6$) δ 11.43 (s, 1H), 10.46 (s, 1H), 9.15 (s, 1H), 8.58 (s, 1H), 7.12 (s, 1H), 6.78 (s, 1H), 6.59 (s, 1H), 4.06-4.00 (m, 3H), 3.85-3.81 (m, 3H), 3.76-3.74 (m, 4H), 3.44 (s, 3H), 2.95-2.93 (m, 4H), 2.08 (s, 3H), 1.26-1.14 (m, 2H). MS (ESI) m/e $[M + 1]^+$ 546. |

Example Q1: Synthesis of N-(5-(2,3-dihydro-[1,4]dioxino[2,3-b]pyridin-6-yl)-4-((4-isopropoxy-6-(methylsulfonyl)pyridine-2-yl)amino)pyridin-2-yl)acetamide

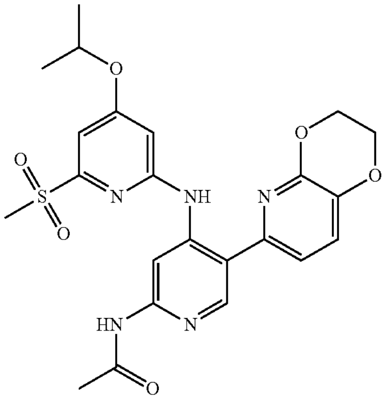 [SMILES: CC(=O)Nc1cc(Nc2cc(OC(C)C)cc(S(C)(=O)=O)n2)c(-c2ccc3c(n2)OCCO3)cn1]

Step 1: 2-chloro-5-(2,3-dihydro-[1,4]dioxino[2,3-b]pyridin-6-yl)pyridin-4-amine

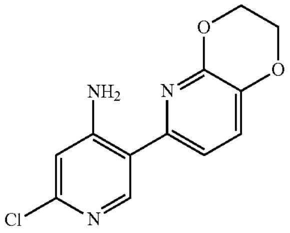 [SMILES: Nc1cc(Cl)ncc1-c1ccc2c(n1)OCCO2]

A mixture of 6-bromo-2,3-dihydro-[1,4]dioxino[2,3-b]pyridine (1 g, 4.63 mmol), 2-chloro-5-(4,4,5,5-tetramethyl-1,3,2-dioxaborolan-2-yl)pyridin-4-amine (1.29 g, 5n10 mmol), Pd(dppf)$Cl_2$ (338 mg, 0.46 mmol) and $K_2CO_3$ (958 mg, 6.95 mmol) in 1,4-dioxane (20 mL) and $H_2$ (2 mL) was charged with nitrogen and heated to 100° C. stirred for 2 h. The reaction was cooled to room temperature and diluted with EA, washed with brine, dried and concentrated. The residue was applied onto a silica gel column with MeOH/DCM (1:100) to afford 2-chloro-5-(2,3-dihydro-[1,4]dioxino[2,3-b]pyridin-6-yl)pyridin-4-amine (141 g). MS (ESI) m/e $[M+1]^+$ 264.

Step 2: N-(4-amino-5-(2,3-dihydro-[1,4]dioxino[2,3-b]pyridin-6-yl)pyridin-2-yl)acetamide

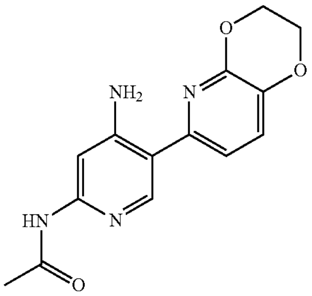 [SMILES: CC(=O)Nc1cc(N)c(-c2ccc3c(n2)OCCO3)cn1]

A mixture of 2-chloro-5-(2,3-dihydro-[1,4]dioxino[2,3-b]pyridin-6-yl)pyridin-4-amine (528 mg, 2 mmol), acetamide (710 mg, 12 mmol), $Pd_2dba_3$ (180 mg, 02 mmol), Xantphos (230 mg, 0.4 mmol) and $Cs_2CO_3$ (1.3 g, 4 mmol) in 1,4-dioxane (10 mL) was heated to 130° C. in a sealed tube stirring overnight under nitrogen atmosphere. The reaction was cooled to room temperature, filtered and the filtration was concentrated under vacuum. The residue was applied onto a silica gel column with DCM/MeOH (100:1) to afford crude N-(4-amino-5-(2,3-dihydro-[1,4]dioxino[2,3-b]pyridin-6-yl)pyridin-2-yl)acetamide (575 mg). MS (ESI) m/e $[M+1]^+$ 287.

Step 3: N-(5-(2,3-dihydro-[1,4]dioxino[2,3-b]pyridin-6-yl)-4-((4-isopropoxy-6-(methylsulfonyl)pyri din-2-yl)amino)pyridin-2-yl)acetamide

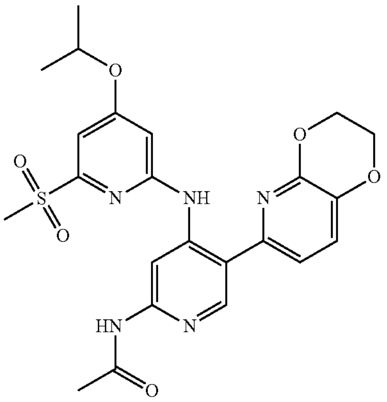 [SMILES: CC(=O)Nc1cc(Nc2cc(OC(C)C)cc(S(C)(=O)=O)n2)c(-c2ccc3c(n2)OCCO3)cn1]

A mixture of N-(4-amino-5-(2,3-dihydro-[1,4]dioxino[2,3-b]pyridin-6-yl)pyridin-2-yl)acetamide (50 mg, 0.17 mmol), 2-bromo-4-isopropoxy-6-(methylsulfonyl)pyridine (77 mg, 0.26 mmol), $Pd_2dba_3$ (16 mg, 0.017 mmol), BINAP (21 mg, 0.034 mmol) and $Cs_2CO_3$ (111 mg, 0.34 mmol) in 1,4-dioxane (6 mL) was heated to 130° C. in a sealed tube stirring for 5 h under nitrogen atmosphere. The reaction was cooled to room temperature, filtered and the filtration was concentrated under vacuum. The residue was applied onto Prep-TLC with DCM/MeOH (20:1) to afford N-(5-(2,3-dihydro-[1,4]dioxino[2,3-b]pyridin-6-yl)-4-((4-isopropoxy-6-(methyl sulfonyl)pyridin-2-yl)amino)pyridin-2-yl)acetamide (17 mg, 20%). $^1H$ NMR (400 MHz, DMSO-$d_6$) δ 11.83 (s, 1H), 10.49 (s, 1H), 9.03 (s, 1H), 8.61 (s, 1H), 7.58

(d, J=8.0 Hz, 1H), 7.48 (d, J=8.0 Hz, 1H), 7.08 (s, 1H), 6.59 (s, 1H), 4.85-4.80 (m, 1H), 4.55-4.52 (m, 2H), 4.36-4.32 (m, 2H), 3.42 (s, 3H), 2.11 (s, 3H), 1.34 (d, J=4.9 Hz, 6H). MS (ESI) m/e $[M+1]^+$ 500.

Example Q21: Synthesis of compound N-(5-(2,2-dimethyl-2,3-dihydro-[1,4]dioxino[2,3-b]pyridin-6-yl)-4-((4-methyl-6-(methylsulfonyl)pyridin-2-yl)amino)pyridin-2-yl)acetamide Method A

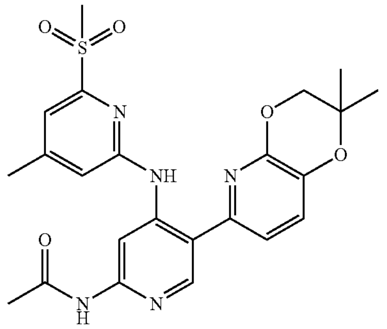

Step 1: 1-(2,6-dibromopyridin-3-yloxy)-2-methylpropan-2-ol

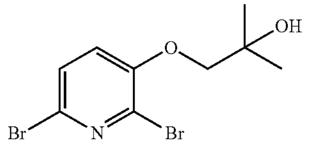

Into a 100-mL round-bottom flask, were placed 2,6-dibromopyridin-3-ol (2.00 g, 7.90 mmol), DMF (30 mL), $K_2CO_3$ (3.28 g, 23.73 mmol), 2,2-dimethyloxirane (0.68 g, 9.43 mmol). The resulting solution was stirred for 5 hr at 100° C. in an oil bath. After cooled to room temperature, the resulting solution was diluted with 50 mL of $H_2O$, extracted with 3×30 mL of ethyl acetate and the organic layers were combined and concentrated. The residue was purified by combi-flash (EtOAc/PE=1:4) to give the product (2.2 g, 85% yield). LCMS (ESI, m/z) $[M+1]^+$ 324.

Step 2: 6-bromo-2,2-dimethyl-2,3-dihydro-[1,4]dioxino[2,3-b]pyridine

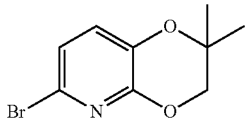

Into a 100-mL round-bottom flask, were placed 1-[(2,6-dibromopyridin-3-yl)oxy]-2-methylpropan-2-ol (2.00 g, 6.15 mmol), DMF (30 mL). This was followed by the addition of NaH (0.49 g, 60% in mineral oil, 12.30 mmol) in portions at 0° C. The resulting solution was stirred for 3 hr at 90° C. in an oil bath. After cooled to room temperature, the reaction was then quenched by the addition of 50 mL of $NH_4Cl$ (aq). The resulting solution was extracted with 3×30 mL of ethyl acetate and the organic layers were combined and concentrated. The residue was purified by combi-flash (EtOAc/PE=1:6) to give the product (1.06 g, 71% yield).

$^1H$ NMR (400 MHz, $CD_3Cl$) δ 7.06-7.02 (m, 2H), 4.08 (s, 2H), 1.38 (s, 6H). LCMS (ESI, m/z) $[M+1]^+$ 244, 246.

Step 3: 2-chloro-5-(2,2-dimethyl-2,3-dihydro-[1,4]dioxino[2,3-b]pyridin-6-yl)pyridin-4-amine

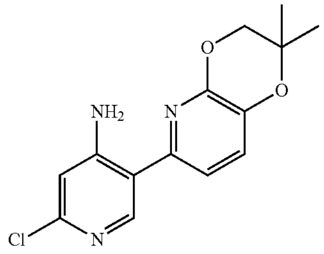 [SMILES: CC1(C)COc2nc(-c3cnc(Cl)cc3N)ccc2O1]

A solution of 2-chloro-5-(4,4,5,5-tetramethyl-1,3,2-dioxaborolan-2-yl)pyridin-4-amine (626.8 mg, 2.46 mmol), 6-bromo-2,2-dimethyl-2,3-dihydro-[1,4]dioxino[2,3-b]pyridine (500 mg, 2.05 mmol), Pd (dppf)$Cl_2$ (300 mg, 0.41 mmol), K3PO4 (869.2 mg, 4.1 mmol) in dioxane (8 mL) and $H_2O$ (2 mL) was stirred at 75° C. for 2 hours. The mixture was cooled to rt and extracted between EA and $H_2O$. The organic layer was concentrated. The crude product was purified by silica gel column chromatography (PE/EA=1:1) to give the desired product (440 mg, 73.57%). MS (ESI) m/e $[M+1]^+$ 292.

Step 4: N-(4-amino-5-(2,2-dimethyl-2,3-dihydro-[1,4]dioxino[2,3-b]pyridin-6-yl)pyridin-2-yl)acetamide

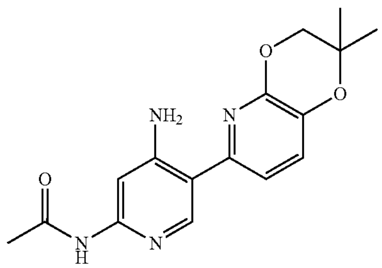 [SMILES: CC(=O)Nc1cc(N)c(-c2ccc3c(n2)OCC(C)(C)O3)cn1]

A solution of 2-chloro-5-(2,2-dimethyl-2,3-dihydro-[1,4]dioxino[2,3-b]pyridin-6-yl)pyridin-4-amine (440 mg, 1.51 mmol), acetamide (445.4 mg, 7.54 mmol), $Pd_2(dba)_3$ (276.6 mg, 0.3 mmol), Xant-phos (349.5 mg, 0.6 mmol) and $Cs_2CO_3$ (984.5 mg, 3 mmol) in dioxane (20 mL) was stirred at 130° C. for 5 hours. The mixture was cooled to r.t and filtered through celite. The filtrate was concentrated under reduced pressure. The crude product was purified by silica gel column chromatography (DCM/MeOH=20:1) to give the desired product (305 mg, 64.26%). MS (ESI) m/e $[M+1]^+$ 315.

Step 5: N-(5-(2,2-dimethyl-2,3-dihydro-[1,4]dioxino[2,3-b]pyridin-6-yl)-4-((4-methyl-6-(methylsulfonyl)pyridin-2-yl)amino)pyridin-2-yl)acetamide

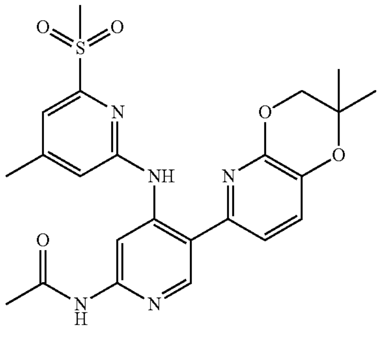

A solution of N-(4-amino-5-(2,2-dimethyl-2,3-dihydro-[1,4]dioxino[2,3-b]pyridin-6-yl)pyridin-2-yl)acetamide (50 mg, 0.16 mmol), 2-bromo-4-methyl-6-(methylsulfonyl)pyridine (48 mg, 0.19 mmol), $Pd_2(dba)_3$ (29.3 mg, 0.032 mmol), Xant-phos (37 mg, 0.064 mmol) and $Cs_2CO_3$ (104.3 mg, 0.32 mmol) in dioxane (3 mL) was stirred at 130° C. for 5 hours. The mixture was cooled to rt and the solid was removed by filtration. The filtrate was concentrated under reduced pressure. The crude product was purified by silica gel column chromatography (DCM/MeOH=15:1) to give the desired product (22.37 mg, 28.91%). $^1$H NMR (400 MHz, DMSO-$d_6$) δ 11.97 (s, 1H), 10.47 (s, 1H), 9.11 (s, 1H), 8.63 (s, 1H), 7.61 (d, J=8.3 Hz, 1H), 7.46-7.41 (m, 2H), 6.97 (s, 1H), 4.26 (s, 2H), 3.43 (s, 3H), 2.42 (s, 3H), 2.11 (s, 3H), 1.37 (s, 6H). MS (ESI) m/e $[M+1]^+$ 484.

Method B

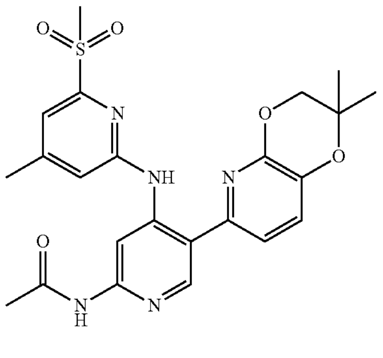

Step 1: 1-(2,6-dibromopyridin-3-yloxy)-2-methylpropan-2-ol

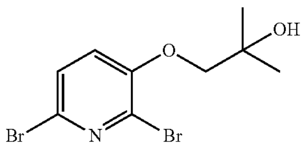

Into a 100-mL round-bottom flask, were placed 2,6-dibromopyridin-3-ol (2.00 g, 7.90 mmol), DMF (30 mL), $K_2CO_3$ (3.28 g, 23.73 mmol), 2,2-dimethyloxirane (0.68 g, 9.43 mmol). The resulting solution was stirred for 5 hr at 100° C. in an oil bath. After cooled to room temperature, the resulting solution was diluted with 50 mL of $H_2O$, extracted with 3×30 mL of ethyl acetate and the organic layers were combined and concentrated. The residue was purified by combi-flash (EtOAc/PE=1/4) to give the product (2.2 g, 85% yield). LCMS (ESI, m/z) $[M+1]^+$ 324.

Step 2: 6-bromo-3,3-dimethyl-2,3-dihydro-[1,4]dioxino[2,3-b]pyridine and 6-bromo-2,2-dimethyl-2,3-dihydro-[1,4]dioxino[2,3-b]pyridine

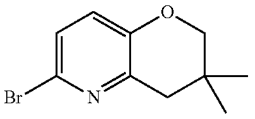

and

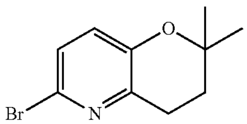

Into a 100-mL round-bottom flask purged and maintained with an inert atmosphere of nitrogen, were placed 1-[(2,6-dibromopyridin-3-yl)oxy]-2-methylpropan-2-ol (1.00 g, 3.07 mmol) and THF (15 mL). This was followed by the addition of NaH (186 mg, 4.58 mmol, 60% wt) in portions at 0° C. The resulting solution was stirred for 16 hr at 55° C. After cooled to room temperature, 20 mL of $NH_4Cl$ (aq) was added to quench the reaction and the resulting solution was extracted with 3×10 mL of ethyl acetate and the organic layers were combined and concentrated. The residue was purified by combi-flash (EtOAc/PE=0-35%) to give the product.

The mixture was separated by Chiral-Prep-HPLC with the following conditions, to obtain two resulted compounds: Column: CHIRAL ART Cellulose-SB, 3×25 cm, 5 um; Mobile Phase A: $CO_2$, Mobile Phase B: MeOH (0.1% 2M $NH_3$-MeOH); Flow rate: 60 mL/min; Gradient: 15% B; Column Temperature: 35° C.; Back Pressure: 100 bar; 220 nm. This resulted in 60 mg of 6-bromo-3,3-dimethyl-2,3-dihydro-[1,4]dioxino[2,3-b]pyridine ($RT_1$: 3.94 min) and 210 mg of 6-bromo-2,2-dimethyl-2,3-dihydro-[1,4]dioxino[2,3-b]pyridine ($RT_2$: 4.51 min).

6-Bromo-3,3-dimethyl-2,3-dihydro-[1,4]dioxino[2,3-b]pyridine: $^1$H NMR (300 MHz, $CD_3Cl$) 57.06 (d, J=8.0 Hz, 1H), 6.97 (d, J=8.0 Hz, 1H), 3.88 (s, 2H), 1.39 (s, 6H). $^1$H NMR (400 MHz, DMSO-$d_6$) δ 7.30 (d, J=8.0 Hz, 1H), 7.11 (d, J=8.0 Hz, 1H), 3.99 (s, 2H), 1.32 (s, 6H); LCMS (ESI, m/z): $[M+H]^+$ 244, 246.

6-bromo-2,2-dimethyl-2,3-dihydro-[1,4]dioxino[2,3-b]pyridine: $^1$H NMR (300 MHz, $CD_3Cl$) δ 7.04-7.03 (m, 2H), 4.08 (s, 2H), 1.39 (s, 6H). LCMS (ESI, m/z): $[M+H]^+$ 244, 246. And, the structure of the compound was further confirmed by single crystal structure determination.

Step 3: 2-chloro-5-(2,2-dimethyl-2,3-dihydro-[1,4]dioxino[2,3-b]pyridin-6-yl)pyridin-4-amine

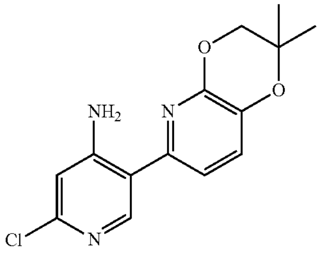 [SMILES: CC1(C)COc2nc(-c3cnc(Cl)cc3N)ccc2O1]

A solution of 2-chloro-5-(4,4,5,5-tetramethyl-1,3,2-dioxaborolan-2-yl)pyridin-4-amine (626.8 mg, 2.46 mmol), 6-bromo-2,2-dimethyl-2,3-dihydro-[1,4]dioxino[2,3-b]pyridine (500 mg, 2.05 mmol), Pd (dppf)$Cl_2$ (300 mg, 0.41 mmol), $K_3PO_4$ (869.2 mg, 4.1 mmol) in dioxane (8 mL) and $H_2O$ (2 mL) was stirred at 75° C. for 2 hr. The mixture was cooled to rt and extracted between EA and $H_2O$. The organic layer was concentrated. The crude product was purified by silica gel column chromatography (PE/EA=1/1) to give the desired product (440 mg, 73.57%). $^1H$ NMR (400 MHz, DMSO-$d_6$) δ 8.26 (s, 1H), 7.40 (d, J=8.2 Hz, 2H), 7.33 (d, J=12.4 Hz, 2H), 6.64 (s, 1H), 4.12 (s, 2H), 1.28 (s, 6H). MS (ESI) m/e $[M+1]^+$ 292.

Step 4: N-(4-amino-5-(2,2-dimethyl-2,3-dihydro-[1,4]dioxino[2,3-b]pyridin-6-yl)pyridin-2-yl)acetamide

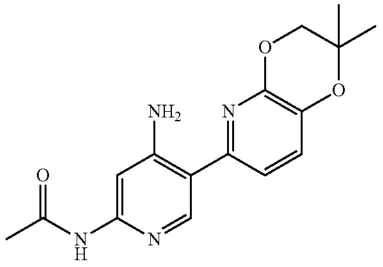 [SMILES: CC(=O)Nc1cc(N)c(-c2ccc3c(n2)OCC(C)(C)O3)cn1]

A solution of 2-chloro-5-(2,2-dimethyl-2,3-dihydro-[1,4]dioxino[2,3-b]pyridin-6-yl)pyridin-4-amine (440 mg, 1.51 mmol), acetamide (445.4 mg, 7.54 mmol), $Pd_2(dba)_3$ (276.6 mg, 0.3 mmol), Xant-phos (349.5 mg, 0.6 mmol) and $Cs_2CO_3$ (984.5 mg, 3 mmol) in dioxane (20 mL) was stirred at 130° C. for 5 hours. The mixture was cooled to r.t and filtered through celite. The filtrate was concentrated under reduced pressure. The crude product was purified by silica gel column chromatography (DCM/MeOH=20/1) to give the desired product (305 mg, 64.26%). $^1H$ NMR (400 MHz, DMSO-$d_6$) δ 10.07 (s, 1H), 8.26 (s, 1H), 7.48-7.35 (m, 2H), 7.33-7.17 (m, 3H), 4.11 (s, 2H), 2.01 (s, 3H), 1.28 (s, 6H). MS (ESI) m/e $[M+1]^+$ 315.

Step 5: N-(5-(2,2-dimethyl-2,3-dihydro-[1,4]dioxino[2,3-b]pyridin-6-yl)-4-((4-methyl-6-(methylsulfonyl)pyridin-2-yl)amino)pyridin-2-yl)acetamide

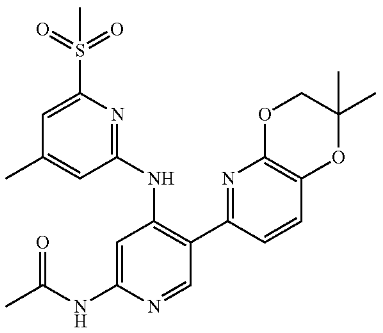

A solution of N-(4-amino-5-(2,2-dimethyl-2,3-dihydro-[1,4]dioxino[2,3-b]pyridin-6-yl)pyridin-2-yl)acetamide (50 mg, 0.16 mmol), 2-bromo-4-methyl-6-(methylsulfonyl)pyridine (48 mg, 0.19 mmol), $Pd_2(dba)_3$ (29.3 mg, 0.032 mmol), Xant-phos (37 mg, 0.064 mmol) and $Cs_2CO_3$ (104.3 mg, 0.32 mmol) in dioxane (3 mL) was stirred at 130° C. for 5 hours. The mixture was cooled to rt and the solid was removed by filtration. The filtrate was concentrated under reduced pressure. The crude product was purified by silica gel column chromatography (DCM/MeOH=15/1) to give the desired product (22.37 mg, 28.91%). $^1H$ NMR (400 MHz, DMSO-$d_6$) δ 11.97 (s, 1H), 10.47 (s, 1H), 9.11 (s, 1H), 8.63 (s, 1H), 7.61 (d, J=8.3 Hz, 1H), 7.46-7.41 (m, 2H), 6.97 (s, 1H), 4.26 (s, 2H), 3.43 (s, 3H), 2.42 (s, 3H), 2.11 (s, 3H), 1.37 (s, 6H). MS (ESI) m/e $[M+1]^+$ 484.

Example Q22: Synthesis of compound N-(5-(2,2-dimethyl-2,3-dihydro-[1,4]dioxino[2,3-b]pyridin-6-yl)-4-((6-(methylsulfonyl)-4-morpholinopyridin-2-yl)amino)pyridin-2-yl)acetamide

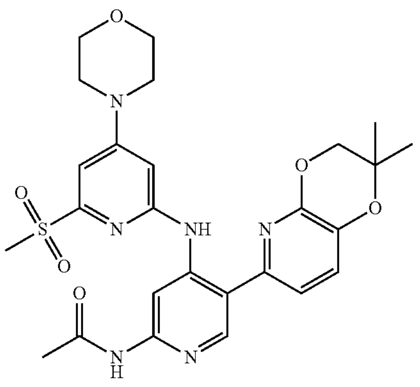

A solution of N-(4-amino-5-(2,2-dimethyl-2,3-dihydro-[1,4]dioxino[2,3-b]pyridin-6-yl)pyridin-2-yl)acetamide (600 mg, 2 mmol), 4-(2-bromo-6-(methylsulfonyl)pyridin-4-yl)morpholine (964 mg, 3 mmol), $Pd_2(dba)_3$ (366 mg, 0.4 mmol), Xantphos (463 mg, 0.8 mmol) and $Cs_2CO_3$ (1304 mg, 4 mmol) in dioxane (30 mL) was stirred at 130° C. for 5 hours. The mixture was cooled to r.t and the solid was filtered through celite. The filtrate was concentrated under reduced pressure. The crude product was purified by silica gel column chromatography (DCM/MeOH=15/1) to give the product (65.36 mg, 59%). $^1H$ NMR (400 MHz, DMSO-$d_6$) δ 11.39 (s, 1H), 10.44 (s, 1H), 8.87 (s, 1H), 8.56 (s, 1H), 7.55 (d, J=8.3 Hz, 1H), 7.42 (d, J=8.3 Hz, 1H), 7.10 (s, 1H), 6.52 (s, 1H), 4.24 (s, 2H), 3.77-3.68 (m, 4H), 3.41-3.36 (m, 4H), 3.35 (s, 3H), 2.09 (s, 3H), 1.36 (s, 6H). MS (ESI) m/e $[M+1]^+$ 555.

Example Q23: Synthesis of compound N-(5-(2,2-dimethyl-2,3-dihydro-[1,4]dioxino[2,3-b]pyridin-6-yl)-4-((6-(methylsulfonyl)-4-(tetrahydro-2H-pyran-4-yl)pyridin-2-yl)amino)pyridin-2-yl)acetamide

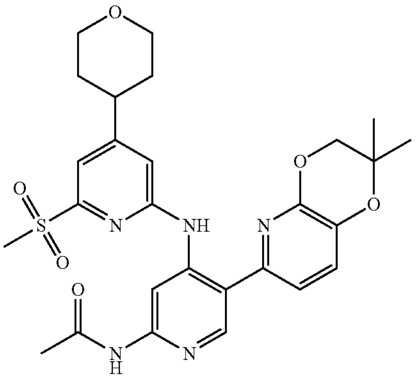

A solution of N-(4-amino-5-(2,2-dimethyl-2,3-dihydro-[1,4]dioxino[2,3-b]pyridin-6-yl)pyridin-2-yl)acetamide (60 mg, 0.2 mmol), 2-bromo-6-(methylsulfonyl)-4-(tetrahydro-2H-pyran-4-yl)pyridine (96 mg, 0.3 mmol), $Pd_2(dba)_3$ (36.6 mg, 0.04 mmol), Xantphos (46.3 mg, 0.08 mmol) and $Cs_2CO_3$ (130.4 mg, 0.4 mmol) in dioxane (3 mL) was stirred at 130° C. for 5 hr. The mixture was cooled to RT and the solid was removed by filtration. The filtrate was concentrated under reduced pressure. The crude product was purified by silica gel column chromatography (DCM/MeOH=15/1) to give the product (63.6 mg, 57%). $^1$H NMR (400 MHz, DMSO-$d_6$) δ 11.86 (s, 1H), 10.49 (s, 1H), 9.06 (s, 1H), 8.62 (s, 1H), 7.59 (d, J=8.5 Hz, 1H), 7.52-7.38 (m, 2H), 7.05 (s, 1H), 4.26 (s, 2H), 4.01-3.92 (m, 2H), 3.49-3.44 (m, 2H), 3.43 (s, 3H), 3.02-2.89 (m, 1H), 2.11 (s, 3H), 1.84-1.74 (m, 2H), 1.72-1.59 (m, 2H), 1.37 (s, 6H). MS (ESI) m/e [M+1]$^+$ 554.

Example Q24: Synthesis of compound N-(5-(2,2-dimethyl-2,3-dihydro-[1,4]dioxino[2,3-b]pyridin-6-yl)-4-((4-(methoxy-d3)-6-(methylsulfonyl)pyridin-2-yl)amino)pyridin-2-yl)acetamide

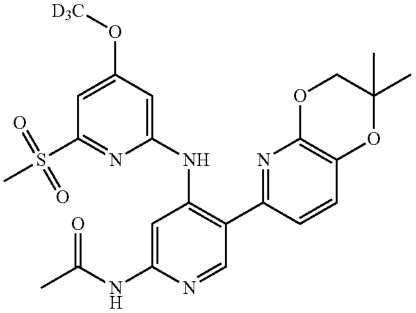

A solution of N-(4-amino-5-(2,2-dimethyl-2,3-dihydro-[1,4]dioxino[2,3-b]pyridin-6-yl)pyridin-2-yl)acetamide (60 mg, 0.2 mmol), 2-bromo-4-(methoxy-d3)-6-(methylsulfonyl)pyridine (80.7 mg, 0.3 mmol), $Pd_2(dba)_3$ (36.6 mg, 0.04 mmol), Xantphos (46.3 mg, 0.08 mmol) and $Cs_2CO_3$ (130.4 mg, 0.4 mmol) in dioxane (3 mL) was stirred at 130° C. for 5 hours. The mixture was cooled to RT and filtered through celite. The filtrate was concentrated under reduced pressure. The crude product was purified by silica gel column chromatography (DCM/MeOH=15/1) to give the product (26.04 mg, 26%). $^1$H NMR (400 MHz, DMSO-$d_6$) δ 11.76 (s, 1H), 10.49 (s, 1H), 8.99 (s, 1H), 8.61 (s, 1H), 7.58 (d, J=8.3 Hz, 1H), 7.43 (d, J=8.3 Hz, 1H), 7.12 (s, 1H), 6.68 (s, 1H), 4.25 (s, 2H), 3.41 (s, 3H), 2.11 (s, 3H), 1.36 (s, 6H). MS (ESI) m/e [M+1]$^+$ 503.

Example Q25: Synthesis of Compound N-(5-(2,2-dimethyl-2,3-dihydro-[1,4]dioxino[2,3-b]pyridin-6-yl)-4-((4-methoxy-6-(methylsulfonyl)pyridin-2-yl)amino)pyridin-2-yl)acetamide

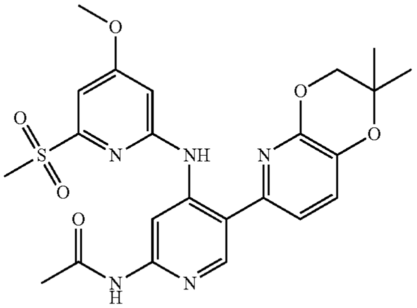

A solution of N-(4-amino-5-(2,2-dimethyl-2,3-dihydro-[1,4]dioxino[2,3-b]pyridin-6-yl)pyridin-2-yl)acetamide (60 mg, 0.2 mmol), 2-bromo-4-methoxy-6-(methylsulfonyl)pyridine (79.8 mg, 0.3 mmol), $Pd_2(dba)_3$ (36.6 mg, 0.04 mmol), Xant-phos (46.3 mg, 0.08 mmol) and $Cs_2CO_3$ (130.4 mg, 0.4 mmol) in dioxane (3 mL) was stirred at 130° C. for 5 hr. The mixture was cooled to rt and filtered through celite. The filtrate was concentrated under reduced pressure. The crude product was purified by silica gel column chromatography (DCM/MeOH=15/1) to give the product (25.21 mg, 25%). $^1$H NMR (400 MHz, DMSO-$d_6$) δ 11.77 (s, 1H), 10.49 (s, 1H), 8.99 (s, 1H), 8.61 (s, 1H), 7.58 (d, J=8.4 Hz, 1H), 7.43 (d, J=8.4 Hz, 1H), 7.12 (s, 1H), 6.69 (s, 1H), 4.25 (s, 2H), 3.93 (s, 3H), 3.41 (s, 3H), 2.11 (s, 3H), 1.36 (s, 6H). MS (ESI) m/e [M+1]$^+$ 500.

Example Q26: Synthesis of Compound N-(4-((3,4-dimethoxy-6-(methylsulfonyl)pyridin-2-yl)amino)-5-(2,2-dimethyl-2,3-dihydro-[1,4]dioxino[2,3-b]pyridin-6-yl)pyridin-2-yl)acetamide

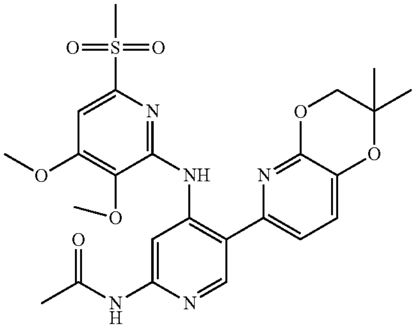

A solution of N-(4-amino-5-(2,2-dimethyl-2,3-dihydro-[1,4]dioxino[2,3-b]pyridin-6-yl)pyridin-2-yl)acetamide (60 mg, 0.2 mmol), 2-bromo-3,4-dimethoxy-6-(methylsulfonyl)pyridine (88.8 mg, 0.3 mmol), $Pd_2(dba)_3$ (36.6 mg, 0.04 mmol), Xant-phos (46.3 mg, 0.08 mmol) and $Cs_2CO_3$ (130.4 mg, 0.4 mmol) in dioxane (3 mL) was stirred at 130° C. for 5 hr. The mixture was cooled to rt and filtered through celite. The filtrate was concentrated under reduced pressure. The crude product was purified by silica gel column chromatography (DCM/MeOH=15/1) to give the product (17.35 mg, 17%). $^1$H NMR (400 MHz, DMSO-$d_6$) δ 12.11 (s, 1H), 10.47 (s, 1H), 9.34 (s, 1H), 8.59 (s, 1H), 7.57 (d, J=8.3 Hz, 1H), 7.46 (d, J=8.3 Hz, 1H), 7.37 (s, 1H), 4.28 (s, 2H), 4.01 (s, 3H), 3.95 (s, 3H), 3.48 (s, 3H), 2.12 (s, 3H), 1.37 (s, 6H). MS (ESI) m/e $[M+1]^+$ 530.

Example Q35: Synthesis of compound (S)—N-(5-(2,2-dimethyl-2,3-dihydro-[1,4]dioxino[2,3-b]pyridin-6-yl)-4-((4-(3-methyl-morpholino)-6-(methylsulfonyl)pyridin-2-yl)amino)-pyridin-2-yl)acetamide

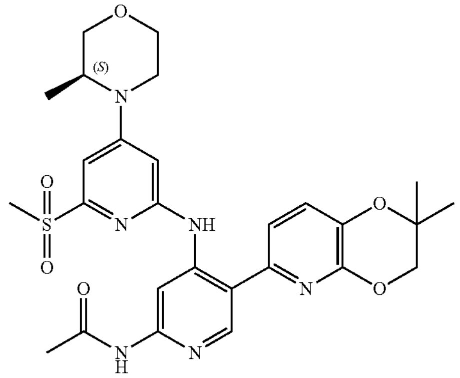

N-(4-amino-5-(2,2-dimethyl-2,3-dihydro-[1,4]dioxino[2,3-b]pyridin-6-yl)pyri-din-2-yl)acetamide (50 mg, 0.16 mmol), (S)-4-(2-chloro-6-(methylsulfonyl)pyridin-4-yl)-3-methyl-morpholine (50.8 mg, 0.18 mmol), $Pd_2dba_3$ (14.6 mg, 0.02 mmol), BINAP (20 mg, 0.03 mmol) and $Cs_2CO_3$ (78 mg, 0.24 mmol) were added into 1,4-dioxane (10 mL). The resulting mixture was degassed with nitrogen and heated to 130° C. with stirring for 2 hr. The reaction was cooled to room temperature. The solids were filtered out. The filtration was concentrated under vacuum. The residue was first applied onto Prep-TLC with DCM/MeOH (20/1) to give the product (65.71 mg, yield: 72.6%). $^1$H NMR (400 MHz, DMSO-$d_6$) δ 11.48 (s, 1H), 10.44 (s, 1H), 8.88 (s, 1H), 8.56 (s, 1H), 7.56 (d, J=8.3 Hz, 1H), 7.42 (d, J=8.3 Hz, 1H), 7.06 (s, 1H), 6.45 (s, 1H), 4.24 (s, 2H), 4.03 (d, J=5.1 Hz, 1H), 3.99-3.90 (m, 1H), 3.70 (d, J=10.3 Hz, 2H), 3.52 (t, J=10.3 Hz, 2H), 3.36 (s, 3H), 3.16 (d, J=10.9 Hz, 1H), 2.10 (s, 3H), 1.36 (s, 6H), 1.16 (d, J=6.6 Hz, 3H). MS (ESI) m/e $[M+1]^+$ 569.

Example Q36: Synthesis of compound (R)—N-(5-(2,2-dimethyl-2,3-dihydro-[1,4]dioxino[2,3-b]pyridin-6-yl)-4-((4-(3-methyl-morpholino)-6-(methylsulfonyl)pyridin-2-yl)amino)-pyridin-2-yl)acetamide

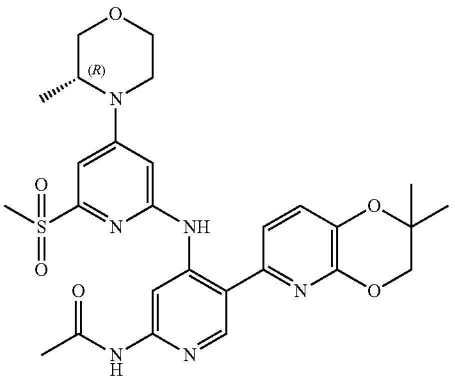

N-(4-amino-5-(2,2-dimethyl-2,3-dihydro-[1,4]dioxino[2,3-b]pyridin-6-yl)pyri-din-2-yl)acetamide (50 mg, 0.16 mmol), (R)-4-(2-chloro-6-(methylsulfonyl)pyridin-4-yl)-3-methyl-morpholine (50.8 mg, 0.18 mmol), $Pd_2dba_3$ (14.6 mg, 0.02 mmol), BINAP (20 mg, 0.03 mmol) and $Cs_2CO_3$ (78 mg, 0.24 mmol) were added into 1,4-dioxane (10 mL). The resulting mixture was degassed with nitrogen and heated to 130° C. with stirring for 2 hr. The reaction was cooled to room temperature. The solids were filtered out. The filtration was concentrated under vacuum. The residue was first applied onto Prep-TLC with DCM/MeOH (20/1) to give the product (49.19 mg, yield: 54.4%). $^1$H NMR (400 MHz, DMSO-$d_6$) δ 11.48 (s, 1H), 10.43 (s, 1H), 8.88 (s, 1H), 8.56 (s, 1H), 7.55 (d, J=8.2 Hz, 1H), 7.42 (d, J=8.2 Hz, 1H), 7.05 (s, 1H), 6.45 (s, 1H), 4.23 (s, 2H), 4.03-4.01 (m, 1H), 3.95 (d, J=10.6 Hz, 1H), 3.69 (dd, J=11.4 Hz, 2H), 3.55-3.49 (m, 2H), 3.35 (s, 3H), 3.17 (t, J=11.4 Hz, 1H), 2.09 (s, 3H), 1.35 (s, 6H), 1.16 (d, J=4.1 Hz, 3H). MS (ESI) m/e $[M+1]^+$ 569.

Example Q37: Synthesis of Compound N-(5-(3,3-dimethyl-2,3-dihydro-[1,4]dioxino[2,3-b]pyridin-6-yl)-4-((4-(methoxy-d3)-6-(methylsulfonyl)pyridin-2-yl)amino)pyridin-2-yl)acetamide

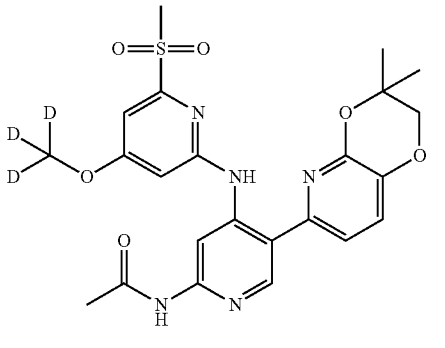 [SMILES: [2H]C([2H])([2H])Oc1cc(Nc2cc(NC(C)=O)ncc2-c2ccc3c(n2)OC(C)(C)CO3)nc(S(C)(=O)=O)c1]

A mixture of N-(4-amino-5-(3,3-dimethyl-2,3-dihydro-[1,4]dioxino[2,3-b]pyridin-6-yl)pyridin-2-yl)acetamide (50 mg, 0.16 mmol), 2-bromo-4-(methoxy-d3)-6-(methylsulfonyl)pyridine (51 mg, 0.19 mmol), $Pd_2(dba)_3$ (15 mg, 0.016 mmol), BINAP (10 mg, 0.016 mmol) and $Cs_2CO_3$ (156 mg, 0.48 mmol) in dioxane (10 mL) was stirred for 5 h at 130° C. under nitrogen atmosphere. After cooled to room temperature, the solid was removed by filtration and the filtrate was concentrated under reduced pressure. The residue was purified by combi-flash (MeOH/DCM=0-10%) to give the product (29.01 mg, 36.4%). H NMR (400 MHz, DMSO-$d_6$) δ 12.03 (s, 1H), 10.44 (s, 1H), 8.93 (s, 1H), 8.57 (s, 1H), 7.51 (d, J=8.0 Hz, 1H), 7.44 (d, J=8.0 Hz, 1H), 7.03 (s, 1H), 6.57 (s, 1H), 4.01 (s, 2H), 3.35 (s, 3H), 2.05 (s, 3H), 1.33 (s, 6H). MS (ESI) m/e $[M+1]^+$ 503.

Example Q38: Synthesis of Compound N-(5-(3,3-dimethyl-2,3-dihydro-[1,4]dioxino[2,3-b]pyridin-6-yl)-4-((4-methoxy-6-(methylsulfonyl)pyridin-2-yl)amino)pyridin-2-yl)acetamide

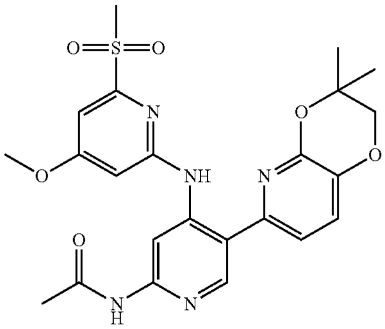

A mixture of N-(4-amino-5-(3,3-dimethyl-2,3-dihydro-[1,4]dioxino[2,3-b]pyridin-6-yl)pyridin-2-yl)acetamide (50 mg, 0.16 mmol), 2-bromo-4-methoxy-6-(methylsulfonyl)pyridine (51 mg, 0.19 mmol), $Pd_2(dba)_3$ (15 mg, 0.016 mmol), BINAP (10 mg, 0.016 mmol) and $Cs_2CO_3$ (156 mg, 0.48 mmol) in dioxane (10 mL) was stirred for 5 h at 130° C. under nitrogen atmosphere After cooled to room temperature, the solid was removed by filtration and the filtrate was concentrated under reduced pressure. The residue was purified by combi-flash (MeOH/DCM=0-10%) to give the product (39.76 mg, 50.1%). $^1H$ NMR (400 MHz, DMSO-$d_6$) δ 12.06 (s, 1H), 10.46 (s, 1H), 8.95 (s, 1H), 8.59 (s, 1H), 7.53 (d, J=8.0 Hz, 1H), 7.46 (d, J=8.0 Hz, 1H), 7.05 (s, 1H), 6.59 (s, 1H), 4.03 (s, 2H), 3.89 (s, 3H), 3.37 (s, 3H), 2.06 (s, 3H), 1.35 (s, 6H). MS (ESI) m/e $[M+1]^+$ 500.

Example Q40: Synthesis of Compound N-(5-(3,3-dimethyl-2,3-dihydro-[1,4]dioxino[2,3-b]pyridin-6-yl)-4-((6-(methylsulfonyl)-4-(tetrahydro-2H-pyran-4-yl)pyridin-2-yl)amino)pyridin-2-yl)acetamide

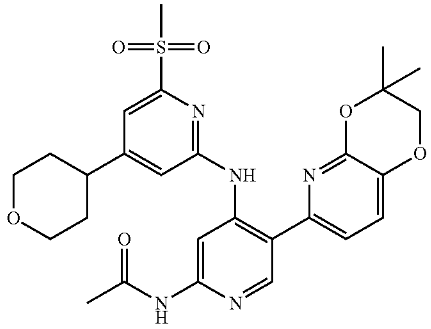 [SMILES: CC(=O)Nc1cc(Nc2cc(C3CCOCC3)cc(S(C)(=O)=O)n2)c(-c2ccc3c(n2)OC(C)(C)CO3)cn1]

A mixture of N-(4-amino-5-(3,3-dimethyl-2,3-dihydro-[1,4]dioxino[2,3-b]pyridin-6-yl)pyridin-2-yl)acetamide (50 mg, 0.16 mmol), 2-chloro-6-(methylsulfonyl)-4-(tetrahydro-2H-pyran-4-yl)pyridine (53 mg, 0.19 mmol), $Pd_2(dba)_3$ (15 mg, 0.016 mmol), BINAP (10 mg, 0.016 mmol) and $Cs_2CO_3$ (156 mg, 0.48 mmol) in dioxane (10 mL) was stirred for 5 h at 130° C. under nitrogen atmosphere. After cooled to room temperature, the solid was removed by filtration and the filtrate was concentrated under reduced pressure. The residue was purified by combi-flash (MeOH/DCM=0-10%) to give the product (33.12 mg, 37.7%). $^1H$ NMR (400 MHz, DMSO-$d_6$) δ 12.43 (s, 1H), 10.45 (s, 1H), 9.04 (s, 1H), 8.62 (s, 1H), 7.56 (d, J=8.0 Hz, 1H), 7.47 (d, J=8.0 Hz, 1H), 7.42 (s, 1H), 6.94 (s, 1H), 4.04 (s, 2H), 3.93-3.90 (m, 2H), 3.44-3.40 (m, 5H), 2.91-2.90 (m, 1H), 2.07 (s, 3H), 1.80-1.77 (m, 2H), 1.63-1.57 (m, 2H), 1.36 (s, 6H). MS (ESI) m/e $[M+1]^+$ 554.

Example Q43: Synthesis of Compound (S)—N-(5-(3,3-dimethyl-2,3-dihydro-[1,4]dioxino[2,3-b]pyridin-6-yl)-4-((4-(1-methoxyethyl)-6-(methylsulfonyl)pyridin-2-yl)amino)pyridin-2-yl)acetamide

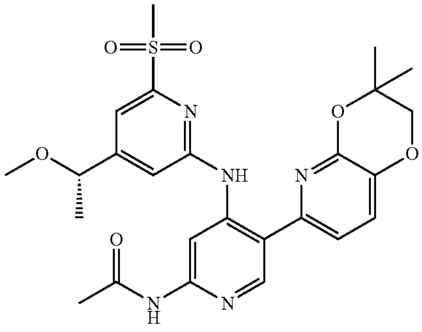

Step 1. 2-chloro-5-(3,3-dimethyl-2,3-dihydro-[1,4]dioxino[2,3-b]pyridin-6-yl)pyridin-4-amine

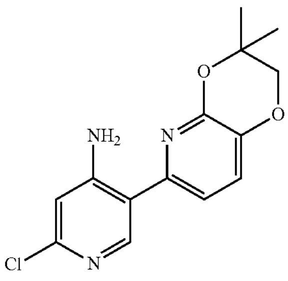 [SMILES: CC1(C)COc2ccc(-c3cnc(Cl)cc3N)nc2O1]

A mixture of 6-bromo-3,3-dimethyl-2,3-dihydro-[1,4]dioxino[2,3-b]pyridine (400 mg, 1.65 mmol), 2-chloro-5-(4,4,5,5-tetramethyl-1,3,2-dioxaborolan-2-yl)pyridin-4-amine (439 mg, 1.73 mmol), $Pd(dppf)Cl_2$ (120 mg, 0.16 mmol) and $K_3PO_4$ (1.05 g, 4.94 mmol) in dioxane (15 mL) and $H_2O$ (3 mL) was stirred for 2 h at 90° C. under nitrogen atmosphere. After cooled to room temperature, the solid was removed by filtration. The filtrate was concentrated under reduced pressure and the residue was purified by combi-flash (EA/PE=0-60%) to give the product (450 mg, 94.1%). MS (ESI) m/e $[M+1]^+$ 292.

Step 2. N-(4-amino-5-(3,3-dimethyl-2,3-dihydro-[1,4]dioxino[2,3-b]pyridin-6-yl)pyridin-2-yl)acetamide

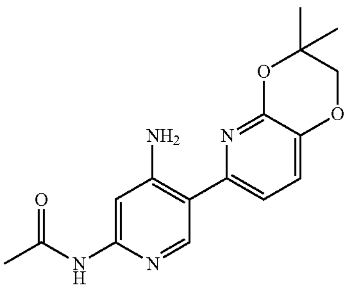 [SMILES: CC(=O)Nc1cc(N)c(-c2ccc3c(n2)OC(C)(C)CO3)cn1]

A mixture of 2-chloro-5-(3,3-dimethyl-2,3-dihydro-[1,4]dioxino[2,3-b]pyridin-6-yl)pyridin-4-amine (450 mg, 1.55 mmol), acetamide (639 mg, 10.8 mmol), $Pd_2(dba)_3$ (142 mg, 0.15 mmol), Xantphos (89 mg, 0.15 mmol) and $Cs_2CO_3$ (1.51 g, 4.64 mmol) in dioxane (15 mL) was stirred for 5 h at 130° C. under nitrogen atmosphere. After cooled to room temperature, the solid was removed by filtration and the filtrate was concentrated under reduced pressure. The residue was purified by combi-flash (MeOH/DCM=0-10%) to give the product (220 mg, 45.4%). MS (ESI) m/e $[M+1]^+$ 315.

Step 3. (S)—N-(5-(3,3-dimethyl-2,3-dihydro-[1,4]dioxino[2,3-b]pyridin-6-yl)-4-((4-(1-methoxyethyl)-6-(methylsulfonyl)pyridin-2-yl)amino)pyridin-2-yl)acetamide

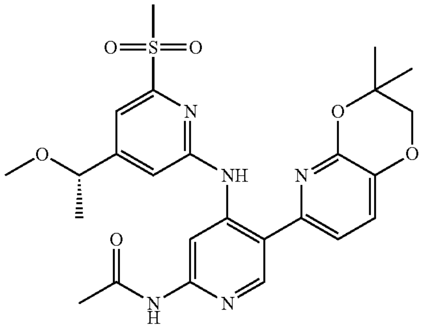

A mixture of N-(4-amino-5-(3,3-dimethyl-2,3-dihydro-[1,4]dioxino[2,3-b]pyridin-6-yl)pyridin-2-yl)acetamide (50 mg, 0.16 mmol), (S)-2-bromo-4-(1-methoxyethyl)-6-(methylsulfonyl)pyridine (56 mg, 0.19 mmol), $Pd_2(dba)_3$ (15 mg, 0.016 mmol), BINAP (10 mg, 0.016 mmol) and $Cs_2CO_3$ (156 mg, 0.48 mmol) in dioxane (10 mL) was stirred for 5 h at 130° C. under nitrogen atmosphere. After cooled to room temperature, the solid was removed by filtration and the filtrate was concentrated under reduced pressure. The residue was purified by combi-flash (MeOH/DCM=0-10%) to give the crude product. The crude product was washed with acetonitrile to give the product (7.29 mg, 8.7%). $^1H$ NMR (400 MHz, DMSO-$d_6$) δ 12.26 (s, 1H), 10.47 (s, 1H), 9.05 (s, 1H), 8.61 (s, 1H), 7.55 (d, J=8.0 Hz, 1H), 7.47 (d, J=8.0 Hz, 1H), 7.42 (s, 1H), 7.05 (s, 1H), 4.45-4.44 (m, 1H), 4.04 (s, 2H), 3.41 (s, 3H), 3.22 (s, 3H), 2.07 (s, 3H), 1.40-1.29 (m, 9H). MS (ESI) m/e $[M+1]^+$ 528.

Example Q46: Synthesis of (S)—N-(5-(2,2-dimethyl-2,3-dihydro-[1,4]dioxino[2,3-b]pyridin-6-yl)-4-((4-(3-methoxypyrrolidin-1-yl)-6-(methylsulfonyl)pyridin-2-yl)amino)pyridin-2-yl)acetamide

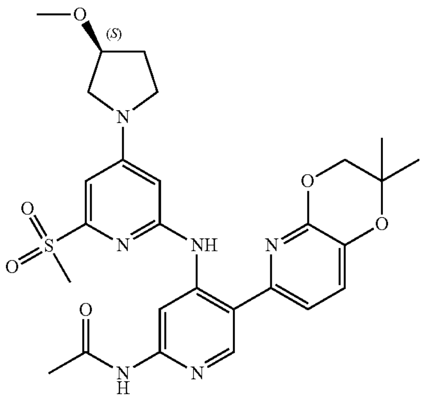

Step 1: (S)-2,6-dichloro-4-(3-methoxypyrrolidin-1-yl)pyridine

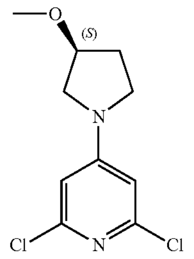

To a round bottom flask was added 2,6-dichloro-4-iodopyridine (5.0 g, 18.3 mmol), (S)-3-methoxypyrrolidine (2.6 g, 19.2 mmol), $Pd_2dba_3$ (503 mg, 0.6 mmol), Xantphos (318 mg, 0.6 mmol), t-BuOK (4.4 g, 45.8 mmol) and 1,4-dioxane (100 mL). The resulting mixture was charged into nitrogen and heated to 40° C. with stirring for 13 h. The reaction was cooled to room temperature. Solids were filtered out. The filtration was concentrated. The residue was applied onto a silica gel column with EtOAc/PE to afford (S)-2,6-dichloro-4-(3-methoxypyrrolidin-1-yl)pyridine as dark brown oil (3.8 g, 84.4%). MS (ESI) m/e $[M+1]^+$ 247.

Step 2: (S)-2-chloro-4-(3-methoxypyrrolidin-1-yl)-6-(methylthio)pyridine

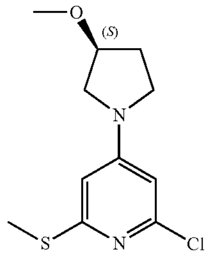

To a solution of (S)-2,6-dichloro-4-(3-methoxypyrrolidin-1-yl)pyridine (3.6 g, 14.6 mmol) in DMF (40 mL) was added $CH_3SNa$ (1.3 g, 17.6 mmol). The resulting reaction was heated to 100° C. with stirring for 2 hours. The reaction mixture was cooled to room temperature. The reaction was quenched by water/ice (200 mL). The resulting solution was extracted with EtOAc (40 mL×5). The organic layer was washed with water and brine, dried and concentrated. This resulted in 4.5 g of (S)-2-chloro-4-(3-methoxypyrrolidin-1-yl)-6-(methylthio)pyridine 4.5 g as yellow crude oil. MS (ESI) m/e $[M+1]^+$ 259.

Step 3: (S)-2-chloro-4-(3-methoxypyrrolidin-1-yl)-6-(methylsulfonyl)pyridine

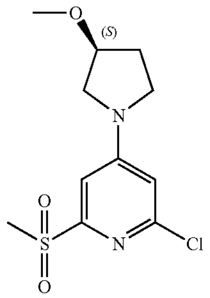

To a solution of (S)-2-chloro-4-(3-methoxypyrrolidin-1-yl)-6-(methylthio)py-ridine (4.5 g, 17.4 mmol) in MeOH (30 mL) was added a solution of Oxone (12.8 g, 20.8 mmol) in $H_2O$ (30 mL) at room temperature dropwise with stirring. The resulting solution was stirred at room temperature for 1.5 h. The reaction was diluted with water (150 mL). The resulting solution was extracted with EtOAc (30 mL×5). The organic layer was washed with water and brine, dried and concentrated. The residue was applied onto a silica gel column with DCM/EtOAc (1:1). This resulted in 3.5 g of (S)-2-chloro-4-(3-methoxypyrrolidin-1-yl)-6-(methylsulfonyl)pyridine as a light yellow solid (Yield=78.1% for two steps). MS (ESI) m/e $[M+1]^+$ 291.

Step 4: (S)—N-(5-(2,2-dimethyl-2,3-dihydro-[1,4]dioxino[2,3-b]pyridin-6-yl)-4-((4-(3-methoxypyrrolidin-1-yl)-6-(methylsulfonyl)pyridin-2-yl)amino)pyridin-2-yl)acetamide

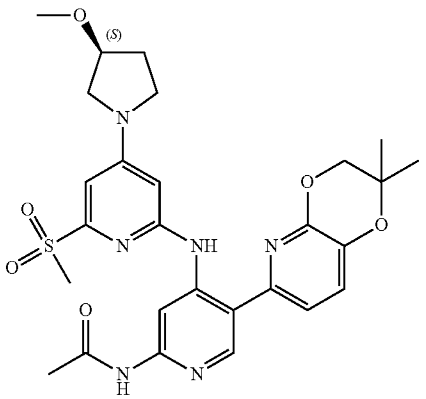

(S)-2-chloro-4-(3-methoxypyrrolidin-1-yl)-6-(methylsulfonyl)pyridine (100 mg, 0.3 mmol), N-(4-amino-5-(2,2-dimethyl-2,3-dihydro-[1,4]dioxino[2,3-b]pyridin-6-yl)pyridin-2-yl)acetamide (102 mg, 0.35 mmol), $Pd_2dba_3$ (29.2 mg, 0.03 mmol), Xantphos (37 mg, 0.06 mmol) and $K_3PO_4$ (135 mg, 0.6 mmol) were added into 2-methyltetrahydrofuran (9.0 mL) and $H_2O$ (1.0 mL). The resulting mixture was degassed with nitrogen and heated to 90° C. with stirring for 16 h. The reaction was cooled to room temperature. The solids were filtered out. The filtration was concentrated under vacuum. The residue was applied onto Prep-TLC with DCM/MeOH (17:1) to afford (S)—N-(5-(2,2-dimethyl-2,3-dihydro-[1,4]dioxino[2,3-b]pyridin-6-yl)-4-((4-(3-methoxypyrrolidin-1-yl)-6-(methylsulfonyl)pyridin-2-yl)amino)pyridin-2-yl)acetamide as a white solid (71.97 mg, yield: 40.0%). $^1$H NMR (400 MHz, DMSO-$d_6$) δ 11.48 (s, 1H), 10.45 (s, 1H), 8.85 (s, 1H), 8.57 (s, 1H), 7.57 (d, J=8.3 Hz, 1H), 7.43 (d, J=8.3 Hz, 1H), 6.78 (s, 1H), 6.21 (s, 1H), 4.25 (s, 2H), 4.11 (s, 1H), 3.59-3.35 (m, 7H), 3.28 (s, 3H), 2.12-2.06 (m, 5H), 1.35 (s, 6H). MS (ESI) m/e [M+1]$^+$ 569.

Example Q49: Synthesis of N-(5-(2,2-dimethyl-2,3-dihydro-[1,4]dioxino[2,3-b]pyridin-6-yl)-4-((4-(3-methoxyazetidin-1-yl)-6-(methylsulfonyl)pyridin-2-yl)amino)pyridin-2-yl)acetamide

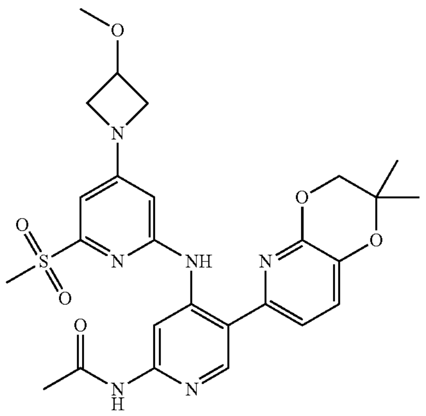

A mixture of N-(4-amino-5-(2,2-dimethyl-2,3-dihydro-[1,4]dioxino[2,3-b]pyridin-6-yl)pyridin-2-yl)acetamide (100 mg, 0.32 mmol), 2-chloro-4-(3-methoxyazetidin-1-yl)-6-(methylsulfonyl)pyridine (105 mg, 0.38 mmol), $Pd_2(dba)_3$ (29 mg, 0.032 mmol), BINAP (20 mg, 0.032 mmol) and $Cs_2CO_3$ (311 mg, 0.96 mmol) in 1,4-dioxane (10 mL) was stirred for 5 h at 130° C. under nitrogen atmosphere. The mixture was allowed to cool down to room temperature. The resulting mixture was filtered and the filtrate was concentrated under reduced pressure. The residue was purified by combi-flash (MeOH/DCM=0-10%) to give the crude product. The crude product was suspended in acetonitrile to give the product (46 mg, 26.4%). $^1$H NMR (400 MHz, DMSO-$d_6$) δ 11.43 (s, 1H), 10.40 (s, 1H), 8.79 (s, 1H), 8.52 (s, 1H), 7.51 (d, J=8.0 Hz, 1H), 7.37 (d, J=8.0 Hz, 1H), 6.58 (s, 1H), 6.01 (s, 1H), 4.33-4.32 (m, 1H), 4.19-4.18 (m, 4H), 3.81 (d, J=8.0 Hz, 2H), 3.29 (s, 3H), 3.21 (s, 3H), 2.05 (s, 3H), 1.31 (s, 6H). LCMS (ESI) m/e [M+1]$^+$=555.

Example Q50: Synthesis of (R/S)—N-(4-((4-(1,4-dioxan-2-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide

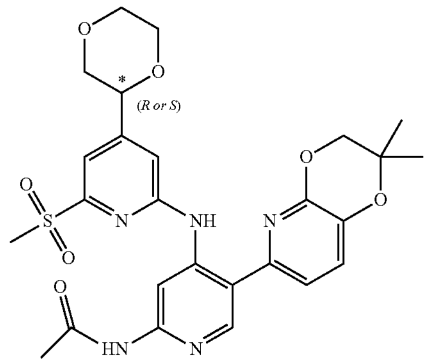

A mixture of N-(4-amino-5-(2,2-dimethyl-2,3-dihydro-[1,4]dioxino[2,3-b]pyridin-6-yl)pyridin-2-yl)acetamide (100 mg, 0.32 mmol), (R or S)-2-chloro-4-(1,4-dioxan-2-yl)-6-(methylsulfonyl)pyridine (98 mg, 0.35 mmol), $Pd_2(dba)_3$ (30 mg, 0.032 mmol), BINAP (20 mg, 0.032 mmol) and $Cs_2CO_3$ (312 mg, 0.96 mmol) in dioxane (10 mL) was stirred for 5 h at 130° C. under nitrogen atmosphere. The mixture was allowed to cool down to room temperature. The resulting mixture was filtered. The filtrate was concentrated under reduced pressure. The residue was purified by combi-flash (MeOH/DCM=0-10%) to give the crude product. The crude product was suspended in acetonitrile to give the product (32 mg, 17.9%). $^1$H NMR (400 MHz, DMSO-do) δ 11.78 (s, 1H), 10.44 (s, 1H), 8.98 (s, 1H), 8.55 (s, 1H), 7.57-7.44 (m, 2H), 7.37 (d, J=8.0 Hz, 1H), 7.12 (s, 1H), 4.71-4.70 (m, 1H), 4.19 (s, 2H), 3.90-3.88 (m, 2H), 3.78-3.66 (m, 2H), 3.54-3.53 (m, 1H), 3.36 (s, 3H), 3.23-3.19 (m, 1H), 2.04 (s, 3H), 1.30 (s, 6H). MS (ESI) m/e [M+1]$^+$ 556.

Example Q51: Synthesis of (S/R)—N-(4-((4-(1,4-dioxan-2-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide

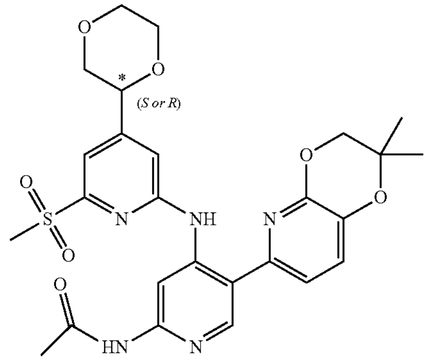

A mixture of N-(4-amino-5-(2,2-dimethyl-2,3-dihydro-[1,4]dioxino[2,3-b]pyridin-6-yl)pyridin-2-yl)acetamide (50 mg, 0.15 mmol), (S or R)-2-chloro-4-(1,4-dioxan-2-yl)-6-(methylsulfonyl)pyridine (51 mg, 0.19 mmol), $Pd_2(dba)_3$ (15 mg, 0.015 mmol), BINAP (10 mg, 0.015 mmol) and $Cs_2CO_3$ (78 mg, 0.238 mmol) in dioxane (10 mL) was stirred for 5 h at 130° C. under nitrogen atmosphere. The mixture was allowed to cool down to room temperature. The resulting mixture was filtered. The filtrate was concentrated under reduced pressure. The residue was purified by combi-flash (MeOH/DCM=0-10%) to give the crude product. The crude product was suspended in acetonitrile to give the product (50 mg, 60%). $^1$H NMR (400 MHz, DMSO-$d_6$) δ 11.80 (s, 1H), 10.46 (s, 1H), 9.00 (s, 1H), 8.57 (s, 1H), 7.60-7.45 (m, 2H), 7.39 (d, J=7.9 Hz, 1H), 7.14 (s, 1H), 4.72 (d, J=9.0 Hz, 1H), 4.21 (s, 2H), 3.96-3.88 (m, 2H), 3.82-3.67 (m, 2H), 3.58-3.55 (m, 1H), 3.38 (s, 3H), 2.06 (s, 3H), 1.32 (s, 6H). MS (ESI) m/e $[M+1]^+$=556.

Example Q52: Synthesis of N-(5-(2,2-dimethyl-2,3-dihydro-[1,4]dioxino[2,3-b]pyridin-6-yl)-4-((4-(4-methoxypiperidin-1-yl)-6-(methylsulfonyl)pyridin-2-yl)amino)pyridin-2-yl)acetamide

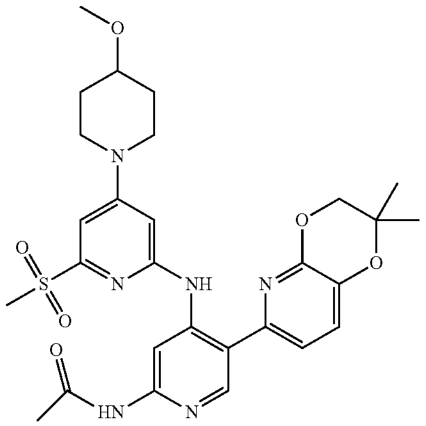

A mixture of N-(4-amino-5-(2,2-dimethyl-2,3-dihydro-[1,4]dioxino[2,3-b]pyridin-6-yl)pyridin-2-yl)acetamide (100 mg, 0.32 mmol), 2-chloro-4-(4-methoxypiperidin-1-yl)-6-(methylsulfonyl)pyridine (116 mg, 0.38 mmol), $Pd_2(dba)_3$ (29 mg, 0.032 mmol), BINAP (20 mg, 0.032 mmol) and $Cs_2CO_3$ (311 mg, 0.96 mmol) in dioxane (10 mL) was stirred for 5 h at 130° C. under nitrogen atmosphere. The mixture was allowed to cool down to room temperature. The resulting mixture was filtered. The filtrate was concentrated under reduced pressure. The residue was purified by combi-flash (MeOH/DCM=0-10%) to give the crude product. The crude product was suspended in acetonitrile to give the product (41 mg, 22%). $^1$H NMR (400 MHz, DMSO-$d_6$) δ 11.35 (s, 1H), 10.37 (s, 1H), 8.81 (s, 1H), 8.49 (s, 1H), 7.49 (d, J=8.0 Hz, 1H), 7.36 (d, J=8.0 Hz, 1H), 7.00 (s, 1H), 6.44 (s, 1H), 4.17 (s, 2H), 3.60-3.59 (m, 2H), 3.39-3.38 (m, 1H), 3.28 (s, 3H), 3.31-3.16 (m, 5H), 2.03 (s, 3H), 1.83-1.82 (m, 2H), 1.43-1.42 (m, 2H), 1.29 (s, 6H). MS (ESI) m/e $[M+1]^+$ 583.

Example Q53: N-(5-(2,2-dimethyl-2,3-dihydro-[1,4]dioxino[2,3-b]pyridin-6-yl)-4-((4-((cis)-3-methoxy-cyclobutyl)-6-(methylsulfonyl)pyridin-2-yl)amino)pyridin-2-yl)acetamide

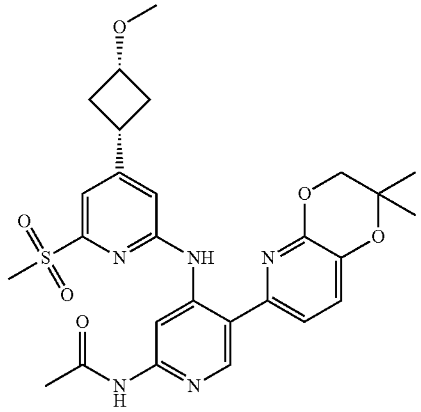

A mixture of N-(4-amino-5-(2,2-dimethyl-2,3-dihydro-[1,4]dioxino[2,3-b]pyridin-6-yl)pyridin-2-yl)acetamide (53 mg, 0.17 mmol), 2-bromo-4-((cis)-3-methoxycyclobutyl)-6-(methylsulfonyl)pyridine (47 mg, 0.17 mmol), $Pd_2(dba)_3$ (16 mg, 0.017 mmol), Xantphos (10 mg, 0.017 mmol), $Cs_2CO_3$ (110 mg, 0.34 mmol) in 5 mL 1,4-dioxane was stirred at 130° C. under nitrogen atmosphere for 2 h. After cooled to rt, the solution was concentrated in vacuo and the residue was purified by Prep TLC to give the product (20 mg). $^1$H NMR (400 MHz, DMSO-$d_6$) δ 11.85 (s, 1H), 10.50 (s, 1H), 9.06 (s, 1H), 8.61 (s, TH), 7.58 (d, J=8.0 Hz, 1H), 7.43 (d, J=8.0 Hz, 1H), 7.39 (s, 1H), 7.01 (s, 1H), 4.25 (s, 2H), 3.89 (m, 1H), 3.43 (s, 3H), 3.18 (m, 4H), 2.68 (m, 2H), 2.10 (s, 3H), 1.91 (m, 2H), 1.36 (s, 6H). MS (ESI) m/e $[M+1]^+$=554.

Example Q54: Synthesis of N-(5-(2,2-dimethyl-2,3-dihydro-[1,4]dioxino[2,3-b]pyridin-6-yl)-4-((4-((trans)-3-methoxycyclobutyl-6-(methylsulfonyl)pyridin-2-yl)amino)pyridin-2-yl)acetamide

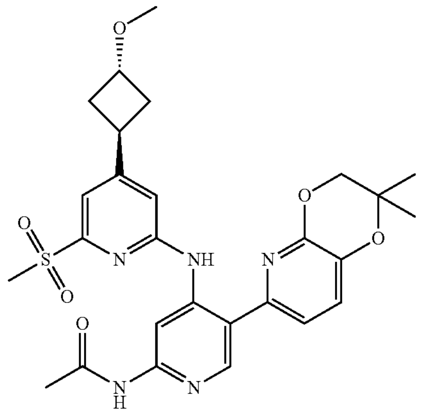

This compound was synthesized by using the similar procedure as example Q53. $^1$H NMR (400 MHz, DMSO-$d_6$) δ 11.95 (s, 1H), 10.50 (s, 1H), 9.07 (s, 1H), 8.63 (s, 1H), 7.60 (d, J=8.4 Hz, 1H), 7.43 (m, 2H), 7.06 (s, 1H), 4.25 (s, 2H), 4.12-3.97 (m, 1H), 3.71-3.56 (m, 1H), 3.44 (s, 3H), 3.19 (s, 3H), 2.43-2.32 (m, 4H), 2.11 (s, 3H), 1.36 (s, 6H). MS (ESI) m/e [M+1]$^+$ 554.

Example Q55: Synthesis of N-(5-(2,2-dimethyl-2,3-dihydro-[1,4]dioxino[2,3-b]pyridin-6-yl)-4-((4-(4-hydroxy-4-methylpiperidin-1-yl)-6-(methylsulfonyl)pyridin-2-yl)amino)pyridin-2-yl)acetamide

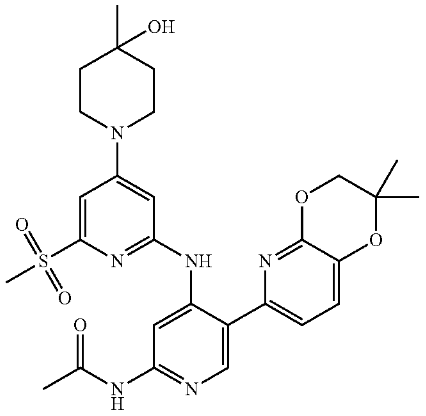

A mixture of N-(4-amino-5-(2,2-dimethyl-2,3-dihydro-[1,4]dioxino[2,3-b]pyridin-6-yl)pyridin-2-yl)acetamide (50 mg, 0.16 mmol), 1-(2-bromo-6-(methylsulfonyl)pyridin-4-yl)-4-methylpiperidin-4-ol (66 mg, 0.19 mmol), $Pd_2(dba)_3$ (7 mg, 0.008 mmol), XantPhos (9 mg, 0.016 mmol) and $K_3PO_4$ (68 mg, 0.32 mmol) in 2-MeTHF (5 mL) and water (0.5 mL) was stirred at 90° C. for 4 h under nitrogen atmosphere. After cooled to rt, the reaction mixture was concentrated and the residue was purified by Prep-TLC (MeOH:DCM=1:20) to give the product (39 mg, 42%). $^1$H NMR (400 MHz, DMSO-$d_6$) δ 11.42 (s, 1H), 10.46 (s, 1H), 8.86 (s, 1H), 8.55 (s, 1H), 7.56 (d, J=8.4 Hz, 1H), 7.43 (d, J=8.3 Hz, 1H), 7.06 (s, 1H), 6.50 (s, 1H), 4.47 (s, 1H), 4.24 (s, 2H), 3.61 (d, J=13.2 Hz, 2H), 3.37-3.34 (m, 5H), 2.10 (s, 3H), 1.57-1.49 (m, 4H), 1.36 (s, 6H), 1.15 (s, 3H). MS (ESI) m/e [M+H]$^+$=583.

Example Q63: Synthesis of N-(4-((4-cyano-6-(methylsulfonyl)pyridin-2-yl)amino)-5-(2,2-dimethyl-2,3-dihydro-[1,4]dioxino[2,3-b]pyridin-6-yl)pyridin-2-yl)acetamide

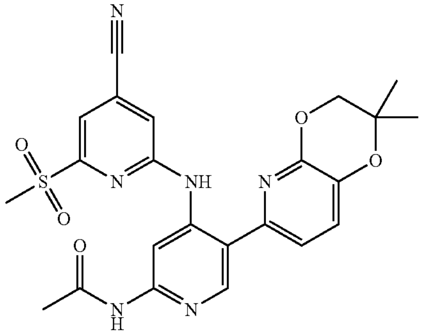

A mixture of N-(4-amino-5-(2,2-dimethyl-2,3-dihydro-[1,4]dioxino[2,3-b]pyridin-6-yl)pyridin-2-yl)acetamide (80 mg, 0.25 mmol), 2-bromo-6-(methylsulfonyl)isonicotinonitrile (80 mg, 0.31 mmol), $Pd_2(dba)_3$ (23 mg, 0.025 mmol), BINAP (16 mg, 0.025 mmol) and $Cs_2CO_3$ (249 mg, 0.76 mmol) in dioxane (10 mL) was stirred for 5 h at 130° C. under nitrogen atmosphere. The mixture was allowed to cool to room temperature. The resulting mixture was filtered. The filtrate was concentrated under reduced pressure. The residue was purified by combi-flash (MeOH/DCM=0-10%) to give the crude product. The crude product was suspended in acetonitrile to give the product (11.09 mg). $^1$H NMR (400 MHz, DMSO-$d_6$) δ 11.94 (s, 1H), 10.59 (s, 1H), 9.05 (s, 1H), 8.65 (s, 1H), 7.82 (s, 1H), 7.63-7.50 (m, 2H), 7.43 (d, J=8.0 Hz, 1H), 4.25 (s, 2H), 3.47 (s, 3H), 2.12 (s, 3H), 1.37 (s, 6H). MS (ESI) m/e [M+1]$^+$ 495.

The following Examples were prepared in a similar manner to the product Example Q1:

| Example | Compound | Chemical Name | $^1$H NMR and LC/MS m/z (M + 1) |
|---|---|---|---|
| Q2 | 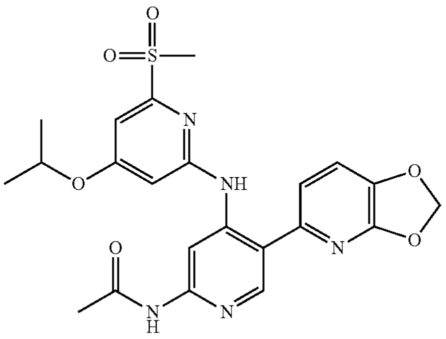 [SMILES: CC(=O)Nc1cc(Nc2cc(OC(C)C)cc(S(C)(=O)=O)n2)c(-c2ccc3c(n2)OCO3)cn1] | N-(5-([1,3]dioxolo[4,5-b]pyridin-5-yl)-4-((4-isopropoxy-6-(methylsulfonyl)pyridin-2-yl)amino)pyridin-2-yl)acetamide | $^1$H NMR (400 MHz, DMSO-$d_6$) δ 10.43 (s, 1H), 10.13 (s, 1H), 8.85 (s, 1H), 8.35 (s, 1H), 7.35 (d, J = 8.0 Hz, 1H), 7.26 (d, J = 8.0 Hz, 1H), 6.98 (s, 1H), 6.67 (s, 1H), 6.19 (s, 2H), 4.79-4.43 (m, 1H), 3.32 (s, 3H), 2.05 (s, 3H), 1.27 (d, J = 5.9 Hz, 6H). MS (ESI) m/e [M + 1]$^+$ 486. |

-continued

| Example | Compound | Chemical Name | $^1$H NMR and LC/MS m/z (M + 1) |
|---|---|---|---|
| Q3 | 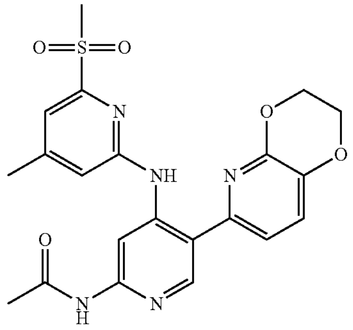 [SMILES: CC(=O)Nc1cc(Nc2cc(C)cc(S(C)(=O)=O)n2)c(-c2ccc3c(n2)OCCO3)cn1] | N-(5-(2,3-dihydro-[1,4]dioxino[2,3-b]pyridin-6-yl)-4-((4-methyl-6-(methylsulfonyl)pyridin-2-yl)amino)pyridin-2-yl)acetamide | $^1$H NMR (400 MHz, DMSO-$d_6$) δ 11.98 (s, 1H), 10.49 (s, 1H), 9.13 (s, 1H), 8.64 (s, 1H), 7.60 (d, J = 8.1 Hz, 1H), 7.54-7.38 (m, 2H), 6.96 (s, 1H), 4.55-4.52 (m, 2H), 4.38-4.35 (m, 2H), 3.43 (s, 3H), 2.42 (s, 3H), 2.11 (s, 3H). MS (ESI) m/e [M + 1]$^+$ 456. |
| Q4 | 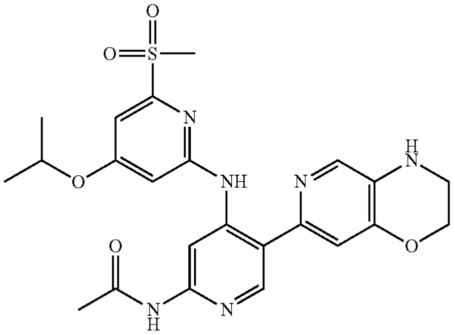 [SMILES: CC(=O)Nc1cc(Nc2cc(OC(C)C)cc(S(C)(=O)=O)n2)c(-c2cc3c(cn2)NCCO3)cn1] | N-(5-(3,4-dihydro-2H-pyrido[4,3-b][1,4]oxazin-7-yl)-4-((4-isopropoxy-6-(methylsulfonyl)pyridin-yl)amino)pyridin-2-yl)acetamide | $^1$H NMR (400 MHz, DMSO-$d_6$) δ 12.31 (s, 1H), 10.41 (s, 1H), 9.03 (s, 1H), 8.53 (s, 1H), 7.51 (s, 1H), 7.12-7.04 (m, 3H), 6.94 (s, 1H), 5.06-4.79 (m, 1H), 4.19 (s, 2H), 3.53 (s, 2H), 3.41 (s, 3H), 2.09 (s, 3H), 1.34 (d, J = 5.9 Hz, 6H). MS (ESI) m/e [M + 1]$^+$ 499. |
| Q5 | 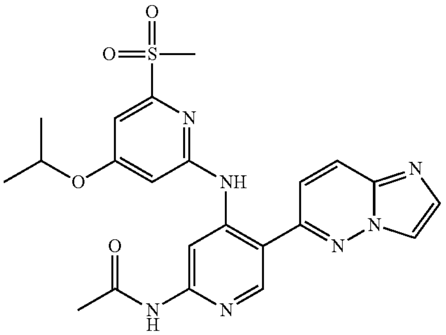 [SMILES: CC(=O)Nc1cc(Nc2cc(OC(C)C)cc(S(C)(=O)=O)n2)c(-c2ccc3nccn3n2)cn1] | N-(5-(imidazo[1,2-b]pyridazin-6-yl)-4-((4-isopropoxy-6-(methylsulfonyl)pyridin-2-yl)amino)pyridin-2-yl)acetamide | $^1$H NMR (400 MHz, DMSO-$d_6$) δ 10.61 (s, 1H), 9.81 (s, 1H), 8.97 (s, 1H), 8.50 (s, 1H), 8.44 (s, 1H), 8.18 (d, J = 12.0 Hz, 1H), 7.82 (s, 1H), 7.54 (d, J = 12.0 Hz, 1H), 7.02-7.01 (m, 1H), 6.82-6.81 (m, 1H), 4.77-4.76 (m, 1H), 3.35 (s, 3H), 2.12 (s, 3H), 1.31 (d, J = 4.0 Hz, 6H). MS (ESI) m/e [M + 1]$^+$ 482. |
| Q6 | 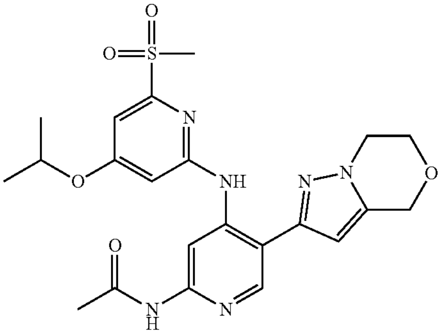 [SMILES: CC(=O)Nc1cc(Nc2cc(OC(C)C)cc(S(C)(=O)=O)n2)c(-c2cc3n(n2)CCOC3)cn1] | N-(5-(6,7-dihydro-4H-pyrazolo[5,1-c][1,4]oxazin-2-yl)-4-((4-isopropoxy-6-(methylsulfonyl)pyridin-2-yl)amino)pyridin-2-yl)acetamide | $^1$H NMR (400 MHz, DMSO-$d_6$) δ 11.21 (s, 1H), 10.42 (s, 1H), 9.16 (s, 1H), 8.59 (s, 1H), 7.09 (d, J = 1.6 Hz, 1H), 6.77 (s, 1H), 6.73 (s, 1H), 4.89 (s, 3H), 4.32 (s, 2H), 4.16-4.12 (m, 2H), 3.46 (s, 3H), 2.11 (s, 3H), 1.34 (d, J = 5.9 Hz, 6H). MS (ESI) m/e [M + 1]$^+$ 487. |

-continued

| Example | Compound | Chemical Name | $^1$H NMR and LC/MS m/z (M + 1) |
|---|---|---|---|
| Q7 | 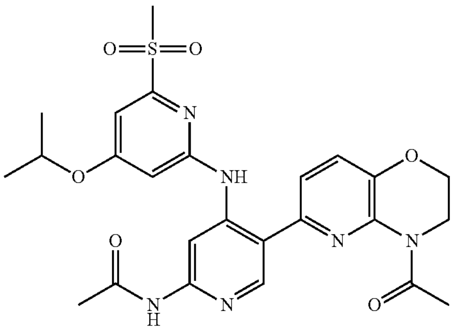 [SMILES: CC(=O)Nc1cc(Nc2cc(OC(C)C)cc(S(C)(=O)=O)n2)c(-c2ccc3c(n2)N(C(C)=O)CCO3)cn1] | N-(5-(4-actyl-3,4-dihydro-2H-pyrido[3,2-b][1,4]oxazin-6-yl)-4-((4-isopropoxy-6-(methylsulfonyl)pyridin-2-yl)amino)pyridin-2-yl)acetamide | $^1$H NMR (400 MHz, $CDCl_3$) δ 11.30 (s, 1H), 9.11 (s, 1H), 8.86 (s, 1H), 8.37 (s, 1H), 7.45-7.40 (m, 2H), 6.67 (s, 1H), 4.75-4.71 (m, 1H), 4.40-4.35 (m, 2H), 4.15-4.10 (m, 2H), 3.38 (s, 3H), 2.56 (s, 3H), 2.23 (s, 3H), 1.39 (d, J = 6.0 Hz, 6H). MS (ESI) m/e [M + 1]$^+$ 541. |
| Q8 | 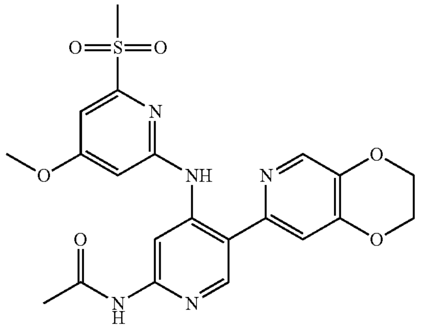 [SMILES: COc1cc(Nc2cc(NC(C)=O)ncc2-c2cc3c(cn2)OCCO3)nc(S(C)(=O)=O)c1] | N-(5-(2,3-dihydro-[1,4]dioxino[2,3-c]pyridin-7-yl)-4-((4-methoxy-6-(methylsulfonyl)pyridin-2-yl)amino)pyridin-2-yl)acetamide | $^1$H NMR (400 MHz, DMSO-$d_6$) δ 12.51 (s, 1H), 10.46 (s, 1H), 9.10 (s, 1H), 8.63 (s, 1H), 8.38 (s, 1H), 7.61 (s, 1H), 7.09 (s, 1H), 6.84 (s, 1H), 4.43-4.39 (m, 4H), 3.95 (s, 3H), 3.43 (s, 3H), 2.11 (s, 3H). MS (ESI) m/e [M + 1]$^+$ 472. |
| Q9 | 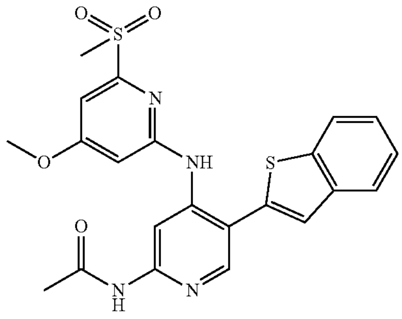 [SMILES: COc1cc(Nc2cc(NC(C)=O)ncc2-c2cc3ccccc3s2)nc(S(C)(=O)=O)c1] | N-(5-(benzo[b]thiophen-2-yl)-4-((4-methoxy-6-(methylsulfonyl)pyridin-2-yl)amino)pyridin-2-yl)acetamide | $^1$H NMR (400 MHz, DMSO-$d_6$) δ 10.51 (s, 1H), 8.92 (s, 1H), 8.60 (s, 1H), 8.14 (s, 1H), 8.10-8.05 (m, 1H), 7.91 (s, 1H), 7.49-7.46 (m, 1H), 7.42-7.38 (m, 1H), 7.35-7.33 (m, 1H), 7.02 (s, 1H), 6.71 (s, 1H), 3.77 (s, 3H), 3.35 (s, 3H), 2.12 (s, 3H). MS (ESI) m/e [M + 1]$^+$ 469. |
| Q10 | 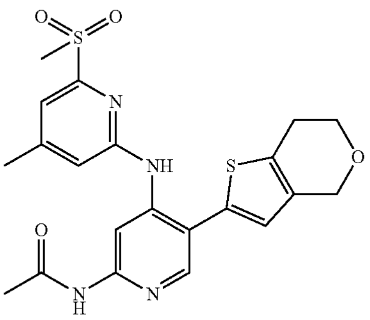 [SMILES: CC(=O)Nc1cc(Nc2cc(C)cc(S(C)(=O)=O)n2)c(-c2cc3c(s2)CCOC3)cn1] | N-(5-(6,7-dihydro-4H-thieno[3,2-c]pyran-2-yl)-4-((4-methyl-6-(methylsulfonyl)pyridin-2-yl)amino)pyridin-2-yl)acetamide | 1H NMR (400 MHz, DMSO-d6) δ 10.49 (s, 1H), 8.97 (s, 1H), 8.73 (s, 1H), 8.23 (s, 1H), 7.36 (s, 1H), 7.14 (s, 1H), 7.05 (s, 1H), 4.65-4.60 (m, 2H), 3.95-3.90 (m, 2H), 3.28 (s, 3H), 2.85-2.80 (m, 2H), 2.36 (s, 3H), 2.08 (s, 3H). MS (ESI) m/e [M + 1]$^+$ 459. |

-continued

| Example | Compound | Chemical Name | $^1$H NMR and LC/MS m/z (M + 1) |
|---|---|---|---|
| Q11 | 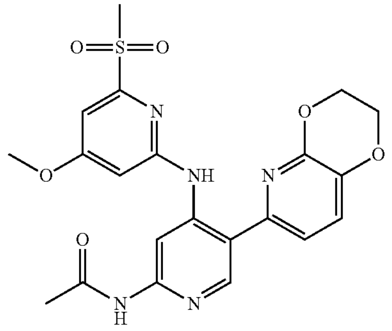 [SMILES: COc1cc(Nc2cc(NC(C)=O)ncc2-c2ccc3c(n2)OCCO3)nc(S(C)(=O)=O)c1] | N-(5-(2,3-dihydro-[1,4]dioxino[2,3-b]pyridin-6-yl)-4-((4-methoxy-6-(methylsulfonyl)pyridin-2-yl)amino)pyridin-2-yl)acetamide | MS (ESI) m/e [M + 1]$^+$ 472. |
| Q12 | 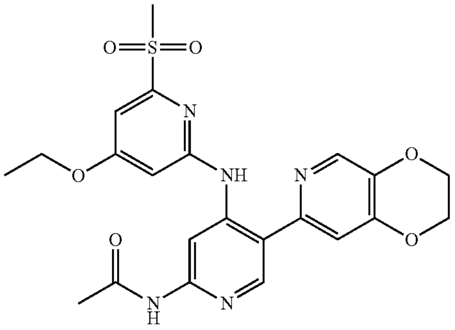 [SMILES: CCOc1cc(Nc2cc(NC(C)=O)ncc2-c2cc3c(cn2)OCCO3)nc(S(C)(=O)=O)c1] | N-(5-(2,3-dihydro-[1,4]dioxino[2,3-c]pyridin-7-yl)-4-((4-ethoxy-6-(methylsulfonyl)pyridin-2-yl)amino)pyridin-2-yl)acetamide | MS (ESI) m/e [M + 1]$^+$ 486. |
| Q13 | 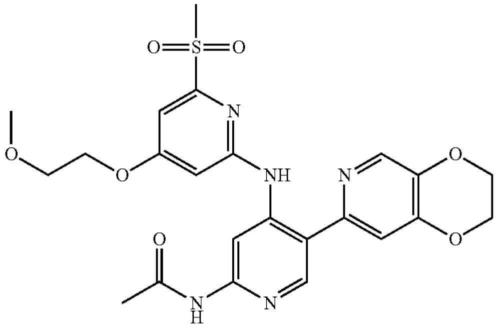 [SMILES: COCCOc1cc(Nc2cc(NC(C)=O)ncc2-c2cc3c(cn2)OCCO3)nc(S(C)(=O)=O)c1] | N-(5-(2,3-dihydro-[1,4]dioxino[2,3-c]pyridin-7-yl)-4-((4-(2-methoxyethoxy)-6-(methylsulfonyl)pyridin-2-yl)amino)pyridin-2-yl)acetamide | MS (ESI) m/e [M + 1]$^+$ 516. |
| Q14 | 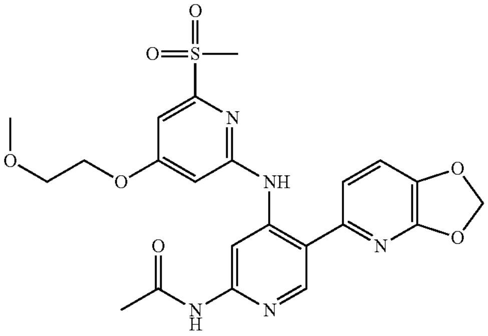 [SMILES: COCCOc1cc(Nc2cc(NC(C)=O)ncc2-c2ccc3c(n2)OCO3)nc(S(C)(=O)=O)c1] | N-(5-([1,3]dioxolo[4,5-b]pyridin-5-yl)-4-((4-(2-methoxyethoxy)-6-(methylsulfonyl)pyridin-2-yl)amino)pyridin-2-yl)acetamide | MS (ESI) m/e [M + 1]$^+$ 502. |

-continued

| Example | Compound | Chemical Name | $^1$H NMR and LC/MS m/z (M + 1) |
|---|---|---|---|
| Q15 | 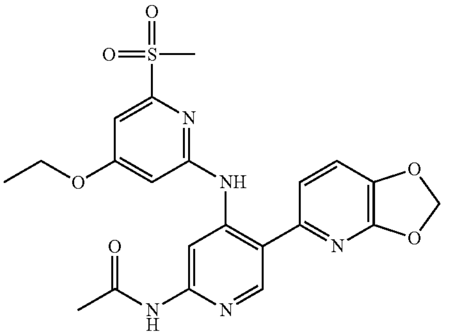 [SMILES: CCOc1cc(Nc2cc(NC(C)=O)ncc2-c2ccc3c(n2)OCO3)nc(S(C)(=O)=O)c1] | N-(5-([1,3]dioxolo[4,5-b]pyridin-5-yl)-4-((4-ethoxy-6-(methylsulfonyl)pyridin-2-yl)amino)pyridin-2-yl)acetamide | MS (ESI) m/e [M + 1]$^+$ 472. |
| Q16 | 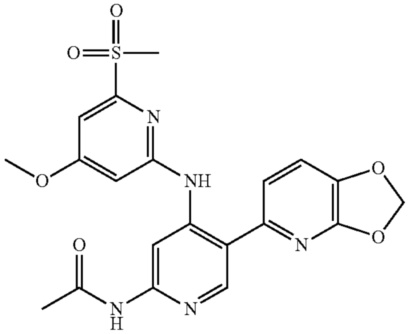 [SMILES: COc1cc(Nc2cc(NC(C)=O)ncc2-c2ccc3c(n2)OCO3)nc(S(C)(=O)=O)c1] | N-(5-([1,3]dioxolo[4,5-b]pyridin-5-yl)-4-((4-methoxy-6-(methylsulfonyl)pyridin-2-yl)amino)pyridin-2-yl)acetamide | MS (ESI) m/e [M + 1]$^+$ 458. |
| Q17 | 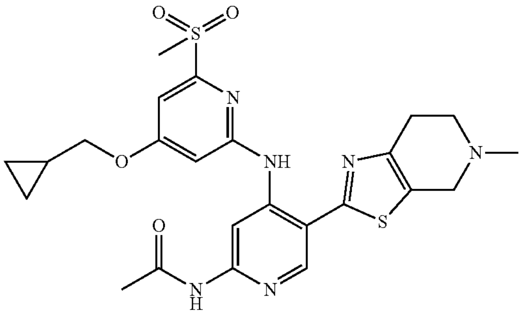 [SMILES: CC(=O)Nc1cc(Nc2cc(OCC3CC3)cc(S(C)(=O)=O)n2)c(-c2nc3c(s2)CN(C)CC3)cn1] | N-(4-((4-(cyclopropylmethoxy)-6-(methylsulfonyl)pyridin-2-yl)amion)-5-(5-methyl-4,5,6,7-tetrahydrothiazolo[5,4-c]pyridin-2-yl)pyridin-2-yl)acetamide | MS (ESI) m/e [M + 1]$^+$ 529 |
| Q18 | 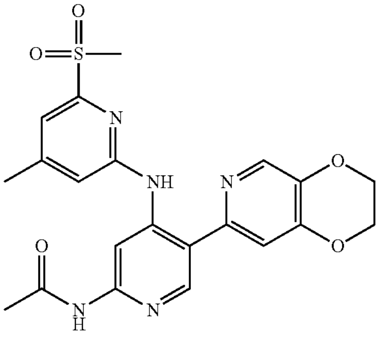 [SMILES: CC(=O)Nc1cc(Nc2cc(C)cc(S(C)(=O)=O)n2)c(-c2cc3c(cn2)OCCO3)cn1] | N-(5-(2,3-dihydro-[1,4]dioxino[2,3-c]pyridin-7-yl)-4-((4-methyl-6-(methylsulfonyl)pyridin-2-yl)amino)pyridin-2-yl)acetamide | Molecular Weight: 455 |

-continued

| Example | Compound | Chemical Name | $^1$H NMR and LC/MS m/z (M + 1) |
|---|---|---|---|
| Q19 | 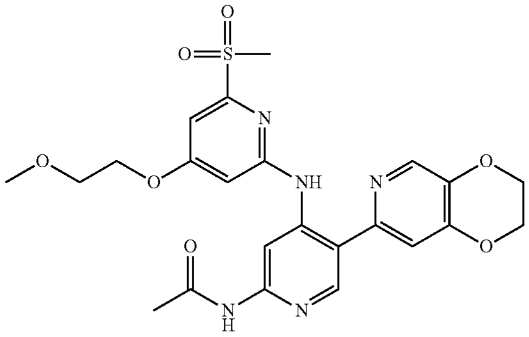 [SMILES: COCCOc1cc(Nc2cc(NC(C)=O)ncc2-c2cc3c(cn2)OCCO3)nc(S(C)(=O)=O)c1] | N-(5-(2,3-dihydro-[1,4]dioxino[2,3-c]pyridin-7-yl)-4-((4-(2-methoxyethoxy)-6-(methylsulfonyl)pyridin-2-yl)amino)pyridin-2-yl)acetamide | Molecular Weight: 516 |
| Q20 | 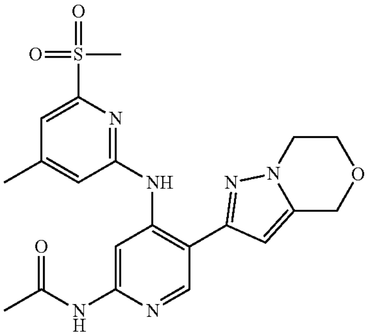 [SMILES: CC(=O)Nc1cc(Nc2cc(C)cc(S(C)(=O)=O)n2)c(-c2cc3n(n2)CCOC3)cn1] | N-(5-(6,7-dihydro-4H-pyrazolo[5,1-c][1,4]oxazin-2-yl)-4-((4-methyl-6-(methylsulfonyl)pyridin-2-yl)amino)pyridin-2-yl)acetamide | Molecular Weight: 442 |
| Q27 | 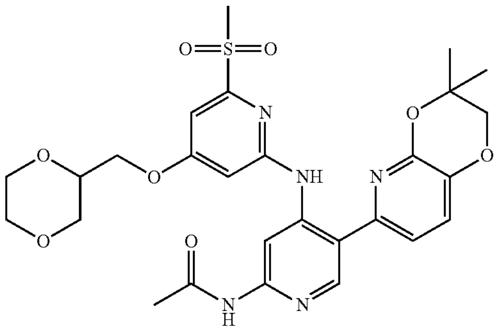 [SMILES: CC(=O)Nc1cc(Nc2cc(OCC3COCCO3)cc(S(C)(=O)=O)n2)c(-c2ccc3c(n2)OC(C)(C)CO3)cn1] | N-(4-((4-((1,4-dioxan-2-yl)methoxy)-6-(methylsulfonyl)pyridin-2-yl)amino)-5-(3,3-dimethyl-2,3-dihydro-[1,4]dioxino[2,3-b]pyridin-6-yl)pyridin-2-yl)acetamide | Molecular Weight: 586 |
| Q28 | 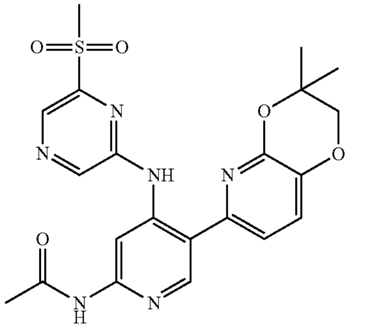 [SMILES: CC(=O)Nc1cc(Nc2cncc(S(C)(=O)=O)n2)c(-c2ccc3c(n2)OC(C)(C)CO3)cn1] | N-(5-(3,3-dimethyl-2,3-dihydro-[1,4]dioxino[2,3-b]pyridine-6-yl)-4-((6-(methylsulfonyl)pyrazin-2-yl)amino)pyridine-2-yl)acetamide | Molecular Weight: 471 |

-continued

| Example | Compound | Chemical Name | $^1$H NMR and LC/MS m/z (M + 1) |
|---|---|---|---|
| Q29 | 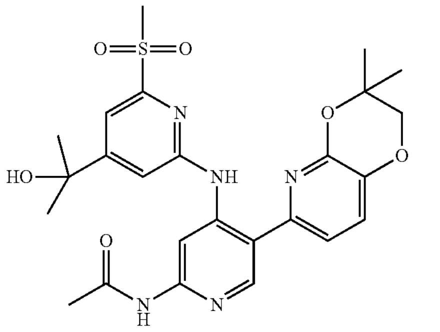 [SMILES: CC(=O)Nc1cc(Nc2cc(C(C)(C)O)cc(S(C)(=O)=O)n2)c(-c2ccc3c(n2)OC(C)(C)CO3)cn1] | N-(5-(3,3-dimethyl-2,3-dihydro-[1,4]dioxino[2,3-b]yridine-6-yl)-4-((4-(2-hydroxypropan-2-yl)-6-(methylsulfonyl)pyridine-2-yl)amino)pyridine-2-yl)acetamide | Molecular Weight: 528 |
| Q30 | 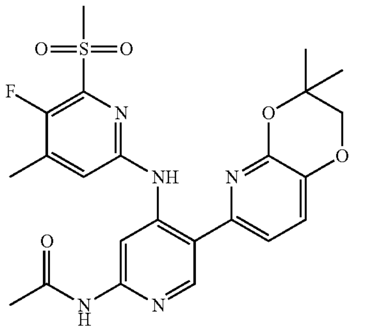 [SMILES: CC(=O)Nc1cc(Nc2cc(C)c(F)c(S(C)(=O)=O)n2)c(-c2ccc3c(n2)OC(C)(C)CO3)cn1] | N-(5-(3,3-dimethyl-2,3-dihydro-[1,4]dioxino[2,3-b]pyridine-6-yl)-4-((5-fluoro-4-methyl-6-(methylsulfonyl)pyridine-2-yl)amino)pyridine-2-yl)acetamide | Molecular Weight: 502 |
| Q39 | 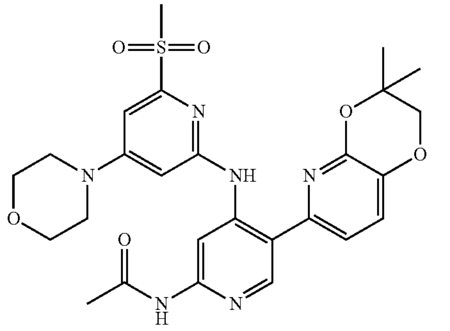 [SMILES: CC(=O)Nc1cc(Nc2cc(N3CCOCC3)cc(S(C)(=O)=O)n2)c(-c2ccc3c(n2)OC(C)(C)CO3)cn1] | N-(5-(3,3-dimethyl-2,3-dihydro-[1,4]dioxino[2,3-b]pyridin-6-yl)-4-((6-(methylsulfonyl)-4-morpholinopyridin-2-yl)amino)pyridin-2-yl)acetamide | Molecular Weight: 555 |
| Q41 | 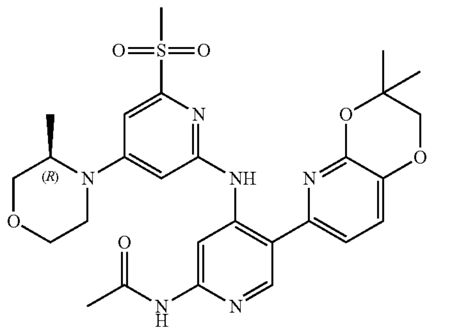 | (R)-N-(5-(3,3-dimethyl-2,3-dihydro-[1,4]dioxino[2,3-b]pyridin-6-yl)-4-((4-(3-methylmorpholino)-6-(methylsulfonyl)pyridin-2-yl)amino)pyridin-2-yl)acetamide | Molecular Weight: 569 |

-continued

| Example | Compound | Chemical Name | $^1$H NMR and LC/MS m/z (M + 1) |
|---|---|---|---|
| Q42 | 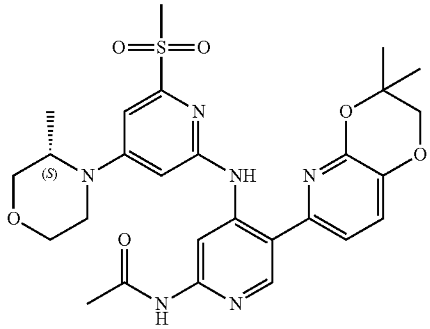 | (S)-N-(5-(3,3-dimethyl-2,3-dihydro-[1,4]dioxino[2,3-b]pyridin-6-yl)-4-((4-(3-methylmorpholino)-6-(methylsulfonyl)pyridin-2-yl)amino)pyridin-2-yl)acetamide | Molecular Weight: 569 |
| Q44 | 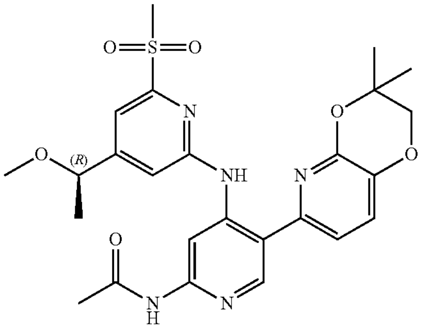 | (R)-N-(5-(3,3-dimethyl-2,3-dihydro-[1,4]dioxino[2,3-b]pyridin-6-yl)-4-((4-(1-methoxyethyl)-6-(methylsulfonyl)pyridin-2-yl)amino)pyridin-2-yl)acetamide | Molecular Weight: 528 |
| Q45 | 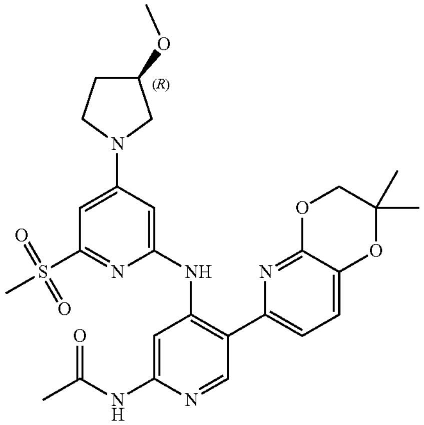 | (R)-N-(5-(2,2-dimethyl-2,3-dihydro-[1,4]dioxino[2,3-b]pyridin-6-yl)-4-((4-(3-methoxypyrrolidin-1-yl)-6-(methylsulfonyl)pyridin-2-yl)amino)pyridin-2-yl)acetamide | $^1$H NMR (400 MHz, DMSO-$d_6$) δ 11.41 (s, 1H), 10.40 (s, 1H), 8.77 (s, 1H), 8.50 (s, 1H), 7.50 (d, J = 8.4 Hz, 1H), 7.36 (d, J = 8.3 Hz, 1H), 6.71 (s, 1H), 6.15 (s, 1H), 4.18 (s, 2H), 4.05 (s, 1H), 3.47-3.34 (m, 4H), 3.26 (s, 3H), 3.22 (s, 3H), 2.03-2.01 (m, 5H), 1.29 (s, 6H). MS (ESI) m/e [M + H]$^+$ = 569. |
| Q47 | 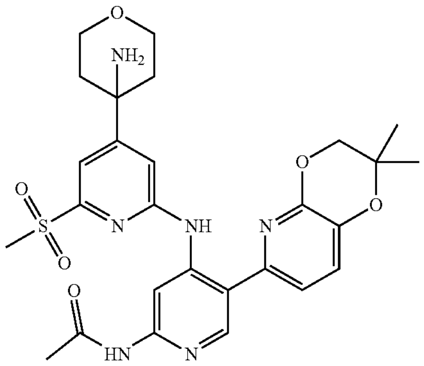 | N-(4-((4-(4-aminotetrahydro-2H-pyran-4-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | Molecular Weight: 569 |

-continued

| Example | Compound | Chemical Name | $^1$H NMR and LC/MS m/z (M + 1) |
|---|---|---|---|
| Q48 | 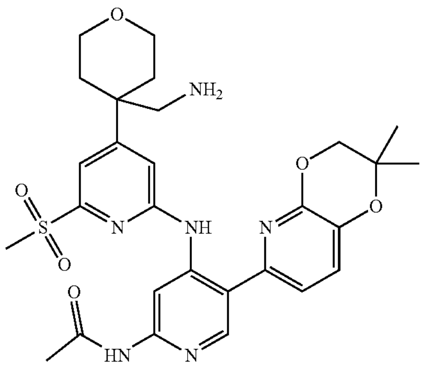 | N-(4-((4-(4-(aminomethyl)tetrahydro-2H-pyran-4-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | Molecular Weight: 583 |
| Q56 | 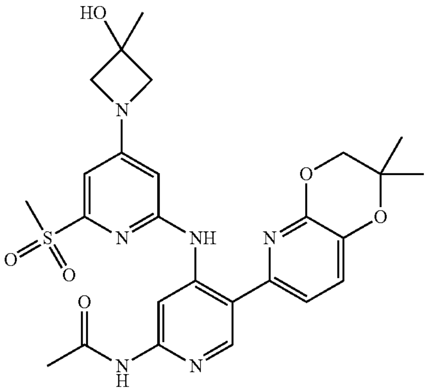 [SMILES: CC(=O)Nc1cc(Nc2cc(N3CC(C)(O)C3)cc(S(C)(=O)=O)n2)c(-c2ccc3c(n2)OCC(C)(C)O3)cn1] | N-(5-(2,2-dimethyl-2,3-dihydro-[1,4]dioxino[2,3-b]pyridin-6-yl)-4-((4-(3-hydroxy-3-methylazetidin-1-yl)-6-(methylsulfonyl)pyridin-2-yl)amino)pyrid-in-2-yl)acetamide | $^1$H NMR (400 MHz, DMSO-$d_6$) δ 11.58 (s, 1H), 10.51 (s, 1H), 8.84 (s, 1H), 8.57 (s, 1H), 7.57 (d, J = 8.4 Hz, 1H), 7.44 (d, J = 8.4 Hz, 1H), 6.63 (s, 1H), 6.04 (s, 1H), 5.78 (s, 1H), 4.25 (s, 2H), 3.95-3.90 (m, 2H), 3.86-3.84 (m, 2H), 3.34 (s, 3H), 2.11 (s, 3H), 1.45 (s, 3H), 1.36 (s, 6H). MS (ESI) m/e [M + 1]$^+$ 555. |
| Q57 | 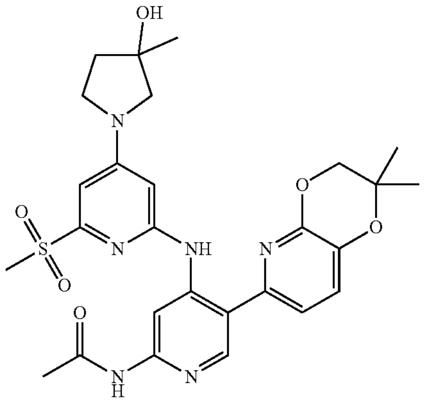 | N-(5-(2,2-dimethyl-2,3-dihydro-[1,4]dioxino[2,3-b]pyridin-6-yl)-4-((4-(3-hydroxy-3-methylpyrrolidin-1-yl)-6-(methyl sulfonyl)pyridin-2-yl)amino)pyridin-2-yl) acetamide | $^1$H NMR (400 MHz, DMSO-$d_6$) δ 11.50 (s, 1H), 10.44 (s, 1H), 8.88 (s, 1H), 8.57 (s, 1H), 7.57 (d, J = 8.0 Hz, 1H), 7.43 (d, J = 8.0 Hz, 1H), 6.72 (s, 1H), 6.14 (s, 1H), 4.93 (s, 1H), 4.25 (s, 2H), 3.50-3.45 (m, 2H), 3.34 (s, 3H), 3.30-3.25 (m, 2H), 2.09 (s, 3H), 2.00-1.95 (m, 2H), 1.36 (s, 9H). MS (ESI) m/e [M + 1]$^+$ 569. |
| Q58 | 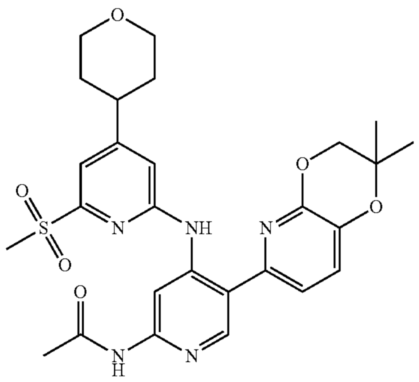 | N-(6-(2,2-dimethyl-2,3-dihydro-[1,4]dioxino[2,3-b]pyridin-6-yl)-5-((6-(methylsulfonyl)-4-(tetrahydro-2H-pyran-4-yl)pyridin-2-yl)amino)pyridazin-3-yl)acetamide | $^1$H NMR (400 MHz, DMSO-$d_6$) δ 12.89 (s, 1H), 11.07 (s, 1H), 9.48 (s, 1H), 8.24 (d, J = 8.0 Hz, 1H), 7.62-7.53 (m, 2H), 7.08 (s, 1H), 4.33 (s, 2H), 4.02-3.96 (m, 2H), 3.55-3.44 (m, 5H), 3.05-3.00 (m, 1H), 2.18 (s, 3H), 1.86-1.82 (m, 2H), 1.70-1.65 (m, 2H), 1.40 (s, 6H). MS (ESI) m/e [M + 1]$^+$ 555. |

-continued

| Example | Compound | Chemical Name | $^1$H NMR and LC/MS m/z (M + 1) |
|---|---|---|---|
| Q59 | 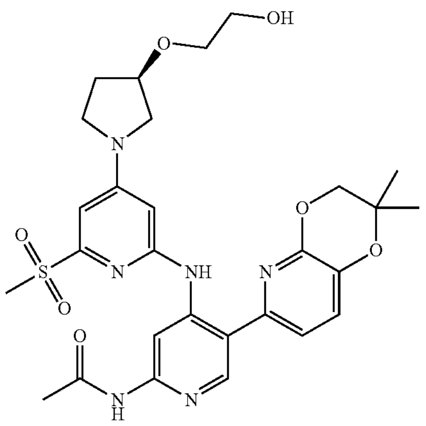 | (R)-N-(5-(2,2-dimethyl-2,3-dihydro-[1,4]dioxino[2,3-b]pyridin-6-yl)-4-((4-(3-(2-hydroxyethoxy)pyrrolidin-1-yl)-6-(methylsulfonyl)pyridin-2-yl)amino)pyridin-2-yl) acetamide | $^1$H NMR (400 MHz, DMSO-$d_6$) δ 11.54 (s, 1H), 10.65 (s, 1H), 8.73 (s, 1H), 8.55 (s, 1H), 7.56 (d, J = 8.0 Hz, 1H), 7.45 (d, J = 8.0 Hz, 1H), 6.80 (s, 1H), 6.24 (s, 1H), 4.28-4.22 (m, 2H), 3.56-3.38 (m, 9H), 3.33 (s, 3H), 2.15-2.10 (m, 5H), 1.36 (s, 6H). MS (ESI) m/e [M + 1]$^+$ 599. |
| Q60 | 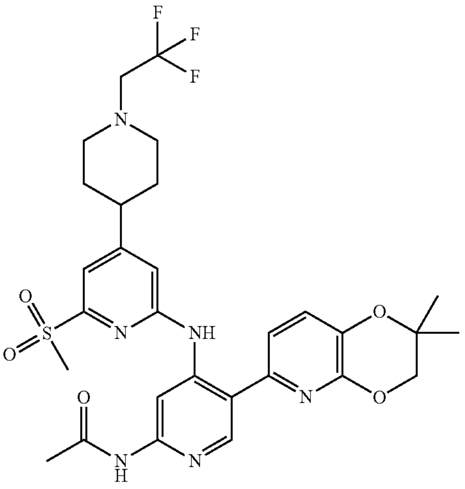 [SMILES: CC(=O)Nc1cc(Nc2cc(C3CCN(CC(F)(F)F)CC3)cc(S(C)(=O)=O)n2)c(-c2ccc3c(n2)OCC(C)(C)O3)cn1] | N-(5-(2,2-dimethyl-2,3-dihydro-[1,4]dioxino[2,3-b]pyridin-6-yl)-4-((6-(methylsulfonyl)-4-(1-(2,2,2-trifluoroethyl)piperidin-4-yl)pyridin-2-yl)amino)pyridin-2-yl) acetamide | $^1$H NMR (400 MHz, DMSO-$d_6$) δ 11.76 (s, 1H), 10.50 (s, 1H), 9.05 (s, 1H), 8.61 (s, 1H), 7.59 (d, J = 8.3 Hz, 1H), 7.46 (s, 1H), 7.44 (d, J = 8.3 Hz, 1H), 7.05 (s, 1H), 4.26 (s, 2H), 3.42 (s, 3H), 3.27-3.19 (m, 2H), 3.05-3.00 (m, 2H), 2.74-2.64 (m, 1H), 2.50-2.46 (m, 2H), 2.11 (s, 3H), 1.85-1.80 (m, 2H), 1.70-1.61 (m, 2H), 1.37 (s, 6H). MS (ESI) m/e [M + 1]$^+$ 635. |
| Q61 | 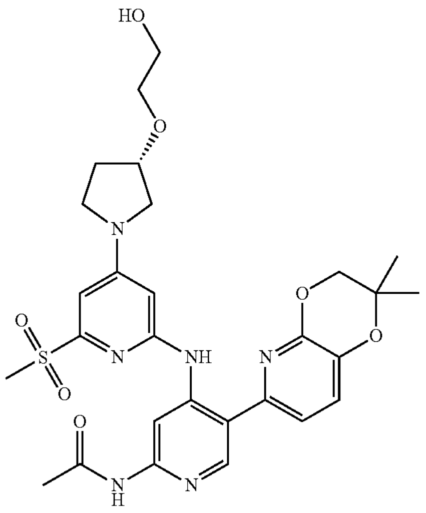 | (S)-N-(5-(2,2-dimethyl-2,3-dihydro-[1,4]dioxino[2,3-b]pyridin-6-yl)-4-((4-(3-(2-hydroxyethoxy)pyrrolidin-1-yl)-6-(methylsulfonyl)pyridin-2-yl)amino)pyridin-2-yl)acetamide | $^1$H NMR (400 MHz, DMSO-$d_6$) δ 11.49 (s, 1H), 10.45 (s, 1H), 8.86 (s, 1H), 8.57 (s, 1H), 7.57 (d, J = 8.0 Hz, 1H), 7.43 (d, J = 8.0 Hz, 1H), 6.78 (s, 1H), 6.21 (s, 1H), 4.62-4.60 (m, 1H), 4.25-4.20 (m, 3H), 3.54-3.49 (m, 6H), 3.43-3.41 (m, 4H), 3.35-3.32 (m, 1H), 2.12-2.10 (m, 5H), 1.36 (s, 6H). MS (ESI) m/e [M + 1]$^+$ 599. |

-continued

| Example | Compound | Chemical Name | $^1$H NMR and LC/MS m/z (M + 1) |
|---|---|---|---|
| Q62 | 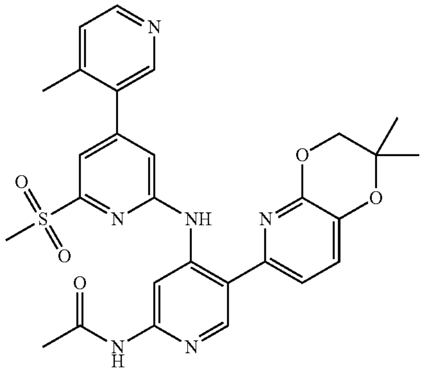 | N-(5-(2,2-dimethyl-2,3-dihydro-[1,4]dioxino[2,3-b]pyridin-6-yl)-4-((4-methyl-6'-(methylsulfonyl)-[3,4'-bipyridin]-2'-yl)amino)pyridin-2-yl)acetamide | $^1$H NMR (400 MHz, DMSO-$d_6$) δ 12.01 (s, 1H), 10.54 (s, 1H), 9.16 (s, 1H), 8.65 (s, 1H), 8.55 (d, J = 4.0 Hz, 1H), 8.52 (s, 1H), 7.61 (d, J = 8.0 Hz, 1H), 7.54 (s, 1H), 7.46-7.40 (m, 2H), 7.17 (s, 1H), 4.20 (s, 2H), 3.50 (s, 3H), 2.34 (s, 3H), 2.13 (s, 3H), 1.33 (s, 6H). MS (ESI) m/e [M + 1]$^+$ 561. |
| Q64 | 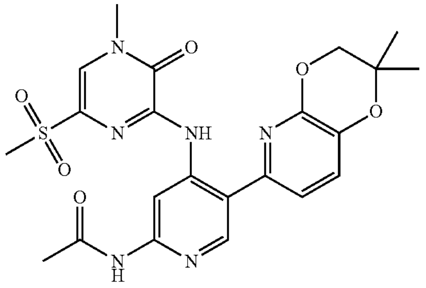 | N-(5-(2,2-dimethyl-2,3-dihydro-[1,4]dioxino[2,3-b]pyridin-6-yl)-4-((4-methyl-6-(methylsulfonyl)-3-oxo-3,4-dihydropyrazin-2-yl)amino)pyridin-2-yl)acetamide | [M + 1]$^+$ 501 |
| Q65 | 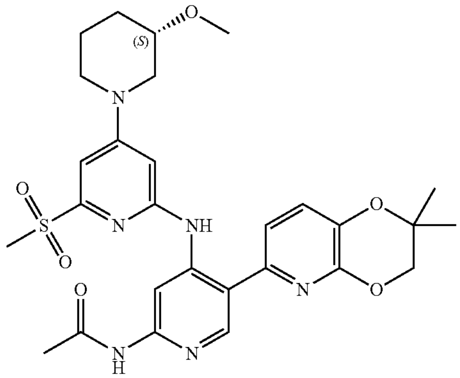 | (S)-N-(5-(2,2-dimethyl-2,3-dihydro-[1,4]dioxino[2,3-b]pyridin-6-yl)-4-((4-(3-methoxypiperidin-1-yl)-6-(methylsulfonyl)pyridin-2-yl)amino)pyridin-2-yl)acetamide | $^1$H NMR (400 MHz, DMSO-$d_6$) δ 11.52 (s, 1H), 10.43 (s, 1H), 8.95 (s, 1H), 8.57 (s, 1H), 7.57 (d, J = 8.4 Hz, 1H), 7.43 (d, J = 8.3 Hz, 1H), 7.05 (d, J = 1.8 Hz, 1H), 6.48 (d, J = 1.8 Hz, 1H), 4.22 (s, 2H), 3.72 (d, J = 12.7 Hz, 1H), 3.66-3.50 (m, 1H), 3.36 (s, 3H), 3.33-3.19 (m, 6H), 2.10 (s, 3H), 1.98-1.87 (m, 1H), 1.75-1.73 (m, 1H), 1.55-1.43 (m, 2H), 1.36 (s, 6H). MS (ESI) m/e [M + 1]$^+$ 583 |
| Q66 | 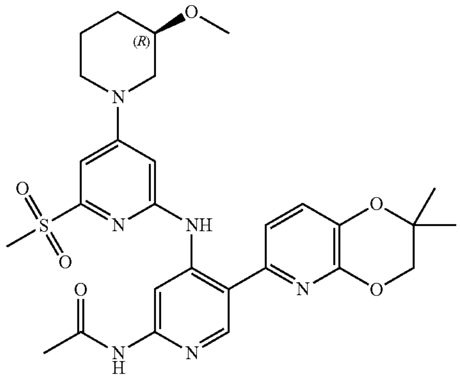 | (R)-N-(5-(2,2-dimethyl-2,3-dihydro-[1,4]dioxino[2,3-b]pyridin-6-yl)-4-((4-(3-methoxypiperidin-1-yl)-6-(methylsulfonyl)pyridin-2-yl)amino)pyridin-2-yl)acetamide | $^1$H NMR (400 MHz, DMSO-$d_6$) δ 11.51 (s, 1H), 10.43 (s, 1H), 8.94 (s, 1H), 8.57 (s, 1H), 7.57 (d, J = 8.4 Hz, 1H), 7.43 (d, J = 8.3 Hz, 1H), 7.05 (d, J = 1.7 Hz, 1H), 6.48 (d, J = 1.7 Hz, 1H), 4.21 (s, 2H), 3.73 (d, J = 11.3 Hz, 1H), 3.58-3.52 (m, 1H), 3.36 (s, 3H), 3.32-3.19 (m, 5H), 2.09 (s, 3H), 1.96-1.89 (m, 1H), 1.76-1.74 (m, 1H), 1.63-1.42 (m, 2H), 1.35 (s, 6H). MS (ESI) m/e [M + 1]$^+$ 583 |

-continued

| Example | Compound | Chemical Name | $^1$H NMR and LC/MS m/z (M + 1) |
|---|---|---|---|
| Q67 | 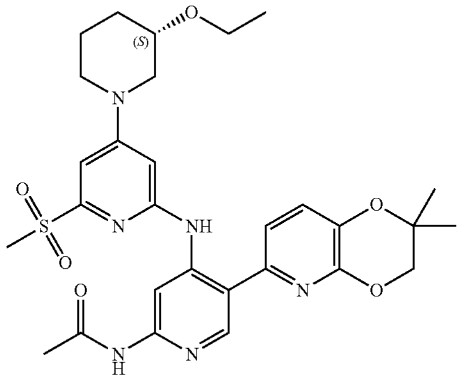 | (S)-N-(5-(2,2-dimethyl-2,3-dihydro-[1,4]dioxino[2,3-b]pyridin-6-yl)-4-((4-(3-ethoxypiperidin-1-yl)-6-(methylsulfonyl)pyridin-2-yl)amino)pyridin-2-yl)acetamide | MS (ESI) m/e [M + 1]$^+$ 597 |
| Q68 | 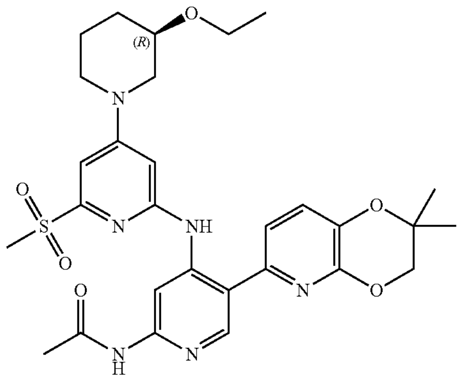 | (R)-N-(5-(2,2-dimethyl-2,3-dihydro-[1,4]dioxino[2,3-b]pyridin-6-yl)-4-((4-(3-ethoxypiperidin-1-yl)-6-(methylsulfonyl)pyridin-2-yl)amino)pyridin-2-yl)acetamide | MS (ESI) m/e [M + 1]$^+$ 597 |
| Q69 | 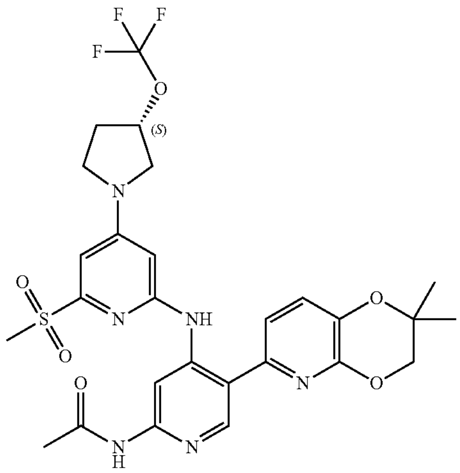 | (S)-N-(5-(2,2-dimethyl-2,3-dihydro-[1,4]dioxino[2,3-b]pyridin-6-yl)-4-((6-(methylsulfonyl)-4-(3-(trifluoromethoxy)pyrrolidin-1-yl)pyridin-2-yl)amino)pyridin-2-yl)acetamide | MS (ESI) m/e [M + 1]$^+$ 623 |

-continued

| Example | Compound | Chemical Name | ¹H NMR and LC/MS m/z (M + 1) |
|---|---|---|---|
| Q70 | 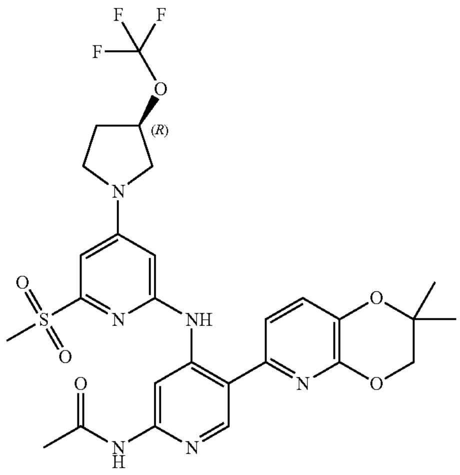 | (R)-N-(5-(2,2-dimethyl-2,3-dihydro-[1,4]dioxino[2,3-b]pyridin-6-yl)-4-((6-(methylsulfonyl)-4-(3-(trifluoromethoxy)pyrrolidin-1-yl)pyridin-2-yl)amino)pyridin-2-yl)acetamide | MS (ESI) m/e $[M + 1]^+$ 623 |
| Q71 | 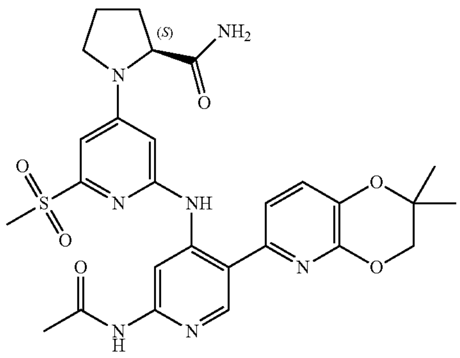 | (S)-1-(2-((2-acetamido-5-(2,2-dimethyl-2,3-dihydro-[1,4]dioxino[2,3-b]pyridin-6-yl)pyridin-4-yl)amino)-6-(methylsulfonyl)pyridin-4-yl)pyrrolidine-2-carboxamide | MS (ESI) m/e $[M + 1]^+$ 582 |
| Q72 | 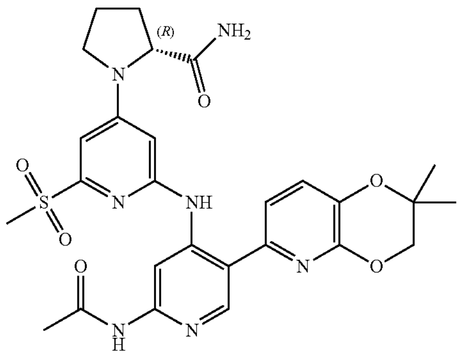 | (R)-1-(2-((2-acetamido-5-(2,2-dimethyl-2,3-dihydro-[1,4]dioxino[2,3-b]pyridin-6-yl)pyridin-4-yl)amino)-6-(methylsulfonyl)pyridin-4-yl)pyrrolidine-2-carboxamide | MS (ESI) m/e $[M + 1]^+$ 582 |

-continued

| Example | Compound | Chemical Name | $^1$H NMR and LC/MS m/z (M + 1) |
|---|---|---|---|
| Q73 | 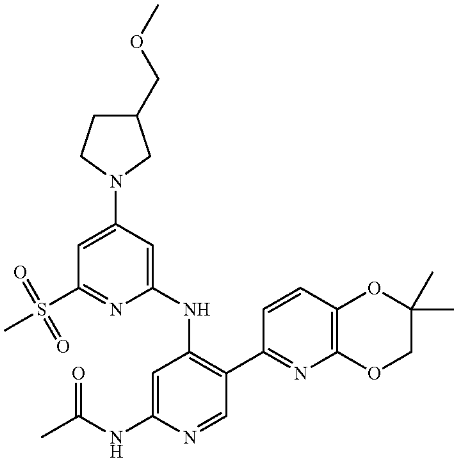 | N-(5-(2,2-dimethyl-2,3-dihydro-[1,4]dioxino[2,3-b]pyridin-6-yl)-4-((4-(3-(methoxymethyl)pyrrolidin-1-yl)-6-(methylsulfonyl)pyridin-2-yl)amino)pyridin-2-yl)acetamide | $^1$H NMR (400 MHz, DMSO-$d_6$) δ 11.45 (s, 1H), 10.43 (s, 1H), 8.88 (s, 1H), 8.56 (s, 1H), 7.57 (d, J = 8.4 Hz, 1H), 7.43 (d, J = 8.3 Hz, 1H), 6.75 (d, J = 1.5 Hz, 1H), 6.17 (s, 1H), 4.24 (s, 2H), 3.56-3.42 (m, 2H), 3.42-3.35 (m, 3H), 3.31 (s, 3H), 3.28 (s, 3H), 3.15-3.11 (m, 1H), 2.61 (m, 1H), 2.13-2.06 (m, 4H), 1.78 (m, 1H), 1.36 (s, 6H). MS (ESI) m/e [M + 1]$^+$ 583 |
| Q73A | 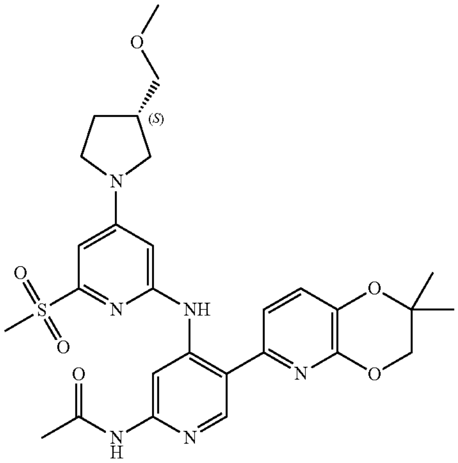 | (S)-N-(5-(2,2-dimethyl-2,3-dihydro-[1,4]dioxino[2,3-b]pyridin-6-yl)-4-((4-(3-(methoxymethyl)pyrrolidin-1-yl)-6-(methylsulfonyl)pyridin-2-yl)amino)pyridin-2-yl)acetamide | MS (ESI) m/e [M + 1]$^+$ 583 |
| Q74 | 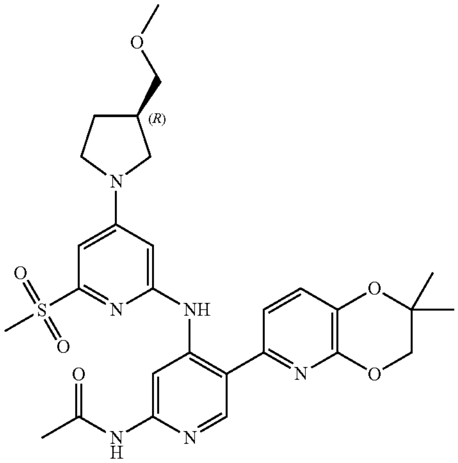 | (R)-N-(5-(2,2-dimethyl-2,3-dihydro-[1,4]dioxino[2,3-b]pyridin-6-yl)-4-((4-(3-(methoxymethyl)pyrrolidin-1-yl)-6-(methylsulfonyl)pyridin-2-yl)amino)pyridin-2-yl)acetamide | MS (ESI) m/e [M + 1]$^+$ 583 |

-continued

| Example | Compound | Chemical Name | $^1$H NMR and LC/MS m/z (M + 1) |
|---|---|---|---|
| Q75 | 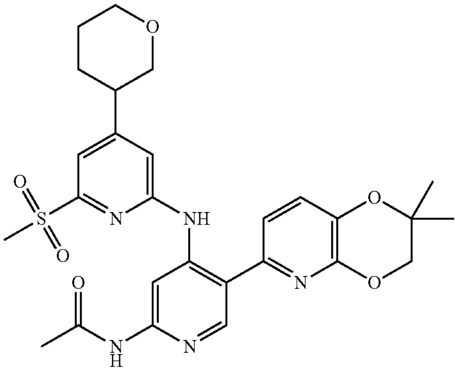 | N-(5-(2,2-dimethyl-2,3-dihydro-[1,4]dioxino[2,3-b]pyridin-6-yl)-4-((6-(methylsulfonyl)-4-(tetrahydro-2H-pyran-3-yl)pyridin-2-yl)amino)pyridin-2-yl)acetamide | $^1$H NMR (400 MHz, DMSO-$d_6$) δ 11.88 (s, 1H), 10.50 (s, 1H), 9.03 (s, 1H), 8.62 (s, 1H), 7.59 (d, J = 8.3 Hz, 1H), 7.50 (s, 1H), 7.44 (d, J = 8.3 Hz, 1H), 7.10 (s, 1H), 4.26 (s, 2H), 3.90-3.83 (m, 2H), 3.56-3.38 (m, 5H), 2.98-2.92 (m, 1H), 2.11 (s, 3H), 2.01-1.98 (m, 1H), 1.91-1.56 (m, 3H), 1.37 (s, 6H). MS (ESI) m/e [M + 1]$^+$ 554 |
| Q75A | 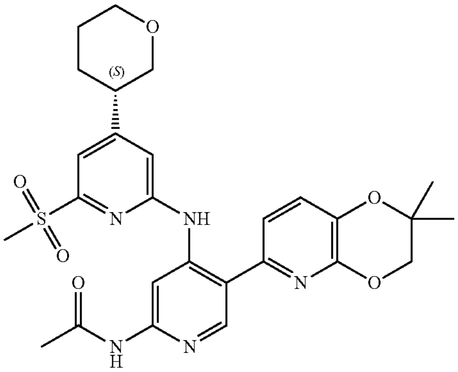 | (S)-N-(5-(2,2-dimethyl-2,3-dihydro-[1,4]dioxino[2,3-b]pyridin-6-yl)-4-((6-(methylsulfonyl)-4-(tetrahydro-2H-pyran-3-yl)pyridin-2-yl)amino)pyridin-2-yl)acetamide | MS (ESI) m/e [M + 1]$^+$ 554 |
| Q76 | 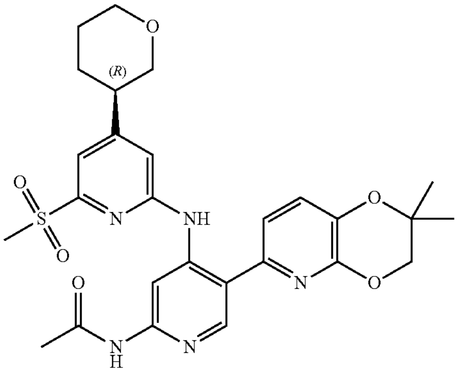 | (R)-N-(5-(2,2-dimethyl-2,3-dihydro-[1,4]dioxino[2,3-b]pyridin-6-yl)-4-((6-(methylsulfonyl)-4-(tetrahydro-2H-pyran-3-yl)pyridin-2-yl)amino)pyridin-2-yl)acetamide | MS (ESI) m/e [M + 1]$^+$ 554 |
| Q77 | 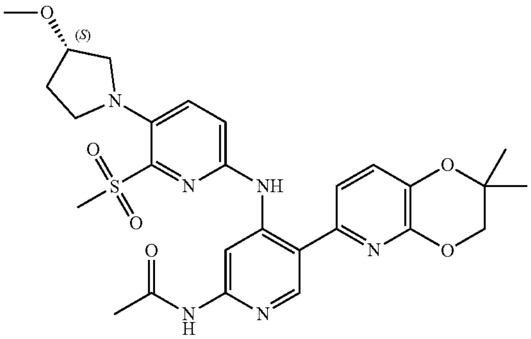 | (S)-N-(5-(2,2-dimethyl-2,3-dihydro-[1,4]dioxino[2,3-b]pyridin-6-yl)-4-((5-(3-methoxypyrrolidin-1-yl)-6-(methylsulfonyl)pyridin-2-yl)amino)pyridin-2-yl)acetamide | MS (ESI) m/e [M + 1]$^+$ 569 |

-continued

| Example | Compound | Chemical Name | $^1$H NMR and LC/MS m/z (M + 1) |
|---|---|---|---|
| Q78 | 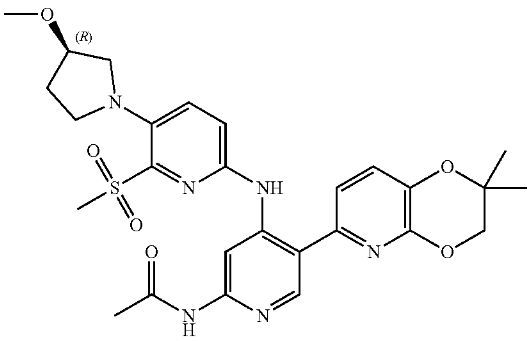 | (R)-N-(5-(2,2-dimethyl-2,3-dihydro-[1,4]dioxino[2,3-b]pyridin-6-yl)-4-((5-(3-methoxypyrrolidin-1-yl)-6-(methylsulfonyl)pyridin-2-yl)amino)pyridin-2-yl)acetamide | MS (ESI) m/e [M + 1]$^+$ 569 |
| Q79 | 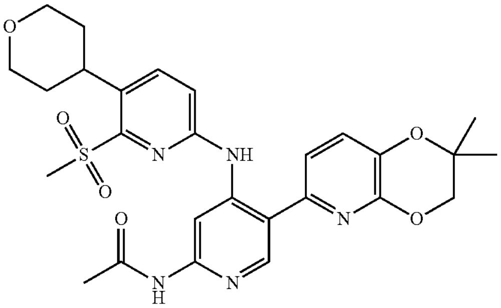 [SMILES: CC(=O)Nc1cc(Nc2ccc(C3CCOCC3)c(S(C)(=O)=O)n2)c(-c2ccc3c(n2)OCC(C)(C)O3)cn1] | N-(5-(2,2-dimethyl-2,3-dihydro-[1,4]dioxino[2,3-b]pyridin-6-yl)-4-((6-(methylsulfonyl)-5-(tetrahydro-2H-pyran-4-yl)pyridin-2-yl)amino)pyridin-2-yl)acetamide | $^1$H NMR (400 MHz, DMSO-$d_6$) δ 11.76 (s, 1H), 10.51 (s, 1H), 8.78 (s, 1H), 8.62 (s, 1H), 8.10 (d, J = 8.6 Hz, 1H), 7.58 (d, J = 8.4 Hz, 1H), 7.42 (d, J = 8.3 Hz, 1H), 7.17 (d, J = 8.6 Hz, 1H), 4.23 (s, 2H), 3.97 (dd, J = 11.2, 3.1 Hz, 2H), 3.78-3.70 (m, 1H), 3.43-3.36 (m, 5H), 2.10 (s, 3H), 1.84-1.61 (m, 4H), 1.36 (s, 6H). MS (ESI) m/e [M + 1]$^+$ 554 |
| Q80 | 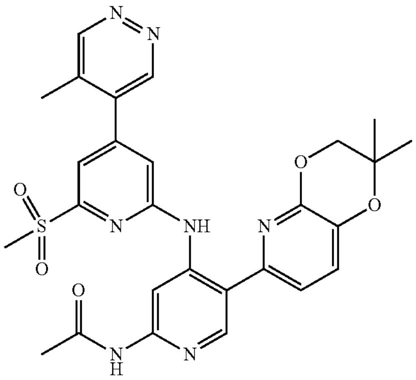 | N-(5-(2,2-dimethyl-2,3-dihydro-[1,4]dioxino[2,3-b]pyridin-6-yl)-4-((4-(5-methylpyridazin-4-yl)-6-(methylsulfonyl)pyridin-2-yl)amino)pyridin-2-yl)acetamide | MS (ESI) m/e [M + 1]$^+$ = 562. |
| Q81 | 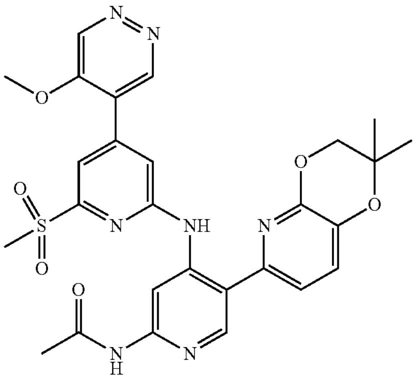 | N-(5-(2,2-dimethyl-2,3-dihydro-[1,4]dioxino[2,3-b]pyridin-6-yl)-4-((4-(5-methoxypyridazin-4-yl)-6-(methylsulfonyl)pyridin-2-yl)amino)pyridin-2-yl)acetamide | MS (ESI) m/e [M + 1]$^+$ = 578. |

-continued

| Example | Compound | Chemical Name | $^1$H NMR and LC/MS m/z (M + 1) |
|---|---|---|---|
| Q82 | 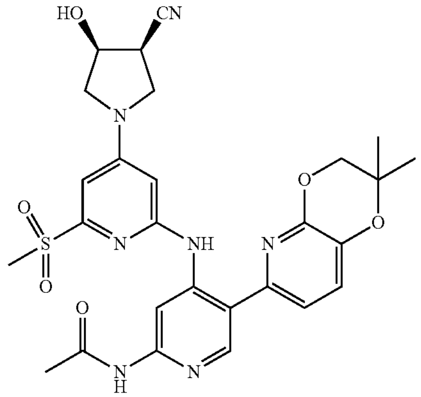 | N-(4-((4-(cis-3-cyano-4-hydroxypyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e [M + 1]$^+$ = 580. |
| Q83 | 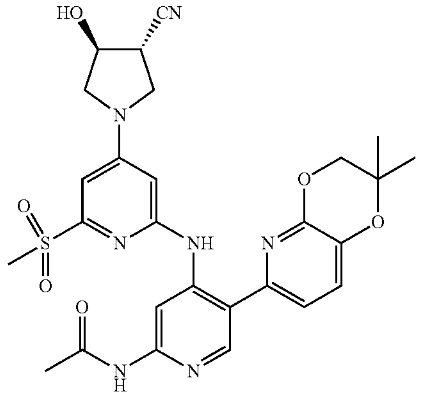 | N-(4-((4-(trans-3-cyano-4-hydroxypyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e [M + 1]$^+$ = 580. |
| Q84 | 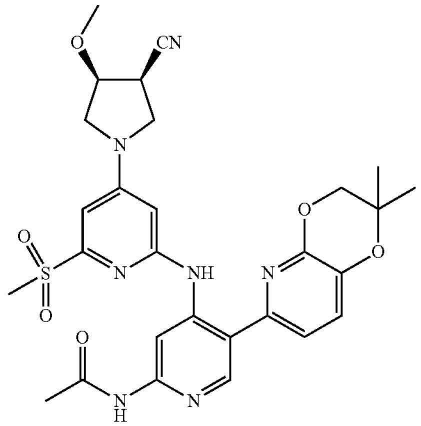 | N-(4-((4-(cis-3-cyano-4-methoxypyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e [M + 1]$^+$ = 594. |

-continued

| Example | Compound | Chemical Name | $^1$H NMR and LC/MS m/z (M + 1) |
|---|---|---|---|
| Q85 | 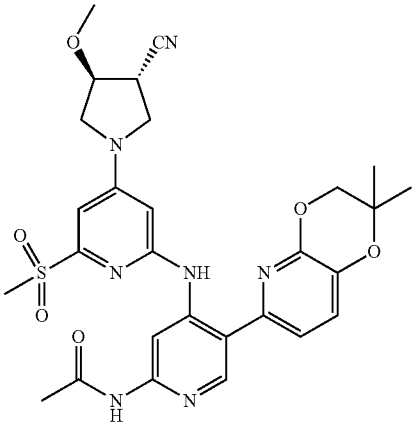 | N-(4-((4-(trans-3-cyano-4-methoxypyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e [M + 1]$^+$ = 594. |
| Q86 | 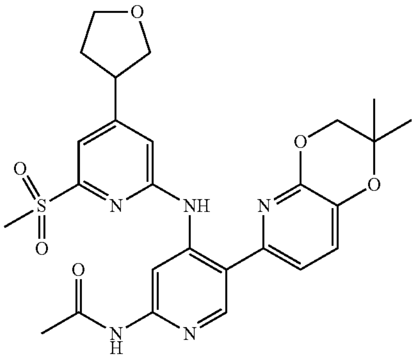 | N-(5-(2,2-dimethyl-2,3-dihydro-[1,4]dioxino[2,3-b]pyridin-6-yl)-4-((6-(methylsulfonyl)-4-(tetrahydrofuran-3-yl)pyridin-2-yl)amino)pyridin-2-yl)acetamde | MS (ESI) m/e [M + 1]$^+$ = 540. |
| Q86A | 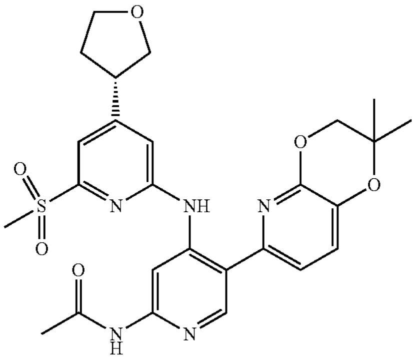 | (S)-N-(5-(2,2-dimethyl-2,3-dihydro-[1,4]dioxino[2,3-b]pyridin-6-yl)-4-((6-(methylsulfonyl)-4-(tetrahydrofuran-3-yl)pyridin-2-yl)amino)pyridin-2-yl)acetamide | MS (ESI) m/e [M + 1]$^+$ = 540. |
| Q87 | 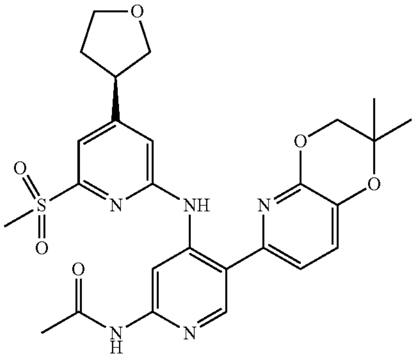 | (R)-N-(5-(2,2-dimethyl-2,3-dihydro-[1,4]dioxino[2,3-b]pyridin-6-yl)-4-((6-(methylsulfonyl)-4-(tetrahydrofuran-3-yl)pyridin-2-yl)amino)pyridin-2-yl)acetamide | MS (ESI) m/e [M + 1]$^+$ = 540. |

-continued

| Example | Compound | Chemical Name | $^1$H NMR and LC/MS m/z (M + 1) |
|---|---|---|---|
| Q88 | 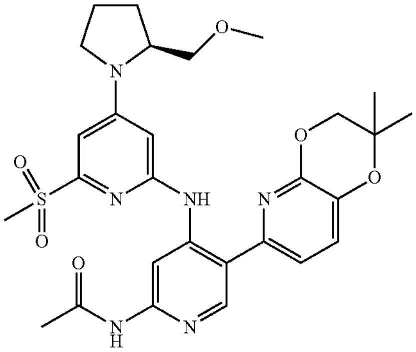 | (S)-N-(5-(2,2-dimethyl-2,3-dihydro-[1,4]dioxino[2,3-b]pyridin-6-yl)-4-((4-(2-(methoxymethyl)pyrrolidin-1-yl)-6-(methylsulfonyl)pyridin-2-yl)amino)pyridin-2-yl)acetamide | MS (ESI) m/e $[M + 1]^+$ = 583. |
| Q89 | 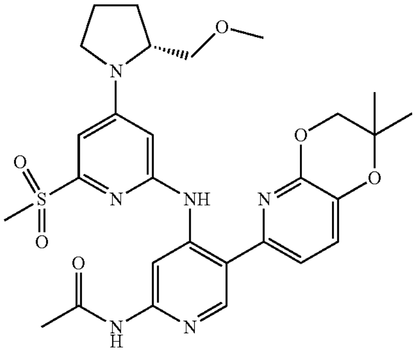 | (R)-N-(5-(2,2-dimethyl-2,3-dihydro-[1,4]dioxino[2,3-b]pyridin-6-yl)-4-((4-(2-(methoxymethyl)pyrrolidin-1-yl)-6-(methylsulfonyl)pyridin-2-yl)amino)pyridin-2-yl)acetamide | MS (ESI) m/e $[M + 1]^+$ = 583. |
| Q90 | 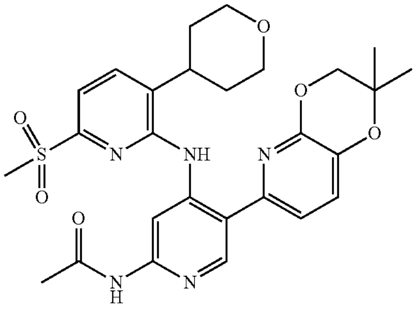 | N-(5-(2,2-dimethyl-2,3-dihydro-[1,4]dioxino[2,3-b]pyridin-6-yl)-4-((6-(methylsulfonyl)-3-(tetrahydro-2H-pyran-4-yl)pyridin-2-yl)amino)pyridin-2-yl)acetamide | MS (ESI) m/e $[M + 1]^+$ = 554. |
| Q91 | 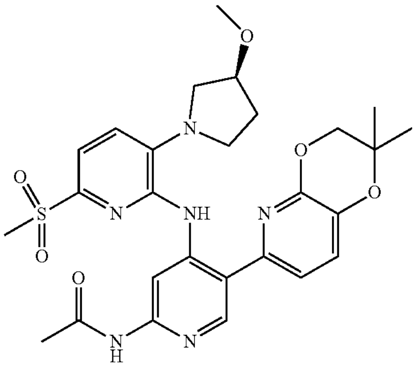 | (S)-N-(5-(2,2-dimethyl-2,3-dihydro-[1,4]dioxino[2,3-b]pyridin-6-yl)-4-((3-(3-methoxypyrrolidin-1-yl)-6-(methylsulfonyl)pyridin-2-yl)amino)pyridin-2-yl)acetamide | MS (ESI) m/e [M + 1] = 569. |

-continued

| Example | Compound | Chemical Name | $^1$H NMR and LC/MS m/z (M + 1) |
|---|---|---|---|
| Q92 | 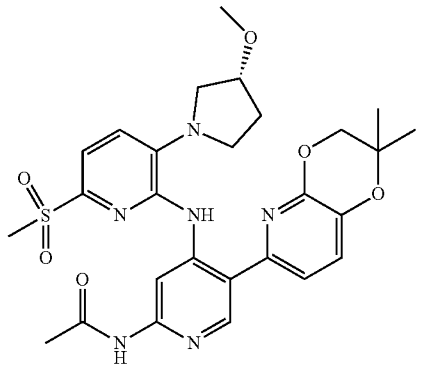 | (R)-N-(5-(2,2-dimethyl-2,3-dihydro-[1,4]dioxino[2,3-b]pyridin-6-yl)-4-((3-(3-methoxypyrrolidin-1-yl)-6-(methylsulfonyl)pyridin-2-yl)amino)pyridin-2-yl)acetamide | MS (ESI) m/e $[M + 1]^+$ = 569. |
| Q93 | 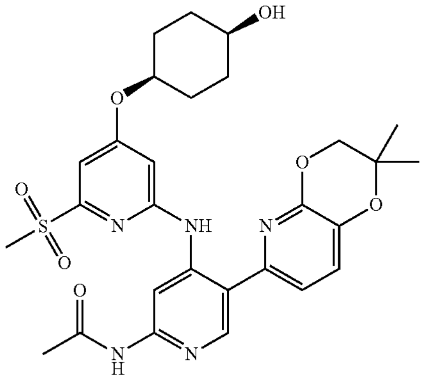 | cis-N-(5-(2,2-dimethyl-2,3-dihydro-[1,4]dioxino[2,3-dihydro-[1,4]dioxino[2,3-b]pyridin-6-yl)-4-((4-((cis-4-hydroxycyclohexyl)oxy)-6-(methylsulfonyl)pyridin-2-yl)amino)pyridin-2-yl)acetamide | MS (ESI) m/e $[M + H]^+$ = 584 |
| Q94 | 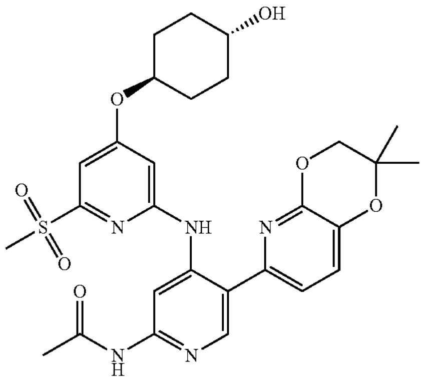 | N-(5-(2,2-dimethyl-2,3-dihydro-[1,4]dioxino[2,3-b]pyridin-6-yl)-4-((4-((trans-4-hydroxycyclohexyl)oxy)-6-(methylsulfonyl)pyridin-2-yl)amino)pyridin-2-yl)acetamide | MS (ESI) m/e $[M + H]^+$ = 584 |
| Q95 | 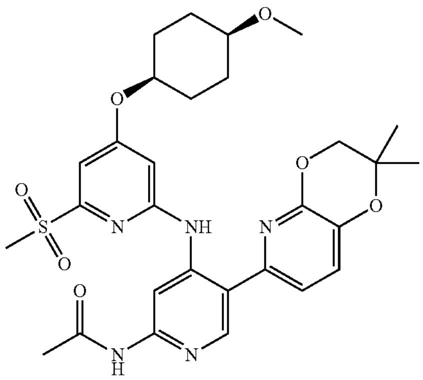 | N-(5-(2,2-dimethyl-2,3-dihydro-[1,4]dioxino[2,3-b]pyridin-6-yl)-4-((4-((cis-4-methoxycyclohexyl)oxy)-6-(methylsulfonyl)pyridin-2-yl)amino)pyridin-2-yl)acetamide | MS (ESI) m/e $[M + H]^+$ = 598 |

-continued

| Example | Compound | Chemical Name | $^1$H NMR and LC/MS m/z (M + 1) |
|---|---|---|---|
| Q96 | 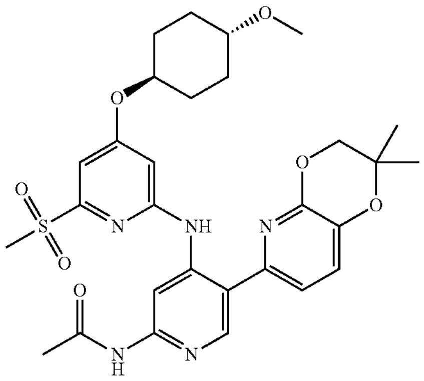 | N-(5-(2,2-dimethyl-2,3-dihydro-[1,4]dioxino[2,3-b]pyridin-6-yl)-4-((4-((trans-4-methoxycyclohexyl)oxy)-6-(methylsulfonyl)pyridin-2-yl)amino)pyridin-2-yl)acetamide | MS (ESI) m/e $[M + H]^+$ = 598 |
| Q97 | 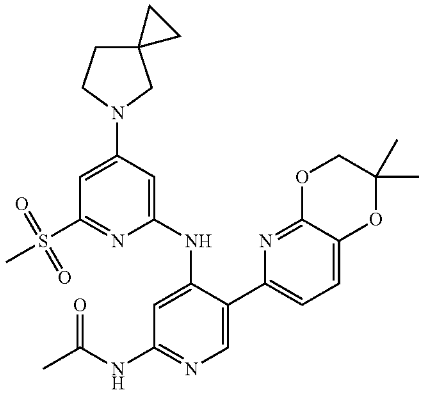 | N-(5-(2,2-dimethyl-2,3-dihydro-[1,4]dioxino[2,3-b]pyridin-6-yl)-4-((6-(methylsulfonyl)-4-(5-azaspiro[2.4]heptan-5-yl)pyridin-2-yl)amino)pyridin-2-yl)acetamide | MS (ESI) m/e $[M + H]^+$ = 565 |
| Q98 | 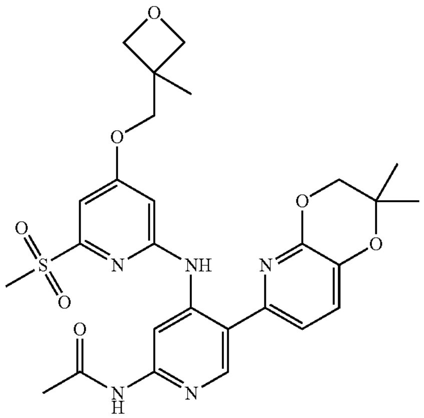 | N-(5-(2,2-dimethyl-2,3-dihydro-[1,4]dioxino[2,3-b]pyridin-6-yl)-4-((4-((3-methyloxetan-3-yl)methoxy)-6-(methylsulfonyl)pyridin-2-yl)amino)pyridin-2-yl)acetamide | $^1$H NMR (400 MHz, DMSO-$d_6$) δ 11.66 (s, 1H), 10.50 (s, 1H), 9.00 (s, 1H), 8.60 (s, 1H), 7.57 (d, J = 8.0 Hz, 1H), 7.43 (d, J = 8.0 Hz, 1H), 7.18 (s, 1H), 6.72 (s, 1H), 4.52 (s, 2H), 4.32 (s, 2H), 4.26 (s, 4H), 3.42 (s, 3H), 2.11 (s, 3H), 1.38-1.36 (m, 9H). MS (ESI) m/e $[M + 1]^+$ 570. |
| Q99 | 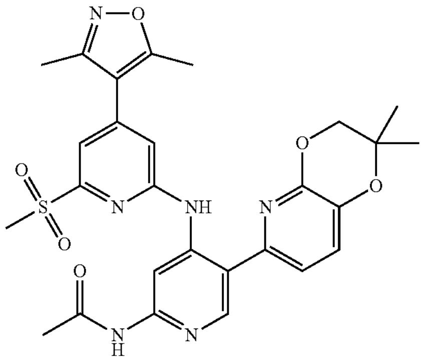 | N-(5-(2,2-dimethyl-2,3-dihydro-[1,4]dioxino[2,3-b]pyridin-6-yl)-4-((4-(3,5-dimethylisoxazol-4-yl)-6-(methylsulfonyl)pyridin-2-yl)amino)pyridin-2-yl)acetamide | MS (ESI) m/e $[M + H]^+$ = 565 |

-continued

| Example | Compound | Chemical Name | $^{1}H$ NMR and LC/MS m/z (M + 1) |
|---|---|---|---|
| Q100 | 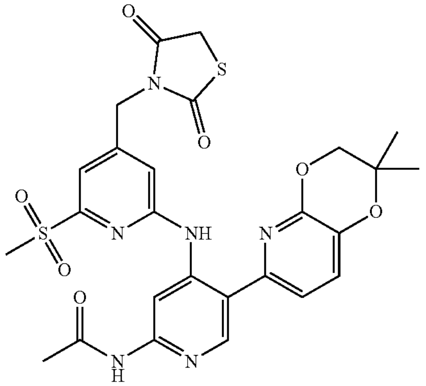 | N-(5-(2,2-dimethyl-2,3-dihydro-[1,4]dioxino[2,3-b]pyridin-6-yl)-4-((4-((2,4-dioxothiazolidin-3-yl)methyl)-6-(methylsulfonyl)pyridin-2-yl)amino)pyridin-2-yl)acetamide | MS (ESI) m/e $[M + H]^+$ = 599 |
| Q101 | 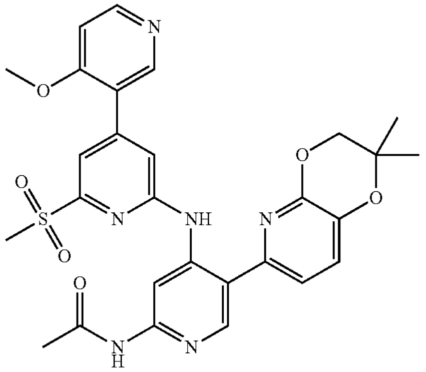 | N-(5-(2,2-dimethyl-2,3-dihydro-[1,4]dioxino[2,3-b]pyridin-6-yl)-4-((4-methoxy-6'-(methylsulfonyl)-[3,4'-bipyridin]-2'-yl)amino)pyridin-2-yl)acetamide | MS (ESI) m/e $[M + H]^+$ = 577 |
| Q102 | 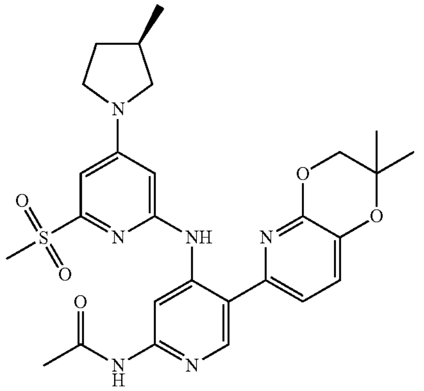 | (R)-N-(5-(2,2-dimethyl-2,3-dihydro-[1,4]dioxino[2,3-b]pyridin-6-yl)-4-((4-(3-methylpyrrolidin-1-yl)-6-(methylsulfonyl)pyridin-2-yl)amino)pyridin-2-yl)acetamide | MS (ESI) m/e $[M + H]^+$ = 553 |
| Q103 | 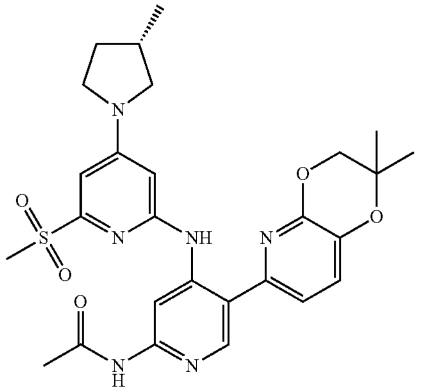 | (S)-N-(5-(2,2-dimethyl-2,3-dihydro-[1,4]dioxino[2,3-b]pyridin-6-yl)-4-((4-(3-methylpyrrolidin-1-yl)-6-(methylsulfonyl)pyridin-2-yl)amino)pyridin-2-yl)acetamide | MS (ESI) m/e $[M + H]^+$ = 553 |

-continued

| Example | Compound | Chemical Name | $^1H$ NMR and LC/MS m/z (M + 1) |
|---|---|---|---|
| Q104 | 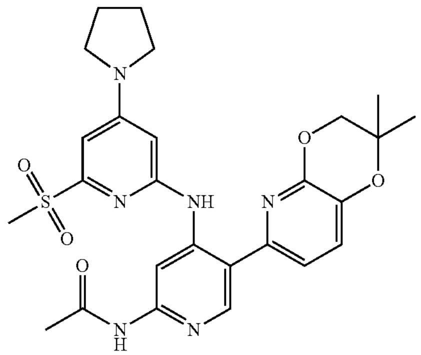 | N-(5-(2,2-dimethyl-2,3-dihydro-[1,4]dioxino[2,3-b]pyridin-6-yl)-4-((6-(methylsulfonyl)-4-(pyrrolidin-1-yl)pyridin-2-yl)amino)pyridin-2-yl)acetamide | MS (ESI) m/e $[M + H]^+$ = 539 |
| Q105 | 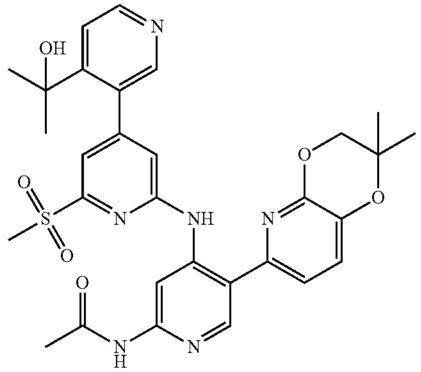 | N-(5-(2,2-dimethyl-2,3-dihydro-[1,4]dioxino[2,3-b]pyridin-6-yl)-4-((4-(2-hydroxypropan-2-yl)-6'-(methylsulfonyl)-[3,4'-bipyridin]-2'-yl)amino)pyridin-2-yl)acetamide | MS (ESI) m/e $[M + H]^+$ = 605 |
| Q106 | 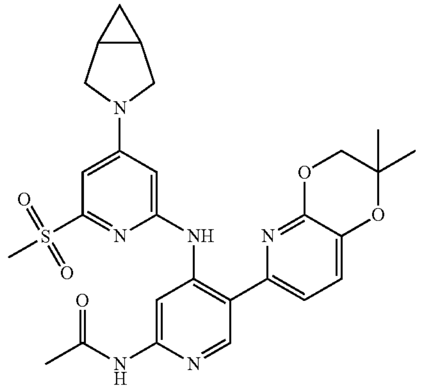 | N-(4-((4-(3-azabicyclo[3.1.0]hexan-3-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | $^1H$ NMR (400 MHz, DMSO-$d_6$) δ 11.52 (s, 1H), 10.43 (s, 1H), 8.88 (s, 1H), 8.57 (s, 1H), 7.57 (d, J = 8.4 Hz, 1H), 7.43 (d, J = 8.3 Hz, 1H), 6.75 (d, J = 1.6 Hz, 1H), 6.16 (d, J = 1.6 Hz, 1H), 4.26 (s, 2H), 3.54 (d, J = 9.9 Hz, 2H), 3.44 (d, J = 9.3 Hz, 2H), 3.33 (s, 3H), 2.10 (s, 3H), 1.76-1.74 (m, 2H), 1.36 (s, 6H), 0.83-0.78 (m, 1H), 0.21-0.19 (m, 1H). MS (ESI) m/e $[M + H]^+$ = 551. |
| Q107 | 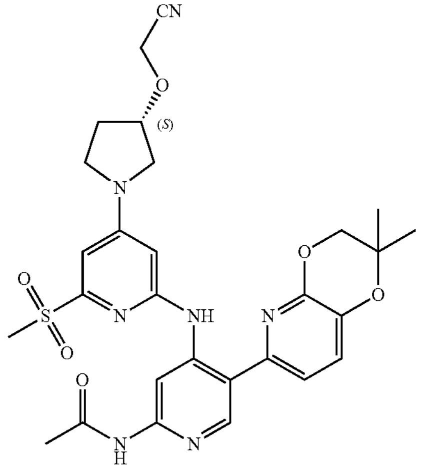 | (S)-N-(4-((4-(3-(cyanomethoxy)pyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e $[M + H]^+$ = 594 |

-continued

| Example | Compound | Chemical Name | $^1$H NMR and LC/MS m/z (M + 1) |
|---|---|---|---|
| Q108 | 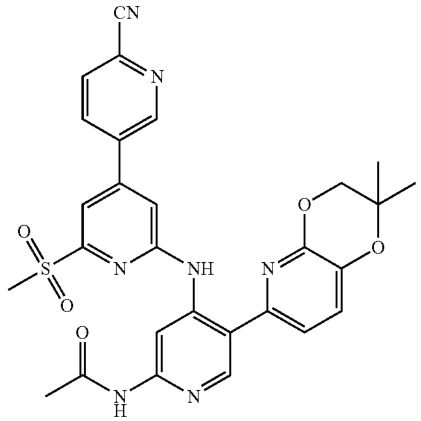 | N-(4-((6-cyano-6'-(methylsulfonyl)-[3,4'-bipyridin]-2'-yl)amino)-5-(2,2-dimethyl-2,3-dihydro-[1,4]dioxino[2,3-b]pyridin-6-yl)pyridin-2-yl)acetamide | $^1$H NMR (400 MHz, DMSO-$d_6$) δ 11.88 (s, 1H), 10.63 (s, 1H), 9.28 (d, J = 1.7 Hz, 1H), 9.12 (s, 1H), 8.70 (s, 1H), 8.61-8.59 (m, 1H), 8.31 (d, J = 8.2 Hz, 1H), 7.95 (s, 1H), 7.65-7.64 (m, 2H), 7.50 (d, J = 8.3 Hz, 1H), 4.29 (s, 2H), 3.54 (s, 3H), 2.19 (s, 3H), 1.42 (s, 6H). MS (ESI) m/e $[M + H]^+$ = 572. |
| Q109 | 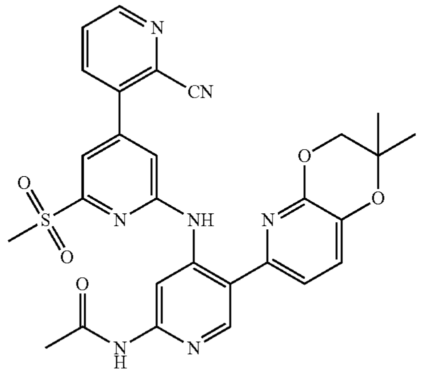 | N-(4-((2-cyano-6'-(methylsulfonyl)-[3,4'-bipyridin]-2'-yl)amino)-5-(2,2-dimethyl-2,3-dihydro-[1,4]dioxino[2,3-b]pyridin-6-yl)pyridin-2-yl)acetamide | MS (ESI) m/e $[M + H]^+$ = 572 |
| Q110 | 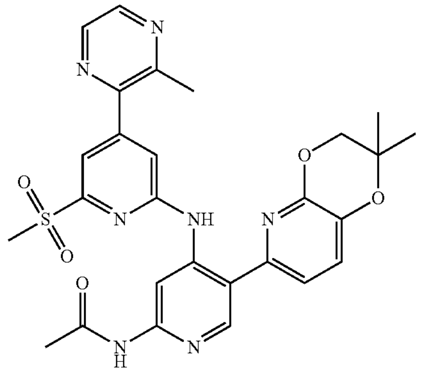 | N-(5-(2,2-dimethyl-2,3-dihydro-[1,4]dioxino[2,3-b]pyridin-6-yl)-4-((4-(3-methylpyrazin-2-yl)-6-(methylsulfonyl)pyridin-2-yl)amino)pyridin-2-yl)acetamide | $^1$H NMR (400 MHz, DMSO-$d_6$) δ 12.21 (s, 1H), 10.55 (s, 1H), 9.20 (s, 1H), 8.67 (d, J = 3.6 Hz, 3H), 7.81 (s, 1H), 7.62 (d, J = 8.4 Hz, 1H), 7.44 (d, J = 8.4 Hz, 2H), 4.23 (s, 2H), 3.52 (s, 3H), 2.69 (s, 3H), 2.13 (s, 3H), 1.35 (s, 6H). MS (ESI) m/e $[M + H]^+$ = 562. |
| Q111 | 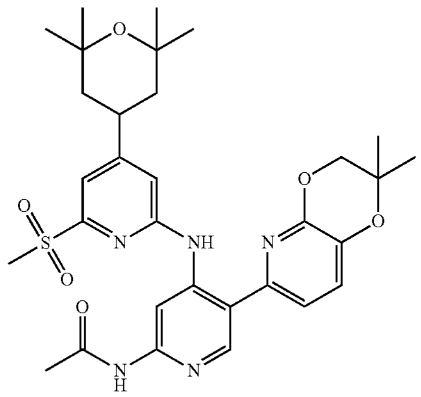 | N-(5-(2,2-dimethyl-2,3-dihydro-[1,4]dioxino[2,3-b]pyridin-6-yl)-4-((6-(methylsulfonyl)-4-(2,2,6,6-tetramethyltetrahydro-2H-pyran-4-yl)pyridin-2-yl)amino)pyridin-2-yl)acetamide | $^1$H NMR (400 MHz, DMSO-$d_6$) δ 11.80 (s, 1H), 10.51 (s, 1H), 9.03 (s, 1H), 8.61 (s, 1H), 7.58 (d, J = 8.3 Hz, 1H), 7.51 (s, 1H), 7.44 (d, J = 8.3 Hz, 1H), 7.11 (s, 1H), 4.25 (s, 2H), 3.43 (s, 3H), 3.34-3.33 (m, 1H), 2.11 (s, 3H), 1.78 (d, J = 12.7 Hz, 2H), 1.41-1.39 (m, 2H), 1.37 (s, 6H), 1.31 (s, 6H), 1.17 (s, 6H). MS (ESI) m/e $[M + H]^+$ = 610. |

-continued

| Example | Compound | Chemical Name | $^1$H NMR and LC/MS m/z (M + 1) |
|---|---|---|---|
| Q112 | 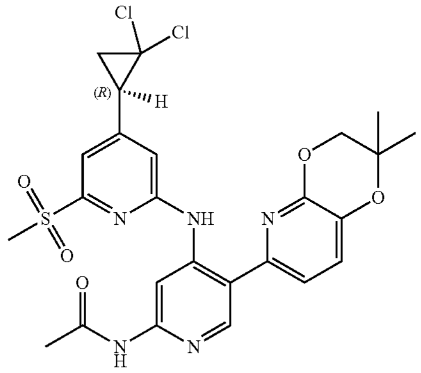 | (R)-N-(4-((4-(2,2-dichlorocyclopropyl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e [M + H]$^+$ = 578 |
| Q113 | 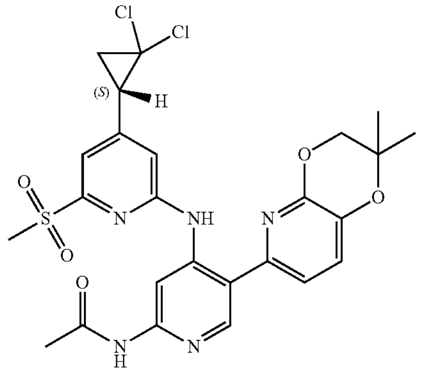 | (S)-N-(4-((4-(2,2-dichlorocyclopropyl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e [M + H]$^+$ = 578 |
| Q114 | 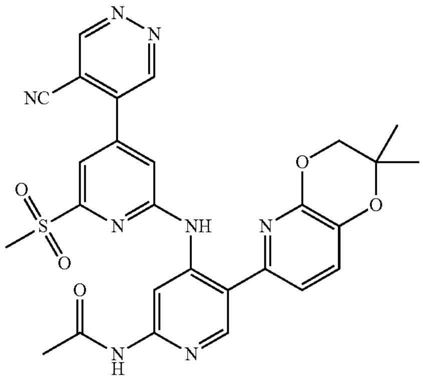 | N-(4-((4-(5-cyanopyridazin-4-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e [M + H]$^+$ = 573 |
| Q115 | 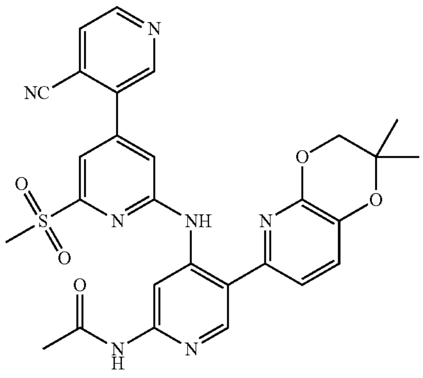 | N-(4-((4-cyano-6'-(methyslulfonyl)-[3,4'-bipyridin]-2'-yl)amino)-5-(2,2-dimethyl-2,3-dihydro-[1,4]dioxino[2,3-b]pyridin-6-yl)pyridin-2-yl)acetamide | $^1$H NMR (400 MHz, DMSO-$d_6$) δ 12.01 (s, 1H), 10.57 (s, 1H), 9.13 (s, 1H), 9.06 (s, 1H), 8.96 (d, J = 4 Hz, 1H), 8.65 (s, 1H), 8.09 (d, J = 8 Hz, 1H), 7.83 (s, 1H), 7.60 (d, J = 8 Hz, 1H), 7.48-7.38 (m, 2H), 4.20 (s, 2H), 3.50 (s, 3H), 2.13 (s, 3H), 1.34 (s, 6H). MS (ESI) m/e [M + H]$^+$ = 572 |

-continued

| Example | Compound | Chemical Name | $^1$H NMR and LC/MS m/z (M + 1) |
|---|---|---|---|
| Q116 | 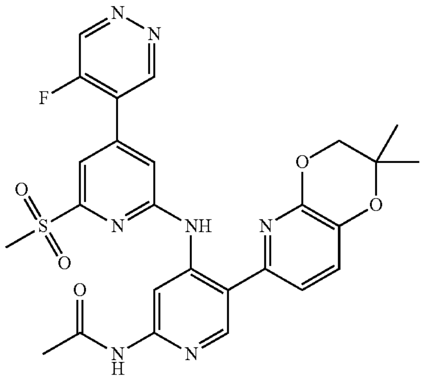 | N-(5-(2,2-dimethyl-2,3-dihydro-[1,4]dioxino[2,3-b]pyridin-6-yl)-4-((4-(5-fluoropyridazin-4-yl)-6-(methylsulfonyl)pyridin-2-yl)amino)pyridin-2-yl)acetamide | MS (ESI) m/e [M + H]$^+$ = 566 |
| Q117 | 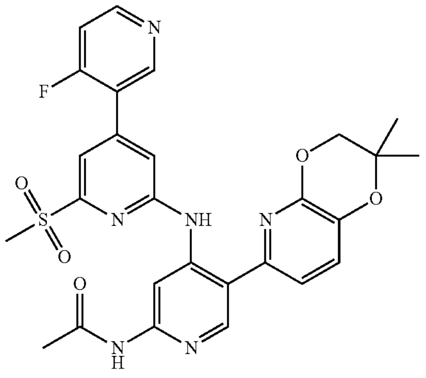 | N-(5-(2,2-dimethyl-2,3-dihydro-[1,4]dioxino[2,3-b]pyridin-6-yl)-4-((4-fluoro-6'-(methylsulfonyl)-[3,4'-bipyridin]-2'-yl)amino)pyridin-2-yl)acetamide | MS (ESI) m/e [M + H]$^+$ = 565 |
| Q118 | 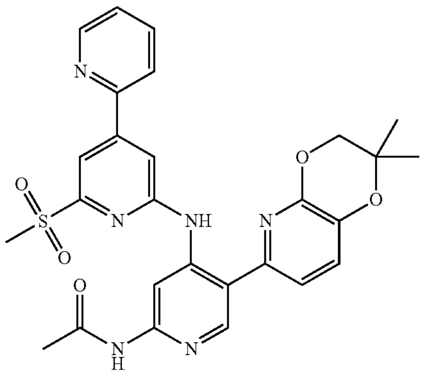 | N-(5-(2,2-dimethyl-2,3-dihydro-[1,4]dioxino[2,3-b]pyridin-6-yl)-4-((6'-(methylsulfonyl)-[2,4'-bipyridin]-2'-yl)amino)pyridin-2-yl)acetamide | MS (ESI) m/e [M + H]$^+$ = 547 |
| Q119 | 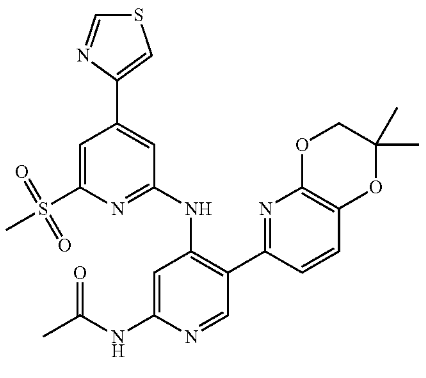 | N-(5-(2,2-dimethyl-2,3-dihydro-[1,4]dioxino[2,3-b]pyridin-6-yl)-4-((6-(methylsulfonyl)-4-(thiazol-4-yl)pyridin-2-yl)amino)pyridin-2-yl)acetamide | $^1$H NMR (400 MHz, DMSO-$d_6$) δ 11.93 (s, 1H), 10.52 (s, 1H), 9.32 (d, J = 1.7 Hz, 1H), 9.11 (s, 1H), 8.73 (d, J = 1.7 Hz, 1H), 8.64 (s, 1H), 8.06 (s, 1H), 7.78 (s, 1H), 7.60 (d, J = 8 Hz, 1H), 7.44 (d, J = 8 Hz, 1H), 4.27 (s, 2H), 3.48 (s, 3H), 2.12 (s, 3H), 1.37 (s, 6H). MS (ESI) m/e [M + H]$^+$ = 553 |

-continued

| Example | Compound | Chemical Name | $^1H$ NMR and LC/MS m/z (M + 1) |
|---|---|---|---|
| Q120 | 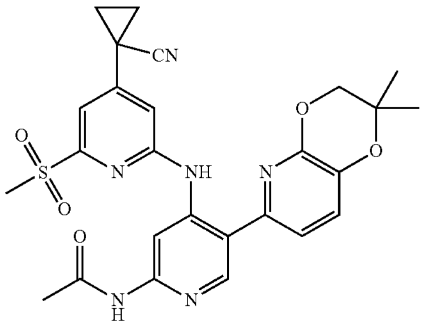 | N-(4-((4-(1-cyanocyclopropyl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | $^1H$ NMR (400 MHz, DMSO-$d_6$) 11.84 (s, 1H), 10.54 (s, 1H), 8.99 (s, 1H), 8.61 (s, 1H), 7.56 (d, J = 8 Hz, 1H), 7.43 (d, J = 8.0 Hz, 1H), 7.29 (d, J = 4.0 Hz, 1H), 7.14 (d, J = 4.0 Hz, 1H), 4.23 (s, 2H), 3.43 (s, 3H), 2.11 (s, 3H), 2.03-1.93 (m, 2H), 1.79-1.96 (m, 2H), 1.36 (s, 6H). MS (ESI) m/e $[M + H]^+$ = 535 |
| Q121 | 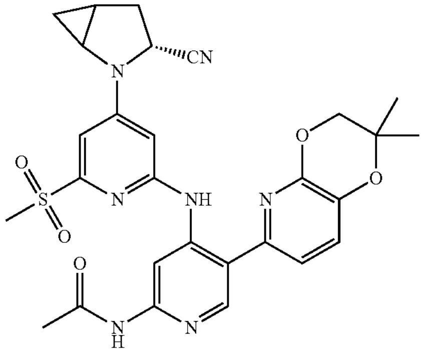 | N-(4-((4-((3R)-3-cyano-2-azabicyclo[3.1.0]hexan-2-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e $[M + H]^+$ = 576 |
| Q122 | 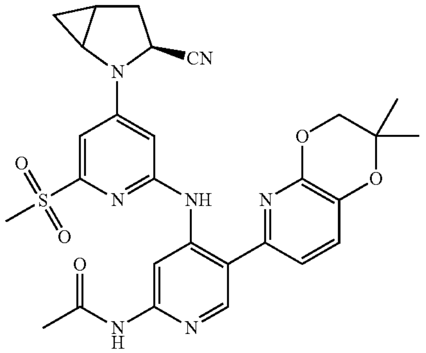 | N-(4-((4-((3S)-3-cyano-2-azabicyclo[3.1.0]hexan-2-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e $[M + H]^+$ = 576 |
| Q123 | 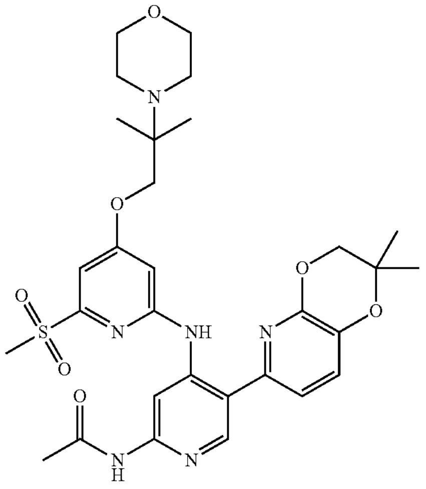 | N-(5-(2,2-dimethyl-2,3-dihydro-[1,4]dioxino[2,3-b]pyridin-6-yl)-4-((4-(2-methyl-2-morpholinopropoxy)-6-(methylsulfonyl)pyridin-2-yl)amino)pyridin-2-yl)acetamide | MS (ESI) m/e $[M + H]^+$ = 627 |

-continued

| Example | Compound | Chemical Name | $^1$H NMR and LC/MS m/z (M + 1) |
|---|---|---|---|
| Q124 | 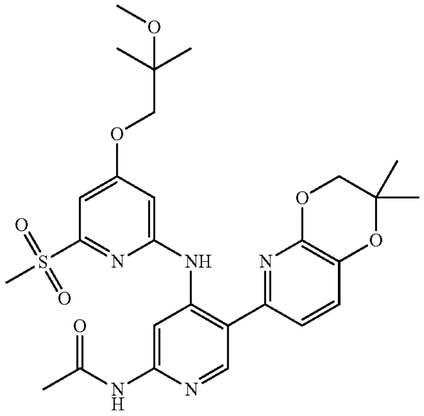 | N-(5-(2,2-dimethyl-2,3-dihydro-[1,4]dioxino[2,3-b]pyridin-6-yl)-4-((4-(2-methoxy-2-methylpropoxy)-6-(methylsulfonyl)pyridin-2-yl)amino)pyridin-2-y)acetamide | MS (ESI) m/e $[M + H]^+$ = 572 |
| Q125 | 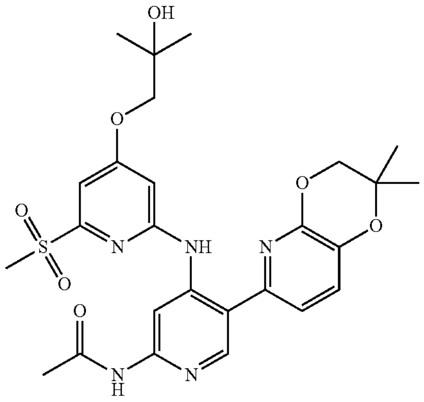 | N-(5-(2,2-dimethyl-2,3-dihydro-[1,4]dioxino[2,3-b]pyridin-6-yl)-4-((4-(2-hydroxy-2-methylpropoxy)-6-(methylsulfonyl)pyridin-2-yl)amino)pyridin-2-yl)acetamide | MS (ESI) m/e $[M + H]^+$ = 558 |
| Q126 | 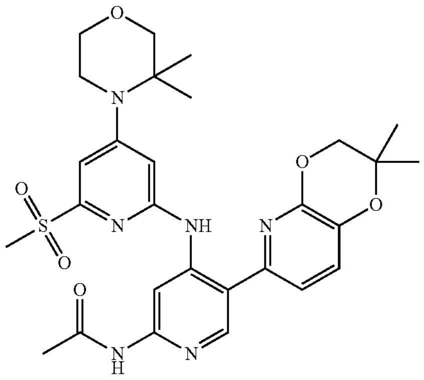 | N-(5-(2,2-dimethyl-2,3-dihydro-[1,4]dioxino[2,3-b]pyridin-6-yl)-4-((4-(3,3-dimethylmorpholino)-6-(methylsulfonyl)pyridin-2-yl)amino)pyridin-2-yl)acetamide | 1H NMR (400 MHz, DMSO-d6) δ 12.11 (s, 1H), 10.46 (s, 1H), 9.07 (s, 1H), 8.63 (s, 1H), 7.61 (d, J = 8.4 Hz, 1H), 7.44 (d, J = 8.3 Hz, 1H), 7.20 (d, J = 1.7 Hz, 1H), 6.68 (d, J = 1.8 Hz, 1H), 4.24 (s, 2H), 3.78-3.77 (m, 2H), 3.42-3.41 (m, 5H), 3.36-3.35 (m, 2H), 2.10 (s, 3H), 1.36 (s, 6H), 1.30 (s, 6H). MS (ESI) m/e [M + H]+ = 583. |
| Q127 | 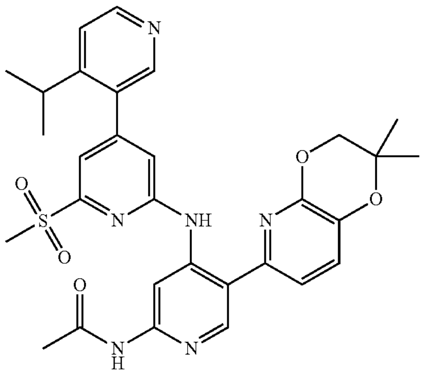 | N-(5-(2,2-dimethyl-2,3-dihydro-[1,4]dioxino[2,3-b]pyridin-6-yl)-4-((4-isopropyl-6'-(methylsulfonyl)-[3,4'-bipyridin]-2'-yl)amino)pyridin-2-yl)acetamide | $^1$H NMR (400 MHz, DMSO-$d_6$) δ 12.24 (s, 1H), 10.55 (s, 1H), 9.21 (s, 1H), 8.68 (s, 1H), 8.63 (d, J = 4 Hz, 1H), 8.47 (s, 1H), 7.64 (d, J = 8.4 Hz, 1H), 7.57 (d, J = 4 Hz, 1H), 7.53-7.36 (m, 2H), 7.11 (s, 1H), 4.18 (s, 2H), 3.53 (s, 3H), 3.01-2.96 (m, 1H), 2.13 (s, 3H), 1.33 (s, 6H), 1.21 (d, J = 8 Hz, 6H). MS (ESI) m/e $[M + H]^+$ = 589 |

-continued

| Example | Compound | Chemical Name | $^1$H NMR and LC/MS m/z (M + 1) |
|---|---|---|---|
| Q128 | 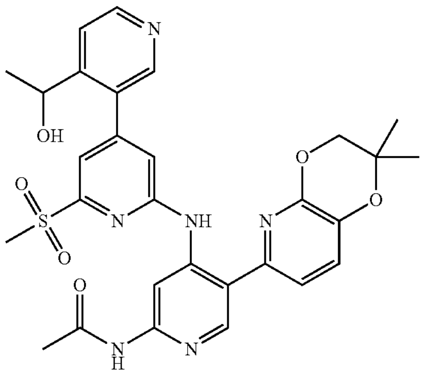 | N-(5-(2,2-dimethyl-2,3-dihydro-[1,4]dioxino[2,3-b]pyridin-6-yl)-4-((4-(1-hydroxyethyl)-6'-(methylsulfonyl)-[3,4'-bipyridin]-2'-yl)amino)pyridin-2-yl)acetamide | MS (ESI) m/e $[M + H]^+$ = 591 |
| Q129 | 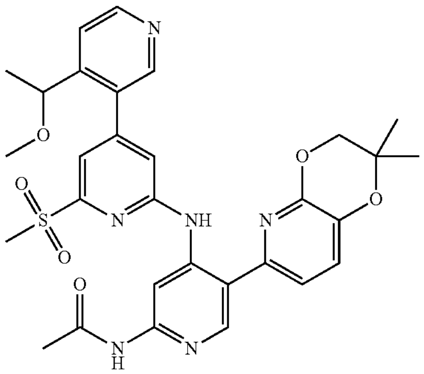 | N-(5-(2,2-dimethyl-2,3-dihydro-[1,4]dioxino[2,3-b]pyridin-6-yl)-4-((4-(1-methoxyethyl)-6'-(methylsulfonyl)-[3,4'-bipyridin]-2'-yl)amino)pyridin-2-yl)acetamide | MS (ESI) m/e $[M + H]^+$ = 605 |
| Q130 | 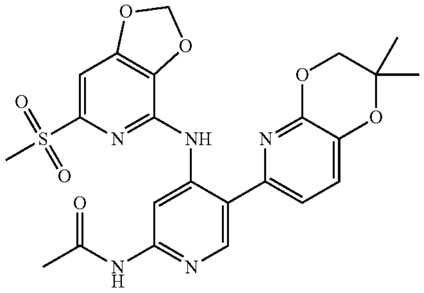 | N-(5-(2,2-dimethyl-2,3-dihydro-[1,4]dioxino[2,3-b]pyridin-6-yl)-4-((6-(methylsulfonyl)-[1,3]dioxolo[4,5-c]pyridin-4-yl)amino)pyridin-2-yl)acetamide | MS (ESI) m/e $[M + H]^+$ = 514 |
| Q131 | 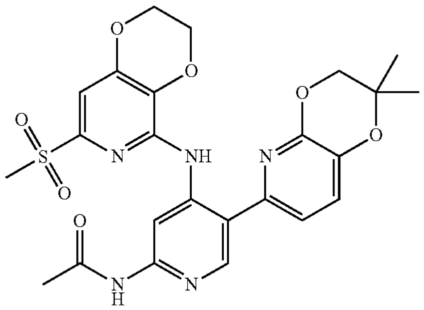 | N-(5-(2,2-dimethyl-2,3-dihydro-[1,4]dioxino[2,3-b]pyridin-6-yl)-4-((7-(methylsulfonyl)-2,3-dihydro-[1,4]dioxino[2,3-c]pyridin-5-yl)amino)pyridin-2-yl)acetamide | MS (ESI) m/e $[M + H]^+$ = 528 |

-continued

| Example | Compound | Chemical Name | $^1$H NMR and LC/MS m/z (M + 1) |
|---|---|---|---|
| Q132 | 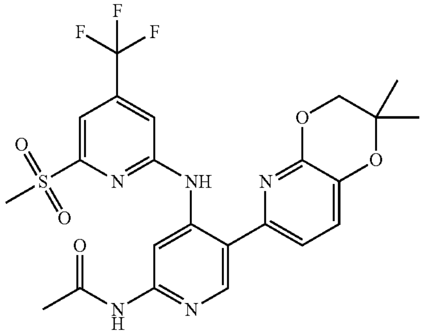 | N-(5-(2,2-dimethyl-2,3-dihydro-[1,4]dioxino[2,3-b]pyridin-6-yl)-4-((6-(methylsulfonyl)-4-(trifluoromethyl)pyridin-2-yl)amino)pyridin-2-yl)acetamide | MS (ESI) m/e $[M + H]^+$ = 538 |
| Q133 | 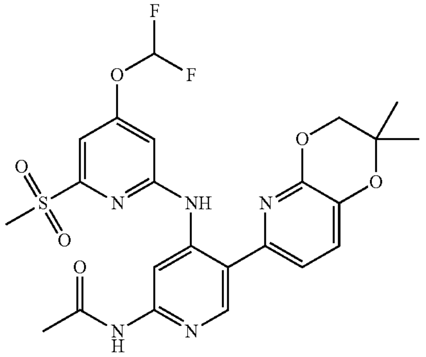 | N-(4-((4-(difluoromethoxy)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e $[M + H]^+$ = 536 |
| Q134 | 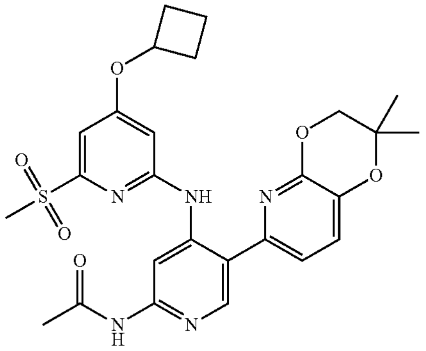 | N-(4-((4-cyclobutoxy-6-(methylsulfonyl)pyridin-2-yl)amino)-5-(2,2-dimethyl-2,3-dihydro-[1,4]dioxino[2,3-b]pyridin-6-yl)pyridin-2-yl)acetamide | MS (ESI) m/e $[M + H]^+$ = 540 |
| Q135 | 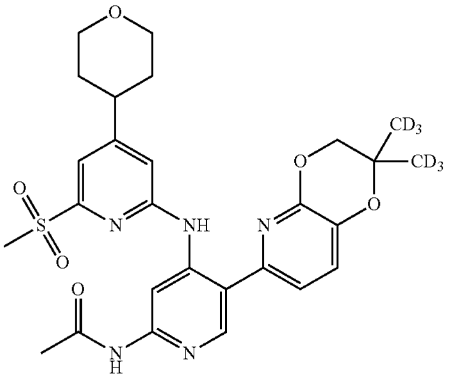 [SMILES: [2H]C([2H])([2H])C1(C([2H])([2H])[2H])COc2nc(-c3cnc(NC(C)=O)cc3Nc3cc(C4CCOCC4)cc(S(C)(=O)=O)n3)ccc2O1] | N-(5-(2,2-bis(methyl-d3)-2,3-dihydro-[1,4]dioxino[2,3-b]pyridin-6-yl)-4-((6-(methylsulfonyl)-4-(tetrahydro-2H-pyran-4-yl)pyridin-2-yl)amino)pyridin-2-yl)acetamide | MS (ESI) m/e [M + H]+ = 560 |

-continued

| Example | Compound | Chemical Name | $^1$H NMR and LC/MS m/z (M + 1) |
|---|---|---|---|
| Q136 | 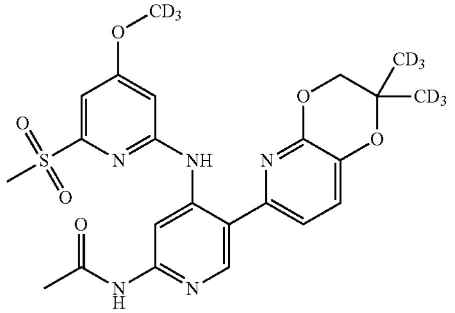 [SMILES: [2H]C([2H])([2H])Oc1cc(Nc2cc(NC(C)=O)ncc2-c2ccc3c(n2)OCC(C([2H])([2H])[2H])(C([2H])([2H])[2H])O3)nc(S(C)(=O)=O)c1] | N-(5-(2,2-bis(methyl-d3)-2,3-dihydro-[1,4]dioxino[2,3-b]pyridin-6-yl)-4-((4-(methoxy-d3)-6-(methylsulfonyl)pyridin-2-yl)amino)pyridin-2-yl)acetamide | MS (ESI) m/e [M + H]+ = 509. |

Example R1: Synthesis of N-(5-(4,4-dimethyl-4,5-dihydrothiazol-2-yl)-4-((6-(methylsulfonyl)pyridin-2-yl)amino)pyridin-2-yl)acetamide Step 1: Synthesis of methyl 6-chloro-4-(4-methoxybenzyl)amino)nicotinate

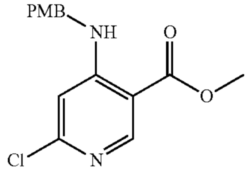

To a solution of methyl 4,6-dichloronicotinate (2 g, 9.7 mmol) and $PMBNH_2$ (2.1 g, 15.3 mmol) in DMF (20 mL) was added TEA (3 g, 29.7 mmol) at rt. The mixture was stirred at rt for 3 h. Then $H_2O$ was added and the mixture was extracted with EA. The organic layer was concentrated and the crude product was used in the next step without purification. MS (ESI) m/e $[M+H]^+$=307.

Step 2: Synthesis of 6-chloro-4-((4-methoxybenzyl)amino)nicotinic acid

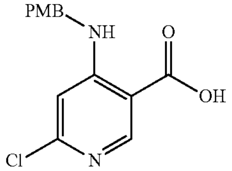

A solution of 6-chloro-4-((4-methoxybenzyl)amino)nicotinate (3.43 g, 11.2 mmol) in THF (100 mL) was added $LiOH{\cdot}H_2O$ (1.5 g, 35.7 mmol) in $H_2O$ (50 mL). The mixture was stirred at rt for overnight. The mixture was concentrated, and the aqueous layer was acidified by HCl (1N). The white solid was collected by filtration and the filter cake was washed with $H_2O$, then dried to give the desired product (2.56 g, yield 90% for two steps). MS (ESI) m/e $[M+H]^+$=293.

Step 3: Synthesis of 6-chloro-N-(1-hydroxy-2-methylpropan-2-yl)-4-((4-methoxybenzyl)amino)nicotinamide

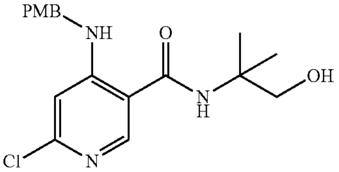

To a solution of 6-chloro-4-((4-methoxybenzyl)amino) nicotinic acid (300 mg, 1 mmol), 2-amino-2-methylpropan-1-ol (115.7 mg, 1.3 mmol), HOBT (148.5 mg, 1.1 mmol) and EDCI (383 mg, 2 mmol) in DMF (5 mL) was added DIEA (322.5 mg, 2.5 mmol) in one portion at rt. The mixture was stirred at rt for 5 h. Then the reaction was quenched with $H_2O$ and extracted with EA. The organic layer was concentrated. The crude product was purified on Prep-TLC (PE: EA=1:1) to give the desired product (90 mg, yield 24.7%) as a colorless oil. MS (ESI) m/e $[M+H]^+$=364.

Step 3: Synthesis of 6-acetamido-N-(1-hydroxy-2-methylpropan-2-yl)-4-((4-methoxybenzyl)amino) nicotinamide

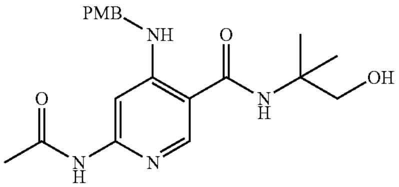

A slurry of 6-chloro-N-(1-hydroxy-2-methylpropan-2-yl)-4-((4-methoxybenzyl)amino)nicotinamide (90 mg, 0.25 mmol), acetamide (73.8 mg, 1.25 mmol), $Pd_2(dba)_3$ (22.9 mg, 0.025 mmol), Xantphos (28.9 mg, 0.05 mmol) and $Cs_2CO_3$ (163 mg, 0.05 mmol) in 1,4-dioxane (5 mL) was stirred at 120° C. under $N_2$ for 5 h. The mixture was cooled to rt and filtered through celite. The filtrate was concentrated under vacuum and the crude product was purified by Prep- TLC (DCM:MeOH=15:1) to give the desired product as a colorless oil (230 mg, crude). MS (ESI) m/e $[M+H]^+$=387.

Step 4: Synthesis of N-(5-(4,4-dimethyl-4,5-dihydrothiazol-2-yl)-4-((4-methoxybenzyl)amino)pyridin-2-yl)acetamide

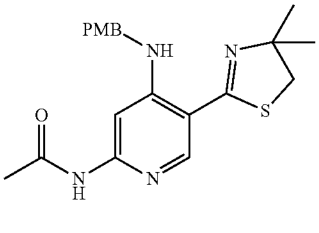

A solution of 6-acetamido-N-(1-hydroxy-2-methylpropan-2-yl)-4-((4-methoxybenzyl)amino)nicotinamide (230 mg, 0.6 mmol), Lawesson reagent (720 mg, 1.8 mmol) in dioxane (8 mL) was irritated at 100° C. under microwave for 1 h. The mixture was cooled to rt and the solvent was removed under reduced pressure. The crude product was purified by silica gel column chromatography (DCM: MeOH=15:1) to give the desired product as a yellow solid (80 mg, yield 83% for two steps). MS (ESI) m/e $[M+H]^+$ =385.

Step 5: Synthesis of N-(4-amino-5-(4,4-dimethyl-4,5-dihydrothiazol-2-yl)pyridin-2-yl)acetamide

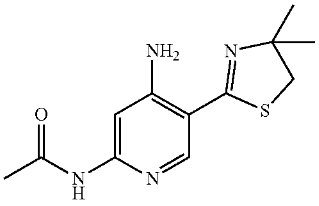 [SMILES: CC(=O)Nc1cc(N)c(C2=NC(C)(C)CS2)cn1]

A solution of N-(5-(4,4-dimethyl-4,5-dihydrothiazol-2-yl)-4-((4-methoxybenzyl)amino)pyridin-2-yl)acetamide (80 mg, 0.21 mmol) in TFA (5 mL) was stirred at 50° C. for 16 h and 70° C. for 5 h. The mixture was cooled to rt and the solvent was removed under reduced pressure. The crude product was used in the next step without further purification. MS (ESI) m/e $[M+H]^+$=265.

Step 6: Synthesis of N-(5-(4,4-dimethyl-4,5-dihydrothiazol-2-yl)-4-((6-(methylsulfonyl)pyridin-2-yl)amino)pyridin-2-yl)acetamide

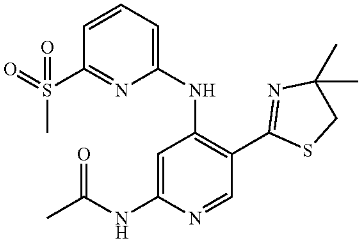 [SMILES: CC(=O)Nc1cc(Nc2cccc(S(C)(=O)=O)n2)c(C2=NC(C)(C)CS2)cn1]

A solution of N-(4-amino-5-(4,4-dimethyl-4,5-dihydrothiazol-2-yl)pyridin-2-yl)acetamide (70 mg, 0.26 mmol), 2-bromo-6-(methylsulfonyl)pyridine (94 mg, 0.4 mmol), $Pd_2(dba)_3$ (24.7 mg, 0.027 mmol), Xantphos (31 mg, 0.053 mmol) and $Cs_2CO_3$ (173 mg, 0.53 mmol) in dioxane (5 mL) was stirred at 120° C. under $N_2$ for 7 h. The mixture was cooled to rt and filtered through celite. The filtrate was concentrated under reduced pressure. The crude product was purified by silica gel column chromatography (DCM: MeOH=15:1) to give the desired product (3.19 mg, yield 3.62% for two steps) as a white solid. $^1H$ NMR (400 MHz, DMSO-$d_6$) δ 12.75 (s, TH), 10.63 (s, 1H), 9.27 (s, 1H), 8.32 (s, JH), 7.98 (t, J=7.9 Hz, TH), 7.56 (d, J=7.4 Hz, 1H), 7.17 (d, J=8.3 Hz, 1H), 3.44 (s, 3H), 3.22 (s, 2H), 2.06 (s, 3H), 1.44 (s, 6H). MS (ESI) m/e $[M+H]^+$=420.

The following Examples were prepared in a similar manner to the product Example R1:

| | | | |
|---|---|---|---|
| R2 | 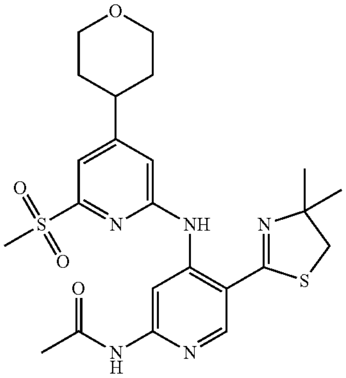 | N-(5-(4,4-dimethyl-4,5-dihydrothiazol-2-yl)-4-((6-(methylsulfonyl)-4-(tetrahydro-2H-pyran-4-yl)pyridin-2-yl)amino)pyridin-2-yl)acetamide | MS (ESI) m/e $[M + H]^+$ = 504 |

Furtherly, all the following compounds can be obtained by similar methods of preparing the example compounds disclosed in the present disclosure.

| # | Compound | Chemical Name | Molecular Weight |
|---|---|---|---|
| 1. | 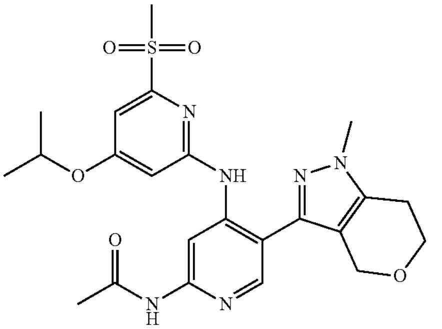 [SMILES: CC(=O)Nc1cc(Nc2cc(OC(C)C)cc(S(C)(=O)=O)n2)c(-c2nn(C)c3c2COCC3)cn1] | N-(4-((4-isopropoxy-6-(methylsulfonyl)pyridin-2-yl)amino)-5-(1-methyl-1,3a,4,6,7,7a-hexahydropyrano[4,3-c]pyrazol-3-yl)pyridin-2-yl)acetamide | Molecular Weight: 502 |
| 2. | 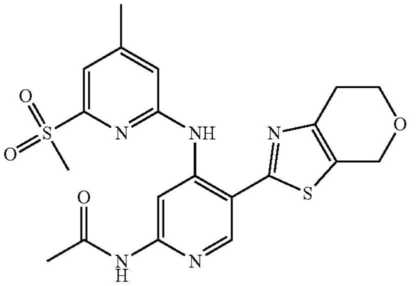 [SMILES: CC(=O)Nc1cc(Nc2cc(C)cc(S(C)(=O)=O)n2)c(-c2nc3c(s2)COCC3)cn1] | N-(5-(6,7-dihydro-4H-pyrano[4,3-d]thiazol-2-yl)-4-((4-methyl-6-(methylsulfonyl)pyridin-2-yl)amino)pyridin-2-yl)acetamide | Molecular Weight: 459 |
| 3. | 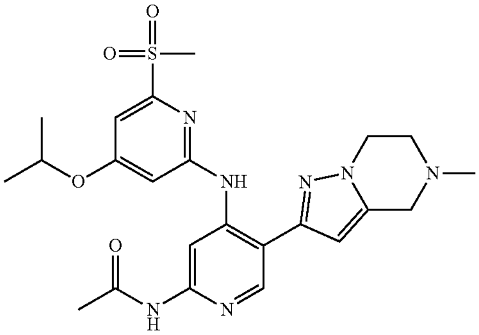 [SMILES: CC(=O)Nc1cc(Nc2cc(OC(C)C)cc(S(C)(=O)=O)n2)c(-c2cc3n(n2)CCN(C)C3)cn1] | N-(4-((4-isopropoxy-6-(methylsulfonyl)pyridin-2-yl)amino)-5-(5-methyl-4,5,6,7-tetrahydropyrazolo[1,5-a]pyrazin-2-yl)pyridin-2-yl)acetamide | Molecular Weight: 499 |
| 4. | 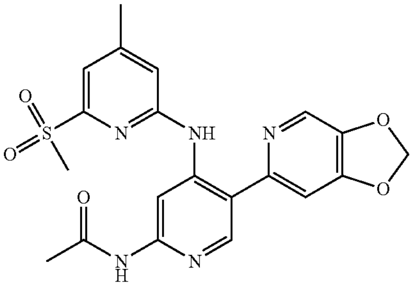 [SMILES: CC(=O)Nc1cc(Nc2cc(C)cc(S(C)(=O)=O)n2)c(-c2cc3c(cn2)OCO3)cn1] | N-(5-([1,3]dioxolo[4,5-c]pyridin-6-yl)-4-((4-methyl-6-(methylsulfonyl)pyridin-2-yl)amino)pyridin-2-yl)acetamide | Molecular Weight: 441 |
| 5. | 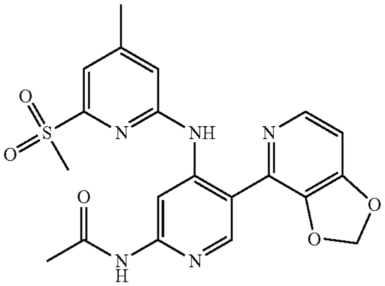 [SMILES: CC(=O)Nc1cc(Nc2cc(C)cc(S(C)(=O)=O)n2)c(-c2nccc3c2OCO3)cn1] | N-(5-([1,3]dioxolo[4,5-c]pyridin-4-yl)-4-((4-methyl-6-(methylsulfonyl)pyridin-2-yl)amino)pyridin-2-yl)acetamide | Molecular Weight: 441 |

-continued

| # | Compound | Chemical Name | Molecular Weight |
|---|---|---|---|
| 6. | 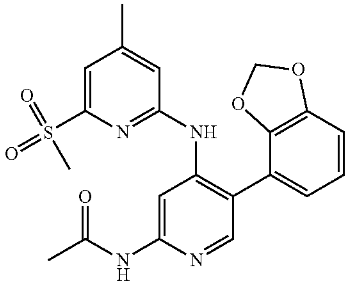 [SMILES: CC(=O)Nc1cc(Nc2cc(C)cc(S(C)(=O)=O)n2)c(-c2cccc3c2OCO3)cn1] | N-(5-(benzo[d][1,3]dioxol-4-yl)-4-((4-methyl-6-(methylsulfonyl)pyridin-2-yl)amino)pyridin-2-yl)acetamide | Molecular Weight: 440 |
| 7. | 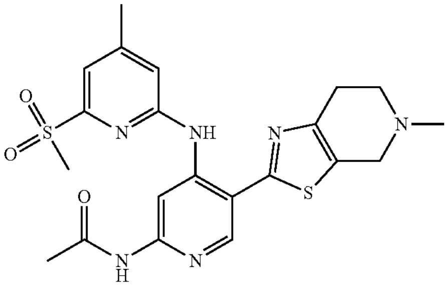 [SMILES: CC(=O)Nc1cc(Nc2cc(C)cc(S(C)(=O)=O)n2)c(-c2nc3c(s2)CN(C)CC3)cn1] | N-(5-(5-methyl-4,5,6,7-tetrahydrothiazolo[5,4-c]pyridin-2-y1)-4-((4-methyl-6-(methylsulfonyl)pyridin-2-yl)amino)pyridin-2-yl)acetamide | Molecular Weight: 472 |
| 8. | 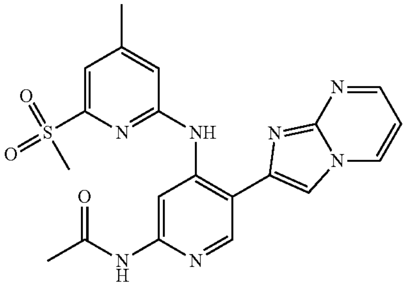 [SMILES: CC(=O)Nc1cc(Nc2cc(C)cc(S(C)(=O)=O)n2)c(-c2cn3cccnc3n2)cn1] | N-(5-(imidazo[1,2-a]pyrimidin-2-yl)-4-((4-methyl-6-(methylsulfonyl)pyridin-2-y1)amino)pyridin-2-yl)acetamide | Molecular Weight: 437 |
| 9. | 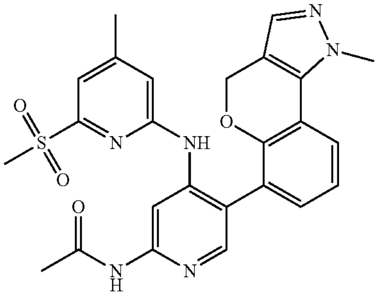 | N-(5-(1-methyl-1,4-dihydrochromeno[4,3-c]pyrazol-6-yl)-4-((4-methyl-6-(methylsulfonyl)pyridin-2-yl)amino)pyridin-2-yl)acetamide | Molecular Weight: 504 |
| 10. | 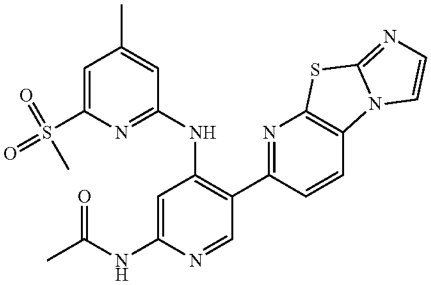 [SMILES: CC(=O)Nc1cc(Nc2cc(C)cc(S(C)(=O)=O)n2)c(-c2ccc3c(n2)sc2nccn23)cn1] | N-(5-(imidazo[2',l':2,3]thiazolo[5,4-b]pyridin-7-yl)-4-((4-methyl-6-(methylsulfonyl)pyridin-2-yl)amino)pyridin-2-yl)acetamide | Molecular Weight: 493 |

-continued

| # | Compound | Chemical Name | Molecular Weight |
|---|---|---|---|
| 11. | 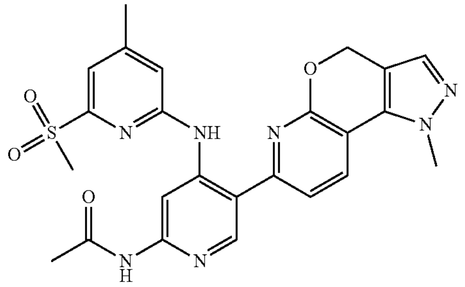 [SMILES: CC(=O)Nc1cc(Nc2cc(C)cc(S(C)(=O)=O)n2)c(-c2ccc3c(n2)OCc2cnn(C)c2-3)cn1] | N-(5-(1-methyl-1,4-dihydropyrazolo[3',4':4,5]pyrano[2,3-b]pyridin-7-yl)-4-((4-methyl-6-(methylsulfonyl)pyridin-2-yl)amino)pyridin-2-yl)acetamide | Molecular Weight: 505 |
| 12. | 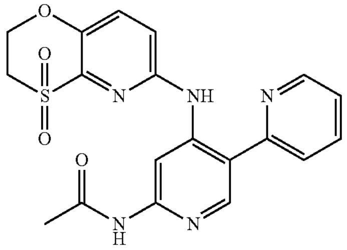 | N-(4'-((4,4-dioxido-2,3-dihydro-[1,4]oxathiino[3,2-b]pyridin-6-yl)amino)-[2,3'-bipyridin]-6'-yl)acetamide | Molecular Weight: 411 |
| 13. | 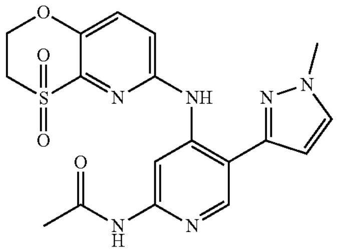 | N-(4-((4,4-dioxido-2,3-dihydro-[1,4]oxathiino[3,2-b]pyridin-6-yl)amino)-5-(1-methyl-1H-pyrazol-3-yl)pyridin-2-yl)acetamide | Molecular Weight: 414 |
| 14. | 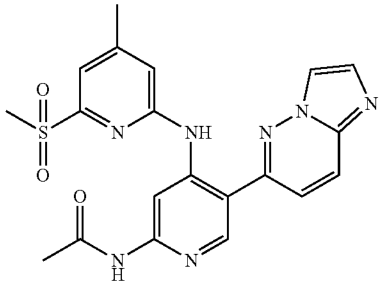 [SMILES: CC(=O)Nc1cc(Nc2cc(C)cc(S(C)(=O)=O)n2)c(-c2ccc3nccn3n2)cn1] | N-(5-(imidazo[1,2-b]pyridazin-6-yl)-4-((4-methyl-6-(methylsulfonyl)pyridin-2-yl)amino)pyridin-2-yl)acetamide | Molecular Weight: 437 |
| 15. | 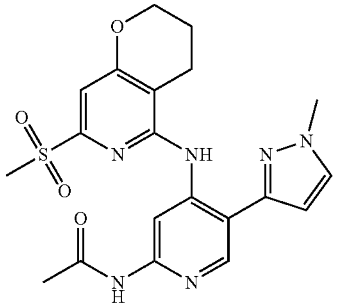 [SMILES: CC(=O)Nc1cc(Nc2nc(S(C)(=O)=O)cc3c2CCCO3)c(-c2ccn(C)n2)cn1] | N-(5-(1-methyl-1H-pyrazol-3-yl)-4-((7-(methylsulfonyl)-3,4-dihydro-2H-pyrano[3,2-c]pyridin-5-yl)amino)pyridin-2-yl)acetamide | Molecular Weight: 442 |

-continued

| # | Compound | Chemical Name | Molecular Weight |
|---|---|---|---|
| 16. | 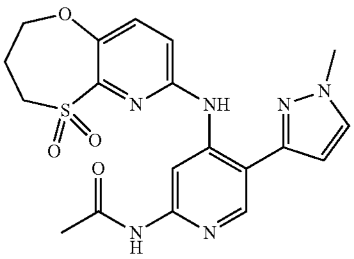 [SMILES: CC(=O)Nc1cc(Nc2ccc3c(n2)S(=O)(=O)CCCO3)c(-c2ccn(C)n2)cn1] | N-(4-((5,5-dioxido-3,4-dihydro-2H-[1,4]oxathiepino[3,2-b]pyridin-7-yl)amino)-5-(1-methyl-1H-pyrazol-3-yl)pyridin-2-yl)acetamide | Molecular Weight: 428 |
| 17. | 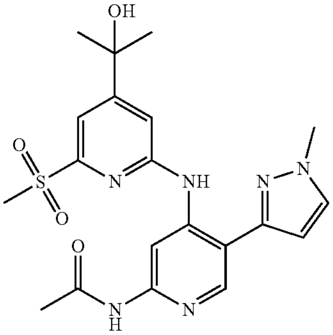 [SMILES: CC(=O)Nc1cc(Nc2cc(C(C)(C)O)cc(S(C)(=O)=O)n2)c(-c2ccn(C)n2)cn1] | N-(4-((4-(2-hydroxypropan-2-yl)-6-(methylsulfonyl)pyridin-2-yl)amino)-5-(1-methyl-1H-pyrazol-3-yl)pyridin-2-yl)acetamide | Molecular Weight: 444 |
| 18. | 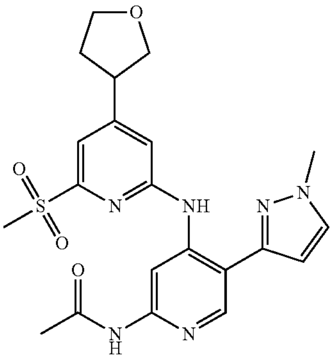 [SMILES: CC(=O)Nc1cc(Nc2cc(C3CCOC3)cc(S(C)(=O)=O)n2)c(-c2ccn(C)n2)cn1] | N-(5-(1-methyl-1H-pyrazol-3-yl)-4-((6-(methylsulfonyl)-4-(tetrahydrofuran-3-yl)pyridin-2-yl)amino)pyridin-2-yl)acetamide | Molecular Weight: 456 |
| 19. | 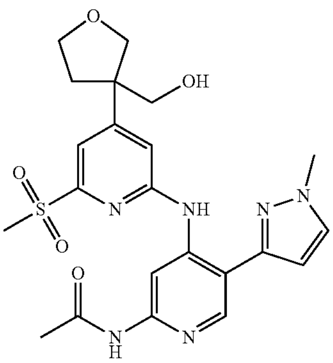 [SMILES: CC(=O)Nc1cc(Nc2cc(C3(CO)CCOC3)cc(S(C)(=O)=O)n2)c(-c2ccn(C)n2)cn1] | N-(4-((4-(3-(hydroxymethyl)tetrahydrofuran-3-yl)-6-(methylsulfonyl)pyridin-2-yl)amino)-5-(1-methyl-1H-pyrazol-3-yl)pyridin-2-yl)acetamide | Molecular Weight: 486 |

-continued

| # | Compound | Chemical Name | Molecular Weight |
|---|---|---|---|
| 20. | 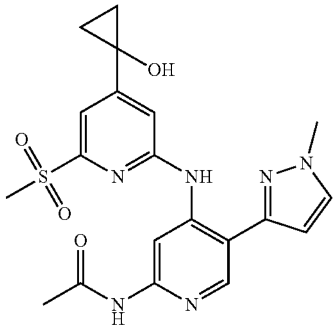 [SMILES: CC(=O)Nc1cc(Nc2cc(C3(O)CC3)cc(S(C)(=O)=O)n2)c(-c2ccn(C)n2)cn1] | N-(4-((4-(1-hydroxycyclopropyl)-6-(methylsulfonyl)pyridin-2-yl)amino)-5-(1-methyl-1H-pyrazol-3-yl)pyridin-2-yl)acetamide | Molecular Weight: 442 |
| 21. | 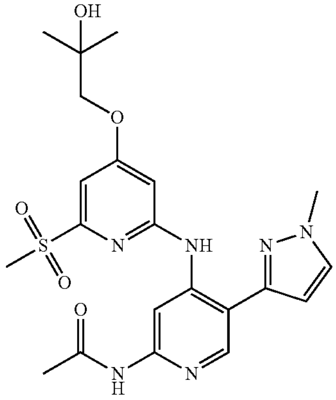 [SMILES: CC(=O)Nc1cc(Nc2cc(OCC(C)(C)O)cc(S(C)(=O)=O)n2)c(-c2ccn(C)n2)cn1] | N-(4-((4-(2-hydroxy-2-methylpropoxy)-6-(methylsulfonyl)pyridin-2-yl)amino)-5-(1-methyl-1H-pyrazol-3-yl)pyridin-2-yl)acetamide | Molecular Weight: 474 |
| 22. | 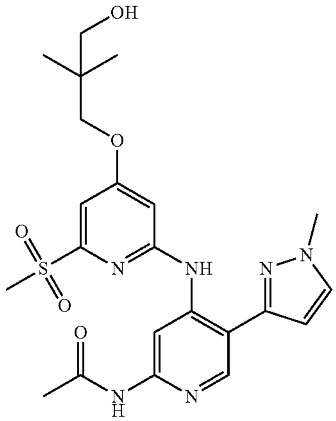 [SMILES: CC(=O)Nc1cc(Nc2cc(OCC(C)(C)CO)cc(S(C)(=O)=O)n2)c(-c2ccn(C)n2)cn1] | N-(4-((4-(3-hydroxy-2,2-dimethylpropoxy)-6-(methylsulfonyl)pyridin-2-yl)amino)-5-(1-methyl-1H-pyrazol-3-yl)pyridin-2-yl)acetamide | Molecular Weight: 488 |
| 23. | 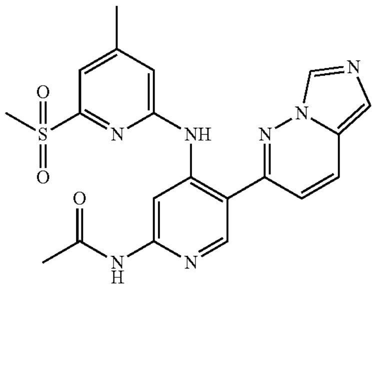 [SMILES: CC(=O)Nc1cc(Nc2cc(C)cc(S(C)(=O)=O)n2)c(-c2ccc3cncn3n2)cn1] | N-(5-(imidazo[1,5-b]pyridazin-2-y1)-4-((4-methyl-6-(methylsulfonyl)pyridin-2-yl)amino)pyridin-2-yl)acetamide | Molecular Weight: 437 |

-continued

| # | Compound | Chemical Name | Molecular Weight |
|---|---|---|---|
| 24. | 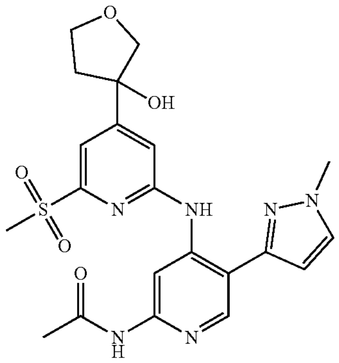 [SMILES: CC(=O)Nc1cc(Nc2cc(C3(O)CCOC3)cc(S(C)(=O)=O)n2)c(-c2ccn(C)n2)cn1] | N-(4-((4-(3-hydroxytetrahydrofuran-3-yl)-6-(methylsulfonyl)pyridin-2-yl)amino)-5-(1-methyl-1H-pyrazol-3-yl)pyridin-2-yl)acetamide | Molecular Weight: 472 |
| 25. | 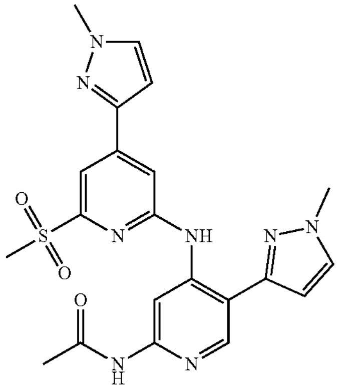 [SMILES: CC(=O)Nc1cc(Nc2cc(-c3ccn(C)n3)cc(S(C)(=O)=O)n2)c(-c2ccn(C)n2)cn1] | N-(5-(1-methyl-1H-pyrazol-3-yl)-4-((4-(1-methyl-1H-pyrazol-3-yl)-6-(methylsulfonyl)pyridin-2-yl)amino)pyridin-2-yl)acetamide | Molecular Weight: 466 |
| 26. | 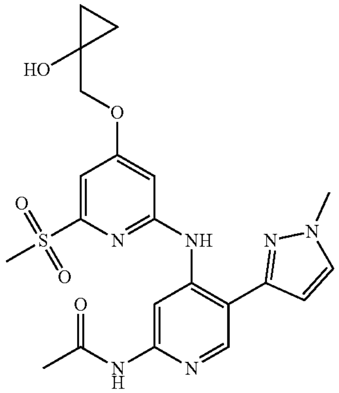 [SMILES: CC(=O)Nc1cc(Nc2cc(OCC3(O)CC3)cc(S(C)(=O)=O)n2)c(-c2ccn(C)n2)cn1] | N-(4-((4-((1-hydroxycyclopropyl)methoxy)-6-(methylsulfonyl)pyridin-2-yl)amino)-5-(1-methyl-1H-pyrazol-3-yl)pyridin-2-yl)acetamide | Molecular Weight: 472 |
| 27. | 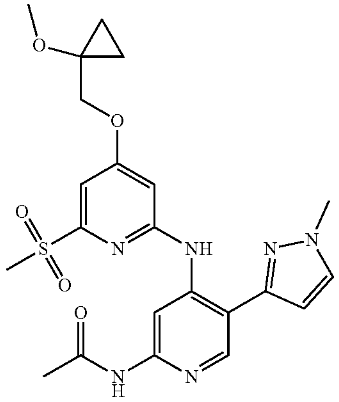 [SMILES: COC1(COc2cc(Nc3cc(NC(C)=O)ncc3-c3ccn(C)n3)nc(S(C)(=O)=O)c2)CC1] | N-(4-((4-((1-methoxycyclopropyl)methoxy)-6-(methylsulfonyl)pyridin-2-yl)amino)-5-(1-methyl-1H-pyrazol-3-yl)pyridin-2-yl)acetamide | Molecular Weight: 486 |

-continued

| # | Compound | Chemical Name | Molecular Weight |
|---|---|---|---|
| 28. | 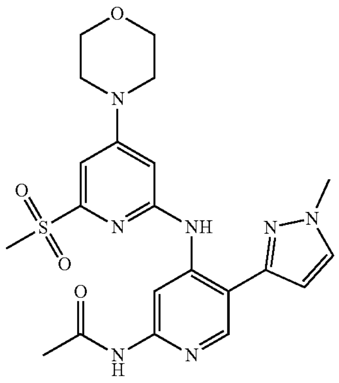 [SMILES: CC(=O)Nc1cc(Nc2cc(N3CCOCC3)cc(S(C)(=O)=O)n2)c(-c2ccn(C)n2)cn1] | N-(5-(1-methyl-1H-pyrazol-3-yl)-4-((6-(methylsulfonyl)-4-morpholinopyridin-2-yl)amino)pyridin-2-yl)acetamide | Molecular Weight: 471 |
| 29. | 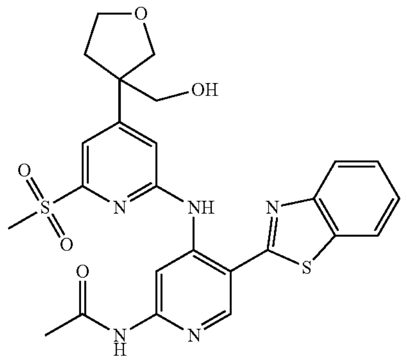 [SMILES: CC(=O)Nc1cc(Nc2cc(C3(CO)CCOC3)cc(S(C)(=O)=O)n2)c(-c2nc3ccccc3s2)cn1] | N-(5-(benzo[d]thiazol-2-y1)-4-((4-(3-(hydroxymethyl)tetrahydrofuran-3-yl)-6-(methylsulfonyl)pyridin-2-yl)amino)pyridin-2-yl)acetamide | Molecular Weight: 540 |
| 30. | 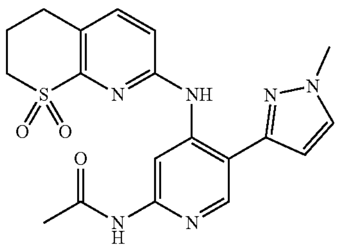 [SMILES: CC(=O)Nc1cc(Nc2ccc3c(n2)S(=O)(=O)CCC3)c(-c2ccn(C)n2)cn1] | N-(4-((1,1-dioxido-3,4-dihydro-2H-thiopyrano[2,3-b]pyridin-7-yl)amino)-5-(1-methyl-1H-pyrazol-3-yl)pyridin-2-yl)acetamide | Molecular Weight: 412 |
| 31. | 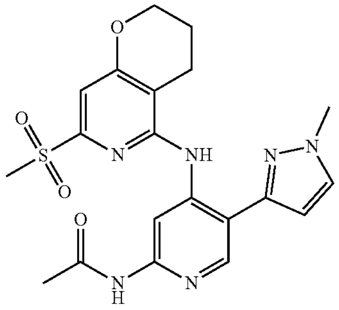 [SMILES: CC(=O)Nc1cc(Nc2nc(S(C)(=O)=O)cc3c2CCCO3)c(-c2ccn(C)n2)cn1] | N-(5-(1-methyl-1H-pyrazol-3-yl)-4-((7-(methylsulfonyl)-3,4-dihydro-2H-pyrano[3,2-c]pyridin-5-yl)amino)pyridin-2-yl)acetamide | Molecular Weight: 442 |

-continued

| # | Compound | Chemical Name | Molecular Weight |
|---|---|---|---|
| 32. | 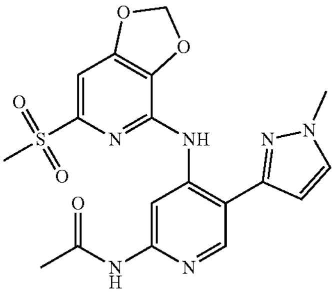 [SMILES: CC(=O)Nc1cc(Nc2nc(S(C)(=O)=O)cc3c2OCO3)c(-c2ccn(C)n2)cn1] | N-(5-(1-methyl-1H-pyrazol-3-yl)-4-((6-(methylsulfonyl)-[1,3]dioxolo[4,5-c]pyridin-4-yl)amino)pyridin-2-yl)acetamide | Molecular Weight: 430 |
| 33. | 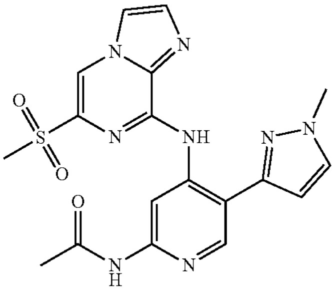 [SMILES: CC(=O)Nc1cc(Nc2nc(S(C)(=O)=O)cn3ccnc23)c(-c2ccn(C)n2)cn1] | N-(5-(1-methyl-1H-pyrazol-3-yl)-4-((6-(methylsulfonyl)imidazo[1,2-a]pyrazin-8-yl)amino)pyridin-2-yl)acetamide | Molecular Weight: 423 |
| 34. | 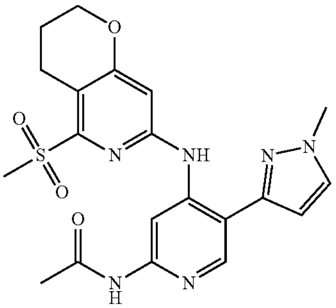 [SMILES: CC(=O)Nc1cc(Nc2cc3c(c(S(C)(=O)=O)n2)CCCO3)c(-c2ccn(C)n2)cn1] | N-(5-(1-methyl-1H-pyrazol-3-yl)-4-((5-(methylsulfonyl)-3,4-dihydro-2H-pyrano[3,2-c]pyridin-7-yl)amino)pyridin-2-yl)acetamide | Molecular Weight: 442 |
| 35. | 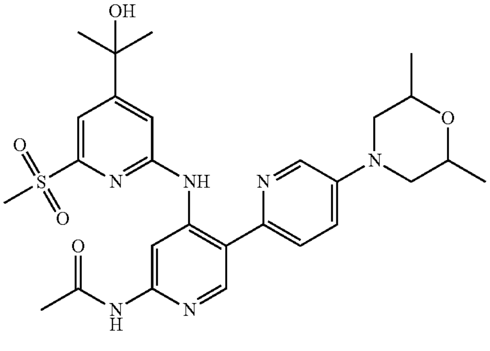 | N-(5-(2,6-dimethylmorpholino)-4'-((4-(2-hydroxypropan-2-yl)-6-(methylsulfonyl)pyridin-2-yl)amino)-[2,3'-bipyridin]-6'-yl)acetamide | Molecular Weight: 554 |

-continued

| # | Compound | Chemical Name | Molecular Weight |
|---|---|---|---|
| 36. | 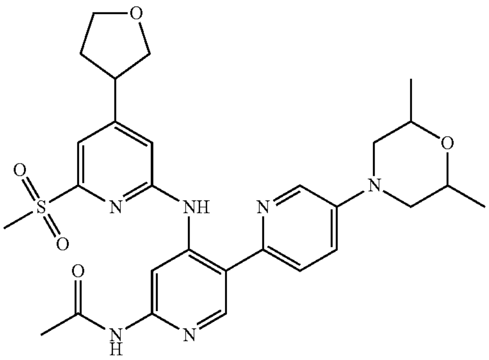 | N-(5-(2,6-dimethylmorpholino)-4'-((6-(methylsulfonyl)-4-(tetrahydrofuran-3-yl)pyridin-2-yl)amino)-[2,3'-bipyridin]-6'-yl)acetamide | Molecular Weight: 566 |
| 37. | 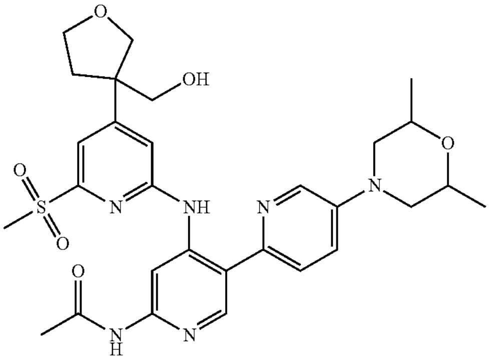 | N-(5-(2,6-dimethylmorpholino)-4'-((4-(3-(hydroxymethyl)tetrahydrofuran-3-yl)-6-(methylsulfonyl)pyridin-2-yl)amino)-[2,3'-bipyridin]-6'-yl)acetamide | Molecular Weight: 596 |
| 38. | 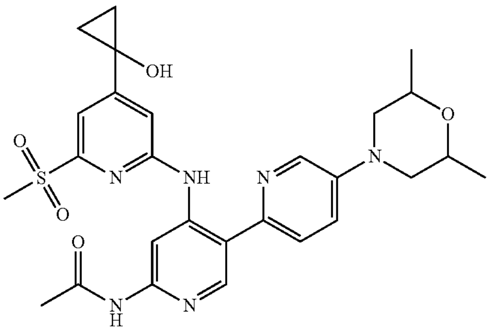 | N-(5-(2,6-dimethylmorpholino)-4'-((4-(1-hydroxycyclopropyl)-6-(methylsulfonyl)pyridin-2-yl)amino)-[2,3'-bipyridin]-6'-yl)acetamide | Molecular Weight: 552 |
| 39. | 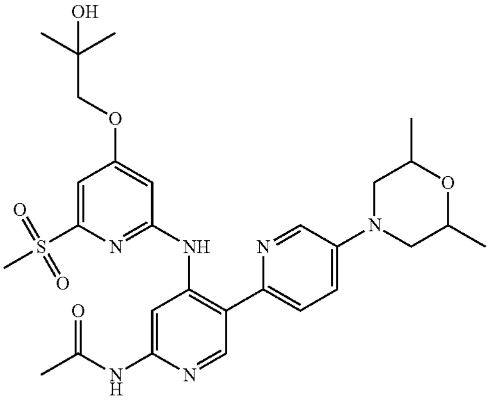 | N-(5-(2,6-dimethylmorpholino)-4'-((4-(2-hydroxy-2-methylpropoxy)-6-(methylsulfonyl)pyridin-2-yl)amino)-[2,3'-bipyridin]-6'-yl)acetamide | Molecular Weight: 584 |

-continued

| # | Compound | Chemical Name | Molecular Weight |
|---|---|---|---|
| 40. | 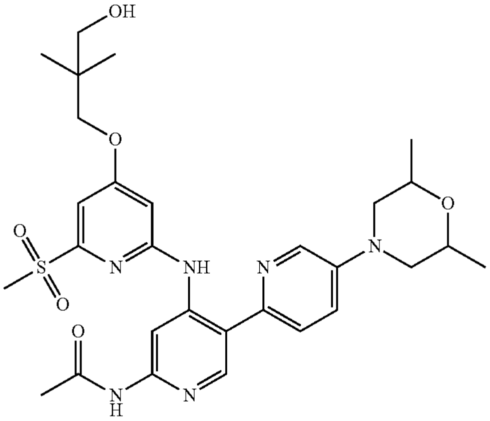 | N-(5-(2,6-dimethylmorpholino)-4'-((4-(3-hydroxy-2,2-dimethylpropoxy)-6-(methylsulfonyl)pyridin-2-yl)amino)-[2,3'-bipyridin]-6'-yl)acetamide | Molecular Weight: 598 |
| 41. | 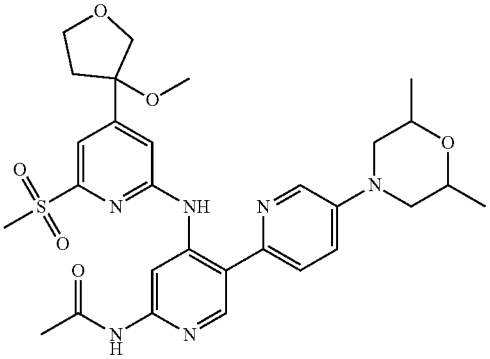 | N-(5-(2,6-dimethylmorpholino)-4'-((4-(3-methoxytetrahydrofuran-3-yl)-6-(methylsulfonyl)pyridin-2-yl)amino)-[2,3'-bipyridin]-6'-yl)acetamide | Molecular Weight: 596.70 |
| 42. | 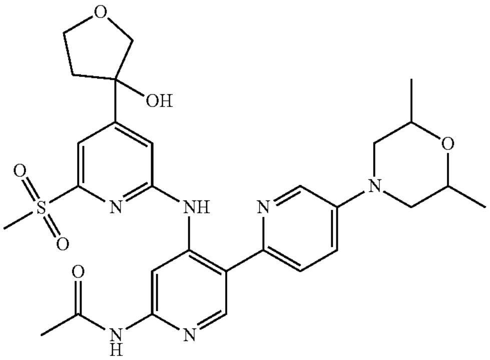 | N-(5-(2,6-dimethylmorpholino)-4'-((4-(3-hydroxytetrahydrofuran-3-yl)-6-(methylsulfonyl)pyridin-2-yl)amino)-[2,3'-bipyridin]-6'-yl)acetamide | Molecular Weight: 582 |
| 43. | 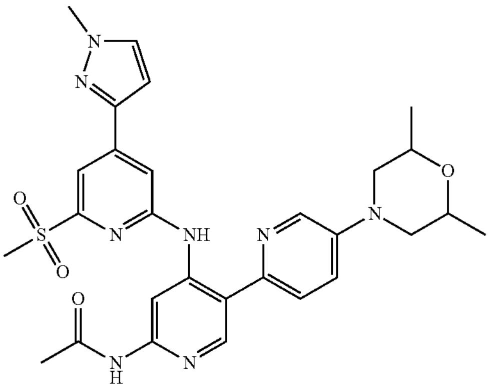 | N-(5-(2,6-dimethylmorpholino)-4'-((4-(1-methyl-1H-pyrazol-3-yl)-6-(methylsulfonyl)pyridin-2-yl)amino)-[2,3'-bipyridin]-6'-yl)acetamide | Molecular Weight: 576 |

-continued

| # | Compound | Chemical Name | Molecular Weight |
|---|---|---|---|
| 44. | 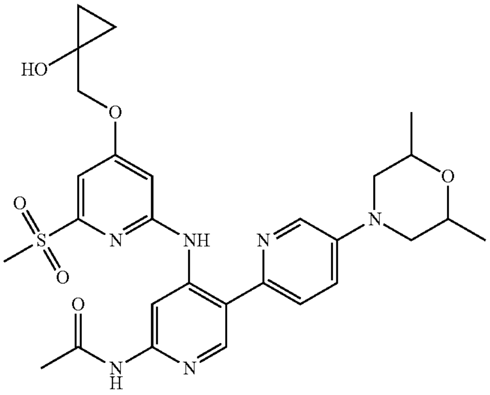 | N-(5-(2,6-dimethylmorpholino)-4'-((4-((1-hydroxycyclopropyl)methoxy)-6-(methylsulfonyl)pyridin-2-yl)amino)-[2,3'-bipyridin]-6'-yl)acetamide | Molecular Weight: 582 |
| 45. | 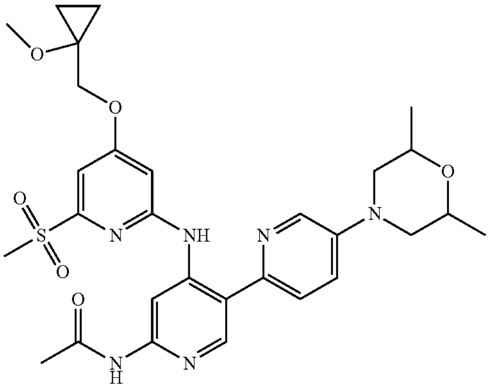 | N-(5-(2,6-dimethylmorpholino)-4'-((4-((1-methoxycyclopropyl)methoxy)-6-(methylsulfonyl)pyridin-2-yl)amino)-[2,3'-bipyridin]-6'-yl)acetamide | Molecular Weight: 596 |
| 46. | 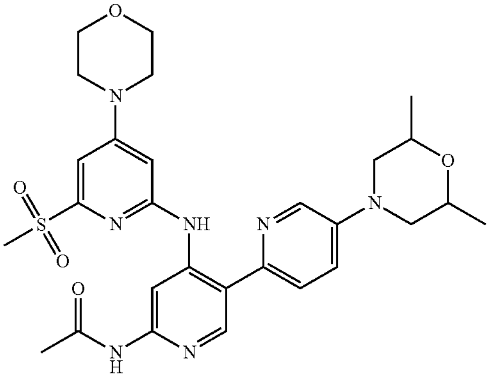 | N-(5-(2,6-dimethylmorpholino)-4'-((6-(methylsulfonyl)-4-morpholinopyridin-2-yl)amino)-[2,3'-bipyridin]-6'-yl)acetamide | Molecular Weight: 581 |
| 47. | 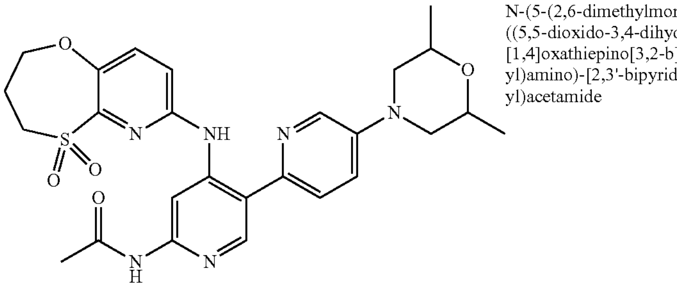 | N-(5-(2,6-dimethylmorpholino)-4'-((5,5-dioxido-3,4-dihydro-2H-[1,4]oxathiepino[3,2-b]pyridin-7-yl)amino)-[2,3'-bipyridin]-6'-yl)acetamide | Molecular Weight: 538 |

-continued

| # | Compound | Chemical Name | Molecular Weight |
|---|---|---|---|
| 48. | 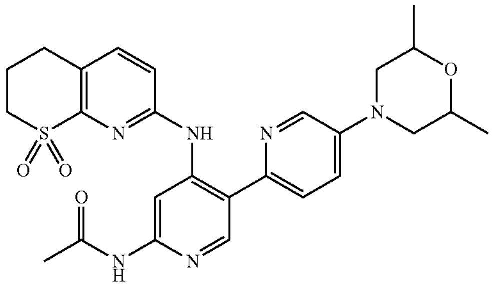 [SMILES: CC(=O)Nc1cc(Nc2ccc3c(n2)S(=O)(=O)CCC3)c(-c2ccc(N3CC(C)OC(C)C3)cn2)cn1] | N-(5-(2,6-dimethylmorpholino)-4'-((1,1-dioxido-3,4-dihydro-2H-thiopyrano[2,3-b]pyridin-7-yl)amino)-[2,3'-bipyridin]-6'-yl)acetamide | Molecular Weight: 522 |
| 49. | 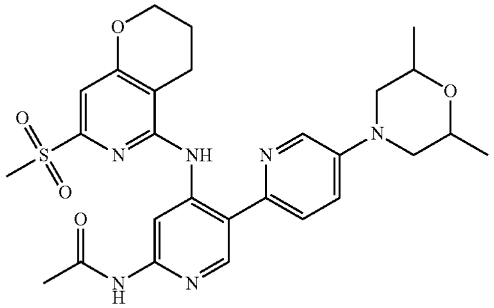 | N-(5-(2,6-dimethylmorpholino)-4'-((7-(methylsulfonyl)-3,4-dihydro-2H-pyrano[3,2-c]pyridin-5-yl)amino)-[2,3'-bipyridin]-6'-yl)acetamide | Molecular Weight: 552 |
| 50. | 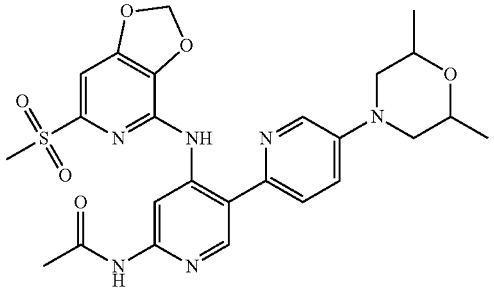 | N-(5-(2,6-dimethylmorpholino)-4'-((6-(methylsulfonyl)-[1,3]dioxolo[4,5-c]pyridin-4-yl)amino)-[2,3'-bipyridin]-6'-yl)acetamide | Molecular Weight: 540 |
| 51. | 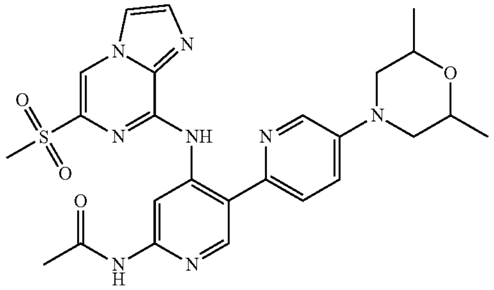 | N-(5-(2,6-dimethylmorpholino)-4'-((6-(methylsulfonyl)imidazo[1,2-a]pyrazin-8-yl)amino)-[2,3'-bipyridin]-6'-yl)acetamide | Molecular Weight: 536 |
| 52. | 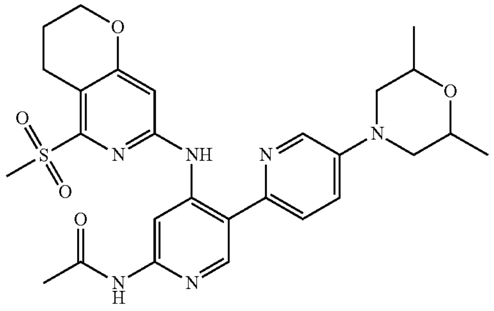 | N-(5-(2,6-dimethylmorpholino)-4'-((5-(methylsulfonyl)-3,4-dihydro-2H-pyrano[3,2-c]pyridin-7-yl)amino)-[2,3'-bipyridin]-6'-y1)acetamide | Molecular Weight: 552 |

-continued

| # | Compound | Chemical Name | Molecular Weight |
|---|---|---|---|
| 53. | 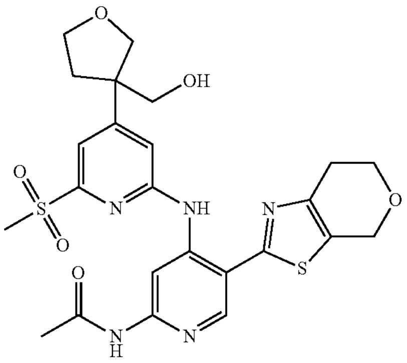 [SMILES: CC(=O)Nc1cc(Nc2cc(C3(CO)CCOC3)cc(S(C)(=O)=O)n2)c(-c2nc3c(s2)COCC3)cn1] | N-(5-(6,7-dihydro-4H-pyrano[4,3-d]thiazol-2-y1)-4-((4-(3-(hydroxymethyl)tetrahydrofuran-3-yl)-6-(methylsulfonyl)pyridin-2-yl)amino)pyridin-2-yl)acetamide | Molecular Weight: 545 |
| 54. | 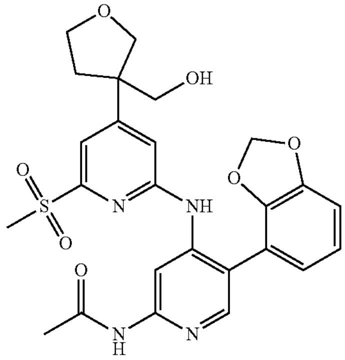 [SMILES: CC(=O)Nc1cc(Nc2cc(C3(CO)CCOC3)cc(S(C)(=O)=O)n2)c(-c2cccc3c2OCO3)cn1] | N-(5-(benzo[d][1,3]dioxol-4-yl)-4-((4-(3-(hydroxymethyl)tetrahydrofuran-3-yl)-6-(methylsulfonyl)pyridin-2-yl)amino)pyridin-2-y1)acetamide | Molecular Weight: 526 |
| 55. | 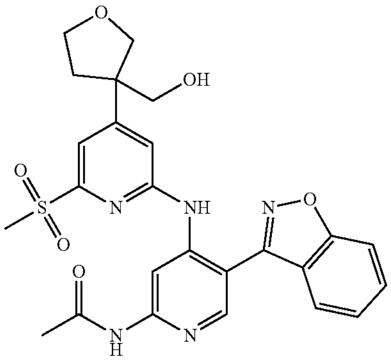 [SMILES: CC(=O)Nc1cc(Nc2cc(C3(CO)CCOC3)cc(S(C)(=O)=O)n2)c(-c2noc3ccccc23)cn1] | N-(5-(benzo[d]isoxazol-3-yl)-4-((4-(3-(hydroxymethyl)tetrahydrofuran-3-yl)-6-(methylsulfonyl)pyridin-2-yl)amino)pyridin-2-y1)acetamide | Molecular Weight: 523 |
| 56. | 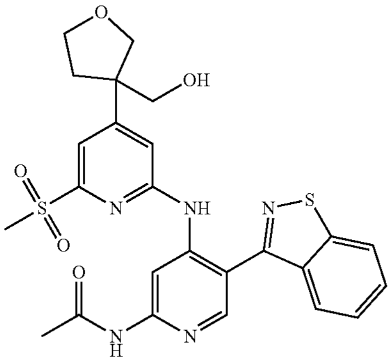 [SMILES: CC(=O)Nc1cc(Nc2cc(C3(CO)CCOC3)cc(S(C)(=O)=O)n2)c(-c2nsc3ccccc23)cn1] | N-(5-(benzo[d]isothiazol-3-y1)-4-((4-(3-(hydroxymethyl)tetrahydrofuran-3-yl)-6-(methylsulfonyl)pyridin-2-yl)amino)pyridin-2-y1)acetamide | Molecular Weight: 539 |

-continued

| # | Compound | Chemical Name | Molecular Weight |
|---|---|---|---|
| 57. | 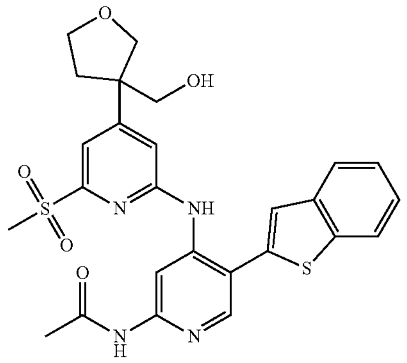 [SMILES: CC(=O)Nc1cc(Nc2cc(C3(CO)CCOC3)cc(S(C)(=O)=O)n2)c(-c2cc3ccccc3s2)cn1] | N-(5-(benzo[b]thiophen-2-yl)-4-((4-(3-(hydroxymethyl)tetrahydrofuran-3-yl)-6-(methylsulfonyl)pyridin-2-yl)amino)pyridin-2-yl)acetamide | Molecular Weight: 538 |
| 58. | 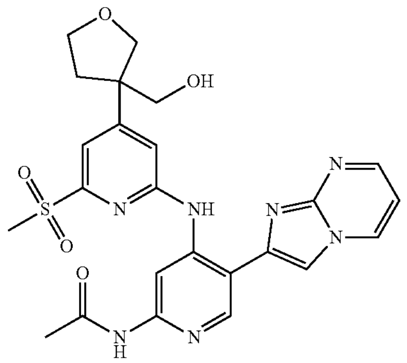 [SMILES: CC(=O)Nc1cc(Nc2cc(C3(CO)CCOC3)cc(S(C)(=O)=O)n2)c(-c2cn3cccnc3n2)cn1] | N-(4-((4-(3-(hydroxymethyl)tetrahydrofuran-3-yl)-6-(methylsulfonyl)pyridin-2-yl)amino)-5-(imidazo[1,2-alpyrimidin-2-y1)pyridin-2-yl)acetamide | Molecular Weight: 523 |
| 59. | 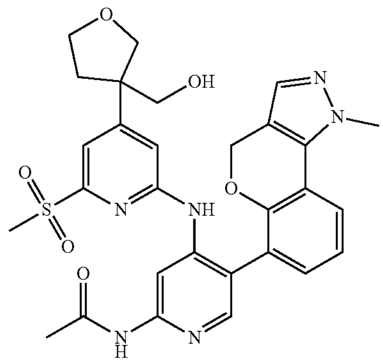 | N-(4-((4-(3-(hydroxymethyl)tetrahydrofuran-3-yl)-6-(methylsulfonyl)pyridin-2-yl)amino)-5-(1-methyl-1,4-dihydrochromeno[4,3-c]pyrazol-6-yl)pyridin-2-yl)acetamide | Molecular Weight: 590 |
| 60. | 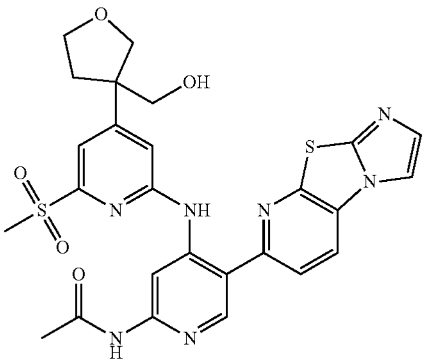 [SMILES: CC(=O)Nc1cc(Nc2cc(C3(CO)CCOC3)cc(S(C)(=O)=O)n2)c(-c2ccc3c(n2)sc2nccn23)cn1] | N-(4-((4-(3-(hydroxymethyl)tetrahydrofuran-3-yl)-6-(methylsulfonyl)pyridin-2-yl)amino)-5-(imidazo[2',l':2,3]thiazolo[5,4-b]pyridin-7-y1)pyridin-2-yl)acetamide | Molecular Weight: 579 |

-continued

| # | Compound | Chemical Name | Molecular Weight |
|---|---|---|---|
| 61. | 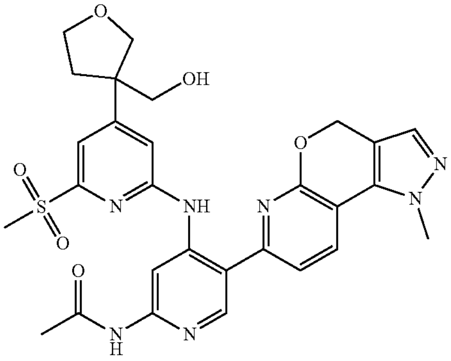 [SMILES: CC(=O)Nc1cc(Nc2cc(C3(CO)CCOC3)cc(S(C)(=O)=O)n2)c(-c2ccc3c(n2)OCc2cnn(C)c2-3)cn1] | N-(4-((4-(3-(hydroxymethyl)tetrahydrofuran-3-yl)-6-(methylsulfonyl)pyridin-2-yl)amino)-5-(1-methyl-1,4-dihydropyrazolo[3',4':4,5]pyrano[2,3-b]pyridin-7-yl)pyridin-2-yl)acetamide | Molecular Weight: 591 |
| 62. | 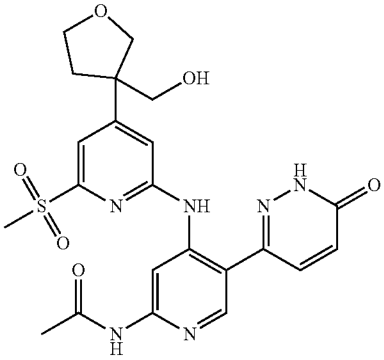 [SMILES: CC(=O)Nc1cc(Nc2cc(C3(CO)CCOC3)cc(S(C)(=O)=O)n2)c(-c2ccc(=O)[nH]n2)cn1] | N-(4-((4-(3-(hydroxymethyl)tetrahydrofuran-3-yl)-6-(methylsulfonyl)pyridin-2-yl)amino)-5-(6-oxo-1,6-dihydropyridazin-3-yl)pyridin-2-yl)acetamide | Molecular Weight: 500 |
| 63. | 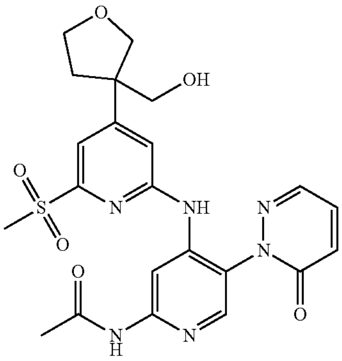 [SMILES: CC(=O)Nc1cc(Nc2cc(C3(CO)CCOC3)cc(S(C)(=O)=O)n2)c(-n2ncccc2=O)cn1] | N-(4-((4-(3-(hydroxymethyl)tetrahydrofuran-3-y1)-6-(methylsulfonyl)pyridin-2-yl)amino)-5-(6-oxopyridazin-1(6H)-yl)pyridin-2-yl)acetamide | Molecular Weight: 500 |
| 64. | 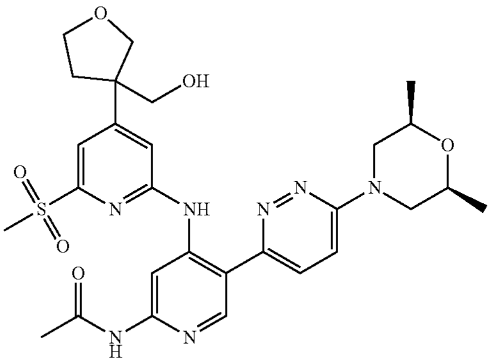 | N-(5-(6-((2S,6R)-2,6-dimethylmorpholino)pyridazin-3-y1)-4-((4-(3-(hydroxymethyl)tetrahydrofuran-3-yl)-6-(methylsulfonyl)pyridin-2-yl)amino)pyridin-2-yl)acetamide | Molecular Weight: 597 |

-continued

| # | Compound | Chemical Name | Molecular Weight |
|---|---|---|---|
| 65. | 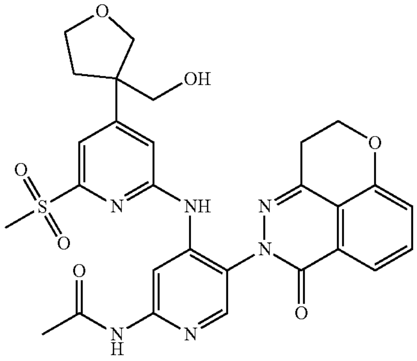 [SMILES: CC(=O)Nc1cc(Nc2cc(C3(CO)CCOC3)cc(S(C)(=O)=O)n2)c(-n2nc3c4c(cccc4c2=O)OCC3)cn1] | N-(4-((4-(3-(hydroxymethyl)tetrahydrofuran-3-yl)-6-(methylsulfonyl)pyridin-2-yl)amino)-5-(3-oxo-8,9-dihydropyrano[4,3,2-de]phthalazin-2(3H)-yl)pyridin-2-yl)acetamide | Molecular Weight: 592 |
| 66. | 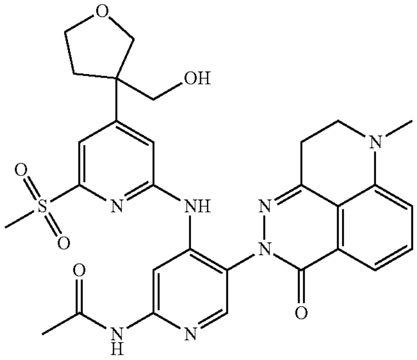 | N-(4-((4-(3-(hydroxymethyl)tetrahydrofuran-3-yl)-6-(methylsulfonyl)pyridin-2-yl)amino)-5-(7-methyl-3-oxo-8,9-dihydro-3H-pyrido[4,3,2-de]phthalazin-2(7H)-yl)pyridin-2-yl)acetamide | Molecular Weight: 605 |
| 67. | 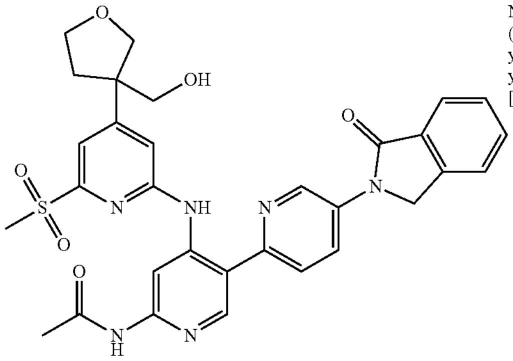 [SMILES: CC(=O)Nc1cc(Nc2cc(C3(CO)CCOC3)cc(S(C)(=O)=O)n2)c(-c2ccc(N3Cc4ccccc4C3=O)cn2)cn1] | N-(4'-((4-(3-(hydroxymethyl)tetrahydrofuran-3-yl)-6-(methylsulfonyl)pyridin-2-yl)amino)-5-(1-oxoisoindolin-2-yl)-[2,3'-bipyridin]-6'-yl)acetamide | Molecular Weight: 614 |
| 68. | 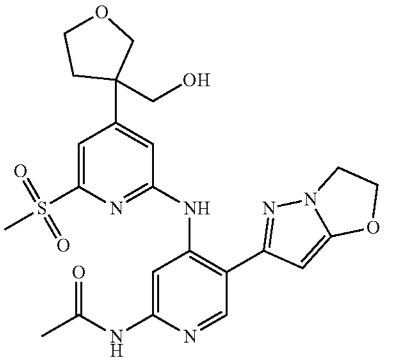 [SMILES: CC(=O)Nc1cc(Nc2cc(C3(CO)CCOC3)cc(S(C)(=O)=O)n2)c(-c2cc3n(n2)CCO3)cn1] | N-(5-(2,3-dihydropyrazolo[5,1-b]oxazol-6-yl)-4-((4-(3-(hydroxymethyl)tetrahydrofuran-3-yl)-6-(methylsulfonyl)pyridin-2-yl)amino)pyridin-2-yl)acetamide | Molecular Weight: 514 |

-continued

| # | Compound | Chemical Name | Molecular Weight |
|---|---|---|---|
| 69. | 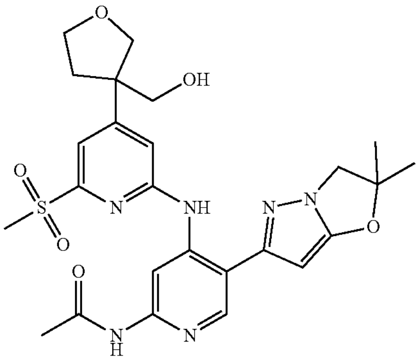 | N-(5-(2,2-dimethyl-2,3-dihydropyrazolo[5,1-b]oxazol-6-yl)-4-((4-(3-(hydroxymethyl)tetrahydrofuran-3-yl)-6-(methylsulfonyl)pyridin-2-yl)amino)pyridin-2-yl)acetamide | Molecular Weight: 542 |
| 70. | 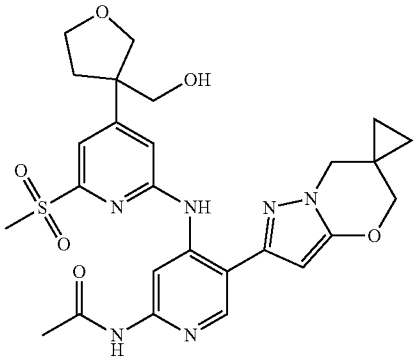 [SMILES: CC(=O)Nc1cc(Nc2cc(C3(CO)CCOC3)cc(S(C)(=O)=O)n2)c(-c2cc3n(n2)CC2(CC2)CO3)cn1] | N-(4-((4-(3-(hydroxymethyl)tetrahydrofuran-3-yl)-6-(methylsulfonyl)pyridin-2-yl)amino)-5-(5'H, 7'H-spiro[cyclopropane-1,6'-pyrazolo[5,1-b][1,3]oxazin]-2'-yl)pyridin-2-yl)acetamide | Molecular Weight: 554 |
| 71. | 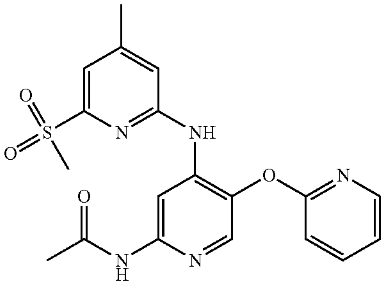 [SMILES: CC(=O)Nc1cc(Nc2cc(C)cc(S(C)(=O)=O)n2)c(Oc2ccccn2)cn1] | N-(4-((4-methyl-6-(methylsulfonyl)pyridin-2-yl)amino)-5-(pyridin-2-yloxy)pyridin-2-yl)acetamide | Molecular Weight: 413 |
| 72. | 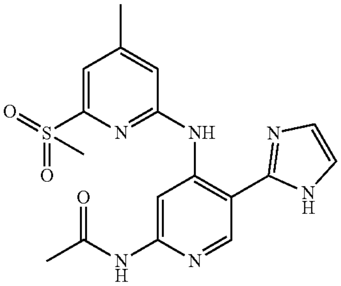 [SMILES: CC(=O)Nc1cc(Nc2cc(C)cc(S(C)(=O)=O)n2)c(-c2ncc[nH]2)cn1] | N-(5-(1H-imidazol-2-yl)-4-((4-methyl-6-(methylsulfonyl)pyridin-2-yl)amino)pyridin-2-yl)acetamide | Molecular Weight: 386 |

-continued

| # | Compound | Chemical Name | Molecular Weight |
|---|---|---|---|
| 73. | 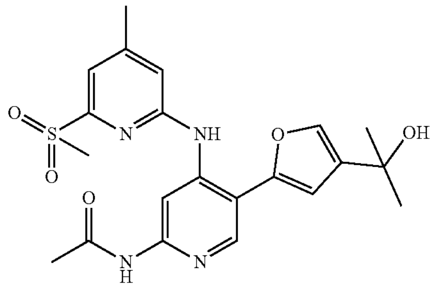 [SMILES: CC(=O)Nc1cc(Nc2cc(C)cc(S(C)(=O)=O)n2)c(-c2cc(C(C)(C)O)co2)cn1] | N-(5-(4-(2-hydroxypropan-2-yl)furan-2-yl)-4-((4-methyl-6-(methylsulfonyl)pyridin-2-yl)amino)pyridin-2-yl)acetamide | Molecular Weight: 444 |
| 74. | 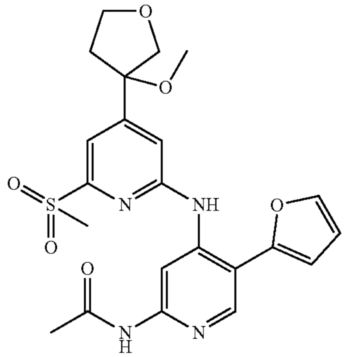 [SMILES: COC1(c2cc(Nc3cc(NC(C)=O)ncc3-c3ccco3)nc(S(C)(=O)=O)c2)CCOC1] | N-(5-(furan-2-yl)-4-((4-(3-methoxytetrahydrofuran-3-yl)-6-(methylsulfonyl)pyridin-2-yl)amino)pyridin-2-yl)acetamide | Molecular Weight: 472 |
| 75. | 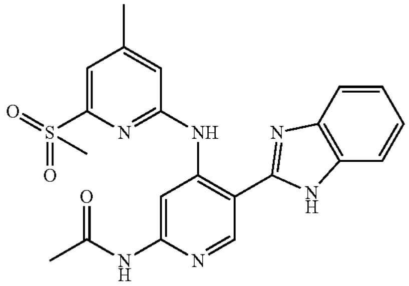 [SMILES: CC(=O)Nc1cc(Nc2cc(C)cc(S(C)(=O)=O)n2)c(-c2nc3ccccc3[nH]2)cn1] | N-(5-(1H-benzo[d]imidazol-2-yl)-4-((4-methyl-6-(methylsulfonyl)pyridin-2-yl)amino)pyridin-2-yl)acetamide | Molecular Weight: 436 |
| 76. | 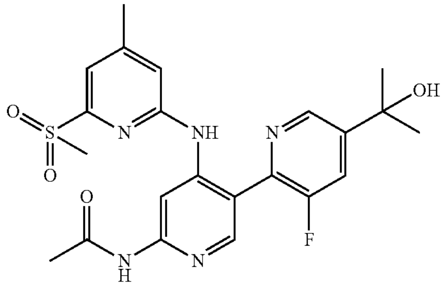 [SMILES: CC(=O)Nc1cc(Nc2cc(C)cc(S(C)(=O)=O)n2)c(-c2ncc(C(C)(C)O)cc2F)cn1] | N-(3-fluoro-5-(2-hydroxypropan-2-yl)-4'-((4-methyl-6-(methylsulfonyl)pyridin-2-yl)amino)-[2,3'-bipyridin]-6'-yl)acetamide | Molecular Weight: 473 |
| 77. | 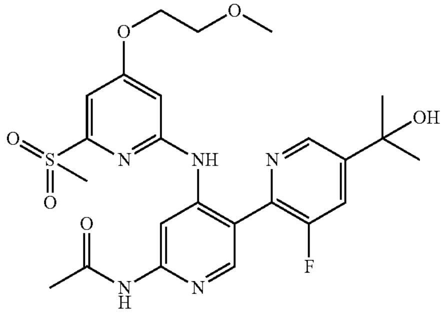 [SMILES: COCCOc1cc(Nc2cc(NC(C)=O)ncc2-c2ncc(C(C)(C)O)cc2F)nc(S(C)(=O)=O)c1] | N-(3-fluoro-5-(2-hydroxypropan-2-yl)-4'-((4-methyl-6-(methylsulfonyl)pyridin-2-yl)amino)-[2,3'-bipyridin]-6'-yl)acetamide | Molecular Weight: 473 |

-continued

| # | Compound | Chemical Name | Molecular Weight |
|---|---|---|---|
| 78. | 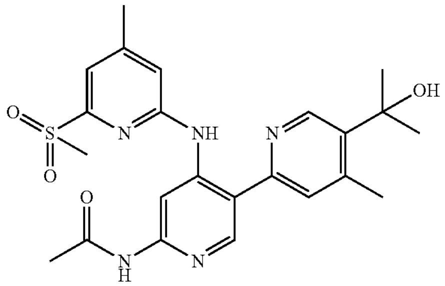 [SMILES: CC(=O)Nc1cc(Nc2cc(C)cc(S(C)(=O)=O)n2)c(-c2cc(C)c(C(C)(C)O)cn2)cn1] | N-(5-(2-hydroxypropan-2-yl)-4-methyl-4'-((4-methyl-6-(methylsulfonyl)pyridin-2-yl)amino)-[2,3'-bipyridin]-6'-yl)acetamide | Molecular Weight: 469 |
| 79. | 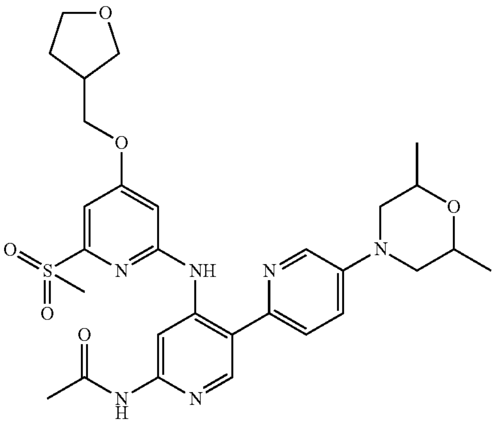 [SMILES: CC(=O)Nc1cc(Nc2cc(OCC3CCOC3)cc(S(C)(=O)=O)n2)c(-c2ccc(N3CC(C)OC(C)C3)cn2)cn1] | N-(5-(2,6-dimethylmorpholino)-4'-((6-(methylsulfonyl)-4-((tetrahydrofuran-3-yl)methoxy)pyridin-2-yl)amino)-[2,3'-bipyridin]-6'-yl)acetamide | Molecular Weight: 596 |
| 80. | 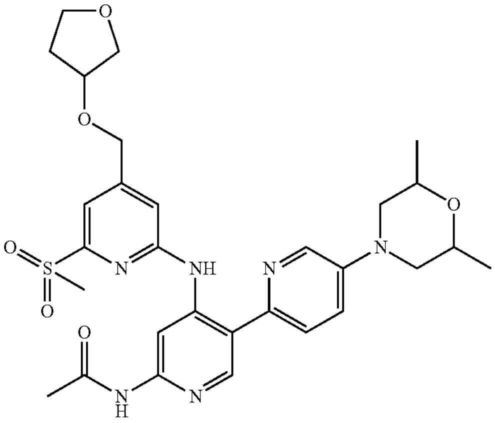 [SMILES: CC(=O)Nc1cc(Nc2cc(COC3CCOC3)cc(S(C)(=O)=O)n2)c(-c2ccc(N3CC(C)OC(C)C3)cn2)cn1] | N-(5-(2,6-dimethylmorpholino)-4'-((6-(methylsulfonyl)-4-(((tetrahydrofuran-3-yl)oxy)methyl)pyridin-2-yl)amino)-[2,3'-bipyridin]-6'-yl)acetamide | Molecular Weight: 596 |
| 81. | 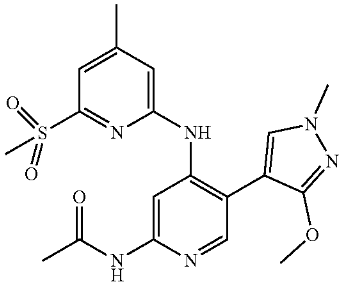 [SMILES: COc1nn(C)cc1-c1cnc(NC(C)=O)cc1Nc1cc(C)cc(S(C)(=O)=O)n1] | N-(5-(3-methoxy-1-methyl-1H-pyrazol-4-yl)-4-((4-methyl-6-(methylsulfonyl)pyridin-2-yl)amino)pyridin-2-yl)acetamide | Molecular Weight: 430 |

-continued

| # | Compound | Chemical Name | Molecular Weight |
|---|---|---|---|
| 82. | 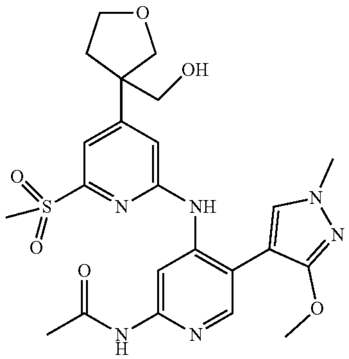 [SMILES: COc1nn(C)cc1-c1cnc(NC(C)=O)cc1Nc1cc(C2(CO)CCOC2)cc(S(C)(=O)=O)n1] | N-(4-((4-(3-(hydroxymethyl)tetrahydrofuran-3-yl)-6-(methylsulfonyl)pyridin-2-yl)amino)-5-(3-methoxy-1-methyl-1H-pyrazol-4-yl)pyridin-2-yl)acetamide | Molecular Weight: 516 |
| 83. | 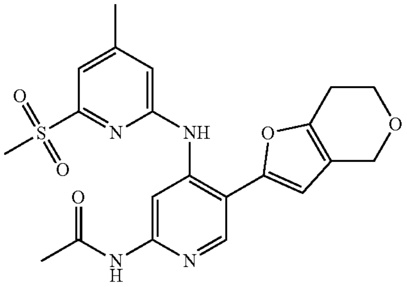 [SMILES: CC(=O)Nc1cc(Nc2cc(C)cc(S(C)(=O)=O)n2)c(-c2cc3c(o2)CCOC3)cn1] | N-(5-(6,7-dihydro-4H-furo[3,2-c]pyran-2-yl)-4-((4-methyl-6-(methylsulfonyl)pyridin-2-yl)amino)pyridin-2-yl)acetamide | Molecular Weight: 442 |
| 84. | 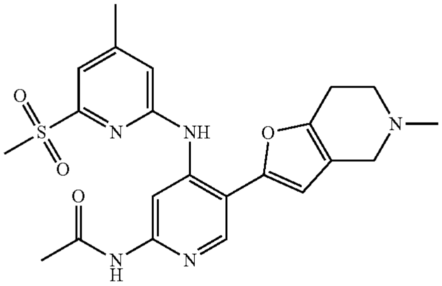 | N-(5-(5-methyl-4,5,6,7-tetrahydrofuro[3,2-c]pyridin-2-yl)-4-((4-methyl-6-(methylsulfonyl)pyridin-2-yl)amino)pyridin-2-yl)acetamide | Molecular Weight: 455 |
| 85. | 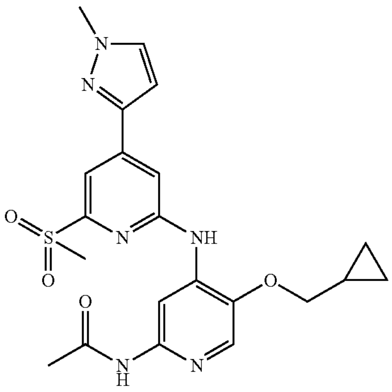 [SMILES: CC(=O)Nc1cc(Nc2cc(-c3ccn(C)n3)cc(S(C)(=O)=O)n2)c(OCC2CC2)cn1] | N-(5-(cyclopropylmethoxy)-4-((4-(1-methyl-1H-pyrazol-3-yl)-6-(methylsulfonyl)pyridin-2-yl)amino)pyridin-2-yl)acetamide | Molecular Weight: 456 |

-continued

| # | Compound | Chemical Name | Molecular Weight |
|---|---|---|---|
| 86. | 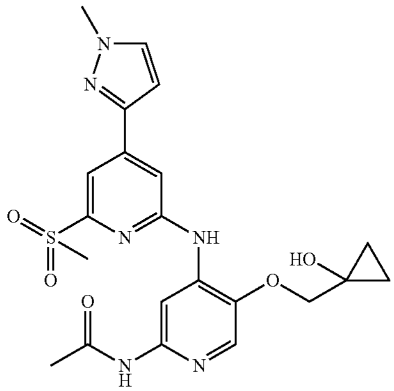 [SMILES: CC(=O)Nc1cc(Nc2cc(-c3ccn(C)n3)cc(S(C)(=O)=O)n2)c(OCC2(O)CC2)cn1] | N-(5-((1-hydroxycyclopropyl)methoxy)-4-((4-(1-methyl-1H-pyrazol-3-yl)-6-(methylsulfonyl)pyridin-2-yl)amino)pyridin-2-yl)acetamide | Molecular Weight: 472 |
| 87. | 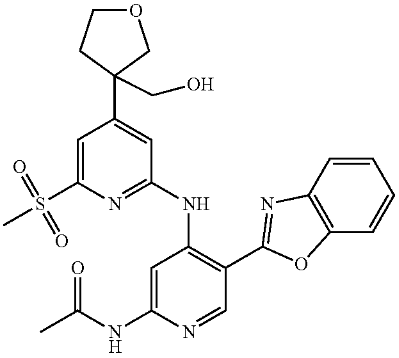 [SMILES: CC(=O)Nc1cc(Nc2cc(C3(CO)CCOC3)cc(S(C)(=O)=O)n2)c(-c2nc3ccccc3o2)cn1] | N-(5-(benzo[d]oxazol-2-yl)-4-((4-(3-(hydroxymethyl)tetrahydrofuran-3-yl)-6-(methylsulfonyl)pyridin-2-yl)amino)pyridin-2-y1)acetamide | Molecular Weight: 524 |
| 88. | 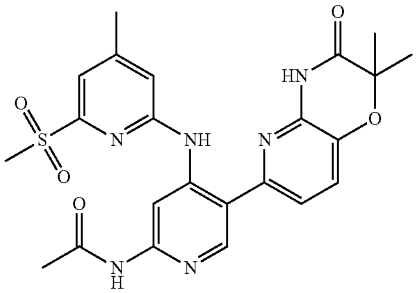 | N-(5-(2,2-dimethyl-3-oxo-3,4-dihydro-2H-pyrido[3,2-b][1,4]oxazin-6-yl)-4-((4-methyl-6-(methylsulfonyl)pyridin-2-yl)amino)pyridin-2-yl)acetamide | Molecular Weight: 497 |
| 89. | 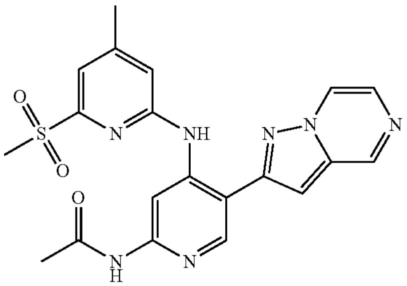 [SMILES: CC(=O)Nc1cc(Nc2cc(C)cc(S(C)(=O)=O)n2)c(-c2cc3cnccn3n2)cn1] | N-(4-((4-methyl-6-(methylsulfonyl)pyridin-2-yl)amino)-5-(pyrazolo[1,5-a]pyrazin-2-yl)pyridin-2-yl)acetamide | Molecular Weight: 437 |

-continued

| # | Compound | Chemical Name | Molecular Weight |
|---|---|---|---|
| 90. | 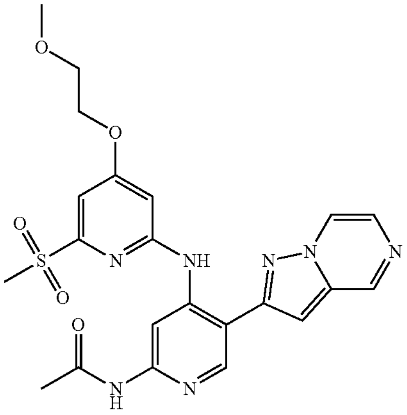 [SMILES: COCCOc1cc(Nc2cc(NC(C)=O)ncc2-c2cc3cnccn3n2)nc(S(C)(=O)=O)c1] | N-(4-((4-(2-methoxyethoxy)-6-(methylsulfonyl)pyridin-2-yl)amino)-5-(pyrazolo[1,5-a]pyrazin-2-yl)pyridin-2-yl)acetamide | Molecular Weight: 498 |
| 91. | 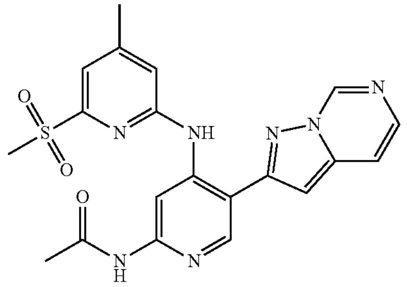 [SMILES: CC(=O)Nc1cc(Nc2cc(C)cc(S(C)(=O)=O)n2)c(-c2cc3ccncn3n2)cn1] | N-(4-((4-methyl-6-(methylsulfonyl)pyridin-2-yl)amino)-5-(pyrazolo[1,5-c]pyrimidin-2-yl)pyridin-2-yl)acetamide | Molecular Weight: 437 |
| 92. | 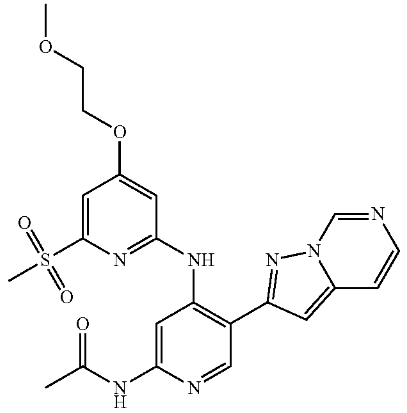 [SMILES: COCCOc1cc(Nc2cc(NC(C)=O)ncc2-c2cc3ccncn3n2)nc(S(C)(=O)=O)c1] | N-(4-((4-(2-methoxyethoxy)-6-(methylsulfonyl)pyridin-2-yl)amino)-5-(pyrazolo[1,5-c]pyrimidin-2-yl)pyridin-2-y1)acetamide | Molecular Weight: 498 |
| 93. | 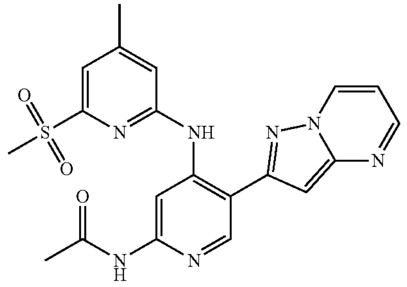 [SMILES: CC(=O)Nc1cc(Nc2cc(C)cc(S(C)(=O)=O)n2)c(-c2cc3ncccn3n2)cn1] | N-(4-((4-methyl-6-(methylsulfonyl)pyridin-2-yl)amino)-5-(pyrazolo[1,5-a]pyrimidin-2-yl)pyridin-2-yl)acetamide | Molecular Weight: 437 |

-continued

| # | Compound | Chemical Name | Molecular Weight |
|---|---|---|---|
| 94. | 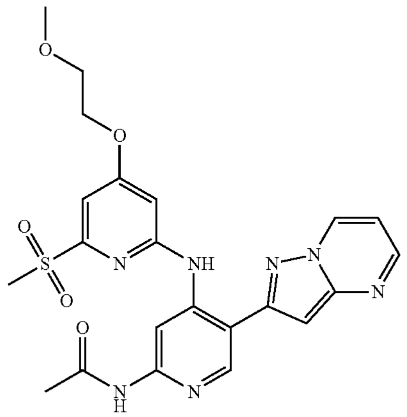 [SMILES: COCCOc1cc(Nc2cc(NC(C)=O)ncc2-c2cc3ncccn3n2)nc(S(C)(=O)=O)c1] | N-(4-((4-(2-methoxyethoxy)-6-(methylsulfonyl)pyridin-2-yl)amino)-5-(pyrazolo[1,5-a]pyrimidin-2-yl)pyridin-2-yl)acetamide | Molecular Weight: 498 |
| 95. | 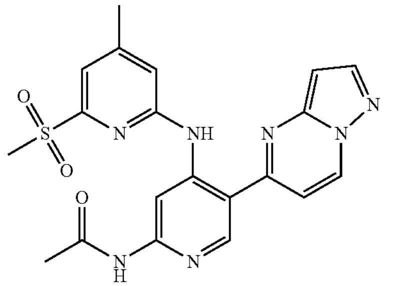 [SMILES: CC(=O)Nc1cc(Nc2cc(C)cc(S(C)(=O)=O)n2)c(-c2ccn3nccc3n2)cn1] | N-(4-((4-methyl-6-(methylsulfonyl)pyridin-2-yl)amino)-5-(pyrazolo[1,5-a]pyrimidin-5-yl)pyridin-2-yl)acetamide | Molecular Weight: 437 |
| 96. | 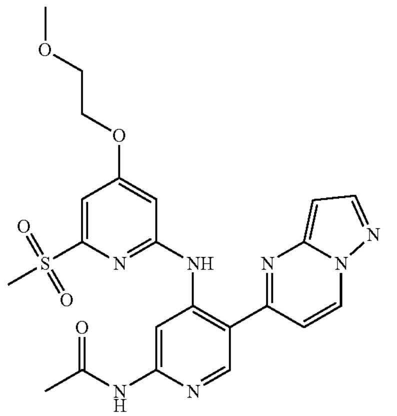 [SMILES: COCCOc1cc(Nc2cc(NC(C)=O)ncc2-c2ccn3nccc3n2)nc(S(C)(=O)=O)c1] | N-(4-((4-(2-methoxyethoxy)-6-(methylsulfonyl)pyridin-2-yl)amino)-5-(pyrazolo[1,5-a]pyrimidin-5-yl)pyridin-2-yl)acetamide | Molecular Weight: 498 |
| 97. | 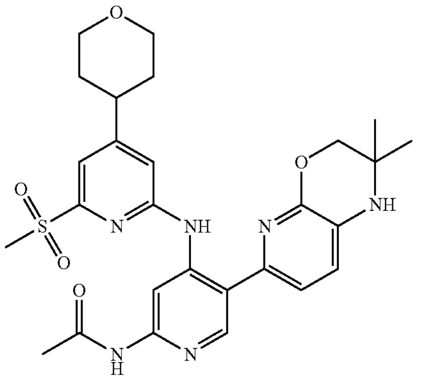 | N-(5-(2,2-dimethyl-2,3-dihydro-1H-pyrido[2,3-b][1,4]oxazin-6-yl)-4-((6-(methylsulfonyl)-4-(tetrahydro-2H-pyran-4-yl)pyridin-2-yl)amino)pyridin-2-yl)acetamide | Molecular Weight: 553 |

Biochemical Assay and Cellular Assay

Assay A: TYK2-JH2 Biochemical Assay

Compounds disclosed herein were tested for blocking of TYK2-JH2 (aa 575-869, in-house) protein with its probe in an assay based on Homogeneous Time Resolved Fluorescence. Compound dilution is done according to the following protocol: (1) Prepare 500× compounds solution in DMSO from 500 uM by 5-fold dilution, total 10 doses were included; (2) Prepare 10× compounds solution in an assay buffer containing 20 mM HEPES, pH 7.5, 10 mM MgCl2, 0.005% BSA, 2 mM DTT, 0.015% Brij-35 by transferring 1 μl serial 500× stock solution into 49 μl assay buffer. 4 d of 0.2 nM recombinant TYK2-JH2 protein was pre-incubated with 1 μl of 10× serial dilution of compounds at room temperature for 0.5 hour. Then 5 μl of 10 nM in-house Probe 1 (6-((3,5-dimethylphenyl)amino)-8-((4,26-dioxo-30-((3aS,4S,6aR)-2-oxohexahydro-1H-thieno[3,4-d]imidazol-4-yl)-7,10,13,16,19,22-hexaoxa-3,25-diazatriacontyl)amino)imidazo[1,2-b]pyridazine-3-carboxamide, KD=10 nM), 5 μl Mab Anti-6His Tb cryptate Gold (Cat: 61HI2TLB, Cisbio Bioassays) and Streptavidin-XL665 (Cat: 610SAXLB, Cisobio Bioassays) mixture were added to plate and further incubated at room temperature for 1 hour. The HTRF signals (ex337 nm, em620 nm/665 nm) were read on BMG PHERAstar FS instrument. The inhibition percentage of TYK2 interaction with its probe in presence of increasing concentrations of compounds was calculated based on the ratio of fluorescence at 615 nm to that at 665 nm. The IC50 for each compound was derived from fitting the data to the four-parameter logistic equation by Dotmatics.

Assay B: JAK1-JH2 Biochemical Assay

Compounds disclosed herein were tested for blocking of JAK1-JH2 protein (aa 561-860, in-house) with its probe in an assay based on Homogeneous Time Resolved Fluorescence. Compound dilution is done according to the following protocol: (1) Prepare 500× compounds solution in DMSO from 500 uM by 5-fold dilution, total 10 doses were included; (2) Prepare 10× compounds solution in an assay buffer containing 20 mM HEPES, pH 7.5, 10 mM MgCl2, 0.005% BSA, 2 mM DTT, 0.015% Brij-35 by transferring 1 μl serial 500× stock solution into 49 μl assay buffer. 4 μL of 1.17 nM recombinant JAK1-JH2 protein was pre-incubated with 1 μl of 10× serial dilution of compounds at room temperature for 0.5 hour. Then 5 μL of 2.9 nM in-house Probe 2 (N-(2-(4-(2-(methyl(4-((((Z)-2-oxoindolin-3-ylidene)(phenyl)methyl)amino)phenyl)amino)-2-oxoethyl)piperazin-1-yl)ethyl)-1-(5-((3aS,4S,6aR)-2-oxohexahydro-1H-thieno[3,4-d]imidazol-4-yl)pentanamido)-3,6,9,12,15,18-hexaoxahenicosan-21-amide, KD=2.9 nM), 5 μl Mab Anti-6His Tb cryptate Gold (Cat: 61HI2TLB, Cisbio Bioassays) and Streptavidin-XL665 (Cat: 610SAXLB, Cisobio Bioassays) mixture were added to plate and further incubated at room temperature for 1 hour. The HTRF signals (ex337 nm, em620 nm/665 nm) were read on BMG PHERAstar FS instrument. The inhibition percentage of JAK1 interaction with its probe in presence of increasing concentrations of compounds was calculated based on the ratio of fluorescence at 615 nm to that at 665 nm. The IC50 for each compound was derived from fitting the data to the four-parameter logistic equation by Dotmatics.

The probes herein used in assays can also be prepared according to the conventional synthesis methods well-known by a chemist.

Assay C: IL-12-JAK2, TYK2/p-STAT4 (Tyr693) Inhibition IC50 Cellular Assay

To evaluate the inhibition effect of compounds disclosed herein on JAK2, TYK2/p-STAT4 (Tyr693) activated by IL-12 in NK-92 cell line, NK-92 cells were collected and washed 3 times by DPBS and resuspended in MEM-α (GIBCO, Cat #12561056) with 10% FBS (Gibco, Cat #10099, Lot #1891605), without IL-2 (R&D systems, Cat #202-IL), starved overnight. Cells were collected and resuspended in 1640 medium (phenol red free, Gibco, Cat #11835-030) with 0.1% BSA, and 12.5 μl/5×10$^4$/well cell suspension were seeded to the 96-well plate (Corning, Cat #3799). Then cells were treated with compounds diluted in 0.2% DMSO 1640 medium, at 37° C., 1 h. Dilution is done according to the following protocol: (1) make 500× compounds solution in DMSO from 5 mM by 4-fold dilution, total 8 doses were included; (3) make 2× compounds solution in assay medium by transferring 0.5 μl serial 500× stock solution into 125 μl assay medium; (4) 15 μl of 2× serial solution is added to cells and incubate at 37° C. for 1 h, the final compound conc. is 10000, 2500, 625, 156.25, 39, 9.8, 2.4 and 0.61 nM, respectively. After 1 h, cells were treated with 2.5 μl medium containing IL-12 at 37° C. (R&D systems, Cat #219-IL-005, final conc. 40 ng/ml), 30 min. Following cells were lysed with 7.5 μl lysis buffer at RT, shaking on shaker for 1 h. 10 μL of cell lysate were transferred to a PE 384-well Proxiplate detection plate, and 5 μL of pre-mixed Alphascreen beads were added to each well. Covered the plate with a plate sealer, span 1000 rpm for 1 min, mix, Incubated overnight at room temperature. Read on BMG PheraStar with Alphascreen protocol. IC 50 values were calculated by fitting dependent data to the four-parameter logistic model using dotmatics software. The assay was performed by using AlphaLISA SureFire Ultra p-STAT4 (Tyr693) Assay Kit—High Volume (PE, Cat #ALSU-PST4-A-HV).

Assay D: IL-6-JAK1/p-STAT3 (Tyr705) Inhibition IC50 Cellular Assay

To evaluate the inhibition effect of compounds disclosed herein on JAK1/p-STAT3 (Tyr705) activated by IL-6 in TF-1 cell line, TF-1 cells were collected and washed 3 times by DPBS and resuspended in RPMI-1640 (phenol red free, Gibco, Cat #11835-030) with 0.1% FBS (Gibco, Cat #10099, Lot #1891605), without GM-CSF (R&D systems, Cat #215-GM-050), starved overnight. Cells were collected and resuspended in 1640 medium (phenol red free, Gibco, Cat #11835-030) with 0.1% BSA, and 12.5 μl/10×10$^4$/well cell suspension were seeded to the 96-well plate (Corning, Cat #3799). Then cells were treated with compounds diluted in 0.2% DMSO 1640 medium, at 37° C., 1 h. Dilution is done according to the following protocol: (1) make 500× compounds solution in DMSO from 5 mM by 4-fold dilution, total 8 doses were included; (3) make 2× compounds solution in assay medium by transferring 0.5 μl serial 500× stock solution into 1251 assay medium; (4) 15 μl of 2× solution is added to cells and incubate at 37° C. for 1 h, the final compound cone. is 10000, 2500, 625, 156.25, 39, 9.8, 2.4 and 0.61 nM, respectively. After 1 h, cells were treated with 2.5 μl medium containing IL-6 at 37° C. (R&D systems, Cat #206-LL-010, final conc. 50 ng/ml), 30 min. Following cells were lysed with 10 μl lysis buffer at RT, shaking on shaker for 1 h. 16 μL of cell lysate were transferred to a PE 384-well HTRF detection plate, and 4 μL of pre-mixed HTRF antibodies were added to each well. Covered the plate with a plate sealer, span 1000 rpm for 1 min, mix, Incubated overnight at room temperature. Read on BMG PheraStar with HTRF protocol (337 nm-665 nm-620 nm). IC 50 values were calculated by fitting dependent data to the four-parameter logistic model using dotmatics software. The assay was performed by using HTRF Phospho-STAT3 (Tyr705) Cellular Assay Kit (Cisbio, Cat #62AT3PEG).

Compounds disclosed herein showed picomolar to nanomolar bio-chemical activity in TYK2-JH2 binding assay and also showed nanomolar activity in cellular assay. In the meanwhile, these compounds showed excellent selectivity in TYK2 bio-chemical assay against JAK1 and in TYK2 cellular assay against JAK2. See the following Tables from 1 to 14.

TABLE 1

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| A1 | 0.052 | 15 | 288 | 79.5 | >10000 | >125 |
| A2 | 5.2 | 828 | 159 | — | — | — |
| A3 | 0.035 | — | — | 2.53 | >10000 | >3952 |
| A4 | 0.52 | 59 | 113 | — | — | — |
| A5 | 0.49 | 59 | 120 | 296 | >10000 | >33 |
| A6 | 0.14 | 18 | 128 | 51 | >10000 | >196 |
| A7 | 670 | >10000 | 14 | — | — | — |
| A8 | 0.26 | — | — | — | — | — |
| A9 | 0.041 | — | — | 1.33 | >10000 | >7518 |
| A10 | 2.4 | — | — | 2996 | — | — |
| A11 | 0.063 | — | — | 41.7 | >10000 | >239 |
| A12 | 0.037 | — | — | 16.8 | >10000 | >595 |
| A13 | 0.08 | — | — | — | — | — |
| A14 | 0.022 | — | — | 0.969 | >10000 | >10319 |
| A15 | 0.04 | — | — | 0.687 | 3462 | 5039 |
| A16 | 0.021 | — | — | 0.667 | >10000 | >14992 |
| A17 | 0.028 | — | — | 1.64 | >10000 | >6097 |
| A18 | 8.15 | — | — | — | — | — |
| A19 | 0.034 | — | — | 1.53 | >10000 | >6535 |
| A20 | 0.03 | — | — | 1.12 | 2379 | 2124 |
| A21 | — | — | — | — | — | — |
| A22 | — | — | — | — | — | — |
| A23 | — | — | — | — | — | — |
| A24 | 0.027 | — | — | 1.85 | >10000 | >5405 |
| A25 | 0.027 | — | — | 0.596 | >10000 | >16778 |
| A26 | 0.032 | — | — | 0.405 | >10000 | >24691 |
| A27 | 0.034 | — | — | 2.1 | >10000 | >4761 |
| A28 | 0.033 | — | — | 1.52 | >10000 | >6578 |
| A29 | 0.042 | — | — | 0.452 | >10000 | >22123 |
| A30 | — | — | — | — | — | — |
| A31 | — | — | — | — | — | — |

TABLE 2

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| B1 | 0.038 | 7.4 | 194 | 9.89 | >10000 | >1011 |
| B2 | 5.8 | — | — | — | — | — |
| B3 | 1.1 | 9 | 8.1 | — | — | — |
| B4 | 0.019 | — | — | 2.53 | >10000 | >3952 |
| B5 | 0.016 | 0.31 | 19 | 0.243 | >10000 | >41152 |
| B6 | 0.018 | 1.2 | 666 | 1.21 | >10000 | >8264 |
| B7 | 0.016 | — | — | 5.58 | >10000 | >1792 |
| B8 | 0.047 | — | — | 1.68 | >10000 | >5952 |
| B9 | 0.53 | — | — | — | — | — |
| B10 | 0.045 | — | — | — | — | — |
| B11 | 0.019 | — | — | — | — | — |
| B12 | 0.034 | — | — | 0.74 | 610 | 824 |
| B13 | 0.43 | 18 | 42 | 183 | >10000 | >54 |
| B14 | 80 | 145 | 1 | — | — | — |
| B15 | 117 | 234 | 1 | — | — | — |
| B16 | 0.03 | — | — | 0.513 | 4292 | 8366 |
| B17 | 0.035 | — | — | 2.05 | >10000 | >4878 |
| B18 | 0.036 | — | — | 1.05 | >10000 | >9523 |
| B19 | 18 | 257 | 14.2 | — | — | — |

TABLE 2-continued

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| B20 | 1.5 | 76 | 50 | — | — | — |
| B21 | 0.047 | — | — | 0.443 | 2490 | 5620 |
| B22 | 0.025 | — | — | 12.61 | 2490 | 197 |
| B23 | 0.04 | — | — | 0.307 | 1001 | 3260 |
| B24 | — | — | — | — | — | — |
| B25 | — | — | — | — | — | — |

TABLE 3

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| C1 | 0.027 | — | — | 0.881 | 563 | 639 |
| C2 | 0.026 | — | — | 0.312 | 962 | 3083 |
| C3 | 0.032 | — | — | 5.81 | >10000 | >1721 |
| C4 | 0.034 | — | — | 4.35 | >10000 | >2298 |
| C5 | 0.032 | — | — | 21.9 | >10000 | >456 |
| C6 | 0.054 | — | — | 26.02 | >10000 | >381 |
| C7 | — | — | — | — | — | — |
| C8 | — | — | — | — | — | — |
| C9 | 0.027 | — | — | 0.672 | >10000 | >14880 |
| C10 | — | — | — | — | — | — |
| C11 | — | — | — | — | — | — |
| C12 | — | — | — | — | — | — |
| C13 | — | — | — | — | — | — |
| C14 | — | — | — | — | — | — |
| C15 | — | — | — | — | — | — |
| C16 | — | — | — | — | — | — |
| C17 | 0.022 | — | — | 0.605 | >10000 | >16528 |
| C18 | 0.023 | — | — | 0.639 | 4873 | 7625 |
| C19 | 0.023 | — | — | — | — | — |
| C20 | 0.023 | — | — | — | — | — |
| C21 | 0.024 | — | — | 0.995 | >10000 | >10050 |
| C22 | 0.023 | — | — | 0.476 | >10000 | >21008 |
| C23 | 0.022 | — | — | 0.63 | 2600 | 4126 |
| C24 | — | — | — | — | — | — |
| C25 | 0.037 | — | — | 0.827 | 1065 | 1288 |

TABLE 4

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| D1 | 0.047 | — | — | 0.251 | >10000 | >39840 |
| D2 | 0.038 | — | — | 15.6 | >10000 | >641 |
| D3 | 0.08 | — | — | 4.8 | >10000 | >2083 |
| D4 | 0.044 | — | — | 0.262 | >10000 | >38167 |
| D5 | 0.036 | — | — | 0.99 | >10000 | >10101 |
| D6 | 0.025 | — | — | 0.593 | >10000 | >16863 |
| D7 | 0.031 | — | — | 0.805 | >10000 | >12422 |
| D8 | 0.036 | — | — | 0.443 | >10000 | >22573 |
| D9 | 0.021 | — | — | 0.479 | >10000 | >20876 |
| D10 | 0.052 | — | — | 12.67 | >10000 | >789 |
| D11 | — | — | — | — | — | — |

TABLE 5

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| E1 | 0.022 | — | — | 4.55 | >10000 | >2197 |
| E2 | 0.017 | — | — | 0.325 | 5807 | 17867 |
| E3 | 0.035 | — | — | 0.645 | >10000 | >15503 |
| E4 | 0.022 | — | — | 0.536 | >10000 | >18656 |
| E5 | 0.022 | — | — | 0.501 | >10000 | >19960 |
| E6 | 0.029 | — | — | 2.72 | >10000 | >3676 |
| E7 | 0.02 | — | — | 0.447 | >10000 | >22371 |
| E8 | 0.034 | — | — | 2.86 | >10000 | >3496 |
| E9 | 0.022 | — | — | 0.504 | >10000 | >19960 |

TABLE 6

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| F1 | 0.046 | — | — | 1.23 | >10000 | >8130 |
| F2 | 0.051 | — | — | 22.14 | >10000 | >451 |
| F3 | 0.068 | — | — | — | — | — |
| F4 | 0.324 | — | — | — | — | — |
| F5 | 0.061 | — | — | — | — | — |
| F6 | 0.532 | — | — | — | — | — |
| F7 | 0.085 | — | — | — | — | — |
| F8 | 0.087 | — | — | — | — | — |
| F9 | 0.06 | — | — | 5.45 | >10000 | > 1834 |
| F10 | 0.04 | — | — | — | — | — |
| F11 | 0.037 | — | — | 0.705 | >10000 | >14184 |
| F12 | 0.034 | — | — | 1.35 | >10000 | >7407 |
| F13 | 0.21 | — | — | — | — | — |
| F14 | 0.13 | — | — | — | — | — |
| F15 | 0.073 | — | — | — | — | — |
| F16 | 0.027 | — | — | — | — | — |
| F17 | 0.054 | — | — | 1.25 | >10000 | >8000 |
| F18 | 0.052 | — | — | — | — | — |
| F19 | 0.036 | — | — | 3.06 | >10000 | >3267 |
| F20 | 0.031 | — | — | 1.45 | >10000 | >6896 |
| F21 | 0.026 | — | — | 3.54 | >10000 | >2814 |
| F22 | 0.026 | — | — | 1.82 | >10000 | >5494 |
| F23 | 0.020 | — | — | 1.07 | >10000 | >9345 |
| F24 | 0.033 | — | — | 0.82 | >10000 | >12195 |
| F25 | 0.029 | — | — | 0.446 | >10000 | >22421 |

TABLE 7

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| G1 | 0.026 | 4.9 | 188 | 14.4 | >10000 | >694 |
| G2 | 0.067 | — | — | 14.2 | >10000 | >704 |
| G3 | 0.05 | — | — | 224 | >10000 | >44 |
| G4 | 0.048 | — | — | 16 | >10000 | >625 |

TABLE 8

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| H1 | 0.016 | 1.4 | 87.5 | 2.6 | >10000 | >3846 |
| H2 | 0.036 | — | — | 0.939 | >10000 | >10649 |
| H3 | 0.048 | — | — | 8.52 | 7185 | >843 |
| H4 | 0.047 | — | — | | | |
| H5 | 0.015 | — | — | 0.323 | 1675 | 5185 |
| H6 | 0.014 | — | — | 1.25 | 8872 | 7097 |
| H7 | 0.046 | — | — | 1.22 | >10000 | >8196 |
| H8 | 0.041 | — | — | 21.66 | >10000 | >461 |
| H9 | 0.016 | — | — | 0.503 | 1583 | 3147 |
| H10 | 0.017 | — | — | 16.45 | >10000 | 607 |
| H11 | 0.027 | — | — | 1 | >10000 | >10000 |
| H12 | 0.022 | — | — | 5.1 | >10000 | >1960 |
| H13 | 0.042 | — | — | 0.676 | 4075 | 6028 |
| H14 | 0.034 | — | — | 0.727 | >10000 | >13755 |
| H15 | 0.029 | — | — | 4.89 | >10000 | >2044 |
| H16 | 0.028 | — | — | 7.51 | >10000 | >1331 |
| H17 | 0.034 | — | — | 67 | >10000 | >149 |
| H18 | 0.032 | — | — | 5.54 | >10000 | >1805 |
| H19 | 0.028 | — | — | 3.2 | >10000 | >3125 |
| H20 | 0.046 | — | — | 35.2 | >10000 | >284 |
| H21 | 0.024 | — | — | 2.24 | >10000 | >4464 |
| H22 | 0.038 | — | — | 2.76 | >10000 | >3623 |
| H23 | 0.034 | — | — | 5.7 | >10000 | >1754 |
| H24 | 0.034 | — | — | 5.39 | >10000 | >1855 |
| H25 | 0.038 | — | — | 7.53 | >10000 | >1328 |
| H26 | 0.039 | — | — | 11.7 | >10000 | >854 |
| H27 | 0.031 | — | — | 2.72 | >10000 | >3676 |
| H28 | 0.03 | — | — | 29.2 | >10000 | >342 |
| H29 | 0.022 | — | — | 1.77 | 8491 | 4797 |
| H30 | 0.023 | — | — | 0.972 | >10000 | >10288 |
| H31 | 0.023 | — | — | 0.935 | >10000 | >10695 |
| H32 | 0.023 | — | — | 0.447 | >10000 | >22371 |
| H33 | 0.019 | — | — | 0.777 | >10000 | >22371 |
| H34 | 0.023 | — | — | 1.12 | >10000 | >8928 |
| H35 | 0.028 | — | — | 3.17 | >10000 | >3154 |
| H36 | 0.022 | — | — | 1.95 | >10000 | >5128 |
| H37 | — | — | — | — | — | — |
| H38 | — | — | — | — | — | — |
| H39 | — | — | — | — | — | — |
| H40 | — | — | — | — | — | — |
| H41 | — | — | — | — | — | — |
| H42 | — | — | — | — | — | — |
| H43 | 0.034 | — | — | 5.39 | >10000 | >1855 |

TABLE 9

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| J1 | 0.019 | — | — | 0.446 | >10000 | >22421 |
| J2 | 0.022 | — | — | 3 | >10000 | >3333 |
| J3 | 0.026 | — | — | 0.286 | >10000 | >34965 |
| J4 | 0.028 | — | — | 4.94 | >10000 | >2024 |
| J5 | 0.022 | — | — | 2.05 | >10000 | >4878 |
| J6 | 0.033 | — | — | 7.94 | >10000 | >1259 |
| J7 | 0.19 | — | — | 66.23 | >10000 | >150 |
| J8 | 0.073 | — | — | 7.67 | >10000 | >1303 |
| J9 | 0.083 | — | — | 6.54 | >10000 | >1529 |
| J10 | 0.05 | — | — | 6.34 | >10000 | >1577 |
| J11 | 0.017 | — | — | 0.275 | 6415 | 23327 |
| J12 | 0.017 | — | — | 0.847 | >10000 | >11806 |
| J13 | 0.054 | — | — | 1.18 | >10000 | >8474 |
| J14 | 0.033 | — | — | 0.792 | >10000 | >12626 |

TABLE 9-continued

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| J15 | 0.016 | — | — | 5.9 | >10000 | >1694 |
| J16 | 0.015 | — | — | 2.52 | >10000 | >3968 |
| J17 | 0.043 | — | — | 6.8 | >10000 | >1470 |
| J18 | 0.028 | — | — | 0.399 | >10000 | >25062 |
| J19 | 0.015 | — | — | 0.882 | >10000 | >1137 |
| J20 | 0.026 | — | — | 3 | >10000 | >3333 |
| J21 | 0.017 | — | — | 0.72 | >10000 | >13888 |
| J22 | 0.037 | — | — | 1.93 | >10000 | >5181 |
| J23 | 0.044 | — | — | 0.862 | 1354 | 1570 |
| J24 | 0.028 | — | — | 6.05 | >10000 | >1652 |
| J25 | 0.025 | — | — | 2.91 | >10000 | >3436 |
| J26 | 0.023 | — | — | 5.5 | >10000 | >1818 |
| J27 | 0.04 | — | — | 0.439 | >10000 | >22779 |
| J28 | 0.053 | — | — | 3.14 | >10000 | >3184 |
| J29 | 0.045 | — | — | 12.41 | >10000 | >805 |
| J30 | 0.054 | — | — | 4.82 | >10000 | >2074 |
| J31 | 0.076 | — | — | 14.97 | >10000 | >668 |
| J32 | 0.079 | — | — | 8.79 | >10000 | >1137 |
| J33 | 0.12 | — | — | — | — | — |
| J34 | 0.067 | — | — | 9.69 | >10000 | >1031 |
| J35 | 0.036 | — | — | 8.13 | >10000 | >1230 |
| J36 | 0.043 | — | — | 5.05 | >10000 | >1980 |
| J37 | 0.035 | — | — | 19.1 | >10000 | >523 |
| J38 | 0.024 | — | — | 1.98 | >10000 | >5050 |
| J39 | 0.036 | — | — | 10.69 | >10000 | >935 |
| J40 | 0.029 | — | — | 0.326 | >10000 | >30674 |
| J41 | 0.027 | — | — | 2.98 | >10000 | >3355 |
| J42 | 0.05 | — | — | 0.796 | >10000 | >12562 |
| J43 | 0.025 | — | — | 0.744 | >10000 | >13440 |
| J44 | 0.022 | — | — | 0.358 | >10000 | >27932 |
| J45 | 0.028 | — | — | 0.398 | >10000 | >25125 |
| J46 | 0.033 | — | — | 2.35 | >10000 | >4255 |
| J47 | 0.037 | — | — | 4.73 | >10000 | >2114 |
| J48 | 0.035 | — | — | 70.2 | >10000 | >1421411 |
| J49 | 0.13 | — | — | — | — | — |
| J50 | 0.049 | — | — | 27.68 | >10000 | >361 |
| J51 | 0.043 | — | — | 1.58 | >10000 | >6329 |
| J52 | 0.021 | — | — | 1.43 | >10000 | >699 |
| J53 | 0.033 | — | — | 3.47 | >10000 | >2881 |
| J54 | 0.028 | — | — | 2.03 | >10000 | >4926 |
| J55 | 0.033 | — | — | 11.38 | >10000 | >878 |
| J56 | 0.044 | — | — | 30.07 | >10000 | >332 |
| J57 | 0.045 | — | — | 15.3 | >10000 | >653 |
| J58 | 0.025 | — | — | 0.497 | >10000 | >20120 |
| J59 | 0.029 | — | — | 1.31 | >10000 | >7633 |
| J60 | 0.021 | — | — | 0.797 | >10000 | >12547 |
| J61 | 0.019 | — | — | 1.42 | >10000 | >7042 |
| J62 | 0.037 | — | — | 4.85 | >10000 | >2061 |
| J63 | 0.018 | — | — | 0.462 | >10000 | >21645 |
| J64 | — | — | — | — | — | — |
| J65 | — | — | — | — | — | — |

TABLE 10

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| M1 | 0.055 | — | — | 0.174 | 2010 | 11551 |
| M2 | 0.032 | — | — | 1.04 | >10000 | >9615 |
| M3 | 0.031 | — | — | 0.526 | 8351 | 15876 |
| M4 | 0.026 | — | — | 0.681 | >10000 | >14684 |
| M5 | 0.032 | — | — | 0.189 | 1551 | 8206 |
| M6 | 0.032 | — | — | 1.21 | >10000 | >8264 |

TABLE 10-continued

| Example | Biochemical assay TYK2-JH2 IC50 (nM) | JAK1-JH2 IC50 (nM) | Selectivity fold (TYK2/JAK1) | Cellular assay pSTAT4/IL-12 IC50 (nM) | pSTAT5/GM-CSF IC50 (nM) | Selectivity fold (TYK2/JAK2) |
|---|---|---|---|---|---|---|
| M7 | 0.026 | — | — | 0.537 | >10000 | >18621 |
| M8 | 0.04 | — | — | 1.64 | >10000 | >6097 |
| M9 | 0.035 | — | — | 7.06 | >10000 | >1416 |
| M10 | 0.099 | — | — | — | — | — |
| M11 | 0.034 | — | — | 9.03 | >10000 | >1107 |
| M12 | 0.03 | — | — | 9.12 | >10000 | >1096 |
| M13 | 0.11 | — | — | — | — | — |
| M14 | 0.03 | — | — | 9.46 | >10000 | >1057 |
| M15 | 0.048 | — | — | 10.23 | >10000 | >977 |
| M16 | 0.048 | — | — | — | — | — |
| M17 | 0.041 | — | — | 1.09 | >10000 | >9174 |
| M18 | 0.026 | — | — | 0.989 | >10000 | >10111 |
| M19 | 0.032 | — | — | 2.55 | >10000 | >3921 |
| M20 | 0.062 | — | — | 1.01 | >10000 | >9900 |
| M21 | 0.035 | — | — | 1.69 | >10000 | >5917 |
| M22 | 0.027 | — | — | 0.316 | 532 | 1683 |
| M23 | 0.031 | — | — | 1.08 | 3749 | 3471 |
| M24 | 0.032 | — | — | 0.487 | 2175 | 4466 |
| M25 | 0.096 | — | — | 15.17 | >10000 | >659 |
| M26 | 0.046 | — | — | 4.33 | >10000 | >2309 |
| M27 | 0.035 | — | — | 3.85 | >10000 | >2597 |
| M28 | 0.032 | — | — | 16.62 | >10000 | >601 |
| M29 | — | — | — | — | — | — |
| M30 | 0.049 | — | — | 11.2 | >10000 | >892 |
| M31 | 0.031 | — | — | 0.828 | 1421 | 1714 |
| M32 | 0.074 | — | — | — | — | — |
| M33 | 0.027 | — | — | 0.648 | >10000 | >15432 |
| M34 | 0.024 | — | — | 0.402 | >10000 | >24875 |
| M35 | 0.036 | — | — | 50.24 | >10000 | >199 |

TABLE 11

| Example | Biochemical assay TYK2-JH2 IC50 (nM) | JAK1-JH2 IC50 (nM) | Selectivity fold (TYK2/JAK1) | Cellular assay pSTAT4/IL-12 IC50 (nM) | pSTAT5/GM-CSF IC50 (nM) | Selectivity fold (TYK2/JAK2) |
|---|---|---|---|---|---|---|
| N1 | 0.077 | — | — | 0.247 | 2133 | 8635 |
| N2 | 0.021 | — | — | 0.641 | >10000 | >15600 |
| N3 | 0.033 | — | — | 12.63 | >10000 | >791 |
| N4 | 0.029 | — | — | 0.137 | >10000 | >72992 |
| N5 | 0.039 | — | — | 0.212 | >10000 | >47169 |
| N6 | 0.039 | — | — | 0.274 | >10000 | >36496 |
| N7 | 0.024 | — | — | 1.43 | >10000 | >6993 |

TABLE 12

| Example | Biochemical assay TYK2-JH2 IC50 (nM) | JAK1-JH2 IC50 (nM) | Selectivity fold (TYK2/JAK1) | Cellular assay pSTAT4/IL-12 IC50 (nM) | pSTAT5/GM-CSF IC50 (nM) | Selectivity fold (TYK2/JAK2) |
|---|---|---|---|---|---|---|
| O1 | 0.017 | — | — | 0.414 | 1213 | 2929 |
| O2 | 0.016 | — | — | 1.12 | 7007 | 6265 |
| O3 | 0.031 | — | — | 6.86 | 8295 | 2109 |

TABLE 13

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| Q1 | 0.023 | — | — | 1.76 | >10000 | >5681 |
| Q2 | 0.021 | — | — | 1.7 | >10000 | >5882 |
| Q3 | 0.023 | — | — | 1.14 | >10000 | >8771 |
| Q4 | 0.037 | — | — | 1.10 | >10000 | >9090 |
| Q5 | 0.065 | — | — | — | — | — |
| Q6 | 0.028 | — | — | 0.45 | >10000 | >22222 |
| Q7 | — | — | — | — | — | — |
| Q8 | — | — | — | — | — | — |
| Q9 | — | — | — | — | — | — |
| Q10 | — | — | — | — | — | — |
| Q11 | — | — | — | — | — | — |
| Q12 | — | — | — | — | — | — |
| Q13 | — | — | — | — | — | — |
| Q14 | — | — | — | — | — | — |
| Q15 | — | — | — | — | — | — |
| Q16 | — | — | — | — | — | — |
| Q17 | — | — | — | — | — | — |
| Q18 | 0.023 | — | — | 0.91 | >10000 | >10989 |
| Q19 | 0.025 | — | — | 3.02 | >10000 | >3311 |
| Q20 | 0.022 | — | — | 0.16 | 1767 | 11043 |
| Q21 | 0.037 | — | — | 0.411 | 1572 | 3824 |
| Q22 | 0.025 | — | — | 0.584 | 3959 | 6779 |
| Q23 | 0.028 | — | — | 0.605 | 8101 | 13390 |
| Q24 | 0.033 | — | — | 0.559 | 620 | 1109 |
| Q25 | 0.026 | — | — | 0.530 | 1822 | 3437 |
| Q26 | 0.032 | — | — | 1.53 | 700 | 457 |
| Q27 | 0.033 | — | — | — | — | — |
| Q28 | 0.026 | — | — | 0.329 | >10000 | >30395 |
| Q29 | 0.037 | — | — | — | — | — |
| Q30 | 0.065 | — | — | — | — | — |
| Q35 | 0.020 | — | — | 0.679 | 1810 | 2665 |
| Q36 | — | — | — | — | — | — |
| Q49 | 0.029 | — | — | 0.827 | 379 | 458 |
| Q50 | 0.019 | — | — | 0.626 | 2023 | 3231 |
| Q51 | 0.034 | — | — | 0.979 | >10000 | >10214 |
| Q52 | 0.038 | — | — | 1.33 | 3420 | 2571 |
| Q53 | 0.047 | — | — | 0.581 | >10000 | >17211 |
| Q54 | 0.037 | — | — | 0.560 | 3985 | 7116 |
| Q55 | 0.019 | — | — | — | — | — |
| Q56 | 0.031 | — | — | — | — | — |
| Q57 | 0.031 | — | — | — | — | — |
| Q58 | 0.097 | — | — | — | — | — |
| Q59 | 0.033 | — | — | — | — | — |
| Q60 | 0.059 | — | — | — | — | — |
| Q61 | 0.022 | — | — | — | — | — |
| Q62 | 0.047 | — | — | 1.79 | >10000 | >5586 |
| Q63 | 0.051 | — | — | 0.755 | 459 | 608 |
| Q64 | 0.034 | — | — | 4.61 | >10000 | >2169 |
| Q65 | 0.029 | — | — | 0.685 | 1642 | 2397 |
| Q66 | 0.029 | — | — | 0.792 | 3046 | 3845 |
| Q73 | 0.025 | — | — | 2.84 | 2354 | 828 |
| Q75 | 0.024 | — | — | 0.637 | 473 | 742 |
| Q79 | 0.32 | — | — | — | — | — |
| Q86 | 0.031 | — | — | 1.48 | 91 | 615 |
| Q90 | — | — | — | 44 | >10000 | 227 |
| Q97 | — | — | — | 3.29 | >10000 | 3039 |
| Q98 | 0.026 | — | — | 1.15 | >10000 | 8695 |
| Q99 | 0.033 | — | — | — | — | — |
| Q101 | 0.03 | — | — | 0.904 | 373 | 412 |
| Q104 | 0.029 | — | — | — | — | — |
| Q106 | 0.015 | — | — | — | — | — |
| Q108 | — | — | — | 1.18 | >10000 | >8474 |
| Q110 | — | — | — | 1.08 | >10000 | >9259 |
| Q115 | 0.034 | — | — | 0.302 | >10000 | >33112 |
| Q119 | 0.031 | — | — | 1.19 | 1149 | 965 |
| Q120 | 0.032 | — | — | — | — | — |

TABLE 14

| | Biochemical assay | | | Cellular assay | | |
|---|---|---|---|---|---|---|
| Example | TYK2-JH2 IC50 (nM) | JAK1-JH2 IC50 (nM) | Selectivity fold (TYK2/JAK1) | pSTAT4/IL-12 IC50 (nM) | pSTAT5/GM-CSF IC50 (nM) | Selectivity fold (TYK2/JAK2) |
| R1 | 0.041 | — | — | 2.18 | >10000 | >4587 |

Binding Pose of Compounds in Tyk2 JH2 Domain

The X-ray crystal structure of human Tyk2 JH12 domain in complex with BMS986165 (PDB ID: 6NZP) was downloaded from the RCSB protein data bank and prepared by the Protein Preparation Wizard in Schrödinger 2020, including removing crystallographic waters, fixing bond orders, adding hydrogens, assigning partial charges with the OPLS3e force field, and minimizing the added hydrogens. The 3D structure of the Example B5 was processed by LigPrep module of Schrödinger 2020 at pH7.4. And then the ligand was docked into the binding pocket (with a radius of 10 Å around BMS986165 binding site) of the above prepared Tyk2 JH2 domain using Glide SP (standard precision). Standard default settings were used for other parameters.

The binding pose of Example B5 in Tyk2 JH2 domain showed importance of substituted position of methylsulfonyl group and acetamide group on the two pyridine rings, for the Tyk2 inhibitors of the present disclosure (Scheme 1). The substituted position of methylsulfonyl group was essential for potency, meta position was much better than orth position, for example, Examples B1 and B5 showed Tyk2 JH2 domain bio-chemical potency at 0.038 nM and 0.016 nM, respectively, whereas Examples B15 and B14 were 3079-fold and 5000-fold less potent, respectively, that was due to the strong interaction between methylsulfonyl group on the pyridine ring and Lys642 residue of Tyk2 (Scheme 1). The acetamide group on the other pyridine ring can also form crucial interaction with Lys642 of Tyk2. Furtherly, the substitution R of acetamide group on the other pyridine ring effected the Tyk2 inhibition potency, for example, the potency dramatically decreased when replacing R from methyl group (Example B1) to cyclopropane group (Example B20). and. In addition, the nitrogen (N) atom of the pyridine ring, which is at the adjacent position of methylsulfonyl, was essential for coplanarity of the two pyridine rings, for example, Example B5 is 2-fold more potent than Example B1 in bio-chemical assay and 40-fold more potent in cellular assay.

Scheme 1 example B5

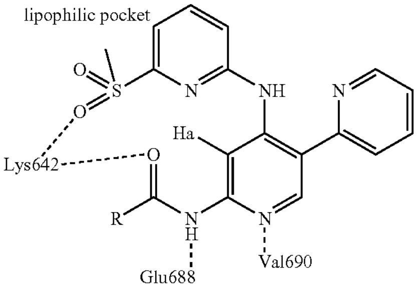

Biological Assay: Mouse PK Study

The pharmacokinetics of compounds were evaluated in male CD-1 mouse via Oral Administration (dose of 10 mg/kg). For oral administration study, test compounds were added in 0.5% MC in water and administrated to mice at 10 mg/kg by gavage. Blood was collected into EDTA-K2 anticoagulant tube at 15, and 30 min and 1, 2, 4, 8 and 24 h after administration. Approximately 30 μL blood was collected at each time point. And then the blood was centrifuged at 2000 g for 5 min at 4° C. using a centrifuge to obtain the plasma. The plasma sample was transferred into a tube and stored in a freezer at approximately −70° C. until the determination of concentration by LC-MS/MS. Pharmacokinetic parameters were estimated by using WinNonlin software (version 8.1, Pharsight Corporation, CA, USA) with non-compartmental method. The following pharmacokinetic parameters were calculated, whenever possible from the plasma concentration-time data: $T_{max}$, $C_{max}$, $AUC_{last}$, $AUC_{inf}$, $T_{1/2}$ for PO administration. All animals were fasted before experiment. The results are shown in Table 15.

TABLE 15

| | Po dosing (10 mg/kg) | | |
|---|---|---|---|
| Compound | $T_{1/2}$ | Cmax (ng/ml) | $AUC_{last}$ (h · ng/mL) |
| Example F22 | 1.48 | 911 | 2098 |
| Example H11 | 2.07 | 8.73 | 19.3 |
| Example Q25 | 3.01 | 2820 | 16245 |

The compounds disclosed herein with pyridine fused ring part showed significantly good PK. As in Table 15, taking Example Q25 with pyridine fused ring part as an example, showed significantly better PK than Examples F22 and H11. The $A_{UC}$ (16245 h-ng/mL) and $C_{max}$ (2820 ng/mL) data of Example Q25 in the table were at least 3-fold higher than those of Example F22 ($C_{max}$: 911 ng/mL; $A_{UC}$: 2098 h-ng/mL) and H11 ($C_{max}$: 7 ng/mL; $A_{UC}$: 19.4 h ng/mL).

It is to be understood that, if any prior art publication is referred to herein, such reference does not constitute an admission that the publication forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of Formula (I)

(I)

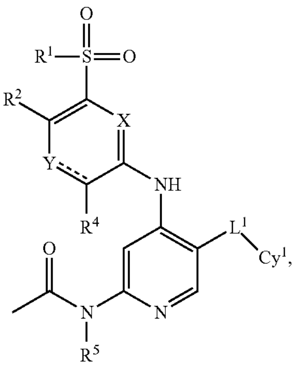

or a stereoisomer or a pharmaceutically acceptable salt thereof, wherein:

X is N or CH;

Y is N, $NR^3$ or $CR^3$;

$L^1$ is a direct bond, $—(CR^aR^b)_q—$, —O—, —S—, —S(O)—, $—SO_2—$, —C(O)—, C(O)O—, —OC(O)—, $—NR^a—$, $—O—(CR^aR^b)_q—$, $—S—(CR^aR^b)_q—$, $—S(O)—(CR^aR^b)_q—$, $—SO_2—(CR^aR^b)_q—$, $—C(O)—(CR^aR^b)_q—$, $C(O)O—(CR^aR^b)_q—$, $—OC(O)—(CR^aR^b)_q—$, $—NR^a—(CR^aR^b)_q—$, $—C(O)NR^a—$, $—NR^aC(O)—$, $—NR^aC(O)O—$, $—NR^aC(O)NR^b—$, $—SO_2NR^a—$, $—NR^aSO_2—$, $—NR^aS(O)_2NR^b—$, $—NR^aS(O)NR^b—$, $—C(O)NR^aSO_2—$, $—C(O)NR^aSO—$, or $—C(═NR^a)NR^b—$, wherein q is a number from 1 to 7, and $R^a$ and $R^b$ are independently hydrogen, $—C_{1-6}$alkyl, $—C_{2-6}$alkenyl, $—C_{2-6}$alkynyl, cycloalkyl, heterocyclyl, aryl, or heteroaryl;

$R^1$ is $—C_{1-6}$alkyl, —halo$C_{1-6}$alkyl, $—C_{1-6}$ alkoxy, —halo$C_{1-6}$ alkoxy, $—C_{3-6}$ cycloalkyl, aryl, or $—NR'''R''$;

each of $R^2$, $R^3$, and $R^4$ is independently hydrogen, cyano, halogen, $—C_{1-6}$alkyl, $—C_{2-6}$alkenyl, $—C_{2-6}$alkynyl, $—C_{3-8}$cycloalkyl, heterocyclyl, aryl, heteroaryl, oxo, $—NO_2$, $—OR^e$, $—SO_2R^e$, $—COR^e$, $—CO_2R^e$, $—CONR^eR^f$, $—C(═NR^e)NR^fR^g$, $—NR^eR^f$, $—NR^eCOR^f$, $—NR^eCONR^fR^g$, $—NR^eCO_2R^f$, $—NR^eSONR^fR^g$, $—NR^eSO_2NR^fR^g$, or $—NR^eSO_2R^f$, wherein each of $—C_{1-6}$alkyl, $—C_{2-6}$alkenyl, $—C_{2-6}$alkynyl, $—C_{3-8}$cycloalkyl, heterocyclyl, aryl, or heteroaryl is independently and optionally substituted with at least one substituent selected from i) cyano, oxo, halogen, $—NR'''R''$, $—OR^h$, $—C(O)NR'''R''$;

ii) heterocyclyl optionally substituted with at least one substituent independently selected from cyano, oxo, halogen, hydroxy, $—NR'''R''$, substituted or unsubstituted $—C_{1-6}$alkyl, substituted or unsubstituted $—C_{1-6}$alkoxy or $—C(O)NR'''R''$; or, iii) $C_{1-6}$alkyl optionally substituted with at least one substituent independently selected from cyano, halogen, hydroxy, $—NH_2$ or $C_{1-6}$alkoxy;

wherein $R^h$ is hydrogen, hydroxy, $—NH_2$, $—C_{1-6}$alkyl, $C_{1-6}$alkyl substituted with hydroxy, or heterocyclyl, $R^e$, $R^f$, and $R^g$ are each independently hydrogen, $—C_{1-6}$ alkyl, $—C_{1-6}$alkoxy, $—C_{2-6}$alkenyl, $—C_{2-6}$alkynyl, cycloalkyl, heterocyclyl, aryl, or heteroaryl, wherein each of $—C_{1-6}$alkyl, $—C_{2-6}$alkenyl, $—C_{2-6}$alkynyl, cycloalkyl, heterocyclyl, aryl, or heteroaryl is optionally independently substituted with one to three substituents selected from cyano, oxo, halogen, hydroxy, $—NR'''R''$, $—C_{1-6}$alkyl, $—C_{1-6}$alkoxy, $—C_{3-6}$cycloalkyl optionally substituted with halogen, hydroxy or $—C_{1-6}$alkoxy, $—C(O)NR'''R''$, or heterocyclyl;

$R^5$ is hydrogen or $C_{1-6}$alkyl;

$Cy^1$ is 6- to 12-membered aryl or 5- to 14-membered heteroaryl, or 5- to 14-membered heterocyclyl, each of which is optionally substituted with at least one substituent $R^i$, $R^i$ is independently halogen, cyano, $—C_{1-6}$alkyl, $—C_{2-6}$ alkenyl, $—C_{2-6}$alkynyl, $—C_{3-8}$cycloalkyl, heterocyclyl, aryl, heteroaryl, oxo, $—NO_2$, $—OR^j$, $—SO_2R^j$, $—COR^j$, $—CO_2R^k$, $—CONR^jR^k$, $—C(═NR^j)NR^kR^l$, $—NR^jR^k$, $—NR^jCOR^k$, $—NR^jCONR^kR^l$, $—NR^jCO_2R^k$, $—NR^jSONR^kR^l$, $—NR^jSO_2NR^kR^l$, or $—NR^jSO_2R^k$, wherein each of $—C_{1-6}$alkyl, $—C_{2-6}$alkenyl, $—C_{2-6}$alkynyl, $—C_{3-8}$cycloalkyl, heterocyclyl, aryl, or heteroaryl is optionally substituted with halogen, $—OR'''$, $—C(O)R'''$, $—NR'''R''$, $—C_{1-6}$alkyl, $C_{1-6}$alkoxy-, $C_{1-6}$alkyl substituted with $—C_{1-6}$alkoxy or oxo;

$R^j$, $R^k$, $R^l$, $R'''$, $R''$ are each independently hydrogen, $—C_{1-6}$alkyl, $C_{1-6}$alkoxy-$C_{1-6}$alkyl-, $—C_{2-6}$alkenyl, $—C_{2-6}$alkynyl, cycloalkyl, heterocyclyl, aryl, or heteroaryl;

or ($R^1$ and $R^2$), or ($R^2$ and $R^3$), or ($R^3$ and $R^4$), together with the atoms to which they are attached, form a fused ring system, said fused ring system comprises 0-4 heteroatoms selected from oxygen (O), nitrogen (N) or sulfur (S) as ring member(s) and is optionally and independently substituted with halogen, $—C_{1-6}$alkyl, $—C_{1-6}$alkoxy, $C_{1-6}$alkyl substituted with halogen, $C_{1-6}$alkoxy substituted with halogen, or $—C_{3-6}$cycloalkyl;

wherein any of said alkyl or alkoxy is optionally enriched in deuterium.

2. The compound of claim 1, wherein the compound of Formula (I) is compound of Formula (I-A)

(I-A)

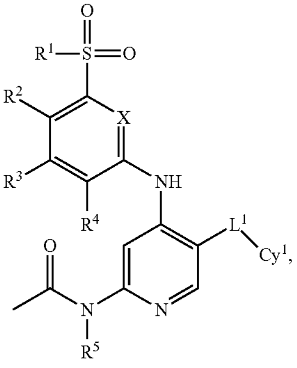

or a stereoisomer or a pharmaceutically acceptable salt thereof, wherein:

X is N or CH;

$L^1$ is a direct bond, $-(CR^aR^b)_q-$, —O—, —S—, —S(O)—, $-SO_2-$, —C(O)—, C(O)O—, —OC(O)—, $-NR^a-$, $-O-(CR^aR^b)_q-$, $-S-(CR^aR^b)_q-$, $-S(O)-(CR^aR^b)_q-$, $-SO_2-(CR^aR^b)_q-$, $-C(O)-(CR^aR^b)_q-$, $C(O)O-(CR^aR^b)_q$, $-OC(O)-(CR^aR^b)_q-$, $-NR^a-(CR^aR^b)_q-$, $-C(O)NR^a-$, $-NR^aC(O)-$, $-NR^aC(O)O-$, $-NR^aC(O)NR^b-$, $-SO_2NR^a-$, $-NR^aSO_2-$, $-NR^aS(O)_2NR^b-$, $-NR^aS(O)NR^b-$, $-C(O)NR^aSO_2-$, $-C(O)NR^aSO-$, or $-C(=NR^a)NR^b-$, wherein q is a number from 1 to 7, and $R^a$ and $R^b$ are independently hydrogen, $-C_{1-6}$alkyl, $-C_{2-6}$alkenyl, $-C_{2-6}$alkynyl, cycloalkyl, heterocyclyl, aryl, or heteroaryl;

$R^1$ is $-C_{1-6}$alkyl, -halo$C_{1-6}$alkyl, $-C_{1-6}$ alkoxy, —halo$C_{1-6}$ alkoxy, $-C_{3-6}$ cycloalkyl, aryl, or $-NR'''R''$;

each of $R^2$, $R^3$, and $R^4$ is independently hydrogen, halogen, $-C_{1-6}$alkyl, $-C_{2-6}$alkenyl, $-C_{2-6}$ alkynyl, $-C_{3-8}$ cycloalkyl, heterocyclyl, aryl, heteroaryl, oxo, cyano, $-NO_2$, $-OR^e$, $-SO_2R^e$, $-COR^e$, $-CO_2R^e$, $-CONR^eR^f$, $-C(=NR^e)NR^fR^g$, $-NR^eR^f$, $-NR^eCOR^f$, $-NR^eCONR^fR^g$, $-NR^eCO_2R^f$, $-NR^eSONR^fR^g$, $-NR^eSO_2NR^fR^g$, or $-NR^eSO_2R^f$, wherein each of $-C_{1-6}$alkyl, $-C_{2-6}$alkenyl, $-C_{2-6}$alkynyl, $-C_{3-8}$cycloalkyl, heterocyclyl, aryl, or heteroaryl is independently and optionally substituted with at least one substituents selected from cyano, oxo, halogen, $C_{1-6}$alkyl optionally substituted with halogen, $-C_{1-6}$alkyl substituted with hydroxy $-OR^h$, $-C(O)NR'''R''$, $-NH_2$, $C_{1-6}$alkyl substituted with $NH_2$ or $-C_{1-6}$alkyl substituted with $C_{1-6}$alkoxy;

wherein $R^h$ is hydrogen, $-C_{1-6}$alkyl, hydroxy-$C_{1-6}$alkyl or heterocyclyl, $R^e$, $R^f$, and $R^g$ are each independently hydrogen, $-C_{1-6}$ alkyl, $-C_{1-6}$alkoxy, $-C_{2-6}$alkenyl, $-C_{2-6}$alkynyl, cycloalkyl, heterocyclyl, aryl, or heteroaryl, wherein each of $-C_{1-6}$alkyl, $-C_{2-6}$alkenyl, $-C_{2-6}$alkynyl, cycloalkyl, heterocyclyl, aryl, or heteroaryl is optionally independently substituted with one to three substituents selected from halogen, hydroxy, cyano, or $-C_{1-6}$alkoxy; $-C_{3-6}$cycloalkyl optionally substituted with halogen, hydroxy, or $C_{1-6}$alkoxy, or heterocyclyl;

$R^5$ is hydrogen or $C_{1-6}$alkyl;

$Cy^1$ is 6- to 12-membered aryl or 5- to 14-membered heteroaryl, or 5- to 14-membered heterocyclyl, each of which is optionally substituted with at least one substituent R, $R^i$ is independently halogen, cyano, $-C_{1-6}$alkyl, $-C_{2-6}$ alkenyl, $-C_{2-6}$alkynyl, $-C_{3-8}$cycloalkyl, heterocyclyl, aryl, heteroaryl, oxo, $-NO_2$, —OR, $-SO_2R$, —COR, $-CO_2R^k$, $-CONR^jR^k$, $-C(=NR^j)NR^kR^l$, $-NR^jR^k$, $-NR^jCOR^k$, $-NR^jCONR^kR^l$, $-NR^jCO_2R^k$, $-NR^jSONR^kR^l$, $-NR^jSO_2NR^kR^l$, or $-NR^jSO_2R^k$, wherein each of said $-C_{1-6}$alkyl, $-C_{2-6}$alkenyl, $-C_{2-6}$alkynyl, $-C_{3-8}$cycloalkyl, heterocyclyl, aryl, or heteroaryl is optionally substituted with halogen, $OR'''$, $C(O)R'''$, $-NR'''R''$, $-C_{1-6}$alkyl, $C_{1-6}$alkoxy-, $C_{1-6}$alkoxy-$C_{1-6}$alkyl-, or oxo;

$R^j$, $R^k$, $R^l$, $R'''$, $R''$ are each independently hydrogen, $-C_{1-6}$alkyl, $-C_{1-6}$alkyl substituted with $C_{1-6}$alkoxy, $-C_{2-6}$alkenyl, $-C_{2-6}$alkynyl, cycloalkyl, heterocyclyl, aryl, or heteroaryl;

or ($R^1$ and $R^2$), or ($R^2$ and $R^3$), or ($R^3$ and $R^4$), together with the atoms to which they are attached, form a fused ring system, said fused ring system comprises 0-4 heteroatoms selected from oxygen, nitrogen or sulfur as ring member(s) and is optionally and independently substituted with halogen, $-C_{1-6}$alkyl, $-C_{1-6}$alkoxy, -halo$C_{1-6}$alkyl, -halo$C_{1-6}$alkoxy, or $-C_{3-6}$cycloalkyl;

wherein any of said alkyl or alkoxy is optionally enriched in deuterium.

3. The compound of claim 2, wherein $R^1$ is $-C_{1-3}$ alkyl, $-NR'''R''$ or $-C_{3-6}$ cycloalkyl.

4. The compound of claim 2, wherein $R^2$ and $R^4$ are each independently hydrogen, halogen, $-C_{1-6}$alkyl, or $-C_{1-6}$alkoxy.

5. The compound of claim 2, wherein $R^3$ is hydrogen;

cyano;

halogen;

$-C_{1-4}$ alkyl optionally substituted with at least one substituent independently selected from halogen, or $-OR^h$, wherein $R^h$ is hydrogen, $-C_{1-6}$alkyl, or heterocyclyl;

$-C_{3-6}$cycloalkyl, optionally substituted with at least one substituent independently selected from cyano, oxo, halogen, $-C_{1-6}$alkyl, or $-C(O)NR'''R''$, wherein $-C_{1-6}$alkyl is substituted with at least one substituent independently selected from halogen, hydroxy, $-NH_2$, or $C_{1-6}$alkoxy;

heterocyclyl comprising one or two heteroatoms selected from oxygen (O), nitrogen (N) or sulfur (S) as ring member(s), optionally substituted with at least one substituent independently selected from cyano, oxo, halogen, hydroxy, $C_{1-6}$alkyl, or $-C(O)NR'''R''$, and wherein $-C_{1-6}$alkyl is substituted with at least one substituent independently selected from halogen, hydroxy, $-NH_2$, or $C_{1-6}$alkoxy;

$-OR^e$, wherein $R^e$ is $-C_{1-6}$alkyl, $-C_{3-6}$cycloalkyl, 3- to 6-membered heterocyclyl, or aryl, wherein i) $-C_{1-6}$alkyl is optionally substituted with cyano, halogen, hydroxy, or $-C_{1-6}$alkoxy; and, ii) $-C_{3-6}$cycloalkyl or 3- to 6-membered heterocyclyl is optionally substituted with cyano, halogen, hydroxy, or $C_{1-6}$alkoxy;

$C_{5-10}$aryl; or heteroaryl comprising one oxygen (O), nitrogen (N) or sulfur (S) heteroatom as ring member, optionally substituted with at least one substituent independently selected from cyano, -oxo, halogen, hydroxy, $-C_{1-6}$ alkyl, $-C_{1-6}$alkoxy or $-C(O)NR'''R''$, wherein $-C_{1-6}$ alkyl is substituted with at least one substituent independently selected from halogen, hydroxy, $-NH_2$, or $C_{1-6}$alkoxy;

and wherein $R'''$ and $R''$ are independently selected from hydrogen or $C_{1-3}$alkyl;

wherein any of said alkyl or alkoxy is optionally enriched in deuterium.

6. The compound of claim 5, wherein $R^3$ is hydrogen;

cyano;

halogen;

$-C_{1-4}$ alkyl optionally substituted with at least one substituent independently selected from halogen, or $-OR^h$, and, $R^h$ is hydrogen, $-C_{1-6}$alkyl or heterocyclyl;

$-C_{3-6}$cycloalkyl, optionally substituted with at least one substituent independently selected from cyano, oxo, halogen, $-C_{1-6}$alkyl, or $-C(O)NR'''R''$, wherein —$C_{1-6}$alkyl is substituted with at least one substituent independently selected from halogen, hydroxy, —$NH_2$, or $C_{1-6}$alkoxy;

heterocyclyl, optionally substituted with at least one substituent independently selected from cyano, oxo, halogen, hydroxy, —$C_{1-6}$alkyl, or —C(O)NR‴R″, and wherein —$C_{1-6}$alkyl is substituted with at least one substituent independently selected from halogen, hydroxy, —$NH_2$, or $C_{1-6}$alkoxy;

—$OR^e$, wherein $R^e$ is —$C_{1-6}$alkyl, —$C_{3-6}$cycloalkyl, 3- to 6-membered heterocyclyl, or aryl, wherein i) —$C_{1-6}$alkyl is optionally substituted with cyano, halogen, hydroxy, or —$C_{1-6}$alkoxy-; and, ii) —$C_{3-6}$cycloalkyl or 3- to 6-membered heterocyclyl is optionally substituted with cyano, halogen, hydroxy, or $C_{1-6}$alkoxy;

$C_{5-10}$aryl; or heteroaryl optionally substituted with at least one substituent independently selected from cyano, oxo, halogen, hydroxy, —$C_{1-6}$alkyl, —$C_{1-6}$alkoxy or —C(O)NR‴R″, wherein —$C_{1-6}$alkyl is substituted with at least one substituent independently selected from halogen, hydroxy, —$NH_2$, or $C_{1-6}$alkoxy;

and wherein R‴ and R″ are independently selected from hydrogen or $C_{1-3}$alkyl.

7. The compound of claim 5, wherein $R^3$ is hydrogen, cyano, halogen;

—$C_{1-4}$ alkyl optionally substituted with at least one substituent independently selected from halogen, or —$OR^h$, and, $R^h$ is hydrogen, $C_{1-6}$alkyl or 3- to 6-membered heterocyclyl;

—$C_{3-6}$cycloalkyl, optionally substituted with at least one substituent independently selected from cyano, oxo, halogen, —$C_{1-6}$alkyl, or —C(O)NR‴R″, wherein —$C_{1-6}$alkyl is substituted with at least one substituent independently selected from halogen, hydroxy, —$NH_2$, or $C_{1-6}$alkoxy;

heterocyclyl is selected from morpholinyl, tetrahydrofuranyl, tetrahydropyranyl, pyrrolidinyl, 1,4-dioxanyl, piperidinyl or azetidinyl, optionally substituted with at least one substituent independently selected from cyano, oxo, halogen, hydroxy, $C_{1-6}$alkyl, or —C(O)NR‴R″, and wherein —$C_{1-6}$alkyl is substituted with at least one substituent independently selected from halogen, hydroxy, —$NH_2$, or —$C_{1-6}$alkoxy;

—$OR^e$, wherein $R^e$ is —$C_{1-6}$alkyl, —$C_{3-6}$cycloalkyl, 4- to 6-membered monocyclic saturated heterocyclyl comprising one oxygen heteroatom as ring member, or $C_{6-10}$aryl, wherein i) —$C_{1-6}$alkyl is optionally substituted with deuterium, cyano, halogen, hydroxy, or —$C_{1-6}$alkoxy-; and, ii) —$C_{3-6}$cycloalkyl or 3- to 6-membered heterocyclyl is optionally substituted with cyano, halogen, hydroxy, or $C_{1-6}$alkoxy;

—$C_{6-10}$aryl; or 5- to 6-membered heteroaryl selected from pyridinyl, pyridazinyl, pyrazinyl, thiazolyl or isoxazolyl, each of which is optionally substituted with at least one substituent independently selected from cyano, oxo, halogen, hydroxy, —$C_{1-6}$alkyl, or —C(O)NR‴R″, wherein —$C_{1-6}$alkyl is substituted with at least one substituent independently selected from halogen, hydroxy, —$NH_2$, or $C_{1-6}$alkoxy;

and wherein R‴ and R″ are independently selected from hydrogen or —$C_{1-3}$alkyl.

8. The compound of claim 5, wherein $R^3$ is hydrogen, cyano, halogen;

—$C_{1-4}$ alkyl optionally substituted with at least one substituent independently selected from halogen, hydroxy, or $C_{1-3}$alkoxy;

—$C_{3-6}$cycloalkyl, optionally substituted with at least one substituent independently selected from cyano, oxo, halogen, or —$C_{1-6}$alkyl, wherein —$C_{1-6}$alkyl is substituted with at least one substitution independently selected from halogen, hydroxy, —$NH_2$, or —$C_{1-3}$alkoxy;

heterocyclyl is selected from morpholinyl, tetrahydrofuranyl, tetrahydropyranyl, pyrrolidinyl, 1,4-dioxanyl, piperidinyl or azetidinyl, optionally substituted with at least one substituent independently selected from cyano, oxo, halogen, hydroxy, $C_{1-6}$alkyl, or —C(O)NR‴R″, and wherein —$C_{1-6}$alkyl is substituted with at least one substituent independently selected from halogen, hydroxy, —$NH_2$, or —$C_{1-6}$alkoxy;

—$OR^e$, wherein $R^e$ is —$C_{1-6}$alkyl, —$C_{3-6}$cycloalkyl, 4- to 6-membered monocyclic saturated heterocyclyl comprising one oxygen heteroatom as ring member, or $C_{6-10}$aryl, wherein i) —$C_{1-6}$alkyl is optionally substituted with cyano, halogen, hydroxy, or —$C_{1-6}$alkoxy-; and ii) —$C_{3-6}$cycloalkyl or 3- to 6-membered heterocyclyl is optionally substituted with cyano, halogen, hydroxy, or —$C_{1-6}$alkoxy;

—$C_{6-10}$aryl; or 5- to 6-membered heteroaryl selected from pyridinyl, pyridazinyl, pyrazinyl, thiazolyl or isoxazolyl, each of which is optionally substituted with at least one substituent independently selected from cyano, oxo, halogen, hydroxy, —$C_{1-6}$alkyl, —$C_{1-6}$alkoxy or —C(O)NR‴R″, wherein —$C_{1-6}$alkyl is substituted with at least one substituent independently selected from halogen, hydroxy, —$NH_2$, or —$C_{1-6}$alkoxy;

and wherein R‴ and R″ are independently selected from hydrogen or —$C_{1-3}$alkyl.

9. The compound of claim 5, wherein $R^3$ is hydrogen, cyano, halogen;

methyl, ethyl, propyl or butyl, each of which optionally substituted with at least one substituent independently selected from halogen, hydroxy, methoxy, ethoxy, or propoxy;

heterocyclyl is selected from morpholin-2-yl, morpholin-3-yl, morpholin-4-yl, tetrahydrofuran-2-yl, tetrahydrofuran-3-yl, tetrahydropyran-2-yl, tetrahydropyran-3-yl, tetrahydropyran-4-yl, pyrrolidine-1-yl, pyrrolidin-2-yl, pyrrolidin-3-yl, 1,4-dioxan-2-yl, piperidin-1-yl, piperidin-2-yl, piperidin-3-yl, piperidin-4-yl, azetidin-1-yl, azetidine-2-yl, azetidin-3-yl, 5-azaspiro[2.4]heptanyl, 3-azabicyclo[3.1.0]hexan-3-yl or 2-azabicyclo[3.1.0]hexan-2-yl, each of which is optionally substituted with at least one substituent independently selected from cyano, oxo, halogen, hydroxy, —$C_{1-6}$alkyl, or —C(O)NR‴R″, and wherein —$C_{1-6}$alkyl is substituted with at least one substituent independently selected from halogen, hydroxy, —$NH_2$, or —$C_{1-6}$alkoxy;

—$OR^e$, wherein $R^e$ is i) methyl, ethyl, propyl, butyl, pentyl or hexyl, each of which is optionally substituted with deuterium, cyano, halogen, hydroxy, or —$C_{1-3}$alkoxy-; or ii) cyclopropyl, cyclobutyl, cyclopentyl, cyclohexyl, morpholin-2-yl, morpholin-3-yl, morpholin-4-yl, tetrahydrofuran-2-yl, tetrahydrofuran-3-yl, tetrahydropyran-2-yl, tetrahydropyran-3-yl, tetrahydropyran-4-yl, pyrrolidin-1-yl, pyrrolidin-2-yl, pyrrolidin-3-yl, 1,4-dioxan-2-yl, piperidin-1-yl, piperidin-2-yl, piperidin-3-yl, piperidin-4-yl, azetidin-1-yl, azetidine-2-yl or azetidin-3-yl, each of which is optionally substituted with cyano, halogen, hydroxy, —$C_{1-3}$alkoxy;

—$C_{6-10}$aryl; or 5- to 6-membered heteroaryl selected from pyridin-1-yl, pyridin-2-yl, pyridin-3-yl, pyridin-4-yl, pyridazin-1-yl, pyridazin-2-yl, pyridazin-3-yl, pyridazin-4-yl, pyrazin-1-yl, pyrazin-2-yl, thiazol-2-yl, thiazol-3-yl, thiazol-4-yl, isoxazol-2-yl, isoxazol-3-yl or isoxazol-4-yl, each of which is optionally substituted with at least one substituent independently selected from cyano, oxo, halogen, hydroxy, —$C_{1-3}$alkyl, —$C_{1-3}$alkoxy or —C(O)NR‴R″, wherein —$C_{1-3}$alkyl is substituted with at least one substituent independently selected from halogen, hydroxy, —$NH_2$, or $C_{1-3}$alkoxy;

and wherein R‴ and R″ are independently selected from hydrogen or —$C_{1-3}$alkyl.

10. The compound of claim 5, wherein $R^3$ is hydrogen;

methyl, 2-hydroxypropan-2-yl, or 1-methoxyethyl;

isopropoxy, methoxy-d3, methoxy, ethoxy, difluoromethoxy, 2-methoxyethoxy, 2-methoxy-2-methylpropoxy, 2-hydroxy-2-methylpropoxy, cyclobutoxy, (4-hydroxycyclohexyl)oxy, (cis-4-hydroxycyclohexyl)oxy, (trans-4-hydroxycyclohexyl)oxy, (4-methoxycyclohexyl)oxy, (cis-4-methoxycyclohexyl)oxy, (trans-4-methoxycyclohexyl)oxy, cyano;

2,2-dichlorocyclopropyl or 1-cyanocyclopropyl;

morpholino, 3-methyl-morpholino, 3(R)-methyl-morpholino, 3(S)-methyl-morpholino, or 3,3-dimethylmorpholino;

tetrahydro-2H-pyran-4-yl, tetrahydro-2H-pyran-3-yl, (R)-tetrahydro-2H-pyran-3-yl, (S)-tetrahydro-2H-pyran-3-yl, or 2,2,6,6-tetramethyltetrahydro-2H-pyran-4-yl;

3-hydroxy-3-methylpyrrolidin-1-yl, 2-(aminocarbonyl)pyrrolidin-1-yl, 2(R)-(aminocarbonyl)pyrrolidin-1-yl, 2(S)-(aminocarbonyl)pyrrolidin-1-yl, 3-(methoxymethyl)pyrrolidin-1-yl, 3(R)-(methoxymethyl)pyrrolidin-1-yl, 3(S)-(methoxymethyl)pyrrolidin-1-yl, 3-cyano-4-hydroxypyrrolidin-1-yl, cis-3-cyano-4-hydroxypyrrolidin-1-yl, trans-3-cyano-4-hydroxypyrrolidin-1-yl, 2-(methoxymethyl)pyrrolidin-1-yl, 2(R)-(methoxymethyl)pyrrolidin-1-yl, 2(S)-(methoxymethyl)pyrrolidin-1-yl, 3-methylpyrrolidin-1-yl, 3(R)-methylpyrrolidin-1-yl, 3(S)-methylpyrrolidin-1-yl, or pyrrolidin-1-yl;

5-azaspiro[2.4]heptan-5-yl;

tetrahydrofuran-3-yl;

3-hydroxy-3-methylazetidin-1-yl;

1,4-dioxan-2-yl;

4-(aminomethyl)tetrahydro-2H-pyran-4-yl;

4-hydroxy-4-methylpiperidin-1-yl or 1-(2,2,2-trifluoroethyl)piperidin-4-yl;

3-cyano-2-azabicyclo[3.1.0]hexan-2-yl, (3R)-3-cyano-2-azabicyclo[3.1.0]hexan-2-yl, (3S)-3-cyano-2-azabicyclo[3.1.0]hexan-2-yl, 3-azabicyclo[3.1.0]hexan-3-yl; 4-methylpyridin-3-yl, 5-methylpyridazin-4-yl, 5-methoxypyridazin-4-yl, 3,5-dimethylisoxazol-4-yl, 4-methoxypyridin-3-yl, 4-(2-hydroxypropan-2-yl)pyridin-3-yl, 6-cyanopyridin-3-yl, 4-cyanopyridin-3-yl, 2-cyanopyridin-3-yl, 3-methylpyrazin-2-yl, 5-cyanopyridazin-4-yl, 5-fluoropyridazin-4-yl, 4-fluoropyridin-3-yl, 4-isopropylpyridin-3-yl, 4-(1-hydroxyethyl)pyridin-3-yl, 4-(1-methoxyethyl)pyridin-3-yl, pyridin-2-yl, or thiazol-4-yl.

11. The compound of claim 2, wherein $R^1$ and $R^2$, or $R^2$ and $R^3$, or $R^3$ and $R^4$, together with the atoms to which they are attached, form a fused 5- to 7-membered ring system, said fused ring system comprises 0-2 oxygen heteroatoms as ring member(s) and is optionally and independently substituted with halogen, —$C_{1-6}$alkyl, —$C_{1-6}$alkoxy, -halo$C_{1-6}$alkyl, -halo$C_{1-6}$alkoxy, or —$C_{3-6}$cycloalkyl.

12. The compound of claim 2, wherein $R^1$ and $R^2$, together with the atoms to which they are attached, form a fused ring system selected from

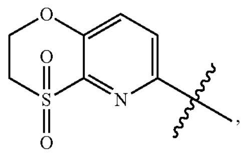
,
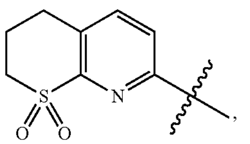
, or
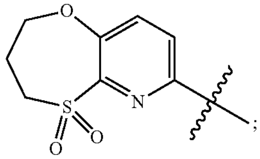
;

or $R^2$ and $R^3$, together with the atoms to which they are attached, form a fused ring system

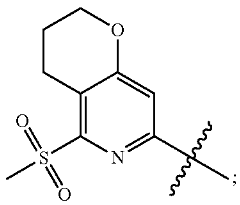 [SMILES: *c1cc2c(c(S(C)(=O)=O)n1)CCCO2]
;

$R^3$ and $R^4$, together with the atoms to which they are attached, form a fused ring system selected from

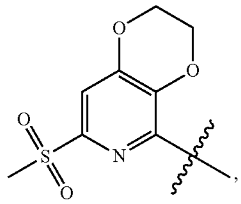
,
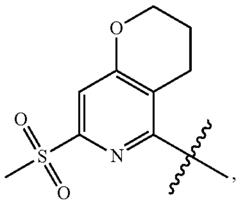
,
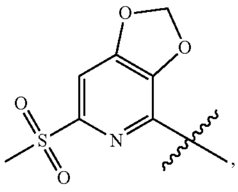
, or
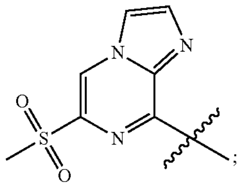
;

and wherein each fused ring system is optionally and independently substituted with halogen, —$C_{1-6}$alkyl, —$C_{1-6}$alkoxy, -halo$C_{1-6}$alkyl, -halo$C_{1-6}$alkoxy, or —$C_{3-6}$cycloalkyl.

13. The compound of claim 2, wherein $L^1$ is a direct bond.

14. The compound of claim 2, wherein $Cy^1$ is a) a 5- to 7-membered monocyclic heterocyclyl or heteroaryl comprising 1, 2, 3 or 4 heteroatoms selected from oxygen, nitrogen or sulfur as ring member(s), or b) 7- to 14-membered bicyclic or tricyclic heterocyclyl or heteroaryl having 1, 2, or 3 heteroatoms selected from oxygen, nitrogen or sulfur as ring member(s), each of which is optionally substituted with at least one substituent $R^i$.

15. The compound of claim 14, wherein $Cy^1$ is a) 5- to 7-membered monocyclic heteroaryl comprising 1, 2, 3 or 4 heteroatom(s) selected from oxygen (O), nitrogen (N) or sulfur (S) as ring member(s), wherein said monocyclic heteroaryl is optionally substituted with one or two substituents selected from i) halogen;

ii) cyano;

iii) —$C_{1-6}$alkyl optionally substituted with halogen, hydroxy, —$C_{1-6}$alkoxy, —C(O)R‴, or —NR‴R″;

iv) heterocyclyl optionally substituted with halogen, $C_{1-6}$alkyl-, —$C_{1-6}$alkyl substituted with —$C_{1-6}$ alkoxy, or oxo;

v) —$C_{3-6}$cycloalkyl optionally substituted with halogen, oxo, —$C_{1-6}$alkyl, $C_{1-6}$alkoxy-, or —$C_{1-6}$alkyl substituted with —$C_{1-6}$alkoxy;

vi) —$OR^j$, wherein $R^j$ is —$C_{1-6}$alkyl, —$C_{1-6}$alkyl substituted with —$C_{1-6}$alkoxy, or heterocyclyl; or vii) oxo;

b) 7- to 14-membered bicyclic or tricyclic heteroaryl comprising 1, 2, or 3 heteroatom(s) selected from oxygen, nitrogen or sulfur as ring member(s), optionally substituted with halogen, —$C_{1-6}$alkyl, —$NH_2$, or —$COR^j$, wherein $R^j$ is $C_{1-6}$alkyl; and wherein any of said alkyl is optionally enriched in deuterium.

16. The compound of claim 14, wherein $Cy^1$ is a 7- to 14-membered bicyclic heteroaryl which is a pyridinyl, pyrazolyl, thienyl, or thiazolyl ring fused with a 5- or 6-membered heterocyclyl ring, wherein said 5- or 6-membered heterocyclyl ring comprises one or two heteroatoms selected from oxygen or nitrogen as ring member(s) and said 5- or 6-membered heterocyclyl ring is optionally substituted with one or two $C_{1-6}$alkyl or oxo.

17. The compound of claim 14, wherein $Cy^1$ is a)

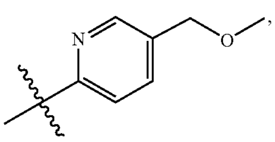,
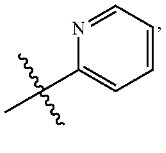,
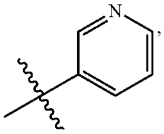,
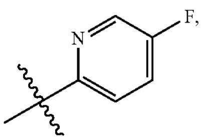
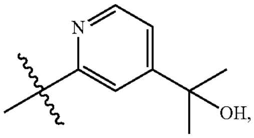
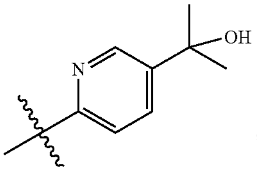,
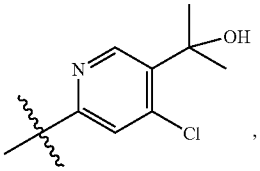,
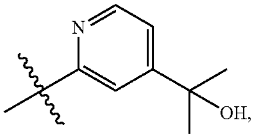

-continued

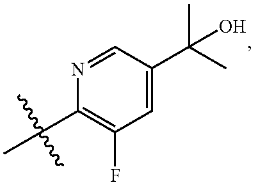,
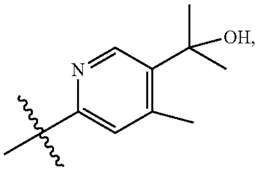
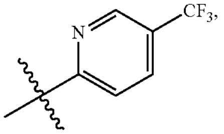
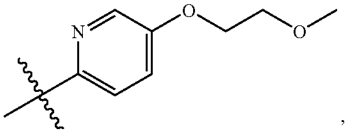,
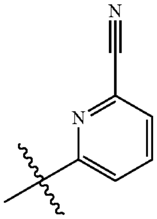
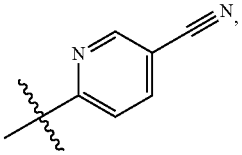
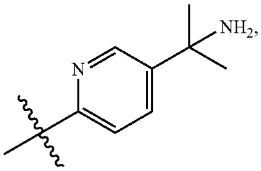
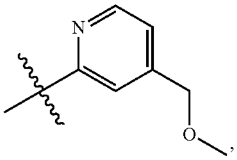
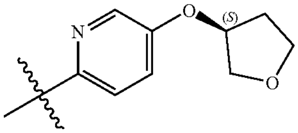,
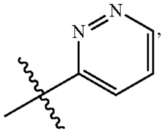
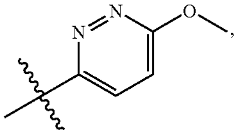
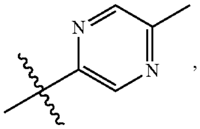,
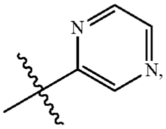 or
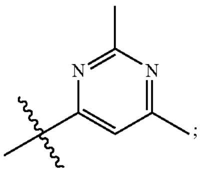;

b)

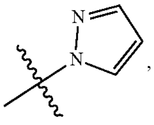,
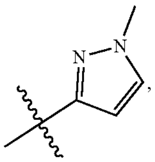
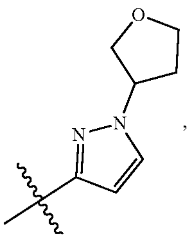,

-continued
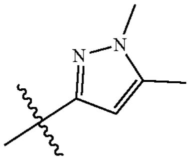, 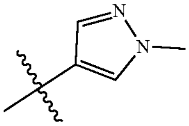,
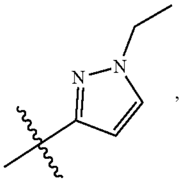, 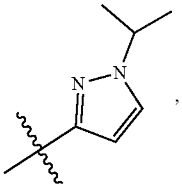, 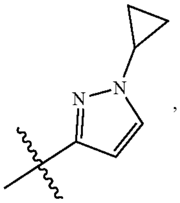,
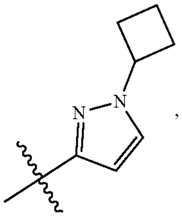, 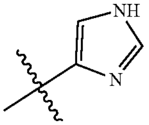, 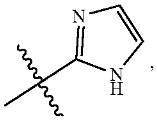,
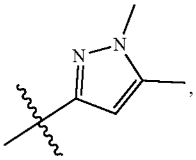, 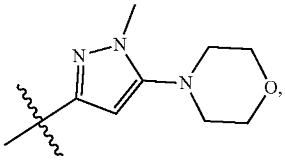
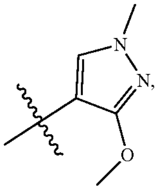 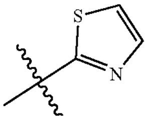, 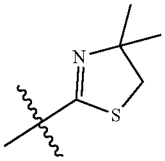,
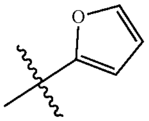, 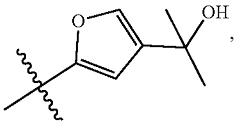,
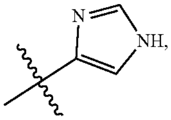 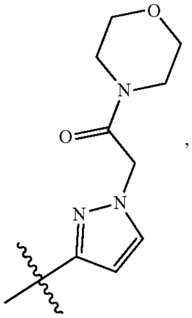, 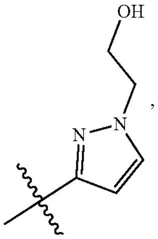,
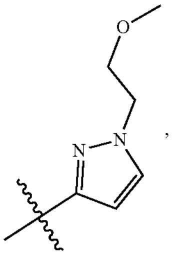, or 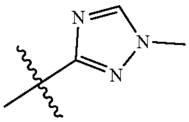;
-continued
c)
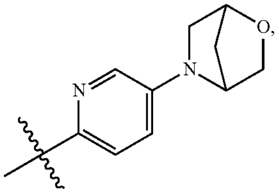
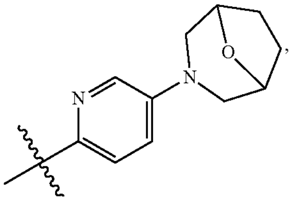
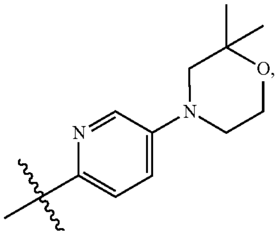
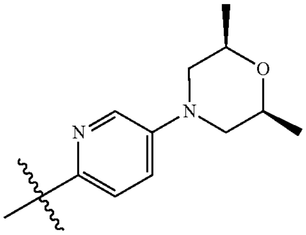
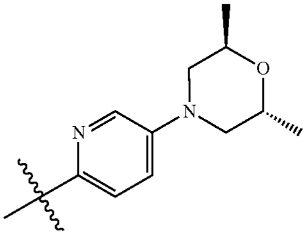
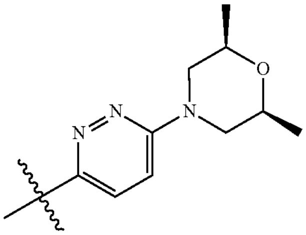
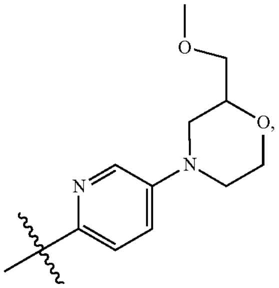

-continued
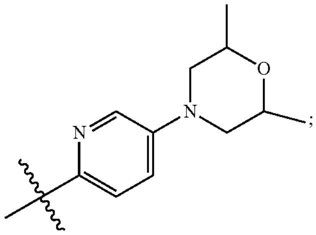;
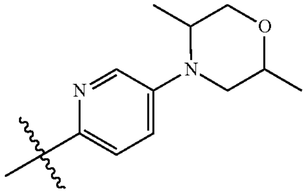,
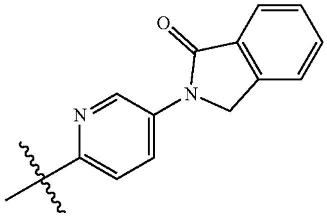
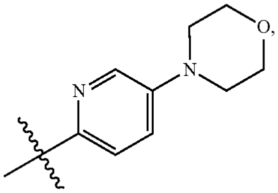, or
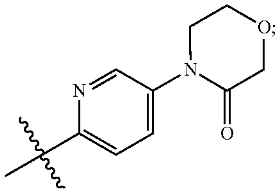;
d)
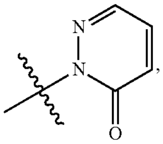, or 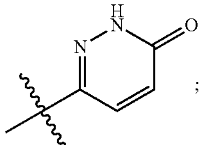;
e)
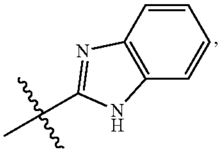, 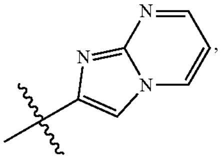,
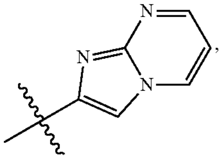, 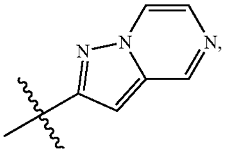,
-continued
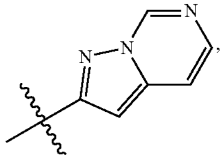, 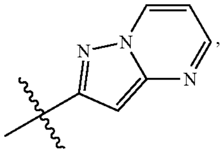,
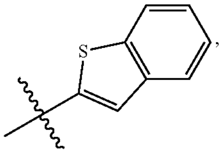, 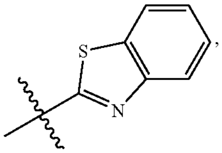,
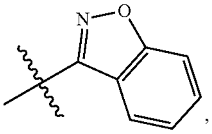, 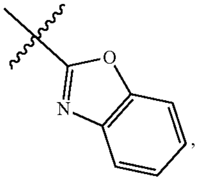,
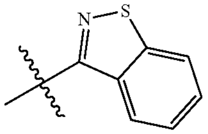, 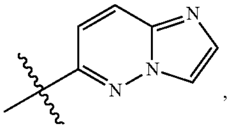,
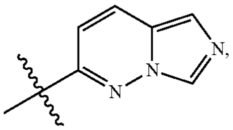, 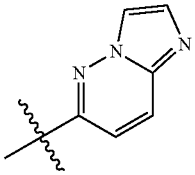,
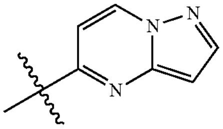, or 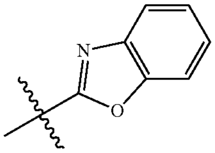
f)
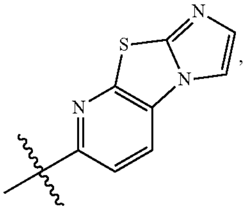, 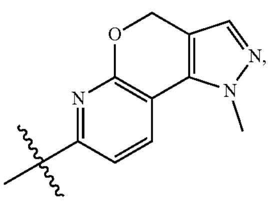, or
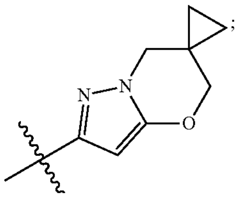;
g)
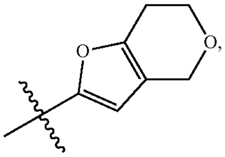, 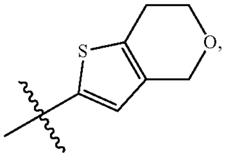, -continued

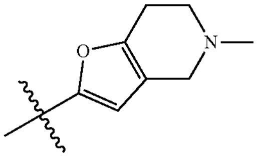,
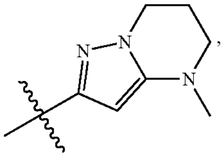,
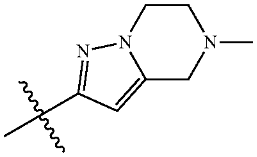,
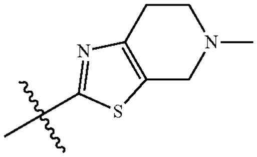,
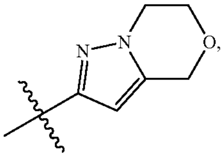
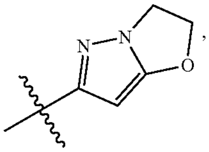,
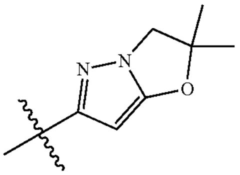,
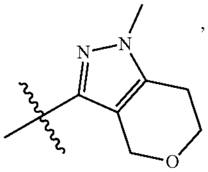,
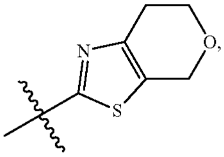
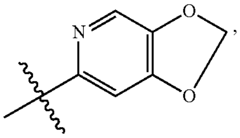,
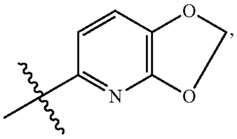,
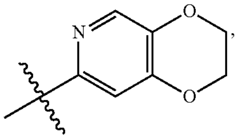,
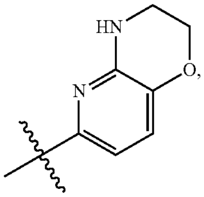
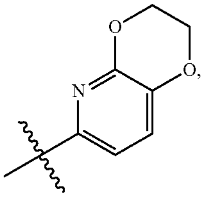
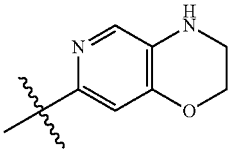,
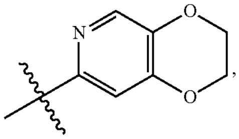,
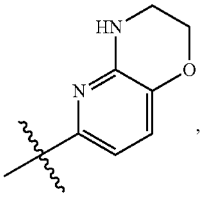,
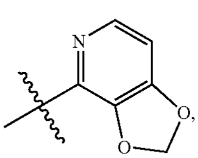
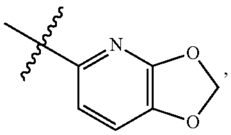,
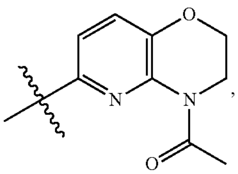, -continued

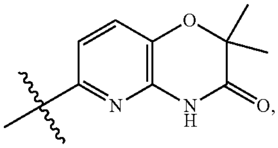
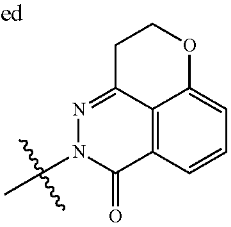,
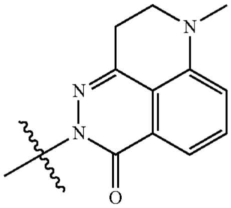,
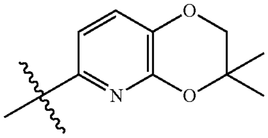,
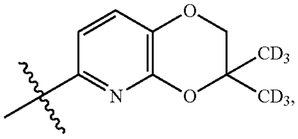
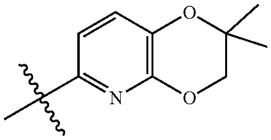, or
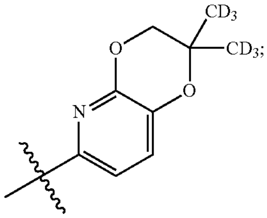

h)

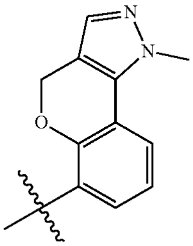, or 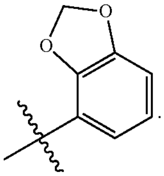.

18. A compound, or pharmaceutically acceptable salt thereof, selected from the group consisting of:

N-(4-((3-(methylsulfonyl)phenyl)amino)-5-(pyridazin-3-yl)pyridin-2-yl)acetamide;

N-[4-[(3-methanesulfonylphenyl)amino]-5-(oxolan-2-yl)pyridin-2-yl]acetamide;

N-(5-(1H-imidazol-4-yl)-4-((6-(methylsulfonyl)pyridin-2-yl)amino)pyridin-2-yl)acetamide;

N-(5-(5-methylpyrazin-2-yl)-4-((3-(methylsulfonyl)phenyl)amino)pyridin-2-yl)acetamide;

N-(4-((3-(methylsulfonyl)phenyl)amino)-5-(pyrazin-2-yl)pyridin-2-yl)acetamide;

N-(5-(2,6-dimethylpyrimidin-4-yl)-4-((3-(methylsulfonyl)phenyl)amino)pyridin-2-yl)acetamide;

N-(4-((3-(methylsulfonyl)phenyl)amino)-5-(2-oxopyrrolidin-1-yl)pyridin-2-yl)acetamide;

N-(5-(1-methyl-1H-pyrazol-4-yl)-4-((6-(methylsulfonyl)pyridin-2-yl)amino)pyridin-2-yl)acetamide;

N-(5-(furan-2-yl)-4-((4-methyl-6-(methylsulfonyl)pyridin-2-yl)amino)pyridin-2-yl)acetamide;

N-(5-(1-methyl-1H-1,2,4-triazol-3-yl)-4-((3-(methylsulfonyl)phenyl)amino)pyridin-2-yl)acetamide;
N-(4-((3-methoxy-6-(methylsulfonyl)pyridin-2-yl)amino)-5-(1-methyl-1H-pyrazol-4-yl)pyridin-2-yl)acetamide;
N-(4-((4-isopropoxy-6-(methylsulfonyl)pyridin-2-yl)amino)-5-(1H-pyrazol-1-yl)pyridin-2-yl)acetamide;
N-(4-((4-methyl-6-(methylsulfonyl)pyridin-2-yl)amino)-5-(1-(2-morpholino-2-oxoethyl)-1H-pyrazol-3-yl)pyridin-2-yl)acetamide;
N-(5-(1-(2-hydroxyethyl)-1H-pyrazol-3-yl)-4-((4-isopropoxy-6-(methylsulfonyl)pyridin-2-yl)amino)pyridin-2-yl)acetamide;
N-(5-(1-(2-methoxyethyl)-1H-pyrazol-3-yl)-4-((4-methyl-6-(methylsulfonyl)pyridin-2-yl)amino)pyridin-2-yl)acetamide;
N-(6-cyano-4'-((4-isopropoxy-6-(methylsulfonyl)pyridin-2-yl)amino)-[2,3'-bipyridin]-6'-yl)acetamide;
N-(5-cyano-4'-((4-isopropoxy-6-(methylsulfonyl)pyridin-2-yl)amino)-[2,3'-bipyridin]-6'-yl)acetamide;
N-(5-(1H-imidazol-1-yl)-4-((4-isopropoxy-6-(methylsulfonyl)pyridin-2-yl)amino)pyridin-2-yl)acetamide;
N-(5-(1-cyclobutyl-1H-pyrazol-3-yl)-4-((4-isopropoxy-6-(methylsulfonyl)pyridin-2-yl)amino)pyridin-2-yl)acetamide;
N-(5-(2-aminopropan-2-yl)-4'-((4-methyl-6-(methylsulfonyl)pyridin-2-yl)amino)-[2,3'-bipyridin]-6'-yl)acetamide;
N-(5-(1H-imidazol-4-yl)-4-((4-(2-methoxyethoxy)-6-(methylsulfonyl)pyridin-2-yl)amino)pyridin-2-yl)acetamide;
N-(5-(1H-imidazol-4-yl)-4-((4-methyl-6-(methylsulfonyl)pyridin-2-yl)amino)pyridin-2-yl)acetamide;
N-(5-(1H-imidazol-4-yl)-4-((4-isopropoxy-6-(methylsulfonyl)pyridin-2-yl)amino)pyridin-2-yl)acetamide;
N-(4-((6-(methylsulfonyl)pyridin-2-yl)amino)-5-(pyridazin-3-yl)pyridin-2-yl)acetamide;
N-(4-((4-(cyclopropylmethoxy)-6-(methylsulfonyl)pyridin-2-yl)amino)-5-(6-methoxypyridazin-3-yl)pyridin-2-yl)acetamide;
N-(4-((4-isopropoxy-6-(methylsulfonyl)pyridin-2-yl)amino)-5-(6-methoxypyridazin-3-yl)pyridin-2-yl)acetamide;
N-(4-((4-((2S,6R)-2,6-dimethylmorpholino)-6-(methylsulfonyl)pyridin-2-yl)amino)-5-(6-methoxypyridazin-3-yl)pyridin-2-yl)acetamide;
N-(5-(6-methoxypyridazin-3-yl)-4-((6-(methylsulfonyl)-[1,3]dioxolo[4,5-c]pyridin-4-yl)amino)pyridin-2-yl)acetamide;
N-(5-(6-isopropoxypyridazin-3-yl)-4-((4-methyl-6-(methylsulfonyl)pyridin-2-yl)amino)pyridin-2-yl)acetamide;
N-(5-(6-isopropoxypyridazin-3-yl)-4-((4-methoxy-6-(methylsulfonyl)pyridin-2-yl)amino)pyridin-2-yl)acetamide;
N-(5-(6-isopropoxypyridazin-3-yl)-4-(4-(methoxy-d3)-6-(methylsulfonyl)pyridin-2-ylamino)pyridin-2-yl)acetamide;
N-(4'-((3-(methylsulfonyl)phenyl)amino)-[2,3'-bipyridin]-6'-yl)acetamide;
N-(4-((6-(methylsulfonyl)pyridin-2-yl)amino)-[3,3'-bipyridin]-6-yl)acetamide;
N-(4'-(phenylamino)-[2,3'-bipyridin]-6'-yl)acetamide;
N-(4'-((6-sulfamoylpyridin-2-yl)amino)-[2,3'-bipyridin]-6'-yl)acetamide;
N-(4'-((6-(methylsulfonyl)pyridin-2-yl)amino)-[2,3'-bipyridin]-6'-yl)acetamide;
N-(4'-((4-(2-methoxyethoxy)-6-(methylsulfonyl)pyridin-2-yl)amino)-[2,3'-bipyridin]-6'-yl)acetamide;
N-(4'-((4-(2-hydroxyethoxy)-6-(methylsulfonyl)pyridin-2-yl)amino)-[2,3'-bipyridin]-6'-yl)acetamide;
N-(4-(methoxymethyl)-4'-((6-(methylsulfonyl)pyridin-2-yl)amino)-[2,3'-bipyridin]-6'-yl)acetamide;
N-(4-(2-hydroxypropan-2-yl)-4'-((3-(methylsulfonyl)phenyl)amino)-[2,3'-bipyridin]-6'-yl)acetamide;
N-(4-(2-hydroxypropan-2-yl)-4'-((4-methyl-6-(methylsulfonyl)pyridin-2-yl)amino)-[2,3'-bipyridin]-6'-yl)acetamide;
N-(4'-((3-(methylsulfonyl)phenyl)amino)-5-morpholino-[2,3'-bipyridin]-6'-yl)acetamide;
N-(5-(2,2-dimethylmorpholino)-4'-((6-(methylsulfonyl)pyridin-2-yl)amino)-[2,3'-bipyridin]-6'-yl)acetamide;
N-(4'-((3-methoxyphenyl)amino)-[2,3'-bipyridin]-6'-yl)acetamide;
N-(4'-((3-(methylsulfonyl)pyridin-2-yl)amino)-[2,3'-bipyridin]-6'-yl)acetamide;
N-(4'-((2-(methylsulfonyl)phenyl)amino)-[2,3'-bipyridin]-6'-yl)acetamide;
N-(5-(2-oxa-5-azabicyclo[2.2.1]heptan-5-yl)-4'-((4-isopropoxy-6-(methylsulfonyl)pyridin-2-yl)amino)-[2,3'-bipyridin]-6'-yl)acetamide;
N-(4-chloro-5-(2-hydroxypropan-2-yl)-4'-((6-(methylsulfonyl)pyridin-2-yl)amino)-[2,3'-bipyridin]-6'-yl)acetamide;
N-(4'-((4-isopropoxy-6-(methylsulfonyl)pyridin-2-yl)amino)-5-(2-(methoxymethyl)morpholino)-[2,3'-bipyridin]-6'-yl)acetamide;
N4'-(3-(methylsulfonyl)phenyl)-[2,3'-bipyridine]-4',6'-diamine;
N-(4'-((3-(methylsulfonyl)phenyl)amino)-[2,3'-bipyridin]-6'-yl)cyclopropanecarboxamide;
(S)—N-(4'-((4-methyl-6-(methylsulfonyl)pyridin-2-yl)amino)-5-((tetrahydrofuran-3-yl)oxy)-[2,3'-bipyridin]-6'-yl)acetamide;
N-(4'-((4-(2-hydroxyethoxy)-6-(methylsulfonyl)pyridin-2-yl)amino)-5-((tetrahydrofuran-3-yl)oxy)-[2,3'-bipyridin]-6'-yl)acetamide;
N-(4'-((6-(methylsulfonyl)pyridin-2-yl)amino)-5-((tetrahydrofuran-3-yl)oxy)-[2,3'-bipyridin]-6'-yl)acetamide;
N-(5-(8-oxa-3-azabicyclo[3.2.1]octan-3-yl)-4'-((4-methyl-6-(methylsulfonyl)pyridin-2-yl)amino)-[2,3'-bipyridin]-6'-yl)acetamide;
N-(5-(2,5-dimethylmorpholino)-4'-((4-methyl-6-(methylsulfonyl)pyridin-2-yl)amino)-[2,3'-bipyridin]-6'-yl)acetamide;
N-(5-(cis-2,6-dimethylmorpholino)-4'-((4-methyl-6-(methylsulfonyl)pyridin-2-yl)amino)-[2,3'-bipyridin]-6'-yl)acetamide;
N-(5-((cis)-2,6-dimethylmorpholino)-4'-((6-(methylsulfonyl)pyridin-2-yl)amino)-[2,3'-bipyridin]-6'-yl)acetamide;
N-(5-((cis)-2,6-dimethylmorpholino)-4'-((3-(methylsulfonyl)phenyl)amino)-[2,3'-bipyridin]-6'-yl)acetamide;
N-(5-((cis)-2,6-dimethylmorpholino)-4'-((4-isopropoxy-6-(methylsulfonyl)pyridin-2-yl)amino)-[2,3'-bipyridin]-6'-yl)acetamide;
N-(4'-((4-(cyclopropylmethoxy)-6-(methylsulfonyl)pyridin-2-yl)amino)-5-((cis)-2,6-dimethylmorpholino)-[2,3'-bipyridin]-6'-yl)acetamide;
N-(4'-((3-(cyclopropylmethoxy)-5-(methylsulfonyl)phenyl)amino)-5-((cis)-2,6-dimethylmorpholino)-[2,3'-bipyridin]-6'-yl)acetamide;

N-(5-((trans)-2,6-dimethylmorpholino)-4'-((4-methyl-6-(methylsulfonyl)pyridin-2-yl)amino)-[2,3'-bipyridin]-6'-yl)acetamide;

N-(5-(Cis-2,6-dimethylmorpholino)-4'-((7-(methylsulfonyl)-2,3-dihydro-[1,4]dioxino[2,3-c]pyridin-5-yl)amino)-[2,3'-bipyridin]-6'-yl)acetamide;

N-(5-((cis)-2,6-dimethylmorpholino)-4'-((4-methoxy-6-(methylsulfonyl)pyridin-2-yl)amino)-[2,3'-bipyridin]-6'-yl)acetamide;

N-(5-((cis)-2,6-dimethylmorpholino)-4'-((4-ethoxy-6-(methylsulfonyl)pyridin-2-yl)amino)-[2,3'-bipyridin]-6'-yl)acetamide;

N-(5-((cis)-2,6-dimethylmorpholino)-4'-((4-(2-methoxyethoxy)-6-(methylsulfonyl)pyridin-2-yl)amino)-[2,3'-bipyridin]-6'-yl)acetamide;

N-(5-((cis)-2,6-dimethylmorpholino)-4'-((4-((R)-2-hydroxypropoxy)-6-(methylsulfonyl)pyridin-2-yl)amino)-[2,3'-bipyridin]-6'-yl)acetamide;

N-(4'-((4-((R)-sec-butoxy)-6-(methylsulfonyl)pyridin-2-yl)amino)-5-((cis)-2,6-dimethylmorpholino)-[2,3'-bipyridin]-6'-yl)acetamide;

N-(5-((cis)-2,6-dimethylmorpholino)-4'-((3-methoxy-5-(methylsulfonyl)phenyl)amino)-[2,3'-bipyridin]-6'-yl)acetamide;

N-(5-((cis)-2,6-dimethylmorpholino)-4'-((3-fluoro-5-(methylsulfonyl)phenyl)amino)-[2,3'-bipyridin]-6'-yl)acetamide;

N-(4'-((3-cyano-5-(methylsulfonyl)phenyl)amino)-5-((cis)-2,6-dimethylmorpholino)-[2,3'-bipyridin]-6'-yl)acetamide;

N-(5-((cis)-2,6-dimethylmorpholino)-4'-((4-(methoxy-d3)-6-(methylsulfonyl)pyridin-2-yl)amino)-[2,3'-bipyridin]-6'-yl)acetamide;

N-(5-(cis-2,6-dimethylmorpholino)-4'-((4-(1-methoxyethyl)-6-(methylsulfonyl)pyridin-2-yl)amino)-[2,3'-bipyridin]-6'-yl)acetamide;

N-(5-((cis)-2,6-dimethylmorpholino)-4'-((4-((R or S)-1-methoxyethyl)-6-(methylsulfonyl)pyridin-2-yl)amino)-[2,3'-bipyridin]-6'-yl)acetamide;

N-(5-((cis)-2,6-dimethylmorpholino)-4'-((4-((R or S)-1-methoxyethyl)-6-(methylsulfonyl)pyridin-2-yl)amino)-[2,3'-bipyridin]-6'-yl)acetamide;

N-(5-(cis-2,6-dimethylmorpholino)-4'-((6-(methylsulfonyl)-4-(tetrahydro-2H-pyran-4-yl)pyridin-2-yl)amino)-[2,3'-bipyridin]-6'-yl)acetamide;

N-(5-(cis-2,6-dimethylmorpholino)-4'-((6-(methylsulfonyl)pyrazin-2-yl)amino)-[2,3'-bipyridin]-6'-yl)acetamide;

N-(5-(cis-2,6-dimethylmorpholino)-4'-((4-((S)-3-methylmorpholino)-6-(methylsulfon-yl)pyridin-2-yl)amino)-[2,3'-bipyridin]-6'-yl) acetamide;

N-(5-(cis-2,6-dimethylmorpholino)-4'-((4-((R)-3-methylmorpholino)-6-(methylsulfon-yl)pyridin-2-yl)amino)-[2,3'-bipyridin]-6'-yl) acetamide;

N-(5-(cis-2,6-dimethyl morpholino)-4'-((4-(3-methoxy azetidin-1-yl)-6-(methylsulfonyl)pyridin-2-yl)amino)-[2,3'-bipyridin]-6'-yl)acetamide;

N-(5-(2-methoxyethoxy)-4'-((6-(methylsulfonyl)pyridin-2-yl)amino)-[2,3'-bipyridin]-6'-yl)acetamide;

N-(5-(2-methoxyethoxy)-4'-((3-(methylsulfonyl)phenyl)amino)-[2,3'-bipyridin]-6'-yl)acetamide;

N-(5-(2-methoxyethoxy)-4'-((3-(methylsulfonyl)-5-(trifluoromethyl)phenyl)amino)-[2,3'-bipyridin]-6'-yl)acetamide;

N-(5-(2-methoxyethoxy)-4'-((4-methyl-6-(methylsulfonyl)pyridin-2-yl)amino)-[2,3'-bipyridin]-6'-yl)acetamide;

N-(4'-((4-methoxy-6-(methylsulfonyl)pyridin-2-yl)amino)-5-(2-methoxyethoxy)-[2,3'-bipyridin]-6'-yl)acetamide;

N-(4'-((4-isopropoxy-6-(methylsulfonyl)pyridin-2-yl)amino)-5-(2-methoxyethoxy)-[2,3'-bipyridin]-6'-yl)acetamide;

(R)—N-(5-(2-methoxyethoxy)-4'-((4-(2-methoxypropoxy)-6-(methylsulfonyl)pyridin-2-yl)amino)-[2,3'-bipyridin]-6'-yl)acetamide;

N-(5-(2-methoxyethoxy)-4'-((4-(2-methoxyethoxy)-6-(methylsulfonyl)pyridin-2-yl)amino)-[2,3'-bipyridin]-6'-yl)acetamide;

N-(4'-((4-ethoxy-6-(methylsulfonyl)pyridin-2-yl)amino)-5-(2-methoxyethoxy)-[2,3'-bipyridin]-6'-yl)acetamide;

N-(4'-((3-(cyclopropylmethoxy)-5-(methylsulfonyl)phenyl)amino)-5-(2-methoxyethoxy)-[2,3'-bipyridin]-6'-yl)acetamide;

N-(4'-((4-(cyclopropylmethoxy)-6-(methylsulfonyl)pyridin-2-yl)amino)-5-(2-methoxyethoxy)-[2,3'-bipyridin]-6'-yl)acetamide;

N-(5-(methoxymethyl)-4'-((3-(methylsulfonyl) phenyl)amino)-[2,3'-bipyridin]-6'-yl)acetamide;

N-(5-(methoxymethyl)-4'-((4-methyl-6-(methylsulfonyl)pyridin-2-yl)amino)-[2,3'-bipyridin]-6'-yl)acetamide;

(R)—N-(5-(methoxymethyl)-4'-((4-(2-methoxypropoxy)-6-(methylsulfonyl)pyridin-2-yl)amino)-[2,3'-bipyridin]-6'-yl)acetamide;

N-(4'-((4-isopropoxy-6-(methylsulfonyl)pyridin-2-yl)amino)-5-(methoxymethyl)-[2,3'-bipyridin]-6'-yl)acetamide;

N-(4'-((4-(2-methoxyethoxy)-6-(methylsulfonyl)pyridin-2-yl)amino)-5-(methoxymethyl)-[2,3'-bipyridin]-6'-yl)acetamide;

N-(4'-((4-(2-hydroxyethoxy)-6-(methylsulfonyl)pyridin-2-yl)amino)-5-(methoxymethyl)-[2,3'-bipyridin]-6'-yl)acetamide;

N-(4'-((4-methoxy-6-(methylsulfonyl)pyridin-2-yl)amino)-5-(methoxymethyl)-[2,3'-bipyridin]-6'-yl)acetamide;

N-(4'-((4-((1r,3r)-3-hydroxycyclobutoxy)-6-(methylsulfonyl)pyridin-2-yl)amino)-5-(methoxymethyl)-[2,3'-bipyridin]-6'-yl)acetamide;

N-(5-(methoxymethyl)-4'-((4-(methoxymethyl)-6-(methylsulfonyl)pyridin-2-yl)amino)-[2,3'-bipyridin]-6'-yl)acetamide;

N-(4'-((4-methyl-6-(methylsulfonyl)pyridin-2-yl)amino)-5-(trifluoromethyl)-[2,3'-bipyridin]-6'-yl)acetamide;

N-(4'-((3-(methylsulfonyl)phenyl)amino)-5-(trifluoromethyl)-[2,3'-bipyridin]-6'-yl)acetamide;

N-(4'-((3-methyl-5-(methylsulfonyl)phenyl)amino)-5-(trifluoromethyl)-[2,3'-bipyridin]-6'-yl)acetamide;

N-(4'-((3-cyano-5-(methylsulfonyl)phenyl)amino)-5-(trifluoromethyl)-[2,3'-bipyridin]-6'-yl)acetamide;

N-(4'-((3-((trans)-3-hydroxycyclobutoxy)-5-(methylsulfonyl)phenyl)amino)-5-(trifluoromethyl)-[2,3'-bipyridin]-6'-yl)acetamide;

N-(4'-((3-(cyclopropylmethoxy)-5-(methylsulfonyl)phenyl)amino)-5-(trifluoromethyl)-[2,3'-bipyridin]-6'-yl)acetamide;

N-(4'-((3-(2-hydroxyethoxy)-5-(methylsulfonyl)phenyl)amino)-5-(trifluoromethyl)-[2,3'-bipyridin]-6'-yl)acetamide;

N-(4'-((3-(2-methoxyethoxy)-5-(methylsulfonyl)phenyl)amino)-5-(trifluoromethyl)-[2,3'-bipyridin]-6'-yl)acetamide;

N-(4'-((4-isopropoxy-6-(methylsulfonyl)pyridin-2-yl)amino)-5-(trifluoromethyl)-[2,3'-bipyridin]-6'-yl)acetamide;

N-(4'-((4-ethoxy-6-(methylsulfonyl)pyridin-2-yl)amino)-5-(trifluoromethyl)-[2,3'-bipyridin]-6'-yl)acetamide;

N-(4'-((4-(2-methoxyethoxy)-6-(methylsulfonyl)pyridin-2-yl)amino)-5-(trifluoromethyl)-[2,3'-bipyridin]-6'-yl)acetamidecarboxamide;

N-(4'-((4-(2-hydroxyethoxy)-6-(methylsulfonyl)pyridin-2-yl)amino)-5-(trifluoromethyl)-[2,3'-bipyridin]-6'-yl)acetamide;

N-(5-fluoro-4'-((3-(methylsulfonyl)-5-(trifluoromethyl)phenyl)amino)-[2,3'-bipyridin]-6'-yl)acetamide;

N-(5-fluoro-4'-((3-isopropoxy-5-(methylsulfonyl)phenyl)amino)-[2,3'-bipyridin]-6'-yl)acetamide;

N-(5-fluoro-4'-((3-((trans)-3-hydroxycyclobutoxy)-5-(methylsulfonyl)phenyl)amino)-[2,3'-bipyridin]-6'-yl)acetamide;

N-(5-fluoro-4'-((4-(2-methoxyethoxy)-6-(methylsulfonyl)pyridin-2-yl)amino)-[2,3'-bipyridin]-6'-yl)acetamide;

N-(5-fluoro-4'-((4-methyl-6-(methylsulfonyl)pyridin-2-yl)amino)-[2,3'-bipyridin]-6'-yl)acetamide;

N-(5-fluoro-4'-((4-isopropoxy-6-(methylsulfonyl)pyridin-2-yl)amino)-[2,3'-bipyridin]-6'-yl)acetamide;

N-(4'-((4-ethoxy-6-(methylsulfonyl)pyridin-2-yl)amino)-5-fluoro-[2,3'-bipyridin]-6'-yl)acetamide;

N-(4'-((4-methoxy-6-(methylsulfonyl)pyridin-2-yl)amino)-5-(trifluoromethyl)-[2,3'-bipyridin]-6'-yl)acetamide;

(S)—N-(4'-((4-(2-hydroxypropoxy)-6-(methylsulfonyl)pyridin-2-yl)amino)-5-(trifluoromethyl)-[2,3'-bipyridin]-6'-yl)acetamide;

N-(5-fluoro-4'-((4-methoxy-6-(methylsulfonyl)pyridin-2-yl)amino)-[2,3'-bipyridin]-6'-yl)acetamide;

N-(4'-((3,4-dimethoxy-6-(methylsulfonyl)pyridin-2-yl)amino)-5-fluoro-[2,3'-bipyridin]-6'-yl)acetamide;

N-(5-fluoro-4'-((4-(methoxy-d3)-6-(methylsulfonyl)pyridine-2-yl)amino)-[2,3'-bipyridin]-6'-yl)acetamide;

N-(4'-((4-cyclopropyl-6-(methylsulfonyl)pyridin-2-yl)amino)-5-fluoro-[2,3'-bipyridin]-6'-yl)acetamide;

N-(4'-((3-(methylsulfonyl)phenyl)amino)-5-(3-oxomorpholino)-[2,3'-bipyridin]-6'-yl)acetamide;

N-(4'-((6-(methylsulfonyl)pyridin-2-yl)amino)-5-(3-oxomorpholino)-[2,3'-bipyridin]-6'-yl)acetamide;

N-(4'-((4-(2-hydroxyethoxy)-6-(methylsulfonyl)pyridin-2-yl)amino)-5-(3-oxomorpholino)-[2,3'-bipyridin]-6'-yl)acetamide;

N-(4'-((4-(2-methoxyethoxy)-6-(methylsulfonyl)pyridin-2-yl)amino)-5-(3-oxomorpholino)-[2,3'-bipyridin]-6'-yl)acetamide;

N-(5-(2-hydroxypropan-2-yl)-4'-((3-(methylsulfonyl)phenyl)amino)-[2,3'-bipyridin]-6'-yl)acetamide;

N-(5-(2-hydroxypropan-2-yl)-4'-((4-isopropoxy-6-(methylsulfonyl)pyridin-2-yl)amino)-[2,3'-bipyridin]-6'-yl)acetamide;

N-(5-(2-hydroxypropan-2-yl)-4'-((3-(methylsulfonyl)-5-(trifluoro methyl)phenyl)amino)-[2,3'-bipyridin]-6'-yl)acetamide;

N-(5-(2-hydroxypropan-2-yl)-4'-((3-methoxy-5-(methylsulfonyl)phenyl)amino)-[2,3'-bipyridin]-6'-yl)acetamide;

N-(5-(2-hydroxypropan-2-yl)-4'-((6-(methylsulfonyl)pyridin-2-yl)amino)-[2,3'-bipyridin]-6'-yl)acetamide;

N-(5-(2-hydroxypropan-2-yl)-4'-((4-(2-methoxyethoxy)-6-(methylsulfonyl)pyridin-2-yl)amino)-[2,3'-bipyridin]-6'-yl)acetamide;

N-(5-(2-hydroxypropan-2-yl)-4'-((4-(2-methoxypropoxy)-6-(methylsulfonyl)pyridin-2-yl)amino)-[2,3'-bipyridin]-6'-yl)acetamide;

N-(4'-((4-(2-hydroxyethoxy)-6-(methylsulfonyl)pyridin-2-yl)amino)-5-(2-hydroxypropan-2-yl)-[2,3'-bipyridin]-6'-yl)acetamide;

N-(5-(2-hydroxypropan-2-yl)-4'-((4-methyl-6-(methylsulfonyl)pyridin-2-yl)amino)-[2,3'-bipyridin]-6'-yl)acetamide;

N-(4'-((4-(trans)-3-hydroxycyclobutoxy)-6-(methylsulfonyl)pyridin-2-yl)amino)-5-(2-hydroxypropan-2-yl)-[2,3'-bipyridin]-6'-ylacetamide;

N-(5-(2-hydroxypropan-2-yl)-4'-((4-methoxy-6-(methylsulfonyl)pyridin-2-yl)amino)-[2,3'-bipyridin]-6'-yl)acetamide;

N-(5-(2-hydroxypropan-2-yl)-4'-((6-(methylsulfonyl)-4-(oxetan-3-ylmethoxy)pyridin-2-yl)amino)-[2,3'-bipyridin]-6'-yl)acetamide;

N-(5-(2-hydroxypropan-2-yl)-4'-((4-(methoxymethyl)-6-(methylsulfonyl)pyridin-2-yl)amino)-[2,3'-bipyridin]-6'-yl)acetamide;

N-(4'-((4-cyano-6-(methylsulfonyl)pyridin-2-yl)amino)-5-(2-hydroxypropan-2-yl)-[2,3'-bipyridin]-6'-yl)acetamide;

N-(5-(2-hydroxypropan-2-yl)-4'-((3-(2-methoxyethoxy)-5-(methylsulfonyl)phenyl)amino)-[2,3'-bipyridin]-6'-yl)acetamide;

N-(5-(2-hydroxypropan-2-yl)-4'-((3-(methoxymethyl)-5-(methylsulfonyl)phenyl)amino)-[2,3'-bipyridin]-6'-yl)acetamide;

N-(5-(2-hydroxypropan-2-yl)-4'-((3-(3-hydroxypyrrolidin-1-yl)-5-(methylsulfonyl)phenyl)amino)-[2,3'-bipyridin]-6'-yl)acetamide;

N-(5-(2-hydroxypropan-2-yl)-4'-((3-(methylsulfonyl)-5-(trifluoromethoxy)phenyl)amino)-[2,3'-bipyridin]-6'-yl)acetamide;

N-(4'-((3-fluoro-5-(methylsulfonyl)phenyl)amino)-5-(2-hydroxypropan-2-yl)-[2,3'-bipyridin]-6'-yl)acetamide;

N-(4'-((3-cyano-5-(methylsulfonyl)phenyl)amino)-5-(2-hydroxypropan-2-yl)-[2,3'-bipyridin]-6'-yl)acetamide;

N-(5-(2-hydroxypropan-2-yl)-4'-((3-methyl-5-(methylsulfonyl)phenyl)amino)-[2,3'-bipyridin]-6'-yl)acetamide;

N-(4'-((3-(cyclopropylmethoxy)-5-(methylsulfonyl)phenyl)amino)-5-(2-hydroxypropan-2-yl)-[2,3'-bipyridin]-6'-yl)acetamide;

N-(4'-((3-cyclopropoxy-5-(methylsulfonyl)phenyl)amino)-5-(2-hydroxypropan-2-yl)-[2,3'-bipyridin]-6'-yl)acetamide;

N-(5-(2-hydroxypropan-2-yl)-4'-((3-isopropoxy-5-(methylsulfonyl)phenyl)amino)-[2,3'-bipyridin]-6'-yl)acetamide;

N-(4'-((3-(difluoromethyl)-5-(methylsulfonyl)phenyl)amino)-5-(2-hydroxypropan-2-yl)-[2,3'-bipyridin]-6'-yl)acetamide;

N-(5-(2-hydroxypropan-2-yl)-4'-((4-(2-hydroxypropoxy)-6-(methylsulfonyl)pyridin-2-yl)amino)-[2,3'-bipyridin]-6'-yl)acetamide;

N-(5-(2-hydroxypropan-2-yl)-4'-((6-(methylsulfonyl)-4-(oxetan-3-yloxy)pyridin-2-yl)amino)-[2,3'-bipyridin]-6'-yl)acetamide;

N-(4'-((4-(cis-3-hydroxycyclobutoxy)-6-(methylsulfonyl)pyridin-2-yl)amino)-5-(2-hydroxypropan-2-yl)-[2,3'-bipyridin]-6'-yl)acetamide;

N-(5-(2-hydroxypropan-2-yl)-4'-((4-(3-methoxycyclobutoxy)-6-(methylsulfonyl)pyridin-2-yl)amino)-[2,3'-bipyridin]-6'-yl)acetamide;

N-(4'-((4-(cyclopropylmethoxy)-6-(methylsulfonyl)pyridin-2-yl)amino)-5-(2-hydroxypropan-2-yl)-[2,3'-bipyridin]-6'-yl)acetamide;
N-(4'-((4-cyclobutoxy-6-(methylsulfonyl)pyridin-2-yl)amino)-5-(2-hydroxypropan-2-yl)-[2,3'-bipyridin]-6'-yl)acetamide;
N-(5-(2-hydroxypropan-2-yl)-4'-((3-methyl-6-(methylsulfonyl)pyridin-2-yl)amino)-[2,3'-bipyridin]-6'-yl)acetamide;
N-(4'-((4-ethoxy-6-(methylsulfonyl)pyridin-2-yl)amino)-5-(2-hydroxypropan-2-yl)-[2,3'-bipyridin]-6'-yl)acetamide;
N-(4'-((5-fluoro-6-(methylsulfonyl)pyridin-2-yl)amino)-5-(2-hydroxypropan-2-yl)-[2,3'-bipyridin]-6'-yl)acetamide;
N-(5-(2-hydroxypropan-2-yl)-4'-((2-methyl-5-(methylsulfonyl)phenyl)amino)-[2,3'-bipyridin]-6'-yl)acetamide;
N-(4'-((6-(ethylsulfonyl)-4-isopropoxypyridin-2-yl)amino)-5-(2-hydroxypropan-2-yl)-[2,3'-bipyridin]-6'-yl)acetamide;
N-(5-(2-hydroxypropan-2-yl)-4'-((7-(methylsulfonyl)-2,3-dihydro-[1,4]dioxino[2,3-c]pyridin-5-yl)amino)-[2,3'-bipyridin]-6'-yl)acetamide;
(R)—N-(5-(2-hydroxypropan-2-yl)-4'-((4-(2-hydroxypropoxy)-6-(methylsulfonyl)pyridin-2-yl)amino)-[2,3'-bipyridin]-6'-yl)acetamide;
N-(5-(2-hydroxypropan-2-yl)-4'-((6-(methylsulfonyl)-4-(tetrahydro-2H-pyran-4-yl)pyridin-2-yl)amino)-[2,3'-bipyridin]-6'-yl)acetamide;
N-(5-(2-hydroxypropan-2-yl)-4'-((4-isobutoxy-6-(methylsulfonyl)pyridin-2-yl)amino)-[2,3'-bipyridin]-6'-yl)acetamide;
(S)—N-(4'-((4-(sec-butoxy)-6-(methylsulfonyl)pyridin-2-yl)amino)-5-(2-hydroxypropan-2-yl)-[2,3'-bipyridin]-6'-yl)acetamide;
(R)—N-(4'-((4-(sec-butoxy)-6-(methylsulfonyl)pyridin-2-yl)amino)-5-(2-hydroxypropan-2-yl)-[2,3'-bipyridin]-6'-yl)acetamide;
N-(5-(2-hydroxypropan-2-yl)-4'-((3-isopropoxy-5-(methylsulfonyl)phenyl)amino)-[2,3'-bipyridin]-6'-yl)acetamide;
N-(5-(1-methyl-1H-pyrazol-3-yl)-4-((4-methyl-6-(methylsulfonyl)pyridin-2-yl)amino)pyridin-2-yl)acetamide;
N-(4-((4-isopropoxy-6-(methylsulfonyl)pyridin-2-yl)amino)-5-(1-methyl-1H-pyrazol-3-yl)pyridin-2-yl)acetamide;
N-(4-((4-(cyclopropylmethoxy)-6-(methylsulfonyl)pyridin-2-yl)amino)-5-(1-methyl-1H-pyrazol-3-yl)pyridin-2-yl)acetamide;
N-(5-(1-methyl-1H-pyrazol-3-yl)-4-((6-sulfamoylpyridin-2-yl)amino)pyridin-2-yl)acetamide;
N-(4-((6-(ethylsulfonyl)pyridin-2-yl)amino)-5-(1-methyl-1H-pyrazol-3-yl)pyridin-2-yl)acetamide;
N-(5-(1-methyl-1H-pyrazol-3-yl)-4-((3-(methylsulfonyl)phenyl)amino)pyridin-2-yl)acetamide;
N-(4-((3-cyano-5-(methylsulfonyl)phenyl)amino)-5-(1-methyl-1H-pyrazol-3-yl)pyridin-2-yl)acetamide;
N-(5-(1-methyl-1H-pyrazol-3-yl)-4-((3-methyl-5-(methylsulfonyl)phenyl)amino)pyridin-2-yl)acetamide;
N-(4-((3-methoxy-5-(methylsulfonyl)phenyl)amino)-5-(1-methyl-1H-pyrazol-3-yl)pyridin-2-yl)acetamide;
N-(5-(1-methyl-1H-pyrazol-3-yl)-4-((3-(methylsulfonyl)-5-(trifluoromethoxy)phenyl)amino)pyridin-2-yl)acetamide;
N-(5-(1-methyl-1H-pyrazol-3-yl)-4-((6-(methylsulfonyl)pyridin-2-yl)amino)pyridin-2-yl)acetamide;
N-(4-((4-(2-methoxyethoxy)-6-(methylsulfonyl)pyridin-2-yl)amino)-5-(1-methyl-1H-pyrazol-3-yl)pyridin-2-yl)acetamide;
N-(4-((4-(2-methoxypropoxy)-6-(methylsulfonyl)pyridin-2-yl)amino)-5-(1-methyl-1H-pyrazol-3-yl)pyridin-2-yl)acetamide;
(R)—N-(4-((4-(2-methoxypropoxy)-6-(methylsulfonyl)pyridin-2-yl)amino)-5-(1-methyl-1H-pyrazol-3-yl)pyridin-2-yl)acetamide;
N-(4-((4-(2-hydroxyethoxy)-6-(methylsulfonyl)pyridin-2-yl)amino)-5-(1-methyl-1H-pyrazol-3-yl)pyridin-2-yl)acetamide;
N-(4-((4-((trans)-3-hydroxycyclobutoxy)-6-(methylsulfonyl)pyridin-2-yl)amino)-5-(1-methyl-1H-pyrazol-3-yl)pyridin-2-yl)acetamide;
N-(4-((4-((cis)-3-hydroxycyclobutoxy)-6-(methylsulfonyl)pyridin-2-yl)amino)-5-(1-methyl-1H-pyrazol-3-yl)pyridin-2-yl)acetamide;
N-(4-((4-(3-methoxycyclobutoxy)-6-(methylsulfonyl)pyridin-2-yl)amino)-5-(1-methyl-1H-pyrazol-3-yl)pyridin-2-yl)acetamide;
N-(4-((4-(methoxymethyl)-6-(methylsulfonyl)pyridin-2-yl)amino)-5-(1-methyl-1H-pyrazol-3-yl)pyridin-2-yl)acetamide;
N-(4-((4-(cyanomethoxy)-6-(methylsulfonyl)pyridin-2-yl)amino)-5-(1-methyl-1H-pyrazol-3-yl)pyridin-2-yl)acetamide;
N-(4-((4-methoxy-6-(methylsulfonyl)pyridin-2-yl)amino)-5-(1-methyl-1H-pyrazol-3-yl)pyridin-2-yl)acetamide;
N-(5-(1-methyl-1H-pyrazol-3-yl)-4-((6-(methylsulfonyl)-4-(oxetan-3-yloxy)pyridin-2-yl)amino)pyridin-2-yl)acetamide;
N-(4-((3-methoxy-6-(methylsulfonyl)pyridin-2-yl)amino)-5-(1-methyl-1H-pyrazol-3-yl)pyridin-2-yl)acetamide;
N-(4-((4-(2-hydroxypropoxy)-6-(methylsulfonyl)pyridin-2-yl)amino)-5-(1-methyl-1H-pyrazol-3-yl)pyridin-2-yl)acetamide;
N-(5-(1-methyl-1H-pyrazol-3-yl)-4-((6-(methylsulfonyl)-4-(oxetan-3-ylmethoxy)pyridin-2-yl)amino)pyridin-2-yl)acetamide;
N-(4-((4-cyano-6-(methylsulfonyl)pyridin-2-yl)amino)-5-(1-methyl-1H-pyrazol-3-yl)pyridin-2-yl)acetamide;
N-(5-(1-methyl-1H-pyrazol-3-yl)-4-((3-methyl-6-(methylsulfonyl)pyridin-2-yl)amino)pyridin-2-yl)acetamide;
N-(4-((6-(cyclopropylsulfonyl)pyridin-2-yl)amino)-5-(1-methyl-1H-pyrazol-3-yl)pyridin-2-yl)acetamide;
N-(4-((6-(isopropylsulfonyl)pyridin-2-yl)amino)-5-(1-methyl-1H-pyrazol-3-yl)pyridin-2-yl)acetamide;
N-(4-((3-fluoro-5-(methylsulfonyl)phenyl)amino)-5-(1-methyl-1H-pyrazol-3-yl)pyridin-2-yl)acetamide;
N-(4-((3-chloro-5-(methylsulfonyl)phenyl)amino)-5-(1-methyl-1H-pyrazol-3-yl)pyridin-2-yl)acetamide;
N-(4-((3-(difluoromethyl)-5-(methylsulfonyl)phenyl)amino)-5-(1-methyl-1H-pyrazol-3-yl)pyridin-2-yl)acetamide;
N-(5-(1-methyl-1H-pyrazol-3-yl)-4-((3-(methylsulfonyl)-5-(trifluoromethyl)phenyl)amino)pyridin-2-yl)acetamide;
N-(4-((3-(methoxymethyl)-5-(methylsulfonyl)phenyl)amino)-5-(1-methyl-1H-pyrazol-3-yl)pyridin-2-yl)acetamide;
N-(4-((3-(2-methoxyethoxy)-5-(methylsulfonyl)phenyl)amino)-5-(1-methyl-1H-pyrazol-3-yl)pyridin-2-yl)acetamide;

N-(4-((3-cyclopropoxy-5-(methylsulfonyl)phenyl)amino)-5-(1-methyl-1H-pyrazol-3-yl)pyridin-2-yl)acetamide;

N-(4-((3-((trans)-3-hydroxycyclobutoxy)-5-(methylsulfonyl)phenyl)amino)-5-(1-methyl-1H-pyrazol-3-yl)pyridin-2-yl)acetamide;

N-(5-(1-methyl-1H-pyrazol-3-yl)-4-((6-(methylsulfonyl)-4-phenylpyridin-2-yl)amino)pyridin-2-yl)acetamide;

N-(5-(1-methyl-1H-pyrazol-3-yl)-4-((6-(methylsulfonyl)-4-phenoxypyridin-2-yl)amino)pyridin-2-yl)acetamide;

N-(4-((4-chloro-6-(methylsulfonyl)pyridin-2-yl)amino)-5-(1-methyl-1H-pyrazol-3-yl)pyridin-2-yl)acetamide;

N-(4-((4-(1-methoxyethyl)-6-(methylsulfonyl)pyridin-2-yl)amino)-5-(1-methyl-1H-pyrazol-3-yl)pyridin-2-yl)acetamide;

N-(4-((4-(difluoromethyl)-6-(methylsulfonyl)pyridin-2-yl)amino)-5-(1-methyl-1H-pyrazol-3-yl)pyridin-2-yl)acetamide;

N-(4-((4-ethoxy-6-(methylsulfonyl)pyridin-2-yl)amino)-5-(1-methyl-1H-pyrazol-3-yl)pyridin-2-yl)acetamide;

N-(4-((4-cyclobutoxy-6-(methylsulfonyl)pyridin-2-yl)amino)-5-(1-methyl-1H-pyrazol-3-yl)pyridin-2-yl)acetamide;

N-(4-((4-(cyclopentyloxy)-6-(methylsulfonyl)pyridin-2-yl)amino)-5-(1-methyl-1H-pyrazol-3-yl)pyridin-2-yl)acetamide;

N-(5-(1-methyl-1H-pyrazol-3-yl)-4-((6-(methylsulfonyl)-4-((tetrahydrofuran-3-yl)oxy)pyridin-2-yl)amino)pyridin-2-yl)acetamide;

(R)—N-(4-((4-(2-hydroxypropoxy)-6-(methylsulfonyl)pyridin-2-yl)amino)-5-(1-methyl-1H-pyrazol-3-yl)pyridin-2-yl)acetamide;

N-(4-((4-(2,3-dihydroxypropoxy)-6-(methylsulfonyl)pyridin-2-yl)amino)-5-(1-methyl-1H-pyrazol-3-yl)pyridin-2-yl)acetamide;

N-(4-((3-isopropoxy-6-(methylsulfonyl)pyridin-2-yl)amino)-5-(1-methyl-1H-pyrazol-3-yl)pyridin-2-yl)acetamide;

N-(4-((5-methoxy-6-(methylsulfonyl)pyridin-2-yl)amino)-5-(1-methyl-1H-pyrazol-3-yl)pyridin-2-yl)acetamide;

N-(5-(1-methyl-1H-pyrazol-3-yl)-4-((5-methyl-6-(methylsulfonyl)pyridin-2-yl)amino)pyridin-2-yl)acetamide;

N-(5-(1-methyl-1H-pyrazol-3-yl)-4-((6-(methylsulfonyl)-4-(trifluoromethyl)pyridin-2-yl)amino)pyridin-2-yl)acetamide;

N-(4-((6-(ethylsulfonyl)-4-isopropoxypyridin-2-yl)amino)-5-(1-methyl-1H-pyrazol-3-yl)pyridin-2-yl)acetamide;

N-(4-((5-fluoro-6-(methylsulfonyl)pyridin-2-yl)amino)-5-(1-methyl-1H-pyrazol-3-yl)pyridin-2-yl)acetamide;

(S)—N-(4-((3-(2-hydroxypropoxy)-5-(methylsulfonyl)phenyl)amino)-5-(1-methyl-1H-pyrazol-3-yl)pyridin-2-yl)acetamide;

N-(4-((3-(2-hydroxyethoxy)-5-(methylsulfonyl)phenyl)amino)-5-(1-methyl-1H-pyrazol-3-yl)pyridin-2-yl)acetamide;

(R)—N-(4-((3-(2-hydroxypropoxy)-5-(methylsulfonyl)phenyl)amino)-5-(1-methyl-1H-pyrazol-3-yl)pyridin-2-yl)acetamide;

N-(4-((4-(difluoromethoxy)-6-(methylsulfonyl)pyridin-2-yl)amino)-5-(1-methyl-1H-pyrazol-3-yl)pyridin-2-yl)acetamide;

N-(4-((4-isobutoxy-6-(methylsulfonyl)pyridin-2-yl)amino)-5-(1-methyl-1H-pyrazol-3-yl)pyridin-2-yl)acetamide;

(S)—N-(4-((4-(sec-butoxy)-6-(methylsulfonyl)pyridin-2-yl)amino)-5-(1-methyl-1H-pyrazol-3-yl)pyridin-2-yl)acetamide;

N-(5-(1-methyl-1H-pyrazol-3-yl)-4-((6-(methylsulfonyl)-4-(tetrahydro-2H-pyran-4-yl)pyridin-2-yl)amino)pyridin-2-yl)acetamide;

N-(4-((3-(difluoromethoxy)-5-(methylsulfonyl)phenyl)amino)-5-(1-methyl-1H-pyrazol-3-yl)pyridin-2-yl)acetamide;

N-(4-((3-(difluoromethoxy)-6-(methylsulfonyl)pyridin-2-yl)amino)-5-(1-methyl-1H-pyrazol-3-yl)pyridin-2-yl)acetamide;

N-(5-(1-methyl-1H-pyrazol-3-yl)-4-((7-(methylsulfonyl)-2,3-dihydro-[1,4]dioxino[2,3-c]pyridin-5-yl)amino)pyridin-2-yl)acetamide;

(R)—N-(4-((4-(sec-butoxy)-6-(methylsulfonyl)pyridin-2-yl)amino)-5-(1-methyl-1H-pyrazol-3-yl)pyridin-2-yl)acetamide;

N-(5-(1-cyclopropyl-1H-pyrazol-3-yl)-4-((6-(methylsulfonyl)pyridin-2-yl)amino)pyridin-2-yl)acetamide;

N-(5-(1-cyclopropyl-1H-pyrazol-3-yl)-4-((4-isopropoxy-6-(methylsulfonyl)pyridin-2-yl)amino)pyridin-2-yl)acetamide;

N-(5-(1-cyclopropyl-1H-pyrazol-3-yl)-4-((4-methyl-6-(methylsulfonyl)pyridin-2-yl)amino)pyridin-2-yl)acetamide;

N-(5-(1-cyclopropyl-1H-pyrazol-3-yl)-4-((4-(2-methoxyethoxy)-6-(methylsulfonyl)pyridin-2-yl)amino)pyridin-2-yl)acetamide;

N-(5-(1-ethyl-1H-pyrazol-3-yl)-4-((6-(methylsulfonyl)pyridin-2-yl)amino)pyridin-2-yl)acetamide;

N-(5-(1-ethyl-1H-pyrazol-3-yl)-4-((4-isopropoxy-6-(methylsulfonyl)pyridin-2-yl)amino)pyridin-2-yl)acetamide;

N-(5-(1-ethyl-1H-pyrazol-3-yl)-4-((4-(methoxymethyl)-6-(methylsulfonyl)pyridin-2-yl)amino)pyridin-2-yl)acetamide;

N-(5-(1-ethyl-1H-pyrazol-3-yl)-4-((3-(methylsulfonyl)phenyl)amino)pyridin-2-yl)acetamide;

N-(5-(1-ethyl-1H-pyrazol-3-yl)-4-((3-methoxy-5-(methylsulfonyl)phenyl)amino)pyridin-2-yl)acetamide;

N-(4-((3-cyano-5-(methylsulfonyl)phenyl)amino)-5-(1-ethyl-1H-pyrazol-3-yl)pyridin-2-yl)acetamide;

N-(5-(1-ethyl-1H-pyrazol-3-yl)-4-((3-methyl-5-(methylsulfonyl)phenyl)amino)pyridin-2-yl)acetamide;

N-(5-(1-ethyl-1H-pyrazol-3-yl)-4-((3-(methoxymethyl)-5-(methylsulfonyl)phenyl)amino)pyridin-2-yl)acetamide;

N-(5-(1-ethyl-1H-pyrazol-3-yl)-4-((3-(methylsulfonyl)-5-(trifluoromethyl)phenyl)amino)pyridin-2-yl)acetamide;

N-(5-(1-ethyl-1H-pyrazol-3-yl)-4-((3-(2-methoxyethoxy)-5-(methylsulfonyl)phenyl)amino)pyridin-2-yl)acetamide;

N-(5-(1-ethyl-1H-pyrazol-3-yl)-4-((3-(2-hydroxyethoxy)-5-(methylsulfonyl)phenyl)amino)pyridin-2-yl)acetamide;

N-(4-((3-(cyclopropylmethoxy)-5-(methylsulfonyl)phenyl)amino)-5-(1-ethyl-1H-pyrazol-3-yl)pyridin-2-yl)acetamide;

N-(4-((4-(cyclopentyloxy)-6-(methylsulfonyl)pyridin-2-yl)amino)-5-(1-ethyl-1H-pyrazol-3-yl)pyridin-2-yl)acetamide;

N-(4-((4-ethoxy-6-(methylsulfonyl)pyridin-2-yl)amino)-5-(1-ethyl-1H-pyrazol-3-yl)pyridin-2-yl)acetamide;
N-(5-(1-ethyl-1H-pyrazol-3-yl)-4-((4-(2-hydroxyethoxy)-6-(methylsulfonyl)pyridin-2-yl)amino)pyridin-2-yl)acetamide;
N-(5-(1-ethyl-1H-pyrazol-3-yl)-4-((4-(2-methoxyethoxy)-6-(methylsulfonyl)pyridin-2-yl)amino)pyridin-2-yl)acetamide;
N-(5-(1-ethyl-1H-pyrazol-3-yl)-4-((3-isopropoxy-6-(methylsulfonyl)pyridin-2-yl)amino)pyridin-2-yl)acetamide;
N-(5-(1-isopropyl-1H-pyrazol-3-yl)-4-((6-(methylsulfonyl)pyridin-2-yl)amino)pyridin-2-yl)acetamide;
N-(4-((4-isopropoxy-6-(methylsulfonyl)pyridin-2-yl)amino)-5-(1-isopropyl-1H-pyrazol-3-yl)pyridin-2-yl)acetamide;
N-(5-(1-isopropyl-1H-pyrazol-3-yl)-4-((4-(2-methoxyethoxy)-6-(methylsulfonyl)pyridin-2-yl)amino)pyridin-2-yl)acetamide;
N-(5-(1-isopropyl-1H-pyrazol-3-yl)-4-((3-(methylsulfonyl)-5-(trifluoromethyl)phenyl)amino)pyridin-2-yl)acetamide;
N-(4-((3-isopropoxy-5-(methylsulfonyl)phenyl)amino)-5-(1-isopropyl-1H-pyrazol-3-yl)pyridin-2-yl)acetamide;
N-(5-(1-isopropyl-1H-pyrazol-3-yl)-4-((3-methoxy-5-(methylsulfonyl)phenyl)amino)pyridin-2-yl)acetamide;
N-(4-((4-(2-hydroxyethoxy)-6-(methylsulfonyl)pyridin-2-yl)amino)-5-(1-isopropyl-1H-pyrazol-3-yl)pyridin-2-yl)acetamide;
N-(4-((3-(2-hydroxyethoxy)-5-(methylsulfonyl)phenyl)amino)-5-(1-isopropyl-1H-pyrazol-3-yl)pyridin-2-yl)acetamide;
N-(4-((3-(methylsulfonyl)phenyl)amino)-5-(1-(tetrahydrofuran-3-yl)-1H-pyrazol-3-yl)pyridin-2-yl)acetamide;
N-(4-((4-methyl-6-(methylsulfonyl)pyridin-2-yl)amino)-5-(1-(tetrahydrofuran-3-yl)-1H-pyrazol-3-yl)pyridin-2-yl)acetamide;
(R)—N-(4-((3-(methylsulfonyl)-5-(trifluoromethyl)phenyl)amino)-5-(1-(tetrahydrofuran-3-yl)-1H-pyrazol-3-yl)pyridin-2-yl)acetamide;
(S)—N-(4-((4-isopropoxy-6-(methylsulfonyl)pyridin-2-yl)amino)-5-(1-(tetrahydrofuran-3-yl)-1H-pyrazol-3-yl)pyridin-2-yl)acetamide;
(R)—N-(4-((4-isopropoxy-6-(methylsulfonyl)pyridin-2-yl)amino)-5-(1-(tetrahydrofuran-3-yl)-1H-pyrazol-3-yl)pyridin-2-yl)acetamide;
(R)—N-(4-((4-methoxy-6-(methylsulfonyl)pyridin-2-yl)amino)-5-(1-(tetrahydrofuran-3-yl)-1H-pyrazol-3-yl)pyridin-2-yl)acetamide;
N-(5-(1,5-dimethyl-1H-pyrazol-3-yl)-4-((6-(methylsulfonyl)pyridin-2-yl)amino)pyridin-2-yl)acetamide;
N-(5-(1,5-dimethyl-1H-pyrazol-3-yl)-4-((4-isopropoxy-6-(methylsulfonyl)pyridin-2-yl)amino)pyridin-2-yl)acetamide;
N-(5-(1,5-dimethyl-1H-pyrazol-3-yl)-4-((3-(2-hydroxyethoxy)-5-(methylsulfonyl)phenyl)amino)pyridin-2-yl)acetamide;
N-(5-(1,5-dimethyl-1H-pyrazol-3-yl)-4-((4-methoxy-6-(methylsulfonyl)pyridin-2-yl)amino)pyridin-2-yl)acetamide;
N-(5-(1,5-dimethyl-1H-pyrazol-3-yl)-4-((4-(2-methoxyethoxy)-6-(methylsulfonyl)pyridin-2-yl)amino)pyridin-2-yl)acetamide;
(R)—N-(5-(1,5-dimethyl-1H-pyrazol-3-yl)-4-((4-(2-methoxypropoxy)-6-(methylsulfonyl)pyridin-2-yl)amino)pyridin-2-yl)acetamide;
N-(5-(1,5-dimethyl-1H-pyrazol-3-yl)-4-((4-ethoxy-6-(methylsulfonyl)pyridin-2-yl)amino)pyridin-2-yl)acetamide;
N-(5-(1-methyl-5-morpholino-1H-pyrazol-3-yl)-4-((6-(methylsulfonyl)pyridin-2-yl)amino)pyridin-2-yl)acetamide;
N-(4-((4-(2-methoxyethoxy)-6-(methylsulfonyl)pyridin-2-yl)amino)-5-(1-methyl-5-morpholino-1H-pyrazol-3-yl)pyridin-2-yl)acetamide;
N-(4-((4-(2-hydroxypropoxy)-6-(methylsulfonyl)pyridin-2-yl)amino)-5-(1-methyl-5-morpholino-1H-pyrazol-3-yl)pyridin-2-yl)acetamide;
N-(5-(2,3-dihydro-[1,4]dioxino[2,3-b]pyridin-6-yl)-4-((4-isopropoxy-6-(methylsulfonyl)pyridine-2-yl)amino)pyridin-2-yl)acetamide;
N-(5-([1,3]dioxolo[4,5-b]pyridin-5-yl)-4-((4-isopropoxy-6-(methylsulfonyl)pyridin-2-yl)amino)pyridin-2-yl)acetamide;
N-(5-(2,3-dihydro-[1,4]dioxino[2,3-b]pyridin-6-yl)-4-((4-methyl-6-(methylsulfonyl)pyridin-2-yl)amino)pyridin-2-yl)acetamide;
N-(5-(3,4-dihydro-2H-pyrido[4,3-b][1,4]oxazin-7-yl)-4-((4-isopropoxy-6-(methylsulfonyl)pyridin-2-yl)amino)pyridin-2-yl)acetamide;
N-(5-(imidazo[1,2-b]pyridazin-6-yl)-4-((4-isopropoxy-6-(methylsulfonyl)pyridin-2-yl)amino)pyridin-2-yl)acetamide;
N-(5-(6,7-dihydro-4H-pyrazolo[5,1-c][1,4]oxazin-2-yl)-4-((4-isopropoxy-6-(methylsulfonyl)pyridin-2-yl)amino)pyridin-2-yl)acetamide;
N-(5-(4-acetyl-3,4-dihydro-2H-pyrido[3,2-b][1,4]oxazin-6-yl)-4-((4-isopropoxy-6-(methylsulfonyl)pyridin-2-yl)amino)pyridin-2-yl)acetamide;
N-(5-(2,3-dihydro-[1,4]dioxino[2,3-c]pyridin-7-yl)-4-((4-methoxy-6-(methylsulfonyl)pyridin-2-yl)amino)pyridin-2-yl)acetamide;
N-(5-(benzo[b]thiophen-2-yl)-4-((4-methoxy-6-(methylsulfonyl)pyridin-2-yl)amino)pyridin-2-yl)acetamide;
N-(5-(6,7-dihydro-4H-thieno[3,2-c]pyran-2-yl)-4-((4-methyl-6-(methylsulfonyl)pyridin-2-yl)amino)pyridin-2-yl)acetamide;
N-(5-(2,3-dihydro-[1,4]dioxino[2,3-b]pyridin-6-yl)-4-((4-methoxy-6-(methylsulfonyl)pyridin-2-yl)amino)pyridin-2-yl)acetamide;
N-(5-(2,3-dihydro-[1,4]dioxino[2,3-c]pyridin-7-yl)-4-((4-ethoxy-6-(methylsulfonyl)pyridin-2-yl)amino)pyridin-2-yl)acetamide;
N-(5-(2,3-dihydro-[1,4]dioxino[2,3-c]pyridin-7-yl)-4-((4-(2-methoxyethoxy)-6-(methylsulfonyl)pyridin-2-yl)amino)pyridin-2-yl)acetamide;
N-(5-([1,3]dioxolo[4,5-b]pyridin-5-yl)-4-((4-(2-methoxyethoxy)-6-(methylsulfonyl)pyridin-2-yl)amino)pyridin-2-yl)acetamide;
N-(5-([1,3]dioxolo[4,5-b]pyridin-5-yl)-4-((4-ethoxy-6-(methylsulfonyl)pyridin-2-yl)amino)pyridin-2-yl)acetamide;
N-(5-([1,3]dioxolo[4,5-b]pyridin-5-yl)-4-((4-methoxy-6-(methylsulfonyl)pyridin-2-yl)amino)pyridin-2-yl)acetamide;
N-(4-((4-(cyclopropylmethoxy)-6-(methylsulfonyl)pyridin-2-yl)amino)-5-(5-methyl-4,5,6,7-tetrahydrothiazolo[5,4-c]pyridin-2-yl)pyridin-2-yl)acetamide;

N-(5-(2,3-dihydro-[1,4]dioxino[2,3-c]pyridin-7-yl)-4-((4-methyl-6-(methylsulfonyl)pyridin-2-yl)amino)pyridin-2-yl)acetamide;

N-(5-(6,7-dihydro-4H-pyrazolo[5,1-c][1,4]oxazin-2-yl)-4-((4-methyl-6-(methylsulfonyl)pyridin-2-yl)amino)pyridin-2-yl)acetamide;

N-(4-((4-((1,4-dioxan-2-yl)methoxy)-6-(methylsulfonyl)pyridin-2-yl)amino)-5-(3,3-dimethyl-2,3-dihydro-[1,4]dioxino[2,3-b]pyridin-6-yl)pyridin-2-yl)acetamide;

N-(5-(3,3-dimethyl-2,3-dihydro-[1,4]dioxino[2,3-b]pyridine-6-yl)-4-((6-(methylsulfonyl)pyrazin-2-yl)amino)pyridine-2-yl)acetamide;

N-(5-(3,3-dimethyl-2,3-dihydro-[1,4]dioxino[2,3-b]pyridine-6-yl)-4-((4-(2-hydroxypropan-2-yl)-6-(methylsulfonyl)pyridine-2-yl)amino)pyridine-2-yl)acetamide;

N-(5-(3,3-dimethyl-2,3-dihydro-[1,4]dioxino[2,3-b]pyridine-6-yl)-4-((5-fluoro-4-methyl-6-(methylsulfonyl)pyridine-2-yl)amino)pyridine-2-yl)acetamide;

N-(5-(3,3-dimethyl-2,3-dihydro-[1,4]dioxino[2,3-b]pyridin-6-yl)-4-((6-(methylsulfonyl)-4-morpholinopyridin-2-yl)amino)pyridin-2-yl)acetamide;

N-(5-(2,2-dimethyl-2,3-dihydro-[1,4]dioxino[2,3-b]pyridin-6-yl)-4-((4-methyl-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-4-morpholinopyridin-2-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-4-(tetrahydro-2H-pyran-4-yl)pyridin-2-yl)amino)pyridin-2-yl)acetamide;

N-(5-(2,2-dimethyl-2,3-dihydro-[1,4]dioxino[2,3-b]pyridin-6-yl)-4-((4-(methoxy-d3)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-methoxy-6-(methylsulfonyl)pyridin-2-yl)amino)pyridin-2-yl)acetamide;

N-(4-((3,4-dimethoxy-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

(S)—N-(5-(2,2-dimethyl-2,3-dihydro-[1,4]dioxino[2,3-b]pyridin-6-yl)-4-((4-(3-methyl-morpholino)-6-(methylsulfonyl)pyridin-2-yl)amino)-pyridin-2-yl)acetamide;

(R)—N-(5-(2,2-dimethyl-2,3-dihydro-[1,4]dioxino[2,3-b]pyridin-6-yl)-4-((4-(3-methyl-morpholino)-6-(methylsulfonyl)pyridin-2-yl)amino)-pyridin-2-yl)acetamide;

N-(5-(3,3-dimethyl-2,3-dihydro-[1,4]dioxino[2,3-b]pyridin-6-yl)-4-((4-(methoxy-d3)-6-(methylsulfonyl)pyridin-2-yl)amino)pyridin-2-yl)acetamide;

N-(5-(3,3-dimethyl-2,3-dihydro-[1,4]dioxino[2,3-b]pyridin-6-yl)-4-((4-methoxy-6-(methylsulfonyl)pyridin-2-yl)amino)pyridin-2-yl)acetamide;

N-(5-(3,3-dimethyl-2,3-dihydro-[1,4]dioxino[2,3-b]pyridin-6-yl)-4-((6-(methylsulfonyl)-4-(tetrahydro-2H-pyran-4-yl)pyridin-2-yl)amino)pyridin-2-yl)acetamide;

(R)—N-(5-(3,3-dimethyl-2,3-dihydro-[1,4]dioxino[2,3-b]pyridin-6-yl)-4-((4-(3-methylmorpholino)-6-(methylsulfonyl)pyridin-2-yl)amino)pyridin-2-yl)acetamide;

(S)—N-(5-(3,3-dimethyl-2,3-dihydro-[1,4]dioxino[2,3-b]pyridin-6-yl)-4-((4-(3-methylmorpholino)-6-(methylsulfonyl)pyridin-2-yl)amino)pyridin-2-yl)acetamide;

(S)—N-(5-(3,3-dimethyl-2,3-dihydro-[1,4]dioxino[2,3-b]pyridin-6-yl)-4-((4-(1-methoxyethyl)-6-(methylsulfonyl)pyridin-2-yl)amino)pyridin-2-yl)acetamide;

(R)—N-(5-(3,3-dimethyl-2,3-dihydro-[1,4]dioxino[2,3-b]pyridin-6-yl)-4-((4-(1-methoxyethyl)-6-(methylsulfonyl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((4-(3-methoxypyrrolidin-1-yl)-6-(methylsulfonyl)pyridin-2-yl)amino)pyridin-2-yl)acetamide;

(S)—N-(5-(2,2-dimethyl-2,3-dihydro-[1,4]dioxino[2,3-b]pyridin-6-yl)-4-((4-(3-methoxypyrrolidin-1-yl)-6-(methylsulfonyl)pyridin-2-yl)amino)pyridin-2-yl)acetamide;

N-(4-((4-(4-aminotetrahydro-2H-pyran-4-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((4-(4-(aminomethyl)tetrahydro-2H-pyran-4-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(5-(2,2-dimethyl-2,3-dihydro-[1,4]dioxino[2,3-b]pyridin-6-yl)-4-((4-(3-methoxyazetidin-1-yl)-6-(methylsulfonyl)pyridin-2-yl)amino)pyridin-2-yl)acetamide;

(R/S)—N-(4-((4-(1,4-dioxan-2-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

(S/R)—N-(4-((4-(1,4-dioxan-2-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(5-(2,2-dimethyl-2,3-dihydro-[1,4]dioxino[2,3-b]pyridin-6-yl)-4-((4-(4-methoxypiperidin-1-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-((cis)-3-methoxycyclobutyl)-6-(methylsulfonyl)pyridin-2-yl)amino)pyridin-2-yl) acetamide;

N-(5-(2,2-dimethyl-2,3-dihydro-[1,4]dioxino[2,3-b]pyridin-6-yl)-4-((4-((trans)-3-methoxycyclobutyl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-(4-hydroxy-4-methylpiperidin-1-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-(3-hydroxy-3-methylazetidin-1-yl)-6-(methylsulfonyl)pyridin-2-yl)amino) pyridin-2-yl)acetamide;

N-(5-(2,2-dimethyl-2,3-dihydro-[1,4]dioxino[2,3-b]pyridin-6-yl)-4-((4-(3-hydroxy-3-methylpyrrolidin-1-yl)-6-(methyl sulfonyl)pyridin-2-yl)amino)pyridin-2-yl)acetamide;

N-(6-(2,2-dimethyl-2,3-dihydro-[1,4]dioxino[2,3-b]pyridin-6-yl)-5-((6-(methylsulfonyl)-4-(tetrahydro-2H-pyran-4-yl)pyridin-2-yl)amino)pyridazin-3-yl)acetamide;

(R)—N-(5-(2,2-dimethyl-2,3-dihydro-[1,4]dioxino[2,3-b]pyridin-6-yl)-4-((4-(3-(2-hydroxyethoxy)pyrrolidin-1-yl)-6-(methylsulfonyl)pyridin-2-yl)amino)pyridin-2-yl) acetamide;

N-(5-(2,2-dimethyl-2,3-dihydro-[1,4]dioxino[2,3-b]pyridin-6-yl)-4-((6-(methylsulfonyl)-4-(1-(2,2,2-trifluoroethyl)piperidin-4-yl)pyridin-2-yl)amino)pyridin-2-yl)acetamide;

(S)—N-(5-(2,2-dimethyl-2,3-dihydro-[1,4]dioxino[2,3-b]pyridin-6-yl)-4-((4-(3-(2-hydroxyethoxy)pyrrolidin-1-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-methyl-6'-(methylsulfonyl)-[3,4'-bipyridin]-2'-yl)amino)pyridin-2-yl)acetamide;

N-(4-((4-cyano-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(5-(2,2-dimethyl-2,3-dihydro-[1,4]dioxino[2,3-b]pyridin-6-yl)-4-((4-methyl-6-(methylsulfonyl)-3-oxo-3,4-dihydropyrazin-2-yl)amino)pyridin-2-yl)acetamide;

(S)—N-(5-(2,2-dimethyl-2,3-dihydro-[1,4]dioxino[2,3-b]pyridin-6-yl)-4-((4-(3-methoxypiperidin-1-yl)-6-(methylsulfonyl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((4-(3-methoxypiperidin-1-yl)-6-(methylsulfonyl)pyridin-2-yl)amino)pyridin-2-yl)acetamide;

(S)—N-(5-(2,2-dimethyl-2,3-dihydro-[1,4]dioxino[2,3-b]pyridin-6-yl)-4-((4-(3-ethoxypiperidin-1-yl)-6-(methylsulfonyl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((4-(3-ethoxypiperidin-1-yl)-6-(methylsulfonyl)pyridin-2-yl)amino)pyridin-2-yl)acetamide;

(S)—N-(5-(2,2-dimethyl-2,3-dihydro-[1,4]dioxino[2,3-b]pyridin-6-yl)-4-((6-(methylsulfonyl)-4-(3-(trifluoromethoxy)pyrrolidin-1-yl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((6-(methylsulfonyl)-4-(3-(trifluoromethoxy)pyrrolidin-1-yl)pyridin-2-yl)amino)pyridin-2-yl)acetamide;

(S)-1-(2-((2-acetamido-5-(2,2-dimethyl-2,3-dihydro-[1,4]dioxino[2,3-b]pyridin-6-yl)pyridin-4-yl)amino)-6-(methylsulfonyl)pyridin-4-yl)pyrrolidine-2-carboxamide;

(R)-1-(2-((2-acetamido-5-(2,2-dimethyl-2,3-dihydro-[1,4]dioxino[2,3-b]pyridin-6-yl)pyridin-4-yl)amino)-6-(methylsulfonyl)pyridin-4-yl)pyrrolidine-2-carboxamide;

(S)—N-(5-(2,2-dimethyl-2,3-dihydro-[1,4]dioxino[2,3-b]pyridin-6-yl)-4-((4-(3-(methoxymethyl)pyrrolidin-1-yl)-6-(methylsulfonyl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((4-(3-(methoxymethyl)pyrrolidin-1-yl)-6-(methylsulfonyl)pyridin-2-yl)amino)pyridin-2-yl)acetamide;

(S)—N-(5-(2,2-dimethyl-2,3-dihydro-[1,4]dioxino[2,3-b]pyridin-6-yl)-4-((6-(methylsulfonyl)-4-(tetrahydro-2H-pyran-3-yl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((6-(methylsulfonyl)-4-(tetrahydro-2H-pyran-3-yl)pyridin-2-yl)amino)pyridin-2-yl)acetamide;

(S)—N-(5-(2,2-dimethyl-2,3-dihydro-[1,4]dioxino[2,3-b]pyridin-6-yl)-4-((5-(3-methoxypyrrolidin-1-yl)-6-(methylsulfonyl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((5-(3-methoxypyrrolidin-1-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-5-(tetrahydro-2H-pyran-4-yl)pyridin-2-yl)amino)pyridin-2-yl)acetamide;

N-(5-(2,2-dimethyl-2,3-dihydro-[1,4]dioxino[2,3-b]pyridin-6-yl)-4-((4-(5-methylpyridazin-4-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-(5-methoxypyridazin-4-yl)-6-(methylsulfonyl)pyridin-2-yl)amino)pyridin-2-yl)acetamide;

N-(4-((4-(cis-3-cyano-4-hydroxypyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((4-(trans-3-cyano-4-hydroxypyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((4-(cis-3-cyano-4-methoxypyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((4-(trans-3-cyano-4-methoxypyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

(S)—N-(5-(2,2-dimethyl-2,3-dihydro-[1,4]dioxino[2,3-b]pyridin-6-yl)-4-((6-(methylsulfonyl)-4-(tetrahydrofuran-3-yl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((6-(methylsulfonyl)-4-(tetrahydrofuran-3-yl)pyridin-2-yl)amino)pyridin-2-yl)acetamide;

(S)—N-(5-(2,2-dimethyl-2,3-dihydro-[1,4]dioxino[2,3-b]pyridin-6-yl)-4-((4-(2-(methoxymethyl)pyrrolidin-1-yl)-6-(methylsulfonyl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((4-(2-(methoxymethyl)pyrrolidin-1-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-3-(tetrahydro-2H-pyran-4-yl)pyridin-2-yl)amino)pyridin-2-yl)acetamide;

(S)—N-(5-(2,2-dimethyl-2,3-dihydro-[1,4]dioxino[2,3-b]pyridin-6-yl)-4-((3-(3-methoxypyrrolidin-1-yl)-6-(methylsulfonyl)pyridin-2-yl)amino)pyridin-2-yl)acetamide;

(R)—N-(5-(2,2-dimethyl-2,3-dihydro-[1,4]dioxino[2,3-b]pyridin-6-yl)-4-((3-(3-methoxypyrrolidin-1-yl)-6-(methylsulfonyl)pyridin-2-yl)amino)pyridin-2-yl)acetamide;

cis-N-(5-(2,2-dimethyl-2,3-dihydro-[1,4]dioxino[2,3-b]pyridin-6-yl)-4-((4-((cis-4-hydroxycyclohexyl)oxy)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-((trans-4-hydroxycyclohexyl)oxy)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-((cis-4-methoxycyclohexyl)oxy)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-((trans-4-methoxycyclohexyl)oxy)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-4-(5-azaspiro[2.4]heptan-5-yl)pyridin-2-yl)amino)pyridin-2-yl)acetamide;

N-(5-(2,2-dimethyl-2,3-dihydro-[1,4]dioxino[2,3-b]pyridin-6-yl)-4-((4-((3-methyloxetan-3-yl)methoxy)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-(3, 5-dimethylisoxazol-4-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-((2,4-dioxothiazolidin-3-yl)methyl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-methoxy-6'-(methylsulfonyl)-[3,4'-bipyridin]-2'-yl)amino)pyridin-2-yl)acetamide;

(R)—N-(5-(2,2-dimethyl-2,3-dihydro-[1,4]dioxino[2,3-b]pyridin-6-yl)-4-((4-(3-methylpyrrolidin-1-yl)-6-(methylsulfonyl)pyridin-2-yl)amino)pyridin-2-yl)acetamide;

(S)—N-(5-(2,2-dimethyl-2,3-dihydro-[1,4]dioxino[2,3-b]pyridin-6-yl)-4-((4-(3-methylpyrrolidin-1-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-4-(pyrrolidin-1-yl)pyridin-2-yl)amino)pyridin-2-yl)acetamide;

N-(5-(2,2-dimethyl-2,3-dihydro-[1,4]dioxino[2,3-b]pyridin-6-yl)-4-((4-(2-hydroxypropan-2-yl)-6'-(methylsulfonyl)-[3,4'-bipyridin]-2'-yl)amino)pyridin-2-yl)acetamide;

N-(4-((4-(3-azabicyclo[3.1.0]hexan-3-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

(S)—N-(4-((4-(3-(cyanomethoxy)pyrrolidin-1-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((6-cyano-6'-(methylsulfonyl)-[3,4'-bipyridin]-2'-yl)amino)-5-(2,2-dimethyl-2,3-dihydro-[1,4]dioxino[2,3-b]pyridin-6-yl)pyridin-2-yl)acetamide;

N-(4-((2-cyano-6'-(methylsulfonyl)-[3,4'-bipyridin]-2'-yl)amino)-5-(2,2-dimethyl-2,3-dihydro-[1,4]dioxino[2,3-b]pyridin-6-yl)pyridin-2-yl)acetamide;

N-(5-(2,2-dimethyl-2,3-dihydro-[1,4]dioxino[2,3-b]pyridin-6-yl)-4-((4-(3-methylpyrazin-2-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-4-(2,2,6,6-tetramethyltetrahydro-2H-pyran-4-yl)pyridin-2-yl)amino)pyridin-2-yl)acetamide;

(R)—N-(4-((4-(2,2-dichlorocyclopropyl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

(S)—N-(4-((4-(2,2-dichlorocyclopropyl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((4-(5-cyanopyridazin-4-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((4-cyano-6'-(methylsulfonyl)-[3,4'-bipyridin]-2'-yl)amino)-5-(2,2-dimethyl-2,3-dihydro-[1,4]dioxino[2,3-b]pyridin-6-yl)pyridin-2-yl)acetamide;

N-(5-(2,2-dimethyl-2,3-dihydro-[1,4]dioxino[2,3-b]pyridin-6-yl)-4-((4-(5-fluoropyridazin-4-yl)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-fluoro-6'-(methylsulfonyl)-[3,4'-bipyridin]-2'-yl)amino)pyridin-2-yl)acetamide;

N-(5-(2,2-dimethyl-2,3-dihydro-[1,4]dioxino[2,3-b]pyridin-6-yl)-4-((6'-(methylsulfonyl)-[2,4'-bipyridin]-2'-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-4-(thiazol-4-yl)pyridin-2-yl)amino)pyridin-2-yl)acetamide;

N-(4-((4-(1-cyanocyclopropyl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((4-((3R)-3-cyano-2-azabicyclo[3.1.0]hexan-2-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((4-((3S)-3-cyano-2-azabicyclo[3.1.0]hexan-2-yl)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(5-(2,2-dimethyl-2,3-dihydro-[1,4]dioxino[2,3-b]pyridin-6-yl)-4-((4-(2-methyl-2-morpholinopropoxy)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-(2-methoxy-2-methylpropoxy)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-(2-hydroxy-2-methylpropoxy)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-(3,3-dimethylmorpholino)-6-(methylsulfonyl)pyridin-2-yl)amino)pyridin-2-yl)acetamide;

N-(5-(2,2-dimethyl-2,3-dihydro-[1,4]dioxino[2,3-b]pyridin-6-yl)-4-((4-isopropyl-6'-(methylsulfonyl)-[3,4'-bipyridin]-2'-yl)amino)pyridin-2-yl)acetamide;

N-(5-(2,2-dimethyl-2,3-dihydro-[1,4]dioxino[2,3-b]pyridin-6-yl)-4-((4-(1-hydroxyethyl)-6'-(methylsulfonyl)-[3,4'-bipyridin]-2'-yl)amino)pyridin-2-yl)acetamide;

N-(5-(2,2-dimethyl-2,3-dihydro-[1,4]dioxino[2,3-b]pyridin-6-yl)-4-((4-(1-methoxyethyl)-6'-(methylsulfonyl)-[3,4'-bipyridin]-2'-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-[1,3]dioxolo[4,5-c]pyridin-4-yl)amino)pyridin-2-yl)acetamide;

N-(5-(2,2-dimethyl-2,3-dihydro-[1,4]dioxino[2,3-b]pyridin-6-yl)-4-((7-(methylsulfonyl)-2,3-dihydro-[1,4]dioxino[2,3-c]pyridin-5-yl)amino)pyridin-2-yl)acetamide;

N-(5-(2,2-dimethyl-2,3-dihydro-[1,4]dioxino[2,3-b]pyridin-6-yl)-4-((6-(methylsulfonyl)-4-(trifluoromethyl)pyridin-2-yl)amino)pyridin-2-yl)acetamide;

N-(4-((4-(difluoromethoxy)-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(4-((4-cyclobutoxy-6-(methylsulfonyl)pyridin-2-yl)amino)-5-(2,2-dimethyl-2,3-dihydro-[1,4]dioxino[2,3-b]pyridin-6-yl)pyridin-2-yl)acetamide;

N-(5-(2,2-bis(methyl-d3)-2,3-dihydro-[1,4]dioxino[2,3-b]pyridin-6-yl)-4-((6-(methylsulfonyl)-4-(tetrahydro-2H-pyran-4-yl)pyridin-2-yl)amino)pyridin-2-yl)acetamide;

N-(5-(2,2-bis(methyl-d3)-2,3-dihydro-[1,4]dioxino[2,3-b]pyridin-6-yl)-4-((4-(methoxy-d3)-6-(methylsulfonyl)pyridin-2-yl)amino)pyridin-2-yl)acetamide;

N-(5-(4,4-dimethyl-4,5-dihydrothiazol-2-yl)-4-((6-(methylsulfonyl)pyridin-2-yl)amino)pyridin-2-yl)acetamide;

N-(5-(4,4-dimethyl-4,5-dihydrothiazol-2-yl)-4-((6-(methylsulfonyl)-4-(tetrahydro-2H-pyran-4-yl)pyridin-2-yl)amino)pyridin-2-yl)acetamide;

N-(4-((4-isopropoxy-6-(methylsulfonyl)pyridin-2-yl)amino)-5-(1-methyl-1,3a,4,6,7,7a-hexahydropyrano[4,3-c]pyrazol-3-yl)pyridin-2-yl)acetamide;

N-(5-(6,7-dihydro-4H-pyrano[4,3-d]thiazol-2-yl)-4-((4-methyl-6-(methylsulfonyl)pyridin-2-yl)amino)pyridin-2-yl)acetamide;

N-(4-((4-isopropoxy-6-(methylsulfonyl)pyridin-2-yl)amino)-5-(5-methyl-4,5,6,7-tetrahydropyrazolo[1,5-a]pyrazin-2-yl)pyridin-2-yl)acetamide;

N-(5-([1,3]dioxolo[4,5-c]pyridin-6-yl)-4-((4-methyl-6-(methylsulfonyl)pyridin-2-yl)amino)pyridin-2-yl)acetamide;

N-(5-([1,3]dioxolo[4,5-c]pyridin-4-yl)-4-((4-methyl-6-(methylsulfonyl)pyridin-2-yl)amino)pyridin-2-yl)acetamide;

N-(5-(benzo[d][1,3]dioxol-4-yl)-4-((4-methyl-6-(methylsulfonyl)pyridin-2-yl)amino)pyridin-2-yl)acetamide;

N-(5-(5-methyl-4,5,6,7-tetrahydrothiazolo[5,4-c]pyridin-2-yl)-4-((4-methyl-6-(methylsulfonyl)pyridin-2-yl)amino)pyridin-2-yl)acetamide;

N-(5-(imidazo[1,2-a]pyrimidin-2-yl)-4-((4-methyl-6-(methylsulfonyl)pyridin-2-yl)amino)pyridin-2-yl)acetamide;

N-(5-(1-methyl-1,4-dihydrochromeno[4,3-c]pyrazol-6-yl)-4-((4-methyl-6-(methylsulfonyl)pyridin-2-yl)amino)pyridin-2-yl)acetamide;

N-(5-(imidazo[2',1':2,3]thiazolo[5,4-b]pyridin-7-yl)-4-((4-methyl-6-(methylsulfonyl)pyridin-2-yl)amino)pyridin-2-yl)acetamide;

N-(5-(1-methyl-1,4-dihydropyrazolo[3',4':4,5]pyrano[2,3-b]pyridin-7-yl)-4-((4-methyl-6-(methylsulfonyl)pyridin-2-yl)amino)pyridin-2-yl)acetamide;

N-(4'-((4,4-dioxido-2,3-dihydro-[1,4]oxathiino[3,2-b]pyridin-6-yl)amino)-[2,3'-bipyridin]-6'-yl)acetamide;

N-(4-((4,4-dioxido-2,3-dihydro-[1,4]oxathiino[3,2-b]pyridin-6-yl)amino)-5-(1-methyl-1H-pyrazol-3-yl)pyridin-2-yl)acetamide;

N-(5-(imidazo[1,2-b]pyridazin-6-yl)-4-((4-methyl-6-(methylsulfonyl)pyridin-2-yl)amino)pyridin-2-yl)acetamide;

N-(5-(1-methyl-1H-pyrazol-3-yl)-4-((7-(methylsulfonyl)-3,4-dihydro-2H-pyrano[3,2-c]pyridin-5-yl)amino)pyridin-2-yl)acetamide;

N-(4-((5,5-dioxido-3,4-dihydro-2H-[1,4]oxathiepino[3,2-b]pyridin-7-yl)amino)-5-(1-methyl-1H-pyrazol-3-yl)pyridin-2-yl)acetamide;

N-(4-((4-(2-hydroxypropan-2-yl)-6-(methylsulfonyl)pyridin-2-yl)amino)-5-(1-methyl-1H-pyrazol-3-yl)pyridin-2-yl)acetamide;

N-(5-(1-methyl-1H-pyrazol-3-yl)-4-((6-(methylsulfonyl)-4-(tetrahydrofuran-3-yl)pyridin-2-yl)amino)pyridin-2-yl)acetamide;

N-(4-((4-(3-(hydroxymethyl)tetrahydrofuran-3-yl)-6-(methylsulfonyl)pyridin-2-yl)amino)-5-(1-methyl-1H-pyrazol-3-yl)pyridin-2-yl)acetamide;

N-(4-((4-(1-hydroxycyclopropyl)-6-(methylsulfonyl)pyridin-2-yl)amino)-5-(1-methyl-1H-pyrazol-3-yl)pyridin-2-yl)acetamide;

N-(4-((4-(2-hydroxy-2-methylpropoxy)-6-(methylsulfonyl)pyridin-2-yl)amino)-5-(1-methyl-1H-pyrazol-3-yl)pyridin-2-yl)acetamide;

N-(4-((4-(3-hydroxy-2,2-dimethylpropoxy)-6-(methylsulfonyl)pyridin-2-yl)amino)-5-(1-methyl-1H-pyrazol-3-yl)pyridin-2-yl)acetamide;

N-(5-(imidazo[1,5-b]pyridazin-2-yl)-4-((4-methyl-6-(methylsulfonyl)pyridin-2-yl)amino)pyridin-2-yl)acetamide;

N-(4-((4-(3-hydroxytetrahydrofuran-3-yl)-6-(methylsulfonyl)pyridin-2-yl)amino)-5-(1-methyl-1H-pyrazol-3-yl)pyridin-2-yl)acetamide;

N-(5-(1-methyl-1H-pyrazol-3-yl)-4-((4-(1-methyl-1H-pyrazol-3-yl)-6-(methylsulfonyl)pyridin-2-yl)amino)pyridin-2-yl)acetamide;

N-(4-((4-((1-hydroxycyclopropyl)methoxy)-6-(methylsulfonyl)pyridin-2-yl)amino)-5-(1-methyl-1H-pyrazol-3-yl)pyridin-2-yl)acetamide;

N-(4-((4-((1-methoxycyclopropyl)methoxy)-6-(methylsulfonyl)pyridin-2-yl)amino)-5-(1-methyl-1H-pyrazol-3-yl)pyridin-2-yl)acetamide;

N-(5-(1-methyl-1H-pyrazol-3-yl)-4-((6-(methylsulfonyl)-4-morpholinopyridin-2-yl)amino)pyridin-2-yl)acetamide;

N-(5-(benzo[d]thiazol-2-yl)-4-((4-(3-(hydroxymethyl)tetrahydrofuran-3-yl)-6-(methylsulfonyl)pyridin-2-yl)amino)pyridin-2-yl)acetamide;

N-(4-((1,1-dioxido-3,4-dihydro-2H-thiopyrano[2,3-b]pyridin-7-yl)amino)-5-(1-methyl-1H-pyrazol-3-yl)pyridin-2-yl)acetamide;

N-(5-(1-methyl-1H-pyrazol-3-yl)-4-((6-(methylsulfonyl)-[1,3]dioxolo[4,5-c]pyridin-4-yl)amino)pyridin-2-yl)acetamide;

N-(5-(1-methyl-1H-pyrazol-3-yl)-4-((6-(methylsulfonyl)imidazo[1,2-a]pyrazin-8-yl)amino)pyridin-2-yl)acetamide;

N-(5-(1-methyl-1H-pyrazol-3-yl)-4-((5-(methylsulfonyl)-3,4-dihydro-2H-pyrano[3,2-c]pyridin-7-yl)amino)pyridin-2-yl)acetamide;

N-(5-(2,6-dimethylmorpholino)-4'-((4-(2-hydroxypropan-2-yl)-6-(methylsulfonyl)pyridin-2-yl)amino)-[2,3'-bipyridin]-6'-yl)acetamide;

N-(5-(2,6-dimethylmorpholino)-4'-((6-(methylsulfonyl)-4-(tetrahydrofuran-3-yl)pyridin-2-yl)amino)-[2,3'-bipyridin]-6'-yl)acetamide;

N-(5-(2,6-dimethylmorpholino)-4'-((4-(3-(hydroxymethyl)tetrahydrofuran-3-yl)-6-(methylsulfonyl)pyridin-2-yl)amino)-[2,3'-bipyridin]-6'-yl)acetamide;

N-(5-(2,6-dimethylmorpholino)-4'-((4-(1-hydroxycyclopropyl)-6-(methylsulfonyl)pyridin-2-yl)amino)-[2,3'-bipyridin]-6'-yl)acetamide;

N-(5-(2,6-dimethylmorpholino)-4'-((4-(2-hydroxy-2-methylpropoxy)-6-(methylsulfonyl)pyridin-2-yl)amino)-[2,3'-bipyridin]-6'-yl)acetamide;

N-(5-(2,6-dimethylmorpholino)-4'-((4-(3-hydroxy-2,2-dimethylpropoxy)-6-(methylsulfonyl)pyridin-2-yl)amino)-[2,3'-bipyridin]-6'-yl)acetamide;

N-(5-(2,6-dimethylmorpholino)-4'-((4-(3-methoxytetrahydrofuran-3-yl)-6-(methylsulfonyl)pyridin-2-yl)amino)-[2,3'-bipyridin]-6'-yl)acetamide;

N-(5-(2,6-dimethylmorpholino)-4'-((4-(3-hydroxytetrahydrofuran-3-yl)-6-(methylsulfonyl)pyridin-2-yl)amino)-[2,3'-bipyridin]-6'-yl)acetamide;

N-(5-(2,6-dimethylmorpholino)-4'-((4-(1-methyl-1H-pyrazol-3-yl)-6-(methylsulfonyl)pyridin-2-yl)amino)-[2,3'-bipyridin]-6'-yl)acetamide;

N-(5-(2,6-dimethylmorpholino)-4'-((4-((1-hydroxycyclopropyl)methoxy)-6-(methylsulfonyl)pyridin-2-yl)amino)-[2,3'-bipyridin]-6'-yl)acetamide;

N-(5-(2,6-dimethylmorpholino)-4'-((4-((1-methoxycyclopropyl)methoxy)-6-(methylsulfonyl)pyridin-2-yl)amino)-[2,3'-bipyridin]-6'-yl)acetamide;

N-(5-(2,6-dimethylmorpholino)-4'-((6-(methylsulfonyl)-4-morpholinopyridin-2-yl)amino)-[2,3'-bipyridin]-6'-yl)acetamide;

N-(5-(2,6-dimethylmorpholino)-4'-((5,5-dioxido-3,4-dihydro-2H-[1,4]oxathiepino[3,2-b]pyridin-7-yl)amino)-[2,3'-bipyridin]-6'-yl)acetamide;

N-(5-(2,6-dimethylmorpholino)-4'-((1,1-dioxido-3,4-dihydro-2H-thiopyrano[2,3-b]pyridin-7-yl)amino)-[2,3'-bipyridin]-6'-yl)acetamide;

N-(5-(2,6-dimethylmorpholino)-4'-((7-(methylsulfonyl)-3,4-dihydro-2H-pyrano[3,2-c]pyridin-5-yl)amino)-[2,3'-bipyridin]-6'-yl)acetamide;

N-(5-(2,6-dimethylmorpholino)-4'-((6-(methylsulfonyl)-[1,3]dioxolo[4,5-c]pyridin-4-yl)amino)-[2,3'-bipyridin]-6'-yl)acetamide;

N-(5-(2,6-dimethylmorpholino)-4'-((6-(methylsulfonyl)imidazo[1,2-a]pyrazin-8-yl)amino)-[2,3'-bipyridin]-6'-yl)acetamide;

N-(5-(2,6-dimethylmorpholino)-4'-((5-(methylsulfonyl)-3,4-dihydro-2H-pyrano[3,2-c]pyridin-7-yl)amino)-[2,3'-bipyridin]-6'-yl)acetamide;

N-(5-(6,7-dihydro-4H-pyrano[4,3-d]thiazol-2-yl)-4-((4-(3-(hydroxymethyl)tetrahydrofuran-3-yl)-6-(methylsulfonyl)pyridin-2-yl)amino)pyridin-2-yl)acetamide;

N-(5-(benzo[d][1,3]dioxol-4-yl)-4-((4-(3-(hydroxymethyl)tetrahydrofuran-3-yl)-6-(methylsulfonyl)pyridin-2-yl)amino)pyridin-2-yl)acetamide;

N-(5-(benzo[d]isoxazol-3-yl)-4-((4-(3-(hydroxymethyl)tetrahydrofuran-3-yl)-6-(methylsulfonyl)pyridin-2-yl)amino)pyridin-2-yl)acetamide;

N-(5-(benzo[d]isothiazol-3-yl)-4-((4-(3-(hydroxymethyl)tetrahydrofuran-3-yl)-6-(methylsulfonyl)pyridin-2-yl)amino)pyridin-2-yl)acetamide;

N-(5-(benzo[b]thiophen-2-yl)-4-((4-(3-(hydroxymethyl)tetrahydrofuran-3-yl)-6-(methylsulfonyl)pyridin-2-yl)amino)pyridin-2-yl)acetamide;

N-(4-((4-(3-(hydroxymethyl)tetrahydrofuran-3-yl)-6-(methylsulfonyl)pyridin-2-yl)amino)-5-(imidazo[1,2-a]pyrimidin-2-yl)pyridin-2-yl)acetamide;

N-(4-((4-(3-(hydroxymethyl)tetrahydrofuran-3-yl)-6-(methylsulfonyl)pyridin-2-yl)amino)-5-(1-methyl-1,4-dihydrochromeno[4,3-c]pyrazol-6-yl)pyridin-2-yl)acetamide;

N-(4-((4-(3-(hydroxymethyl)tetrahydrofuran-3-yl)-6-(methylsulfonyl)pyridin-2-yl)amino)-5-(imidazo[2',1':2,3]thiazolo[5,4-b]pyridin-7-yl)pyridin-2-yl)acetamide;

N-(4-((4-(3-(hydroxymethyl)tetrahydrofuran-3-yl)-6-(methylsulfonyl)pyridin-2-yl)amino)-5-(1-methyl-1,4-dihydropyrazolo[3',4':4,5]pyrano[2,3-b]pyridin-7-yl)pyridin-2-yl)acetamide;

N-(4-((4-(3-(hydroxymethyl)tetrahydrofuran-3-yl)-6-(methylsulfonyl)pyridin-2-yl)amino)-5-(6-oxo-1,6-dihydropyridazin-3-yl)pyridin-2-yl)acetamide;

N-(4-((4-(3-(hydroxymethyl)tetrahydrofuran-3-yl)-6-(methylsulfonyl)pyridin-2-yl)amino)-5-(6-oxopyridazin-1(6H)-yl)pyridin-2-yl)acetamide;

N-(5-(6-((2S,6R)-2,6-dimethylmorpholino)pyridazin-3-yl)-4-((4-(3-(hydroxymethyl)tetrahydrofuran-3-yl)-6-(methylsulfonyl)pyridin-2-yl)amino)pyridin-2-yl)acetamide;

N-(4-((4-(3-(hydroxymethyl)tetrahydrofuran-3-yl)-6-(methylsulfonyl)pyridin-2-yl)amino)-5-(3-oxo-8,9-dihydropyrano[4,3,2-de]phthalazin-2(3H)-yl)pyridin-2-yl)acetamide;

N-(4-((4-(3-(hydroxymethyl)tetrahydrofuran-3-yl)-6-(methylsulfonyl)pyridin-2-yl)amino)-5-(7-methyl-3-oxo-8,9-dihydro-3H-pyrido[4,3,2-de]phthalazin-2(7H)-yl)pyridin-2-yl)acetamide;

N-(4'-((4-(3-(hydroxymethyl)tetrahydrofuran-3-yl)-6-(methylsulfonyl)pyridin-2-yl)amino)-5-(1-oxoisoindolin-2-yl)-[2,3'-bipyridin]-6'-yl)acetamide;

N-(5-(2,3-dihydropyrazolo[5,1-b]oxazol-6-yl)-4-((4-(3-(hydroxymethyl)tetrahydrofuran-3-yl)-6-(methylsulfonyl)pyridin-2-yl)amino)pyridin-2-yl)acetamide;

N-(5-(2,2-dimethyl-2,3-dihydropyrazolo[5,1-b]oxazol-6-yl)-4-((4-(3-(hydroxymethyl)tetrahydrofuran-3-yl)-6-(methylsulfonyl)pyridin-2-yl)amino)pyridin-2-yl)acetamide;

N-(4-((4-(3-(hydroxymethyl)tetrahydrofuran-3-yl)-6-(methylsulfonyl)pyridin-2-yl)amino)-5-(5'H, 7'H-spiro[cyclopropane-1,6'-pyrazolo[5,1-b][1,3]oxazin]-2'-yl)pyridin-2-yl)acetamide;

N-(4-((4-methyl-6-(methylsulfonyl)pyridin-2-yl)amino)-5-(pyridin-2-yloxy)pyridin-2-yl)acetamide;

N-(5-(1H-imidazol-2-yl)-4-((4-methyl-6-(methylsulfonyl)pyridin-2-yl)amino)pyridin-2-yl)acetamide;

N-(5-(4-(2-hydroxypropan-2-yl)furan-2-yl)-4-((4-methyl-6-(methylsulfonyl)pyridin-2-yl)amino)pyridin-2-yl)acetamide;

N-(5-(furan-2-yl)-4-((4-(3-methoxytetrahydrofuran-3-yl)-6-(methylsulfonyl)pyridin-2-yl)amino)pyridin-2-yl)acetamide;

N-(5-(1H-benzo[d]imidazol-2-yl)-4-((4-methyl-6-(methylsulfonyl)pyridin-2-yl)amino)pyridin-2-yl)acetamide;

N-(3-fluoro-5-(2-hydroxypropan-2-yl)-4'-((4-methyl-6-(methylsulfonyl)pyridin-2-yl)amino)-[2,3'-bipyridin]-6'-yl)acetamide;

N-(5-(2-hydroxypropan-2-yl)-4-methyl-4'-((4-methyl-6-(methylsulfonyl)pyridin-2-yl)amino)-[2,3'-bipyridin]-6'-yl)acetamide;

N-(5-(2,6-dimethylmorpholino)-4'-((6-(methylsulfonyl)-4-((tetrahydrofuran-3-yl)methoxy)pyridin-2-yl)amino)-[2,3'-bipyridin]-6'-yl)acetamide;

N-(5-(2,6-dimethylmorpholino)-4'-((6-(methylsulfonyl)-4-(((tetrahydrofuran-3-yl)oxy)methyl)pyridin-2-yl)amino)-[2,3'-bipyridin]-6'-yl)acetamide;

N-(5-(3-methoxy-1-methyl-1H-pyrazol-4-yl)-4-((4-methyl-6-(methylsulfonyl)pyridin-2-yl)amino)pyridin-2-yl)acetamide;

N-(4-((4-(3-(hydroxymethyl)tetrahydrofuran-3-yl)-6-(methylsulfonyl)pyridin-2-yl)amino)-5-(3-methoxy-1-methyl-1H-pyrazol-4-yl)pyridin-2-yl)acetamide;

N-(5-(6,7-dihydro-4H-furo[3,2-c]pyran-2-yl)-4-((4-methyl-6-(methylsulfonyl)pyridin-2-yl)amino)pyridin-2-yl)acetamide;

N-(5-(5-methyl-4,5,6,7-tetrahydrofuro[3,2-c]pyridin-2-yl)-4-((4-methyl-6-(methylsulfonyl)pyridin-2-yl)amino)pyridin-2-yl)acetamide;
N-(5-(cyclopropylmethoxy)-4-((4-(1-methyl-1H-pyrazol-3-yl)-6-(methylsulfonyl)pyridin-2-yl)amino)pyridin-2-yl)acetamide;
N-(5-((1-hydroxycyclopropyl)methoxy)-4-((4-(1-methyl-1H-pyrazol-3-yl)-6-(methylsulfonyl)pyridin-2-yl)amino)pyridin-2-yl)acetamide;
N-(5-(benzo[d]oxazol-2-yl)-4-((4-(3-(hydroxymethyl)tetrahydrofuran-3-yl)-6-(methylsulfonyl)pyridin-2-yl)amino)pyridin-2-yl)acetamide;
N-(5-(2,2-dimethyl-3-oxo-3,4-dihydro-2H-pyrido[3,2-b][1,4]oxazin-6-yl)-4-((4-methyl-6-(methylsulfonyl)pyridin-2-yl)amino)pyridin-2-yl)acetamide;
N-(4-((4-methyl-6-(methylsulfonyl)pyridin-2-yl)amino)-5-(pyrazolo[1,5-a]pyrazin-2-yl)pyridin-2-yl)acetamide;
N-(4-((4-(2-methoxyethoxy)-6-(methylsulfonyl)pyridin-2-yl)amino)-5-(pyrazolo[1,5-a]pyrazin-2-yl)pyridin-2-yl)acetamide;
N-(4-((4-methyl-6-(methylsulfonyl)pyridin-2-yl)amino)-5-(pyrazolo[1,5-c]pyrimidin-2-yl)pyridin-2-yl)acetamide;
N-(4-((4-(2-methoxyethoxy)-6-(methylsulfonyl)pyridin-2-yl)amino)-5-(pyrazolo[1,5-c]pyrimidin-2-yl)pyridin-2-yl)acetamide;
N-(4-((4-methyl-6-(methylsulfonyl)pyridin-2-yl)amino)-5-(pyrazolo[1,5-a]pyrimidin-2-yl)pyridin-2-yl)acetamide;
N-(4-((4-(2-methoxyethoxy)-6-(methylsulfonyl)pyridin-2-yl)amino)-5-(pyrazolo[1,5-a]pyrimidin-2-yl)pyridin-2-yl)acetamide;
N-(4-((4-methyl-6-(methylsulfonyl)pyridin-2-yl)amino)-5-(pyrazolo[1,5-a]pyrimidin-5-yl)pyridin-2-yl)acetamide;
N-(4-((4-(2-methoxyethoxy)-6-(methylsulfonyl)pyridin-2-yl)amino)-5-(pyrazolo[1,5-a]pyrimidin-5-yl)pyridin-2-yl)acetamide; and
N-(5-(2,2-dimethyl-2,3-dihydro-1H-pyrido[2,3-b][1,4]oxazin-6-yl)-4-((6-(methylsulfonyl)-4-(tetrahydro-2H-pyran-4-yl)pyridin-2-yl)amino)pyridin-2-yl)acetamide.

19. A pharmaceutical composition comprising one or more compounds according to claim 2 or a stereoisomer or pharmaceutically acceptable salt thereof, and a pharmaceutically acceptable excipient.

20. A pharmaceutical composition comprising one or more compounds according to claim 18 or pharmaceutically acceptable salt thereof, and a pharmaceutically acceptable excipient.

* * * * *